(12) United States Patent
Kori et al.

(10) Patent No.: US 9,499,568 B2
(45) Date of Patent: Nov. 22, 2016

(54) HETEROCYCLIC COMPOUND AND USE THEREOF

(71) Applicant: Takeda Pharmaceutical Company Limited, Osaka-shi, Osaka (JP)

(72) Inventors: Masakuni Kori, Osaka (JP); Toshihiro Imaeda, Kanagawa (JP); Shinji Nakamura, Kanagawa (JP); Masashi Toyofuku, Kanagawa (JP); Eiji Honda, Kanagawa (JP); Osamu Ujikawa, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 14/804,935

(22) Filed: Jul. 21, 2015

(65) Prior Publication Data

US 2015/0353578 A1    Dec. 10, 2015

Related U.S. Application Data

(63) Continuation of application No. 13/816,137, filed as application No. PCT/JP2011/068497 on Aug. 9, 2011, now Pat. No. 9,150,591.

(30) Foreign Application Priority Data

Aug. 10, 2010 (JP) ................... 2010-179577

(51) Int. Cl.
*C07D 513/04* (2006.01)

(52) U.S. Cl.
CPC ................... *C07D 513/04* (2013.01)

(58) Field of Classification Search
CPC .................................................. C07D 513/04
USPC ......................................... 544/10; 514/222.8
See application file for complete search history.

(56) References Cited

U.S. PATENT DOCUMENTS

| | | | |
|---|---|---|---|
| 6,894,043 B1 | 5/2005 | Pirotte et al. | |
| 7,262,190 B2 | 8/2007 | Desos et al. | |
| 9,150,591 B2 * | 10/2015 | Kori ..................... | C07D 513/04 |
| 2004/0242571 A1 | 12/2004 | Gouliaev et al. | |
| 2005/0065146 A1 | 3/2005 | Cordi et al. | |
| 2005/0165008 A1 | 7/2005 | Francotte et al. | |
| 2006/0128697 A1 | 6/2006 | Dosos et al. | |
| 2007/0004709 A1 | 1/2007 | Francotte et al. | |
| 2009/0163545 A1 | 6/2009 | Goldfarb | |
| 2010/0010090 A1 | 1/2010 | Dominguez-Manzanares | |
| 2010/0240635 A1 | 9/2010 | Cordi et al. | |
| 2011/0118236 A1 | 5/2011 | Mochizuki et al. | |
| 2012/0142672 A1 | 6/2012 | Koike et al. | |

FOREIGN PATENT DOCUMENTS

| | | |
|---|---|---|
| JP | 2-085851 | 3/1990 |
| JP | 4-037742 | 2/1992 |
| JP | 4-119890 | 4/1992 |
| JP | 7-137462 | 5/1995 |
| JP | 2009-248543 | 10/2009 |
| WO | 01/40210 | 6/2001 |
| WO | 2004/099217 | 11/2004 |
| WO | 2009/061699 | 5/2009 |
| WO | 2009/119088 | 10/2009 |
| WO | 2009/147167 | 12/2009 |
| WO | 2010/054067 | 5/2010 |
| WO | 2010/083141 | 7/2010 |
| WO | 2010/098495 | 9/2010 |
| WO | 2010/106249 | 9/2010 |
| WO | 2010/140339 | 12/2010 |
| WO | 2011/036885 | 3/2011 |
| WO | 2011/036889 | 3/2011 |

OTHER PUBLICATIONS

Dingledine, et al., "The Glutamate Receptor Ion Channels", Pharmacological Reviews, vol. 51, No. 1, pp. 7-61, 1999.
Bettler, et al., "Review: Neurotransmitter Receptors II AMPA and Kainate Receptors", Neuropharmacology, vol. 34, pp. 123-139, 1995.
Malinow, et al., "AMPA Receptor Trafficking and Synaptic Plasticity", Ann. Rev. Neurosci, vol. 25, pp. 103-126, 2002.
Bowie, et al., "Ionotropic Glutamate Receptors & CNS Disorders", CNS & Neurological Disorders—Drug Target, vol. 7, pp. 129-143, 2008.
Morrow, et al., "Recent advances in positive allosteric modulators of the AMPA receptor", Current Opinion in Drug Discovery and Development, vol. 9, pp. 571-579, 2006.
L'abbé, et al., "Synthesis of Fused Dihydro-1,2,4-thiadiazolimines from Cyano-substituted Azides and Acyl Isothiocyanates", Journal of the Chemical Society, Perkin Transactions 1: Organic and Bio-Organic Chemistry, vol. 1, pp. 27-29, 1993.
Database Registry [Online] Chemical Abstracts Service, Columbus, Ohio, US; 2004, XP002661033.

(Continued)

*Primary Examiner* — Kahsay Habte
(74) *Attorney, Agent, or Firm* — Hamre, Schumann, Mueller & Larson, P.C.

(57) ABSTRACT

Provided is a compound represented by the formula (I):

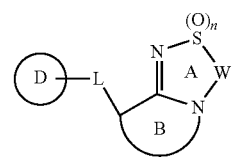

(I)

wherein each symbol is as defined in the specification, or a salt thereof, which has an AMPA (α-amino-3-hydroxy-5-methyl-4-isoxazolepropionic acid) receptor potentiating action. The compound of the present invention is useful as a prophylactic or therapeutic drug for depression, schizophrenia, Alzheimer's disease or attention deficit hyperactivity disorder (ADHD) and the like.

17 Claims, 1 Drawing Sheet

(56) References Cited

OTHER PUBLICATIONS

Ward, et al., "Recent Advances in the Discovery of Selective AMPA Receptor Positive Allosteric Modulators", Current Medicinal Chemistry, vol. 17, No. 30, pp. 3503-3513, 2010.
STN Registry No. 728898-87-1, entered Aug. 19, 2014; STN Registry No. 726155-61-9, entered Aug. 13, 2004; STN Registry No. 565192-84-9, entered Aug. 12, 2003; STN Registry No. 554406-78-9, entered Jul. 25, 2003; STN Registry No. 315677-93-1, entered Jan. 22, 2001; STN Registry No. 303019-30-9, entered Nov. 16 2000; STN Registry No. 303018-15-7, entered Nov. 16, 2000; STN Registry No. 71518-03-1, entered Nov. 16, 1984—STN International, 8 pages.

* cited by examiner

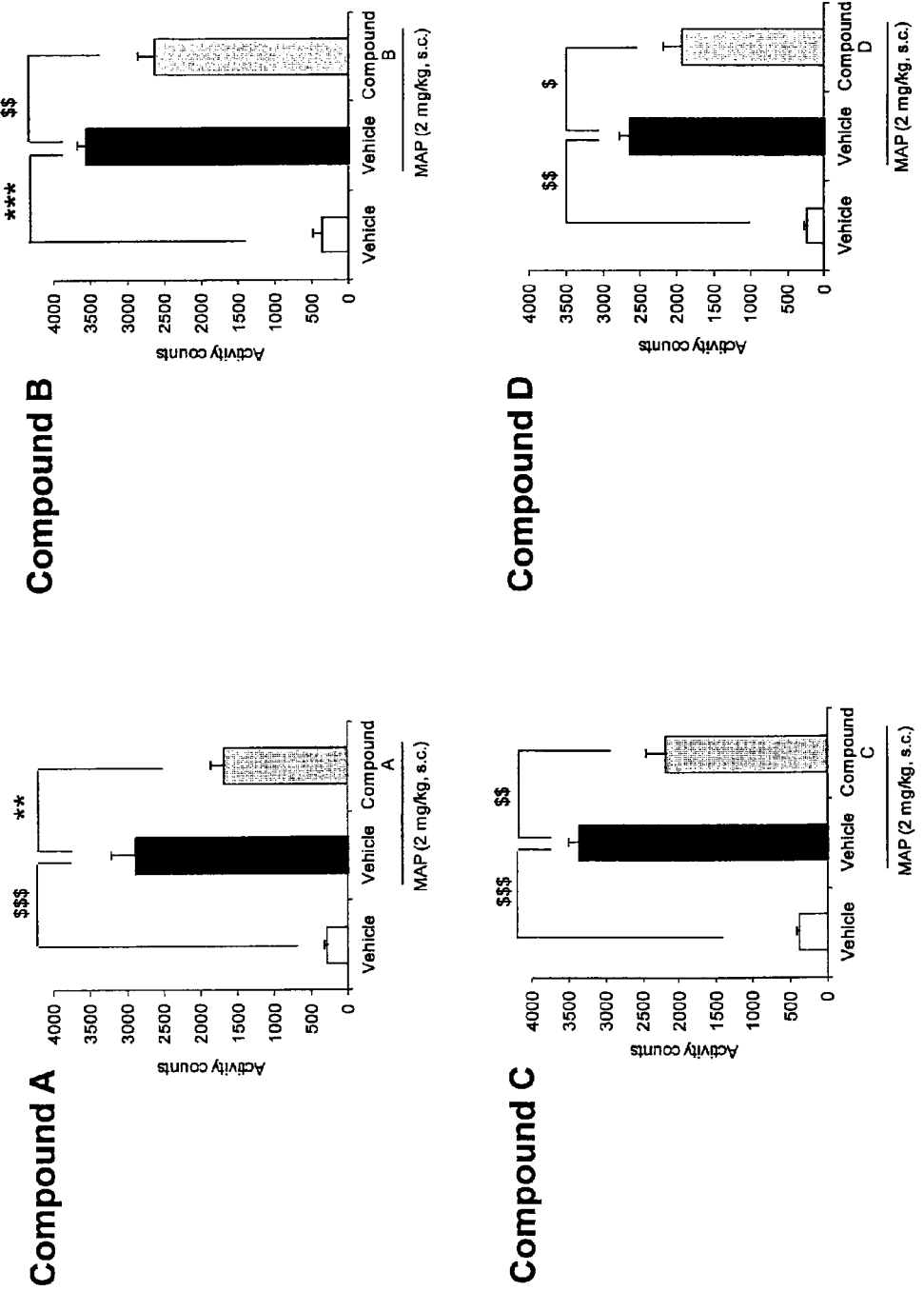

SEQUENCE LISTING

```
<160> NUMBER OF SEQ ID NOS: 4

<210> SEQ ID NO 1
<211> LENGTH: 42
<212> TYPE: DNA
<213> ORGANISM: Artificial
<220> FEATURE:
<223> OTHER INFORMATION: Forward primer for GluR1 flip cDNA
```

```
<400> SEQUENCE: 1
actgaattcg ccaccatgca gcacattttt gccttcttct gc            42

<210> SEQ ID NO 2
<211> LENGTH: 32
<212> TYPE: DNA
<213> ORGANISM: Artificial
<220> FEATURE:
<223> OTHER INFORMATION: Reverse primer for GluR1 flip cDNA

<400> SEQUENCE: 2
ccgcggccgc ttacaatccc gtggctccca ag                       32

<210> SEQ ID NO 3
<211> LENGTH: 41
<212> TYPE: DNA
<213> ORGANISM: Artificial
<220> FEATURE:
<223> OTHER INFORMATION: Forward primer for stargazin cDNA

<400> SEQUENCE: 3
ggtctcgagg ccaccatggg gctgtttgat cgaggtgttc a             41

<210> SEQ ID NO 4
<211> LENGTH: 40
<212> TYPE: DNA
<213> ORGANISM: Artificial
<220> FEATURE:
<223> OTHER INFORMATION: Reverse primer for stargazin cDNA

<400> SEQUENCE: 4
gttggatcct tatacggggg tggtccggcg gttggctgtg               40
```

HETEROCYCLIC COMPOUND AND USE THEREOF

TECHNICAL FIELD

The present invention relates to a heterocyclic compound, particularly a heterocyclic compound having an AMPA (α-amino-3-hydroxy-5-methyl-4-isoxazolepropionic acid) receptor potentiating action.

BACKGROUND OF THE INVENTION

Glutamate is the most abundant excitatory neurotransmitter in the mammalian central nervous system. Glutamate plays a pivotal role in cognition, mood, and motor function, and its neurotransmission becomes unstable in psychiatric diseases and neurological disorder. Glutamate receptors are divided into ligand gated ion channels and G protein-coupled receptors, and the ligand gated ion channels are further divided into α-amino-3-hydroxy-5-methyl-4-isoxazolepropionic acid (AMPA) receptors, N-methyl-D-aspartic acid (NMDA) receptors, and kainic acid (KA) receptors. (non-patent document 1)

AMPA receptor is one kind of receptor for excitatory neurotransmitter glutamate, and was named for the selective activation of the receptor by AMPA. AMPA receptors are composed of 4 subunits (GluR1, GluR2, GluR3, GluR4). Each subunit exists in flip and flop alternatively spliced variants. AMPA receptors form homo- or hetero-tetramers composed of these subunits in vivo. The physiological property of AMPA receptor has been reported to change depending on the subunit composition. (non-patent documents 1, 2, 3)

The importance of AMPA receptor in cerebrophysiology is well known, and a compound having an AMPA receptor potentiating action is expected to be useful as a prophylactic or therapeutic drug for psychiatric diseases, neurodegenerative diseases, cognitive disorders, sleep disorders and the like. (non-patent documents 4, 5)

As a heterocyclic compound, patent document 1 discloses disodium {4-(acetylamino)-8-[(3-{2-[4-(acetylamino)-2,2-dioxido-7-(sulfonatomethyl)-6H-pyrazolo[5,1-c][1,2,4]thiadiazin-8-yl]ethenyl}-5,5-dimethylcyclohex-2-en-1-yl)methylidene]-2,2-dioxido-8H-pyrazolo[5,1-c][1,2,4]thiadiazin-7-yl}methanesulfonate.

In addition, non-patent document 6 discloses 2,2,2-trichloro-N-(7,7-diphenyl-6,7-dihydro-5H-pyrrolo[2,1-c][1,2,4]thiadiazol-3-ylidene)acetamide.

DOCUMENT LIST

Patent Document

[patent document 1] JP-A-H4-37742

Non-Patent Documents

[Non-Patent Document 1]
Pharmacological Reviews, Vol. 51, 7-61, 1999
[Non-Patent Document 2]
Neuropharmacology, Vol. 34, 123-139, 1995
[Non-Patent Document 3]
Ann. Rev. Neurosci., Vol. 25, 103-126, 2002
[Non-Patent Document 4]
CNS & Neurological Disorders-Drug Targets, Vol. 7, 129-143, 2008
[Non-Patent Document 5]
Current Opinion in Drug Discovery and Development, Vol. 9, 571-579, 2006
[Non-Patent Document 6]
Journal of the Chemical Society, Perkin Transactions 1: Organic and Bio-Organic Chemistry (1993), (1), 27-9

SUMMARY OF THE INVENTION

Problems to be Solved by the Invention

The present invention aims to provide a heterocyclic compound having an AMPA receptor potentiating action (AMPA receptor potentiator; sometimes to be also referred to as AMPA receptor positive modulator, AMPAkine, AMPA receptor allosteric modulator, AMPA receptor positive allosteric modulator, or positive allosteric activator of AMPA receptor).

Means of Solving the Problems

The present inventors have found that a compound represented by the following formula (I') or a salt thereof (compound (I') in the present specification, or sometimes to be referred to as the compound of the present invention) has an AMPA receptor potentiating action, and conducted further studies and completed the present invention. In the present specification, compound (I') and a prodrug thereof are sometimes to be collectively referred to as the compound of the present invention.

A compound represented by the following formula (I) and a salt thereof, which are encompassed in the scope of compound (I'), are novel compounds.

Accordingly, the present invention provides the following and the like.

[1] A compound represented by the formula (I):

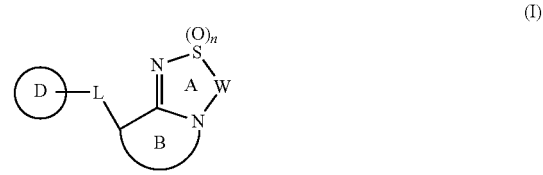

(I)

wherein
ring A is an optionally substituted 5-7-membered heterocycle,
ring B is an optionally substituted 5-8-membered heterocycle having, as a ring-constituting atom besides carbon atom, one nitrogen atom, and optionally further having 1 to 3 hetero atoms selected from a nitrogen atom, an oxygen atom and a sulfur atom,
ring D is an optionally substituted non-aromatic hydrocarbon ring, an optionally substituted non-aromatic heterocycle, an optionally substituted aromatic hydrocarbon ring, or an optionally substituted aromatic heterocycle,
W is optionally substituted $C_{1-3}$ alkylene, or optionally substituted $C_{2-3}$ alkenylene,
L is a bond, or a spacer having the main chain having an atom number of 1-8, and
n is 0, 1 or 2, provided when
a partial structural formula represented by the formula (I):

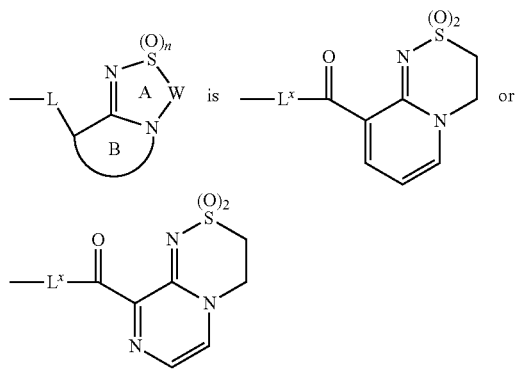 is 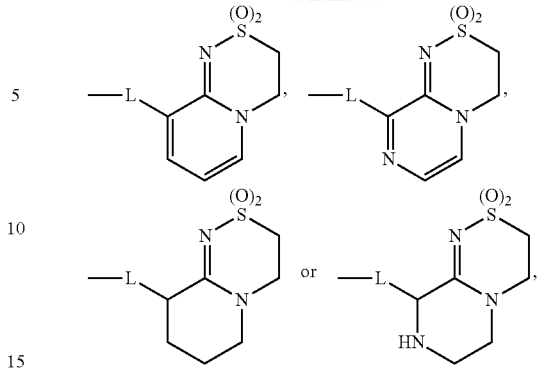

wherein L^x is a bond or a spacer having the main chain having an atom number of 1-7, one or both of ring A and ring B has(have) substituent(s),
excluding the following compounds;
2,2,2-trichloro-N-(7,7-diphenyl-6,7-dihydro-5H-pyrrolo[2,1-c][1,2,4]thiadiazol-3-ylidene)acetamide,
{4-(acetylamino)-8-[(3-{2-[4-(acetylamino)-2,2-dioxido-7-(sulfonatomethyl)-6H-pyrazolo[5,1-c][1,2,4]thiadiazin-8-yl]ethenyl}-5,5-dimethylcyclohex-2-en-1-yl)methylidene]-2,2-dioxido-8H-pyrazolo[5,1-c][1,2,4]thiadiazin-7-yl}methanesulfonic acid,
3-tert-butyl-5-[(7-tert-butyl-2,2-dioxido-3,4-dihydro-6H-pyrazolo[5,1-c][1,2,4]thiadiazin-8-yl)diazenyl]-1H-pyrazole-4-carbonitrile,
ethyl 2-[(4-{[(2-butoxy-4-octylphenyl)sulfonyl]amino}-3-ethyl-7-methyl-2,2-dioxido-6H-pyrazolo[5,1-c][1,2,4]thiadiazin-8-yl)diazenyl]benzoate,
7-methyl-4,8-diphenyl-6H-pyrazolo[5,1-c][1,2,4]thiadiazine 2,2-dioxide,
or a salt thereof (hereinafter sometimes to be referred to as compound (I));
[2] the compound of [1], wherein ring A and ring B are each an optionally substituted 6-membered ring,
ring B has, as a ring-constituting atom besides carbon atom, one nitrogen atom, and optionally further has 1 to 3 nitrogen atoms,
L is a bond, —O—, —O—CH$_2$—, —CH$_2$—O—, —CO—NH—, —CO—N(C$_{1-6}$ alkyl)-, —S—, —SO—, —SO$_2$—, C$_{1-6}$ alkylene, C$_{2-6}$ alkenylene or C$_{2-6}$ alkynylene,
or a salt thereof;
[3] the compound of [2], wherein W is optionally substituted —CH$_2$—CH$_2$—, and
n is 2,
or a salt thereof;
[4] the compound of [2] or [3], wherein the partial structural formula represented by the formula (I):

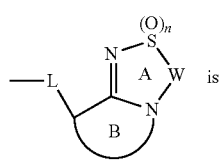 is ring B is optionally substituted by substituent(s) selected from
a halogen atom;
hydroxy;
C$_{1-6}$ alkyl optionally substituted by a halogen atom;
C$_{1-6}$ alkoxy; and
C$_{1-6}$ alkyl-carbonyl,
or a salt thereof;
[5] the compound of any one of [2]-[4], wherein L is a bond, or a salt thereof;
[6] the compound of any one of [2]-[5], wherein ring D is an optionally substituted 3-8-membered monocyclic non-aromatic hydrocarbon ring, an optionally substituted 6-14-membered aromatic hydrocarbon ring, an optionally substituted 6-14-membered non-aromatic hydrocarbon ring, an optionally substituted 5-6-membered monocyclic aromatic heterocycle, an optionally substituted 3-8-membered monocyclic non-aromatic heterocycle, an optionally substituted 8-14-membered condensed aromatic heterocycle or an optionally substituted 6-14-membered condensed non-aromatic heterocycle, or a salt thereof;
[7] the compound of any one of [2]-[6], wherein ring D is optionally substituted C$_{3-7}$ cycloalkane,
optionally substituted C$_{6-14}$ arene,
optionally substituted dihydronaphthalene,
optionally substituted tetrahydronaphthalene,
optionally substituted dihydroinden,
optionally substituted thiophene,
optionally substituted azetidine,
optionally substituted piperidine,
optionally substituted furan,
optionally substituted pyridine,
optionally substituted pyrazole,
optionally substituted 1,2,4-oxadiazole,
optionally substituted dihydrobenzodioxin,
optionally substituted dihydrobenzofuran,
optionally substituted benzodioxole,
optionally substituted benzofuran,
optionally substituted indole,
optionally substituted quinoline,
optionally substituted benzimidazole,
optionally substituted benzothiazole,
optionally substituted indazole, or
optionally substituted dibenzothiophene,
or a salt thereof;
[8] the compound of any one of [2]-[7], wherein ring D is C$_{3-7}$ cycloalkane, C$_{6-14}$ arene, dihydronaphthalene, tetrahydronaphthalene, dihydroinden, thiophene, azetidine, piperidine, furan, pyridine, pyrazole, 1,2,4-oxadiazole, dihydrobenzodioxin, dihydrobenzofuran, benzodioxole, benzofuran, indole, quinoline, benzimidazole, benzothiazole, indazole or dibenzothiophene, optionally substituted by 1-4 substituents selected from
(1) a halogen atom;
(2) cyano;
(3) hydroxy;
(4) oxo;
(5) $C_{1-6}$ alkyl optionally substituted by substituent(s) selected from 1) a halogen atom, 2) phenyl optionally substituted by substituent(s) selected from a halogen atom and $C_{1-6}$ alkyl and 3) $C_{2-6}$ alkoxycarbonyl;
(6) $C_{3-7}$ cycloalkyl optionally substituted by $C_{2-6}$ alkoxycarbonyl or phenyl;
(7) $C_{1-6}$ alkyl-carbonyl;
(8) phenyl-carbonyl optionally substituted by $C_{1-6}$ alkoxy;
(9) $C_{2-6}$ alkenyl substituted by phenyl;
(10) phenyl optionally substituted by 1 to 3 substituents selected from a halogen atom, $C_{1-6}$ alkyl, $C_{3-7}$ cycloalkyl and $C_{1-6}$ alkoxy;
(11) pyrazole optionally substituted by 1 to 3 substituents selected from $C_{1-6}$ alkyl optionally substituted by a halogen atom, and $C_{3-7}$ cycloalkyl;
(12) pyrrolidine;
(13) dihydrobenzofuran;
(14) morpholine;
(15) oxetane substituted by a halogen atom;
(16) sulfanyl substituted by a halogen atom or $C_{1-6}$ alkyl;
(17) $C_{1-6}$ alkylsulfonyloxy substituted by a halogen atom;
(18) di-$C_{1-6}$ alkylcarbamoyl;
(19) 4,4,5,5-tetramethyl-1,3,2-dioxaborolane;
(20) $C_{1-6}$ alkoxy optionally substituted by substituent(s) selected from a halogen atom, $C_{3-7}$ cycloalkyl, phenyl optionally substituted by a halogen atom, tetrahydrofuran and tetrahydropyran;
(21) $C_{3-7}$ cycloalkyloxy optionally substituted by $C_{1-6}$ alkyl, oxo or $C_{2-6}$ alkylenedioxy;
(22) $C_{3-7}$ cycloalkenyloxy optionally substituted by $C_{1-6}$ alkyl;
(23) phenyloxy optionally substituted by 1 to 3 substituents selected from a halogen atom, cyano, hydroxy, $C_{2-6}$ alkyl optionally substituted by a halogen atom, and $C_{1-6}$ alkoxy optionally substituted by a halogen atom;
(24) pyridyloxy optionally substituted by a halogen atom, or $C_{1-6}$ alkyl optionally substituted by a halogen atom;
(25) silyloxy substituted by $C_{1-6}$ alkyl;
(26) tetrahydrofuranyloxy;
(27) tetrahydropyranyloxy; and
(28) dihydrobenzofuranyloxy,
or a salt thereof;
[9] the compound of any one of [2]-[8], wherein ring D is benzene optionally substituted by 1-3 substituents selected from
(1) a halogen atom;
(2) cyano;
(3) hydroxy;
(4) $C_{1-6}$ alkyl optionally substituted by substituent(s) selected from 1) a halogen atom, 2) phenyl optionally substituted by substituent(s) selected from a halogen atom and $C_{1-6}$ alkyl and 3) $C_{2-6}$ alkoxycarbonyl;
(5) $C_{3-7}$ cycloalkyl optionally substituted by $C_{1-6}$ alkoxycarbonyl or phenyl;
(6) $C_{1-6}$ alkyl-carbonyl;
(7) phenyl-carbonyl optionally substituted by $C_{1-6}$ alkoxy;
(8) $C_{2-6}$ alkenyl substituted by phenyl;
(9) phenyl optionally substituted by a halogen atom or $C_{1-6}$ alkyl;

(10) pyrazole optionally substituted by 1 to 3 substituents selected from $C_{1-6}$ alkyl optionally substituted by a halogen atom, and $C_{3-7}$ cycloalkyl;
(11) pyrrolidine;
(12) dihydrobenzofuran;
(13) morpholine;
(14) oxetane substituted by a halogen atom;
(15) sulfanyl substituted by a halogen atom or $C_{1-6}$ alkyl;
(16) $C_{1-6}$ alkylsulfonyloxy substituted by a halogen atom;
(17) di-$C_{1-6}$ alkylcarbamoyl;
(18) 4,4,5,5-tetramethyl-1,3,2-dioxaborolane;
(19) $C_{1-6}$ alkoxy optionally substituted by substituent(s) selected from a halogen atom, $C_{3-7}$ cycloalkyl, phenyl optionally substituted by a halogen atom, tetrahydrofuran and tetrahydropyran;
(20) $C_{3-7}$ cycloalkyloxy optionally substituted by $C_{1-6}$ alkyl, oxo or $C_{2-6}$ alkylenedioxy;
(21) $C_{3-7}$ cycloalkenyloxy optionally substituted by $C_{1-6}$ alkyl;
(22) phenyloxy optionally substituted by substituent(s) selected from a halogen atom, cyano, hydroxy, $C_{1-6}$ alkyl optionally substituted by a halogen atom, and $C_{1-6}$ alkoxy optionally substituted by a halogen atom;
(23) pyridyloxy optionally substituted by a halogen atom, or $C_{1-6}$ alkyl optionally substituted by a halogen atom;
(24) silyloxy substituted by $C_{1-6}$ alkyl;
(25) tetrahydrofuranyloxy;
(26) tetrahydropyranyloxy; and
(27) dihydrobenzofuranyloxy,
or a salt thereof;
[10] the compound of any one of [2]-[4] and [6]-[7], wherein the partial structural formula represented by the formula (I):

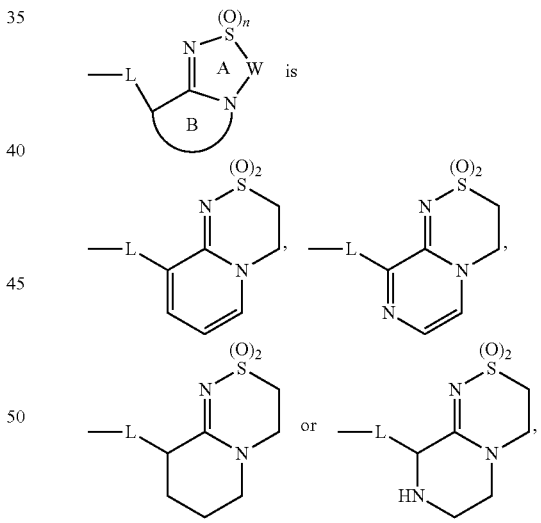

ring B is optionally substituted by substituent(s) selected from
a halogen atom;
hydroxy;
$C_{1-6}$ alkyl optionally substituted by a halogen atom;
$C_{1-6}$ alkoxy; and
$C_{1-6}$ alkyl-carbonyl,
ring D is $C_{3-7}$ cycloalkane, $C_{6-14}$ arene, dihydronaphthalene, tetrahydronaphthalene, dihydroinden, thiophene, azetidine, piperidine, furan, pyridine, pyrazole, 1,2,4-oxadiazole, dihydrobenzodioxin, dihydrobenzofuran, benzodioxole, benzofuran, indole, quinoline, benzimidazole, benzothiazole, indazole or dibenzothiophene, each optionally substituted by 1-4 substituents selected from
(1) a halogen atom;
(2) cyano;
(3) hydroxy;
(4) oxo;
(5) optionally substituted $C_{1-6}$ alkyl;
(6) optionally substituted $C_{3-7}$ cycloalkyl;
(7) substituted carbonyl;
(8) substituted $C_{2-6}$ alkenyl;
(9) optionally substituted $C_{6-14}$ aryl;
(10) optionally substituted $C_{7-16}$ aralkyl;
(11) optionally substituted pyrazole
(12) pyrrolidine;
(13) dihydrobenzofuran;
(14) morpholine;
(15) substituted oxetane;
(16) substituted sulfanyl;
(17) substituted $C_{2-6}$ alkylsulfonyloxy;
(18) di-$C_{1-6}$ alkyl-carbamoyl;
(19) substituted dioxaborolane;
(20) optionally substituted $C_{1-6}$ alkoxy;
(21) $C_{3-7}$ cycloalkyloxy;
(22) optionally substituted $C_{3-7}$ cycloalkenyloxy;
(23) optionally substituted $C_{6-14}$ aryloxy;
(24) optionally substituted $C_{7-16}$ aralkyloxy;
(25) optionally substituted pyridyloxy;
(26) substituted silyloxy;
(27) tetrahydrofuranyloxy;
(28) tetrahydropyranyloxy; and
(29) dihydrobenzofuranyloxy, and L is a bond, —O—, —O—CH$_2$—, —CH$_2$—O—, —CO—NH—, —CO—N(C$_{1-6}$ alkyl)-, —S—, —SO—, —SO$_2$—, $C_{1-6}$ alkylene, $C_{1-6}$ alkenylene or $C_{2-6}$ alkynylene, or a salt thereof;

[11] the compound of any one of [2]-[4], [6]-[8] and [10], wherein the partial structural formula represented by the formula (I):

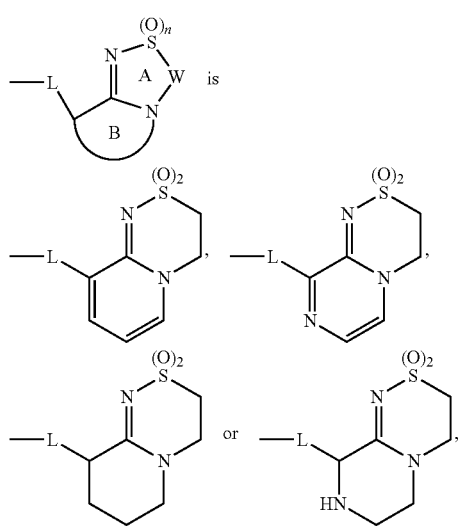

ring B is optionally substituted by substituent(s) (preferably 1-2) selected from
a halogen atom;
hydroxy;
$C_{1-6}$ alkyl optionally substituted by halogen atom(s) (preferably 1-3);
$C_{1-6}$ alkoxy; and
$C_{1-6}$ alkyl-carbonyl, ring D is $C_{3-7}$ cycloalkane, $C_{6-14}$ arene, dihydronaphthalene, tetrahydronaphthalene, dihydroinden, thiophene, azetidine, piperidine, furan, pyridine, pyrazole, 1,2,4-oxadiazole, dihydrobenzodioxin, dihydrobenzofuran, benzodioxole, benzofuran, indole, quinoline, benzimidazole, benzothiazole, indazole or dibenzothiophene, each optionally substituted by 1-4 substituents selected from
(1) a halogen atom;
(2) cyano;
(3) hydroxy;
(4) oxo;
(5) $C_{1-6}$ alkyl optionally substituted by substituent(s) (preferably 1-3) selected from 1) a halogen atom, 2) phenyl optionally substituted by substituent(s) (preferably 1-3) selected from halogen atom(s) (preferably 1-3) and $C_{1-6}$ alkyl (preferably 1-3) and 3) $C_{1-6}$ alkoxycarbonyl;
(6) $C_{3-7}$ cycloalkyl optionally substituted by $C_{1-6}$ alkoxycarbonyl (preferably 1-2) or phenyl (preferably 1-2);
(7) $C_{1-6}$ alkyl-carbonyl;
(8) phenyl-carbonyl optionally substituted by $C_{1-6}$ alkoxy (preferably 1-2);
(9) $C_{2-6}$ alkenyl substituted by phenyl (preferably 1-2);
(10) phenyl optionally substituted by 1 to 3 substituents selected from a halogen atom, $C_{1-6}$ alkyl, $C_{3-7}$ cycloalkyl and $C_{1-6}$ alkoxy;
(11) pyrazole optionally substituted by 1 to 3 substituents selected from $C_{1-6}$ alkyl optionally substituted by halogen atom(s) (preferably 1-3), and $C_{3-7}$ cycloalkyl;
(12) pyrrolidine;
(13) dihydrobenzofuran;
(14) morpholine;
(15) oxetane substituted by halogen atom(s) (preferably 1-3);
(16) sulfanyl substituted by halogen atom(s) (preferably 1-6) or $C_{1-6}$ alkyl (preferably 1-3);
(17) $C_{1-6}$ alkylsulfonyloxy substituted by halogen atom(s) (preferably 1-3);
(18) di-$C_{1-6}$ alkylcarbamoyl;
(19) 4,4,5,5-tetramethyl-1,3,2-dioxaborolane;
(20) $C_{1-6}$ alkoxy optionally substituted by substituent(s) (preferably 1-3) selected from a halogen atom, $C_{3-7}$ cycloalkyl, phenyl optionally substituted by halogen atom(s) (preferably 1-3), tetrahydrofuran and tetrahydropyran;
(21) $C_{3-7}$ cycloalkyloxy optionally substituted (preferably 1-3) by $C_{1-6}$ alkyl, oxo or $C_{2-6}$ alkylenedioxy;
(22) $C_{3-7}$ cycloalkenyloxy optionally substituted by $C_{1-6}$ alkyl (preferably 1-3);
(23) phenyloxy optionally substituted by 1 to 3 substituents selected from a halogen atom, cyano, hydroxy, $C_{2-6}$ alkyl optionally substituted by halogen atom(s) (preferably 1-3), and $C_{1-6}$ alkoxy optionally substituted by halogen atom(s) (preferably 1-3);
(24) pyridyloxy optionally substituted (preferably 1-3) by a halogen atom, or $C_{1-6}$ alkyl optionally substituted by halogen atom(s) (preferably 1-3);
(25) silyloxy substituted by $C_{1-6}$ alkyl (preferably 1-3);
(26) tetrahydrofuranyloxy;
(27) tetrahydropyranyloxy; and
(28) dihydrobenzofuranyloxy, L is a bond, —O—, —O—CH$_2$—, —CH$_2$—O—, —CO—NH—, —CO—N(C$_{1-6}$ alkyl)-, —S—, —SO—, —SO$_2$—, $C_{1-6}$ alkylene, $C_{2-6}$ alkenylene or $C_{2-6}$ alkynylene, or a salt thereof;

[12] the compound of any one of [2]-[4], [6]-[8] and [10]-[11], wherein the partial structural formula represented by the formula (I):

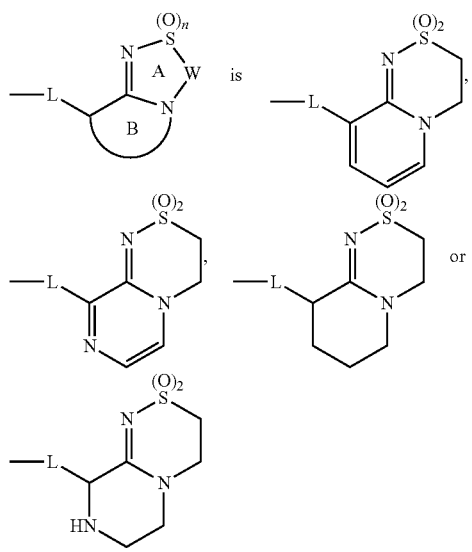

ring B is optionally substituted by substituent(s) (preferably 1-2) selected from a halogen atom, hydroxy, $C_{1-6}$ alkyl and $C_{1-6}$ alkoxy,
ring D is $C_{3-7}$ cycloalkane, benzene, naphthalene, pyridine or thiophene optionally substituted by 1 to 3 substituents selected from
(1) a halogen atom;
(2) hydroxy;
(3) $C_{1-6}$ alkyl optionally substituted by substituent(s) (preferably 1-3) selected from 1) a halogen atom, and 2) phenyl optionally substituted by substituent(s) (preferably 1-3) selected from a halogen atom and $C_{1-6}$ alkyl;
(4) $C_{3-7}$ cycloalkyl;
(5) phenyl-carbonyl;
(6) $C_{2-6}$ alkenyl substituted by phenyl (preferably 1-2);
(7) phenyl optionally substituted by halogen atom(s) (preferably 1-3) or $C_{1-6}$ alkyl (preferably 1-3);
(8) pyrrolidine;
(9) dihydrobenzofuran;
(10) $C_{1-6}$ alkylsulfonyloxy substituted by halogen atom(s) (preferably 1-3);
(11) $C_{1-6}$ alkoxy optionally substituted by substituent(s) (preferably 1-3) selected from a halogen atom, $C_{3-7}$ cycloalkyl, phenyl substituted by halogen atom(s) (preferably 1-3), tetrahydrofuran and tetrahydropyran;
(12) $C_{3-7}$ cycloalkyloxy optionally substituted by $C_{1-6}$ alkyl (preferably 1-3);
(13) $C_{3-7}$ cycloalkenyloxy optionally substituted by $C_{1-6}$ alkyl (preferably 1-3);
(14) phenyloxy optionally substituted by 1 to 3 substituents selected from a halogen atom, cyano, hydroxy, $C_{2-6}$ alkyl optionally substituted by halogen atom(s) (preferably 1-3), and $C_{2-6}$ alkoxy;
(15) pyridyloxy substituted by halogen atom(s) (preferably 1-3), or $C_{1-6}$ alkyl (preferably 1-3) substituted by halogen atom(s) (preferably 1-3);
(16) tetrahydrofuranyloxy;
(17) tetrahydropyranyloxy; and
(18) dihydrobenzofuranyloxy, and
L is a bond, —O—, —O—CH$_2$—, —CO—NH—, $C_{1-6}$ alkylene, or $C_{2-6}$ alkynylene,
or a salt thereof;

[13] the compound of any one of [2]-[12], wherein the partial structural formula represented by the formula (I):

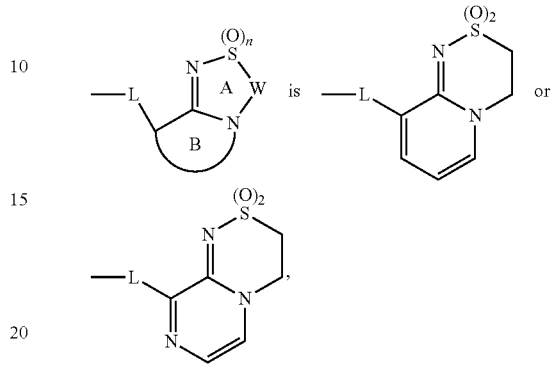

ring B is optionally substituted by $C_{1-6}$ alkyl (preferably 1-2),
ring D is benzene optionally substituted by 1 to 3 substituents selected from
(1) a halogen atom;
(2) hydroxy;
(3) $C_{1-6}$ alkyl optionally substituted by substituent(s) (preferably 1-3) selected from 1) a halogen atom, and 2) phenyl optionally substituted by substituent(s) (preferably 1-3) selected from halogen atom(s) (preferably 1-3) and $C_{1-6}$ alkyl (preferably 1-3);
(4) $C_{3-7}$ cycloalkyl optionally substituted by $C_{1-6}$ alkoxycarbonyl (preferably 1-2) or phenyl (preferably 1-2);
(5) phenyl-carbonyl;
(6) $C_{2-6}$ alkenyl substituted by phenyl (preferably 1-2);
(7) phenyl optionally substituted by halogen atom(s) (preferably 1-3) or $C_{1-6}$ alkyl (preferably 1-3);
(8) pyrrolidine;
(9) dihydrobenzofuran;
(10) $C_{1-6}$ alkylsulfonyloxy substituted by halogen atom(s) (preferably 1-3);
(11) $C_{1-6}$ alkoxy optionally substituted by substituent(s) (preferably 1-3) selected from a halogen atom, $C_{3-7}$ cycloalkyl, phenyl substituted by halogen atom(s) (preferably 1-3), tetrahydrofuran and tetrahydropyran;
(12) $C_{3-7}$ cycloalkyloxy optionally substituted by $C_{1-6}$ alkyl (preferably 1-3);
(13) $C_{3-7}$ cycloalkenyloxy optionally substituted by $C_{1-6}$ alkyl (preferably 1-3);
(14) phenyloxy optionally substituted by 1 to 3 substituents selected from a halogen atom, cyano, hydroxy, $C_{1-6}$ alkyl optionally substituted by halogen atom(s) (preferably 1-3), and $C_{1-6}$ alkoxy;
(15) pyridyloxy substituted (preferably 1-3) by a halogen atom, or $C_{1-6}$ alkyl substituted by halogen atom(s) (preferably 1-3);
(16) tetrahydrofuranyloxy;
(17) tetrahydropyranyloxy; and
(18) dihydrobenzofuranyloxy, and
L is a bond,
or a salt thereof;
[14] 9-(4-phenoxyphenyl)-3,4-dihydropyrido[2,1-c][1,2,4]thiadiazine 2,2-dioxide or a salt thereof;

[15] 9-[4-(4-methylphenoxy)phenyl]-3,4-dihydropyrido[2,1-c][1,2,4]thiadiazine 2,2-dioxide or a salt thereof;
[16] 9-[4-(cyclohexyloxy)phenyl]-3,4-dihydropyrido[2,1-c][1,2,4]thiadiazine 2,2-dioxide or a salt thereof;
[17] 9-[4-(cyclohexyloxy)phenyl]-7-methyl-3,4-dihydropyrazino[2,1-c][1,2,4]thiadiazine 2,2-dioxide or a salt thereof;
[18] a medicament containing a compound represented by the formula (I'):

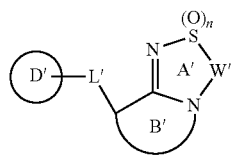
(I')

wherein
ring A' is an optionally substituted 5-7-membered heterocycle,
ring B' is an optionally substituted 5-8-membered heterocycle having, as a ring-constituting atom besides carbon atom, one nitrogen atom, and optionally further having 1 to 3 hetero atoms selected from a nitrogen atom, an oxygen atom and a sulfur atom,
ring D' is an optionally substituted non-aromatic hydrocarbon ring, an optionally substituted non-aromatic heterocycle, an optionally substituted aromatic hydrocarbon ring, or an optionally substituted aromatic heterocycle,
W' is optionally substituted $C_{1-3}$ alkylene, or optionally substituted $C_{2-3}$ alkenyl,
L' is a bond, or a spacer having the main chain having an atom number of 1-8, and
n is 0, 1 or 2
or a salt thereof;
[19] the medicament of [18], which is an AMPA receptor potentiator;
[20] the medicament of [18], which is a prophylactic or therapeutic agent for depression, schizophrenia, Alzheimer's disease or attention deficit hyperactivity disorder;
[21] a method for the prophylaxis or treatment of depression, schizophrenia, Alzheimer's disease or attention deficit hyperactivity disorder, comprising administering an effective amount of a compound represented by the formula (I') or a salt thereof of [18] to a mammal;
[22] use of a compound represented by the formula (I') or a salt thereof of [18] for the production of a prophylactic or therapeutic drug for depression, schizophrenia, Alzheimer's disease or attention deficit hyperactivity disorder;
[23] use of a compound represented by the formula (I') or a salt thereof of [18] for the prophylaxis or treatment of depression, schizophrenia, Alzheimer's disease or attention deficit hyperactivity disorder.

The present invention also provides the following embodiments and the like.
[1A]
A compound represented by the formula (I):

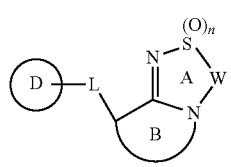
(I)

wherein
ring A is an optionally substituted 5-7-membered heterocycle,
ring B is an optionally substituted 5-8-membered heterocycle having, as a ring-constituting atom besides carbon atom, one nitrogen atom, and optionally further having 1 to 3 hetero atoms selected from a nitrogen atom, an oxygen atom and a sulfur atom,
ring D is an optionally substituted non-aromatic hydrocarbon ring, an optionally substituted non-aromatic heterocycle, an optionally substituted aromatic hydrocarbon ring, or an optionally substituted aromatic heterocycle,
W is optionally substituted $C_{1-3}$ alkylene, or optionally substituted $C_{2-3}$ alkenylene,
L is a bond, or a spacer having the main chain having an atom number of 1-8, and
n is 0, 1 or 2,
provided when
a partial structural formula represented by the formula (I):

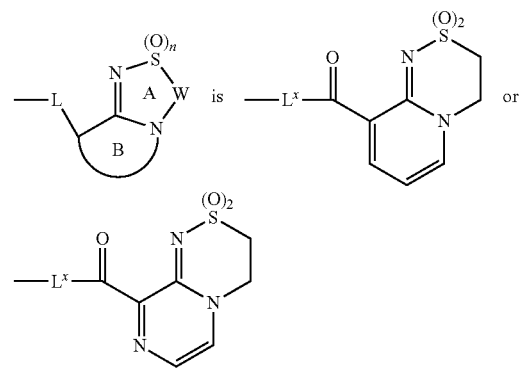

wherein $L^x$ is a bond or a spacer having the main chain having an atom number of 1-7, one or both of ring A and ring B has(have) substituent(s),
excluding the following compounds;
2,2,2-trichloro-N-(7,7-diphenyl-6,7-dihydro-5H-pyrrolo[2,1-c][1,2,4]thiadiazol-3-ylidene)acetamide, and
{4-(acetylamino)-8-[(3-{2-[4-(acetylamino)-2,2-dioxido-7-(sulfonatomethyl)-6H-pyrazolo[5,1-c][1,2,4]thiadiazin-8-yl]ethenyl}-5,5-dimethylcyclohex-2-en-1-yl)methylidene]-2,2-dioxido-8H-pyrazolo[5,1-c][1,2,4]thiadiazin-7-yl}methanesulfonic acid,
or a salt thereof;
[2A] a prodrug of the compound of [1A] or a salt thereof;
[3A] a medicament containing the compound of [1A] or a salt thereof or a prodrug thereof;
[4A] an AMPA receptor potentiator containing a compound represented by the formula (I'):

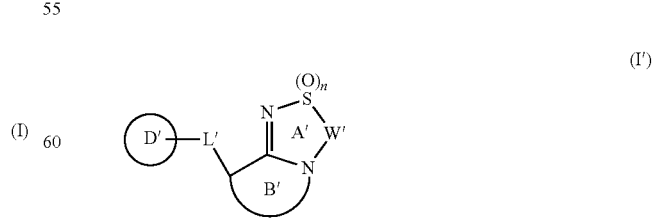
(I')

wherein
ring A' is an optionally substituted 5-7-membered heterocycle, ring B' is an optionally substituted 5-8-membered heterocycle having, as a ring-constituting atom besides carbon atom, one nitrogen atom, and optionally further having 1 to 3 hetero atoms selected from a nitrogen atom, an oxygen atom and a sulfur atom, ring D' is an optionally substituted non-aromatic hydrocarbon ring, an optionally substituted non-aromatic heterocycle, an optionally substituted aromatic hydrocarbon ring, or an optionally substituted aromatic heterocycle, W' is optionally substituted $C_{1-3}$ alkylene, or optionally substituted $C_{2-3}$ alkenylene, L' is a bond, or a spacer having the main chain having an atom number of 1-8, and n is 0, 1 or 2, or a salt thereof, or a prodrug thereof;

[5A] the AMPA receptor potentiator of [4A], which is a prophylactic or therapeutic drug for depression, schizophrenia or attention deficit hyperactivity disorder;

[6A] a method for the prophylaxis or treatment of depression, schizophrenia or attention deficit hyperactivity disorder, comprising administering an effective amount of the compound represented by the formula (I') or a salt thereof of [4A] or a prodrug thereof to a mammal;

[7A] use of the compound represented by the formula (I') or a salt thereof of [4A] or a prodrug thereof for the production of a prophylactic or therapeutic drug for depression, schizophrenia or attention deficit hyperactivity disorder;

[8A] use of the compound represented by the formula (I') or a salt thereof of [4A], or a prodrug thereof for the prophylaxis or treatment of depression, schizophrenia or attention deficit hyperactivity disorder;

[9A] a medicament containing the compound of any one of [1]-[17] or a salt thereof;

[10A] the medicament of [9A], which is an AMPA receptor potentiator;

[11A] the medicament of [9A], which is a prophylactic or therapeutic agent for depression, schizophrenia, Alzheimer's disease or attention deficit hyperactivity disorder;

[12A] a method of potentiating AMPA receptor, comprising administering an effective amount of the compound of any one of [1]-[17] or a salt thereof to a mammal;

[13A] a method for the prophylaxis or treatment of depression, schizophrenia, Alzheimer's disease or attention deficit hyperactivity disorder, comprising administering an effective amount of the compound of any one of [1]-[17] or a salt thereof to a mammal;

[13B] a method for the prophylaxis or treatment of depression, comprising administering an effective amount of 9-(4-phenoxyphenyl)-3,4-dihydropyrido[2,1-c][1,2,4]thiadiazine 2,2-dioxide;

9-[4-(4-methylphenoxy)phenyl]-3,4-dihydropyrido[2,1-c][1,2,4]thiadiazine 2,2-dioxide;

9-[4-(cyclohexyloxy)phenyl]-3,4-dihydropyrido[2,1-c][1,2,4]thiadiazine 2,2-dioxide; or 9-[4-(cyclohexyloxy)phenyl]-7-methyl-3,4-dihydropyrazino[2,1-c][1,2,4]thiadiazine 2,2-dioxide, or a salt thereof, to a mammal;

[13C] a method for the prophylaxis or treatment of schizophrenia, comprising administering an effective amount of 9-(4-phenoxyphenyl)-3,4-dihydropyrido[2,1-c][1,2,4]thiadiazine 2,2-dioxide;

9-[4-(4-methylphenoxy)phenyl]-3,4-dihydropyrido[2,1-c][1,2,4]thiadiazine 2,2-dioxide;

9-[4-(cyclohexyloxy)phenyl]-3,4-dihydropyrido[2,1-c][1,2,4]thiadiazine 2,2-dioxide; or 9-[4-(cyclohexyloxy)phenyl]-7-methyl-3,4-dihydropyrazino[2,1-c][1,2,4]thiadiazine 2,2-dioxide, or a salt thereof, to a mammal;

[13C'] a method for the prophylaxis or treatment of a positive symptom of schizophrenia, comprising administering an effective amount of 9-(4-phenoxyphenyl)-3,4-dihydropyrido[2,1-c][1,2,4]thiadiazine 2,2-dioxide;

9-[4-(4-methylphenoxy)phenyl]-3,4-dihydropyrido[2,1-c][1,2,4]thiadiazine 2,2-dioxide;

9-[4-(cyclohexyloxy)phenyl]-3,4-dihydropyrido[2,1-c][1,2,4]thiadiazine 2,2-dioxide; or 9-[4-(cyclohexyloxy)phenyl]-7-methyl-3,4-dihydropyrazino[2,1-c][1,2,4]thiadiazine 2,2-dioxide, or a salt thereof, to a mammal;

[13C"] a method for the prophylaxis or treatment of a negative symptom of schizophrenia, comprising administering an effective amount of 9-(4-phenoxyphenyl)-3,4-dihydropyrido[2,1-c][1,2,4]thiadiazine 2,2-dioxide;

9-[4-(4-methylphenoxy)phenyl]-3,4-dihydropyrido[2,1-c][1,2,4]thiadiazine 2,2-dioxide;

9-[4-(cyclohexyloxy)phenyl]-3,4-dihydropyrido[2,1-c][1,2,4]thiadiazine 2,2-dioxide; or 9-[4-(cyclohexyloxy)phenyl]-7-methyl-3,4-dihydropyrazino[2,1-c][1,2,4]thiadiazine 2,2-dioxide, or a salt thereof, to a mammal;

[13C'''] a method for the prophylaxis or treatment of cognitive impairment in schizophrenia, comprising administering an effective amount of 9-(4-phenoxyphenyl)-3,4-dihydropyrido[2,1-c][1,2,4]thiadiazine 2,2-dioxide;

9-[4-(4-methylphenoxy)phenyl]-3,4-dihydropyrido[2,1-c][1,2,4]thiadiazine 2,2-dioxide;

9-[4-(cyclohexyloxy)phenyl]-3,4-dihydropyrido[2,1-c][1,2,4]thiadiazine 2,2-dioxide; or 9-[4-(cyclohexyloxy)phenyl]-7-methyl-3,4-dihydropyrazino[2,1-c][1,2,4]thiadiazine 2,2-dioxide, or a salt thereof, to a mammal;

[13D] a method for the prophylaxis or treatment of Alzheimer's disease, comprising administering an effective amount of 9-(4-phenoxyphenyl)-3,4-dihydropyrido[2,1-c][1,2,4]thiadiazine 2,2-dioxide;

9-[4-(4-methylphenoxy)phenyl]-3,4-dihydropyrido[2,1-c][1,2,4]thiadiazine 2,2-dioxide;

9-[4-(cyclohexyloxy)phenyl]-3,4-dihydropyrido[2,1-c][1,2,4]thiadiazine 2,2-dioxide; or 9-[4-(cyclohexyloxy)phenyl]-7-methyl-3,4-dihydropyrazino[2,1-c][1,2,4]thiadiazine 2,2-dioxide, or a salt thereof, to a mammal;

[13E] a method for the prophylaxis or treatment of attention deficit hyperactivity disorder, comprising administering an effective amount of 9-(4-phenoxyphenyl)-3,4-dihydropyrido[2,1-c][1,2,4]thiadiazine 2,2-dioxide;

9-[4-(4-methylphenoxy)phenyl]-3,4-dihydropyrido[2,1-c][1,2,4]thiadiazine 2,2-dioxide;

9-[4-(cyclohexyloxy)phenyl]-3,4-dihydropyrido[2,1-c][1,2,4]thiadiazine 2,2-dioxide; or 9-[4-(cyclohexyloxy)phenyl]-7-methyl-3,4-dihydropyrazino[2,1-c][1,2,4]thiadiazine 2,2-dioxide, or a salt thereof, to a mammal;

[14A] use of the compound of any one of [1]-[17] or a salt thereof for the production of an AMPA receptor potentiator;

[15A] use of the compound of any one of [1]-[17] or a salt thereof for the production of a prophylactic or therapeutic drug for depression, schizophrenia, Alzheimer's disease or attention deficit hyperactivity disorder;

[16A] the compound of any one of [1]-[17] or a salt thereof for use for potentiating AMPA receptor;

[17A] use of the compound of any one of [1]-[17] or a salt thereof for the prophylaxis or treatment of depression, schizophrenia, Alzheimer's disease or attention deficit hyperactivity disorder.

Effect of the Invention

According to the present invention, a useful compound having an AMPA receptor potentiating action and useful as a prophylactic or therapeutic drug for depression, schizophrenia, Alzheimer's disease or attention deficit hyperactivity disorder (ADHD) and the like can be provided.

BRIEF DESCRIPTION OF THE DRAWINGS

FIG. 1 shows inhibition of methamphetamine (MAP)-induced hyperlocomotion by compound A, B, C and D.

DETAILED DESCRIPTION OF THE INVENTION

The present invention is explained in detail in the following.

In the present specification, the hydrogen atoms in the chemical structural formulas are sometimes to be abbreviated according to conventional use in the chemical field.

In the present specification, unless otherwise specified, examples of the "halogen atom" include fluorine, chlorine, bromine, and iodine.

In the present specification, unless otherwise specified, "optionally halogenated" and "halogeno" mean optionally having one or more (e.g., 1 to 3) a halogen atoms as substituents.

In the present specification, unless otherwise specified, examples of the "non-aromatic hydrocarbon ring" include a non-aromatic hydrocarbon ring having a carbon number of 3 to 8 such as $C_{3-8}$ cycloalkane, $C_{5-8}$ cycloalkene, $C_{5-8}$ cycloalkadiene, bridged cyclic hydrocarbon having a carbon number of 5 to 8 and the like.

In the present specification, unless otherwise specified, examples of the "$C_{3-8}$ cycloalkane" include cyclopropane, cyclobutane, cyclopentane, cyclohexane, cycloheptane, and cyclooctane.

In the present specification, unless otherwise specified, examples of the "$C_{5-8}$ cycloalkene" include cyclopentene, cyclohexene, cycloheptene, and cyclooctene.

In the present specification, unless otherwise specified, examples of the "$C_{5-8}$ cycloalkadiene" include cyclopentadiene, cyclohexadiene, cycloheptadiene, and cyclooctadiene.

In the present specification, unless otherwise specified, examples of the "bridged cyclic hydrocarbon having a carbon number of 5 to 8" include bicyclo[2.1.0]pentane, bicyclo[2.2.1]heptane, bicyclo[3.2.1]octane, bicyclo[2.2.1]hept-2-en, and tricyclo[2.2.1.0]heptane.

In the present specification, unless otherwise specified, examples of the "aromatic hydrocarbon ring" include an aromatic hydrocarbon ring having a carbon number of 6 to 14. Specific examples thereof include a benzene ring, a naphthalene ring, an anthracene ring and a phenanthrene ring.

In the present specification, unless otherwise specified, the "aromatic hydrocarbon ring" may be monocyclic, bicyclic or tricyclic.

In the present specification, unless otherwise specified, examples of the "heterocycle" include a 3- to 14-membered heterocycle containing 1 to 4 hetero atoms selected from a nitrogen atom (N), a sulfur atom (S) and an oxygen atom (O).

In the present specification, unless otherwise specified, examples of the "heterocycle" include non-aromatic heterocycle, and aromatic heterocycle.

In the present specification, unless otherwise specified, examples of the "non-aromatic heterocycle" include monocyclic non-aromatic heterocycle, and condensed non-aromatic heterocycle.

In the present specification, unless otherwise specified, examples of the "monocyclic non-aromatic heterocycle" include a 3- to 8-membered non-aromatic heterocycle such as an oxirane ring, an azetidine ring, an oxetane ring, a thietane ring, a pyrrolidine ring, a dihydrofuran ring, a tetrahydrofuran ring, a tetrahydrothiophene ring, an imidazolidine ring, an oxazolidine ring, an isooxazoline ring, a piperidine ring, a dihydropyran ring, a tetrahydropyran ring, a tetrahydrothiopyran ring, a morpholine ring, a thiomorpholine ring, a piperazine ring, a dihydrooxazin ring, a tetrahydrooxazin ring, a dihydropyrimidine ring, a tetrahydropyrimidine ring, an azepane ring, an oxepane ring, a thiepane ring, an oxazepane ring, a thiazepane ring, an azocane ring, an oxocane ring, a thiocane ring, an oxazocane ring, a thiazocane ring and the like.

In the present specification, unless otherwise specified, examples of the "condensed non-aromatic heterocycle" include a monocyclic non-aromatic heterocycle condensed with 1 or 2 rings selected from a non-aromatic hydrocarbon ring having a carbon number of 3 to 8, a benzene ring, a monocyclic non-aromatic heterocycle, and a 5- or 6-membered aromatic heterocycle. Specific examples thereof include a bicyclic condensed non-aromatic heterocycle such as dihydroindole, dihydroisoindole, dihydrobenzofuran, dihydrobenzodioxine, dihydrobenzodioxepine, tetrahydrobenzofuran, chromene, dihydroquinoline, tetrahydroquinoline, dihydroisoquinoline, tetrahydroisoquinoline, dihydrophthalazine, tetrahydrobenzoazepine and the like.

In the present specification, unless otherwise specified, examples of the "aromatic heterocycle" include monocyclic aromatic heterocycle, and condensed aromatic heterocycle.

In the present specification, unless otherwise specified, examples of the "monocyclic aromatic heterocycle" include a 5- or 6-membered aromatic heterocycle such as a furan ring, a thiophene ring, a pyrrole ring, an oxazole ring, an isoxazole ring, a triazole ring, an isothiazole ring, an imidazole ring, a pyrazole ring, a 1,2,3-oxadiazole ring, a 1,2,4-oxadiazole ring, a 1,3,4-oxadiazole ring, a furazan ring, a 1,2,3-thiadiazole ring, a 1,2,4-thiadiazole ring, a 1,3,4-thiadiazole ring, a 1,2,3-triazole ring, a 1,2,4-triazole ring, a tetrazole ring, a pyridine ring, a pyridazine ring, a pyrimidine ring, a pyrazine ring, a triazine ring and the like.

In the present specification, unless otherwise specified, examples of the "condensed aromatic heterocycle" include a monocyclic aromatic heterocycle condensed with 1 or 2 rings selected from a benzene ring, and a 5- or 6-membered aromatic heterocycle. Specific examples thereof include a bicyclic condensed aromatic heterocycle such as quinoline, isoquinoline, quinazoline, quinoxaline, benzofuran, benzothiophene, benzoxazole, benzisoxazole, benzothiazole, benzimidazole, benzotriazole, indole, indolizine, indazole, pyrrolopyrazine (e.g., 1H-pyrrolo[2,3-b]pyrazine, 1H-pyrrolo[2,3-b]pyrazine, pyrrolo[1,2-a]pyrazine), pyrazolopyridine (e.g., pyrazolo[1,5-a]pyridine), imidazopyridine (e.g., 1H-imidazo[4,5-b]pyridine, 1H-imidazo[4,5-c]pyridine, 2H-imidazo[1,2-a]pyridine, imidazo[1,2-a]pyridine, imidazo[1,5-a]pyridine), triazolopyridine (e.g., 1H-[1,2,3]triazolo[4,5-b]pyridine, 1H-[1,2,3]triazolo[4,5-c]pyridine, [1,2,4]triazolo[4,3-a]pyridine, [1,2,4]triazolo[1,5-a]pyridine), imidazopyrazine (e.g., 1H-imidazo[4,5-b]pyrazine, imidazo[1,2-a]pyrazine, imidazo[1,5-a]pyrazine), triazolopyrazine (e.g., [1,2,4]triazolo[1,5-a]pyrazine), pyrazolopyridine (e.g., 1H-pyrazolo[4,3-c]pyridine), pyrazolothiophene (e.g., 2H-pyrazolo[3,4-b]thiophene), pyrazolotriazine (e.g., pyrazolo[5,1-c][1,2,4]triazine) and the like.

In the present specification, unless otherwise specified, examples of the "alkyl (group)" include a $C_{1-6}$ alkyl (group).

In the present specification, unless otherwise specified, examples of the "$C_{1-6}$ alkyl (group)" include methyl, ethyl, n-propyl, isopropyl, n-butyl, isobutyl, sec-butyl, tert-butyl, pentyl, isopentyl, neopentyl, and hexyl.

In the present specification, unless otherwise specified, the "optionally halogenated $C_{1-6}$ alkyl (group)" means a $C_{1-6}$ alkyl (group) optionally substituted by a halogen atom, and specific examples thereof include trifluoromethyl.

In the present specification, unless otherwise specified, examples of the "alkenyl (group)" include a $C_{1-6}$ alkenyl (group).

In the present specification, unless otherwise specified, examples of the "$C_{2-6}$ alkenyl (group)" include vinyl, 1-propen-1-yl, 2-propen-1-yl, isopropenyl, 2-buten-1-yl, 4-penten-1-yl, and 5-hexen-1-yl.

In the present specification, unless otherwise specified, examples of the "alkynyl (group)" include a $C_{2-6}$ alkynyl group. Examples of the "$C_{2-6}$ alkynyl (group)" include ethynyl, 1-propyn-1-yl, 2-propyn-1-yl, 4-pentyn-1-yl, and 5-hexyn-1-yl.

In the present specification, unless otherwise specified, examples of the "$C_{3-7}$ cycloalkyl-$C_{2-6}$ alkynyl (group)" include cyclopropylethynyl.

In the present specification, unless otherwise specified, examples of the "non-aromatic cyclic hydrocarbon group" include a $C_{3-7}$ cycloalkyl (group), a $C_{3-7}$ cycloalkenyl (group) and a $C_{4-10}$ cycloalkadienyl (group), each of which may be condensed with one or more (preferably 1 or 2) hydrocarbon rings.

Examples of the "hydrocarbon ring" include the aforementioned "non-aromatic hydrocarbon ring" and the aforementioned "aromatic hydrocarbon ring".

In the present specification, unless otherwise specified, examples of the "$C_{3-7}$ cycloalkyl (group)" include cyclopropyl, cyclobutyl, cyclopentyl, cyclohexyl, and cycloheptyl.

In the present specification, unless otherwise specified, examples of the "$C_{3-7}$ cycloalkenyl (group)" include cyclopropenyl, cyclobutenyl, cyclopentenyl, cyclohexenyl, and cycloheptenyl.

In the present specification, unless otherwise specified, examples of the "$C_{4-10}$ cycloalkadienyl (group)" include cyclobutadienyl, cyclopentadienyl, cyclohexadienyl, cycloheptadienyl, cyclooctadienyl, cyclononadienyl, and cyclodecadienyl.

In the present specification, unless otherwise specified, the "aromatic cyclic hydrocarbon group" may be monocyclic, bicyclic or tricyclic.

In the present specification, unless otherwise specified, examples of the "aromatic cyclic hydrocarbon group" include $C_{6-14}$ aryl (group) and the like. Specific examples thereof include phenyl, 1-naphthyl, 2-naphthyl, 2-biphenylyl, 3-biphenylyl, 4-biphenylyl, and 2-anthryl.

In the present specification, unless otherwise specified, examples of the "$C_{7-16}$ aralkyl (group)" include benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl, and 4-biphenylylmethyl.

In the present specification, unless otherwise specified, examples of the "$C_{6-14}$ aryl-$C_{2-6}$ alkenyl (group)" include styryl.

In the present specification, unless otherwise specified, examples of the "$C_{1-7}$ alkylene (group)" (i.e., $C_{1-6}$ alkanediyl group) include methylene, ethylene, trimethylene, tetramethylene, 2-butenylene, 2-methyltetramethylene, pentamethylene, and hexamethylene.

In the present specification, unless otherwise specified, examples of the "$C_{2-7}$ alkylene (group)" include an alkylene (group) having a carbon number of 2 to 7 from the aforementioned "$C_{1-7}$ alkylene (group)". Examples of the "$C_{1-3}$ alkylene (group)" include an alkylene (group) having a carbon number of 1 to 3 from the aforementioned "$C_{1-7}$ alkylene (group)".

In the present specification, unless otherwise specified, examples of the "$C_{2-6}$ alkenylene (group)" include —CH=CH—, —CH=C(CH$_3$)—, —C(CH$_3$)=CH—, —CH=CH—CH$_2$—, —CH$_2$—CH=CH—, —C(CH$_3$)$_2$—CH=CH—, —CH$_2$—CH=CH—CH$_2$—, —CH$_2$—CH$_2$—CH=CH—, —CH=CH—CH=CH—, —CH=CH—CH$_2$—CH$_2$—CH$_2$—, and —CH=C(C$_2$H$_5$)—.

In the present specification, unless otherwise specified, examples of the "$C_{2-3}$ alkenylene (group)" include an alkenylene (group) having a carbon number of 2 to 3 from the aforementioned "$C_{2-6}$ alkenylene (group)".

In the present specification, unless otherwise specified, examples of the "$C_{2-6}$ alkynylene (group)" include —C≡C—, —CH$_2$—C≡C—, —CH$_2$—C≡C—CH(CH$_3$)—, and —CH$_2$—C≡C—CH$_2$—CH$_2$—.

In the present specification, unless otherwise specified, the "heterocyclic group" (and heterocycle moiety in substituents) is a non-aromatic heterocyclic group, or an aromatic heterocyclic group (i.e., heteroaryl group).

In the present specification, unless otherwise specified, the "heterocyclic group" may be monocyclic, bicyclic or tricyclic.

In the present specification, unless otherwise specified, the "heterocyclic group" is, for example, a 3- to 14-membered heterocyclic group containing 1 to 4 hetero atoms selected from an oxygen atom, a sulfur atom and a nitrogen atom and the like.

In the present specification, unless otherwise specified, the "non-aromatic heterocyclic group" may be saturated or unsaturated.

In the present specification, unless otherwise specified, examples of the "non-aromatic heterocyclic group" include a 3- to 14-membered non-aromatic heterocyclic group.

In the present specification, unless otherwise specified, examples of the "3- to 14-membered non-aromatic heterocyclic group" include a 3- to 6-membered non-aromatic heterocyclic group containing 1 to 4 hetero atoms selected from an oxygen atom, a sulfur atom and a nitrogen atom, which may be condensed with a 5- or 6-membered ring.

In the present specification, unless otherwise specified, examples of the "3- to 6-membered non-aromatic heterocyclic group containing 1 to 4 hetero atoms selected from an oxygen atom, a sulfur atom and a nitrogen atom" include tetrahydrofuryl, oxazolidinyl, imidazolinyl (e.g., 1-imidazolinyl, 2-imidazolinyl, 4-imidazolinyl), aziridinyl (e.g., 1-aziridinyl, 2-aziridinyl), azetidinyl (e.g., 1-azetidinyl, 2-azetidinyl), pyrrolidinyl (e.g., 1-pyrrolidinyl, 2-pyrrolidinyl, 3-pyrrolidinyl), piperidinyl (e.g., 1-piperidinyl, 2-piperidinyl, 3-piperidinyl), azepanyl (e.g., 1-azepanyl, 2-azepanyl, 3-azepanyl, 4-azepanyl), azocanyl (e.g., 1-azocanyl, 2-azocanyl, 3-azocanyl, 4-azocanyl), piperazinyl (e.g., 1,4-piperazin-1-yl, 1,4-piperazin-2-yl), diazepinyl (e.g., 1,4-diazepin-1-yl, 1,4-diazepin-2-yl, 1,4-diazepin-5-yl, 1,4-diazepin-6-yl), diazocanyl (e.g., 1,4-diazocan-1-yl, 1,4-diazocan-2-yl, 1,4-diazocan-5-yl, 1,4-diazocan-6-yl, 1,5-diazocan-1-yl, 1,5-diazocan-2-yl, 1,5-diazocan-3-yl), tetrahydropyranyl (e.g., tetrahydropyran-4-yl), morpholinyl (e.g., 4-morpholinyl), thiomorpholinyl (e.g., 4-thiomorpholinyl), 2-oxazolidinyl, dihydrofuryl, dihydropyranyl, dihydroquinolyl, and 2,3-dihydro-1H-imidazo[1,2-a]imidazol-1-yl.

In the present specification, unless otherwise specified, examples of the "5- or 6-membered ring" include a hydrocarbon ring having a carbon number of 5 or 6 (e.g., cyclopentane, cyclohexane, cyclopentene, cyclohexene, cyclopentadiene, cyclohexadiene, benzene) and a 5- or 6-membered heterocycle.

In the present specification, unless otherwise specified, examples of the "5- or 6-membered heterocycle" include the aforementioned "heterocycle" which is a 5- or 6-membered ring.

In the present specification, unless otherwise specified, examples of the "3- to 6-membered non-aromatic heterocyclic group containing 1 to 4 hetero atoms selected from an oxygen atom, a sulfur atom and a nitrogen atom which is condensed with a 5- or 6-membered ring" include 2,3-dihydro-1H-imidazo[1,2-a]benzimidazol-1-yl.

In the present specification, unless otherwise specified, examples of the "aromatic heterocyclic group" include 5- or 6-membered monocyclic aromatic heterocyclic group, and 5- to 10-membered aromatic condensed heterocyclic group.

In the present specification, unless otherwise specified, examples of the "5- or 6-membered monocyclic aromatic heterocyclic group" include a 5- or 6-membered monocyclic aromatic heterocyclic group containing 1 to 4 hetero atoms selected from an oxygen atom, a sulfur atom and a nitrogen atom, such as pyrrolyl (e.g., 1-pyrrolyl, 2-pyrrolyl, 3-pyrrolyl), furyl (e.g., 2-furyl, 3-furyl), thienyl (e.g., 2-thienyl, 3-thienyl), pyrazolyl (e.g., 1-pyrazolyl, 3-pyrazolyl, 4-pyrazolyl), imidazolyl (e.g., 1-imidazolyl, 2-imidazolyl, 4-imidazolyl), isoxazolyl (e.g., 3-isoxazolyl, 4-isoxazolyl, 5-isoxazolyl), oxazolyl (e.g., 2-oxazolyl, 4-oxazolyl, 5-oxazolyl), isothiazolyl (e.g., 3-isothiazolyl, 4-isothiazolyl, 5-isothiazolyl), thiazolyl (e.g., 2-thiazolyl, 4-thiazolyl, 5-thiazolyl), triazolyl (e.g., 1,2,3-triazol-4-yl, 1,2,4-triazol-3-yl), oxadiazolyl (e.g., 1,2,4-oxadiazol-3-yl, 1,2,4-oxadiazol-5-yl), thiadiazolyl (e.g., 1,2,4-thiadiazol-3-yl, 1,2,4-thiadiazol-5-yl), tetrazolyl, pyridyl (e.g., 2-pyridyl, 3-pyridyl, 4-pyridyl), pyridazinyl (e.g., 3-pyridazinyl, 4-pyridazinyl), pyrimidinyl (e.g., 2-pyrimidinyl, 4-pyrimidinyl, 5-pyrimidinyl), and pyrazinyl and the like.

In the present specification, unless otherwise specified, examples of the "5- to 10-membered aromatic condensed heterocyclic group" include a 5- to 10-membered aromatic condensed heterocyclic group containing 1 to 4 hetero atoms selected from an oxygen atom, a sulfur atom and a nitrogen atom such as isoindolyl (e.g., 1-isoindolyl, 2-isoindolyl, 3-isoindolyl, 4-isoindolyl, 5-isoindolyl, 6-isoindolyl, 7-isoindolyl), indolyl (e.g., 1-indolyl, 2-indolyl, 3-indolyl, 4-indolyl, 5-indolyl, 6-indolyl, 7-indolyl), benzo[b]furanyl (e.g., 2-benzo[b]furanyl, 3-benzo[b]furanyl, 4-benzo[b]furanyl, 5-benzo[b]furanyl, 6-benzo[b]furanyl, 7-benzo[b]furanyl), benzo[c]furanyl (e.g., 1-benzo[c]furanyl, 4-benzo[c]furanyl, 5-benzo[c]furanyl), benzo[b]thienyl, (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzo[c]thienyl (e.g., 1-benzo[c]thienyl, 4-benzo[c]thienyl, 5-benzo[c]thienyl), indazolyl (e.g., 1-indazolyl, 2-indazolyl, 3-indazolyl, 4-indazolyl, 5-indazolyl, 6-indazolyl, 7-indazolyl), benzimidazolyl (e.g., 1-benzimidazolyl, 2-benzimidazolyl, 4-benzimidazolyl, 5-benzimidazolyl), 1,2-benzoisoxazolyl (e.g., 1,2-benzoisoxazol-3-yl, 1,2-benzoisoxazol-4-yl, 1,2-benzoisoxazol-5-yl, 1,2-benzoisoxazol-6-yl, 1,2-benzoisoxazol-7-yl), benzoxazolyl (e.g., 2-benzoxazolyl, 4-benzoxazolyl, 5-benzoxazolyl, 6-benzoxazolyl, 7-benzoxazolyl), 1,2-benzoisothiazolyl (e.g., 1,2-benzoisothiazol-3-yl, 1,2-benzoisothiazol-4-yl, 1,2-benzoisothiazol-5-yl, 1,2-benzoisothiazol-6-yl, 1,2-benzoisothiazol-7-yl), benzothiazolyl (e.g., 2-benzothiazolyl, 4-benzothiazolyl, 5-benzothiazolyl, 6-benzothiazolyl, 7-benzothiazolyl), isoquinolyl (e.g., 1-isoquinolyl, 3-isoquinolyl, 4-isoquinolyl, 5-isoquinolyl), quinolyl (e.g., 2-quinolyl, 3-quinolyl, 4-quinolyl, 5-quinolyl, 8-quinolyl), cinnolinyl (e.g., 3-cinnolinyl, 4-cinnolinyl, 5-cinnolinyl, 6-cinnolinyl, 7-cinnolinyl, 8-cinnolinyl), phthalazinyl (e.g., 1-phthalazinyl, 4-phthalazinyl, 5-phthalazinyl, 6-phthalazinyl, 7-phthalazinyl, 8-phthalazinyl), quinazolinyl (e.g., 2-quinazolinyl, 4-quinazolinyl, 5-quinazolinyl, 6-quinazolinyl, 7-quinazolinyl, 8-quinazolinyl), quinoxalinyl (e.g., 2-quinoxalinyl, 3-quinoxalinyl, 5-quinoxalinyl, 6-quinoxalinyl, 7-quinoxalinyl, 8-quinoxalinyl), pyrazolo[1,5-a]pyridyl (e.g., pyrazolo[1,5-a]pyridin-2-yl, pyrazolo[1,5-a]pyridin-3-yl, pyrazolo[1,5-a]pyridin-4-yl, pyrazolo[1,5-a]pyridin-5-yl, pyrazolo[1,5-a]pyridin-6-yl, pyrazolo[1,5-a]pyridin-7-yl), imidazo[1,2-a]pyridyl (e.g., imidazo[1,2-a]pyridin-2-yl, imidazo[1,2-a]pyridin-3-yl, imidazo[1,2-a]pyridin-5-yl, imidazo[1,2-a]pyridin-6-yl, imidazo[1,2-a]pyridin-7-yl, imidazo[1,2-a]pyridin-8-yl) and the like.

In the present specification, unless otherwise specified, examples of the "alkoxy (group)" include $C_{1-6}$ alkoxy (group).

In the present specification, unless otherwise specified, examples of the "$C_{1-6}$ alkoxy (group)" include methoxy, ethoxy, n-propoxy, isopropoxy, n-butoxy, isobutoxy, sec-butoxy, tert-butoxy, pentyloxy, and hexyloxy.

In the present specification, unless otherwise specified, examples of the "$C_{3-7}$ cycloalkyloxy (group)" include cyclohexyloxy.

In the present specification, unless otherwise specified, examples of the "$C_{6-14}$ aryloxy (group)" include phenyloxy, 1-naphthyloxy, and 2-naphthyloxy.

In the present specification, unless otherwise specified, examples of the "$C_{7-16}$ aralkyloxy (group)" include benzyloxy, and phenethyloxy.

In the present specification, unless otherwise specified, examples of the "alkyl-carbonyloxy (group)" include a $C_{1-6}$ alkyl-carbonyloxy (group).

In the present specification, unless otherwise specified, examples of the "$C_{1-6}$ alkyl-carbonyloxy (group)" include acetoxy, and propionyloxy.

In the present specification, unless otherwise specified, examples of the "alkoxy-carbonyloxy (group)" include a $C_{1-6}$ alkoxy-carbonyloxy (group).

In the present specification, unless otherwise specified, examples of the "$C_{1-6}$ alkoxy-carbonyloxy (group)" include methoxycarbonyloxy, ethoxycarbonyloxy, propoxycarbonyloxy, and butoxycarbonyloxy.

In the present specification, unless otherwise specified, examples of the "mono-alkyl-carbamoyloxy (group)" include a mono-$C_{1-6}$ alkyl-carbamoyloxy (group).

In the present specification, unless otherwise specified, examples of the "mono-$C_{1-6}$ alkyl-carbamoyloxy (group)" include methylcarbamoyloxy, and ethylcarbamoyloxy.

In the present specification, unless otherwise specified, examples of the "di-alkyl-carbamoyloxy (group)" include a di-$C_{1-6}$ alkyl-carbamoyloxy (group).

In the present specification, unless otherwise specified, examples of the "di-$C_{1-6}$ alkyl-carbamoyloxy (group)" include dimethylcarbamoyloxy, and diethylcarbamoyloxy.

In the present specification, unless otherwise specified, examples of the "$C_{6-14}$ aryl-carbonyloxy (group)" include benzoyloxy and naphthylcarbonyloxy.

In the present specification, unless otherwise specified, examples of the "mono- or di-$C_{6-14}$ aryl-carbamoyloxy (group)" include phenylcarbamoyloxy and naphthylcarbamoyloxy.

In the present specification, unless otherwise specified, examples of the heterocycle moiety of the "heterocyclyl-oxy (group)" include those similar to the aforementioned "heterocyclic group". Specific examples of the "heterocyclyl-oxy (group)" include a 3- to 14-membered heterocyclyl-oxy (group) containing 1 to 5 hetero atoms selected from a nitrogen atom, a sulfur atom, and an oxygen atom.

In the present specification, unless otherwise specified, examples of the aromatic heterocycle moiety of the "aromatic heterocyclyl-oxy (group)" include those similar to the "aromatic heterocyclic group" as an example of the aforementioned "heterocyclic group". Specifically as the "aromatic heterocyclyl-oxy (group)", for example, a 5- to 14-membered aromatic heterocyclyl-oxy containing 1 to 5 hetero atoms selected from a nitrogen atom, a sulfur atom, and an oxygen atom can be mentioned.

In the present specification, unless otherwise specified, examples of the "$C_{1-6}$ alkylsulfonyloxy group" include methylsulfonyloxy, and ethylsulfonyloxy.

In the present specification, unless otherwise specified, examples of the "halogeno $C_{1-6}$ alkylsulfonyloxy group" include halogenomethylsulfonyloxy, and halogenoethylsulfonyloxy.

In the present specification, unless otherwise specified, examples of the "alkylsulfanyl (group)" include a $C_{1-6}$ alkylsulfanyl (group).

In the present specification, unless otherwise specified, examples of the "$C_{1-6}$ alkylsulfanyl (group)" include methylsulfanyl, ethylsulfanyl, n-propylsulfanyl, isopropylsulfanyl, n-butylsulfanyl, sec-butylsulfanyl, and tert-butylsulfanyl.

In the present specification, unless otherwise specified, examples of the "$C_{3-7}$ cycloalkylsulfanyl (group)" include cyclopropylsulfanyl, cyclobutylsulfanyl, cyclopentylsulfanyl, and cyclohexylsulfanyl.

In the present specification, unless otherwise specified, examples of the "$C_{6-14}$ arylsulfanyl (group)" include phenylsulfanyl, 1-naphthylsulfanyl, and 2-naphthylsulfanyl.

In the present specification, unless otherwise specified, examples of the "$C_{7-16}$ aralkylsulfanyl (group)" include benzylsulfanyl, and phenethylsulfanyl.

In the present specification, unless otherwise specified, examples of the heterocycle moiety of the "heterocyclyl-sulfanyl (group)" include those similar to the aforementioned "heterocyclic group". Specifically as the "heterocyclyl-sulfanyl (group)", for example, a 3- to 14-membered heterocyclyl-sulfanyl (group) containing 1 to 5 hetero atoms selected from a nitrogen atom, a sulfur atom, and an oxygen atom can be mentioned.

In the present specification, unless otherwise specified, examples of the "alkyl-carbonyl (group)" include $C_{1-6}$ alkyl-carbonyl.

In the present specification, unless otherwise specified, examples of the "$C_{1-6}$ alkyl-carbonyl (group)" include acetyl, propionyl, and pivaloyl.

In the present specification, unless otherwise specified, examples of the "$C_{3-7}$ cycloalkyl-carbonyl (group)" include cyclopropylcarbonyl, cyclopentylcarbonyl, and cyclohexylcarbonyl.

In the present specification, unless otherwise specified, examples of the "$C_{6-14}$ aryl-carbonyl (group)" include benzoyl, 1-naphthoyl, and 2-naphthoyl.

In the present specification, unless otherwise specified, examples of the "$C_{7-16}$ aralkyl-carbonyl (group)" include phenylacetyl, and 3-phenylpropionyl.

In the present specification, unless otherwise specified, examples of the heterocycle moiety of the "heterocyclyl-carbonyl (group)" include those similar to the aforementioned "heterocyclic group". Specifically, a 3- to 14-membered heterocyclyl-carbonyl (group) containing 1 to 5 hetero atoms selected from a nitrogen atom, a sulfur atom, and an oxygen atom can be mentioned, and more specifically, for example, picolinoyl, nicotinoyl, isonicotinoyl, 2-thenoyl, 3-thenoyl, 2-furoyl, 3-furoyl, 1-morpholinylcarbonyl, 4-thiomorpholinylcarbonyl, aziridin-1-ylcarbonyl, aziridin-2-ylcarbonyl, azetidin-1-ylcarbonyl, azetidin-2-ylcarbonyl, pyrrolidin-1-ylcarbonyl, pyrrolidin-2-ylcarbonyl, pyrrolidin-3-ylcarbonyl, piperidin-1-ylcarbonyl, piperidin-2-ylcarbonyl, piperidin-3-ylcarbonyl, azepan-1-ylcarbonyl, azepan-2-ylcarbonyl, azepan-3-ylcarbonyl, azepan-4-ylcarbonyl, azocan-1-ylcarbonyl, azocan-2-ylcarbonyl, azocan-3-ylcarbonyl, azocan-4-ylcarbonyl, 1,4-piperazin-1-ylcarbonyl, 1,4-piperazin-2-ylcarbonyl, 1,4-diazepan-1-ylcarbonyl, 1,4-diazepan-2-ylcarbonyl, 1,4-diazepan-5-ylcarbonyl, 1,4-diazepan-6-ylcarbonyl, 1,4-diazocan-1-ylcarbonyl, 1,4-diazocan-2-ylcarbonyl, 1,4-diazocan-5-ylcarbonyl, 1,4-diazocan-6-ylcarbonyl, 1,5-diazocan-1-ylcarbonyl, 1,5-diazocan-2-ylcarbonyl, and 1,5-diazocan-3-ylcarbonyl can be mentioned.

In the present specification, unless otherwise specified, examples of the "optionally esterified carboxy (group)" include carboxy, optionally substituted alkoxy-carbonyl, optionally substituted $C_{6-14}$ aryloxy-carbonyl, optionally substituted $C_{7-16}$ aralkyloxy-carbonyl, optionally substituted silyloxy-carbonyl (e.g., TMS-O—CO—, TES-O—CO—, TBS—O—CO—, TIPS—O—CO—, TBDPS-O—CO—) and the like.

In the present specification, unless otherwise specified, examples of the "alkoxy-carbonyl (group)" include a "$C_{1-6}$ alkoxy-carbonyl (group)".

In the present specification, unless otherwise specified, examples of the "$C_{1-6}$ alkoxy-carbonyl (group)" include methoxycarbonyl, ethoxycarbonyl, propoxycarbonyl, and tert-butoxycarbonyl.

In the present specification, unless otherwise specified, examples of the "$C_{6-14}$ aryloxy-carbonyl (group)" include phenoxycarbonyl.

In the present specification, unless otherwise specified, examples of the "$C_{7-16}$ aralkyloxy-carbonyl (group)" include benzyloxycarbonyl, and phenethyloxycarbonyl.

In the present specification, unless otherwise specified, examples of the "alkylsulfonyl (group)" include a $C_{1-6}$ alkylsulfonyl (group).

In the present specification, unless otherwise specified, examples of the "$C_{1-6}$ alkylsulfonyl (group)" include methylsulfonyl, and ethylsulfonyl.

In the present specification, unless otherwise specified, examples of the "$C_{3-7}$ cycloalkylsulfonyl (group)" include cyclopropylsulfonyl, cyclobutylsulfonyl, cyclopentylsulfonyl, and cyclohexylsulfonyl.

In the present specification, unless otherwise specified, examples of the "$C_{6-14}$ arylsulfonyl (group)" include phenylsulfonyl, 1-naphthylsulfonyl, and 2-naphthylsulfonyl.

In the present specification, unless otherwise specified, examples of the heterocycle moiety of the "heterocyclyl-sulfonyl (group)" include those similar to the aforementioned "heterocyclic group". Specifically as the "heterocyclyl-sulfonyl (group)", for example, a 3- to 14-membered heterocyclyl-sulfonyl (group) containing 1 to 5 hetero atoms selected from a nitrogen atom, a sulfur atom, and an oxygen atom can be mentioned.

In the present specification, unless otherwise specified, examples of the "alkylsulfinyl (group)" include a $C_{1-6}$ alkylsulfinyl (group).

In the present specification, unless otherwise specified, examples of the "$C_{1-6}$ alkylsulfinyl (group)" include methylsulfinyl, and ethylsulfinyl.

In the present specification, unless otherwise specified, examples of the "$C_{3-7}$ cycloalkylsulfinyl (group)" include cyclopropylsulfinyl, cyclobutylsulfinyl, cyclopentylsulfinyl, and cyclohexylsulfinyl.

In the present specification, unless otherwise specified, examples of the "$C_{6-14}$ arylsulfinyl (group)" include phenylsulfinyl, 1-naphthylsulfinyl, and 2-naphthylsulfinyl.

In the present specification, unless otherwise specified, examples of the heterocycle moiety of the "heterocyclyl-sulfinyl (group)" include those similar to the aforementioned "heterocyclic group". Specifically as the "heterocyclyl-sulfinyl (group)", for example, a 3- to 14-membered heterocyclyl-sulfinyl (group) containing 1 to 5 hetero atoms selected from a nitrogen atom, a sulfur atom, and an oxygen atom can be mentioned.

In the present specification, unless otherwise specified, examples of the "alkyl-carbamoyl (group)" include mono- or di-$C_{1-6}$ alkyl-carbamoyl (group).

In the present specification, unless otherwise specified, examples of the "mono- or di-$C_{1-6}$ alkyl-carbamoyl (group)" include methylcarbamoyl, dimethylcarbamoyl, ethylcarbamoyl, and propylcarbamoyl.

In the present specification, unless otherwise specified, examples of the "mono- or di-alkylamino (group)" include a mono- or di-$C_{1-6}$ alkylamino (group).

In the present specification, unless otherwise specified, examples of the "mono- or di-$C_{1-6}$ alkylamino (group)" include methylamino, ethylamino, propylamino, dimethylamino, and diethylamino.

In the present specification, unless otherwise specified, examples of the "alkyl-carbonylamino (group)" include $C_{1-6}$ alkyl-carbonylamino (group).

In the present specification, unless otherwise specified, examples of the "$C_{1-6}$ alkyl-carbonylamino (group)" include acetylamino, propionylamino, and pivaloylamino.

In the present specification, unless otherwise specified, examples of the "heterocycle (group)" of the "heterocyclyl-amino (group)" include those similar to the aforementioned "heterocyclic group", and examples of the "heterocyclyl-amino (group)" include 2-pyridyl-amino.

In the present specification, unless otherwise specified, examples of the "heterocyclyl-carbonyl" of the "heterocyclyl-carbonylamino (group)" include those similar to the aforementioned "heterocyclyl-carbonyl", and examples of the "heterocyclyl-carbonylamino (group)" include pyridyl-carbonylamino.

In the present specification, unless otherwise specified, examples of the "heterocycle (group)" of the "heterocyclyl-oxycarbonylamino (group)" include those similar to the aforementioned "heterocyclic group", and examples of the "heterocyclyl-oxycarbonylamino (group)" include 2-pyridyl-oxycarbonylamino.

In the present specification, unless otherwise specified, examples of the "heterocycle (group)" of the "heterocyclyl-sulfonylamino (group)" include those similar to the aforementioned "heterocyclic group", and examples of the "heterocyclyl-sulfonylamino (group)" include 2-pyridyl-sulfonylamino.

In the present specification, unless otherwise specified, examples of the "alkoxy-carbonylamino (group)" include a $C_{1-6}$ alkoxy-carbonylamino (group).

In the present specification, unless otherwise specified, examples of the "$C_{1-6}$ alkoxy-carbonylamino (group)" include methoxycarbonylamino, ethoxycarbonylamino, propoxycarbonylamino, and butoxycarbonylamino.

In the present specification, unless otherwise specified, examples of the "alkylsulfonylamino (group)" include a $C_{1-6}$ alkylsulfonylamino (group).

In the present specification, unless otherwise specified, examples of the "$C_{1-6}$ alkylsulfonylamino (group)" include methylsulfonylamino, and ethylsulfonylamino.

In the present specification, unless otherwise specified, examples of the "mono- or di-$C_{3-7}$ cycloalkylamino (group)" include cyclopropylamino, cyclopentylamino, and cyclohexylamino.

In the present specification, unless otherwise specified, examples of the "$C_{3-7}$ cycloalkyl-carbonylamino (group)" include cyclopropylcarbonylamino, cyclopentylcarbonylamino, and cyclohexylcarbonylamino.

In the present specification, unless otherwise specified, examples of the "$C_{3-7}$ cycloalkyloxy-carbonylamino (group)" include cyclopropoxycarbonylamino, cyclopentyloxycarbonylamino, and cyclohexyloxycarbonylamino.

In the present specification, unless otherwise specified, examples of the "$C_{3-7}$ cycloalkylsulfonylamino (group)" include cyclopropylsulfonylamino, cyclopentylsulfonylamino, and cyclohexylsulfonylamino.

In the present specification, unless otherwise specified, examples of the "mono- or di-$C_{6-14}$ arylamino (group)" include phenylamino, and diphenylamino.

In the present specification, unless otherwise specified, examples of the "mono- or di-$C_{7-16}$ aralkylamino (group)" include benzylamino.

In the present specification, unless otherwise specified, examples of the "$C_{6-14}$ aryl-carbonylamino (group)" include benzoylamino and naphthoylamino.

In the present specification, unless otherwise specified, examples of the "$C_{6-14}$ arylsulfonylamino (group)" include phenylsulfonylamino, 2-naphthylsulfonylamino, and 1-naphthylsulfonylamino.

The substituents of the compound of the present specification are explained in the following. [Substituent group A]

In the present specification, substituent group A consists of the following substituents (1)-(52).

(1) a halogen atom,
(2) a nitro group,
(3) a cyano group,
(4) an optionally esterified carboxy group,
(5) an optionally substituted alkyl group,
(6) an optionally substituted alkenyl group,
(7) an optionally substituted alkynyl group (e.g., an optionally substituted $C_{3-7}$ cycloalkyl-$C_{2-6}$ alkynyl group),
(8) an optionally substituted $C_{3-7}$ cycloalkyl group, (9) an optionally substituted $C_{6-14}$ aryl group,
(10) an optionally substituted $C_{7-16}$ aralkyl group,
(11) an optionally substituted $C_{6-14}$ aryl-$C_{2-6}$ alkenyl group,
(12) an optionally substituted heterocyclic group,
(13) a hydroxy group,
(14) an optionally substituted alkoxy group,
(15) an optionally substituted $C_{3-7}$ cycloalkyloxy group,
(16) an optionally substituted $C_{6-14}$ aryloxy group,
(17) an optionally substituted $C_{7-16}$ aralkyloxy group,
(18) an optionally substituted alkyl-carbonyloxy group,
(19) an optionally substituted alkoxy-carbonyloxy group,
(20) an optionally substituted mono-alkyl-carbamoyloxy group,
(21) an optionally substituted di-alkyl-carbamoyloxy group,
(22) an optionally substituted $C_{6-14}$ aryl-carbonyloxy group,
(23) an optionally substituted mono- or di-$C_{6-14}$ aryl-carbamoyloxy group,
(24) an optionally substituted heterocyclyl-oxy group (e.g., optionally substituted aromatic heterocyclyl-oxy group),
(25) an optionally substituted $C_{1-6}$ alkylsulfonyloxy group (e.g., optionally substituted halogeno $C_{1-6}$ alkylsulfonyloxy group),
(26) a sulfanyl (mercapto) group,
(27) an optionally substituted alkylsulfanyl group,
(28) an optionally substituted $C_{3-7}$ cycloalkylsulfanyl group,
(29) an optionally substituted $C_{6-14}$ arylsulfanyl group,
(30) an optionally substituted $C_{7-16}$ aralkylsulfanyl group,
(31) an optionally substituted heterocyclyl-sulfanyl group,
(32) a formyl group,
(33) an optionally substituted alkyl-carbonyl group,
(34) an optionally substituted $C_{3-7}$ cycloalkyl-carbonyl group,
(35) an optionally substituted $C_{6-14}$ aryl-carbonyl group,
(36) an optionally substituted $C_{7-16}$ aralkyl-carbonyl group,
(37) an optionally substituted heterocyclyl-carbonyl group,
(38) an optionally substituted alkylsulfonyl group,
(39) an optionally substituted $C_{3-7}$ cycloalkylsulfonyl group,
(40) an optionally substituted $C_{6-14}$ arylsulfonyl group,
(41) an optionally substituted heterocyclyl-sulfonyl group,
(42) an optionally substituted alkylsulfinyl group,
(43) an optionally substituted $C_{3-7}$ cycloalkylsulfinyl group,
(44) an optionally substituted $C_{6-14}$ arylsulfinyl group,
(45) an optionally substituted heterocyclyl-sulfinyl group,
(46) a sulfo group,
(47) a sulfamoyl group,
(48) a sulfinamoyl group,
(49) a sulfenamoyl group,
(50) a thiocarbamoyl group,
(51) an optionally substituted carbamoyl group [e.g., an optionally substituted alkyl-carbamoyl group and the like],
(52) an optionally substituted amino group
[e.g.,
an amino,
an optionally substituted mono- or di-alkylamino group,
an optionally substituted mono- or di-$C_{3-7}$ cycloalkylamino group,
an optionally substituted mono- or di-$C_{6-14}$ arylamino group,
an optionally substituted mono- or di-$C_{7-16}$ aralkylamino group,
an optionally substituted heterocyclyl-amino group,
an optionally substituted $C_{6-14}$ aryl-carbonylamino group,
a formylamino group,
an optionally substituted alkyl-carbonylamino group (e.g., mono-($C_{1-6}$ alkyl-carbonyl)-amino group),
an optionally substituted $C_{3-7}$ cycloalkyl-carbonylamino group,
an optionally substituted heterocyclyl-carbonylamino group,
an optionally substituted alkoxy-carbonylamino group,
an optionally substituted $C_{3-7}$ cycloalkyloxy-carbonylamino group,
an optionally substituted heterocyclyl-oxycarbonylamino group,
an optionally substituted carbamoylamino group,
an optionally substituted alkylsulfonylamino group,
an optionally substituted $C_{3-7}$ cycloalkylsulfonylamino group,
an optionally substituted heterocyclyl-sulfonylamino group,
an optionally substituted $C_{6-14}$ arylsulfonylamino group]

In substituent group A, examples of each substituent of "optionally substituted alkoxy-carbonyl group", "optionally substituted alkyl group", "optionally substituted alkenyl group", "optionally substituted alkynyl group", "optionally substituted alkoxy group", "optionally substituted alkyl-carbonyloxy group", "optionally substituted alkoxy-carbonyloxy group", "optionally substituted mono-alkyl-carbamoyloxy group", "optionally substituted di-alkyl-carbamoyloxy group", "optionally substituted alkylsulfanyl group", "optionally substituted alkyl-carbonyl group", "optionally substituted alkylsulfonyl group", "optionally substituted alkylsulfinyl group", "optionally substituted alkyl-carbamoyl group", "optionally substituted mono- or di-alkylamino group", "optionally substituted alkyl-carbonylamino group", "optionally substituted mono-($C_{1-6}$ alkyl-carbonyl)-amino group", "optionally substituted alkoxy-carbonylamino group", and "optionally substituted alkylsulfonylamino group" include substituents selected from the following substituent group B. The number of the substituents is 1 to the maximum substitutable number, more preferably 1 to 3, more preferably 1.

In substituent group A, examples of each substituent of "optionally substituted $C_{6-14}$ aryloxy-carbonyl group", "optionally substituted $C_{7-16}$ aralkyloxy-carbonyl group", "optionally substituted $C_{3-7}$ cycloalkyl-$C_{2-6}$ alkynyl group", "optionally substituted $C_{3-7}$ cycloalkyl group", "optionally substituted $C_{6-14}$ aryl group", "optionally substituted $C_{7-16}$ aralkyl group", "optionally substituted $C_{6-14}$ aryl-$C_{2-6}$ alkenyl group", "optionally substituted heterocyclic group", "optionally substituted $C_{3-7}$ cycloalkyloxy group", "optionally substituted $C_{6-14}$ aryloxy group", "optionally substituted $C_{7-16}$ aralkyloxy group", "optionally substituted $C_{6-14}$ aryl-carbonyloxy group", "optionally substituted mono- or di-$C_{6-14}$ aryl-carbamoyloxy group", "optionally substituted heterocyclyl-oxy group", "optionally substituted aromatic heterocyclyl-oxy group", "optionally substituted $C_{3-7}$ cycloalkylsulfanyl group", "optionally substituted $C_{6-14}$ arylsulfanyl group", "optionally substituted $C_{7-16}$ aralkylsulfanyl group", "optionally substituted heterocyclyl-sulfanyl group", "optionally substituted $C_{3-7}$ cycloalkyl-carbonyl group", "optionally substituted $C_{6-14}$ aryl-carbonyl group", "optionally substituted $C_{7-16}$ aralkyl-carbonyl group", "optionally substituted heterocyclyl-carbonyl group", "optionally substituted $C_{3-7}$ cycloalkylsulfonyl group", "optionally substituted $C_{6-14}$ arylsulfonyl group", "optionally substituted heterocyclyl-sulfonyl group", "optionally substituted $C_{3-7}$ cycloalkylsulfinyl group", "optionally substituted $C_{6-14}$ arylsulfinyl group", "optionally substituted heterocyclyl-sulfinyl group", "optionally substituted carbamoyl group", "optionally substituted amino group", "optionally substituted mono- or di-$C_{3-8}$ cycloalkylamino group", "optionally substituted mono- or di-$C_{6-14}$ arylamino group",
"optionally substituted mono- or di-$C_{7-16}$ aralkylamino group",
"optionally substituted heterocyclyl-amino group",
"optionally substituted $C_{6-14}$ aryl-carbonylamino group",
"optionally substituted $C_{3-8}$ cycloalkyl-carbonylamino group",
"optionally substituted heterocyclyl-carbonylamino group",
"optionally substituted $C_{3-8}$ cycloalkoxy-carbonylamino group",
"optionally substituted heterocyclyl-oxycarbonylamino group",
"optionally substituted carbamoylamino group",
"optionally substituted alkylsulfonylamino group",
"optionally substituted $C_{3-8}$ cycloalkylsulfonylamino group",
"optionally substituted heterocyclyl-sulfonylamino group", and
"optionally substituted $C_{6-14}$ arylsulfonylamino group" include substituents selected from the following substituent group B and the following substituent group B'. The number of the substituents is 1 to the maximum substitutable number, more preferably 1 to 3, more preferably 1.

[Substituent Group B]

In the present specification, substituent group B consists of the following substituents (a)-(bb).

(a) a halogen atom,
(b) a hydroxy group,
(c) a nitro group,
(d) a cyano group,
(e) an optionally substituted $C_{6-14}$ aryl group [for example, a $C_{6-14}$ aryl group optionally substituted by one or more (e.g., 1 to 5) substituents selected from the group consisting of a halogen atom, hydroxy, cyano, amino, optionally halogenated $C_{1-6}$ alkyl, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, and mono- or di-$C_{6-14}$ aryl-carbamoyl and the like],
(f) an optionally substituted $C_{6-14}$ aryloxy group [for example, a $C_{6-14}$ aryloxy group optionally substituted by one or more (e.g., 1 to 5) substituents selected from the group consisting of a halogen atom, hydroxy, cyano, amino, optionally halogenated $C_{1-6}$ alkyl, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, and mono- or di-$C_{6-14}$ aryl-carbamoyl and the like],
(g) an optionally substituted $C_{7-16}$ aralkyloxy group [for example, a $C_{7-16}$ aralkyloxy group optionally substituted by one or more (e.g., 1 to 5) substituents selected from the group consisting of a halogen atom, hydroxy, cyano, amino, optionally halogenated $C_{1-6}$ alkyl, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, and mono- or di-$C_{6-14}$ aryl-carbamoyl and the like],
(h) an optionally substituted mono- or di-5- to 10-membered heterocyclic group containing 1 to 4 hetero atoms selected from a nitrogen atom, a sulfur atom, and an oxygen atom [for example, a mono- or di-5- to 10-membered heterocyclic group containing 1 to 4 hetero atoms selected from a nitrogen atom, a sulfur atom, and an oxygen atom (e.g., furyl, pyridyl, thienyl, pyrrolidino, 1-piperidinyl, 4-piperidyl, piperazinyl, 1-morpholinyl, 4-thiomorpholinyl, azepan-1-yl, azocan-1-yl, azonan-1-yl, 3,4-dihydroisoquinolin-2-yl), which is optionally substituted by one or more (e.g., 1 to 5) substituents selected from the group consisting of a halogen atom, hydroxy, cyano, amino, optionally halogenated $C_{1-6}$ alkyl, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, and mono- or di-$C_{6-14}$ aryl-carbamoyl and the like],
(i) an optionally substituted amino group [for example, an amino group optionally substituted by 1 or 2 substituents selected from the group consisting of $C_{1-6}$ alkyl, $C_{2-6}$ alkenyl, $C_{6-14}$ aryl, $C_{7-16}$ aralkyl, a heterocyclic group, and heterocyclyl-alkyl, each of which is optionally substituted (examples of the substituent of the "$C_{1-6}$ alkyl, $C_{2-6}$ alkenyl, $C_{6-14}$ aryl, $C_{7-16}$ aralkyl, a heterocyclic group, and heterocyclyl-alkyl, each of which is optionally substituted" include a halogen atom, hydroxy, cyano, amino, optionally halogenated $C_{1-6}$ alkyl (which is not substituent of alkyl and alkenyl), mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{3-7}$ cycloalkyloxy-carbonyl, $C_{6-14}$ aryloxy-carbonyl, $C_{7-16}$ aralkyloxy-carbonyl, $C_{1-6}$ alkylsulfanyl, $C_{3-7}$ cycloalkylsulfanyl, $C_{1-6}$ alkylsulfinyl, $C_{3-7}$ cycloalkylsulfinyl, $C_{1-6}$ alkylsulfonyl, $C_{3-7}$ cycloalkylsulfonyl, carbamoyl, thiocarbamoyl, mono- or di-$C_{1-6}$ alkyl-carbamoyl, and mono- or di-$C_{6-14}$ aryl-carbamoyl and the like. The number of the substituents is one or more (e.g., 1 to 5). Examples of the "heterocyclyl-" of the "heterocyclic group" and "heterocyclyl-alkyl" include those similar to the aforementioned "heterocyclic group".)],
(j) a $C_{3-7}$ cycloalkyl,
(k) an optionally substituted $C_{1-6}$ alkoxy group [for example, a $C_{1-6}$ alkoxy group optionally substituted by one or more (e.g., 1 to 5) substituents selected from the group consisting of a halogen atom, hydroxy, amino, mono- or di-$C_{1-6}$ alkylamino, mono- or di-$C_{6-14}$ arylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, and mono- or di-$C_{6-14}$ aryl-carbamoyl, trimethylsilyl (TMS) and the like],
(l) a formyl group,
(m) a $C_{1-6}$ alkyl-carbonyl group (e.g., acetyl etc.),
(n) a $C_{3-7}$ cycloalkyl-carbonyl group,
(o) a $C_{6-14}$ aryl-carbonyl group,
(p) a $C_{7-16}$ aralkyl-carbonyl group,
(q) a $C_{1-6}$ alkoxy-carbonyl group,
(r) a $C_{6-14}$ aryloxy-carbonyl group, (s) a $C_{7-16}$ aralkyloxy-carbonyl group,
(t) a $C_{1-6}$ alkylsulfanyl group,
(u) a $C_{1-6}$ alkylsulfinyl group,
(v) a $C_{1-6}$ alkylsulfonyl group,
(w) a carbamoyl group,
(x) a thiocarbamoyl group,
(y) a mono-$C_{1-6}$ alkyl-carbamoyl group (e.g., methylcarbamoyl, ethylcarbamoyl and the like),
(z) a di-$C_{1-6}$ alkyl-carbamoyl group (e.g., dimethylcarbamoyl, diethylcarbamoyl, ethylmethylcarbamoyl and the like),
(aa) a mono- or di-$C_{6-14}$ aryl-carbamoyl group (e.g., phenylcarbamoyl, 1-naphthylcarbamoyl, 2-naphthylcarbamoyl and the like), and
(bb) a mono- or di-5- to 7-membered heterocyclyl containing 1 to 4 hetero atoms selected from a nitrogen atom, a sulfur atom, and an oxygen atom-carbamoyl group (e.g., 2-pyridylcarbamoyl, 3-pyridylcarbamoyl, 4-pyridylcarbamoyl, 2-thienylcarbamoyl, 3-thienylcarbamoyl and the like).

[Substituent Group B']

In the present specification, substituent group B' consists of the following substituents (a)-(c).

(a) an optionally substituted $C_{1-6}$ alkyl group [for example, a $C_{1-6}$ alkyl group optionally substituted by one or more (e.g., 1 to 5) substituents selected from the group consisting of a halogen atom, hydroxy, cyano, amino, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, and mono- or di-$C_{6-14}$ aryl-carbamoyl and the like], (b) an optionally substituted $C_{2-6}$ alkenyl group [for example, a $C_{2-6}$ alkenyl group optionally substituted by one or more (e.g., 1 to 5) substituents selected from the group consisting of a halogen atom, hydroxy, cyano, amino, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, and mono- or di-$C_{6-14}$ aryl-carbamoyl and the like], and (c) an optionally substituted $C_{2-6}$ alkynyl group [for example, a $C_{2-6}$ alkynyl group optionally substituted by one or more (e.g., 1 to 5) substituents selected from the group consisting of a halogen atom, hydroxy, cyano, amino, mono- or di-$C_{1-6}$ alkylamino, mono- or di-$C_{6-14}$ arylamino, mono- or di-$C_{7-16}$ aralkylamino, $C_{3-7}$ cycloalkyl, $C_{2-6}$ alkoxy, formyl, $C_{1-6}$ alkyl-carbonyl, $C_{3-7}$ cycloalkyl-carbonyl, $C_{6-14}$ aryl-carbonyl, $C_{7-26}$ aralkyl-carbonyl, $C_{2-6}$ alkoxy-carbonyl, $C_{6-14}$ aryloxy-carbonyl, $C_{7-26}$ aralkyloxy-carbonyl, $C_{2-6}$ alkylsulfanyl, $C_{2-6}$ alkylsulfinyl, $C_{1-6}$ alkylsulfonyl, carbamoyl, thiocarbamoyl, mono- or di-$C_{1-6}$ alkyl-carbamoyl, and mono- or di-$C_{6-14}$ aryl-carbamoyl and the like].

[Substituent Group C]

In the present specification, substituent group C consists of the following substituents (1)-(6).

(1) an oxo group,
(2) an imino group,
(3) an imino group optionally substituted by one substituent selected from an optionally substituted alkyl group, an optionally substituted $C_{3-7}$ cycloalkyl group, an optionally substituted $C_{6-14}$ aryl group, an optionally substituted $C_{7-16}$ aralkyl group, an optionally substituted heterocyclic group, a hydroxy group, an optionally substituted alkoxy group, an optionally substituted $C_{3-7}$ cycloalkyloxy group, an optionally substituted $C_{6-14}$ aryloxy group, an optionally substituted $C_{7-16}$ aralkyloxy group, and an optionally substituted heterocyclyl-oxy group, (4) a methylidene group optionally substituted by 1 or 2 substituents selected from an optionally substituted alkyl group, an optionally substituted $C_{3-7}$ cycloalkyl group, an optionally substituted $C_{6-14}$ aryl group, an optionally substituted $C_{7-16}$ aralkyl group, and an optionally substituted heterocyclic group, (5) an optionally substituted $C_{3-7}$ cycloalkylidene group, and (6) a $C_{2-7}$ alkylene group optionally substituted by one or more (e.g., 1-3) substituents selected from an optionally substituted alkyl group, an optionally substituted $C_{3-7}$ cycloalkyl group, an optionally substituted $C_{6-14}$ aryl group, an optionally substituted $C_{7-16}$ aralkyl group, and an optionally substituted heterocyclic group (when the $C_{2-7}$ alkylene group is a divalent group on one carbon atom, in other words, when the $C_{2-7}$ alkylene group substitutes two hydrogen atoms on the aforementioned carbon atom, the $C_{2-7}$ alkylene group forms $C_{3-8}$ cycloalkane together with the aforementioned carbon atom).

Examples of the "optionally substituted alkyl group", "optionally substituted $C_{3-7}$ cycloalkyl group", "optionally substituted $C_{6-14}$ aryl group", "optionally substituted $C_{7-16}$ aralkyl group", "optionally substituted heterocyclic group", "optionally substituted alkoxy group", "optionally substituted $C_{3-7}$ cycloalkyloxy group", "optionally substituted $C_{6-14}$ aryloxy group", "optionally substituted $C_{7-16}$ aralkyloxy group", and "optionally substituted heterocyclyl-oxy group" as the substituent of the substituents constituting substituent group C include those similar to the substituents described as the substituents constituting substituent group A.

In addition, examples of the substituent of the "optionally substituted $C_{3-7}$ cycloalkylidene group" include substituents selected from the above-mentioned substituent group B and the above-mentioned substituent group B'. The number of the substituents is 1 to substitutable maximum number, more preferably 1-3, more preferably 1.

The symbols in the formula (I) and the formula (I') are explained in the following. For simplification of the description, the symbols in the formula (I) are explained, and respective symbols in the formula (I') are the same as the corresponding ones in the formula (I).

Ring A is an optionally substituted 5-7-membered heterocycle.

Ring A is preferably an optionally substituted 6-membered heterocycle. Ring A is, for example, an optionally substituted 5-7-membered (preferably, 6-membered) heterocycle having, as ring-constituting atom besides carbon atom, two nitrogen atoms and one optionally mono- or di-oxidized sulfur atom.

W is optionally substituted $C_{1-3}$ alkylene, or optionally substituted $C_{2-3}$ alkenylene.

W is preferably, for example, optionally substituted ethylene (—CH$_2$—CH$_2$—), more preferably, ethylene (—CH$_2$—CH$_2$—).

As the "5-7-membered heterocycle" of the "optionally substituted 5-7-membered heterocycle" for ring A, for example, 4,5-dihydro-1,2,4-thiadiazole, 5,6-dihydro-4H-1,2,4-thiadiazine, 4H-1,2,4-thiadiazine, 4,5,6,7-tetrahydro-1,2,4-thiadiazepine, 4,5-dihydro-1,2,4-thiadiazepine, and 4,7-dihydro-1,2,4-thiadiazepine, and S-mono or dioxides thereof can be specifically mentioned.

As the substituent of the "optionally substituted 5-7-membered heterocycle" for ring A, substituents selected from the aforementioned substituent group A can be mentioned. The number of the substituents is preferably 0 (i.e., unsubstituted), or 1 to 5.

When two substituents are present on a single atom, the two substituents may be taken together to form a divalent substituent. As the divalent substituent, substituents selected from the aforementioned substituent group C can be mentioned.

Ring A is preferably, for example, 5,6-dihydro-4H-1,2,4-thiadiazine 1,1-dioxide.

Ring B is an optionally substituted 5-8-membered heterocycle having, as a ring-constituting atom besides carbon atom, one nitrogen atom, and optionally further having 1 to 3 hetero atoms selected from a nitrogen atom, an oxygen atom and a sulfur atom.

As the "5-8-membered heterocycle having, as a ring-constituting atom besides carbon atom, one nitrogen atom, and optionally further having 1 to 3 hetero atoms selected from a nitrogen atom, an oxygen atom and a sulfur atom" of the "optionally substituted 5-8-membered heterocycle having, as a ring-constituting atom besides carbon atom, one nitrogen atom, and optionally further having 1 to 3 hetero atoms selected from a nitrogen atom, an oxygen atom and a sulfur atom" for ring B, non-aromatic heterocycle can be mentioned. The non-aromatic heterocycle may be saturated or unsaturated.

Examples of the "non-aromatic heterocycle" include pyrrolidine ring, pyrazolidine ring, imidazolidine ring, 1,3-oxazolidine ring, isoxazolidine ring, 1,3-thiazolidine ring, isothiazolidine ring, piperidine ring, piperazine ring, morpholine ring, thiomorpholine ring, hexahydropyrimidine ring, hexahydropyridazine ring, 3,4-dihydro-2H-1,4-oxazine ring, 4,5-dihydro-1H-imidazole ring, 1,2-dihydropyridine ring, 1,2-dihydropyrazine ring, 3,4-dihydro-2H-1,4-thiazine ring, 1,6-dihydropyrimidine ring, 1,6-dihydropyridazine ring, 2,3-dihydro-1H-pyrazole ring, 2,3-dihydroisoxazole ring, 2,3-dihydroisothiazole ring, 2,5-dihydro-1H-1,2,3-triazole ring, 4,5-dihydro-1H-1,2,3-triazole ring, 2,3-dihydro-1,2,5-oxadiazole ring, 2,3-dihydro-1,2,5-thiadiazole ring, 1,2,3,6-tetrahydropyridine ring, 1,2,3,4-tetrahydropyridine ring, 1,2,3,6-tetrahydropyrazine ring, 1,2,3,4-tetrahydropyrazine ring, 1,2,3,4-tetrahydropyrimidine ring, 1,4,5,6-tetrahydropyrimidine ring, 1,2,5,6-tetrahydropyrimidine ring, 1,2,3,6-tetrahydropyridazine ring, 1,4,5,6-tetrahydropyridazine ring, 1,2,3,4-tetrahydropyridazine ring, 4,5-dihydro-1,2,4-triazine ring, 1,6-dihydro-1,2,3-triazine ring, 1,6-dihydro-1,2,4-triazine ring, azepane ring, 1,4-diazepane ring, 1,4-oxazepane ring, 1,4-thiazepane ring, azocane ring, 1,4-diazocane ring, 1,5-diazocane ring, 1,4-oxazocane ring, 1,5-oxazocane ring, 1,4-thiazocane ring, and 1,5-thiazocane ring and the like. The structures of the above-mentioned "non-aromatic heterocycle" are shown below.

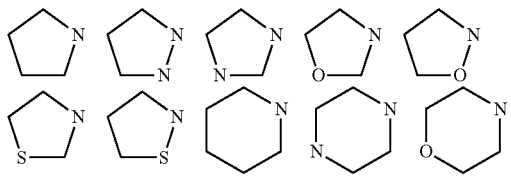

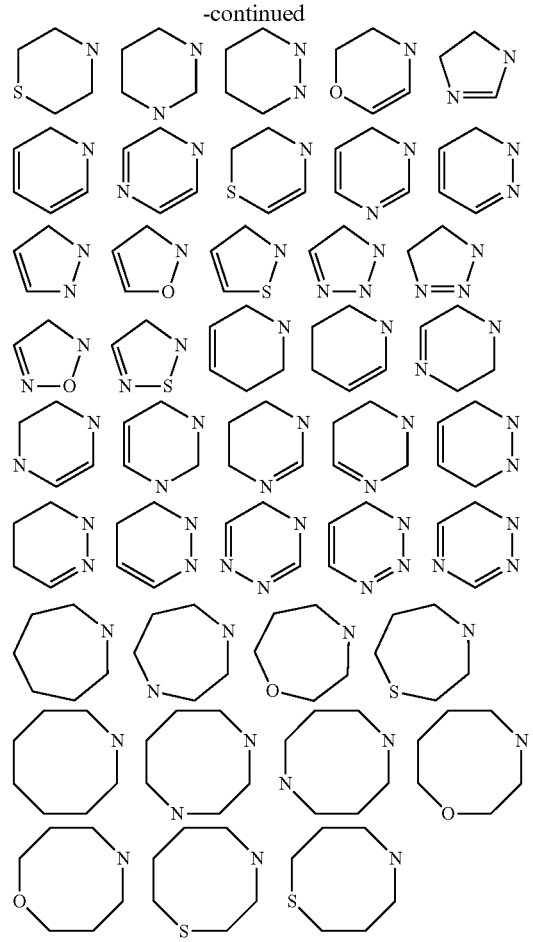

As the substituent of the "optionally substituted 5-8-membered heterocycle having, as a ring-constituting atom besides carbon atom, one nitrogen atom, and optionally further having 1 to 3 hetero atoms selected from a nitrogen atom, an oxygen atom and a sulfur atom" for ring B, substituents selected from the aforementioned substituent group A can be mentioned. The number of the substituents is preferably 0 (i.e., unsubstituted), or 1 to 5.

When two substituents are present on a single atom, the two substituents may be taken together to form a divalent substituent. As the divalent substituent, substituents selected from the aforementioned substituent group C can be mentioned.

Ring B is preferably, for example, a 6-membered heterocycle having, as a ring-constituting atom besides carbon atom, one nitrogen atom, and optionally further having one hetero atom selected from a nitrogen atom, an oxygen atom and a sulfur atom, which is optionally substituted by substituent(s) selected from a fluorine atom, a hydroxy group, a $C_{1-6}$ alkyl group optionally substituted by 1 to 3 halogen atoms, a $C_{1-6}$ alkoxy group and a $C_{1-6}$ alkyl-carbonyl group, more preferably, a 6-membered heterocycle having, as a ring-constituting atom besides carbon atom, one nitrogen atom, and optionally further having 1 to 3 nitrogen atoms, which is optionally substituted by substituent(s) selected from a fluorine atom, a hydroxy group, a $C_{1-6}$ alkyl group optionally substituted by 1 to 3 halogen atoms, a $C_{1-6}$ alkoxy group and a $C_{1-6}$ alkyl-carbonyl group.

The "optionally substituted 6-membered heterocycle" is preferably, for example, a 1,2-dihydropyridine ring, a 1,2-dihydropyrazine ring, a piperazine ring or a piperidine ring.

The substituent of the "optionally substituted 6-membered heterocycle" is preferably, for example, a fluorine atom, a hydroxy group, a $C_{1-6}$ alkyl group optionally substituted by 1 to 3 halogen atoms, a $C_{1-6}$ alkoxy group or a $C_{1-6}$ alkyl-carbonyl group.

Ring D is an optionally substituted non-aromatic hydrocarbon ring, an optionally substituted non-aromatic heterocycle, an optionally substituted aromatic hydrocarbon ring, or an optionally substituted aromatic heterocycle.

As the "non-aromatic hydrocarbon ring" of the "optionally substituted non-aromatic hydrocarbon ring" for ring D, those mentioned above can be mentioned.

As the "non-aromatic heterocycle" of the "optionally substituted non-aromatic heterocycle" for ring D, those mentioned above can be mentioned.

As the "aromatic hydrocarbon ring" of the "optionally substituted aromatic hydrocarbon ring" for ring D, those mentioned above can be mentioned.

As the "aromatic heterocycle" of the "optionally substituted aromatic heterocycle" for ring D, those mentioned above can be mentioned.

As the substituent of each of the "optionally substituted non-aromatic hydrocarbon ring", "optionally substituted non-aromatic heterocycle", "optionally substituted aromatic hydrocarbon ring" and "optionally substituted aromatic heterocycle" for ring D, substituents selected from the aforementioned substituent group A can be mentioned. The number of the substituents is preferably 0 (i.e., unsubstituted), or 1 to 5.

When two substituents are present on a single atom, the two substituents may be taken together to form a divalent substituent. As the divalent substituent, substituents selected from the aforementioned substituent group C can be mentioned.

Ring D is preferably an aromatic hydrocarbon ring having a carbon number of 6 to 14, a 5- or 6-membered aromatic heterocycle or a bicyclic condensed heterocycle, each of which is optionally substituted.

As each of the "aromatic hydrocarbon ring having a carbon number of 6 to 14", "5- or 6-membered aromatic heterocycle" and "bicyclic condensed heterocycle", those mentioned above can be mentioned.

Ring D is preferably a 3-8-membered monocyclic non-aromatic hydrocarbon ring, a 6-14-membered aromatic hydrocarbon ring, a 6-14-membered non-aromatic hydrocarbon ring, a 5-6-membered monocyclic aromatic heterocycle, a 3-8-membered monocyclic non-aromatic heterocycle, a 8-14-membered condensed aromatic heterocycle or a 6-14-membered condensed non-aromatic heterocycle, each of which is optionally substituted.

Ring D is particularly preferably, for example, $C_{3-7}$ cycloalkane, $C_{6-14}$ arene (e.g., benzene ring, naphthalene ring), dihydronaphthalene ring, tetrahydronaphthalene ring, dihydroindene ring, azetidine ring, piperidine ring, furan ring, pyridine ring, pyrazole ring, 1,2,4-oxadiazole ring, dihydrobenzodioxine ring, dihydrobenzofuran ring, benzodioxole ring, benzofuran ring, indole ring, quinoline ring, benzimidazole ring, benzothiazole ring, indazole ring, dibenzothiophene ring or thiophene ring), each of which is optionally substituted.

The substituent of ring D is preferably, for example, 1 to 3 substituents selected from the group consisting of a halogen atom, a cyano group, a $C_{1-6}$ alkyl group optionally substituted by 1 to 3 halogen atoms, a $C_{3-7}$ cycloalkyl group, a $C_{6-14}$ aryl group, a $C_{1-6}$ alkoxy group optionally substituted by 1 to 3 halogen atoms, a $C_{6-14}$ aryloxy group, a $C_{1-6}$ alkyl-carbonyl group, and a mono- or di-$C_{1-6}$ alkyl-carbamoyl group, or, for example, 1 to 3 substituents selected from the group consisting of (1) a halogen atom;
(2) cyano;
(3) hydroxy;
(4) oxo;
(5) $C_{1-6}$ alkyl optionally substituted by substituent(s) selected from 1) a halogen atom, 2) phenyl optionally substituted by substituent(s) selected from a halogen atom and $C_{1-6}$ alkyl and 3) $C_{1-6}$ alkoxycarbonyl;
(6) $C_{3-7}$ cycloalkyl optionally substituted by $C_{1-6}$ alkoxycarbonyl or phenyl;
(7) $C_{1-6}$ alkyl-carbonyl;
(8) phenyl-carbonyl optionally substituted by $C_{1-6}$ alkoxy;
(9) $C_{2-6}$ alkenyl substituted by phenyl;
(10) phenyl optionally substituted by 1 to 3 substituents selected from a halogen atom, $C_{1-6}$ alkyl, $C_{3-7}$ cycloalkyl and $C_{1-6}$ alkoxy;
(11) pyrazole optionally substituted by 1 to 3 substituents selected from $C_{1-6}$ alkyl optionally substituted by a halogen atom, and $C_{3-7}$ cycloalkyl;
(12) pyrrolidine;
(13) dihydrobenzofuran;
(14) morpholine;
(15) oxetane substituted by a halogen atom;
(16) sulfanyl substituted by a halogen atom or $C_{1-6}$ alkyl;
(17) $C_{1-6}$ alkylsulfonyloxy substituted by a halogen atom;
(18) di-$C_{1-6}$ alkylcarbamoyl;
(19) 4,4,5,5-tetramethyl-1,3,2-dioxaborolane;
(20) $C_{1-6}$ alkoxy optionally substituted by substituent(s) selected from a halogen atom, $C_{3-7}$ cycloalkyl, phenyl optionally substituted by a halogen atom, tetrahydrofuran and tetrahydropyran;
(21) $C_{3-7}$ cycloalkyloxy optionally substituted by $C_{1-6}$ alkyl, oxo or $C_{2-6}$ alkylenedioxy;
(22) $C_{3-7}$ cycloalkenyloxy optionally substituted by $C_{1-6}$ alkyl;
(23) phenyloxy optionally substituted by 1 to 3 substituents selected from a halogen atom, cyano, hydroxy, $C_{1-6}$ alkyl optionally substituted by a halogen atom, and $C_{1-6}$ alkoxy optionally substituted by a halogen atom;
(24) pyridyloxy optionally substituted by a halogen atom, or $C_{1-6}$ alkyl optionally substituted by a halogen atom;
(25) silyloxy substituted by $C_{1-6}$ alkyl;
(26) tetrahydrofuranyloxy;
(27) tetrahydropyranyloxy; and
(28) dihydrobenzofuranyloxy.

L is a bond, or a spacer having the main chain having an atom number of 1-8.

The "main chain" of the "spacer having the main chain having an atom number of 1-8" for L mean a divalent straight chain connecting the ring-constituting atom of ring D and the ring-constituting atom of ring B. The "main chain" consists of 1-8 atoms selected from a carbon atom and a hetero atom (e.g., nitrogen atom, oxygen atom, sulfur atom etc.), and may be saturated or unsaturated. The nitrogen atom constituting the main chain is optionally substituted by a substituent (e.g., $C_{1-6}$ alkyl group). S may be oxidized.

The "spacer having the main chain having an atom number of 1-8" for L is preferably, for example, —$Y^a$—$X^a$—, —$X^a$—$Y^a$—, or —$Y^a$—$X^a$—$Y^b$—

($X^a$ is a bond, —O—, —$NR^a$—, —S(O)n-, —CO—$NR^a$—, —$NR^a$—CO—, —$SO_2$—$NR^a$—, —$NR^a$—$SO_2$—, —$NR^a$—CO—$NR^b$—, —$NR^a$—COO—, or —OCO—$NR^a$—;

n is 0, 1 or 2;

$Y^a$ and $Y^b$ are the same or different and each is a bond, an optionally substituted $C_{1-6}$ alkylene group, a $C_{2-6}$ alkenylene group, or a $C_{2-6}$ alkynylene group;

$R^a$ is a hydrogen atom, an optionally substituted $C_{1-6}$ alkyl group, or an optionally substituted $C_{3-6}$ cycloalkyl group.

L is preferably, for example, a bond, —O—, —O—$CH_2$—, —$CH_2$—O—, —CO—NH—, —NH—CO—, —S—, —SO—, —$SO_2$—, $C_{1-6}$ alkylene, $C_{2-6}$ alkenylene, or $C_{2-6}$ alkynylene, particularly preferably a bond.

n is 0, 1 or 2.

n is preferably, for example, 2.

Preferable examples of the substituent, moiety, ring and the like explained in the present specification are more preferably used in combination.

As compound (I'), preferred is a compound wherein, for example, L is a bond and ring D is an optionally substituted benzene ring.

As compound (I'), preferred is, for example, compound (I-A) below.

[Compound (I-A)]

A compound represented by the formula (I-A)

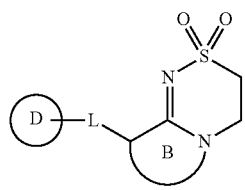

(I-A)

wherein ring B is an optionally substituted 6-membered heterocycle having, as a ring-constituting atom besides carbon atom, one nitrogen atom, and optionally further having 1 hetero atom selected from a nitrogen atom, an oxygen atom and a sulfur atom, ring D is an aromatic hydrocarbon ring having a carbon number of 6 to 14, a 5- or 6-membered aromatic heterocycle, or a bicyclic condensed heterocycle, each of which is optionally substituted by 1-3 substituents selected from a halogen atom, a cyano group, a $C_{1-6}$ alkyl group optionally substituted by 1 to 3 halogen atoms, a $C_{3-7}$ cycloalkyl group, a $C_{6-14}$ aryl group, a $C_{1-6}$ alkoxy group optionally substituted by 1 to 3 halogen atoms, a $C_{6-14}$ aryloxy group, a $C_{1-6}$ alkyl-carbonyl group, and a mono- or di-$C_{1-6}$ alkyl-carbamoyl group, L is a bond, —O—, —CO—NH—, —NH—CO—, —S—, —SO—, —$SO_2$—, $C_{1-6}$ alkylene, $C_{2-6}$ alkenylene, or $C_{2-6}$ alkynylene, and n is 2, or a salt thereof.

As compound (I-A), particularly preferred is a compound wherein ring B is a 6-membered heterocycle, having, as a ring-constituting atom besides carbon atom, one nitrogen atom, and further having one hetero atom selected from a nitrogen atom, an oxygen atom and a sulfur atom, which is optionally substituted by $C_{1-6}$ alkyl group optionally substituted by 1 to 3 halogen atoms, or a salt thereof.

In another embodiment of the present invention, of compounds (I), a compound wherein ring A and ring B are each an optionally substituted 6-membered ring, ring B has, as a ring-constituting atom besides carbon atom, one nitrogen atom, and optionally further has 1 to 3 nitrogen atoms, and L is a bond, —O—, —O—$CH_2$—, —$CH_2$—O—, —CO—NH—, —CO—N($C_{1-6}$ alkyl)-, —S—, —SO—, —$SO_2$—, $C_{1-6}$ alkylene, $C_{2-6}$ alkenylene or $C_{2-6}$ alkynylene (hereinafter sometimes to be referred to as compound (I-i)) is preferable.

Of the above-mentioned compounds (I-i), a compound wherein

W is optionally substituted —$CH_2$—$CH_2$—, and n is 2

(hereinafter sometimes to be referred to as compound (I-ii)) is more preferable.

Of compounds (I-i)-(I-ii), a compound wherein the partial structural formula represented by the formula (I):

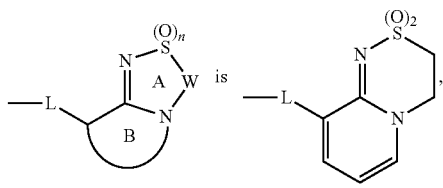

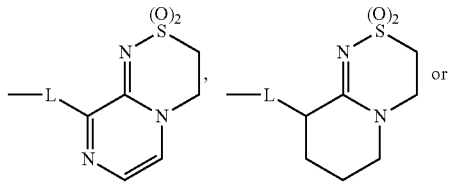

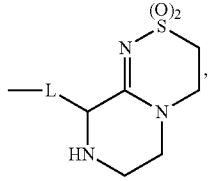

ring B is optionally substituted by substituent(s) selected from a halogen atom;

hydroxy;

$C_{1-6}$ alkyl optionally substituted by a halogen atom;

$C_{1-6}$ alkoxy; and $C_{1-6}$ alkyl-carbonyl (hereinafter sometimes to be referred to as compound (I-iii)) is more preferable.

Alternatively, of compounds (I-i)-(I-iii), a compound wherein the partial structural formula represented by the formula (I):

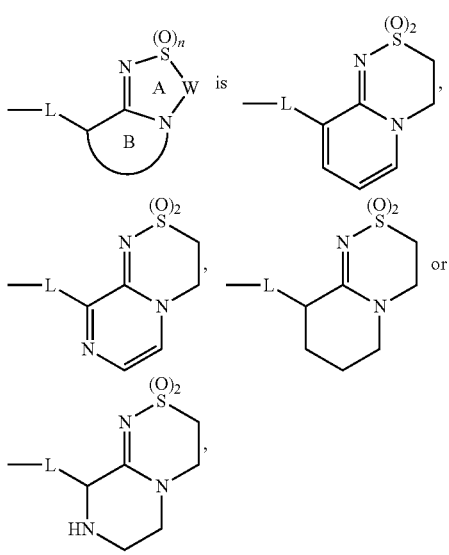

ring B is optionally substituted by substituent(s) selected from a halogen atom, hydroxy, $C_{1-6}$ alkyl and $C_{1-6}$ alkoxy (hereinafter sometimes to be referred to as compound (I-iv)) is more preferable.

Alternatively, of compounds (I-i)-(I-iv), a compound wherein the partial structural formula represented by the formula (I):

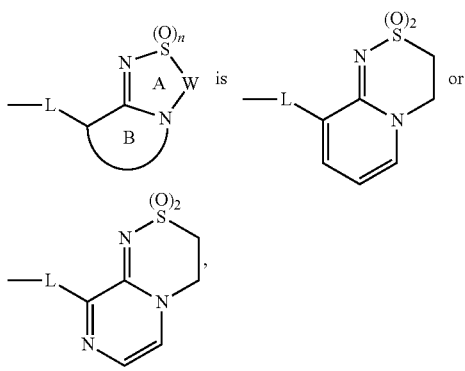

ring B is optionally substituted by $C_{1-6}$ alkyl (hereinafter sometimes to be referred to as compound (I-v)) is more preferable.

Alternatively, of compounds (I-i)-(I-v), a compound wherein

L is a bond, —O—, —O—CH$_2$—, $C_{1-6}$ alkylene or $C_{2-6}$ alkynylene (hereinafter sometimes to be referred to as compound (I-vi)) is more preferable.

Alternatively, of compounds (I-i)-(I-vi), a compound wherein

L is a bond (hereinafter sometimes to be referred to as compound (I-vii)) is more preferable.

Alternatively, of compounds (I-i)-(I-vii), a compound wherein ring D is an optionally substituted 3-8-membered monocyclic non-aromatic hydrocarbon ring, an optionally substituted 6-14-membered aromatic hydrocarbon ring, an optionally substituted 6-14-membered non-aromatic hydrocarbon ring, an optionally substituted 5-6-membered monocyclic aromatic heterocycle, an optionally substituted 3-8-membered monocyclic non-aromatic heterocycle, an optionally substituted 8-14-membered condensed aromatic heterocycle or an optionally substituted 6-14-membered condensed non-aromatic heterocycle (hereinafter sometimes to be referred to as compound (I-viii)) is more preferable.

Alternatively, of compounds (I-i)-(I-viii), a compound wherein ring D is optionally substituted $C_{3-7}$ cycloalkane,
optionally substituted $C_{6-14}$ arene,
optionally substituted dihydronaphthalene,
optionally substituted tetrahydronaphthalene,
optionally substituted dihydroindene,
optionally substituted thiophene,
optionally substituted azetidine,
optionally substituted piperidine,
optionally substituted furan,
optionally substituted pyridine,
optionally substituted pyrazole,
optionally substituted 1,2,4-oxadiazole,
optionally substituted dihydrobenzodioxine,
optionally substituted dihydrobenzofuran,
optionally substituted benzodioxole,
optionally substituted benzofuran,
optionally substituted indole,
optionally substituted quinoline,
optionally substituted benzimidazole,
optionally substituted benzothiazole,
optionally substituted indazole, or
optionally substituted dibenzothiophene
(hereinafter sometimes to be referred to as compound (I-ix)) is more preferable.

Alternatively, of compounds (I-i)-(I-ix), a compound wherein ring D is $C_{3-7}$ cycloalkane, $C_{6-14}$ arene, dihydronaphthalene, tetrahydronaphthalene, dihydroindene, thiophene, azetidine, piperidine, furan, pyridine, pyrazole, 1,2,4-oxadiazole, dihydrobenzodioxine, dihydrobenzofuran, benzodioxole, benzofuran, indole, quinoline, benzimidazole, benzothiazole, indazole or dibenzothiophene, each of which is optionally substituted by 1-4 substituents selected from (1) a halogen atom;
(2) cyano;
(3) hydroxy;
(4) oxo;
(5) $C_{1-6}$ alkyl optionally substituted by substituent(s) selected from 1) a halogen atom, 2) phenyl optionally substituted by substituent(s) selected from a halogen atom and $C_{1-6}$ alkyl and 3) $C_{2-6}$ alkoxycarbonyl;
(6) $C_{3-7}$ cycloalkyl optionally substituted by $C_{2-6}$ alkoxycarbonyl or phenyl;
(7) $C_{1-6}$ alkyl-carbonyl;
(8) phenyl-carbonyl optionally substituted by $C_{1-6}$ alkoxy;
(9) $C_{2-6}$ alkenyl substituted by phenyl;
(10) phenyl optionally substituted by 1 to 3 substituents selected from a halogen atom, $C_{1-6}$ alkyl, $C_{3-7}$ cycloalkyl and $C_{1-6}$ alkoxy;
(11) pyrazole optionally substituted by 1 to 3 substituents selected from $C_{1-6}$ alkyl optionally substituted by a halogen atom, and $C_{3-7}$ cycloalkyl;
(12) pyrrolidine;
(13) dihydrobenzofuran;
(14) morpholine;
(15) oxetane substituted by a halogen atom;

(16) sulfanyl substituted by a halogen atom or $C_{1-6}$ alkyl;
(17) $C_{1-6}$ alkylsulfonyloxy substituted by a halogen atom;
(18) di-$C_{1-6}$ alkylcarbamoyl;
(19) 4,4,5,5-tetramethyl-1,3,2-dioxaborolane;
(20) $C_{1-6}$ alkoxy optionally substituted by substituent(s) selected from a halogen atom, $C_{3-7}$ cycloalkyl, phenyl optionally substituted by a halogen atom, tetrahydrofuran and tetrahydropyran;
(21) $C_{3-7}$ cycloalkyloxy optionally substituted by $C_{1-6}$ alkyl, oxo or $C_{2-6}$ alkylenedioxy;
(22) $C_{3-7}$ cycloalkenyloxy optionally substituted by $C_{1-6}$ alkyl;
(23) phenyloxy optionally substituted by 1 to 3 substituents selected from a halogen atom, cyano, hydroxy, $C_{1-6}$ alkyl optionally substituted by a halogen atom, and $C_{1-6}$ alkoxy optionally substituted by a halogen atom;
(24) pyridyloxy optionally substituted by a halogen atom, or $C_{1-6}$ alkyl optionally substituted by a halogen atom;
(25) silyloxy substituted by $C_{1-6}$ alkyl;
(26) tetrahydrofuranyloxy;
(27) tetrahydropyranyloxy; and
(28) dihydrobenzofuranyloxy
(hereinafter sometimes to be referred to as compound (I-x)) is more preferable.

Alternatively, of compounds (I-i)-(I-ix), a compound wherein
ring D is $C_{3-7}$ cycloalkane, benzene, naphthalene, pyridine or thiophene, each of which is optionally substituted (hereinafter sometimes to be referred to as compound (I-xi)) is more preferable.

Alternatively, of compounds (I-i)-(I-xi), a compound wherein
ring D is benzene optionally substituted by 1-3 substituents selected from
(1) a halogen atom;
(2) cyano;
(3) hydroxy;
(4) $C_{1-6}$ alkyl optionally substituted by substituent(s) selected from 1) a halogen atom, 2) phenyl optionally substituted by substituent(s) selected from a halogen atom and $C_{1-6}$ alkyl, and 3) $C_{1-6}$ alkoxycarbonyl;
(5) $C_{3-7}$ cycloalkyl optionally substituted by $C_{1-6}$ alkoxycarbonyl or phenyl;
(6) $C_{1-6}$ alkyl-carbonyl;
(7) phenyl-carbonyl optionally substituted by $C_{1-6}$ alkoxy;
(8) $C_{2-6}$ alkenyl substituted by phenyl;
(9) phenyl optionally substituted by a halogen atom or $C_{1-6}$ alkyl;
(10) pyrazole optionally substituted by 1 to 3 substituents selected from $C_{1-6}$ alkyl optionally substituted by a halogen atom, and $C_{3-7}$ cycloalkyl;
(11) pyrrolidine;
(12) dihydrobenzofuran;
(13) morpholine;
(14) oxetane substituted by a halogen atom;
(15) sulfanyl substituted by a halogen atom or $C_{1-6}$ alkyl;
(16) $C_{1-6}$ alkylsulfonyloxy substituted by a halogen atom;
(17) di-$C_{1-6}$ alkylcarbamoyl;
(18) 4,4,5,5-tetramethyl-1,3,2-dioxaborolane;
(19) $C_{1-6}$ alkoxy optionally substituted by substituent(s) selected from a halogen atom, $C_{3-7}$ cycloalkyl, phenyl optionally substituted by a halogen atom, tetrahydrofuran and tetrahydropyran;
(20) $C_{3-7}$ cycloalkyloxy optionally substituted by $C_{1-6}$ alkyl, oxo or $C_{2-6}$ alkylenedioxy;
(21) $C_{3-7}$ cycloalkenyloxy optionally substituted by $C_{1-6}$ alkyl;
(22) phenyloxy optionally substituted by substituent(s) selected from a halogen atom, cyano, hydroxy, $C_{1-6}$ alkyl optionally substituted by a halogen atom, and $C_{1-6}$ alkoxy optionally substituted by a halogen atom;
(23) pyridyloxy optionally substituted by a halogen atom, or $C_{1-6}$ alkyl optionally substituted by a halogen atom;
(24) silyloxy substituted by $C_{1-6}$ alkyl;
(25) tetrahydrofuranyloxy;
(26) tetrahydropyranyloxy; and
(27) dihydrobenzofuranyloxy
(hereinafter sometimes to be referred to as compound (I-xii)) is more preferable.

Alternatively, of compounds (I-i)-(I-xii), a compound wherein
ring D is benzene optionally substituted by 1-3 substituents selected from
(1) a halogen atom;
(2) hydroxy;
(3) $C_{1-6}$ alkyl optionally substituted by substituent(s) selected from 1) a halogen atom and 2) phenyl optionally substituted by substituent(s) selected from a halogen atom and $C_{1-6}$ alkyl;
(4) $C_{3-7}$ cycloalkyl;
(5) phenyl-carbonyl;
(6) $C_{2-6}$ alkenyl substituted by phenyl;
(7) phenyl optionally substituted by a halogen atom or $C_{1-6}$ alkyl;
(8) pyrrolidine;
(9) dihydrobenzofuran;
(10) $C_{1-6}$ alkylsulfonyloxy substituted by a halogen atom;
(11) $C_{1-6}$ alkoxy optionally substituted by substituent(s) selected from a halogen atom, $C_{3-7}$ cycloalkyl, phenyl substituted by a halogen atom, tetrahydrofuran and tetrahydropyran;
(12) $C_{3-7}$ cycloalkyloxy optionally substituted by $C_{1-6}$ alkyl;
(13) $C_{3-7}$ cycloalkenyloxy optionally substituted by $C_{1-6}$ alkyl;
(14) phenyloxy optionally substituted by 1-3 substituent(s) selected from a halogen atom, cyano, hydroxy, $C_{1-6}$ alkyl optionally substituted by a halogen atom, and $C_{1-6}$ alkoxy;
(15) pyridyloxy substituted by a halogen atom, or $C_{1-6}$ alkyl substituted by a halogen atom;
(16) tetrahydrofuranyloxy;
(17) tetrahydropyranyloxy; and
(18) dihydrobenzofuranyloxy
(hereinafter sometimes to be referred to as compound (I-xiii)) is more preferable.

Alternatively, of compounds (I-i)-(I-iii) and (I-viii)-(I-ix), a compound wherein
the partial structural formula represented by the formula (I):

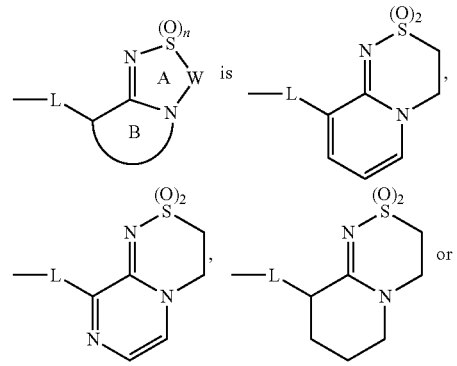

-continued

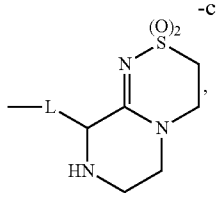

ring B is optionally substituted by substituent(s) selected from
a halogen atom;
hydroxy;
$C_{1-6}$ alkyl optionally substituted by a halogen atom;
$C_{1-6}$ alkoxy; and
$C_{1-6}$ alkyl-carbonyl, ring D is $C_{3-7}$ cycloalkane, $C_{6-14}$ arene, dihydronaphthalene, tetrahydronaphthalene, dihydroindene, thiophene, azetidine, piperidine, furan, pyridine, pyrazole, 1,2,4-oxadiazole, dihydrobenzodioxine, dihydrobenzofuran, benzodioxole, benzofuran, indole, quinoline, benzimidazole, benzothiazole, indazole or dibenzothiophene, each of which is optionally substituted by 1-4 substituents selected from
(1) a halogen atom;
(2) cyano;
(3) hydroxy;
(4) oxo;
(5) optionally substituted $C_{1-6}$ alkyl;
(6) optionally substituted $C_{3-7}$ cycloalkyl;
(7) substituted carbonyl;
(8) substituted $C_{2-6}$ alkenyl;
(9) optionally substituted $C_{6-14}$ aryl;
(10) optionally substituted $C_{7-16}$ aralkyl;
(11) optionally substituted pyrazole;
(12) pyrrolidine;
(13) dihydrobenzofuran;
(14) morpholine;
(15) substituted oxetane;
(16) substituted sulfanyl;
(17) substituted $C_{1-6}$ alkylsulfonyloxy;
(18) di-$C_{1-6}$ alkyl-carbamoyl;
(19) substituted dioxaborolane;
(20) optionally substituted $C_{1-6}$ alkoxy;
(21) $C_{3-7}$ cycloalkyloxy;
(22) optionally substituted $C_{3-7}$ cycloalkenyloxy;
(23) optionally substituted $C_{6-14}$ aryloxy;
(24) optionally substituted $C_{7-16}$ aralkyloxy;
(25) optionally substituted pyridyloxy;
(26) substituted silyloxy;
(27) tetrahydrofuranyloxy;
(28) tetrahydropyranyloxy; and
(29) dihydrobenzofuranyloxy, L is a bond, —O—, —O—CH$_2$—, —CH$_2$—O—, —CO—NH—, —CO—N($C_{1-6}$ alkyl)-, —S—, —SO—, —SO$_2$—, $C_{1-6}$ alkylene, $C_{2-6}$ alkenylene or $C_{2-6}$ alkynylene (hereinafter sometimes to be referred to as compound (I-xiv)) is more preferable.

Alternatively, of compounds (I-i)-(I-iii) and (I-viii)-(I-x), a compound wherein
the partial structural formula represented by the formula (I):

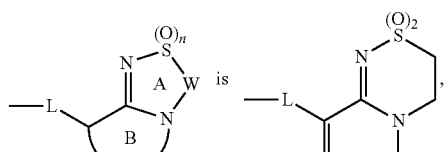 is 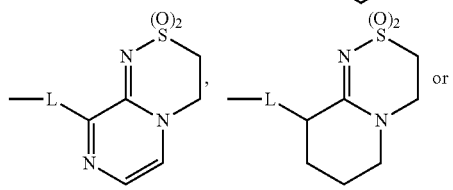,

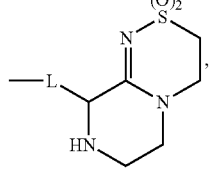, ring B is optionally substituted by substituent(s) selected from
a halogen atom (e.g., a fluorine atom, chlorine atom);
hydroxy;
$C_{1-6}$ alkyl (e.g., methyl) optionally substituted by a halogen atom (e.g., a fluorine atom);
$C_{1-6}$ alkoxy (e.g., methoxy); and
$C_{1-6}$ alkyl-carbonyl (e.g., methylcarbonyl), ring D is $C_{3-7}$ cycloalkane (e.g., cyclohexane), $C_{6-14}$ arene (e.g., benzene, naphthalene), dihydronaphthalene, tetrahydronaphthalene, dihydroindene, thiophene, azetidine, piperidine, furan, pyridine, pyrazole, 1,2,4-oxadiazole, dihydrobenzodioxine, dihydrobenzofuran, benzodioxole, benzofuran, indole, quinoline, benzimidazole, benzothiazole, indazole or dibenzothiophene, each of which is optionally substituted by 1-4 substituents selected from
(1) a halogen atom (e.g., a fluorine atom, chlorine atom);
(2) cyano;
(3) hydroxy;
(4) oxo;
(5) $C_{1-6}$ alkyl (e.g., methyl, ethyl, isopropyl, butyl, isobutyl, sec-butyl, tert-butyl) optionally substituted by substituent(s) selected from 1) a halogen atom (e.g., a fluorine atom), 2) phenyl optionally substituted by substituent(s) selected from a halogen atom (e.g., a fluorine atom) and $C_{1-6}$ alkyl (e.g., methyl) and 3) $C_{2-6}$ alkoxycarbonyl (e.g., methoxycarbonyl);
(6) $C_{3-7}$ cycloalkyl (e.g., cyclopropyl, cyclobutyl, cyclopentyl, cyclohexyl) optionally substituted by $C_{1-6}$ alkoxycarbonyl (e.g., methoxycarbonyl) or phenyl;
(7) $C_{1-6}$ alkyl-carbonyl (e.g., methylcarbonyl);
(8) phenyl-carbonyl optionally substituted by $C_{1-6}$ alkoxy (e.g., methoxy);
(9) $C_{2-6}$ alkenyl (e.g., vinyl) substituted by phenyl;
(10) phenyl optionally substituted by 1 to 3 substituents selected from a halogen atom (e.g., a fluorine atom, chlorine atom), $C_{1-6}$ alkyl (e.g., methyl), $C_{3-7}$ cycloalkyl and $C_{1-6}$ alkoxy (e.g., methoxy);
(11) pyrazole optionally substituted by 1 to 3 substituents selected from $C_{1-6}$ alkyl (e.g., methyl) optionally substituted by a halogen atom (e.g., a fluorine atom), and $C_{3-7}$ cycloalkyl (e.g., cyclopropyl);
(12) pyrrolidine;
(13) dihydrobenzofuran;

(14) morpholine;
(15) oxetane substituted by a halogen atom (e.g., a fluorine atom);
(16) sulfanyl substituted by a halogen atom (e.g., a fluorine atom) or $C_{1-6}$ alkyl (e.g., methyl);
(17) $C_{2-6}$ alkylsulfonyloxy (e.g., methylsulfonyloxy) substituted by a halogen atom (e.g., a fluorine atom);
(18) di-$C_{1-6}$ alkylcarbamoyl (e.g., dimethylcarbamoyl, diethylcarbamoyl);
(19) 4,4,5,5-tetramethyl-1,3,2-dioxaborolane;
(20) $C_{1-6}$ alkoxy (e.g., methoxy, ethoxy, propoxy, isopropoxy, butoxy, isobutoxy, sec-butoxy, tert-butoxy, neopentoxy, 1-ethylpropoxy) optionally substituted by substituent(s) selected from a halogen atom (e.g., a fluorine atom), $C_{3-7}$ cycloalkyl (e.g., cyclopropyl, cyclopentyl, cyclohexyl), phenyl optionally substituted by a halogen atom (e.g., a fluorine atom), tetrahydrofuran and tetrahydropyran;
(21) $C_{3-7}$ cycloalkyloxy (e.g., cyclopropyloxy, cyclobutyloxy, cyclopentyloxy, cyclohexyloxy, cycloheptyloxy) optionally substituted by $C_{1-6}$ alkyl (e.g., methyl), oxo or $C_{2-6}$ alkylenedioxy (e.g., 1,2-ethylenedioxy);
(22) $C_{3-7}$ cycloalkenyloxy (e.g., cyclohexenyloxy) optionally substituted by $C_{2-6}$ alkyl (e.g., methyl);
(23) phenyloxy optionally substituted by 1 to 3 substituents selected from a halogen atom (e.g., a fluorine atom, chlorine atom, bromine atom), cyano, hydroxy, $C_{1-6}$ alkyl (e.g., methyl, ethyl, isopropyl, tert-butyl) optionally substituted by a halogen atom (e.g., a fluorine atom), and $C_{1-6}$ alkoxy (e.g., methoxy, isopropoxy, butoxy) optionally substituted by a halogen atom (e.g., a fluorine atom);
(24) pyridyloxy optionally substituted by a halogen atom (e.g., chlorine atom), or $C_{1-6}$ alkyl (e.g., methyl) optionally substituted by a halogen atom (e.g., a fluorine atom);
(25) silyloxy substituted by $C_{1-6}$ alkyl (e.g., methyl, tert-butyl);
(26) tetrahydrofuranyloxy;
(27) tetrahydropyranyloxy; and
(28) dihydrobenzofuranyloxy, L is a bond, —O—, —O—CH$_2$—, —CH$_2$—O—, —CO—NH—, —NH—CO—, —CO—NH—NH—CO—, —CO—N(C$_{1-6}$ alkyl)-, —N(C$_{1-6}$ alkyl)-CO—, —S—, —SO—, —SO$_2$—, —CH$_2$—S—, —CH$_2$—SO—, —CH$_2$—SO$_2$—, $C_{1-6}$ alkylene (e.g., ethylene), $C_{2-6}$ alkenylene (e.g., ethenylene) or $C_{2-6}$ alkynylene (e.g., ethynylene)
(hereinafter sometimes to be referred to as compound (I-xv)) is more preferable.

Alternatively, of compounds (I-i)-(I-iv), (I-viii)-(I-xi) and (I-xiv)-(I-xv), a compound wherein
the partial structural formula represented by the formula (I):

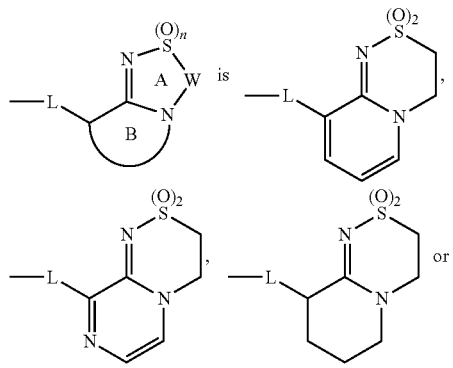

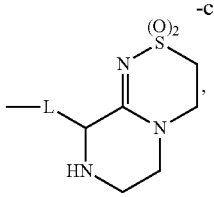

ring B is optionally substituted by substituent(s) (preferably 1-2) selected from a halogen atom, hydroxy, $C_{1-6}$ alkyl and $C_{1-6}$ alkoxy,
ring D is $C_{3-7}$ cycloalkane, benzene, naphthalene, pyridine or thiophene, each of which is optionally substituted by 1 to 3 substituents selected from
(1) a halogen atom;
(2) hydroxy;
(3) $C_{1-6}$ alkyl optionally substituted by substituent(s) (preferably 1-3) selected from 1) a halogen atom, and 2) phenyl optionally substituted by substituent(s) (preferably 1-3) selected from a halogen atom and $C_{1-6}$ alkyl;
(4) $C_{3-7}$ cycloalkyl;
(5) phenyl-carbonyl;
(6) $C_{2-6}$ alkenyl substituted by phenyl (preferably 1-2);
(7) phenyl optionally substituted by halogen atom(s) (preferably 1-3) or $C_{1-6}$ alkyl (preferably 1-3);
(8) pyrrolidine;
(9) dihydrobenzofuran;
(10) $C_{1-6}$ alkylsulfonyloxy substituted by halogen atom(s) (preferably 1-3);
(11) $C_{1-6}$ alkoxy optionally substituted by substituent(s) (preferably 1-3) selected from a halogen atom, $C_{3-7}$ cycloalkyl, phenyl substituted by halogen atom(s) (preferably 1-3), tetrahydrofuran and tetrahydropyran;
(12) $C_{3-7}$ cycloalkyloxy optionally substituted by $C_{1-6}$ alkyl (preferably 1-3);
(13) $C_{3-7}$ cycloalkenyloxy optionally substituted by $C_{1-6}$ alkyl (preferably 1-3);
(14) phenyloxy optionally substituted by 1 to 3 substituents selected from a halogen atom, cyano, hydroxy, $C_{1-6}$ alkyl optionally substituted by halogen atom(s) (preferably 1-3), and $C_{1-6}$ alkoxy;
(15) pyridyloxy substituted by halogen atom(s) (preferably 1-3), or $C_{1-6}$ alkyl (preferably 1-3) substituted by halogen atom(s) (preferably 1-3);
(16) tetrahydrofuranyloxy;
(17) tetrahydropyranyloxy; and
(18) dihydrobenzofuranyloxy, and
L is a bond, —O—, —O—CH$_2$—, —CO—NH—, $C_{1-6}$ alkylene, or $C_{2-6}$ alkynylene
(hereinafter sometimes to be referred to as compound (I-xvi)) is more preferable.

Alternatively, of compounds (I-i)-(I-xvi), a compound wherein
the partial structural formula represented by the formula (I):

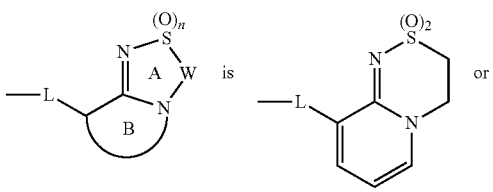

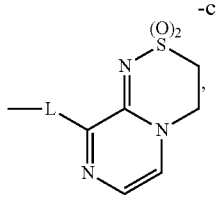

ring B is optionally substituted by one $C_{1-6}$ alkyl,
ring D is benzene optionally mono-substituted by
(1) $C_{3-7}$ cycloalkyloxy, or
(2) phenyloxy optionally mono-substituted by $C_{1-6}$ alkyl, and
L is a bond
(hereinafter sometimes to be referred to as compound (I-xvii)) is more preferable.

Alternatively, of compounds (I-i)-(I-xvi), a compound wherein
the partial structural formula represented by the formula (I):

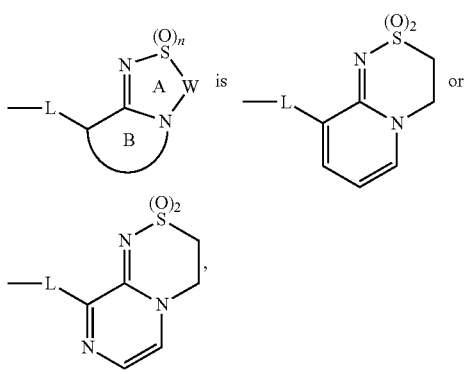

ring B is optionally substituted by $C_{1-6}$ alkyl (preferably 1-2),
ring D is benzene optionally substituted by 1 to 3 substituents selected from
(1) a halogen atom;
(2) hydroxy;
(3) $C_{1-6}$ alkyl optionally substituted by substituent(s) (preferably 1-3) selected from 1) a halogen atom, and 2) phenyl optionally substituted by substituent(s) (preferably 1-3) selected from halogen atom(s) (preferably 1-3) and $C_{1-6}$ alkyl (preferably 1-3);
(4) $C_{3-7}$ cycloalkyl optionally substituted by $C_{1-6}$ alkoxycarbonyl (preferably 1-2) or phenyl (preferably 1-2);
(5) phenyl-carbonyl;
(6) $C_{2-6}$ alkenyl substituted by phenyl (preferably 1-2);
(7) phenyl optionally substituted by halogen atom(s) (preferably 1-3) or $C_{1-6}$ alkyl (preferably 1-3);
(8) pyrrolidine;
(9) dihydrobenzofuran;
(10) $C_{1-6}$ alkylsulfonyloxy substituted by halogen atom(s) (preferably 1-3);
(11) $C_{1-6}$ alkoxy optionally substituted by substituent(s) (preferably 1-3) selected from a halogen atom, $C_{3-7}$ cycloalkyl, phenyl substituted by halogen atom(s) (preferably 1-3), tetrahydrofuran and tetrahydropyran;
(12) $C_{3-7}$ cycloalkyloxy optionally substituted by $C_{1-6}$ alkyl (preferably 1-3);
(13) $C_{3-7}$ cycloalkenyloxy optionally substituted by $C_{1-6}$ alkyl (preferably 1-3);
(14) phenyloxy optionally substituted by 1 to 3 substituents selected from a halogen atom, cyano, hydroxy, $C_{1-6}$ alkyl optionally substituted by halogen atom(s) (preferably 1-3), and $C_{1-6}$ alkoxy;
(15) pyridyloxy substituted (preferably 1-3) by a halogen atom, or $C_{1-6}$ alkyl substituted by halogen atom(s) (preferably 1-3);
(16) tetrahydrofuranyloxy;
(17) tetrahydropyranyloxy; and
(18) dihydrobenzofuranyloxy, and
L is a bond
(hereinafter sometimes to be referred to as compound (I-xviii)) is more preferable.

Alternatively, of compounds (I-i)-(I-iii), (I-viii)-(I-x) and (I-xiv)-(I-xv), a compound wherein
the partial structural formula represented by the formula (I):

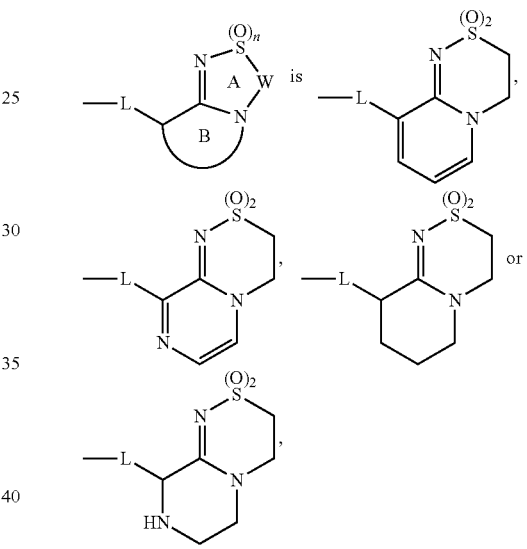

ring B is optionally substituted by substituent(s) selected from
a halogen atom (e.g., a fluorine atom, chlorine atom);
$C_{1-6}$ alkyl (e.g., methyl) optionally substituted by a halogen atom (e.g., a fluorine atom); and
$C_{1-6}$ alkoxy (e.g., methoxy),
ring D is $C_{3-7}$ cycloalkane (e.g., cyclohexane), $C_{6-14}$ arene (e.g., benzene, naphthalene), tetrahydronaphthalene, dihydroindene, thiophene, pyridine, indole or benzothiazole, each of which is optionally substituted by 1 to 3 substituents selected from
(1) a halogen atom (e.g., a fluorine atom, chlorine atom);
(2) hydroxy;
(3) oxo;
(4) $C_{1-6}$ alkyl (e.g., methyl, ethyl, isopropyl, butyl, isobutyl) optionally substituted by substituent(s) selected from 1) a halogen atom (e.g., a fluorine atom), and 2) phenyl optionally substituted by substituent(s) selected from a halogen atom (e.g., a fluorine atom) and $C_{1-6}$ alkyl (e.g., methyl);
(5) $C_{3-7}$ cycloalkyl (e.g., cyclobutyl) optionally substituted by phenyl;
(6) $C_{1-6}$ alkyl-carbonyl (e.g., methylcarbonyl);
(7) phenyl-carbonyl optionally substituted by $C_{1-6}$ alkoxy (e.g., methoxy);

(8) phenyl optionally substituted by 1 to 3 substituents selected from a halogen atom (e.g., a fluorine atom, chlorine atom), $C_{1-6}$ alkyl (e.g., methyl), and $C_{1-6}$ alkoxy (e.g., methoxy);
(9) pyrazole optionally substituted by 1 to 3 substituents selected from $C_{1-6}$ alkyl (e.g., methyl) optionally substituted by a halogen atom (e.g., a fluorine atom), and $C_{3-7}$ cycloalkyl (e.g., cyclopropyl);
(10) pyrrolidine;
(11) morpholine;
(12) oxetane substituted by a halogen atom (e.g., a fluorine atom);
(13) sulfanyl substituted by $C_{1-6}$ alkyl (e.g., methyl);
(14) $C_{1-6}$ alkoxy (e.g., methoxy, ethoxy, propoxy, isopropoxy, butoxy, tert-butoxy, neopentoxy, 1-ethylpropoxy) optionally substituted by substituent(s) selected from a halogen atom (e.g., a fluorine atom), phenyl substituted by a halogen atom (e.g., a fluorine atom), tetrahydrofuran and tetrahydropyran;
(15) $C_{3-7}$ cycloalkyloxy (e.g., cyclopropyloxy, cyclobutyloxy, cyclohexyloxy, cycloheptyloxy) optionally substituted by oxo;
(16) phenyloxy optionally substituted by 1 to 3 substituents selected from a halogen atom (e.g., a fluorine atom, chlorine atom, bromine atom), cyano, hydroxy, $C_{1-6}$ alkyl (e.g., methyl, ethyl) optionally substituted by a halogen atom (e.g., a fluorine atom), and $C_{1-6}$ alkoxy (e.g., methoxy);
(17) pyridyloxy substituted by $C_{1-6}$ alkyl (e.g., methyl) optionally substituted by a halogen atom (e.g., a fluorine atom); and
(18) dihydrobenzofuranyloxy, L is a bond, —O—, —O—CH$_2$—, —CH$_2$—O—, —CO—NH—, $C_{1-6}$ alkylene (e.g., ethylene), $C_{2-6}$ alkenylene (e.g., ethenylene) or $C_{2-6}$ alkynylene (e.g., ethynylene)
(hereinafter sometimes to be referred to as compound (I-xix)) is more preferable.

Moreover, in another embodiment of the present invention, of compounds (I), a compound wherein
ring D is benzene optionally mono-substituted by
(1) $C_{3-7}$ cycloalkyloxy, or
(2) phenyloxy optionally substituted by one $C_{1-6}$ alkyl (hereinafter sometimes to be referred to as compound (I-xix)) is preferable.

Specific examples of compound (I) include the Example compounds. Therefrom
9-(4-phenoxyphenyl)-3,4-dihydropyrido[2,1-c][1,2,4]thiadiazine 2,2-dioxide or a salt thereof;
9-[4-(4-methylphenoxy)phenyl]-3,4-dihydropyrido[2,1-c][1,2,4]thiadiazine 2,2-dioxide or a salt thereof;
9-[4-(cyclohexyloxy)phenyl]-3,4-dihydropyrido[2,1-c][1,2,4]thiadiazine 2,2-dioxide or a salt thereof; and
9-[4-(cyclohexyloxy)phenyl]-7-methyl-3,4-dihydropyrazino[2,1-c][1,2,4]thiadiazine 2,2-dioxide or a salt thereof
are preferable.

When compound (I') is a salt, examples of such salt include metal salt, ammonium salt, salt with organic base, salt with inorganic acid, salt with organic acid, salt with basic or acidic amino acid and the like. Preferable examples of the metal salt include alkali metal salts such as sodium salt, potassium salt and the like; alkaline earth metal salts such as calcium salt, magnesium salt, barium salt and the like; aluminum salt and the like. Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include salts with arginine, lysine, ornithine and the like, and preferable examples of the salt with acidic amino acid include salts with aspartic acid, glutamic acid and the like. Of these, pharmaceutically acceptable salts are preferable. When the compound has an acidic functional group, examples thereof include inorganic salts such as alkali metal salts (e.g., sodium salt, potassium salt, etc.), alkaline earth metal salts (e.g., calcium salt, magnesium salt, barium salt, etc.) and the like, ammonium salts, and the like. When the compound has a basic functional group, examples thereof include salts with inorganic acids such as hydrochloric acid, hydrobromic acid, nitric acid, sulfuric acid, phosphoric acid and the like, and salts with organic acids such as acetic acid, phthalic acid, fumaric acid, oxalic acid, tartaric acid, maleic acid, citric acid, succinic acid, methanesulfonic acid, p-toluenesulfonic acid and the like.

When compound (I') has isomers such as tautomer, optical isomer, stereoisomer, positional isomer, rotational isomer and the like, any isomers and mixture of isomers are encompassed in the compound of the present invention. Furthermore, when compound (I') has an optical isomer, an optical isomer separated from a racemate is also encompassed in compound (I').

Compound (I') may be a crystal, and a single crystal form and a mixture of crystal forms are encompassed in compound (I').

Compound (I') may be a pharmaceutically acceptable cocrystal or a cocrystal salt. Here, the cocrystal or cocrystal salt means a crystalline substance, which is constituted from two or more kinds of specific solids each having different physical properties (e.g., structure, melting point, heat of fusion, hygroscopicity, solubility, stability and the like) at room temperature. The cocrystal and cocrystal salt can be produced according to a cocrystallization method known per se.

Compound (I') may be a solvate (e.g., hydrate etc.) or a non-solvate, both of which are encompassed in the compound (I').

A compound labeled or substituted with an isotope (e.g., $^2H$, $^3H$, $^{11}C$, $^{14}C$, $^{18}F$, $^{35}S$, $^{125}I$ and the like) and the like is also encompassed in compound (I'). The compound labeled with or substituted by an isotope can be used as a tracer (PET tracer) to be used for, for example, Positron Emission Tomography (PET), and is useful in the field of medical diagnosis and the like.

[Production Method]

The production method of compound (I) of the present invention is explained in the following. Compound (I') encompassing compound (I) can also be produced according to the production method of compound (I) explained hereafter.

Compound (I) of the present invention is obtained according to, for example, the method shown in the following Reaction Scheme or a method analogous thereto and the like. Each symbol in the compounds in the reaction schemes is as defined above. Each compound shown in the reaction scheme may form a salt. Examples of the salt include salts similar to the salts of compound (I'). In addition, a reaction mixture of the compound obtained in each step can be used directly or as a crude product for the next reaction. The compound can also be isolated from the reaction mixture according to a conventional method, and can be easily purified by a method known per se, for example, separation means such as extraction, concentration, neutralization, filtration, distillation, recrystallization, distillation, chromatography and the like. Alternatively, as the compound in the scheme, a commercially available product can also be used directly.

Schematic showing of the reaction schemes is given below.

lithium and the like; an organic functional group such as a carboxy group, an ester group, an amino group, an aldehyde group, an amido group, a hydroxy group, a hydroxymethyl group, a sulfanyl(mercapto) group, a sulfanylmethyl(mercaptomethyl) group, an aminomethyl group, an isocyanato group, a carbamate group, an ethynyl group, a hydrazido group and the like; a halogen atom such as fluorine, chlorine, bromine, iodine and the like; hydrogen atom and the like, which is capable of forming a linker (L) by reacting with X or R'. Particularly, when ring D is a saturated ring, Y may be a carbonyl group formed together with the ring-constituting carbon atom, or a ring-constituting nitrogen atom itself. $R^1$ is an optionally substituted alkyl group, an alkylcarbonyl

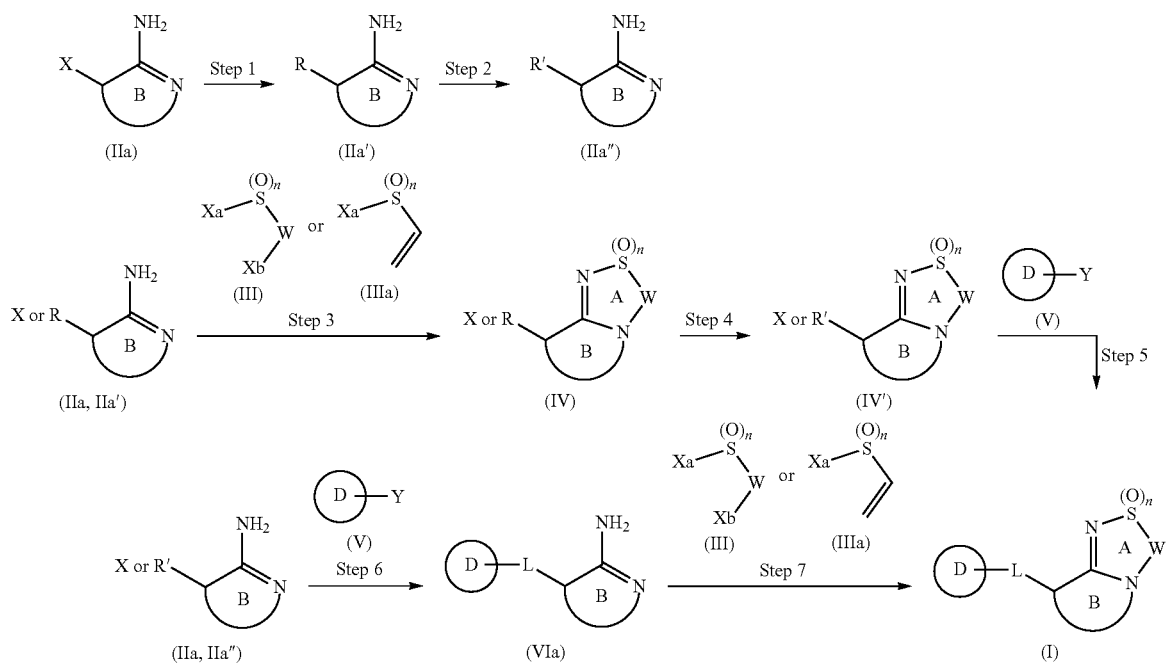

Reaction Scheme 1

In the formulas, X, Xa, Xb are leaving groups. Examples of the "leaving group" include halogen atoms; sulfonyloxy groups such as p-toluenesulfonyloxy group, methanesulfonyloxy group, trifluoromethanesulfonyloxy group and the like, and the like. X is preferably a halogen atom such as chlorine, bromine, iodine and the like. Xa and Xb are each preferably a halogen atom such as fluorine, chlorine and the like. Xc is a halogen atom such as fluorine, chlorine, bromine, iodine and the like. P is a protecting group. Examples of the "protecting group" include a t-butyldimethylsilyl group, a t-butoxy carbamate group, a 1,8-diaminonaphthyl group and the like. R is a functional group such as a cyano group, an ester group, a carboxy group, an amido group, an aldehyde group, an acyl group, an imino group, a protected amino group, an alkoxy group, a nitro group, an azido group, an isocyanato group and the like. R' is a functional group such as an ester group, a carboxy group, an amido group, an aldehyde group, an amino group, an amidine, a hydroxyamidine, an alkylimidate, a hydroxy group, a hydroxymethyl group and the like, which is obtained by converting R. Y is an organic metal functional group such as a boric acid, a borate, a vinylboric acid, a vinylborate, a propenylboric acid, a propenylborate, a magnesium halide, group or a protecting group, $R^2$ is a hydroxy group, an optionally substituted alkyl group, or deuterium, and $R^3$ is an optionally substituted alkyl group. Ring Ba is an unsaturated ring encompassed in the definition of ring B, and ring Bb is a saturated ring encompassed in the definition of ring B. In addition, ring A, ring B, ring D, L and W are as defined in the claims.

The production method of compound (I) is explained below according to the aforementioned Reaction Schemes.

[Step 1]

Compound (IIa') may be a commercially available product, or can also be produced according to a known method or a method analogous thereto. For example, in Step 1, compound (IIa') can be produced by subjecting compound (IIa) to a coupling reaction or nucleophilic substitution reaction with a nucleophilic reagent such as a metal cyanide and the like, or reacting compound (IIa) with an organic metal and the like, and then reacting the resulting compound with an electrophilic reagent such as carbon dioxide and the like.

The coupling reaction with a nucleophilic reagent such as metal cyanide and the like is carried out, for example, using a base and a palladium reagent or a copper reagent. A phosphine ligand may be used as necessary.

Examples of the base used for this reaction include alkali metal hydroxide such as sodium hydroxide, potassium hydroxide and the like; alkali metal hydrogencarbonate such as sodium hydrogen carbonate and the like; alkali metal carbonate such as sodium carbonate, potassium carbonate and the like; cesium salts such as cesium carbonate and the like; alkali metal phosphates such as tripotassium phosphate and the like; alkali metal hydrides such as sodium hydride, potassium hydride and the like; sodium amide; alkali metal alkoxides such as sodium methoxide, sodium ethoxide and the like; amines such as trimethylamine, triethylamine, N-ethyl-N-isopropylpropan-2-amine, diisopropylamine and the like; cyclic amines such as pyridine, 4-dimethylaminopyridine, DBU (1,8-diazabicyclo[5.4.0]undec-7-ene) and the like, and the like.

Examples of the palladium reagent include tetrakis(triphenylphosphine)palladium(0), bis(triphenylphosphine)palladium(II) dichloride, tris(dibenzylideneacetone)dipalladium (0), trans-dichlorobis(tri-o-tolylphosphine)palladium(II), palladium(II) trifluoroacetate, palladium(II) acetate and the like.

Examples of the copper catalyst include copper iodide, copper bromide, copper chloride, copper acetate and the like.

Examples of the phosphine ligand include triphenylphosphine, 2,2'-bis(diphenylphosphino)-1,1'-binaphthyl, 2-(di-tert-butylphosphino)biphenyl, 2-(dicyclohexylphosphino)biphenyl, 2-(dicyclohexylphosphino)-2',6'-dimethoxy-1,1'-biphenyl, 2-(dicyclohexylphosphino)-2',4',6'-triisopropyl-1,1'-biphenyl, 2-(dicyclohexylphosphino)-2'-(N,N-dimethylamino)biphenyl, 1,1'-bis(diphenylphosphino)ferrocene, tri-tert-butylphosphine, tricyclohexylphosphine, (9,9-dimethyl-9H-xanthene-4,5-diyl)bis(diphenylphosphine) and the like.

In this reaction, for example, cyclohexyl-1,2-diamine, N,N'-dimethylcyclohexyl-1,2-diamine or picoline acid and the like may be used as necessary.

This reaction can be carried out without solvent or in a known solvent, for example, water; alcohols such as methanol, ethanol and the like; ethers such as diethyl ether, 1,4-dioxane, 1,2-dimethoxyethane, tetrahydrofuran and the like; aromatic hydrocarbons such as benzene, toluene, xylene and the like; esters such as ethyl acetate and the like; halogenated hydrocarbons such as chloroform, dichloromethane and the like; nitriles such as acetonitrile and the like; amides such as N,N-dimethylformamide, N,N-dimethylacetamide, 1-methyl-2-pyrrolidinone and the like; ketones such as acetone, 2-butanone and the like; sulfoxides such as dimethylsulfoxide and the like, and the like. These solvents may be used alone or mixed at a suitable ratio.

This reaction may be carried out under an atmosphere of, for example, nitrogen, argon and the like as necessary.

In this reaction, per 1 mol of the starting compound, the amount of the nucleophilic reagent such as a metal cyanide and the like is generally about 0.5-about 10 mol, preferably about 1-about 5 mol, the amount of the base is generally about 0.1-about 100 equivalents, preferably about 1-about 5 equivalents, the amount of the palladium reagent or copper reagent is generally about 0.01-about 2 equivalents, preferably about 0.01-about 0.5 equivalents, the amount of the phosphine ligand is generally about 0.01-about 2 equivalents, preferably about 0.01-about 0.5 equivalents, and the amount of the cyclohexyl-1,2-diamine is generally about 0.01-about 2 equivalents, preferably about 0.01-about 1 equivalents. The reaction temperature is generally 0° C.-200° C., preferably 50° C.-150° C. The reaction time is about 0.1-about 100 hr, preferably about 0.5-about 50 hr.

A base may be used in the substitution reaction with a nucleophilic reagent such as metal cyanide and the like as necessary. Examples of the base used for the reaction include alkali metal hydroxide such as sodium hydroxide, potassium hydroxide and the like; alkali metal hydrogencarbonate such as sodium hydrogen carbonate and the like; alkali metal carbonate such as sodium carbonate, potassium carbonate and the like; cesium salts such as cesium carbonate and the like; alkali metal hydrides such as sodium hydride, potassium hydride and the like; sodium amide; alkali metal alkoxides such as sodium methoxide, sodium ethoxide and the like; amine such as trimethylamine, triethylamine, diisopropylamine and the like; cyclic amine such as pyridine, 4-dimethylaminopyridine, DBU and the like, and the like.

This reaction can be carried out without solvent or in a known solvent, for example, water; alcohols such as methanol, ethanol and the like; ethers such as diethyl ether, 1,4-dioxane, tetrahydrofuran and the like; aromatic hydrocarbons such as benzene, toluene, xylene and the like; esters such as ethyl acetate and the like; halogenated hydrocarbons such as chloroform, dichloromethane and the like; nitriles such as acetonitrile and the like; amides such as N,N-dimethylformamide, N,N-dimethylacetamide, 1-methyl-2-pyrrolidinone and the like; ketones such as acetone, 2-butanone and the like; sulfoxides such as dimethylsulfoxide and the like, and the like. These solvents may be used alone or mixed at a suitable ratio.

This reaction may be carried out under atmosphere such as nitrogen, argon and the like, as necessary.

In this reaction, per 1 mol of the starting compound, the amount of the nucleophilic reagent such as a metal cyanide and the like is generally about 1-about 10 mol, preferably about 1-about 5 mol, and the amount of the base is generally about 0.1-about 100 equivalents, preferably about 1-about 5 equivalents. The reaction temperature is generally 0° C.-200° C., preferably 50° C.-150° C. The reaction time is about 0.1-about 100 hr, preferably about 0.5-about 50 hr.

The organic metal and the like used in the step of the reaction with an electrophilic reagent such as carbon dioxide and the like after the reaction with the organic metal and the like include LDA (lithium diisopropylamide), butyllithium, methylmagnesium bromide and the like.

This reaction can be carried out in a suitable solvent such as an aprotonic solvent and the like (e.g., polar compound (e.g., DMF (N,N-dimethylformamide), DMSO (dimethyl sulfoxide), HMPA (hexamethylphosphoric triamide)), a nitrile compound (e.g., acetonitrile, propionitrile), an ether compound (THF (tetrahydrofuran), dioxane, diethyl ether, dibutyl ether, dimethoxyethane), a ketone compound (acetone, methyl ethyl ketone, methyl isobutyl ketone), an aromatic hydrocarbon (e.g., benzene, toluene, xylene and the like), a halogenated aromatic hydrocarbon (e.g., monochlorobenzene, dichlorobenzene and the like), an aliphatic hydrocarbon (hexane, heptane, octane), and a mixed solvent thereof, and the like).

The reaction temperature is generally about −78 to about 60° C., preferably about −20 to about 20° C. A temperature not less than or not more than these temperatures can be employed as necessary. The reaction time is generally about 10 min-about 24 hr, preferably about 30 min-12 hr. A reaction time not less than or not more than the above can be employed as necessary.

[Step 2]

Compound (IIa'') may be a commercially available product, or can also be produced according to a known method or a method analogous thereto. For example, in step 2, compound (IIa") can be produced by converting the functional group R of compound (IIa') into a functional group R' using hydrolysis, oxidation, reduction, nucleophilic addition, deprotection and the like.

The representative examples of some of the functional group R are more specifically explained in the following.

(1) Hydrolysis of Cyano Group, Amido Group or Ester Group

For example, an amido group or an ester group can be converted to a carboxyl group by hydrolysis. A cyano group can be converted to an ester group, an amido group and the like by hydrolysis, and converted to a carboxyl group by employing strong conditions such as heating, prolonged reaction time and the like.

For these reactions, hydrolysis method under basic conditions or acidic conditions is generally employed.

The hydrolysis under basic conditions is carried out, for example, by treatment with an alkali such as lithium hydroxide, sodium hydroxide, potassium hydroxide and the like. The hydrolysis is preferably carried out by dissolving compound (IIa') in an alcohol such as methanol, ethanol and the like; a water-soluble solvent such as tetrahydrofuran, dioxane and the like; or a mixed solvent thereof, and treating the solution with an aqueous alkali solution such as an aqueous sodium hydroxide solution, an aqueous lithium hydroxide solution and the like.

In this reaction, the amount of the aqueous alkali solution is generally about 1-about 10 equivalents, per 1 mol of the starting compound. The reaction temperature is generally 0° C.-100° C., preferably 20° C.-100° C. The reaction time is about 0.1-about 100 hr, preferably about 0.5-about 50 hr.

The hydrolysis under acidic conditions is carried out, for example, by treatment with an acid such as hydrochloric acid, sulfuric acid, nitric acid and the like. The hydrolysis is preferably carried out by dissolving compound (IIa') in an alcohol such as methanol, ethanol and the like; a water-soluble solvent such as tetrahydrofuran, dioxane and the like; or a mixed solvent thereof, and treating the solution with an aqueous acid solution such as hydrochloric acid, sulfuric acid, nitric acid and the like.

In this reaction, the amount of the aqueous acid solution is generally about 1-about 10 equivalents, per 1 mol of the starting compound. The reaction temperature is generally 0° C.-100° C., preferably 20° C.-100° C. The reaction time is about 0.1-about 100 hr, preferably about 0.5-about 50 hr.

(2) Reduction of Cyano Group, Ester Group or Amido Group

Alternatively, for example, a cyano group or an ester group can be converted to an aldehyde group by reduction, an ester group can be converted to a hydroxymethyl group by reduction, and a cyano group or an amido group can be converted to an aminomethyl group by reduction.

Examples of the reducing agent include metal hydrides such as sodium borohydride, lithium aluminum hydride, diisopropyl aluminum hydride and the like; boranes such as borane-tetrahydrofuran complex and the like, and the like. The amount of the reducing agent to be used is about 0.5-about mol, preferably about 1-about 5 mol, per 1 mol of the compound. In addition, an acid catalyst can be added together with the reducing agent when desired. Examples of the acid catalyst include proton acids (e.g., acetic acid, trifluoroacetic acid and the like), Lewis acids (e.g., aluminum chloride and the like) and the like.

This reaction can be advantageously carried out without solvent or in a solvent inert to the reaction. Such solvent is not particularly limited as long as the reaction proceeds, and examples thereof include water; alcohols such as methanol, ethanol, propanol and the like; hydrocarbons such as cyclohexane, hexane, benzene, toluene, xylene, mesitylene and the like; organic acids such as formic acid, acetic acid and the like; ethers such as tetrahydrofuran, dioxane, 1,2-dimethoxyethane, diethyl ether, diisopropyl ether and the like; anilines such as N,N-dimethylaniline, N,N-diethylaniline and the like; halogenated hydrocarbons such as dichloromethane, chloroform, carbon tetrachloride, 1,2-dichloroethane and the like; a mixed solvent thereof and the like.

The reaction temperature is generally about 0 to about 120° C., preferably about 25 to about 60° C. A temperature not less than or not more than these temperatures can be employed as necessary. The reaction time is generally about 10 min-about 24 hr, preferably about 30 min-12 hr. A reaction time not less than or not more than the above can be employed as necessary.

(3) Reduction of Azido Group or Nitro Group

Alternatively, an azido group or a nitro group can be converted to an amino group by reduction. This reaction can be specifically carried out, for example, by reduction with a metal reducing reagent such as lithium borohydride, lithium aluminum hydride and the like as a reducing agent, or catalytic reduction with a transition metal (palladium-carbon, platinum oxide, Raney-nickel, rhodium, ruthenium etc.). Examples of the organic solvent used for the reduction reaction include methanol, ethanol, tertiary butyl alcohol, tetrahydrofuran, diethyl ether, dioxane, acetone, ethyl acetate, acetic acid, benzene, toluene, xylene, dimethylformamide, dimethylsulfoxide and the like.

The reaction temperature for the reduction reaction is generally −20 to 80° C., preferably about 0 to about 40° C. A temperature not less than or not more than these temperatures can be employed as necessary. The reaction time for the reduction reaction is generally 5 min-24 hr, preferably about 30 min-12 hr. A reaction time not less than or not more than the above can be employed as necessary.

(4) Deprotection of Protected Amino Group

Alternatively, a protected amino group can be converted to an amino group by deprotection.

Examples of the deprotection of the protecting group such as an acetyl group, a benzoyl group and the like include deprotection under acidic conditions, deprotection by basic hydrolysis, and the like.

The deprotection under acidic conditions is carried out, for example, without solvent or in an organic solvent (e.g., methylene chloride, chloroform, toluene, fluorobenzene, trifluorobenzene, dioxane, ethyl acetate, anisole, methanol, ethanol, isopropyl alcohol etc.), water or mixed solvent thereof, in the presence of an organic acid (acetic acid, trifluoroacetic acid, methanesulfonic acid etc.), an inorganic acid (hydrochloric acid, sulfuric acid etc.) or a mixture thereof (hydrogen bromide/acetic acid etc.), at 0 to 100° C. A temperature not less than or not more than these temperatures can be employed as necessary.

The deprotection by basic hydrolysis is carried out, for example, in an organic solvent (e.g., an ether (tetrahydrofuran, dioxane, dimethoxyethane, diethyl ether etc.), an alcohol (methanol, ethanol etc.), a benzene (benzene, toluene etc.), a ketone (acetone, methyl ethyl ketone etc.), a nitrile (acetonitrile etc.), an amide (dimethylformamide etc.)), water, or a mixture of two or more kinds thereof, in the presence of an inorganic acid (sodium hydroxide, potassium hydroxide etc.), at 0 to 200° C. A temperature not less than or not more than these temperatures can be employed as necessary.

Examples of the deprotection of a protecting group such as a benzoyl group, a benzyloxycarbonyl group, a t-butoxycarbonyl group and the like include deprotection under acidic conditions, deprotection by hydrogenolysis, and the like.

The deprotection under acidic conditions is carried out, for example, in an organic solvent (methylene chloride, chloroform, toluene, fluorobenzene, trifluorobenzene, dioxane, ethyl acetate, anisole, methanol, ethanol, isopropyl alcohol etc.) or in the absence of an organic solvent, or a aqueous solution thereof, in the presence of an organic acid (acetic acid, trifluoroacetic acid, methanesulfonic acid etc.), an inorganic acid (hydrochloric acid, sulfuric acid etc.) or a mixture thereof (hydrogen bromide/acetic acid etc.), at 0 to 100° C. A temperature not less than or not more than these temperatures can be employed as necessary.

The deprotection by hydrogenolysis is carried out, for example, in a solvent (an ether (tetrahydrofuran, dioxane, dimethoxyethane, diethyl ether etc.), an alcohol (methanol, ethanol etc.), a benzene (benzene, toluene etc.), a ketone (acetone, methyl ethyl ketone etc.), a nitrile (acetonitrile etc.), an amide (dimethylformamide etc.), water, ethyl acetate, acetic acid or a mixture of two or more kinds thereof), in the presence of a catalyst (palladium-carbon, palladium black, palladium hydroxide, platinum oxide, Raney-nickel etc.), under a hydrogen atmosphere, under normal pressure or pressurization, or in the presence of ammonium formate, at 0 to 100° C. A temperature not less than or not more than these temperatures can be employed as necessary.

Examples of the deprotection of a protecting group such as a benzyl group and the like include deprotection by reaction with 1-chloroethyl chlorocarbonate, and reacting the resulting quaternary salt with a solvent such as methanol and the like, or deprotection by hydrogenolysis, and the like.

The reaction with 1-chloroethyl chlorocarbonate is advantageously carried out without solvent or in a solvent inert to the reaction. Such solvent is not particularly limited as long as the reaction proceeds. For example, the reaction is carried out in an organic solvent (methylene chloride, 1,2-dichloroethane, chloroform, toluene, fluorobenzene, trifluorobenzene, dioxane, ethyl acetate etc.), at 0 to 100° C. A temperature not less than or not more than these temperatures can be employed as necessary. And then, the reaction mixture is concentrated to give a quaternary salt, and then the quaternary salt is dissolved in an alcohol such as methanol, ethanol and the like; or in a mixed solvent of the alcohol and a solvent inert to the reaction such as tetrahydrofuran, dioxane and the like.

In this reaction, the reaction temperature is generally 0° C.-100° C., preferably 20° C.-80° C. The reaction time is about 0.1-about 100 hr, preferably about 0.5-about 10 hr.

The deprotection by hydrogenolysis is carried out, for example, in a solvent (a ether (tetrahydrofuran, dioxane, dimethoxyethane, diethyl ether etc.), an alcohol (methanol, ethanol etc.), a benzene (benzene, toluene etc.), a ketone (acetone, methyl ethyl ketone etc.), a nitrile (acetonitrile etc.), an amide (dimethylformamide etc.), water, ethyl acetate, acetic acid or a mixture of two or more kinds thereof), in the presence of a catalyst (palladium-carbon, palladium black, palladium hydroxide, platinum oxide, Raney-nickel etc.), under a hydrogen atmosphere, under normal pressure or pressurization, or in the presence of ammonium formate, at 0 to 100° C. A temperature not less than or not more than these temperatures can be employed as necessary.

The series of reaction time for the deprotection is generally about 10 min-about 72 hr, preferably about 30 min-24 hr. A reaction time not less than or not more than the above can be employed as necessary.

The amino-protecting group is not particularly limited as long as it can be easily and selectively removed, and a group other than the above-mentioned protecting groups may also be employed. For example, those described in T. W. Greene, Protective groups in Organic Synthesis 3rd edition, Wiley, New York, 1999 can be used. These protecting groups can be removed corroding to a known method or a method analogous thereto, for example, by treatment with an acid, a base, ultraviolet rays, hydrazine, phenylhydrazine, sodium N-methyldithiocarbamate, tetrabutylammonium fluoride, palladium acetate and the like, reduction reaction, or hydrolysis. The reduction reaction can be carried out according to a known method or a method analogous thereto, for example, by reduction with a metal reducing reagent such as lithium borohydride, lithium aluminum hydride and the like as a reducing agent, or catalytic reduction with a transition metal (palladium-carbon, platinum oxide, Raney-nickel, rhodium, ruthenium etc.). Examples of the organic solvent used for the reduction reaction include methanol, ethanol, tertiary butyl alcohol, tetrahydrofuran, diethyl ether, dioxane, acetone, ethyl acetate, acetic acid, benzene, toluene, xylene, dimethylformamide, dimethylsulfoxide and the like.

The reaction temperature for the reduction reaction is generally −20 to 150° C., preferably about 20 to about 80° C. A temperature not less than or not more than these temperatures can be employed as necessary. The reaction time for the reduction reaction is generally 5 min-24 hr, preferably about 30 min-12 hr. A reaction time not less than or not more than the above can be employed as necessary.

The hydrolysis can be carried out according to a known method or a method analogous thereto, for example, by treatment with an acid, a base, an enzyme and the like.

[Step 3]

In step 3, compound (IV) is obtained by reacting compound (IIa) or (IIa') with compound (III) or compound (IIIa) according to a known method and the like. In the aforementioned Reaction Scheme, the formulas (IIa, IIa') mean both compound (IIa) and compound (IIa'). When the starting material is compound (IIa), compound (IV) has a leaving group X as a substituent of ring B. On the other hand, when the starting material is compound (IIa'), compound (IV) has functional group R as a substituent of ring B. This reaction is carried out in an organic solvent which does not adversely influence the reaction. As such organic solvent, chloroform, methylene chloride, tetrahydrofuran, 1,4-dioxane, N,N-dimethylformamide, N,N-dimethylacetamide, acetone, ethyl acetate, or a mixed solvent thereof and the like can be used, preferably tetrahydrofuran, N,N-dimethylacetamide and the like.

In addition, this reaction is not particularly limited, and can be carried out in the presence of a suitable base (e.g., cesium carbonate, potassium carbonate, sodium carbonate, potassium t-butoxide, sodium hydride, triethylamine, DBU, DBN (1,5-diazabicyclo[4.3.0]non-5-ene) and the like). When a base is used, preferred are potassium carbonate, potassium tert-butoxide, sodium hydride and the like.

The reaction temperature is generally about −30 to about 150° C., preferably about −10 to about 100° C. A temperature not less than or not more than these temperatures can be employed as necessary. The reaction time is generally about 10 min-about 48 hr, preferably about 30 min-24 hr. A reaction time not less than or not more than the above can be employed as necessary.

[Step 4]

Compound (IV') can be produced, in step 4, in the same manner as in step 2, by performing hydrolysis, oxidation, reduction, nucleophilic addition, deprotection and the like with functional group R of compound (IV) to convert same to functional group R'.

That is, the aforementioned Reaction Scheme describes, for convenience, compound (IV) having leaving group X as a substituent of ring B. In practice, compound (IV) having leaving group X as a substituent of ring B is not subjected to step 4.

[Step 5]

In step 5, compound (I) is obtained by reacting compound (IV') with compound (V) by coupling reaction, addition reaction, substitution reaction, condensation reaction and the like according to a known method and the like.

The coupling reaction is carried out using, for example, base, palladium reagent or copper reagent. Where necessary, a ligand may be used.

Examples of the base used for this reaction include alkali metal hydroxide such as sodium hydroxide, potassium hydroxide and the like; alkali metal hydrogencarbonate such as sodium hydrogen carbonate and the like; alkali metal carbonate such as sodium carbonate, potassium carbonate and the like; cesium salts such as cesium carbonate and the like; alkali metal phosphates such as tripotassium phosphate and the like; alkali metal hydrides such as sodium hydride, potassium hydride and the like; sodium amide; alkali metal alkoxides such as sodium methoxide, sodium ethoxide and the like; amine such as trimethylamine, triethylamine, N-ethyl-N-isopropylpropan-2-amine, diisopropylamine and the like; cyclic amine such as pyridine, 4-dimethylaminopyridine, 1,8-diazabicyclo[5.4.0]undec-7-ene (DBU) and the like, and the like.

Examples of the palladium reagent include palladium-carbon, tetrakis(triphenylphosphine)palladium(0), bis(triphenylphosphine)palladium(II) dichloride, tris(dibenzylideneacetone)dipalladium(0), trans-dichlorobis(tri-o-tolylphosphine)palladium(II), palladium(II) trifluoroacetate, palladium(II) acetate and the like.

Examples of the copper catalyst include copper iodide, copper bromide, copper chloride, copper acetate and the like.

Examples of the ligand include, in addition to phosphine ligand such as triphenylphosphine, 2,2'-bis(diphenylphosphino)-1,1'-binaphthyl, 2-(di-tert-butylphosphino)biphenyl, 2-(dicyclohexylphosphino)biphenyl, 2-(dicyclohexylphosphino)-2',6'-dimethoxy-1,1'-biphenyl, 2-(dicyclohexylphosphino)-2',4',6'-triisopropyl-1,1'-biphenyl, 2-(dicyclohexylphosphino)-2'-(N,N-dimethylamino)biphenyl, 1,1'-bis(diphenylphosphino)ferrocene, tri-tert-butylphosphine, tricyclohexylphosphine, (9,9-dimethyl-9H-xanthene-4,5-diyl)bis(diphenylphosphine) and the like, 2-(dimethylamino)acetic acid, cyclohexyl-1,2-diamine, N,N'-dimethylcyclohexyl-1,2-diamine, or picoline acid and the like.

This reaction can be carried out without solvent or in a known solvent, for example, solvents such as water; alcohols (methanol, ethanol and the like); ethers (diethyl ether, 1,4-dioxane, 1,2-dimethoxyethane, tetrahydrofuran and the like); aromatic hydrocarbons (benzene, toluene, xylene and the like); esters (ethyl acetate and the like); halogenated hydrocarbons (chloroform, dichloromethane and the like); nitriles (acetonitrile and the like); amides (N,N-dimethylformamide, N,N-dimethylacetamide, 1-methyl-2-pyrrolidinone and the like); ketones (acetone, 2-butanone and the like); sulfoxides (dimethylsulfoxide and the like), and the like. These solvents may be used alone or in a mixture at suitable ratio.

In this reaction, molecular sieves may be added as necessary.

This reaction may be performed under microwave irradiation as necessary.

This reaction may be carried out under an atmosphere of, for example, nitrogen, argon and the like, as necessary.

In this reaction, per 1 mol of the starting compound, a nucleophilic reagent is generally used in about 0.5-about 10 mol, preferably about 1-about 5 mol, the amount of the base is generally about 0.1-about 100 equivalents, preferably about 1-about 5 equivalents, the amount of the palladium reagent or copper reagent is about 0.01-about 2 equivalents, preferably about 0.01-about 0.5 equivalents, the amount of the phosphine ligand is generally about 0.01-about 2 equivalents, preferably about 0.01-about 0.5 equivalents, and the amount of the cyclohexyl-1,2-diamine is generally about 0.01-about 2 equivalents, preferably about 0.01-about 1 equivalents. The reaction temperature is generally 0° C.-200° C., preferably 50° C.-150° C. The reaction time is about 0.1-about 100 hr, preferably about 0.5-about 50 hr.

The addition reaction and substitution reaction can be carried out using a nucleophilic reagent such as organic metal (e.g., LDA, butyllithium, methylmagnesium bromide) and the like. These reactions can be carried out in a suitable solvent such as aprotonic solvent and the like (e.g., polar compound (e.g., DMF, DMSO, HMPA), nitrile compound (e.g., acetonitrile, propionitrile), ether compound (THF, dioxane, diethyl ether, dibutyl ether, dimethoxyethane), a ketone compound (acetone, methyl ethyl ketone, methyl isobutyl ketone), an aromatic hydrocarbon (e.g., benzene, toluene, xylene and the like), a halogenated aromatic hydrocarbon (e.g., monochlorobenzene, dichlorobenzene and the like), an aliphatic hydrocarbon (hexane, heptane, octane), and a mixed solvent thereof, and the like).

These reactions may be carried out under an atmosphere such as nitrogen, argon and the like as necessary.

In these reactions, per 1 mol of the starting compound, the amount of the nucleophilic reagent is generally about 1-about 10 mol, preferably about 1-about 5 mol, and the amount of the base is about 0.1-about 100 equivalents, preferably about 1-about 5 equivalents.

The reaction temperature is generally about −78 to about 60° C., preferably about −20 to about 20° C. A temperature not less than or not more than these temperatures can be employed as necessary. The reaction time is generally about 10 min-about 24 hr, preferably about 30 min-12 hr. A reaction time not less than or not more than the above can be employed as necessary.

In addition, when each of compound (V) and compound (IV') has primary or secondary alcohol and a hydroxy group, Mitsunobu reaction can be used.

This reaction can be carried out under conditions generally known. For example, this reaction can be carried out in a suitable solvent such as THF and the like, by adding azodicarboxylic acid derivative such as diisopropylazodicarboxylate, diethylazodicarboxylate and the like, and organic phosphorus reagent such as triphenylphosphine and the like to the above-mentioned two kinds of substrates.

When compound (V) and compound (IV') have a carboxyl group and an amino group, respectively, compound (I), which is a condensation product, can be produced by condensation reaction.

The condensation reaction can be carried out using a dehydrating condensing agent.

Examples of the dehydrating condensing agent to be used in this reaction include N,N'-dicyclohexylcarbodiimide, 1-ethyl-3-(3-dimethylaminopropyl)carbodiimide (EDCI) or a hydrochloride thereof, N,N'-carbonyldiimidazole, 1H-benzotriazol-1-yloxytris(dimethylamino)phosphonium hexafluorophosphate, O-(7-azabenzotriazol-1-yl)-1,1,3,3-tetramethyluronium hexafluorophosphate (HATU), 2-chloro-1,3-dimethylimidazolium chloride, and bromotripyrrolidinophosphonium hexafluorophosphate and the like.

This reaction may be carried out, for example, in the presence of a base such as 1-hydroxybenzotriazole (HOBt), N,N-diisopropylethylamine, N-methylmorpholine, triethylamine, 4-(N,N-dimethylamino)pyridine and the like as necessary.

This reaction is preferably carried out in a known solvent, for example, solvents such as amides (N,N-dimethylformamide, N,N-dimethylacetamide, and N-methylpyrrolidone and the like); halogenated hydrocarbons (dichloromethane and the like); esters (ethyl acetate and the like); hydrocarbons (cyclohexane, n-hexane and the like); aromatic hydrocarbons (toluene and the like); ethers (tetrahydrofuran, diethyl ether, dioxane, and 1,2-dimethoxyethane and the like); or nitriles (acetonitrile and the like), and the like.

In this reaction, per 1 mol of the starting compound, the amount of compound (V) is generally about 1-about 5 mol, and the amount of the dehydrating condensing agent is about 1-about 100 equivalents, preferably 1-5 equivalents. The reaction temperature is generally 0° C.-100° C., preferably 0° C.-60° C. The reaction time is about 0.1-about 100 hr, preferably about 0.5-about 50 hr.

When compound (I) is an amide compound, compound (I) can also be produced by activating a carboxyl group of compound (V) or compound (IV') according to a known activation method, and by reacting the compound with compound (IV') or compound (V), each having an amino group.

As the activation method of a carboxyl group, a general method is adopted, for example, a method of producing an acid anhydride by using chloroformic acid ester, pivaloyl chloride, 2,4,6-trichlorobenzoyl chloride and the like; a method of producing an acid halide by using thionyl chloride, oxalyl chloride and the like; and a method of producing ester of 1-hydroxybenzotriazole, or pentafluorophenol and the like by using a dehydrating condensing agent, and the like.

A representative example is a method of producing an acid halide. For example, acid halide can be produced by treating carboxylic acid with a halogenating agent such as thionyl chloride, oxalyl chloride and the like and, as an additive, for example, N,N-dimethylformamide may be added.

The method of producing an acid halide is preferably carried out in a known solvent, for example, solvent such as halogenated hydrocarbons (dichloromethane and the like); ethers (tetrahydrofuran, diethyl ether and the like); or aromatic hydrocarbons (toluene and the like) and the like, or without solvent.

In this reaction, the amount of the halogenating agent is generally about 1-about 100 equivalents, preferably 1-5 equivalents, per 1 mol of the starting compound. The reaction temperature is generally −78° C. to 100° C., preferably 0° C. to 100° C. The reaction time is about 0.1-about 100 hr, preferably about 0.5-about 50 hr.

After activation of a carboxyl group of compound (V) as mentioned above, it is reacted with an amino group of compound (IV') to give compound (I), which is an amide compound. Alternatively, after activation of a carboxyl group of compound (IV'), it is reacted with an amino group of compound (V) to give compound (I), which is an amide compound. This reaction is preferably carried out in a known solvent, for example, solvent such as halogenated hydrocarbons (dichloromethane and the like); ethers (tetrahydrofuran, diethyl ether and the like); or amides (N,N-dimethylformamide, N,N-dimethylacetamide, N-methylpyrrolidone and the like) and the like.

The reaction temperature is generally −78° C. to 150° C., preferably 0° C. to 100° C. The reaction time is about 0.1-about 100 hr, preferably about 0.5-about 50 hr.

[Step 6]

In step 6, compound (VIa) is obtained by reacting compound (IIa) or (IIa") with compound (V) by coupling reaction, addition reaction, substitution reaction and condensation reaction and the like according to a known method and the like in the same manner as in step 5.

For example, specific examples include a coupling reaction using compound (IIa) and compound (V). This reaction is carried out using a base, and palladium reagent. Where necessary, a phosphine ligand may be used.

Examples of the palladium reagent include palladium-carbon, tetrakis(triphenylphosphine)palladium(0), bis(triphenylphosphine)palladium(II) dichloride, tris(dibenzylideneacetone)dipalladium(0), trans-dichlorobis(tri-o-tolylphosphine)palladium(II), palladium(II) trifluoroacetate, palladium(II) acetate and the like, preferably tetrakis(triphenylphosphine)palladium(0) and the like.

Examples of the base include alkali metal hydroxides such as sodium hydroxide, potassium hydroxide and the like; alkali metal hydrogencarbonates such as sodium hydrogen carbonate and the like; alkali metal carbonate such as sodium carbonate, potassium carbonate and the like; cesium salts such as cesium carbonate and the like; alkali metal phosphates such as tripotassium phosphate and the like; alkali metal hydrides such as sodium hydride, potassium hydride and the like; sodium amide; alkali metal alkoxides such as sodium methoxide, sodium ethoxide and the like; amines such as trimethylamine, triethylamine, N-ethyl-N-isopropylpropan-2-amine, diisopropylamine and the like; cyclic amines such as pyridine, 4-dimethylaminopyridine, 1,8-diazabicyclo[5.4.0]undec-7-ene (DBU) etc. and the like. Preferred are sodium carbonate, cesium carbonate, tripotassium phosphate and the like.

Examples of the phosphine ligand include triphenylphosphine, 2,2'-bis(diphenylphosphino)-1,1'-binaphthyl, 2-(di-tert-butylphosphino)biphenyl, 2-(dicyclohexylphosphino) biphenyl, 2-(dicyclohexylphosphino)-2',6'-dimethoxy-1,1'-biphenyl, 2-(dicyclohexylphosphino)-2',-4',6'-triisopropyl-1,1'-biphenyl, 2-(dicyclohexylphosphino)-2'-(N,N-dimethylamino)biphenyl, 1,1'-bis(diphenylphosphino) ferrocene, tri-tert-butylphosphine, tricyclohexylphosphine, (9,9-dimethyl-9H-xanthene-4,5-diyl)bis(diphenylphosphine) and the like.

This reaction is carried out in a known solvent, for example, solvents such as water; alcohols (methanol, ethanol and the like); ethers (diethyl ether, 1,4-dioxane, 1,2-dimethoxyethane, tetrahydrofuran and the like); aromatic hydrocarbons (benzene, toluene, xylene and the like); esters (ethyl acetate and the like); halogenated hydrocarbons (chloroform, dichloromethane and the like); nitriles (acetonitrile and the like); amides (N,N-dimethylformamide, N,N-dimethylacetamide, 1-methyl-2-pyrrolidinone and the like); ketones (acetone, 2-butanone and the like); sulfoxides (dimethyl sulfoxide and the like), and the like. These solvents may be mixed at suitable ratio or may not be used. Preferred are 1,2-dimethoxyethane-water mixed solvent and the like.

This reaction may be carried out under an atmosphere of, for example, nitrogen, argon and the like, as necessary.

In this reaction, per 1 mol of the starting compound, the palladium reagent is used in about 0.01-about 2 equivalents, preferably about 0.01-about 0.5 equivalents, the base is used in about 0.1-about 100 equivalents, preferably about 1-about 5 equivalents, and the phosphine ligand is used in about 0.01-about 2 equivalents, preferably about 0.01-about 0.5 equivalents. The reaction temperature is generally 0° C. to 200° C., preferably 50° C. to 150° C. The reaction time is about 0.1-about 100 hr, preferably about 0.5-about 50 hr.

[Step 7]

In step 7, compound (I) is obtained by reacting compound (VIa) with compound (III) or compound (IIIa) in the same manner as in step 3.

In any step, when further desired, known protection reaction, deprotection, coupling reaction, acylation reaction, alkylation reaction, cycloalkylation reaction, dehydroxylation reaction, hydrogenation reaction, oxidation reaction, reduction reaction, fluorination reaction, carbon chain extension reaction or substituent exchanging reaction and the like can be used alone or in combination of two or more thereof.

Specific examples of the synthesis of compound (I) are explained in the following.

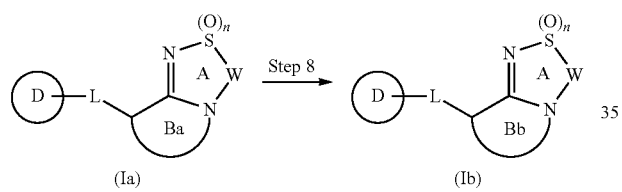

[Step 8]

In step 8, compound (Ib) is obtained from compound (Ia) by reducing unsaturated ring (Ba) in the center to form saturated ring (Bb).

Examples of the reduction reaction include a reaction using a metal reducing reagent such as lithium borohydride, lithium aluminum hydride and the like, and a catalytic reduction using a transition metal (palladium-carbon, platinum-carbon, platinum oxide, Raney-nickel, rhodium, ruthenium etc.) under a hydrogen atmosphere. Of these reactions, the catalytic reduction using a transition metal (palladium-carbon, platinum(IV) oxide, rhodium) is preferable. Examples of the organic solvent to be used for the catalytic reduction include methanol, ethanol, tertiary butyl alcohol, tetrahydrofuran, diethyl ether, dioxane, acetone, ethyl acetate, acetic acid, benzene, toluene, xylene, dimethylformamide, dimethyl sulfoxide and the like. Preferred are methanol, ethanol, tetrahydrofuran and the like.

The reaction temperature of the reduction reaction is generally −20 to 80° C., preferably about 0 to about 40° C. A temperature not less than or not more than these temperatures can be employed as necessary. The reaction time of the reduction reaction is generally 5 min-24 hr, preferably about 30 min-12 hr. A reaction time not less than or not more than the above can be employed as necessary. In addition, the reaction may be carried out under pressurization as necessary. The pressure to be applied is generally 1.1-50 atm, preferably 2-10 atm.

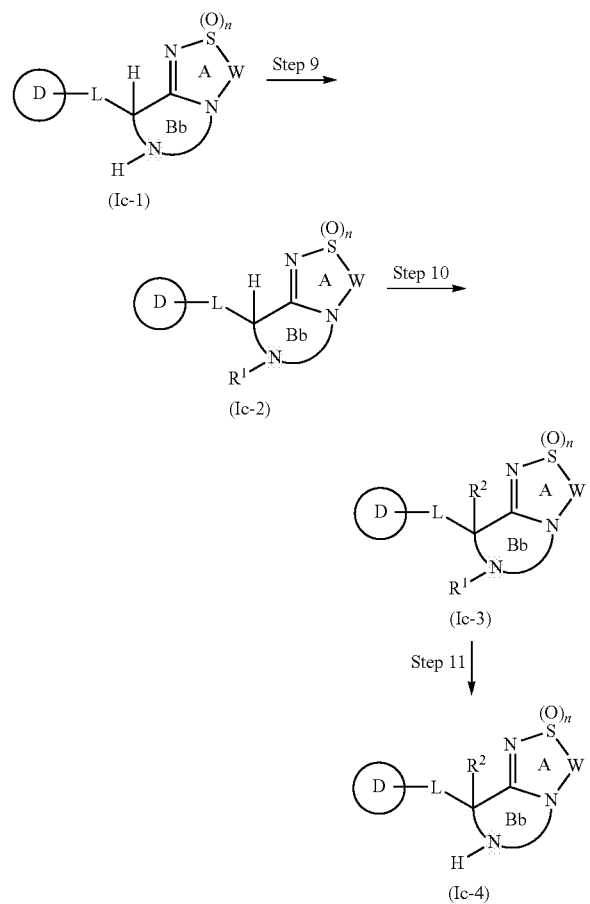

[Step 9]

Furthermore, when one of the saturated ring Bb-constituting atoms is a nitrogen atom, that is, the structure shown in the formula (Ic-1), compound (Ic-2), wherein the nitrogen atom is modified by alkylation of, acylation, protection reaction and the like of step 9, can be obtained.

The alkylation is carried out using a suitable alkylating agent in a suitable solvent. Examples of the alkylating agent include alkylhalide (iodomethane, iodoethane etc.) and the like.

Examples of the solvent include solvents such as water, methanol, ethanol, diethyl ether, tetrahydrofuran, toluene, ethyl acetate, acetonitrile, N,N-dimethylformamide, dimethyl sulfoxide and the like. These solvents may be mixed at a suitable ratio or may not be used.

In addition, this reaction is not particularly limited, and can also be carried out in the presence of a suitable base (e.g., cesium carbonate, potassium carbonate, sodium carbonate, potassium t-butoxide, sodium hydride, triethylamine, DBU, DBN (1,5-diazabicyclo[4.3.0]non-5-ene) and the like). When a base is used, preferred are potassium carbonate, sodium hydride and the like.

The reaction temperature is generally about −30 to about 150° C., preferably about −10 to about 100° C. The reaction time is generally about 10 min-about 48 hr, preferably about 30 min-24 hr.

The acylation can be carried out in the same manner as in the condensation reaction of [Step 5]. Commercially available acid chloride can also be used instead of activating carboxylic acid.

The protection reaction can be carried out according to a method generally known, for example, the method described in T. W. Greene, Protective Groups in Organic Synthesis 3rd edition, Wiley, New York, 1999 and the like.

[Step 10]

This step can be carried out in the same manner as in the alkylation of [Step 9]. In addition, deuteration ($R^2$=D) can also be carried out by reacting a deuterium source such as deuterium, deuterated methanol and the like in a suitable solvent in the presence of a base such as sodium hydride and the like.

[Step 11]

This step can be carried out in the same manner as in (4) deprotection of protected amino group in [Step 2].

In addition, when ring D has a protected hydroxy group, that is, the structure shown in the formula (I-5), compound (I-6), (I-7) and (I-8) can be obtained by the deprotection of step 12, alkylation of step 13, and arylation of step 14, respectively. When ring B is saturated ring Bb in step 14, compound (Ib-9) is sometimes obtained as a byproduct.

[Step 14]

Step 14 can be carried out using the conditions of the coupling reaction of step 5. For example, compound (I-6) and arylhalide, arylboronic acid or arylboroxin as Ar—Y are treated with a base and a copper reagent. Where necessary, a ligand may be used.

Examples of the base used for this reaction include alkali metal hydroxides such as sodium hydroxide, potassium hydroxide and the like; alkali metal hydrogencarbonates such as sodium hydrogen carbonate and the like; alkali metal carbonate such as sodium carbonate, potassium carbonate and the like; cesium salts such as cesium carbonate and the like; alkali metal phosphates such as tripotassium phosphate and the like; alkali metal hydrides such as sodium hydride, potassium hydride and the like; sodium amide; alkali metal alkoxides such as sodium methoxide, sodium ethoxide and the like; amines such as trimethylamine, triethylamine, N-ethyl-N-isopropylpropan-2-amine, diisopropylamine and the like; cyclic amines such as pyridine, 4-dimethylaminopyridine, 1,8-diazabicyclo[5.4.0]undec-7-ene (DBU) etc.,

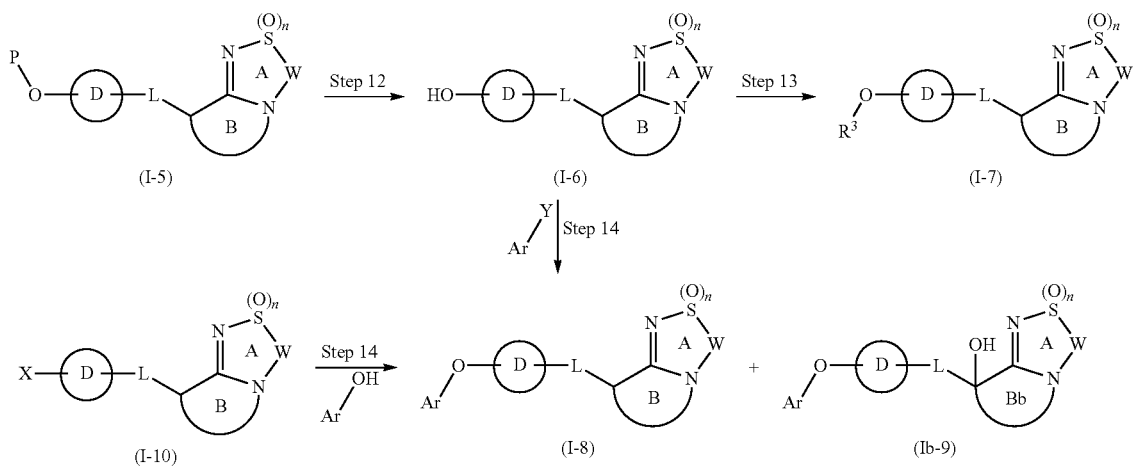

Reaction Scheme 4

[Step 12]

A deprotection can be carried out by an appropriate deprotection reaction of a known protecting group. For example, when protecting group P is a silicon protecting group such as a t-butyldimethylsilyl group and the like, the deprotection can be carried out using TBAF as deprotecting agent, and a reagent having a halogen ion such as hydrochloric acid and the like.

This reaction is carried out in a known solvent, for example, solvents such as halogenated hydrocarbons (dichloromethane and the like); ethers (tetrahydrofuran, diethyl ether and the like) and the like.

The reaction temperature is generally −78° C. to 150° C., preferably 0° C. to 100° C. The reaction time is about 0.1-about 100 hr, preferably about 0.5-about 50 hr.

In addition, the hydroxy-protecting group is not particularly limited as long as it can be removed easily and selectively. For example, those described in T. W. Greene, Protective Groups in Organic Synthesis 3rd edition, Wiley, New York, 1999 can be used.

[Step 13]

Step 13 can be carried out under the conditions of the alkylation reaction of step 9, Mitsunobu reaction of step 5 and the like.

and the like. These bases may be used alone or in a combination of two or more thereof.

Examples of the copper catalyst include copper iodide, copper bromide, copper chloride, copper acetate and the like.

Examples of the ligand include 2-(dimethylamino)acetic acid, picoline acid and the like.

This reaction can be carried out without solvent or in a known solvent, for example, solvents such as water; alcohols (methanol, ethanol and the like); ethers (diethyl ether, 1,4-dioxane, 1,2-dimethoxyethane, tetrahydrofuran and the like); aromatic hydrocarbons (benzene, toluene, xylene and the like); esters (ethyl acetate and the like); halogenated hydrocarbons (chloroform, dichloromethane and the like); nitriles (acetonitrile and the like); amides (N,N-dimethylformamide, N,N-dimethylacetamide, 1-methyl-2-pyrrolidinone and the like); ketones (acetone, 2-butanone and the like); sulfoxides (dimethyl sulfoxide and the like), and the like. These solvents may be used alone or in a mixture at a suitable ratio.

In this reaction, molecular sieves may be added as necessary.

This reaction may be performed under microwave irradiation as necessary.

This reaction may be carried out under an atmosphere of, for example, nitrogen, argon and the like, as necessary.

In this reaction, per 1 mol of the starting compound, arylhalide, arylboronic acid or arylboroxin is generally used in about 0.3-about 10 mol, preferably about 1-about 5 mol, the amount of the base is generally about 0.1-about 100 equivalents, preferably about 1-about 5 equivalents, the amount of the copper reagent is about 0.01-about 5 equivalents, preferably about 0.01-about 2 equivalents, and the amount of the ligand is generally about 0.01-about 5 equivalents, preferably about 0.01-about 2 equivalents. The reaction temperature is generally 0° C. to 200° C., preferably 20° C. to 150° C. The reaction time is about 0.1-about 100 hr, preferably about 0.5-about 50 hr.

1-about 5 equivalents. The reaction temperature is generally 0° C. to 200° C., preferably 20° C. to 150° C. The reaction time is about 0.1-about 100 hr, preferably about 0.5-about 50 hr.

In step 14, when ring D has a halogen atom such as a bromine atom and the like as X, that is, the structure shown in the formula (I-10), compound (I-8) can be produced by using Ar—OH as Ar—Y.

Compound (I-15) can be synthesized from compounds (I-10) and (I-12), arylboronic acid and arylboronic acid ester, or compounds (I-13) and (I-14) and arylhalide, by the coupling reaction of step 18. Compounds (I-12), (I-13) and (I-14) can be synthesized by step 15-step 17, respectively.

Reaction scheme 5

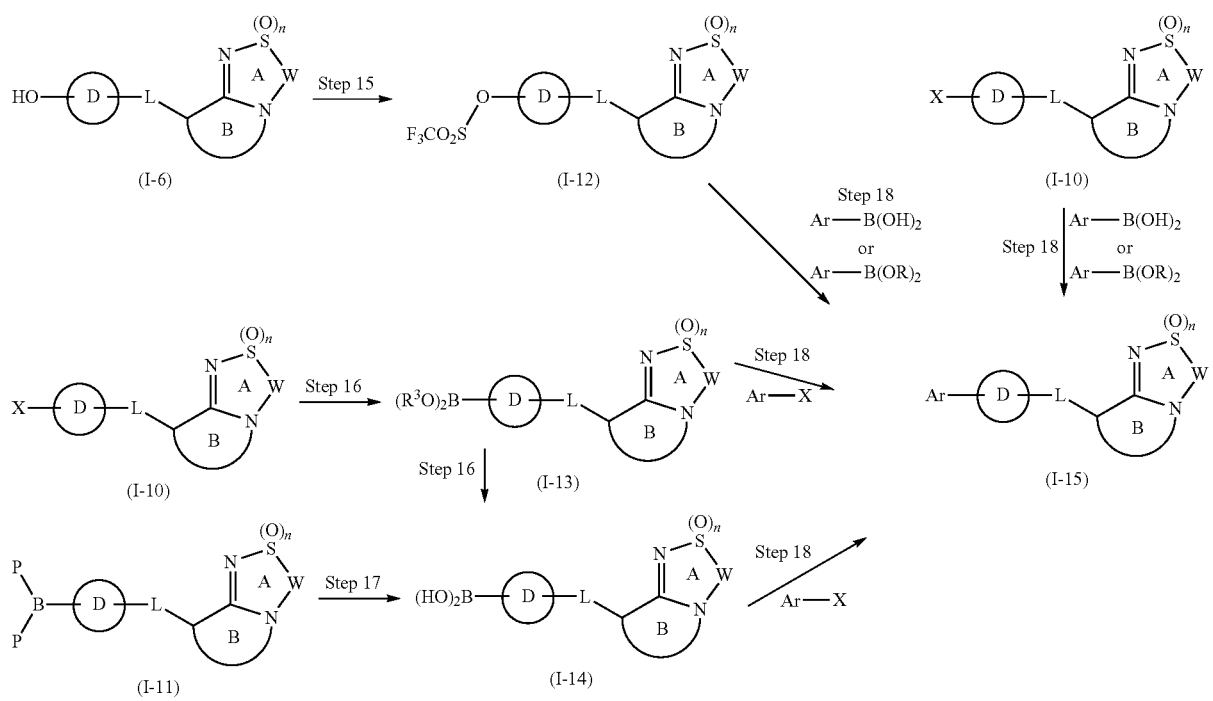

Particularly when Y of Ar—Y in step 14 is a fluorine atom or a chlorine atom, this step may be carried out in a solvent suitable for compound (I-6). In this reaction, a base may be used as necessary.

Examples of the solvent include tetrahydrofuran, toluene, N,N-dimethylformamide, dimethyl sulfoxide and the like. Preferred are N,N-dimethylformamide, dimethyl sulfoxide and the like. These solvents may be used alone or in a mixture at a suitable ratio.

Examples of the base include sodium carbonate, potassium carbonate, cesium carbonate, sodium hydride, triethylamine and the like.

This reaction may be performed under microwave irradiation as necessary.

This reaction may be carried out under an atmosphere of, for example, nitrogen, argon and the like, as necessary.

In this reaction, per 1 mol of the starting compound, Ar—Y is generally used in about 0.3-about 10 mol, preferably about 1-about 5 mol, and the amount of the base is generally about 0.1-about 100 equivalents, preferably about

[Step 15]
When ring D has a hydroxy group, compound (I-12) can be obtained by using a trifluoromethanesulfonylating agent relative to compound (I-6) in a suitable solvent. In this case, a suitable base may also be added.

Examples of the trifluoromethanesulfonylating agent include trifluoromethanesulfonyl chloride, trifluoromethanesulfonic anhydride and the like.

Examples of the base include triethylamine, pyridine, potassium carbonate and the like.

Examples of the solvent include tetrahydrofuran, acetonitrile, ethyl acetate and the like.

[Step 16]
When ring D has a halogen atom, compound (I-13) can be obtained by using boronic acid ester relative to compound (I-10) in the presence of a metal catalyst in a suitable solvent. In this case, a suitable base may also be added. Compound (I-14) may be produced during the reaction. In addition, compound (I-14) can be obtained by hydrolyzing isolated compound (I-13).

Examples of the boronic acid ester include 4,4,4',4',5,5,5',5'-octamethyl-2,2'-bi-1,3,2-dioxaborolane and the like.

Examples of the base include triethylamine, pyridine, potassium carbonate, cesium carbonate and the like.

Examples of the metal catalyst include tris(dibenzylideneacetone)dipalladium(0), [1,1'-bis(diphenylphosphino)ferrocene]dichloropalladium(II) and the like.

Examples of the solvent include 1,2-dimethoxyethane, tetrahydrofuran, acetonitrile, ethyl acetate, N,N-dimethylformamide and the like.

[Step 17]

When ring D has a protected boron atom, compound (I-14) can be obtained by deprotection of compound (I-11). Examples of the protecting group include 1,8-diaminonaphthalene and the like. In this case, the deprotection can be carried out using an acid in a suitable solvent.

Examples of the acid include hydrochloric acid and the like, and examples of the solvent include tetrahydrofuran and the like.

[Step 18]

In step 18, compound (I-15) can be obtained by applying a method similar to the coupling reaction using a palladium reagent in step 6 to compound (I-10), (I-12), (I-13) or (I-14).

In addition, when ring D has a protected nitrogen atom, that is, the structure shown in the formula (I-16), compounds (I-17) and (I-18) can be obtained by the deprotection of step 19 and alkylation of step 20, respectively.

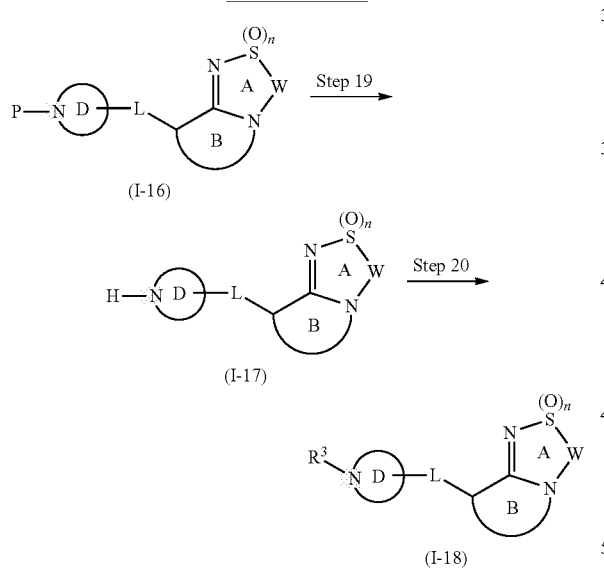

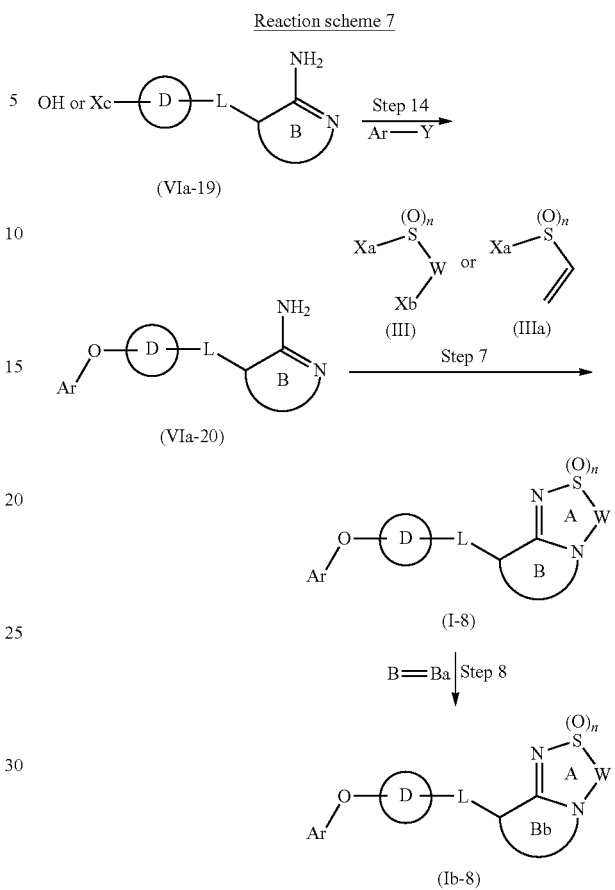

[Step 19]

Step 19 can be carried out in the same manner as in the method of (4) deprotection of protected amino group in step 2.

[Step 20]

Step 20 can be carried out in the same manner as in the method of the alkylation of step 9.

Step 9-step 20 mentioned above can also be applied to compound (VIa) in Reaction Scheme 1, and thereafter compounds (I) and (Ib) can be obtained according to step 7 and step 8.

For example, compound (I-8) can be produced by applying step 14 and step 7 to compound (VIa-19). In addition, when ring B of compound (I-8) is ring Ba, compound (Ib-8) can also be produced by further performing step 8.

The amino group of compounds (IIa), (IIa'), (IIa") and (VIa) in Reaction Scheme 1 may be a halogen atom, and the corresponding halogen atom can be converted to amino group in any step.

For example, as shown in the following formulas, compound (VIa) can also be produced by, besides as shown in Reaction Scheme 1, applying step 21 to compound (VIa-23) obtained by applying step 2 to compound (IIa'-21), and then step 6 to compound (IIa"-22).

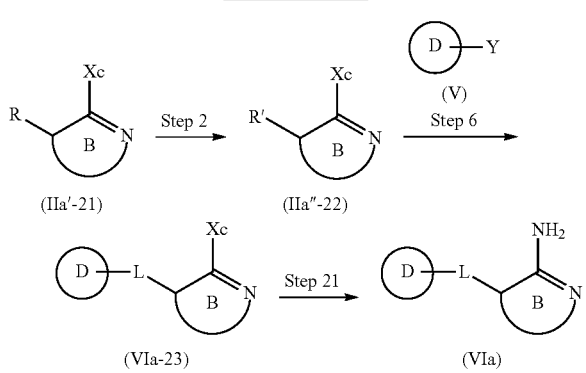

[Step 21]

Step 21 can be carried out in the same manner as in the coupling reaction described in step 5 and using an amino source such as 1,1-diphenylmethanimine and the like.

As the base to be used in this reaction, sodium t-butoxide and the like can be mentioned, as the palladium reagent, tris(dibenzylideneacetone)dipalladium(0) and the like can be mentioned, as the ligand, 2,2'-bis(diphenylphosphino)-1,1'-binaphthyl and the like can be mentioned, and as the solvent, toluene and the like can be mentioned.

When 1,1-diphenylmethanimine is used as an amino source, (4) deprotection of protected amino group described in step 2 needs to be performed after the coupling reaction.

Compound (IIa") can also be produced by a route besides as shown in Reaction Scheme 1. Compound (IIa) wherein X=H, namely, compound (IIa-24), is subjected to the protection reaction described in step 9 to give compound (IIa-25).

[Step 22]

Then, functionalized compound (IIa") can be produced by reacting a base and reacting a suitable functionalizing agent in step 22. In this case, a suitable additive may be added.

ring B to be bonded to ring D is hydroxylated may be obtained in a step using the compound. One example thereof is the byproduct (Ib-9) of step 11.

Byproduct may not be indicated in each Reaction Scheme.

In Reaction Schemes 1-9 mentioned above, in a compound having ring B and ring A, when ring B is ring Ba, step 8 may be performed at this stage to convert ring Ba to ring Bb.

The reactants (arylboronic acid, arylhalide and the like) used in the aforementioned steps may be commercially available products, or can also be prepared by a known method or a method analogous thereto. Arylhalide (V-29), arylboronic acid (V-30), and arylboronic acid ester (V-31) can also be prepared by the following method.

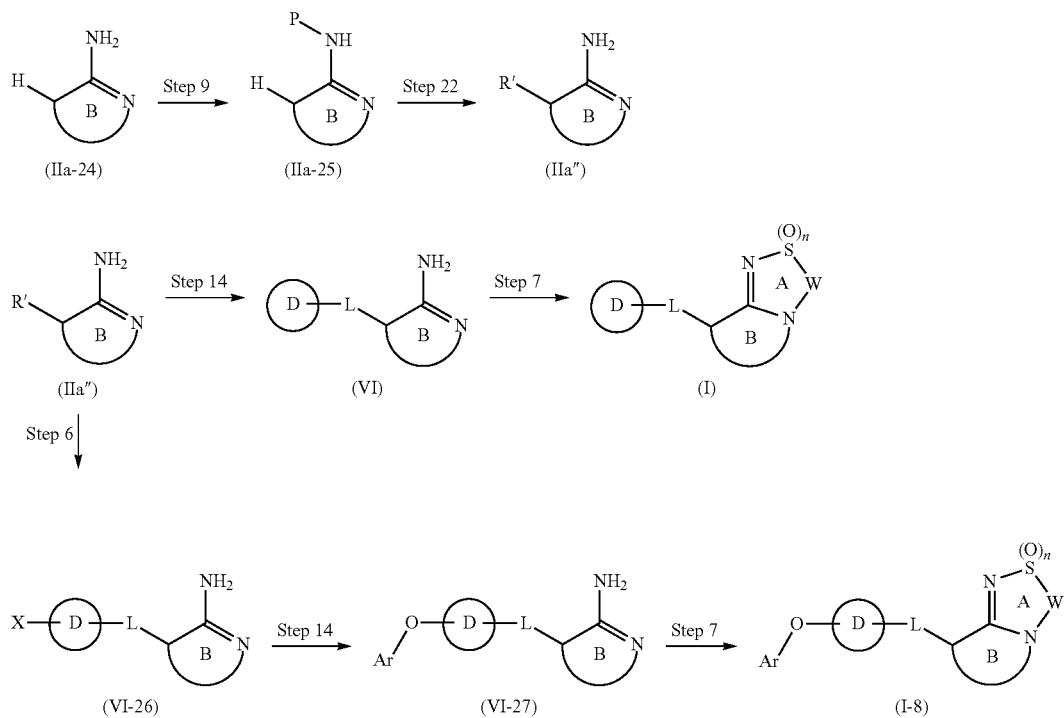

For example, when R'=B(OH)$_2$, n-butyllithium and the like can be mentioned as a base, triisopropyl borate and the like can be mentioned as a functionalizing agent, N,N,N',N'-tetramethylethylenediamine and the like can be mentioned as an additive, and tetrahydrofuran and the like can be mentioned as a solvent. Then, (4) deprotection of protected amino group described in step 2 needs to be performed. Deprotection may proceed during this reaction.

Using the thus-produced compound (IIa"), compound (I) can be produced via, for example, step 14 and step 7. Alternatively, compound (I-8) can also be produced via step 6, step 14 and step 7 and using compound (IIa").

In Reaction Schemes 1-9 mentioned above, in a compound having ring A, ring B and ring D, when ring B is ring Bb and the carbon atom of ring B to be bonded to ring D has a hydrogen atom, a byproduct wherein the carbon atom of

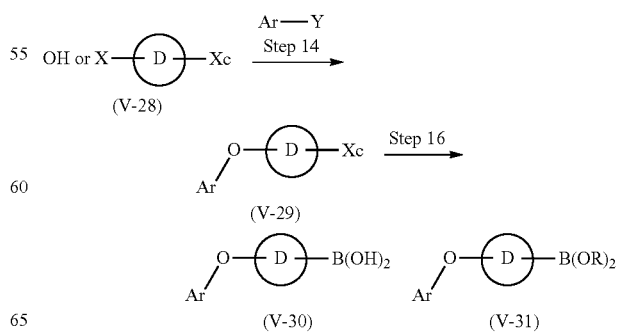

Arylhalide derivative (V-29) can be produced in the same manner as in step 14 and using compound (V-28) having the same or different two halogen atoms and Ar—Y wherein Y is a hydroxy group, or compound (V-28) having a halogen atom and a hydroxy group and Ar—Y wherein Y is a halogen atom. Then, arylboronic acid (V-30) or arylboronic acid ester (V-31) can be produced by performing step 16.

Compound (I) or an intermediate therefor may also be optically resolved by a known method or a method analogous thereto to give an optically active form of compound (I) or an optically active form of the intermediate. As a method of the optical resolution, a method known per se can be mentioned, for example, fractional recrystallization, chiral column method, diastereomer method and the like. In the "fractional recrystallization", a salt is formed from a racemate and an optically active compound [e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine etc.), which is separated by fractional recrystallization and the like and, when desired, subjected to a neutralization step to give a free optical isomer. In the "chiral column method", a racemate or a salt thereof is subjected to a column for separation of optical isomer (chiral column). For example, in liquid chromatography, a racemate is added to a chiral column such as ENANTIO-OVM (manufactured by TOSO) or CHIRAL series manufactured by DAICEL and the like, and developed with water, a buffer (e.g., phosphate buffer), an organic solvent (e.g., hexane, ethanol, methanol, isopropanol, acetonitrile, trifluoroacetic acid, diethylamine, triethylamine and the like), or a mixed solvent thereof to separate an optical isomer. For example, in gas chromatography, a chiral column such as CP-Chirasil-DeX CB (manufactured by GL Sciences Inc.) and the like is used to achieve separation. In the "diastereomer method", a racemate and an optically active reagent are reacted to give a diastereomer mixture, then subjected to a general separation means (e.g., fractional recrystallization, chromatography method etc.) to give one diastereomer, and subjected to a chemical reaction (e.g., acid hydrolysis, base hydrolysis, hydrogenolysis etc.) to dissociate an optically active reagent moiety, whereby the object optical isomer is obtained. Examples of the "optically active reagent" include optically active organic acids such as MTPA [α-methoxy-α-(trifluoromethyl)phenylacetic acid], (−)-menthoxyacetic acid and the like; optically active alkoxymethylhalides such as (1R-endo)-2-(chloromethoxy)-1,3,3-trimethylbicyclo[2.2.1]heptane and the like, and the like.

Compound (I) or an intermediate therefor obtained by the above methods can be isolated and purified by, for example, a general separation means such as recrystallization, distillation, chromatography and the like. When compound (I) is obtained as a free compound, it can be converted to a salt by a method known per se or a method analogous thereto (e.g., neutralization etc.). When compound (I) is obtained as a salt, it can be converted to a free form or other salt by a method known per se or a method analogous thereto.

As a salt of compound (I) or an intermediate therefor, a pharmacologically acceptable salt and the like are used. For example, salts with inorganic bases, salts with organic bases, salts with inorganic acids, salts with organic acids, salts with basic or acidic amino acids and the like are used. Preferable examples of the salts with inorganic bases include alkali metal salts such as sodium salt, potassium salt and the like, alkaline earth metal salts such as calcium salt, magnesium salt and the like, aluminum salt, ammonium salt and the like. Preferable examples of the salts with organic bases include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salts with inorganic acids include salts with hydrochloric acid, hydrobromic acid, nitric acid, sulfuric acid, phosphoric acid and the like. Preferable examples of the salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salts with basic amino acids include salts with arginine, lysine, ornithine and the like. Preferable examples of the salts with acidic amino acids include salts with aspartic acid, glutamic acid and the like. Of these, pharmaceutically acceptable salt is preferable. When compound (I) or intermediate has a basic functional group, examples thereof include salts with inorganic acids such as hydrochloric acid, hydrobromic acid, nitric acid, sulfuric acid, phosphoric acid and the like, salts with organic acids such as acetic acid, phthalic acid, fumaric acid, tartaric acid, maleic acid, citric acid, succinic acid, methanesulfonic acid, p-toluenesulfonic acid and the like. When compound (I) or intermediate has an acidic functional group, examples thereof include alkali metal salts such as sodium salt, potassium salt and the like, alkaline earth metal salts such as calcium salt, magnesium salt and the like, ammonium salt and the like.

When compound (I) contains an isomer, such isomer can be obtained as single products by synthesis method and separation method (concentration, solvent extraction, column chromatography, recrystallization etc.) known per se.

The compound of the present invention is useful as an agent for the prophylaxis or treatment of diseases such as
(1) mental diseases [e.g., depression, major depression, bipolar depression, dysthymic disorder, emotional disorder (seasonal affective disorder and the like), recurrent depression, postpartum depression, stress disorder, depression symptom, mania, anxiety, generalized anxiety disorder, anxiety syndrome, panic disorder, phobia, social phobia, social anxiety disorder, obsessive disorder, post-traumatic stress syndrome, post-traumatic stress disorder, Tourette syndrome, autism, adjustment disorder, bipolar disorder, neurosis, schizophrenia (e.g., positive symptom, negative symptom, cognitive impairment), neurosis, chronic fatigue syndrome, anxiety neurosis, compulsive neurosis, panic disorder, epilepsy, anxiety, anxious mental state, emotional abnormality, cyclothymia, nervous erethism, faint, addiction, low sex drive, attention deficit hyperactivity disorder (ADHD), psychotic major depression, refractory major depression, treatment-resistant depression],
(2) neurodegenerative diseases [e.g., Alzheimer's disease, Alzheimer-type senile dementia, Parkinson's disease, Huntington chorea, multi-infarct dementia, frontotemporal dementia, frontotemporal dementia Parkinson's Type, progressive supranuclear palsy, Pick's syndrome, Niemann-Pick syndrome, corticobasal degeneration, Down's disease, vascular dementia, postencephalitic parkinsonism, Lewy body dementia, HIV dementia, amyotrophic lateral sclerosis (ALS), motor neurogenesis disease (MND), Creutzfeldt-Jakob disease or prion disease, cerebral palsy, progressive supranuclear palsy, multiple sclerosis],
(3) age-related cognition memory disorders [e.g., age-related memory disorders, senile dementia]
(4) sleep disorders [e.g., intrinsic sleep disorders (e.g., psychophysiological insomnia and the like), extrinsic sleep disorder, circadian rhythm disorders (e.g., time zone change syndrome (jet lag), shift work sleep disorder, irregular sleep-wake pattern, delayed sleep phase, advanced sleep phase syndrome, non-24-hour sleep-wake and the like), parasomnia, sleep disorders associated with internal medical or psychiatric disorder (e.g., chronic obstructive pulmonary diseases, Alzheimer's disease, Parkinson's disease, cerebrovascular dementia, schizophrenia, depression, anxiety neurosis), stress insomnia, insomnia, insomniac neurosis, sleep apnea syndrome], (5) respiratory depression caused by anesthetics, traumatic disease, or neurodegenerative disease and the like, (6) traumatic brain injury, neurotic anorexia, eating disorder, anorexia nervosa, hyperorexia, other eating disorder, alcohol dependence, alcohol abuse, alcoholic amnesia, alcohol paranoia, alcohol preference, alcohol withdrawal, alcoholic insanity, alcohol poisoning, alcoholic jealousy, alcoholic mania, alcohol-dependent mental disorder, alcoholic insanity, pharmacophilia, pharmacophobia, pharmacomania, drug withdrawal, migraine, stress headache, tension headache, diabetic neuropathy, obesity, diabetes, muscular spasm, Meniere's disease, autonomic ataxia, alopecia, glaucoma, hypertension, cardiac disease, tachycardia, cardiac failure, hyperventilation, bronchial asthma, apnea, sudden infant death syndrome, inflammatory disease, allergic disease, impotence, climacteric disorder, infertility, cancer, immunodeficiency syndrome caused by HIV infection, immunodeficiency syndrome caused by stress, cerebrospinal meningitis, acromegaly, incontinence, metabolic syndrome, osteoporosis, peptic ulcer, irritable bowel syndrome, inflammatory bowel disease, ulcerative colitis, Crohn's disease, stress gastrointestinal disorder, neurotic vomiting, peptic ulcer, diarrhea, constipation, postoperative ileus, stress gastrointestinal disorder, and the like in mammals (e.g., mouse, rat, hamster, rabbit, cat, dog, bovine, sheep, monkey, human and the like).

Since the compound of the present invention has a superior AMPA receptor potentiating action, it can be expected to provide a superior prophylactic or therapeutic effect for the above-mentioned diseases.

A prodrug of compound (I') may be used in the same manner as with compound (I') encompassing compound (I). A prodrug of compound (I') means a compound which is converted to compound (I') with a reaction due to an enzyme, gastric acid, etc. under the physiological condition in the living body, that is, a compound which is converted to compound (I') by oxidation, reduction, hydrolysis, etc. according to an enzyme; a compound which is converted to compound (I') by hydrolysis etc. due to gastric acid, etc.

A prodrug of compound (I') may be a compound obtained by subjecting an amino group in compound (I') to an acylation, alkylation or phosphorylation (e.g., a compound obtained by subjecting an amino group in compound (I') to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.); a compound obtained by subjecting a hydroxyl group in compound (I') to an acylation, alkylation, phosphorylation or boration (e.g., a compound obtained by subjecting a hydroxyl group in compound (I') to an acetylation, palmitoylation, propanoylation, pivaloylation, succinylation, fumarylation, alanylation, dimethylaminomethylcarbonylation, etc.); a compound obtained by subjecting a carboxy group in compound (I') to an esterification or amidation (e.g., a compound obtained by subjecting a carboxy group in compound (I') to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation, etc.) and the like. Any of these compounds can be produced from compound (I') by a method known per se. A prodrug for compound (I') may also be one which is converted into compound (I') under a physiological condition, such as those described in IYAKUHIN no KAIHATSU (Development of Pharmaceuticals), Vol. 7 (Design of Molecules), p. 163-198 (HIROKAWA SHOTEN).

Since the compound of the present invention is superior in in vivo kinetics (e.g., plasma drug half-life, brain transfer, metabolism stability), shows low toxicity (e.g., more superior as a medicament in terms of acute toxicity, chronic toxicity, genetic toxicity, reproductive toxicity, cardiotoxicity, drug interaction, carcinogenicity and the like), it can be safely administered orally or parenterally to mammals (e.g., human, monkey, bovine, horse, swine, mouse, rat, hamster, rabbit, cat, dog, sheep, goat etc.) directly as a medicament, or a pharmaceutical composition containing pharmaceutically acceptable carrier etc. The "parenteral" includes intravenous, intramuscular, subcutaneous, intraorgan, intranasal, intradermal, instillation, intracerebral, rectal, vaginal, intraperitoneal, intratumor, tumor proximal administration, direct administration to a lesion and the like.

While the daily dose of the compound of the present invention varies depending on the administration route, symptom and the like, it is, for example, 0.001-1000 mg/kg body weight, preferably 0.01-100 mg/kg body weight, more preferably 0.1-10 mg/kg body weight, by, for example, oral administration to patients with schizophrenia (adult, body weight 40-80 kg, for example, 60 kg). This dose can be administered in one to 3 portions a day.

A medicament containing the compound of the present invention can be used singly or in the form of a pharmaceutical composition prepared according to a method known per se as a production method of pharmaceutical preparations (e.g., the method described in the Japanese Pharmacopoeia etc.) by mixing the compound of the present invention and pharmaceutically acceptable carriers. A medicament containing the compound of the present invention can be safely administered orally or parenterally (e.g., intravenous, intramuscular, subcutaneous, intraorgan, intranasal, intradermal, instillation, intracerebral, rectal, vaginal, intraperitoneal, lesion etc.) in the form of, for example, tablet (including sugar-coated tablet, film-coated tablet, sublingual tablet, orally disintegrable tablet, buccal tablet and the like), pill, powder, granule, capsule (including soft capsule, microcapsule), troche, syrup, liquid, emulsion, suspension, controlled release preparation (e.g., immediate-release preparation, sustained-release preparation, sustained-release microcapsule), aerosol, films (e.g., orally disintegrable films, oral mucosal adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like.

As the aforementioned "pharmacologically acceptable carrier", various organic or inorganic carriers conventionally used as starting materials of preparations are used. For example, excipient, lubricant, binder, disintegrant and the like for solid preparations are used, and solvent, solubilizing agent, suspending agent, isotonic agent, buffering agent, soothing agent and the like for liquid preparations are used.

Where necessary, additives for preparations such as preservative, antioxidant, colorant, sweetener and the like can be also used.

Examples of the excipient include lactose, white sugar, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, carboxymethylstarch sodium, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include paraoxybenzoic acid esters, chlorobutanol, benzyl alcohol, phenylethyl alcohol, dehydroacetic acid, sorbic acid and the like.

Examples of the antioxidant include sulfites, ascorbic acid, α-tocopherol and the like.

While the pharmaceutical composition varies depending on the dosage form, the administration method, carrier and the like, the composition can be produced by adding the compound of the present invention in a proportion of generally 0.01-100% (w/w), preferably 0.1-95% (w/w), of the total amount of the preparation according to a conventional method.

The compound of the present invention may be used in combination with other active ingredients (hereinafter to be abbreviated as concomitant drug).

As the concomitant drug, for example, the following can be mentioned.

benzodiazepine (chlordiazepoxide, diazepam, potassium clorazepate, lorazepam, clonazepam, alprazolam etc.), L-type calcium channel inhibitor (pregabalin etc.), tricyclic or tetracyclic antidepressant (imipramine hydrochloride, amitriptyline hydrochloride, desipramine hydrochloride, clomipramine hydrochloride etc.), selective serotonin reuptake inhibitor (fluvoxamine maleate, fluoxetine hydrochloride, citalopram hydrobromide, sertraline hydrochloride, paroxetine hydrochloride, escitalopram oxalate etc.), serotonin-noradrenaline reuptake inhibitor (venlafaxine hydrochloride, duloxetine hydrochloride, desvenlafaxine hydrochloride etc.), noradrenaline reuptake inhibitor (reboxetine mesylate etc.), noradrenaline-dopamine reuptake inhibitor (bupropion hydrochloride etc.), mirtazapine, trazodone hydrochloride, nefazodone hydrochloride, bupropion hydrochloride, setiptiline maleate, 5-HT$_{1A}$ agonist (buspirone hydrochloride, tandospirone citrate, osemozotan hydrochloride etc.), 5-HT$_3$ antagonist (cyamemazine etc.), heart non-selective β inhibitor (propranolol hydrochloride, oxprenolol hydrochloride etc.), histamine H$_1$ antagonist (hydroxyzine hydrochloride etc.), therapeutic drug for schizophrenia (chlorpromazine, haloperidol, sulpiride, clozapine, trifluoperazine hydrochloride, fluphenazine hydrochloride, olanzapine, quetiapine fumarate, risperidone, aripiprazole etc.), CRF antagonist, other antianxiety drug (meprobamate etc.), tachykinin antagonist (MK-869, saredutant etc.), medicament acting on metabotropic glutamate receptor, CCK antagonist, β3 adrenaline antagonist (amibegron hydrochloride etc.), GAT-1 inhibitor (tiagabine hydrochloride etc.), N-type calcium channel inhibitor, carbonic anhydrase II inhibitor, NMDA glycine site agonist, NMDA antagonist (memantine etc.), peripheral type benzodiazepine receptor agonist, vasopressin antagonist, vasopressin V1b antagonist, vasopressin Via antagonist, phospho diesterase inhibitor, opioid antagonist, opioid agonist, uridine, nicotinic acid receptor agonist, thyroid hormone (T3, T4), TSH, TRH, MAO inhibitor (phenelzine sulfate, tranylcypromine sulfate, moclobemide etc.), 5-HT$_{2A}$ antagonist, 5-HT$_{2A}$ inverse agonist, COMT inhibitor (entacapone etc.), therapeutic drug for bipolar disorder (lithium carbonate, sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcohol dependence, therapeutic drug for autism, therapeutic drug for chronic fatigue syndrome, therapeutic drug for spasm, therapeutic drug for fibromyalgia syndrome, therapeutic drug for headache, therapeutic drug for insomnia (etizolam, zopiclone, triazolam, zolpidem, ramelteon, indiplon etc.), therapeutic drug for quit smoking, therapeutic drug for myasthenia gravis, therapeutic drug for cerebral infarction, therapeutic drug for mania, therapeutic drug for hypersomnia, therapeutic drug for pain, therapeutic drug for dysthymia, therapeutic drug for autonomicataxia, therapeutic drug for male and female sexual dysfunction, therapeutic drug for migraine, therapeutic drug for pathological gambler, therapeutic drug for restless legs syndrome, therapeutic drug for substance addiction, therapeutic drug for alcohol-related disease, therapeutic drug for irritable bowel syndrome, therapeutic drug for Alzheimer's disease (donepezil, galanthamine, memantine etc.), therapeutic drug for Parkinson's disease, therapeutic drug for ALS (riluzole etc., neurotrophic factor etc.), therapeutic drug for lipid abnormality like cholesterol-lowering agent (statin series (pravastatin sodium, atrovastatin, simvastatin, rosuvastatin etc.), fibrate (clofibrate etc.), squalene synthetase inhibitor), therapeutic drug for abnormal behavior or suppressant of dromomania due to dementia (sedatives, antianxiety drug etc.), apoptosis inhibitor, antiobesity drug, therapeutic drug for diabetes, therapeutic drug for hypertension, therapeutic drug for hypotension, therapeutic drug for rheumatism (DMARD), anti-cancer agent, therapeutic drug for parathyroid (PTH), calcium receptor antagonist, sex hormone or a derivative thereof (progesterone, estradiol, estradiol benzoate etc.), neuronal differentiation enhancer, nerve regeneration enhancer, non-steroidal anti-inflammatory drug (meloxicam, tenoxicam, indomethacin, ibuprofen, celecoxib, rofecoxib, aspirin, indomethacin etc.), steroid (dexamethasone, cortisone acetate etc.), anti-cytokine drug (TNF inhibitor, MAP kinase inhibitor etc.), antibody medicament, nucleic acid or nucleic acid derivative, aptamer drug and the like.

By combining the compound of the present invention and a concomitant drug, a superior effect such as
(1) the dose can be reduced as compared to single administration of the compound of the present invention or a concomitant drug,
(2) the concomitant drug can be selected according to the condition of patients (mild case, severe case and the like),
(3) the period of treatment can be set longer by selecting a concomitant drug having different action and mechanism from the compound of the present invention,
(4) a sustained treatment effect can be designed by selecting a concomitant drug having different action and mechanism from the compound of the present invention,
(5) a synergistic effect can be afforded by a combined use of the compound of the present invention and a concomitant drug, and the like, can be achieved.

A combined use of the compound of the present invention and a concomitant drug is referred to as "combination agent of the present invention".

When using the combination agent of the present invention, the administration time of the compound of the present invention and the concomitant drug is not restricted, and the compound of the present invention or a pharmaceutical composition thereof and the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the combination agent of the present invention is not particularly restricted, and it is sufficient that the compound of the present invention and the concomitant drug are combined in administration. Examples of such administration mode include the following:
(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The combination agent of the present invention has low toxicity, and for example, the compound of the present invention or (and) the above-mentioned concomitant drug can be mixed, according to a method known per se, with a pharmacologically acceptable carrier to give pharmaceutical compositions, for example, tablets (including a sugar-coated tablet, film-coated tablet), powders, granules, capsules (including a soft capsule), solutions, injections, suppositories, sustained release agents and the like which can be safely administered orally or parenterally (e.g., administration to local, rectum, vein, and the like). An injection can be administered intravenously, intramuscularly, subcutaneously or intraorganly or directly to the lesion.

As the pharmacologically acceptable carrier usable for the production of the combination agent of the present invention, various organic or inorganic carrier substances conventionally used as preparation materials can be mentioned. For example, excipient, lubricant, binder and disintegrant can be used for solid preparations. Solvent, solubilizing agent, suspending agent, isotonic agent, buffering agent and soothing agent and the like can be used for liquid preparations. Where necessary, suitable amounts of general additives such as preservative, antioxidant, colorant, sweetening agent, adsorbent, wetting agent and the like can also be used as appropriate.

Examples of the excipient include lactose, white sugar, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, carboxymethylstarch sodium, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include paraoxybenzoic acid esters, chlorobutanol, benzyl alcohol, phenylethyl alcohol, dehydroacetic acid, sorbic acid and the like.

Examples of the antioxidant include sulfites, ascorbic acid, α-tocopherol and the like.

The compounding ratio of the compound of the present invention to the concomitant drug in the combination agent of the present invention can be appropriately selected depending on an administration subject, administration route, diseases and the like.

For example, the content of the compound of the present invention in the combination agent of the present invention varies depending on the form of a preparation, and usually from about 0.01 to 100 wt %, preferably from about 0.1 to 50 wt %, further preferably from about 0.5 to 20 wt %, based on the whole preparation.

While the content of the concomitant drug in the combination agent of the present invention varies depending on the form of a preparation, it is usually from about 0.01 to 100 wt %, preferably from about 0.1 to 50 wt %, further preferably from about 0.5 to 20 wt %, based on the whole preparation.

While the content of the additives such as carrier and the like in the combination agent of the present invention varies depending on the form of a preparation, it is generally about 1 to 99.99 wt %, preferably about 10 to 90 wt %, based on the whole preparation.

Similar contents can be employed for individual preparations of the compound of the present invention and the concomitant drug.

EXAMPLES

The present invention is explained in detail in the following by referring to Reference Examples, Examples, Experimental Examples and Formulation Examples, which are not to be construed as limitative, and the invention may be changed within the scope of the present invention.

In the following Examples, the "room temperature" generally shows about 10° C. to about 35° C. The ratios for mixed solvents show, unless otherwise specified, volume mixing ratios. Unless otherwise specified, % shows wt %.

In silica gel column chromatography, basic NH means use of aminopropylsilane-bound silica gel. The ratios of elution solvents are volume mixing ratios, unless otherwise specified.

In the following Reference Examples and Examples, the following abbreviations are used.
mp: melting point
DMF: N,N-dimethylformamide
THF: tetrahydrofuran
EDCI: 1-ethyl-3-(3-dimethylaminopropyl)carbodiimide
DMSO: dimethyl sulfoxide
HOBt: 1-hydroxybenzotriazole
DIEA: N,N-diisopropylethylamine
DEAD: diethyl azodicarboxylate
IPE: diisopropyl ether
aq.: aqueous solution
TEA: triethylamine
sat.: saturated
4A MS: 4 angstrom molecular sieves
DME: 1,2-dimethoxyethane
Pd(dppf)Cl$_2$: [1,1'-bis(diphenylphosphino)ferrocene]dichloropalladium(II)
NaH: sodium hydride
BSA: bovine serum albumin
EDTA: ethylenediaminetetraacetic acid
HBSS: Hanks' balanced salt solution
HEPES: 2-[4-(2-hydroxyethyl)-1-piperazinyl]ethanesulfonic acid
HMPA: hexamethylphosphoric triamide
D-MEM: Dulbecco's Modified Eagle Medium
N: normal
% wet: wet weight
$^1$H-NMR (proton nuclear magnetic resonance spectrum) was measured Fourier-transform type NMR. For the analysis, ACD/SpecManager (trade name) and the like were used. Peaks with very mild protons such as a hydroxyl group, an amino group, hydrochloride, hydrobromide and the like are not described. In addition, peaks that matched with signals of water, deuterated solvents or other solvents are not described.

For indication of the measurement results of $^1$H NMR, the following abbreviations are used.

s: singlet, d: doublet, dd: double doublet, dt: double triplet, t: triplet, q: quartet, dq: double quartet, m: multiplet, brs: broad singlet, spt: septet, quin: quintet, sxt: sextet, J: coupling constant, Hz: hertz MS (mass spectrum) was measured by LC/MS (liquid chromatography mass spectrometer). As the ionization method, atmospheric pressure ionization (API) method was used. The API method includes ESI (ElectroSpray Ionization) method, APCI (Atmospheric Pressure Chemical Ionization) method and ESI+APCI mixed ion mode method.

The data indicates those found. Generally, a molecular ion peak is observed; however, it may not be observed in some cases. In the case of a compound having a tert-butoxycarbonyl group (-Boc), a peak after elimination of a tert-butoxycarbonyl group or tert-butyl group may be observed as a fragment ion. In the case of a salt, a molecular ion peak or fragment ion peak of free form is generally observed. In addition, plural molecular ion peaks of isotope may be described.

For elemental analysis values (Anal.), those calculated (Calcd) and those found (Found) are described.

When preparative HPLC was performed for purification and described as C18, an octadecyl-bound silica gel column was used.

Example 1

N-[4-(1-methylpropyl)phenyl]-3,4-dihydropyrazino[2,1-c][1,2,4]thiadiazine-9-carboxamide 2,2-dioxide A) methyl 3,4-dihydropyrazino[2,1-c][1,2,4]thiadiazine-9-carboxylate 2,2-dioxide To a suspension of sodium hydride (60%, 2.0 g) in dry THF (100 mL) were added under ice-cooling methyl 3-aminopyrazine-2-carboxylate (1.53 g) and 2-chloroethanesulfonyl chloride (2.1 mL), and the mixture was stirred at room temperature overnight. To the reaction mixture was added 2-chloroethanesulfonyl chloride (2.1 mL), and the mixture was stirred at room temperature for 3 days. 2-Chloroethanesulfonyl chloride (2.1 mL) was added, and the mixture was stirred at room temperature for 3 days. The reaction mixture was added dropwise to aqueous sodium hydrogen carbonate (15.1 g) solution (400 mL) under ice-cooling, and the mixture was stirred at the same temperature for 1 hr. The precipitated was collected by filtration, washed successively with water and a small amount of methanol, and dried to give the title compound (1.62 g) as a pale-yellow solid.

MS (ESI+). found: 244.1.

B) N-[4-(1-methylpropyl)phenyl]-3,4-dihydropyrazino[2,1-c][1,2,4]thiadiazine-9-carboxamide 2,2-dioxide To a suspension of methyl 3,4-dihydropyrazino[2,1-c][1,2,4]thiadiazine-9-carboxylate 2,2-dioxide (1.58 g) in methanol (13 mL) were added 1N aqueous sodium hydroxide solution (13 mL), and the mixture was stirred at room temperature for 1 hr. To the reaction mixture was added 1N hydrochloric acid (13.2 mL), and methanol was evaporated under reduced pressure. The precipitated was collected by filtration, washed successively with water and methanol, and dried to give a brown solid (866 mg). The obtained solid (734 mg) was dissolved in DMF (20 mL), 4-sec-butylaniline (0.70 mL), HOBt (686 mg) and EDCI HCl (859 mg) were added and the mixture was stirred at room temperature overnight. The reaction mixture was diluted with ethyl acetate, washed successively with 5% aqueous sodium hydrogen carbonate solution and saturated brine, dried over anhydrous sodium sulfate, and concentrated under reduced pressure. The residue was purified by basic silica gel column chromatography (methanol/ethyl acetate), and recrystallized from water-containing ethanol to give the title compound (332 mg) as pale-yellow crystals.

Example 2

7-methyl-N-[4-(1-methylpropyl)phenyl]-3,4-dihydropyrido[2,1-c][1,2,4]thiadiazine-9-carboxamide 2,2-dioxide A) 2-amino-5-methylpyridine-3-carbonitrile To a solution of 2-amino-3-bromo-5-methylpyridine (3.74 g) in DMF (30 mL) was added copper(I) cyanide (4.48 g), and the mixture was stirred under microwave irradiation at 180° C. for 30 min. To the reaction mixture were added ethyl acetate and water, 1N aqueous sodium hydroxide solution (50 mL) was added and the mixture was stirred. Insoluble material was filtered off through celite. The aqueous layer and organic layer were separated, and the aqueous layer was extracted with ethyl acetate. The extract was collected, washed with saturated brine, dried over anhydrous sodium sulfate and concentrated under reduced pressure. The residue was purified by silica gel column chromatography (ethyl acetate/hexane) to give the title compound (357 mg) as a colorless solid.
MS (ESI+). found: 134.1.

B) ethyl 2-amino-5-methylpyridine-3-carboxylate

To a solution of 2-amino-5-methylpyridine-3-carbonitrile (353 mg) in ethanol (10 mL) was added concentrated sulfuric acid (5 mL), and the mixture was stirred at 80° C. for 4 hr. The reaction mixture was added dropwise to a mixture of sodium carbonate (10.6 g), water (50 mL) and ethyl acetate (50 mL) under ice-cooling with stirring. The organic layer was separated, washed with saturated brine, dried over anhydrous sodium sulfate, and concentrated under reduced pressure. The residue was purified by silica gel column chromatography (ethyl acetate/hexane) to give the title compound (373 mg) as a colorless solid.
MS (ESI+). found: 181.1.

C) ethyl 7-methyl-3,4-dihydropyrido[2,1-c][1,2,4]thiadiazine-9-carboxylate 2,2-dioxide To a solution of ethyl 2-amino-5-methylpyridine-3-carboxylate (368 mg) in DMF (20 mL) were added pyridine (0.66 mL) and 2-chloroethanesulfonyl chloride (0.32 mL), and the mixture was stirred at room temperature for 3 hr. To the reaction mixture were added water (50 mL) and sodium carbonate (1 g), sodium chloride was saturated and the mixture was extracted 3 times with ethyl acetate. The extracts were collected, dried over anhydrous sodium sulfate, and concentrated under reduced pressure. The residue was purified by silica gel column chromatography (methanol/ethyl acetate) to give the title compound (111 mg) as a brown solid.
MS (ESI+). found: 271.1.

D) 7-methyl-3,4-dihydropyrido[2,1-c][1,2,4]thiadiazine-9-carboxylic acid 2,2-dioxide To a solution of ethyl 7-methyl-3,4-dihydropyrido[2,1-c][1,2,4]thiadiazine-9-carboxylate 2,2-dioxide (106 mg) in methanol (1 mL) was added 1N aqueous sodium hydroxide solution (1 mL), and the mixture was stirred at room temperature for 1 hr. To the reaction mixture were added 1N hydrochloric acid (1.05 mL) and water (1 mL), and the resulting precipitate was collected by filtration, washed successively with water and a small amount of THF, and dried to give the title compound (79 mg) as a pale-yellow solid.
MS (ESI+). found: 243.1.

E) 7-methyl-N-[4-(1-methylpropyl)phenyl]-3,4-dihydropyrido[2,1-c][1,2,4]thiadiazine-9-carboxamide 2,2-dioxide To a suspension of 7-methyl-3,4-dihydropyrido[2,1-c][1,2,4]thiadiazine-9-carboxylic acid 2,2-dioxide (76 mg) in DMF (3 mL) were added 4-sec-butylaniline (0.069 mL), HOBt (67 mg), and EDCI HCl (84 mg) and the mixture was stirred at room temperature overnight. To the reaction mixture was added water (10 mL), and the resulting precipitate was collected by filtration. The obtained solid was recrystallized from DMSO-ethanol to give the title compound (114 mg) as pale-yellow crystals.

Example 3

In the same manner as in Example 1, the compound of Example 3 was produced.

Example 4

N-(4-cyclopropylphenyl)-3,4-dihydropyrido[2,1-c][1,2,4]thiadiazine-9-carboxamide 2,2-dioxide 3,4-Dihydropyrido[2,1-c][1,2,4]thiadiazine-9-carboxylic acid 2,2-dioxide (150 mg) was dissolved in DMF (5 mL), 4-cyclopropylaniline (131 mg), HOBt (151 mg), EDCI HCl (189 mg) and DIEA (0.23 mL) were added and the mixture was stirred at room temperature overnight. The reaction mixture was diluted with ethyl acetate, washed successively with water and saturated brine, dried over anhydrous sodium sulfate, and concentrated under reduced pressure. The residue was suspended in ethyl acetate, and insoluble crystals were collected by filtration to give the title compound (168 mg) as pale-yellow crystals.
$^1$H NMR (300 MHz, DMSO-$d_6$) δ 0.42-0.78 (2H, m), 0.78-1.09 (2H, m), 1.72-2.06 (1H, m), 3.47-3.85 (2H, m), 4.65-4.85 (2H, m), 6.71-6.98 (1H, m), 6.99-7.32 (2H, m), 7.32-7.70 (2H, m), 8.09 (1H, dd, J=6.4, 1.9 Hz), 8.52 (1H, dd, J=7.6, 1.9 Hz), 12.01 (1H, s). Anal. Calcd for $C_{17}H_{17}N_3O_3S$: C, 59.46; H, 4.99; N, 12.24. Found: C, 59.23; H, 4.91; N, 12.19.

Examples 5-12

In the same manner as in Example 4, the compounds of Examples 5, 6, 7, 8, 9, 10, 11 and 12 were produced.

Example 13

N-(2,2-dioxido-3,4-dihydropyrido[2,1-c][1,2,4]thiadiazin-9-yl)-2,3-dihydro-1,4-benzodioxine-6-carboxamide A) 2,3-dihydrobenzo[b][1,4]dioxine-6-carboxamide To a solution of 2,3-dihydrobenzo[b][1,4]dioxine-6-carboxylic acid (3.54 g) in DMF (80 mL) were added HOBt- NH₃ (4.48 g) and EDCI HCl (5.65 g) at room temperature. The reaction mixture was stirred at room temperature for 3 days, water was added, and the mixture was extracted with ethyl acetate. The extract was washed with saturated aqueous sodium hydrogen carbonate solution and saturated brine, and dried over anhydrous sodium sulfate. The solvent was evaporated under reduced pressure and the residue was washed with hexane to give the title compound (1.10 g).

¹H NMR (300 MHz, DMSO-d₆) δ 4.18-4.35 (4H, m), 6.89 (1H, d, J=8.3 Hz), 7.19 (1H, brs), 7.34-7.44 (2H, m), 7.80 (1H, brs).

B)
9-bromo-3,4-dihydropyrido[2,1-c][1,2,4]thiadiazine 2,2-dioxide

A mixture of 3-bromopyridin-2-amine (3 g) in dehydrated THF (30 mL) was added to a mixture of 2-chloroethanesulfonyl chloride (7.07 g) and sodium hydride (60%, 3.47 g) in dehydrated THF (30 mL) at room temperature, and the reaction mixture was stirred at room temperature overnight. Water was added to the reaction mixture, and THF was removed under reduced pressure. The resulting precipitate was collected by filtration, and washed with water and diethyl ether to give the title compound (3.41 g) as a white solid.

MS (ESI+). found: 262.9.

C) N-(2,2-dioxido-3,4-dihydropyrido[2,1-c][1,2,4]thiadiazin-9-yl)-2,3-dihydro-1,4-benzodioxine-6-carboxamide To a solution of 9-bromo-3,4-dihydropyrido[2,1-c][1,2,4]thiadiazine 2,2-dioxide (100 mg) in DMF (1 mL) were added toluene (2 mL), 2,3-dihydrobenzo[b][1,4]dioxine-6-carboxamide (74.9 mg), cesium carbonate (248 mg), 9,9-dimethyl-4,5-(diphenylphosphino)xanthene (33.0 mg) and tris(dibenzylideneacetone)dipalladium(0) (34.8 mg) at room temperature. The reaction mixture was stirred under a nitrogen atmosphere at 100° C. for 5 hr, and purified by silica gel column chromatography (methanol/ethyl acetate) and recrystallized from (methanol/diisopropyl ether) to give the title compound (25.4 mg).

Example 14

9-biphenyl-4-yl-3,4-dihydropyrido[2,1-c][1,2,4]thiadiazine 2,2-dioxide

A) 3-biphenyl-4-ylpyridin-2-amine

A mixture of 2M aqueous sodium carbonate solution (6.64 mL), tetrakis(triphenylphosphine)palladium(0) (0.512 g), biphenyl-4-ylboronic acid (2.28 g) and 3-bromopyridin-2-amine (1.532 g) in dehydrated THF (30 mL) was heated under reflux overnight. The reaction mixture was added to water, and the mixture was extracted with ethyl acetate. The organic layer was washed with saturated brine, dried over anhydrous magnesium sulfate, and concentrated under reduced pressure to give a solid. The obtained solid was crystallized from toluene, diisopropyl ether and acetonitrile to give the title compound (1.428 g) as a white solid.

MS (ESI+). found: 247.4.

B) 9-biphenyl-4-yl-3,4-dihydropyrido[2,1-c][1,2,4]thiadiazine 2,2-dioxide

A mixture of 3-biphenyl-4-ylpyridin-2-amine (700 mg) in dehydrated THF (30 mL) was added to a mixture of sodium hydride (60%, 568 mg) and 2-chloroethanesulfonyl chloride (1390 mg) in dehydrated THF (30 mL) under ice-cooling. The reaction mixture was stirred at room temperature overnight, and water and hexane were added. The resulting precipitate was collected by filtration, and washed with water and ethyl acetate to give the title compound (652 mg) as a white solid.

¹H NMR (300 MHz, DMSO-d₆) δ 3.42-3.54 (2H, m), 4.60-4.76 (2H, m), 6.73 (1H, t, J=6.8 Hz), 7.34-7.42 (1H, m), 7.44-7.54 (2H, m), 7.59-7.66 (2H, m), 7.66-7.76 (5H, m), 7.80 (1H, dd, J=6.6, 1.7 Hz).

mp 315-316° C.

MS (API+). found: 337.0

Anal. Calcd for C₁₉H₁₆N₂O₂S-0.2H₂O: C, 66.94; H, 4.88; N, 8.22.

Found: C, 67.25; H, 4.82; N, 8.15.

Example 15

9-[4-(1-methylethyl)phenoxy]-3,4-dihydropyrido[2,1-c][1,2,4]thiadiazine 2,2-dioxide A) 3-[4-(1-methylethyl)phenoxy]pyridin-2-amine A mixture of 3-bromopyridin-2-amine (1200 mg), tripotassium phosphate (2945 mg), 4-isopropylphenol (1134 mg), copper iodide(I) (132 mg) and picoline acid (171 mg) in DMSO (40 mL) was stirred under a nitrogen atmosphere at 80° C. overnight. The reaction mixture was added to saturated aqueous ammonium chloride solution, filtered through celite, and the filtrate was extracted with ethyl acetate. The organic layer was washed with saturated brine, dried over anhydrous magnesium sulfate, and concentrated under reduced pressure. The residue was purified by silica gel column chromatography (ethyl acetate/hexane) to give the title compound (180.4 mg) as a pale-brown solid.

MS (ESI+). found: 229.1.

B) 9-[4-(1-methylethyl)phenoxy]-3,4-dihydropyrido[2,1-c][1,2,4]thiadiazine 2,2-dioxide In the same manner as in Example 14, step B, the title compound was obtained from the compound of the above-mentioned A).

Example 16

9-{[4-(1-methylethyl)phenyl]sulfanyl}-3,4-dihydropyrido[2,1-c][1,2,4]thiadiazine 2,2-dioxide A) 3-{[4-(1-methylethyl)phenyl]sulfanyl}pyridin-2-amine A mixture of 4-isopropylbenzenethiol (2.288 g), 3-bromopyridin-2-amine (2.0 g), (9,9-dimethyl-9H-xanthene-4,5-diyl)bis(diphenylphosphine) (0.669 g), tris(dibenzylideneacetone)dipalladium(0) (0.529 g) and DIEA (7.47 mL) in toluene (57.8 mL) was stirred overnight under a nitrogen atmosphere at 120° C. The reaction mixture was added to water, filtered through celite, and the filtrate was extracted with ethyl acetate. The organic layer was washed with saturated brine, dried over anhydrous magnesium sulfate, and concentrated under reduced pressure. The residue was purified by silica gel column chromatography (ethyl acetate/hexane) to give the title compound (2508 mg) as a pale-yellow solid.

MS (ESI+). found: 245.3.

B) 9-{[4-(1-methylethyl)phenyl]sulfanyl}-3,4-dihydropyrido[2,1-c][1,2,4]thiadiazine 2,2-dioxide In the same manner as in Example 14, step B, the title compound was obtained from the compound of the above-mentioned A).

Example 17

The compound of Example 17 was produced in the same manner as in Example 16.

Example 18

The compound of Example 18 was produced in the same manner as in Example 15.

Example 19

9-{[4-(1-methylethyl)phenyl]sulfinyl}-3,4-dihydropyrido[2,1-c][1,2,4]thiadiazine 2,2-dioxide To a mixture of 9-{[4-(1-methylethyl)phenyl]sulfanyl}-3,4-dihydropyrido[2,1-c][1,2,4]thiadiazine 2,2-dioxide (137.4 mg) in dehydrated DMF (3 mL) was added a mixture of 3-chloroperbenzoic acid (75%, 99 mg) in dehydrated DMF (3 mL) under ice-cooling, and the mixture was stirred at room temperature overnight. To the reaction mixture was added saturated aqueous sodium sulfite solution, and the mixture was extracted with ethyl acetate. The organic layer was washed with saturated aqueous sodium hydrogen carbonate solution and saturated brine, dried over anhydrous magnesium sulfate, and concentrated under reduced pressure. The residue was purified by silica gel column chromatography (ethyl acetate/methanol) to give the title compound (67.6 mg) as a white solid.

Example 20

9-{[4-(1-methylethyl)phenyl]sulfonyl}-3,4-dihydropyrido[2,1-c][1,2,4]thiadiazine 2,2-dioxide A mixture of 9-{[4-(1-methylethyl)phenyl]sulfanyl}-3,4-dihydropyrido[2,1-c][1,2,4]thiadiazine 2,2-dioxide (125.5 mg) and 3-chloroperbenzoic acid (75%, 190 mg) in dehydrated DMF (5 mL) was stirred at room temperature overnight. To the reaction mixture was added saturated aqueous sodium sulfite solution, and the mixture was extracted with ethyl acetate. The organic layer was washed with saturated aqueous sodium hydrogen carbonate solution and saturated brine, dried over anhydrous magnesium sulfate, and concentrated under reduced pressure. The residue was purified by silica gel column chromatography (ethyl acetate/methanol) to give the title compound (48.4 mg) as a white solid.

Example 21

9-(benzylsulfinyl)-3,4-dihydropyrido[2,1-c][1,2,4]thiadiazine 2,2-dioxide

In the same manner as in Example 19, the title compound (112.2 mg) was obtained from 9-(benzylsulfanyl)-3,4-dihydropyrido[2,1-c][1,2,4]thiadiazine 2,2-dioxide (220 mg).

Example 22

9-(benzylsulfonyl)-3,4-dihydropyrido[2,1-c][1,2,4]thiadiazine 2,2-dioxide

In the same manner as in Example 20, the title compound (40.3 mg) was obtained from 9-(benzylsulfanyl)-3,4-dihydropyrido[2,1-c][1,2,4]thiadiazine 2,2-dioxide (220 mg).

Example 23

9-[4-(1-methylethyl)phenyl]-3,4-dihydropyrido[2,1-c][1,2,4]thiadiazine 2,2-dioxide A) 3-[4-(1-methylethyl)phenyl]pyridin-2-amine A mixture of 2M aqueous sodium carbonate solution (8.67 mL), tetrakis(triphenylphosphine)palladium(0) (668 mg), 4-isopropylphenylboronic acid (2844 mg) and 3-bromopyridin-2-amine (2.0 g) in 1,2-dimethoxyethane (30 mL) was heated under reflux overnight. The reaction mixture was added to water, and the mixture was extracted with ethyl acetate. The organic layer was washed with saturated brine, dried over anhydrous magnesium sulfate, and concentrated under reduced pressure. The residue was purified by silica gel column chromatography (ethyl acetate/hexane) to give the title compound (2267 mg) as a white solid.

MS (ESI+). found: 213.4

B) 9-[4-(1-methylethyl)phenyl]-3,4-dihydropyrido[2,1-c][1,2,4]thiadiazine 2,2-dioxide A mixture of 3-[4-(1-methylethyl)phenyl]pyridin-2-amine (700 mg) in dehydrated THF (15 mL) was added to a mixture of sodium hydride (60%, 659 mg) and 2-chloroethanesulfonyl chloride (1613 mg) in dehydrated THF (15 mL) under ice-cooling. The reaction mixture was stirred at room temperature overnight, and saturated aqueous sodium hydrogen carbonate solution and ethyl acetate were added. The resulting precipitate was collected by filtration, and washed with water and ethyl acetate to give the title compound (738 mg) as a white solid. The obtained solid was crystallized from acetonitrile and diisopropyl ether to give a white solid.

$^1$H NMR (300 MHz, DMSO-$d_6$) δ 1.23 (6H, d, J=7.2 Hz), 2.92 (1H, spt, J=6.9 Hz), 3.37-3.51 (2H, m), 4.55-4.72 (2H, m), 6.70 (1H, t, J=6.8 Hz), 7.22-7.34 (2H, m), 7.40-7.49 (2H, m), 7.60 (1H, dd, J=7.2, 1.9 Hz), 7.76 (1H, dd, J=6.6, 1.7 Hz).

mp 239-241° C.

Anal. Calcd for $C_{16}H_8N_2O_2S$: C, 63.55; H, 6.00; N, 9.26. Found: C, 63.37; H, 6.00; N, 9.28.

Example 24

The compound of Example 24 was produced in the same manner as in Example 15.

Example 25

9-{2-[4-(1-methylethyl)phenyl]ethyl}-3,4-dihydropyrido[2,1-c][1,2,4]thiadiazine 2,2-dioxide A) 3-{[4-(1-methylethyl)phenyl]ethynyl}pyridin-2-amine A mixture of bis(triphenylphosphine)palladium(0)dichloride (0.811 g), 3-bromopyridin-2-amine (2 g), 1-ethynyl-4- isopropylbenzene (1.667 g) and copper iodide(I) (0.22 g) in triethylamine (38.6 mL) was heated under reflux. Water was added to the reaction mixture, the mixture was filtered through celite, and the filtrate was extracted with ethyl acetate. The organic layer was washed with saturated brine, dried over anhydrous magnesium sulfate, and concentrated under reduced pressure.

The residue was purified by silica gel column chromatography (ethyl acetate/hexane) to give the title compound (1273 mg) as a pale-yellow solid.

MS (ESI+). found: 237.4.

B) 3-{2-[4-(1-methylethyl)phenyl]ethyl}pyridin-2-amine

A mixture of 10% palladium-carbon (50% wet, 50 mg) and 3-{[4-(1-methylethyl)phenyl]ethynyl}pyridin-2-amine (662.8 mg) in methanol (15 mL) was stirred under a hydrogen atmosphere at room temperature for 3 hr. The reaction mixture was filtered, a saturated aqueous sodium hydrogen carbonate solution was added to the filtrate, and the mixture was extracted with ethyl acetate. The organic layer was washed with saturated brine, dried over anhydrous magnesium sulfate, and concentrated under reduced pressure. The residue was purified by silica gel column chromatography (ethyl acetate/hexane) to give the title compound (246.6 mg) as a colorless oil.

MS (ESI+). found: 241.4.

C) 9-{2-[4-(1-methylethyl)phenyl]ethyl}-3,4-dihydropyrido[2,1-c][1,2,4]thiadiazine 2,2-dioxide A mixture of 3-{2-[4-(1-methylethyl)phenyl]ethyl}pyridin-2-amine (150 mg) in dehydrated THF (5 mL) was added to a mixture of sodium hydride (60%, 125 mg) and 2-chloroethanesulfonyl chloride (305 mg) in dehydrated THF (5 mL) under ice-cooling. The reaction mixture was stirred at room temperature for 2 hr, and saturated aqueous sodium hydrogen carbonate solution and ethyl acetate were added. The resulting precipitate was collected by filtration, and washed with water and ethyl acetate to give the title compound (149 mg) as a white solid. The obtained solid was crystallized from acetonitrile and diisopropyl ether to give a white solid.

$^1$H NMR (300 MHz, DMSO-$d_6$) δ 1.18 (6H, d, J=7.2 Hz), 2.63-2.96 (5H, m), 3.37-3.50 (2H, m), 4.50-4.68 (2H, m), 6.56 (1H, t, J=6.8 Hz), 7.03-7.30 (4H, m), 7.45 (1H, dd, J=7.2, 1.5 Hz), 7.65 (1H, dd, J=6.8, 1.5 Hz).

Anal. Calcd for $C_{18}H_{22}N_2O_2S$-0.25$H_2O$: C, 64.55; H, 6.77; N, 8.36.

Found: C, 64.46; H, 6.65; N, 8.34.

Example 26

9-{[4-(1-methylethyl)phenyl]ethynyl}-3,4-dihydropyrido[2,1-c][1,2,4]thiadiazine 2,2-dioxide A mixture of 3-{[4-(1-methylethyl)phenyl]ethynyl}pyridin-2-amine (150 mg) in dehydrated THF (5 mL) was added to a mixture of sodium hydride (60%, 127 mg) and 2-chloroethanesulfonyl chloride (310 mg) in dehydrated THF (5 mL) under ice-cooling. The reaction mixture was stirred at room temperature for 2 hr, and saturated aqueous sodium hydrogen carbonate solution and ethyl acetate were added. The resulting precipitate was collected by filtration, and washed with water and ethyl acetate to give the title compound (110 mg) as a white solid. The obtained solid was crystallized from acetonitrile and diisopropyl ether to give a white solid.

$^1$H NMR (300 MHz, DMSO-$d_6$) δ 1.21 (6H, d, J=7.2 Hz), 2.81-3.07 (1H, m), 3.39-3.56 (2H, m), 4.56-4.67 (2H, m), 6.64 (1H, t, J=7.0 Hz), 7.25-7.36 (2H, m), 7.40-7.49 (2H, m), 7.79 (1H, dd, J=6.8, 1.5 Hz), 7.87 (1H, dd, J=7.2, 1.5 Hz).

mp 258-262° C.

Anal. Calcd for $C_{18}H_{18}N_2O_2S$-0.125$H_2O$: C, 65.78; H, 5.60; N, 8.52.

Found: C, 65.75; H, 5.63; N, 8.51.

Example 27

N-(2,2-dioxido-3,4-dihydropyrido[2,1-c][1,2,4]thiadiazin-9-yl)-2,2,3,3-tetrafluoro-2,3-dihydro-1,4-benzodioxine-6-carboxamide

A) 2,2,3,3-tetrafluoro-2,3-dihydrobenzo[b][1,4]dioxine-6-carboxamide

To 2,2,3,3-tetrafluoro-2,3-dihydrobenzo[b][1,4]dioxine-6-carbonitrile (200 mg) were added concentrated sulfuric acid (2 mL) and water (0.3 mL) at room temperature. The reaction mixture was stirred at 40° C. for 3 hr, water was added and the mixture was stirred for 40 min at room temperature. The resulting solid was collected by filtration, washed with purified water, and dried under reduced pressure to give the title compound (190.6 mg).

$^1$H NMR (300 MHz, CDCl$_3$) δ 5.80 (2H, brs), 7.23 (1H, d, J=8.3 Hz), 7.58-7.70 (2H, m).

B) N-(2,2-dioxido-3,4-dihydropyrido[2,1-c][1,2,4]thiadiazin-9-yl)-2,2,3,3-tetrafluoro-2,3-dihydro-1,4-benzodioxine-6-carboxamide In the same manner as in Example 13, step B, the title compound was obtained from the compound of the above-mentioned A).

Example 28

9-biphenyl-4-yl-3,4,6,7,8,9-hexahydropyrido[2,1-c][1,2,4]thiadiazine 2,2-dioxide A mixture of 10% palladium-carbon (50% wet, 12 mg) and 9-biphenyl-4-yl-3,4-dihydropyrido[2,1-c][1,2,4]thiadiazine 2,2-dioxide (115 mg) in THF (50 mL) was stirred under a hydrogen atmosphere overnight. The reaction mixture was filtered, and the filtrate was concentrated to give the title compound (122 mg) as a white solid. The obtained solid was crystallized from acetonitrile, diisopropyl ether and hexane to give a white solid.

$^1$H NMR (300 MHz, DMSO-$d_6$) δ 1.64-1.91 (3H, m), 1.94-2.15 (1H, m), 3.18-3.38 (2H, m), 3.39-3.67 (2H, m), 3.70-4.06 (3H, m), 7.25-7.32 (2H, m), 7.32-7.40 (1H, m), 7.41-7.52 (2H, m), 7.56-7.63 (2H, m), 7.63-7.69 (2H, m).

mp 238-239° C.

Anal. Calcd for $C_{19}H_{20}N_2O_2S$: C, 67.03; H, 5.92; N, 8.23. Found: C, 66.75; H, 5.91; N, 8.14.

Example 29

9-{5-[4-(1-methylethyl)phenyl]-1,2,4-oxadiazol-3-yl}-3,4-dihydropyrido[2,1-c][1,2,4]thiadiazine 2,2-dioxide

A) 2-amino-N'-hydroxypyridine-3-carboxyamide

To a mixture of 2-aminopyridine-3-carbonitrile (4800 mg) and hydroxyamine hydrochloride (4200 mg) in ethanol (125 mL) was added a solution of sodium carbonate (6406 mg) in water (25 mL) under ice-cooling, and the mixture was stirred at room temperature overnight. The reaction mixture was concentrated under reduced pressure, the residue was added to water, and the mixture was extracted with ethyl acetate. The organic layer was washed with saturated brine, dried over anhydrous magnesium sulfate, and concentrated under reduced pressure to give the title compound (5442 mg) as a white solid.

MS (ESI+). found: 153.4.

B) 3-{5-[4-(1-methylethyl)phenyl]-1,2,4-oxadiazol-3-yl}pyridin-2-amine

A mixture of 2-amino-N'-hydroxypyridine-3-carboxyamide (1070 mg), HOBt.H$_2$O (1185 mg), EDCI HCl (1483 mg) and 4-isopropylbenzoic acid (1270 mg) in dehydrated DMF (40 mL) was stirred at room temperature overnight and at 80° C. for 24 hr. To the reaction mixture was added saturated aqueous sodium hydrogen carbonate solution, and the mixture was extracted with ethyl acetate. The organic layer was washed with saturated aqueous sodium hydrogen carbonate solution and saturated brine, dried over anhydrous magnesium sulfate, and concentrated under reduced pressure. The residue was purified by silica gel column chromatography (ethyl acetate/hexane) to give the title compound (302 mg) as a white solid.

MS (ESI+). found: 281.1.

C) 9-{5-[4-(1-methylethyl)phenyl]-1,2,4-oxadiazol-3-yl}-3,4-dihydropyrido[2,1-c][1,2,4]thiadiazine 2,2-dioxide In the same manner as in Example 14, step B, the title compound was obtained from the compound of the above-mentioned B).

Example 30

9-(4-cyclohexylphenyl)-3,4-dihydropyrido[2,1-c][1,2,4]thiadiazine 2,2-dioxide

A) 3-(4-cyclohexylphenyl)pyridin-2-amine

A mixture of 2M aqueous sodium carbonate solution (0.396 mL), tetrakis(triphenylphosphine)palladium(0) (30.5 mg), 4-cyclohexylphenylboronic acid (140 mg) and 3-bromopyridin-2-amine (91 mg) in 1,2-dimethoxyethane (20 mL) and water (5 mL) was stirred overnight under a nitrogen atmosphere at 80° C. The reaction mixture was added to water, and the mixture was extracted with ethyl acetate. The organic layer was washed with saturated brine, dried over anhydrous magnesium sulfate, and concentrated under reduced pressure. The residue was purified by silica gel column chromatography (ethyl acetate/hexane) to give the title compound (57.4 mg) as a pale-yellow solid.

MS (ESI+). found: 253.2.

B) 9-(4-cyclohexylphenyl)-3,4-dihydropyrido[2,1-c][1,2,4]thiadiazine 2,2-dioxide A mixture of 3-(4-cyclohexylphenyl)pyridin-2-amine (57 mg) in dehydrated THF (5 mL) was added to a mixture of sodium hydride (60%, 45.2 mg) and 2-chloroethanesulfonyl chloride (110 mg) in dehydrated THF (5 mL) under ice-cooling. The reaction mixture was stirred at room temperature overnight, and water was added. The resulting precipitate was collected by filtration, and washed with water and diisopropyl ether to give the title compound (40.3 mg) as a white solid. The obtained solid was crystallized from acetonitrile and diisopropyl ether to give a white solid.

$^1$H NMR (300 MHz, DMSO-d$_6$) δ 1.11-1.57 (5H, m), 1.62-1.93 (5H, m), 2.39-2.58 (1H, m), 3.36-3.54 (2H, m), 4.55-4.70 (2H, m), 6.69 (1H, t, J=6.8 Hz), 7.20-7.30 (2H, m), 7.37-7.46 (2H, m), 7.60 (1H, d, J=6.4 Hz), 7.75 (1H, d, J=6.4 Hz).

mp 294-298° C.

Example 31

9-(4-phenoxyphenyl)-3,4-dihydropyrido[2,1-c][1,2,4]thiadiazine 2,2-dioxide

A) 3-(4-phenoxyphenyl)pyridin-2-amine

A mixture of sodium carbonate (1.905 g), tetrakis(triphenylphosphine)palladium(0) (519 mg), 4-phenoxyphenylboronic acid (2.5 g) and 3-bromopyridin-2-amine (1.555 g) in 1,2-dimethoxyethane (60 mL) and water (12 mL) was stirred overnight at 80° C. The reaction mixture was added to water, and the mixture was extracted with ethyl acetate. The organic layer was washed with saturated brine, dried over anhydrous magnesium sulfate, and concentrated under reduced pressure. The residue was purified by silica gel column chromatography (ethyl acetate/hexane) to give the title compound (2.289 g) as a pale-yellow solid.

MS (ESI+). found: 263.1.

B) 9-(4-phenoxyphenyl)-3,4-dihydropyrido[2,1-c][1,2,4]thiadiazine 2,2-dioxide A mixture of 3-(4-phenoxyphenyl)pyridin-2-amine (47 mg) in dehydrated THF (5 mL) was added to a mixture of sodium hydride (60%, 35.8 mg) and 2-chloroethanesulfonyl chloride (88 mg) in dehydrated THF (5 mL) under ice-cooling. The reaction mixture was stirred at room temperature overnight, and water and hexane were added. The resulting precipitate was collected by filtration, and washed with water and ethyl acetate to give the title compound (53.2 mg) as a white solid. The obtained solid was crystallized from THF and diisopropyl ether to give a white solid.

$^1$H NMR (300 MHz, DMSO-d$_6$) δ 3.40-3.54 (2H, m), 4.59-4.73 (2H, m), 6.65-6.79 (1H, m), 6.96-7.14 (4H, m), 7.14-7.27 (1H, m), 7.34-7.50 (2H, m), 7.50-7.60 (2H, m), 7.60-7.71 (1H, m), 7.74-7.83 (1H, m).

mp 252-253° C.

Anal. Calcd for $C_{19}H_{16}N_2O_3S \cdot 0.25H_2O$: C, 63.94; H, 4.66; N, 7.85.

Found: C, 63.93; H, 4.55; N, 7.78.

Example 32

9-[4-(1-methylpropyl)phenyl]-3,4-dihydropyrido[2,1-c][1,2,4]thiadiazine 2,2-dioxide

A) 3-[4-(1-methylpropyl)phenyl]pyridin-2-amine

A mixture of sodium carbonate (412 mg), tetrakis(triphenylphosphine)palladium(0) (112 mg), 4-(1-methylpropyl)phenylboronic acid (450 mg) and 3-bromopyridin-2-amine (336 mg) in 1,2-dimethoxyethane (15 mL) and water (3 mL) was stirred under a nitrogen atmosphere at 80° C. overnight. The reaction mixture was added to water, and the mixture was extracted with ethyl acetate. The organic layer was washed with saturated brine, dried over anhydrous magnesium sulfate, and concentrated under reduced pressure. The residue was purified by silica gel column chromatography (ethyl acetate/hexane) to give the title compound (392 mg) as a pale-yellow solid.

MS (ESI+). found: 227.3.

B) 9-[4-(1-methylpropyl)phenyl]-3,4-dihydropyrido[2,1-c][1,2,4]thiadiazine 2,2-dioxide A mixture of 3-[4-(1-methylpropyl)phenyl]pyridin-2-amine (300 mg) in dehydrated THF (5 mL) was added to a mixture of sodium hydride (60%, 265 mg) and 2-chloroethanesulfonyl chloride (648 mg) in dehydrated THF (5 mL) under ice-cooling. The reaction mixture was stirred at room temperature overnight, and water and hexane were added. The resulting precipitate was collected by filtration, and washed with water and diisopropyl ether to give the title compound (376 mg) as a white solid. The obtained solid was crystallized from THF, acetonitrile and diisopropyl ether to give a white solid.

$^1$H NMR (300 MHz, DMSO-$d_6$) δ 0.81 (3H, t, J=7.3 Hz), 1.21 (3H, d, J=7.2 Hz), 1.59 (2H, quin, J=7.3 Hz), 2.62 (1H, sxt, J=7.1 Hz), 3.39-3.50 (2H, m), 4.57-4.72 (2H, m), 6.70 (1H, t, J=7.0 Hz), 7.19-7.29 (2H, m), 7.40-7.49 (2H, m), 7.61 (1H, dd, J=7.3, 1.7 Hz), 7.76 (1H, dd, J=6.6, 1.7 Hz).

mp 237-239° C.

Anal. Calcd for $C_{17}H_{20}N_2O_2S$-0.1$H_2O$: C, 64.16; H, 6.40; N, 8.80.

Found: C, 64.21; H, 6.39; N, 8.73.

Example 33

9-[4-(1-methylethoxyl)phenyl]-3,4-dihydropyrido[2,1-c][1,2,4]thiadiazine 2,2-dioxide

A) 3-[4-(1-methylethoxyl)phenyl]pyridin-2-amine

A mixture of sodium carbonate (906 mg), tetrakis(triphenylphosphine)palladium(0) (247 mg), 4-(1-methylethoxyl)phenylboronic acid (1000 mg) and 3-bromopyridin-2-amine (0.739 g) in 1,2-dimethoxyethane (50 mL) and water (10 mL) was stirred under a nitrogen atmosphere at 80° C. overnight. The reaction mixture was added to water, and the mixture was extracted with ethyl acetate. The organic layer was washed with saturated brine, dried over anhydrous magnesium sulfate, and concentrated under reduced pressure. The residue was purified by silica gel column chromatography (ethyl acetate/hexane) to give the title compound (883 mg) as a pale-yellow solid.

MS (ESI+). found: 229.1.

B) 9-[4-(1-methylethoxyl)phenyl]-3,4-dihydropyrido[2,1-c][1,2,4]thiadiazine 2,2-dioxide A mixture of 3-[4-(1-methylethoxyl)phenyl]pyridin-2-amine (350 mg) in dehydrated THF (5 mL) was added to a mixture of sodium hydride (60%, 307 mg) and 2-chloroethanesulfonyl chloride (750 mg) in dehydrated THF (5 mL) under ice-cooling. The reaction mixture was stirred at room temperature overnight, and water and hexane were added. The resulting precipitate was collected by filtration, and washed with water and diisopropyl ether to give the title compound (360 mg) as a white solid. The obtained solid was crystallized from THF, acetonitrile and diisopropyl ether to give a white solid.

$^1$H NMR (300 MHz, DMSO-$d_6$) δ 1.28 (6H, d, J=6.0 Hz), 3.38-3.55 (2H, m), 4.54-4.79 (3H, m), 6.68 (1H, t, J=7.0 Hz), 6.88-7.01 (2H, m), 7.39-7.52 (2H, m), 7.58 (1H, dd, J=7.2, 1.9 Hz), 7.73 (1H, dd, J=6.8, 1.5 Hz).

mp 245-247° C.

Anal. Calcd for $C_{16}H_{18}N_2O_3S$: C, 60.36; H, 5.70; N, 8.80.

Found: C, 60.13; H, 5.57; N, 8.84.

Example 34

9-[4-(trifluoromethoxy)phenyl]-3,4-dihydropyrido[2,1-c][1,2,4]thiadiazine 2,2-dioxide

A) 3-[4-(trifluoromethoxy)phenyl]pyridin-2-amine

A mixture of sodium carbonate (0.903 g), tetrakis(triphenylphosphine)palladium(0) (0.246 g), 4-(trifluoromethoxy)phenylboronic acid (1.14 g) and 3-bromopyridin-2-amine (0.737 g) in 1,2-dimethoxyethane (50 mL) and water (10 mL) was stirred under a nitrogen atmosphere at 80° C. overnight. The reaction mixture was added to water, and the mixture was extracted with ethyl acetate. The organic layer was washed with saturated brine, dried over anhydrous magnesium sulfate, and concentrated under reduced pressure. The residue was purified by silica gel column chromatography (ethyl acetate/hexane) to give the title compound (1.069 g) as a pale-yellow solid.

MS (ESI+). found: 255.1.

B) 9-[4-(trifluoromethoxy)phenyl]-3,4-dihydropyrido[2,1-c][1,2,4]thiadiazine 2,2-dioxide A mixture of 3-[4-(trifluoromethoxy)phenyl]pyridin-2-amine (350 mg) in dehydrated THF (5 mL) was added to a mixture of sodium hydride (60%, 275 mg) and 2-chloroethanesulfonyl chloride (673 mg) in dehydrated THF (5 mL) under ice-cooling. The reaction mixture was stirred at room temperature overnight, and water and hexane were added. The resulting precipitate was collected by filtration, and washed with water and diisopropyl ether to give the title compound (333 mg) as a white solid. The obtained solid was crystallized from THF, acetonitrile and diisopropyl ether to give a white solid.

$^1$H NMR (300 MHz, DMSO-$d_6$) δ 3.39-3.53 (2H, m), 4.56-4.75 (2H, m), 6.73 (1H, t, J=7.0 Hz), 7.35-7.49 (2H, m), 7.58-7.75 (3H, m), 7.81 (1H, dd, J=6.8, 1.5 Hz).

mp 249-251° C.

Anal. Calcd for $C_{14}H_{11}F_3N_2O_3S$-0.2$H_2O$: C, 48.33; H, 3.30; N, 8.05.

Found: C, 48.43; H, 3.12; N, 8.09.

Example 35

9-(4-tert-butylphenyl)-3,4-dihydropyrido[2,1-c][1,2,4]thiadiazine 2,2-dioxide

A) 3-(4-tert-butylphenyl)pyridin-2-amine

A mixture of sodium carbonate (1.31 g), tetrakis(triphenylphosphine)palladium(0) (0.357 g), 4-tert-butylphenylboronic acid (1.43 g) and 3-bromopyridin-2-amine (1.069 g) in 1,2-dimethoxyethane (50 mL) and water (10 mL) was stirred under a nitrogen atmosphere at 80° C. overnight. The reaction mixture was added to water, and the mixture was extracted with ethyl acetate. The organic layer was washed with saturated brine, dried over anhydrous magnesium sulfate, and concentrated under reduced pressure. The residue was purified by silica gel column chromatography (ethyl acetate/hexane) to give the title compound (1.274 g) as a pale-yellow solid.

MS (ESI+). found: 227.0.

B) 9-(4-tert-butylphenyl)-3,4-dihydropyrido[2,1-c][1,2,4]thiadiazine 2,2-dioxide A mixture of 3-(4-tert-butylphenyl)pyridin-2-amine (350 mg) in dehydrated THF (5 mL) was added to a mixture of sodium hydride (60%, 309 mg) and 2-chloroethanesulfonyl chloride (756 mg) in dehydrated THF (5 mL) under ice-cooling. The reaction mixture was stirred at room temperature overnight, and water and hexane were added. The resulting precipitate was collected by filtration, and washed with water and diisopropyl ether to give the title compound (376 mg) as a white solid. The obtained solid was crystallized from THF, acetonitrile and diisopropyl ether to give a white solid.

$^1$H NMR (300 MHz, DMSO-$d_6$) δ 1.31 (9H, s), 3.38-3.52 (2H, m), 4.52-4.75 (2H, m), 6.70 (1H, t, J=6.8 Hz), 7.35-7.53 (4H, m), 7.61 (1H, dd, J=7.2, 1.5 Hz), 7.76 (1H, dd, J=6.8, 1.5 Hz).

mp 291-292° C.

Anal. Calcd for $C_{17}H_{20}N_2O_2S$: C, 64.53; H, 6.37; N, 8.85. Found: C, 64.26; H, 6.38; N, 8.86.

Example 36

N'-{[4-(1-methylethyl)phenyl]carbonyl}-3,4-dihydropyrido[2,1-c][1,2,4]thiadiazine-9-carbohydrazide 2,2-dioxide

A) methyl 4-(1-methylethyl)benzoate

A mixture of 4-isopropylbenzoic acid (10 g) and sulfuric acid (5 mL) in methanol (50 mL) was heated under reflux overnight, hydrazine monohydrate (3.66 g) was added, and the mixture was heated under reflux overnight. The reaction mixture was added to a saturated aqueous sodium hydrogen carbonate solution, and the mixture was extracted with ethyl acetate. The organic layer was washed with saturated aqueous sodium hydrogen carbonate solution and saturated brine, dried over anhydrous magnesium sulfate and concentrated under reduced pressure to give the title compound (10.32 g) as a yellow oil.

MS (ESI+). found: 179.0.

B) 4-(1-methylethyl)benzohydrazide

A mixture of methyl 4-(1-methylethyl)benzoate (10 g) and hydrazine monohydrate (5.62 g) in methanol (50 mL) was heated under reflux overnight. To the reaction mixture was added toluene (50 mL), and the mixture was heated at 120° C. overnight. The reaction mixture was added to a saturated aqueous sodium hydrogen carbonate solution, and the mixture was extracted with ethyl acetate. The organic layer was washed with saturated brine, dried over anhydrous magnesium sulfate and concentrated under reduced pressure. The residue was washed with hexane and diisopropyl ether to give the title compound (9.22 g) as a white solid.

MS (ESI+). found: 179.0.

C) 2-aminopyridine-3-carboxylic acid

A mixture of methyl 2-aminonicotinate (4 g) and 2M aqueous sodium hydroxide solution (35 mL) in THF (50 mL) was stirred at room temperature overnight. The reaction mixture was neutralized with 1M hydrochloric acid, and extracted with ethyl acetate. The aqueous layer was acidified with 1M hydrochloric acid, and extracted with THF. The organic layers were combined, washed with water and saturated brine, dried over anhydrous magnesium sulfate and concentrated under reduced pressure to give the title compound (1.78 g) as a white solid.

MS (ESI+). found: 139.3.

D) 2-amino-N'-{[4-(1-methylethyl)phenyl]carbonyl}pyridine-3-carbohydrazide

A mixture of 4-(1-methylethyl)benzohydrazide (2194 mg), HOBt.H$_2$O (2073 mg), EDCI HCl (2595 mg) and 2-aminopyridine-3-carboxylic acid (1700 mg) in dehydrated DMF (50 mL) was stirred at 60° C. overnight. The reaction mixture was added to a saturated aqueous sodium hydrogen carbonate solution, and the mixture was extracted with ethyl acetate. The organic layer was washed with saturated aqueous sodium hydrogen carbonate solution and saturated brine, dried over anhydrous magnesium sulfate and concentrated under reduced pressure. The residue was crystallized from a mixture of ethyl acetate and diisopropyl ether to give the title compound (2.4489 g) as a white solid. The mother liquor was purified by silica gel column chromatography (ethyl acetate/hexane) to give the title compound (276.1 mg) as a white solid.

MS (ESI+). found: 299.3.

E) N'-{[4-(1-methylethyl)phenyl]carbonyl}-3,4-dihydropyrido[2,1-c][1,2,4]thiadiazine-9-carbohydrazide 2,2-dioxide A mixture of Lawesson reagent (746 mg) and 2-amino-N'-{[4-(1-methylethyl)phenyl]carbonyl}pyridine-3-carbohydrazide (1000 mg) in toluene (50 mL) and dehydrated THF (50 mL) was stirred at 80° C. overnight. The resulting precipitate was collected by filtration, and washed with THF to give a white solid (1082.2 mg). A mixture of the obtained solid (80 mg) in DMSO (15 mL) was added to a mixture of sodium hydride (60%, 32.4 mg) and 2-chloroethanesulfonyl chloride (220 mg) in dehydrated THF (15 mL) under ice-cooling, and the reaction mixture was stirred at room temperature under a nitrogen atmosphere overnight. The reaction mixture was added to water, and the mixture was extracted with ethyl acetate. The organic layer was washed with saturated brine, dried over anhydrous magnesium sulfate and concentrated under reduced pressure. The residue was purified by aminopropyl silica-bound silica gel column chromatography (ethyl acetate/methanol) to give the title compound (27.3 mg) as a white solid.

Example 37

The compound of Example 37 was produced in the same manner as in Example 13.

Example 38

9-(4-tert-butylphenyl)-3,4,6,7,8,9-hexahydropyrido[2,1-c][1,2,4]thiadiazine 2,2-dioxide A mixture of 10% palladium-carbon (50% wet, 15 mg) and 9-(4-tert-butylphenyl)-3,4-dihydropyrido[2,1-c][1,2,4]thiadiazine 2,2-dioxide (150 mg) in THF (25 mL) and ethanol (25 mL) was stirred under a hydrogen atmosphere at room temperature, and stirred under a hydrogen atmosphere (3.5 atm) for 1 hr. To the reaction mixture was added 5% rhodium-carbon (50% wet, 15 mg), and the mixture was stirred under a hydrogen atmosphere (3.5 atm) for 4 hr. To the reaction mixture was added platinum dioxide (15 mg) and the mixture was stirred under a hydrogen atmosphere for 2 hr. The reaction mixture was filtered, the filtrate was concentrated, and the residue was crystallized from THF and diisopropyl ether to give the title compound (35 mg) as a white solid.

$^1$H NMR (300 MHz, DMSO-$d_6$) δ 1.28 (9H, s), 1.61-1.83 (3H, m), 1.83-2.09 (1H, m), 3.22-3.30 (2H, m), 3.38-3.56 (2H, m), 3.66-3.93 (3H, m), 7.06-7.18 (2H, m), 7.28-7.37 (2H, m).

mp 232-236° C.

Anal. Calcd for $C_{17}H_{24}N_2O_2S$-0.125$H_2O$: C, 63.27; H, 7.57; N, 8.68.

Found: C, 63.11; H, 7.71; N, 8.44.

Example 39

9-[4-(1-methylpropyl)phenyl]-3,4,6,7,8,9-hexahydropyrido[2,1-c][1,2,4]thiadiazine 2,2-dioxide A mixture of 5% rhodium-carbon (50% wet, 15 mg) and 9-[4-(1-methylpropyl)phenyl]-3,4-dihydropyrido[2,1-c][1,2,4]thiadiazine 2,2-dioxide (150 mg) in THF (30 mL) and ethanol (30 mL) was stirred under a hydrogen atmosphere (3 atm) at room temperature for 7 hr. The reaction mixture was filtered, and the filtrate was concentrated to give the title compound (132 mg) as a brown solid. The obtained solid was crystallized from THF and diisopropyl ether to give a brown solid.

$^1$H NMR (300 MHz, DMSO-$d_6$) δ 0.78 (3H, t, J=7.4 Hz), 1.18 (3H, d, J=7.2 Hz), 1.54 (2H, quin, J=7.2 Hz), 1.62-1.81 (3H, m), 1.87-2.11 (1H, m), 2.50-2.67 (1H, m), 3.15-3.36 (2H, m), 3.37-3.56 (2H, m), 3.66-3.98 (3H, m), 7.03-7.22 (4H, m).

Anal. Calcd for $C_{17}H_{24}N_2O_2S$-0.25$H_2O$: C, 62.83; H, 7.60; N, 8.62.

Found: C, 62.85; H, 7.56; N, 8.37.

Example 40

9-[4-(1-methylethoxyl)phenyl]-3,4,6,7,8,9-hexahydropyrido[2,1-c][1,2,4]thiadiazine 2,2-dioxide A mixture of 5% rhodium-carbon (50% wet, 10 mg) and 9-[4-(1-methylethoxyl)phenyl]-3,4-dihydropyrido[2,1-c][1,2,4]thiadiazine 2,2-dioxide (110 mg) in THF (30 mL) and ethanol (30 mL) was stirred under a hydrogen atmosphere (3 atm) at room temperature for 7 hr. The reaction mixture was filtered, the filtrate was concentrated to give the title compound (121 mg) as a white solid. The obtained solid was crystallized from THF and diisopropyl ether to give a white solid.

$^1$H NMR (300 MHz, DMSO-$d_6$) δ 1.25 (6H, d, J=6.1 Hz), 1.61-1.81 (3H, m), 1.84-2.07 (1H, m), 3.17-3.30 (2H, m), 3.36-3.55 (2H, m), 3.64-3.72 (1H, m), 3.72-3.94 (2H, m), 4.57 (1H, quin, J=6.1 Hz), 6.76-6.90 (2H, m), 7.02-7.15 (2H, m).

mp 191-192° C.

Anal. Calcd for $C_{16}H_{22}N_2O_3S$-0.25$H_2O$: C, 58.78; H, 6.94; N, 8.57.

Found: C, 58.82; H, 6.93; N, 8.52.

Example 41

9-[4-(trifluoromethoxy)phenyl]-3,4,6,7,8,9-hexahydropyrido[2,1-c][1,2,4]thiadiazine 2,2-dioxide A mixture of 5% rhodium-carbon (50% wet, 15 mg) and 9-[4-(trifluoromethoxy)phenyl]-3,4-dihydropyrido[2,1-c][1,2,4]thiadiazine 2,2-dioxide (150 mg) in THF (30 mL) and ethanol (30 mL) was stirred under a hydrogen atmosphere at room temperature for 7 hr. The reaction mixture was filtered, the filtrate was concentrated to give the title compound (153 mg) as a gray white solid. The obtained solid was crystallized from THF and diisopropyl ether to give a gray white solid.

$^1$H NMR (300 MHz, DMSO-$d_6$) δ 1.64-1.87 (3H, m), 2.02 (1H, d, J=6.0 Hz), 3.22-3.30 (2H, m), 3.38-3.60 (2H, m), 3.70-3.94 (3H, m), 7.24-7.40 (4H, m).

mp 207-208° C.

Anal. Calcd for $C_{14}H_{15}N_2O_3SF_3$-0.2$H_2O$: C, 47.78; H, 4.41; N, 7.96.

Found: C, 47.89; H, 4.38; N, 7.96.

Example 42

9-[4-(1-methylethyl)phenyl]-3,4,6,7,8,9-hexahydropyrido[2,1-c][1,2,4]thiadiazine 2,2-dioxide A mixture of 5% rhodium-carbon (50% wet, 15 mg) and 9-[4-(1-methylethyl)phenyl]-3,4-dihydropyrido[2,1-c][1,2,4]thiadiazine 2,2-dioxide (150 mg) in THF (30 mL) and ethanol (30 mL) was stirred under a hydrogen atmosphere at room temperature for 7 hr. The reaction mixture was filtered, and the filtrate was concentrated to give the title compound (143 mg) as a gray white solid. The obtained solid was crystallized from THF and diisopropyl ether to give a white solid.

$^1$H NMR (300 MHz, DMSO-$d_6$) δ 1.20 (6H, d, J=7.2 Hz), 1.61-1.82 (3H, m), 1.86-2.09 (1H, m), 2.86 (1H, quin, J=6.9 Hz), 3.22-3.30 (2H, m), 3.37-3.58 (2H, m), 3.64-3.96 (3H, m), 7.03-7.14 (2H, m), 7.14-7.24 (2H, m).

mp 198-203° C.

Anal. Calcd for $C_{16}H_{22}N_2O_2S$-0.125$H_2O$: C, 62.26; H, 7.27; N, 9.08.

Found: C, 62.19; H, 7.34; N, 8.99.

Example 43

9-(4-phenoxyphenyl)-3,4,6,7,8,9-hexahydropyrido[2,1-c][1,2,4]thiadiazine 2,2-dioxide A mixture of 9-(4-phenoxyphenyl)-3,4-dihydropyrido[2,1-c][1,2,4]thiadiazine 2,2-dioxide (173 mg) and 5% rhodium-carbon (50% wet, 17 mg) in THF (50 mL) and ethanol (20 mL) was stirred under a hydrogen atmosphere at room temperature overnight. To the reaction mixture was added platinum dioxide (17 mg), and the mixture was stirred under a hydrogen atmosphere at room temperature for 7 hr. The reaction mixture was filtered through celite, and the filtrate was concentrated under reduced pressure. The residue was purified by aminopropyl silica-bound silica gel column chromatography (ethyl acetate/methanol) to give the title compound (153 mg) as a white solid. The obtained solid was crystallized from acetonitrile and diisopropyl ether.

$^1$H NMR (300 MHz, DMSO-$d_6$) δ 1.63-1.84 (3H, m), 1.86-2.07 (1H, m), 3.28 (2H, t, J=6.4 Hz), 3.48 (2H, dq, J=12.4, 6.4 Hz), 3.66-3.90 (3H, m), 6.89-6.98 (2H, m), 6.98-7.05 (2H, m), 7.10-7.18 (1H, m), 7.18-7.27 (2H, m), 7.34-7.46 (2H, m).

Example 44

9-biphenyl-4-yl-3,4-dihydropyrido[2,1-c][1,2,4]thiadiazine 2,2-dioxide

Tetrakis(triphenylphosphine)palladium(0) (32.9 mg) was added to a mixture of 2M aqueous sodium carbonate solution (0.428 mL), 9-bromo-3,4-dihydropyrido[2,1-c][1,2,4]thiadiazine 2,2-dioxide (150 mg) and biphenyl-4-ylboronic acid (135 mg) in 1,2-dimethoxyethane (5.701 mL). The reaction mixture was stirred under a nitrogen atmosphere at 100° C. overnight, added to water, and the mixture was extracted with ethyl acetate. The organic layer was washed with saturated brine, dried over anhydrous magnesium sulfate and concentrated under reduced pressure. The residue was purified by silica gel column chromatography (ethyl acetate/hexane, then ethyl acetate/methanol) to give the title compound (44.5 mg) as a pale-brown solid.

$^1$H NMR (300 MHz, DMSO-$d_6$) δ 3.37-3.53 (2H, m), 4.60-4.74 (2H, m), 6.74 (1H, t, J=7.0 Hz), 7.34-7.44 (1H, m), 7.44-7.54 (2H, m), 7.58-7.67 (2H, m), 7.67-7.76 (5H, m), 7.80 (1H, dd, J=6.8, 1.5 Hz).

MS (API+). found: 337.3

Example 45

The compound of Example 45 was produced in the same manner as in Example 44.

Example 46

9-naphthalen-2-yl-3,4-dihydropyrido[2,1-c][1,2,4]thiadiazine 2,2-dioxide

A) 3-(naphthalen-2-yl)pyridin-2-amine

To a solution of 3-bromopyridin-2-amine (1.0 g) in 1,2-dimethoxyethane (50 mL) were added naphthalen-2-ylboronic acid (1.292 g), sodium carbonate (1.225 g), tetrakis(triphenylphosphine)palladium(0) (0.334 g) and water (10 mL) at room temperature. The reaction mixture was stirred under a nitrogen atmosphere at 80° C. for 5 hr, water was added, and the mixture was extracted with ethyl acetate. The extract was washed with saturated brine, dried over anhydrous sodium sulfate and the solvent was evaporated under reduced pressure. The residue was washed with acetonitrile to give the title compound (0.876 g).

$^1$H NMR (300 MHz, DMSO-$d_6$) δ 5.65 (2H, s), 6.70 (1H, dd, J=7.2, 4.9 Hz), 7.44 (1H, dd, J=7.2, 1.9 Hz), 7.51-7.60 (3H, m), 7.91-8.03 (5H, m).

B) 9-naphthalen-2-yl-3,4-dihydropyrido[2,1-c][1,2,4]thiadiazine 2,2-dioxide

To a suspension of 60% sodium hydride (0.79 g) in THF (20 mL) was added 2-chloroethanesulfonyl chloride (1.93 g) under ice-cooling. The reaction mixture was stirred under ice-cooling for 5 min. Then, a solution of 3-(naphthalen-2-yl)pyridin-2-amine (0.87 g) in THF (20 mL) was added. The reaction mixture was stirred at room temperature overnight and at 50° C. for 1 hr, and water and hexane were added under ice-cooling. The resulting solid was collected by filtration, washed with diisopropyl ether, and dried under reduced pressure to give the title compound (0.88 g).

$^1$H NMR (300 MHz, DMSO-$d_6$) δ 3.43-3.56 (2H, m), 4.62-4.74 (2H, m), 6.76 (1H, t, J=7.0 Hz), 7.50-7.59 (2H, m), 7.68 (1H, dd, J=8.7, 1.5 Hz), 7.75 (1H, dd, J=7.2, 1.1 Hz), 7.83 (1H, dd, J=6.6, 0.9 Hz), 7.88-8.01 (4H, m).

Example 47

9-(3-fluorobiphenyl-4-yl)-3,4-dihydropyrido[2,1-c][1,2,4]thiadiazine 2,2-dioxide A) 3-(3-fluorobiphenyl-4-yl)pyridin-2-amine To a solution of 3-bromopyridin-2-amine (1.0 g) in 1,2-dimethoxyethane (50 mL) were added 3-fluorobiphenyl-4-ylboronic acid (1.623 g), sodium carbonate (1.225 g), tetrakis(triphenylphosphine)palladium(0) (0.334 g), and water (10 mL) at room temperature. The reaction mixture was stirred under a nitrogen atmosphere at 80° C. for 4 hr, water was added, and the mixture was extracted with ethyl acetate. The extract was washed with saturated brine, and dried over anhydrous sodium sulfate. The solvent was evaporated under reduced pressure. The residue was purified by recrystallization (THF/diisopropyl ether) to give the title compound (1.528 g).

$^1$H NMR (300 MHz, DMSO-$d_6$) δ 5.74 (2H, brs), 6.68 (1H, dd, J=7.2, 4.9 Hz), 7.35-7.46 (4H, m), 7.47-7.55 (2H, m), 7.56-7.65 (3H, m), 7.98 (1H, dd, J=4.9, 1.9 Hz).

B) 9-(3-fluorobiphenyl-4-yl)-3,4-dihydropyrido[2,1-c][1,2,4]thiadiazine 2,2-dioxide To a suspension of 60% sodium hydride (0.76 g) in THF (20 mL) was added 2-chloroethanesulfonyl chloride (1.85 g) under ice-cooling. The reaction mixture was stirred under ice-cooling for 5 min, and a solution of 3-(3-fluorobiphenyl-4-yl)pyridin-2-amine (1.0 g) in THF (20 mL) was added. The reaction mixture was stirred at room temperature overnight, and water and hexane were added under ice-cooling. The resulting solid was collected by filtration, washed with diisopropyl ether, and dried under reduced pressure to give the title compound (1.06 g).

$^1$H NMR (300 MHz, DMSO-$d_6$) δ 3.46-3.54 (2H, m), 4.63-4.72 (2H, m), 6.75 (1H, t, J=7.0 Hz), 7.39-7.64 (8H, m), 7.76 (1H, dd, J=7.2, 1.9 Hz), 7.83 (1H, dd, J=6.8, 1.5 Hz).

Example 48

9-(3-fluorobiphenyl-4-yl)-3,4,6,7,8,9-hexahydropyrido[2,1-c][1,2,4]thiadiazine 2,2-dioxide To a solution of 9-(3-fluorobiphenyl-4-yl)-3,4-dihydropyrido[2,1-c][1,2,4]thiadiazine 2,2-dioxide (200 mg) in THF/methanol (30 mL/30 mL) was added 10% palladium carbon (50 mg). The reaction mixture was stirred under a hydrogen atmosphere at 50° C. for 1 day. 5% Rhodium carbon (100 mg) was added, and the reaction mixture was stirred under a hydrogen atmosphere at room temperature for 7 hr, and insoluble material was filtered off through celite. The filtrate was concentrated under reduced pressure, and the obtained residue was purified by recrystallization (methanol-THF/diisopropyl ether) to give the title compound (154.4 mg).

$^1$H NMR (300 MHz, DMSO-d$_6$) δ 1.66-1.92 (3H, m), 1.94-2.13 (1H, m), 3.40-3.67 (3H, m), 3.72-3.99 (3H, m), 7.05-7.28 (2H, m), 7.30-7.70 (7H, m).

Example 49

9-naphthalen-2-yl-3,4,6,7,8,9-hexahydropyrido[2,1-c][1,2,4]thiadiazine 2,2-dioxide To a solution of 9-naphthalen-2-yl-3,4-dihydropyrido[2,1-c][1,2,4]thiadiazine 2,2-dioxide (150 mg) in THF/methanol (30 mL/30 mL) was added platinum (IV) oxide (50 mg). The reaction mixture was stirred under a hydrogen atmosphere at room temperature for 7 hr, and insoluble material was filtered off through celite. The filtrate was concentrated under reduced pressure, and the obtained residue was purified by recrystallization (methanol-THF/diisopropyl ether) to give the title compound (104.7 mg).

$^1$H NMR (300 MHz, CDCl$_3$) δ 1.74-2.29 (4H, m), 3.26-3.37 (2H, m), 3.40-3.60 (2H, m), 3.87-4.10 (3H, m), 7.30 (1H, d, J=1.9 Hz), 7.42-7.51 (2H, m), 7.56-7.63 (1H, m), 7.75-7.85 (3H, m).

Example 50

9-(5-phenylthiophen-2-yl)-3,4-dihydropyrido[2,1-c][1,2,4]thiadiazine 2,2-dioxide A) 3-(5-phenylthiophen-2-yl)pyridin-2-amine A mixture of sodium carbonate (799 mg), tetrakis(triphenylphosphine)palladium(0) (218 mg), 3-bromopyridin-2-amine (652 mg) and 5-phenylthiophen-2-ylboronic acid (1000 mg) in water (10 mL) and 1,2-dimethoxyethane (50 mL) was stirred under a nitrogen atmosphere at 80° C. overnight. The reaction mixture was added to water, and the mixture was extracted with ethyl acetate. The organic layer was washed with saturated brine, dried over anhydrous magnesium sulfate and concentrated under reduced pressure. The residue was purified by silica gel column chromatography (ethyl acetate/hexane) to give the title compound (579 mg) as a dark yellow solid.

MS (ESI+). found: 253.2.

B) 9-(5-phenylthiophen-2-yl)-3,4-dihydropyrido[2,1-c][1,2,4]thiadiazine 2,2-dioxide A mixture of 3-(5-phenylthiophen-2-yl)pyridin-2-amine (250 mg) in dehydrated THF (10 mL) was added to a mixture of sodium hydride (60%, 198 mg) and 2-chloroethanesulfonyl chloride (485 mg) in dehydrated THF (10 mL) under ice-cooling, and the mixture was stirred at room temperature overnight. The reaction mixture was added to water, and the resulting precipitate was washed with water and diisopropyl ether to give the title compound (262 mg) as a yellow solid. The obtained solid was crystallized from acetonitrile to give a yellow solid.

$^1$H NMR (300 MHz, DMSO-d$_6$) δ 3.46-3.63 (2H, m), 4.63-4.76 (2H, m), 6.77 (1H, dd, J=7.6, 6.8 Hz), 7.27-7.39 (1H, m), 7.39-7.50 (2H, m), 7.52 (1H, d, J=4.2 Hz), 7.65-7.75 (2H, m), 7.76-7.85 (2H, m), 8.25 (1H, dd, J=7.6, 1.5 Hz).

mp 241-242° C.

Anal. Calcd for C$_{17}$H$_{14}$N$_2$O$_2$S$_2$: C, 59.63; H, 4.12; N, 8.18. Found: C, 59.37; H, 4.12; N, 8.03.

Example 51

9-{(E)-2-[4-(1-methylethyl)phenyl]ethenyl}-3,4-dihydropyrido[2,1-c][1,2,4]thiadiazine 2,2-dioxide A) 4,4,5,5-tetramethyl-2-{(E)-2-[4-(1-methylethyl)phenyl]ethenyl}-1,3,2-dioxaborolane A mixture of triethylamine (246 mg), 1-ethynyl-4-isopropylbenzene (3500 mg), 4,4,5,5-tetramethyl-1,3,2-dioxaborolane (3417 mg) and zirconocene chloride hydride (626 mg) was stirred at 80° C. overnight. To the reaction mixture was added hexane, and the mixture was filtered. The filtrate was concentrated under reduced pressure, and the residue was purified by silica gel column chromatography (ethyl acetate/hexane) to give the title compound (6030 mg) as a yellow solid.

$^1$H NMR (300 MHz, CDCl$_3$) δ 1.24 (6H, d, J=7.2 Hz), 1.31 (12H, s), 2.78-3.02 (1H, m), 6.11 (1H, d, J=18.1 Hz), 7.20 (2H, d, J=7.9 Hz), 7.31-7.47 (3H, m).

B) 9-{(E)-2-[4-(1-methylethyl)phenyl]ethenyl}-3,4-dihydropyrido[2,1-c][1,2,4]thiadiazine 2,2-dioxide In the same manner as in Example 14, step B, the title compound was obtained from the compound of the above-mentioned A).

Example 52

9-{[4-(1-methylethyl)benzyl]oxy}-3,4-dihydropyrido[2,1-c][1,2,4]thiadiazine 2,2-dioxide A) 3-{[4-(1-methylethyl)benzyl]oxy}pyridin-2-amine A mixture of cesium carbonate (2.82 g), 1,10-phenanthrolin (0.208 g), (4-isopropylphenyl)methanol (8.68 g), 3-bromopyridin-2-amine (1 g) and copper (I) iodide (0.110 g) in toluene (10 mL) was stirred under a nitrogen atmosphere at 110° C. overnight, and at 130° C. for 5 hr. The reaction mixture was added to saturated brine, and the mixture was extracted with ethyl acetate. The organic layer was washed with saturated brine, dried over anhydrous magnesium sulfate and concentrated under reduced pressure. The residue was purified by silica gel column chromatography (ethyl acetate/hexane) to give the title compound (0.92 g) as a pale-yellow solid.

MS (ESI+). found: 243.1.

B) 9-{[4-(1-methylethyl)benzyl]oxy}-3,4-dihydropyrido[2,1-c][1,2,4]thiadiazine 2,2-dioxide In the same manner as in Example 14, step B, the title compound was obtained from the compound of the above-mentioned A).

Example 53

9-(5-phenylfuran-2-yl)-3,4-dihydropyrido[2,1-c][1,2,4]thiadiazine 2,2-dioxide

A) 3-furan-2-ylpyridin-2-amine

In the same manner as in Example 14, step A, the title compound (2600 mg) was obtained as a yellow solid from furan-2-boronic acid (2500 mg) and 3-bromopyridin-2-amine (2974 mg).

MS (ESI+). found: 161.0.

B) 3-(5-bromofuran-2-yl)pyridin-2-amine hydrobromide

A mixture of bromine (1425 mg) in acetic acid (30 mL) was added to a mixture of 3-furan-2-ylpyridin-2-amine (1500 mg) in acetic acid (30 mL) under ice-cooling, and the reaction mixture was stirred at room temperature overnight. To the reaction mixture was added a mixture of hexane and ethyl acetate. The resulting precipitate was collected by filtration and washed with ethyl acetate to give the title compound (2674 mg) as a brown solid.

$^1$H NMR (300 MHz, CDCl$_3$) δ 6.86 (1H, d, J=3.8 Hz), 7.03 (1H, dd, J=7.7, 6.2 Hz), 7.10 (1H, d, J=3.4 Hz), 7.79 (2H, brs), 8.06 (1H, dd, J=6.2, 1.7 Hz), 8.19 (1H, dd, J=7.5, 1.5 Hz).

C) 3-(5-phenylfuran-2-yl)pyridin-2-amine

In the same manner as in Example 14, step A, the title compound (1.19 g) was obtained as a yellow solid from 3-(5-bromofuran-2-yl)pyridin-2-amine hydrobromide and phenylboronic acid.

D) 9-(5-phenylfuran-2-yl)-3,4-dihydropyrido[2,1-c][1,2,4]thiadiazine 2,2-dioxide In the same manner as in Example 14, step B, the title compound was obtained from the compound of the above-mentioned C).

Example 54

9-(2-fluorobiphenyl-4-yl)-3,4-dihydropyrido[2,1-c][1,2,4]thiadiazine 2,2-dioxide

A) 3-(2-fluorobiphenyl-4-yl)pyridin-2-amine

To a solution of 3-bromopyridin-2-amine (1.0 g) in 1,2-dimethoxyethane (50 mL) were added 2-fluorobiphenyl-4-ylboronic acid (1.623 g), sodium carbonate (1.225 g), tetrakis(triphenylphosphine)palladium(0) (0.334 g), and water (10 mL) at room temperature. The reaction mixture was stirred under a nitrogen atmosphere at 80° C. overnight, water was added, and the mixture was extracted with ethyl acetate. The extract was washed with saturated brine, dried over anhydrous sodium sulfate and the solvent was evaporated under reduced pressure. The residue was purified by recrystallization (THF/diisopropyl ether) to give the title compound (1.175 g).

$^1$H NMR (300 MHz, DMSO-d$_6$) δ 5.74 (2H, s), 6.68 (1H, dd, J=7.2, 4.9 Hz), 7.35-7.46 (4H, m), 7.48-7.55 (2H, m), 7.56-7.65 (3H, m), 7.98 (1H, dd, J=4.9, 1.9 Hz).

B) 9-(2-fluorobiphenyl-4-yl)-3,4-dihydropyrido[2,1-c][1,2,4]thiadiazine 2,2-dioxide To a suspension of 60% sodium hydride (0.76 g) in THF (20 mL) was added 2-chloroethanesulfonyl chloride (1.85 g) under ice-cooling. The reaction mixture was stirred under ice-cooling for 5 min, and a solution of 3-(2-fluorobiphenyl-4-yl)pyridin-2-amine (1.0 g) in THF (20 mL) was added. The reaction mixture was stirred at room temperature overnight, and water and hexane were added under ice-cooling. The resulting solid was collected by filtration, washed with ethyl acetate, and dried under reduced pressure to give the title compound (0.724 g).

$^1$H NMR (300 MHz, DMSO-d$_6$) δ 3.45-3.54 (2H, m), 4.64-4.72 (2H, m), 6.75 (1H, t, J=7.0 Hz), 7.39-7.63 (8H, m), 7.75 (1H, dd, J=7.2, 1.9 Hz), 7.83 (1H, dd, J=6.8, 1.5 Hz).

Example 55

9-(2-fluorobiphenyl-4-yl)-3,4,6,7,8,9-hexahydropyrido[2,1-c][1,2,4]thiadiazine 2,2-dioxide To a solution of 9-(2-fluorobiphenyl-4-yl)-3,4-dihydropyrido[2,1-c][1,2,4]thiadiazine 2,2-dioxide (200 mg) in THF/methanol (30 mL/30 mL) was added 5% rhodium carbon (50 mg). The reaction mixture was stirred under a hydrogen atmosphere at room temperature for 1 day. Platinum (IV) oxide (40 mg) was added, and the mixture was stirred under a hydrogen atmosphere at room temperature for 9 hr, and insoluble material was filtered off through celite. The filtrate was concentrated under reduced pressure, the obtained residue was purified by recrystallization (THF-ethyl acetate/diisopropyl ether) to give the title compound (121.2 mg).

$^1$H NMR (300 MHz, DMSO-d$_6$) δ 1.81-2.25 (4H, m), 3.25-3.38 (2H, m), 3.40-3.58 (2H, m), 3.86-3.99 (3H, m), 6.92-7.06 (2H, m), 7.32-7.48 (4H, m), 7.49-7.57 (2H, m).

Example 56

9-[4-(4,4,5,5-tetramethyl-1,3,2-dioxaborolan-2-yl)phenyl]-3,4-dihydropyrido[2,1-c][1,2,4]thiadiazine 2,2-dioxide A suspension of 9-(4-chlorophenyl)-3,4-dihydropyrido[2,1-c][1,2,4]thiadiazine 2,2-dioxide (224 mg), potassium carbonate (149 mg), bis(pinacolato)diboron (232 mg), tricyclohexylphosphine (43 mg), and tris(dibenzylideneacetone)dipalladium(0) (35 mg) in 1,2-dimethoxyethane (5 mL) was stirred at 70° C. overnight. The reaction mixture was cooled to room temperature, purified by silica gel column chromatography (ethyl acetate/hexane), and recrystallized from ethanol/ethyl acetate to give the title compound (142 mg) as a white solid.

Example 57

9-(5-phenylthiophen-2-yl)-3,4,6,7,8,9-hexahydropyrido[2,1-c][1,2,4]thiadiazine 2,2-dioxide A mixture of 10% palladium-carbon (50% wet, 12 mg) and 9-(5-phenylthiophen-2-yl)-3,4-dihydropyrido[2,1-c][1,2,4]thiadiazine 2,2-dioxide (120 mg) in ethanol (10 mL) and dehydrated THF (60 mL) was stirred under a hydrogen atmosphere at room temperature for 4 hr. To the reaction mixture was added 5% rhodium-carbon (50% wet, 12 mg)

and the mixture was stirred under a hydrogen atmosphere at room temperature overnight, and under a hydrogen atmosphere (4 atm) for 6 hr. To the reaction mixture was added 5% ruthenium-alumina (12 mg) and the mixture was stirred under a hydrogen atmosphere at room temperature overnight. To the reaction mixture was added platinum dioxide (12 mg), and the mixture was stirred under a hydrogen atmosphere at room temperature for 24 hr. The reaction mixture was filtered through celite, and the filtrate was concentrated under reduced pressure. The residue was purified by aminopropyl silica-bound silica gel column chromatography (ethyl acetate/methanol) to give the title compound (42.3 mg) as a white solid. The obtained solid was crystallized from acetonitrile and diisopropyl ether.

$^1$H NMR (300 MHz, CDCl$_3$) δ 1.71-2.04 (3H, m), 2.04-2.21 (1H, m), 3.20-3.32 (2H, m), 3.46 (2H, t, J=6.1 Hz), 3.80 (2H, t, J=6.6 Hz), 4.03 (1H, t, J=5.7 Hz), 6.96 (1H, d, J=3.8 Hz), 7.25-7.33 (1H, m), 7.35 (1H, d, J=3.8 Hz), 7.37-7.46 (2H, m), 7.57-7.65 (2H, m).

Example 58

9-{2-[4-(1-methylethyl)phenyl]ethyl}-3,4,6,7,8,9-hexahydropyrido[2,1-c][1,2,4]thiadiazine 2,2-dioxide The title compound was obtained in the same manner as in Example 38.

The compounds of Examples 1-58 produced by the above-mentioned methods or methods analogous thereto are shown in the following Tables. In the Tables, MS means Found.

TABLE 1

| Ex. No. | IUPAC Name | Structure | Salt | MS |
|---|---|---|---|---|
| 1 | N-[4-(1-methylpropyl)phenyl]-3,4-dihydropyrazino[2,1-c][1,2,4]thiadiazine-9-carboxamide 2,2-dioxide | 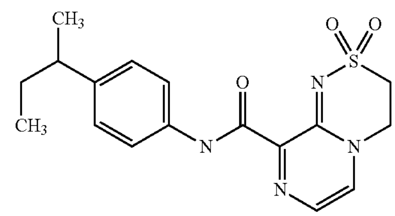 [SMILES: CCC(C)c1ccc(NC(=O)C2=NC=CN3CCS(=O)(=O)N=C23)cc1] | | 361.2 |
| 2 | 7-methyl-N-[4-(1-methylpropyl)phenyl]-3,4-dihydropyrido[2,1-c][1,2,4]thiadiazine-9-carboxamide 2,2-dioxide | 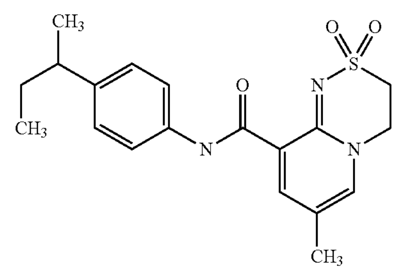 [SMILES: CCC(C)c1ccc(NC(=O)C2=CC(C)=CN3CCS(=O)(=O)N=C23)cc1] | | 374.2 |
| 3 | N-[4-(1-methylpropyl)phenyl]-7-(trifluoromethyl)-3,4-dihydropyrido[2,1-c][1,2,4]thiadiazine-9-carboxamide 2,2-dioxide | 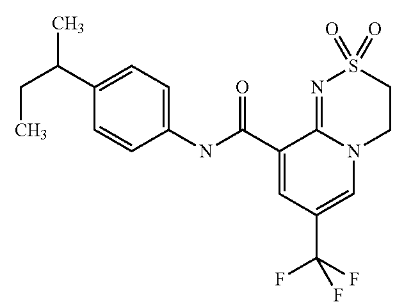 [SMILES: CCC(C)c1ccc(NC(=O)C2=CC(C(F)(F)F)=CN3CCS(=O)(=O)N=C23)cc1] | | 428.1 |
| 4 | N-(4-cyclopropylphenyl)-3,4-dihydropyrido[2,1-c][1,2,4]thiadiazine-9-carboxamide 2,2-dioxide | 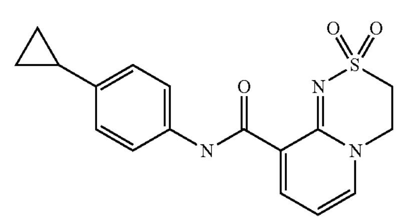 [SMILES: O=C(Nc1ccc(C2CC2)cc1)C1=CC=CN2CCS(=O)(=O)N=C12] | | 344.2 |

TABLE 1-continued

| Ex. No. | IUPAC Name | Structure | Salt | MS |
|---|---|---|---|---|
| 5 | N-[6-(trifluoromethyl)pyridin-3-yl]-3,4-dihydropyrido[2,1-c][1,2,4]thiadiazine-9-carboxamide 2,2-dioxide | 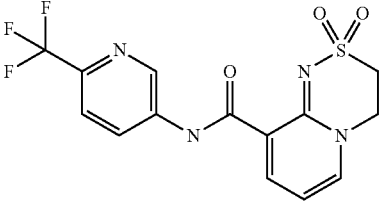 [SMILES: O=C(Nc1ccc(C(F)(F)F)nc1)C1=CC=CN2CCS(=O)(=O)N=C12] | | 373.2 |
| 6 | N-[4-(trifluoromethyl)phenyl]-3,4-dihydropyrido[2,1-c][1,2,4]thiadiazine-9-carboxamide 2,2-dioxide | 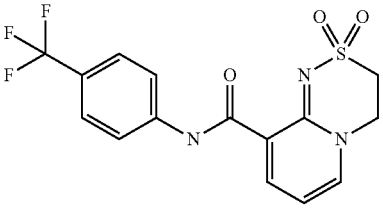 [SMILES: O=C(Nc1ccc(C(F)(F)F)cc1)C1=CC=CN2CCS(=O)(=O)N=C12] | | 372.2 |
| 7 | N-[5-(trifluoromethyl)pyridin-2-yl]-3,4-dihydropyrido[2,1-c][1,2,4]thiadiazine-9-carboxamide 2,2-dioxide | 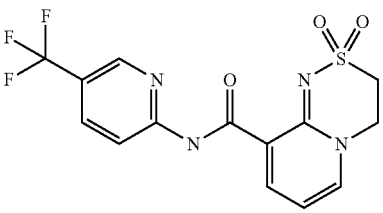 [SMILES: O=C(Nc1ccc(C(F)(F)F)cn1)C1=CC=CN2CCS(=O)(=O)N=C12] | | 373.2 |
| 8 | N-[4-(trifluoromethoxy)phenyl]-3,4-dihydropyrido[2,1-c][1,2,4]thiadiazine-9-carboxamide 2,2-dioxide | 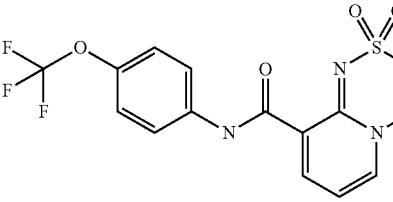 | | 388.2 |

TABLE 2

| | | | | |
|---|---|---|---|---|
| 9 | N-(4-cyanophenyl)-3,4-dihydropyrido[2,1-c][1,2,4]thiadiazine-9-carboxamide 2,2-dioxide | 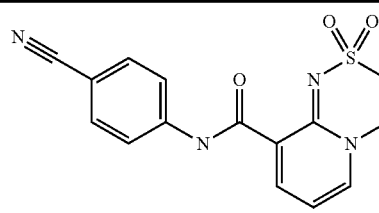 | | 329.2 |
| 10 | N-(4-acetylphenyl)-3,4-dihydropyrido[2,1-c][1,2,4]thiadiazine-9-carboxamide 2,2-dioxide | 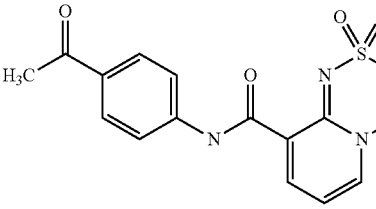 | | 346.2 |

TABLE 2-continued

| | | | |
|---|---|---|---|
| 11 | N-[4-(dimethylcarbamoyl)phenyl]-3,4-dihydropyrido[2,1-c][1,2,4]thiadiazine-9-carboxamide 2,2-dioxide | 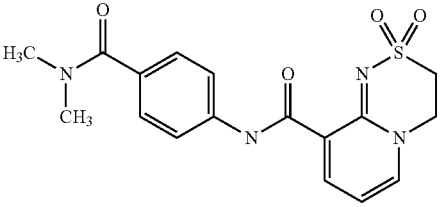 [SMILES: CN(C)C(=O)c1ccc(NC(=O)C2=CC=CN3CCS(=O)(=O)N=C23)cc1] | 375.2 |
| 12 | N-methyl-N-[4-(1-methylethyl)phenyl]-3,4-dihydropyrido[2,1-c][1,2,4]thiadiazine-9-carboxamide 2,2-dioxide | 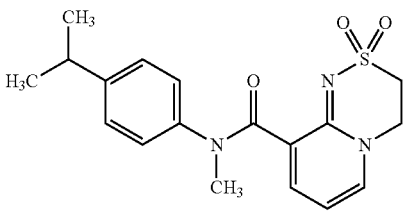 [SMILES: CC(C)c1ccc(N(C)C(=O)C2=CC=CN3CCS(=O)(=O)N=C23)cc1] | 360.0 |
| 13 | N-(2,2-dioxido-3,4-dihydropyrido[2,1-c][1,2,4]thiadiazin-9-yl)-2,3-dihydro-1,4-benzodioxine-6-carboxamide | 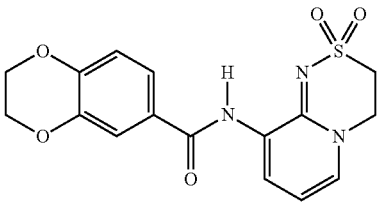 [SMILES: O=C(NC1=CC=CN2CCS(=O)(=O)N=C12)c1ccc2c(c1)OCCO2] | 362.3 |
| 14 | 9-biphenyl-4-yl-3,4-dihydropyrido[2,1-c][1,2,4]thiadiazine 2,2-dioxide | 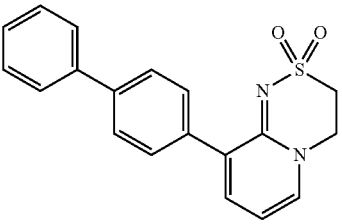 [SMILES: O=S1(=O)CCN2C=CC=C(c3ccc(-c4ccccc4)cc3)C2=N1] | 337.0 |
| 15 | 9-[4-(1-methylethyl)phenoxy]-3,4-dihydropyrido[2,1-c][1,2,4]thiadiazine 2,2-dioxide | 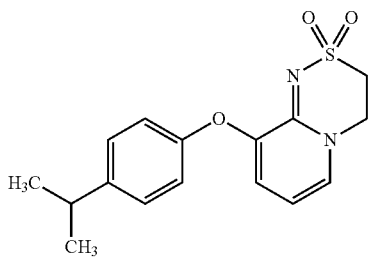 [SMILES: CC(C)c1ccc(OC2=CC=CN3CCS(=O)(=O)N=C23)cc1] | 319.3 |
| 16 | 9-{[4-(1-methylethyl)phenyl]sulfanyl}-3,4-dihydropyrido[2,1-c][1,2,4]thiadiazine 2,2-dioxide | 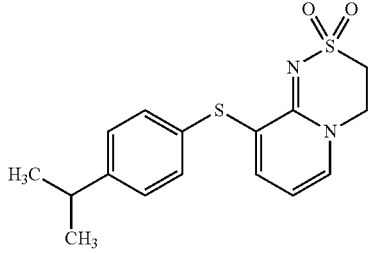 [SMILES: CC(C)c1ccc(SC2=CC=CN3CCS(=O)(=O)N=C23)cc1] | 335.3 |
| 17 | 9-(benzylsulfanyl)-3,4-dihydropyrido[2,1-c][1,2,4]thiadiazine 2,2-dioxide | 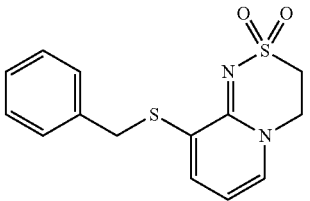 [SMILES: O=S1(=O)CCN2C=CC=C(SCc3ccccc3)C2=N1] | 307.3 |

TABLE 3

| | | | |
|---|---|---|---|
| 18 | 9-(biphenyl-4-yloxy)-3,4-dihydropyrido[2,1-c][1,2,4]thiadiazine 2,2-dioxide | 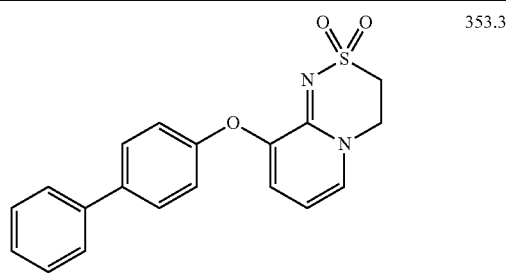 | 353.3 |
| 19 | 9-{[4-(1-methylethyl)phenyl]sulfinyl}-3,4-dihydropyrido[2,1-c][1,2,4]thiadiazine 2,2-dioxide | 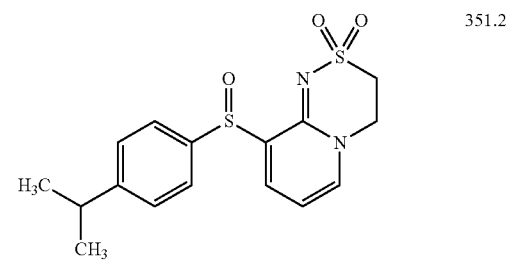 | 351.2 |
| 20 | 9-{[4-(1-methylethyl)phenyl]sulfonyl}-3,4-dihydropyrido[2,1-c][1,2,4]thiadiazine 2,2-dioxide | 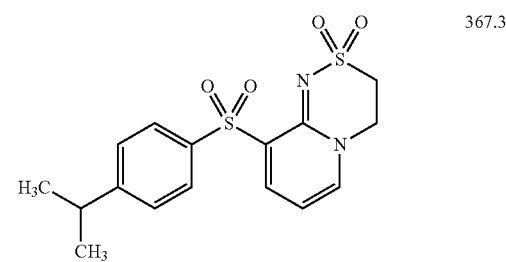 | 367.3 |
| 21 | 9-(benzylsulfinyl)-3,4-dihydropyrido[2,1-c][1,2,4]thiadiazine 2,2-dioxide | 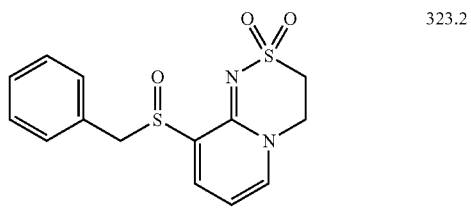 | 323.2 |
| 22 | 9-(benzylsulfonyl)-3,4-dihydropyrido[2,1-c][1,2,4]thiadiazine 2,2-dioxide | 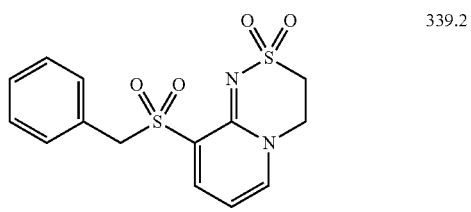 | 339.2 |
| 23 | 9-[4-(1-methylethyl)phenyl]-3,4-dihydropyrido[2,1-c][1,2,4]thiadiazine 2,2-dioxide | 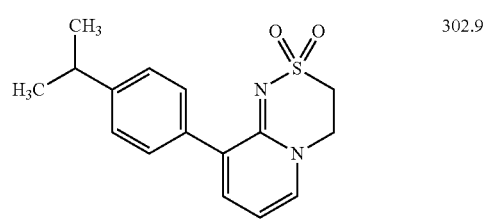 | 302.9 |

TABLE 3-continued

| 24 | 9-[(2-methyl-1,3-benzothiazol-5-yl)oxy]-3,4-dihydropyrido[2,1-c][1,2,4]thiadiazine 2,2-dioxide | 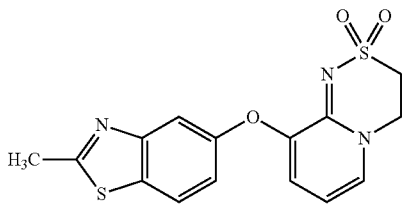 [SMILES: Cc1nc2cc(OC3=CC=CN4CCS(=O)(=O)N=C34)ccc2s1] | 347.9 |
| 25 | 9-{2-[4-(1-methylethyl)phenyl]ethyl}-3,4-dihydropyrido[2,1-c][1,2,4]thiadiazine 2,2-dioxide | 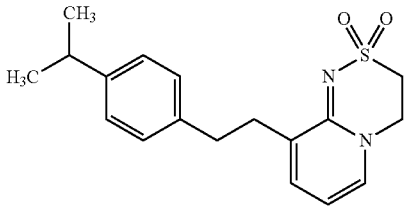 | 331.2 |
| 26 | 9-{[4-(1-methylethyl)phenyl]ethynyl)-3,4-dihydropyrido[2,1-c][1,2,4]thiadiazine 2,2-dioxide | 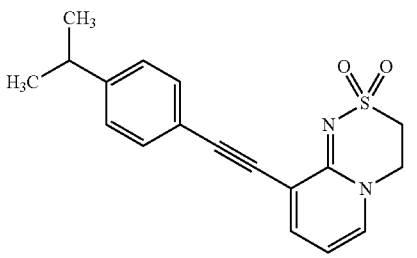 [SMILES: CC(C)c1ccc(C#CC2=CC=CN3CCS(=O)(=O)N=C23)cc1] | 327.1 |

TABLE 4

| 27 | N-(2,2-dioxido-3,4-dihydropyrido[2,1-c][1,2,4]thiadiazin-9-yl)-2,2,3,3-tetrafluoro-2,3-dihydro-1,4-benzodioxine-6-carboxamide | 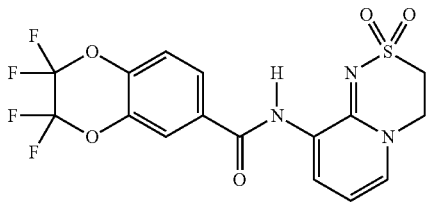 [SMILES: O=C(NC1=CC=CN2CCS(=O)(=O)N=C12)c1ccc2c(c1)OC(F)(F)C(F)(F)O2] | 434.0 |
| 28 | 9-biphenyl-4-yl-3,4,6,7,8,9-hexahydropyrido[2,1-c][1,2,4]thiadiazine 2,2-dioxide | 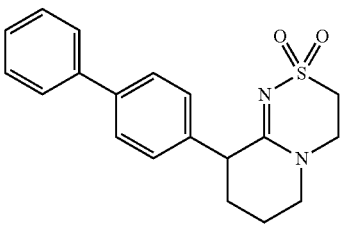 [SMILES: O=S1(=O)CCN2CCCC(c3ccc(-c4ccccc4)cc3)C2=N1] | 341.0 |
| 29 | 9-{5-[4-(1-methylethyl)phenyl]-1,2,4-oxadiazol-3-yl}-3,4-dihydropyrido[2,1-c][1,2,4]thiadiazine 2,2-dioxide | 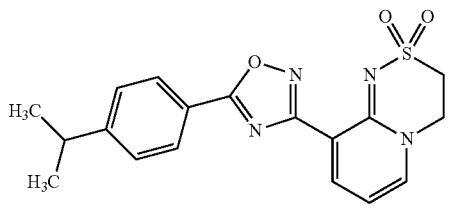 [SMILES: CC(C)c1ccc(-c2nc(C3=CC=CN4CCS(=O)(=O)N=C34)no2)cc1] | |

1H NMR (300 MHz, DMSO-d6) δ 1.26 (6H, d, J = 6.8 Hz), 3.03 (1H, spt, J = 6.8 Hz), 3.43-3.61 (2H, m), 4.61-4.77 (2H, m), 6.78 (1H, t, J = 7.0 Hz), 7.50-7.60 (2H, m), 7.99 (1H, dd, J = 6.8, 1.9 Hz), 8.05-8.14 (2H, m), 8.19 (1H, dd, J = 7.4, 1.7 Hz).

TABLE 4-continued

| | | | |
|---|---|---|---|
| 30 | 9-(4-cyclohexylphenyl)-3,4-dihydropyrido[2,1-c][1,2,4]thiadiazine 2,2-dioxide | 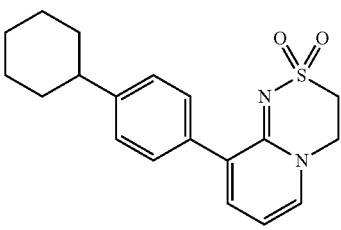 [SMILES: O=S1(=O)CCN2C=CC=C(c3ccc(C4CCCCC4)cc3)C2=N1] | 343.3 |
| 31 | 9-(4-phenoxyphenyl)-3,4-dihydropyrido[2,1-c][1,2,4]thiadiazine 2,2-dioxide | 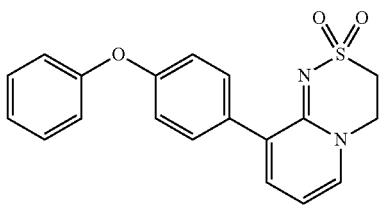 | 353.3 |
| 32 | 9-[4-(1-methylpropyl)phenyl]-3,4-dihydropyrido[2,1-c][1,2,4]thiadiazine 2,2-dioxide | 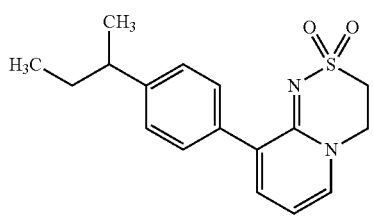 [SMILES: CCC(C)c1ccc(C2=CC=CN3CCS(=O)(=O)N=C23)cc1] | 317.2 |
| 33 | 9-[4-(1-methylethoxy)phenyl]-3,4-dihydropyrido[2,1-c][1,2,4]thiadiazine 2,2-dioxide | 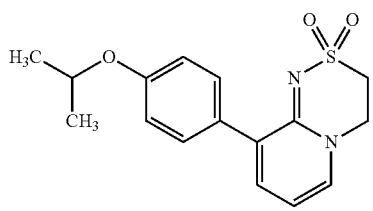 [SMILES: CC(C)Oc1ccc(C2=CC=CN3CCS(=O)(=O)N=C23)cc1] | 319.4 |
| 34 | 9-[4-(trifluoromethoxy)phenyl]-3,4-dihydropyrido[2,1-c][1,2,4]thiadiazine 2,2-dioxide | 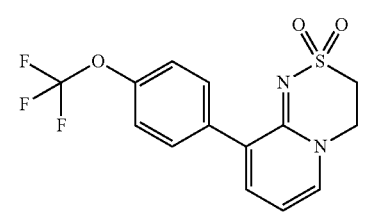 [SMILES: O=S1(=O)CCN2C=CC=C(c3ccc(OC(F)(F)F)cc3)C2=N1] | 345.2 |

TABLE 5

| | | | |
|---|---|---|---|
| 35 | 9-(4-tert-butylphenyl)-3,4-dihydropyrido[2,1-c][1,2,4]thiadiazine 2,2-dioxide | 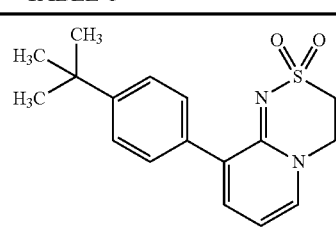 | 317.3 |
| 36 | N'-{[4-(1-methylethyl)phenyl]carbonyl}-3,4-dihydropyrido[2,1-c][1,2,4]thiadiazine-9-carbohydrazide 2,2-dioxide | 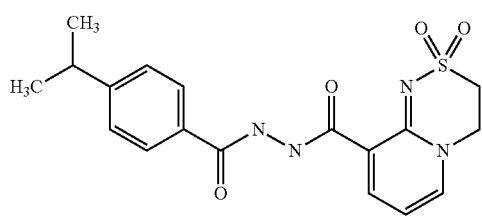 [SMILES: CC(C)c1ccc(C(=O)NNC(=O)C2=CC=CN3CCS(=O)(=O)N=C23)cc1] | 389.3 |

TABLE 5-continued

| | | | |
|---|---|---|---|
| 37 | N-(2,2-dioxido-3,4-dihydropyrido[2,1-c][1,2,4]thiadiazin-9-yl)-4-(1-methylethyl)benzamido | 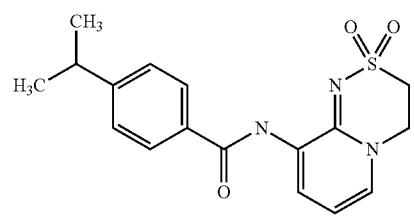 [SMILES: CC(C)c1ccc(C(=O)NC2=CC=CN3CCS(=O)(=O)N=C23)cc1] | 346.1 |
| 38 | 9-(4-tert-butylphenyl)-3,4,6,7,8,9-hexahydropyrido[2,1-c][1,2,4]thiadiazine 2,2-dioxide | 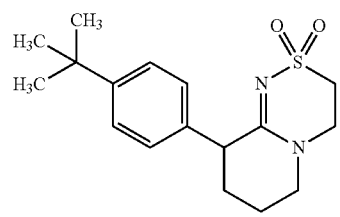 [SMILES: CC(C)(C)c1ccc(C2CCCN3CCS(=O)(=O)N=C23)cc1] | 321.3 |
| 39 | 9-[4-(1-methylpropyl)phenyl]-3,4,6,7,8,9-hexahydropyrido[2,1-c][1,2,4]thiadiazine 2,2-dioxide | 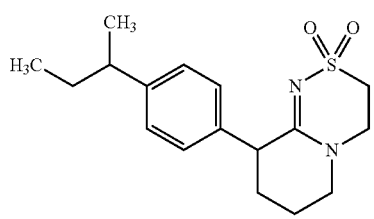 [SMILES: CCC(C)c1ccc(C2CCCN3CCS(=O)(=O)N=C23)cc1] | 321.3 |
| 40 | 9-[4-(1-methylethoxy)phenyl]-3,4,6,7,8,9-hexahydropyrido[2,1-c][1,2,4]thiadiazine 2,2-dioxide | 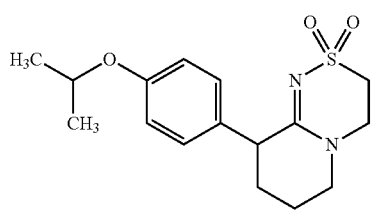 [SMILES: CC(C)Oc1ccc(C2CCCN3CCS(=O)(=O)N=C23)cc1] | 323.3 |
| 41 | 9-[4-(trifluoromethoxy)phenyl]-3,4,6,7,8,9-hexahydropyrido[2,1-c][1,2,4]thiadiazine 2,2-dioxide | 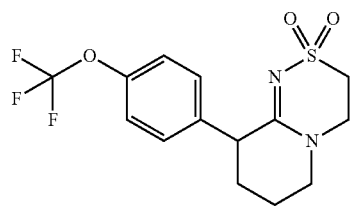 [SMILES: O=S1(=O)CCN2CCCC(c3ccc(OC(F)(F)F)cc3)C2=N1] | 349.2 |
| 42 | 9-[4-(1-methylethyl)phenyl]-3,4,6,7,8,9-hexahydropyrido[2,1-c][1,2,4]thiadiazine 2,2-dioxide | 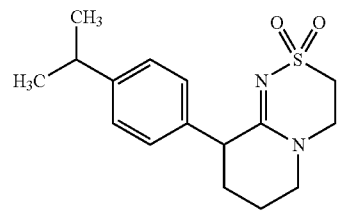 [SMILES: CC(C)c1ccc(C2CCCN3CCS(=O)(=O)N=C23)cc1] | 307.2 |
| 43 | 9-(4-phenoxyphenyl)-3,4,6,7,8,9-hexahydropyrido[2,1-c][1,2,4]thiadiazine 2,2-dioxide | 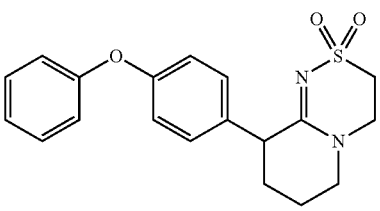 [SMILES: O=S1(=O)CCN2CCCC(c3ccc(Oc4ccccc4)cc3)C2=N1] | 357.1 |

TABLE 6

| 44 | 9-biphenyl-4-yl-3,4-dihydropyrido[2,1-c][1,2,4]thiadiazine 2,2-dioxide | 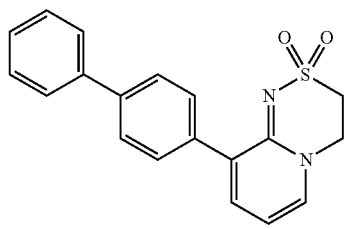 [SMILES: O=S1(=O)CCN2C=CC=C(c3ccc(-c4ccccc4)cc3)C2=N1] | 337.3 |
| 45 | 9-(4-chlorophenyl)-3,4-dihydropyrido[2,1-c][1,2,4]thiadiazine 2,2-dioxide | 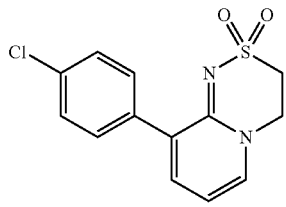 [SMILES: O=S1(=O)CCN2C=CC=C(c3ccc(Cl)cc3)C2=N1] | 295.0 |
| 46 | 9-naphthalen-2-yl-3,4-dihydropyrido[2,1-c][1,2,4]thiadiazine 2,2-dioxide | 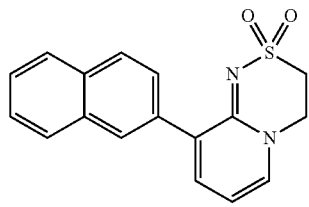 [SMILES: O=S1(=O)CCN2C=CC=C(c3ccc4ccccc4c3)C2=N1] | 311.1 |
| 47 | 9-(3-fluorobiphenyl-4-yl)-3,4-dihydropyrido[2,1-c][1,2,4]thiadiazine 2,2-dioxide | 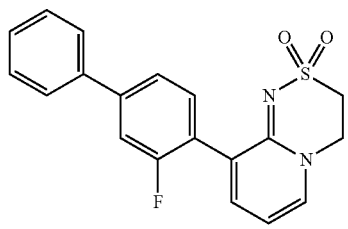 [SMILES: O=S1(=O)CCN2C=CC=C(c3ccc(-c4ccccc4)cc3F)C2=N1] | 355.1 |
| 48 | 9-(3-fluorobiphenyl-4-yl)-3,4,6,7,8,9-hexahydropyrido[2,1-c][1,2,4]thiadiazine 2,2-dioxide | 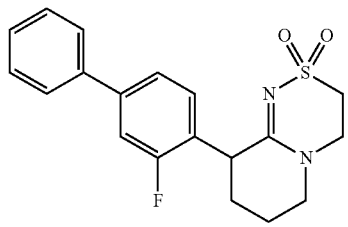 [SMILES: O=S1(=O)CCN2CCCC(c3ccc(-c4ccccc4)cc3F)C2=N1] | 359.1 |
| 49 | 9-naphthalen-2-yl-3,4,6,7,8,9-hexahydropyrido[2,1-c][1,2,4]thiadiazine 2,2-dioxide | 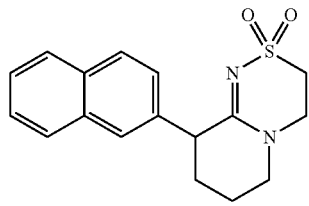 [SMILES: O=S1(=O)CCN2CCCC(c3ccc4ccccc4c3)C2=N1] | 315.1 |
| 50 | 9-(5-phenylthiophen-2-yl)-3,4-dihydropyrido[2,1-c][1,2,4]thiadiazine 2,2-dioxide | 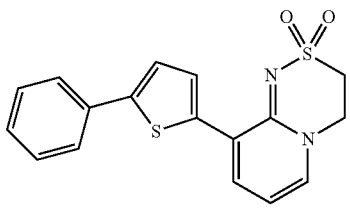 [SMILES: O=S1(=O)CCN2C=CC=C(c3ccc(-c4ccccc4)s3)C2=N1] | 343.3 |

TABLE 6-continued

| | | | |
|---|---|---|---|
| 51 | 9-{(E)-2-[4-(1-methylethyl)phenyl]ethenyl}-3,4-dihydropyrido[2,1-c][1,2,4]thiadiazine 2,2-dioxide | 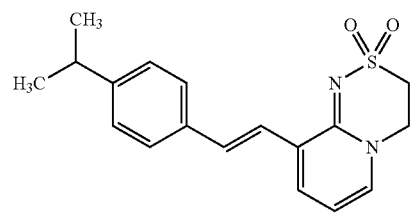 [SMILES: CC(C)c1ccc(/C=C/C2=CC=CN3CCS(=O)(=O)N=C23)cc1] | 329.1 |
| 52 | 9-{[4-(1-methylethyl)benzyl]oxy}-3,4-dihydropyrido[2,1-c][1,2,4]thiadiazine 2,2-dioxide | 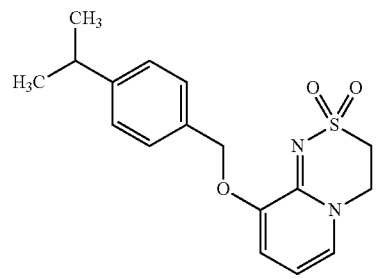 [SMILES: CC(C)c1ccc(COC2=CC=CN3CCS(=O)(=O)N=C23)cc1] | 333.1 |
| 53 | 9-(5-phenylfuran-2-yl)-3,4-dihydropyrido[2,1-c][1,2,4]thiadiazine 2,2-dioxide | 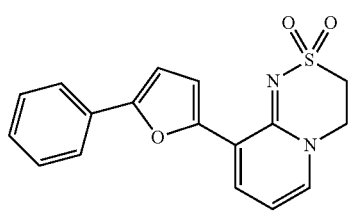 [SMILES: O=S1(=O)CCN2C=CC=C(c3ccc(-c4ccccc4)o3)C2=N1] | 327.1 |

TABLE 7

| | | | |
|---|---|---|---|
| 54 | 9-(2-fluorobiphenyl-4-yl)-3,4-dihydropyrido[2,1-c][1,2,4]thiadiazine 2,2-dioxide | 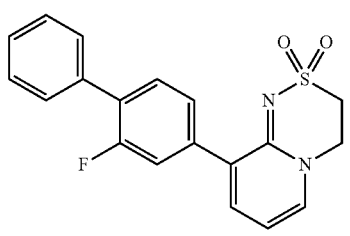 [SMILES: O=S1(=O)CCN2C=CC=C(c3ccc(-c4ccccc4)c(F)c3)C2=N1] | 355.1 |
| 55 | 9-(2-fluorobiphenyl-4-yl)-3,4,6,7,8,9-hexahydropyrido[2,1-c][1,2,4]thiadiazine 2,2-dioxide | 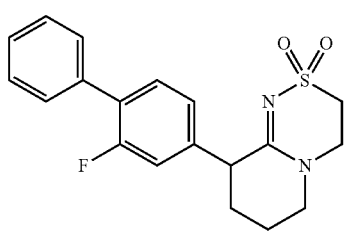 | 359.1 |
| 56 | 9-[4-(4,4,5,5-tetramethyl-1,3,2-dioxaborolan-2-yl)phenyl]-3,4-dihydropyrido[2,1-c][1,2,4]thiadiazine 2,2-dioxide | 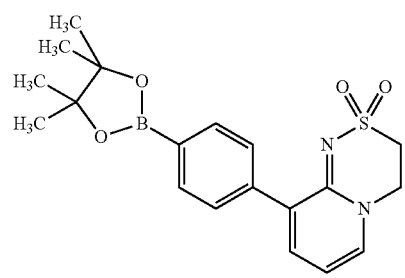 [SMILES: CC1(C)OB(c2ccc(C3=CC=CN4CCS(=O)(=O)N=C34)cc2)OC1(C)C] | 387.1 |

TABLE 7-continued

| | | | |
|---|---|---|---|
| 57 | 9-(5-phenylthiophen-2-yl)-3,4,6,7,8,9-hexahydropyrido[2,1-c][1,2,4]thiadiazine 2,2-dioxide | 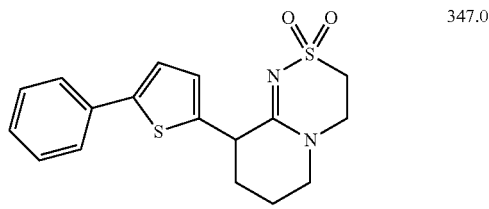 | 347.0 |
| 58 | 9-{2-[4-(1-methylethyl)phenyl]ethyl}-3,4,6,7,8,9-hexahydropyrido[2,1-c][1,2,4]thiadiazine 2,2-dioxide | 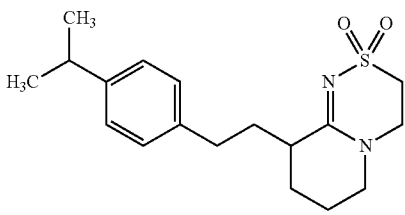 [SMILES: CC(C)c1ccc(CCC2CCCN3CCS(=O)(=O)N=C23)cc1] | 335.2 |

Example 59

9-[(7-methoxynaphthalen-2-yl)oxy]-3,4-dihydro-pyrido[2,1-c][1,2,4]thiadiazine 2,2-dioxide A)
3-[(7-methoxynaphthalen-2-yl)oxy]pyridin-2-amine A mixture of picoline acid (0.427 g), tripotassium phosphate (11.04 g), copper (I) iodide (0.660 g), 7-methoxynaphthalen-2-ol (6.04 g), 3-bromopyridin-2-amine (3 g) and DMSO (50 mL) was stirred under a nitrogen atmosphere at 140° C. overnight. Water was added, and the mixture was filtered through celite, and the filtrate was extracted with ethyl acetate. The organic layer was washed with saturated brine, dried over anhydrous magnesium sulfate and concentrated under reduced pressure. The residue was purified by silica gel column chromatography (ethyl acetate/hexane) and basic silica gel column chromatography (ethyl acetate/hexane) to give the title compound (1.667 g) as a pale-yellow solid.

MS (API+). found: 267.1

B) 9-[(7-methoxynaphthalen-2-yl)oxy]-3,4-dihydro-pyrido[2,1-c][1,2,4]thiadiazine 2,2-dioxide To a mixture of sodium hydride (60%, 375 mg), 2-chloroethanesulfonyl chloride (612 mg) and dehydrated THF (15 mL) was added a mixture of 3-[(7-methoxynaphthalen-2-yl)oxy]pyridin-2-amine (500 mg) and dehydrated THF (15 mL) at room temperature. The reaction mixture was stirred for 2 hr, water was added, and THF was evaporated under reduced pressure. The resulting precipitate was washed with water and diisopropyl ether to give the title compound (348 mg) as a pale-brown solid. The obtained solid was crystallized from acetonitrile and diisopropyl ether to give a pale-brown solid.

$^1$H NMR (300 MHz, DMSO-d$_6$) δ 3.41-3.61 (2H, m), 3.84 (3H, s), 4.56-4.83 (2H, m), 6.61 (1H, t, J=7.2 Hz), 7.03-7.18 (2H, m), 7.20-7.27 (2H, m), 7.29 (1H, dd, J=7.8, 1.3 Hz), 7.66 (1H, dd, J=6.8, 1.1 Hz), 7.81 (1H, d, J=9.1 Hz), 7.86 (1H, d, J=8.7 Hz).

mp 235-237° C.

Anal. Calcd for $C_{18}H_{16}N_2O_4S$-1/3$H_2O$: C, 59.66; H, 4.64; N, 7.73. Found: C, 59.73; H, 4.55; N, 7.80.

Example 60

9-[(7-methoxynaphthalen-2-yl)oxy]-3,4,6,7,8,9-hexahydropyrido[2,1-c][1,2,4]thiadiazine 2,2-dioxide A mixture of 9-[(7-methoxynaphthalen-2-yl)oxy]-3,4-dihydropyrido[2,1-c][1,2,4]thiadiazine 2,2-dioxide (120 mg), platinum (IV) oxide (76 mg) and acetic acid (10 mL) was stirred under a hydrogen atmosphere at room temperature overnight. The reaction mixture was filtered, and concentrated under reduced pressure. To the residue was added a saturated aqueous sodium hydrogen carbonate solution and the mixture was extracted with ethyl acetate. The organic layer was washed with saturated aqueous sodium hydrogen carbonate solution and saturated brine, dried over anhydrous magnesium sulfate, and concentrated under reduced pressure. The residue was crystallized from ethyl acetate and hexane to give the title compound (27.4 mg) as a gray white solid.

$^1$H NMR (300 MHz, DMSO-d$_6$) δ 1.77-2.13 (4H, m), 3.22-3.38 (2H, m), 3.38-3.61 (2H, m), 3.76-3.91 (5H, m), 5.03 (1H, t, J=3.8 Hz), 7.01 (1H, dd, J=8.9, 2.5 Hz), 7.06 (1H, dd, J=8.9, 2.5 Hz), 7.19 (1H, d, J=2.3 Hz), 7.40 (1H, d, J=2.3 Hz), 7.75 (2H, dd, J=9.1, 3.8 Hz).

Example 61

9-{[4-(1-methylethyl)phenoxy]methyl}-3,4-dihydro-pyrido[2,1-c][1,2,4]thiadiazine 2,2-dioxide A) (2-chloropyridin-3-yl)methanol To a mixture of methyl 2-chloronicotinate (5 g), dehydrated THF (30 mL) and ethanol (30 mL) was added sodium borohydride (4.41 g) at 0° C. The reaction mixture was stirred at room temperature overnight, poured into water, and the mixture was extracted with ethyl acetate. The organic layer was washed with saturated brine, dried over anhydrous magnesium sulfate, and concentrated under reduced pressure. The residue was purified by silica gel column chromatography (ethyl acetate/hexane) to give the title compound (3.22 g) as a white solid.

MS (API+). found: 144.0

B) 2-chloro-3-{[4-(1-methylethyl)phenoxy]methyl}pyridine

To a mixture of triphenylphosphine (2740 mg), 4-isopropylphenol (1138 mg), (2-chloropyridin-3-yl)methanol (1000 mg) and dehydrated THF (20 mL) was added DEAD (40% toluene solution, 4549 mg) at room temperature over 30 min. The reaction mixture was stirred at room temperature for 2 hr, DEAD (40% toluene solution, 919 mg) was added at room temperature, and the mixture was stirred for 1 hr. The reaction mixture was concentrated under reduced pressure, and the residue was purified by silica gel column chromatography (ethyl acetate/hexane) to give the title compound (1623 mg) as an orange oil.
MS (API+). found: 262.1

C) 3-{[4-(1-methylethyl)phenoxy]methyl}pyridin-2-amine

A mixture of sodium tert-butoxide (0.617 g), 2,2'-bis(diphenylphosphino)-1,1'-binaphthyl (0.160 g), 1,1-diphenylmethanimine (1.008 g), 2-chloro-3-{[4-(1-methylethyl)phenoxy]methyl}pyridine (1.12 g), tris(dibenzylideneacetone)dipalladium(0) (0.118 g) and toluene (20 mL) was stirred at 110° C. for 6 hr. To the reaction mixture was added THF, and the mixture was filtered through celite, and the filtrate was concentrated under reduced pressure. To the residue were added THF (25 mL) and 1M hydrochloric acid (25 mL) at room temperature, and the mixture was stirred overnight. The reaction mixture was neutralized with saturated aqueous sodium hydrogen carbonate solution, and extracted with ethyl acetate. The organic layer was washed with water and saturated brine, dried over anhydrous magnesium sulfate and concentrated under reduced pressure. The residue was purified by basic silica gel column chromatography (ethyl acetate/hexane) to give the title compound (902.2 mg) containing impurity as a pale-yellow oil.
MS (API+). found: 243.1

D) 9-{[4-(1-methylethyl)phenoxy]methyl}-3,4-dihydropyrido[2,1-c][1,2,4]thiadiazine 2,2-dioxide A mixture of 3-{[4-(1-methylethyl)phenoxy]methyl}pyridin-2-amine (600 mg) and dehydrated THF (10 mL) was added to a mixture of sodium hydride (60%, 495 mg), 2-chloroethanesulfonyl chloride (1211 mg) and dehydrated THF (10 mL) at room temperature. The reaction mixture was stirred for 1 hr, water was added, and the mixture was extracted with ethyl acetate. The organic layer was washed with water and saturated brine, dried over anhydrous magnesium sulfate, and concentrated under reduced pressure. The residue was purified by basic silica gel column chromatography (methanol/ethyl acetate) to give the title compound (303 mg) as a white solid. The obtained solid was crystallized from THF-diisopropyl ether to give a white solid.
$^1$H NMR (300 MHz, DMSO-$d_6$) δ 1.17 (6H, d, J=7.2 Hz), 2.74-3.00 (1H, m), 3.40-3.57 (2H, m), 4.57-4.74 (2H, m), 4.85 (2H, s), 6.68 (1H, t, J=7.0 Hz), 6.86-6.95 (2H, m), 7.12-7.23 (2H, m), 7.68 (1H, dd, J=7.0, 1.3 Hz), 7.76 (1H, d, J=6.4 Hz).
mp 212-214° C.
Anal. Calcd for $C_{17}H_{20}N_2O_3S·1/10H_2O$: C, 61.09; H, 6.09; N, 8.38. Found: C, 61.10; H, 6.12; N, 8.36.

Example 62

(9R)-9-(4-phenoxyphenyl)-3,4,6,7,8,9-hexahydropyrido[2,1-c][1,2,4]thiadiazine 2,2-dioxide A racemate (603 mg) of 9-(4-phenoxyphenyl)-3,4,6,7,8,9-hexahydropyrido[2,1-c][1,2,4]thiadiazine 2,2-dioxide was separated by HPLC (column: CHIRALPAK AD (LF001), 50 mmID×500 mmL, manufactured by DAICEL CHEMICAL INDUSTRIES, LTD., mobile phase:methanol=100) to give the title compound (296 mg) with a shorter retention time.
$^1$H NMR (300 MHz, DMSO-$d_6$) δ 1.60-1.85 (3H, m), 1.87-2.11 (1H, m), 3.20-3.31 (2H, m), 3.36-3.62 (2H, m), 3.63-3.96 (3H, m), 6.90-6.98 (2H, m), 6.98-7.08 (2H, m), 7.09-7.18 (1H, m), 7.18-7.29 (2H, m), 7.33-7.45 (2H, m).
mp 171-176° C.
Anal. Calcd for $C_{19}H_{20}N_2O_3S$: C, 64.02; H, 5.66; N, 7.86. Found: C, 63.86; H, 5.78; N, 7.81.

Example 63

(9S)-9-(4-phenoxyphenyl)-3,4,6,7,8,9-hexahydropyrido[2,1-c][1,2,4]thiadiazine 2,2-dioxide A racemate (603 mg) of 9-(4-phenoxyphenyl)-3,4,6,7,8, 9-hexahydropyrido[2,1-c][1,2,4]thiadiazine 2,2-dioxide was separated by HPLC (column: CHIRALPAK AD (LF001), 50 mmID×500 mmL, manufactured by DAICEL CHEMICAL INDUSTRIES, LTD., mobile phase:methanol=100) to give the title compound (288 mg) with a longer retention time.
$^1$H NMR (300 MHz, DMSO-$d_6$) δ 1.65-1.84 (3H, m), 1.89-2.10 (1H, m), 3.22-3.30 (2H, m), 3.38-3.61 (2H, m), 3.68-3.95 (3H, m), 6.90-6.99 (2H, m), 6.99-7.09 (2H, m), 7.11-7.18 (1H, m), 7.18-7.29 (2H, m), 7.34-7.46 (2H, m).
mp 174-175° C.
Anal. Calcd for $C_{19}H_{20}N_2O_3S$: C, 64.02; H, 5.66; N, 7.86. Found: C, 63.92; H, 5.78; N, 7.82.

Example 64

9-biphenyl-4-yl-3,4,6,7,8,9-hexahydropyrido[2,1-c][1,2,4]thiadiazine 2,2-dioxide 9-Biphenyl-4-yl-3,4,6,7,8,9-hexahydropyrido[2,1-c][1,2,4]thiadiazine 2,2-dioxide (300 mg) was separated by SFC (column: CHIRALPAK ADH (KG010), 20 mmID×250 mmL, manufactured by DAICEL CHEMICAL INDUSTRIES, LTD., mobile phase:carbon dioxide/methanol/acetonitrile=660/170/170 (v/v/v)) to give the title compound (140 mg) with a shorter retention time.
$^1$H NMR (300 MHz, DMSO-$d_6$) δ 1.62-1.89 (3H, m), 1.93-2.14 (1H, m), 3.25-3.31 (2H, m), 3.39-3.66 (2H, m), 3.71-4.00 (3H, m), 7.26-7.40 (3H, m), 7.41-7.51 (2H, m), 7.56-7.63 (2H, m), 7.63-7.71 (2H, m).
mp 220-222° C.
Anal. Calcd for $C_{19}H_{20}N_2O_2S$: C, 67.03; H, 5.92; N, 8.23. Found: C, 66.84; H, 5.92; N, 8.17.

Example 65

9-biphenyl-4-yl-3,4,6,7,8,9-hexahydropyrido[2,1-c][1,2,4]thiadiazine 2,2-dioxide 9-Biphenyl-4-yl-3,4,6,7,8,9-hexahydropyrido[2,1-c][1,2,4]thiadiazine 2,2-dioxide (300 mg) was separated by SFC (column: CHIRALPAK ADH (KG010), 20 mmID×250 mmL, manufactured by DAICEL CHEMICAL INDUS- TRIES, LTD., mobile phase:carbon dioxide/methanol/acetonitrile=660/170/170 (v/v/v)) to give the title compound (138 mg) with a longer retention time.

$^1$H NMR (300 MHz, DMSO-$d_6$) δ 1.63-1.88 (3H, m), 1.92-2.13 (1H, m), 3.24-3.31 (2H, m), 3.41-3.62 (2H, m), 3.71-3.96 (3H, m), 7.26-7.40 (3H, m), 7.41-7.52 (2H, m), 7.57-7.63 (2H, m), 7.63-7.71 (2H, m).

mp 224-227° C.

Anal. Calcd for $C_{19}H_{20}N_2O_2S$-1/5 $H_2O$: C, 66.33; H, 5.98; N, 8.14. Found: C, 66.50; H, 5.93; N, 8.10.

Example 66

9-[4-(cyclopentyloxy)phenyl]-3,4-dihydropyrido[2,1-c][1,2,4]thiadiazine 2,2-dioxide A mixture of potassium carbonate (450 mg), iodocyclopentane (639 mg) and 4-(2,2-dioxido-3,4-dihydropyrido[2,1-c][1,2,4]thiadiazin-9-yl)phenol (300 mg) in DMSO (3 mL) was stirred at 130° C. overnight. Then iodocyclopentane (639 mg) was added and the mixture was stirred at 150° C. for 5 hr. The mixture was poured into 1N NaOH aq. and extracted with EtOAc. The organic layer was separated, washed with 1N NaOH aq. and brine, dried over anhydrous magnesium sulfate and concentrated in vacuo. The residue was purified by column chromatography (NH silica gel, eluted with MeOH in EtOAc) to give crude product (81.1 mg). The crude product was purified by preparative HPLC (C18, eluted with $H_2O$ in acetonitrile containing 0.1% TFA). The desired fraction was neutralized with sat.NaHCO$_3$ aq. and extracted with EtOAc. The organic layer was separated, dried over anhydrous magnesium sulfate and concentrated in vacuo to give the title compound (52.3 mg) as a white solid.

$^1$H NMR (300 MHz, DMSO-$d_6$) δ 1.44-1.84 (6H, m), 1.82-2.04 (2H, m), 3.38-3.52 (2H, m), 4.54-4.74 (2H, m), 4.75-4.94 (1H, m), 6.68 (1H, t, J=7.0 Hz), 6.87-7.04 (2H, m), 7.37-7.52 (2H, m), 7.58 (1H, dd, J=7.2, 1.5 Hz), 7.74 (1H, dd, J=6.6, 1.7 Hz).

mp 254-256° C.

Anal. Calcd for $C_{18}H_{20}N_2O_3S$-1/4$H_2O$: C, 61.96; H, 5.92; N, 8.03. Found: C, 62.20; H, 5.86; N, 7.98.

Example 67

9-[4-(2,2-dimethylpropoxy)phenyl]-3,4-dihydropyrido[2,1-c][1,2,4]thiadiazine 2,2-dioxide A mixture of potassium carbonate (300 mg), 1-iodo-2,2-dimethylpropane (430 mg) and 4-(2,2-dioxido-3,4-dihydropyrido[2,1-c][1,2,4]thiadiazin-9-yl)phenol (200 mg) in DMSO (5 mL) was stirred at 150° C. for 1 hr. Water was added to give a precipitate. The precipitate was collected by filtration and washed with Et$_2$O-water. The precipitate was crystallized from CH$_3$CN-IPE to give the title compound (182 mg) as a white solid.

$^1$H NMR (300 MHz, DMSO-$d_6$) δ 1.01 (9H, s), 3.37-3.56 (2H, m), 3.67 (2H, s), 4.53-4.74 (2H, m), 6.69 (1H, t, J=6.8 Hz), 6.90-7.03 (2H, m), 7.39-7.51 (2H, m), 7.58 (1H, dd, J=7.2, 1.5 Hz), 7.74 (1H, dd, J=6.8, 1.5 Hz).

mp 258-259° C.

Anal. Calcd for $C_{18}H_{22}N_2O_3S$-1/4$H_2O$: C, 61.60; H, 6.46; N, 7.98. Found: C, 61.61; H, 6.33; N, 7.95.

Example 68

9-[4-(cyclohexyloxy)phenyl]-3,4-dihydropyrazino[2,1-c][1,2,4]thiadiazine 2,2-dioxide A) 3-[4-(cyclohexyloxy)phenyl]pyrazin-2-amine A mixture of sodium carbonate (491 mg), tetrakis(triphenylphosphine)palladium(0) (80 mg), 4-(cyclohexyloxy)phenylboronic acid (612 mg) and 3-chloropyrazin-2-amine (300 mg) in water (3 mL) and DME (15 mL) was stirred at 80° C. for 4 hr. Silica gel was added and the mixture was concentrated in vacuo. The residue was purified by column chromatography (silica gel, eluted with EtOAc in hexane) to give 3-[4-(cyclohexyloxy)phenyl]pyrazin-2-amine (485 mg) as a white solid.

MS (API+). found: 270.1

B) 9-[4-(cyclohexyloxy)phenyl]-3,4-dihydropyrazino[2,1-c][1,2,4]thiadiazine 2,2-dioxide A mixture of 3-[4-(cyclohexyloxy)phenyl]pyrazin-2-amine (470 mg) in THF (dry) (25.00 mL) was added to a mixture of NaH (60%, 349 mg) and 2-chloroethanesulfonyl chloride (853 mg) in THF (dry) (25 mL) at room temperature. The mixture was stirred at room temperature overnight and 80° C. for 3 hr. Water was added and THF was removed in vacuo. A precipitate was collected by filtration and washed with water-Et$_2$O to give the title compound (522 mg) as a yellow solid. The solid was crystallized from CH$_3$CN-IPE to give a yellow solid.

$^1$H NMR (300 MHz, DMSO-$d_6$) δ 1.11-1.61 (6H, m), 1.61-1.82 (2H, m), 1.82-2.03 (2H, m), 3.43-3.61 (2H, m), 4.30-4.52 (1H, m), 4.53-4.69 (2H, m), 6.86-7.07 (2H, m), 7.53-7.65 (1H, m), 7.65-7.76 (1H, m), 7.90-8.05 (2H, m).

mp 239-240° C.

Anal. Calcd for $C_{18}H_{21}N_3O_3S$: C, 60.15; H, 5.89; N, 11.69. Found: C, 60.00; H, 5.90; N, 11.66.

Example 69

9-[4-(tetrahydro-2H-pyran-4-ylmethoxy)phenyl]-3,4-dihydropyrido[2,1-c][1,2,4]thiadiazine 2,2-dioxide A mixture of potassium carbonate (602 mg), 4-(bromomethyl)tetrahydro-2H-pyran (780 mg), 4-(bromomethyl)tetrahydro-2H-pyran (780 mg) and 4-(2,2-dioxido-3,4-dihydropyrido[2,1-c][1,2,4]thiadiazin-9-yl)phenol (602 mg) in DMSO (5 mL) was stirred at 130° C. for 3 hr. The mixture was poured into 1N NaOH aq. and extracted with EtOAc. The organic layer was separated, washed with 1N NaOH aq. and brine, dried over anhydrous magnesium sulfate and concentrated in vacuo. The residue was passed through column chromatography (NH silica gel, eluted with MeOH) to give the title compound (357 mg) as a pale yellow solid.

$^1$H NMR (300 MHz, DMSO-$d_6$) δ 1.16-1.45 (2H, m), 1.58-1.77 (2H, m), 1.87-2.11 (1H, m), 3.25-3.40 (2H, m), 3.39-3.52 (2H, m), 3.80-3.94 (4H, m), 4.53-4.74 (2H, m), 6.69 (1H, t, J=7.0 Hz), 6.91-7.02 (2H, m), 7.40-7.50 (2H, m), 7.58 (1H, dd, J=7.0, 1.7 Hz), 7.74 (1H, dd, J=6.8, 1.5 Hz).

mp 268-269° C.

Anal. Calcd for $C_{19}H_{22}N_2O_4S\cdot1/8\ H_2O$: C, 60.58; H, 5.95; N, 7.44. Found: C, 60.49; H, 5.91; N, 7.79.

Example 70

9-[4-(cyclopropyloxy)phenyl]-3,4-dihydropyrido[2,1-c][1,2,4]thiadiazine 2,2-dioxide A mixture of potassium carbonate (450 mg), bromocyclopropane (394 mg) and 4-(2,2-dioxido-3,4-dihydropyrido[2,1-c][1,2,4]thiadiazin-9-yl)phenol (300 mg) in DMSO (3 mL) was stirred at 130° C. overnight. Then bromocyclopropane (788 mg) and sodium iodide (488 mg) were added and the mixture was stirred at 150° C. for 5 hr. The mixture was poured into 1N NaOH aq. and extracted with EtOAc. The organic layer was separated, washed with 1N NaOH aq. and brine, dried over anhydrous magnesium sulfate and concentrated in vacuo to give a brown solid. The solid was purified by column chromatography (NH silica gel, eluted with MeOH in EtOAc) to give 50.9 mg of yellow solid. The solid was purified by preparative HPLC (C18, eluted with $H_2O$ in acetonitrile containing 0.1% TFA). The desired fraction was neutralized with sat.NaHCO$_3$ aq. and extracted with EtOAc. The organic layer was separated, dried over anhydrous magnesium sulfate and concentrated in vacuo to give the title compound (26.8 mg) as a white solid.
$^1$H NMR (300 MHz, DMSO-d$_6$) δ 0.57-0.88 (4H, m), 3.39-3.52 (2H, m), 3.87 (1H, tt, J=6.1, 3.0 Hz), 4.50-4.74 (2H, m), 6.69 (1H, t, J=7.0 Hz), 6.92-7.16 (2H, m), 7.42-7.53 (2H, m), 7.53-7.66 (1H, m), 7.74 (1H, d, J=6.4 Hz).

Example 71

9-[4-(tetrahydro-2H-pyran-4-yloxy)phenyl]-3,4-dihydropyrido[2,1-c][1,2,4]thiadiazine 2,2-dioxide A mixture of potassium carbonate (750 mg), 4-bromotetrahydro-2H-pyran (896 mg), sodium iodide (814 mg) and 4-(2,2-dioxido-3,4-dihydropyrido[2,1-c][1,2,4]thiadiazin-9-yl)phenol (300 mg) in DMSO (5 mL) was stirred at 150° C. overnight and 160° C. for 24 hr. The mixture was poured into 1N NaOH aq. and extracted with EtOAc. The organic layer was separated, washed with 1N NaOH aq. and brine, dried over anhydrous magnesium sulfate and concentrated in vacuo. The residue was purified by column chromatography (NH silica gel, eluted with MeOH in EtOAc) to give a white solid (66.6 mg). The solid was purified by preparative HPLC (C18, eluted with $H_2O$ in acetonitrile containing 0.1% TFA). The desired fraction was neutralized with sat. NaHCO$_3$ aq. and extracted with EtOAc. The organic layer was separated, dried over anhydrous magnesium sulfate and concentrated in vacuo to give the title compound (17.0 mg) as a white solid.
$^1$H NMR (300 MHz, DMSO-d$_6$) δ 1.46-1.73 (2H, m), 1.99 (2H, dd, J=13.1, 4.0 Hz), 3.38-3.58 (4H, m), 3.76-3.99 (2H, m), 4.56-4.75 (3H, m), 6.69 (1H, t, J=6.8 Hz), 6.95-7.08 (2H, m), 7.40-7.52 (2H, m), 7.59 (1H, dd, J=7.2, 1.5 Hz), 7.74 (1H, dd, J=6.4, 1.5 Hz).

Example 72

9-[4-(1-ethylpropoxy)phenyl]-3,4-dihydropyrido[2,1-c][1,2,4]thiadiazine 2,2-dioxide A mixture of potassium carbonate (750 mg), 3-bromopentane (820 mg), sodium iodide (814 mg) and 4-(2,2-dioxido-3,4-dihydropyrido[2,1-c][1,2,4]thiadiazin-9-yl)phenol (300 mg) in DMSO (5 mL) was stirred at 150° C. for 3 hr. The mixture was poured into 1N NaOH aq. and extracted with EtOAc. The organic layer was separated, washed with 1N NaOH aq. and brine, dried over anhydrous magnesium sulfate and concentrated in vacuo. The residue was purified by column chromatography (NH silica gel, eluted with MeOH in EtOAc) to give a solid. This material was purified by preparative HPLC (C18, eluted with $H_2O$ in acetonitrile containing 0.1% TFA). The desired fraction was neutralized with sat.NaHCO$_3$ aq. and extracted with EtOAc. The organic layer was separated, dried over anhydrous magnesium sulfate and concentrated in vacuo to give the title compound (36.1 mg) as a pale yellow solid.
$^1$H NMR (300 MHz, DMSO-d$_6$) δ 0.92 (6H, t, J=7.4 Hz), 1.51-1.76 (4H, m), 3.38-3.55 (2H, m), 4.17-4.37 (1H, m), 4.55-4.73 (2H, m), 6.69 (1H, t, J=7.0 Hz), 6.87-7.02 (2H, m), 7.37-7.51 (2H, m), 7.59 (1H, d, J=7.2 Hz), 7.74 (1H, d, J=6.8 Hz).

Example 73

7-chloro-9-[4-(cyclohexyloxy)phenyl]-3,4-dihydropyrido[2,1-c][1,2,4]thiadiazine 2,2-dioxide A) 5-chloro-3-[4-(cyclohexyloxy)phenyl]pyridin-2-amine A mixture ofسodium carbonate (307 mg), tetrakis(triphenylphosphine)palladium(0) (50.1 mg), 4-(cyclohexyloxy)phenylboronic acid (414 mg) and 3-bromo-5-chloropyridin-2-amine (300 mg) in DME (15 mL) and water (3 mL) was stirred at 80° C. for 5 hr. Silica gel was added and the mixture was concentrated in vacuo. The residue was purified by column chromatography (silica gel, eluted with EtOAc in hexane) to give the title compound (212 mg) as a yellow gum.
MS (API+). found: 303.1

B) 7-chloro-9-[4-(cyclohexyloxy)phenyl]-3,4-dihydropyrido[2,1-c][1,2,4]thiadiazine 2,2-dioxide A mixture of 5-chloro-3-[4-(cyclohexyloxy)phenyl]pyridin-2-amine (210 mg) in THF (dry) (10 mL) was added to a mixture of NaH (60%, 139 mg) and 2-chloroethanesulfonyl chloride (339 mg) in THF (dry) (10.0 mL) at room temperature. The mixture was stirred at room temperature overnight. Water was added and the mixture was concentrated in vacuo. The residue was washed with water and IPE to give the title compound (232 mg) as a pale yellow solid. The solid was crystallized from EtOAc-hexane to give a pale yellow solid.
$^1$H NMR (300 MHz, DMSO-d$_6$) δ 1.16-1.61 (6H, m), 1.63-1.83 (2H, m), 1.83-2.04 (2H, m), 3.40-3.54 (2H, m), 4.27-4.49 (1H, m), 4.51-4.72 (2H, m), 6.87-7.09 (2H, m), 7.38-7.59 (2H, m), 7.65 (1H, d, J=2.6 Hz), 8.05 (1H, d, J=2.3 Hz).
mp 284-287° C.
Anal. Calcd for $C_{19}H_{21}N_2O_3SCl$: C, 58.08; H, 5.39; N, 7.13. Found: C, 57.82; H, 5.41; N, 7.06.

Example 74

9-[4-(cyclopentylmethoxy)phenyl]-3,4-dihydropyrido[2,1-c][1,2,4]thiadiazine 2,2-dioxide A mixture of potassium carbonate (450 mg), (iodomethyl)cyclopentane (684 mg) and 4-(2,2-dioxido-3,4-dihydropyrido[2,1-c][1,2,4]thiadiazin-9-yl)phenol (300 mg) in DMSO (5 mL) was stirred at 130° C. for 2 hr. The mixture was poured into water and extracted with EtOAc. The organic layer was separated, washed with 1N NaOH aq. and brine, dried over anhydrous magnesium sulfate and concentrated in vacuo. The residue was washed with Et$_2$O to give the title compound (311 mg) as a pale yellow solid. The solid was crystallized from CH$_3$CN-IPE to give a pale yellow solid.

$^1$H NMR (300 MHz, DMSO-d$_6$) δ 1.19-1.43 (2H, m), 1.46-1.69 (4H, m), 1.69-1.91 (2H, m), 2.32 (1H, dt, J=14.7, 7.4 Hz), 3.39-3.56 (2H, m), 3.88 (2H, d, J=6.8 Hz), 4.50-4.76 (2H, m), 6.68 (1H, t, J=7.0 Hz), 6.90-7.03 (2H, m), 7.35-7.53 (2H, m), 7.58 (1H, dd, J=7.2, 1.9 Hz), 7.74 (1H, dd, J=6.8, 1.5 Hz).

mp 258-259° C.

Anal. Calcd for C$_{19}$H$_{22}$N$_2$O$_3$S: C, 63.66; H, 6.19; N, 7.82. Found: C, 63.45; H, 6.13; N, 7.81.

Example 75

9-[4-(tetrahydrofuran-2-ylmethoxy)phenyl]-3,4-dihydropyrido[2,1-c][1,2,4]thiadiazine 2,2-dioxide A mixture of potassium carbonate (450 mg), sodium iodide (488 mg), 2-(bromomethyl)tetrahydrofuran (538 mg) and 4-(2,2-dioxido-3,4-dihydropyrido[2,1-c][1,2,4]thiadiazin-9-yl)phenol (300 mg) in DMSO (10 mL) was stirred at 130° C. for 5 hr. The mixture was poured into water and extracted with EtOAc. The organic layer was separated, washed with 1N NaOH aq. and brine, dried over anhydrous magnesium sulfate and concentrated in vacuo. The residue was washed with IPE to give the title compound (332 mg) as a pale yellow solid. The solid was crystallized from CH$_3$CN-IPE to give a pale yellow solid.

$^1$H NMR (300 MHz, DMSO-d$_6$) δ 1.51-2.16 (4H, m), 3.39-3.52 (2H, m), 3.59-3.74 (1H, m), 3.73-3.88 (1H, m), 3.88-4.08 (2H, m), 4.08-4.25 (1H, m), 4.52-4.78 (2H, m), 6.69 (1H, t, J=7.0 Hz), 6.86-7.11 (2H, m), 7.36-7.52 (2H, m), 7.58 (1H, dd, J=7.0, 1.7 Hz), 7.74 (1H, dd, J=6.6, 1.7 Hz).

mp 222-223° C.

Anal. Calcd for C$_{18}$H$_{20}$N$_2$O$_4$S.0.25H$_2$O: C, 59.24; H, 5.66; N, 7.68. Found: C, 59.32; H, 5.54; N, 7.71.

Example 76

7-chloro-9-(4-{[4-(trifluoromethyl)pyridin-2-yl]oxy}phenyl)-3,4-dihydropyrido[2,1-c][1,2,4]thiadiazine 2,2-dioxide A) 4-(2-amino-5-chloropyridin-3-yl)phenol A mixture of sodium carbonate (4.09 g), tetrakis(triphenylphosphine)palladium(0) (0.668 g), 4-(tert-butyldimethylsilyloxy)phenylboronic acid (6.32 g) and 3-bromo-5-chloropyridin-2-amine (4.00 g) in DME (100 mL) and water (20 mL) was stirred at 80° C. overnight. Silica gel was added and the mixture was concentrated in vacuo. The residue was purified by column chromatography (silica gel, eluted with EtOAc in hexane) to give 4-(2-amino-5-chloropyridin-3-yl) phenol (3.05 g) as a pale yellow solid and 3-(4-{[tert-butyl(dimethyl)silyl]oxy}phenyl)-5-chloropyridin-2-amine (1.55 g) as a yellow solid.

4-(2-amino-5-chloropyridin-3-yl)phenol

MS (API+). found: 221.1

3-(4-{[tert-butyl(dimethyl)silyl]oxy}phenyl)-5-chloropyridin-2-amine

MS (API+). found: 335.2

B) 5-chloro-3-(4-{[4-(trifluoromethyl)pyridin-2-yl]oxy}phenyl)pyridin-2-amine

A mixture of potassium carbonate (376 mg), 2-fluoro-4-(trifluoromethyl)pyridine (269 mg) and 4-(2-amino-5-chloropyridin-3-yl)phenol (300 mg) in DMSO (5 mL) was stirred at 120° C. for 2 hr. The mixture was neutralized with sat.NaHCO$_3$ aq. and extracted with EtOAc. The organic layer was separated, washed with 1N NaOH aq. and brine, dried over anhydrous magnesium sulfate and concentrated in vacuo. The residue was purified by column chromatography (NH silica gel, eluted with EtOAc in hexane) to give the title compound (484 mg) as a pale yellow solid.

MS (API+). found: 366.1

C) 7-chloro-9-(4-{[4-(trifluoromethyl)pyridin-2-yl]oxy}phenyl)-3,4-dihydropyrido[2,1-c][1,2,4]thiadiazine 2,2-dioxide 5-Chloro-3-(4-(4-(trifluoromethyl)pyridin-2-yloxy)phenyl)pyridin-2-amine (470 mg) was added to a mixture of NaH (60%, 257 mg) and 2-chloroethanesulfonyl chloride (628 mg) in THF (dry) (10 mL) at room temperature. The mixture was stirred at room temperature overnight and 80° C. for 3 hr. Water was added and the mixture was concentrated in vacuo. The residue was washed with IPE to give the title compound (502 mg) as a yellow solid. The solid was crystallized from CH$_3$CN-IPE to give a pale yellow solid (1st crop impure, 2nd crop (254 mg)). The 1st crop was purified by column chromatography (NH silica gel, eluted with MeOH in EtOAc) to give the title compound (263 mg) as a white solid.

$^1$H NMR (300 MHz, DMSO-d$_6$) δ 3.44-3.61 (2H, m), 4.57-4.72 (2H, m), 7.17-7.29 (2H, m), 7.46-7.57 (2H, m), 7.57-7.66 (2H, m), 7.77 (1H, d, J=2.3 Hz), 8.11 (1H, d, J=2.7 Hz), 8.45 (1H, d, J=5.3 Hz).

mp 238-239° C.

Anal. Calcd for C$_{19}$H$_3$N$_3$O$_3$SClF$_3$-0.2EtOAc: C, 500.23; H, 3.11; N, 8.88.

Found: C, 49.97; H, 3.26; N, 8.86.

Example 77

7-chloro-9-{4-[(5-chloropyridin-2-yl)oxy]phenyl}-3,4-dihydropyrido[2,1-c][1,2,4]thiadiazine 2,2-dioxide A) 5-chloro-3-{4-[(5-chloropyridin-2-yl)oxy]phenyl}pyridin-2-amine A mixture of potassium carbonate (376 mg), 5-chloro-2-fluoropyridine (215 mg) and 4-(2-amino-5-chloropyridin-3-yl)phenol (300 mg) in DMSO (10 mL) was stirred at 120° C. for 5 hr. The mixture was poured into water and extracted with EtOAc. The organic layer was separated, washed with 1N NaOH aq. and brine, dried over anhydrous magnesium sulfate and concentrated in vacuo. The residue was purified by column chromatography (NH silica gel, eluted with EtOAc in hexane) to give the title compound (450 mg) as a pale yellow solid.

MS (API+). found: 332.0

B) 7-chloro-9-{4-[(5-chloropyridin-2-yl)oxy]phenyl}-3,4-dihydropyrido[2,1-c][1,2,4]thiadiazine 2,2-dioxide A mixture of 5-chloro-3-{4-[(5-chloropyridin-2-yl)oxy]phenyl}pyridin-2-amine (440 mg) in THF (dry) (10 mL) was added to a mixture of NaH (60%, 265 mg) and 2-chloroethanesulfonyl chloride (648 mg) in THF (dry) (10 mL) at room temperature. The mixture was stirred at room temperature overnight and 80° C. for 3 hr. Water was added and the mixture was concentrated in vacuo. The residue was washed with water and $Et_2O$ to give an off-white solid. The solid was purified by column chromatography (NH silica gel, eluted with MeOH in EtOAc) to give the title compound (520 mg) as an off-white solid. The solid was crystallized from $CH_3CN$-IPE to give a white solid.

$^1$H NMR (300 MHz, DMSO-$d_6$) δ 3.42-3.55 (2H, m), 4.52-4.70 (2H, m), 7.13-7.24 (3H, m), 7.55-7.66 (2H, m), 7.76 (1H, d, J=2.3 Hz), 7.98 (1H, dd, J=8.7, 2.7 Hz), 8.11 (1H, d, J=2.7 Hz), 8.25 (1H, d, J=2.7 Hz).

mp 228-229° C.

Anal. Calcd for $C_{28}H_{23}N_3O_3SCl_2$: C, 51.20; H, 3.10; N, 9.95. Found: C, 51.16; H, 3.17; N, 9.95.

Example 78

7-chloro-9-(4-{[3-(trifluoromethyl)pyridin-2-yl]oxy}phenyl)-3,4-dihydropyrido[2,1-c][1,2,4]thiadiazine 2,2-dioxide

A) 5-chloro-3-(4-{[3-(trifluoromethyl)pyridin-2-yl]oxy}phenyl)pyridin-2-amine A mixture of potassium carbonate (376 mg), 2-fluoro-3-(trifluoromethyl)pyridine (269 mg) and 4-(2-amino-5-chloropyridin-3-yl)phenol (300 mg) in DMSO (10 mL) was stirred at 120° C. for 3 hr. The mixture was poured into water and extracted with EtOAc. The organic layer was separated, washed with 1N NaOH aq. and brine, dried over anhydrous magnesium sulfate and concentrated in vacuo. The residue was purified by column chromatography (NH silica gel, eluted with EtOAc in hexane) to give the title compound (470 mg) as a pale yellow solid.

MS (API+). found: 366.0

B) 7-chloro-9-(4-{[3-(trifluoromethyl)pyridin-2-yl]oxy}phenyl)-3,4-dihydropyrido[2,1-c][1,2,4]thiadiazine 2,2-dioxide A mixture of 5-chloro-3-(4-{[3-(trifluoromethyl)pyridin-2-yl]oxy}phenyl)pyridin-2-amine (450 mg) in THF (dry) (10 mL) was added to a mixture of NaH (60%, 246 mg) and 2-chloroethanesulfonyl chloride (602 mg) in THF (dry) (10.0 mL) at room temperature. The mixture was stirred at 70° C. for 3 hr. Water was added and the mixture was concentrated in vacuo. The residue was washed with water and $Et_2O$ to give an off-white solid. The solid was purified by column chromatography (NH silica gel, eluted with MeOH in EtOAc) to give the title compound (315 mg) as a white solid. The solid was crystallized from $CH_3CN$-IPE to give a white solid.

$^1$H NMR (300 MHz, DMSO-$d_6$) δ 3.38-3.62 (2H, m), 4.53-4.78 (2H, m), 7.14-7.30 (2H, m), 7.36 (1H, dd, J=7.6, 4.9 Hz), 7.51-7.68 (2H, m), 7.77 (1H, d, J=2.3 Hz), 8.12 (1H, d, J=2.6 Hz), 8.29 (1H, dd, J=7.6, 1.1 Hz), 8.45 (1H, dd, J=4.9, 1.1 Hz).

mp 264-265° C.

Anal. Calcd for $C_{19}H_{13}N_3O_3SClF_3$—$CH_3CN$: C, 50.76; H, 3.25; N, 11.28.

Found: C, 50.67; H, 3.27; N, 11.21.

Example 79

7-chloro-9-(4-{[2-(trifluoromethyl)pyridin-4-yl]oxy}phenyl)-3,4-dihydropyrido[2,1-c][1,2,4]thiadiazine 2,2-dioxide

A) 5-chloro-3-(4-{[2-(trifluoromethyl)pyridin-4-yl]oxy}phenyl)-1,2-dihydropyridin-2-amine A mixture of 4-bromo-2-(trifluoromethyl)pyridine (282 mg), tripotassium phosphate (481 mg), picolinic acid (27.9 mg), copper(I) iodide (21.58 mg) and 4-(2-amino-5-chloropyridin-3-yl)phenol (250 mg) in DMSO (5 mL) was stirred at 140° C. under $N_2$ overnight. The mixture was poured into sat.$NH_4Cl$ aq. and extracted with EtOAc. The organic layer was separated, washed with brine, dried over anhydrous magnesium sulfate and concentrated in vacuo. The residue was purified by column chromatography (NH silica gel, eluted with EtOAc in hexane) to give the title compound (230 mg) as a pale yellow solid.

MS (API+). found: 366.0

B) 7-chloro-9-(4-{[2-(trifluoromethyl)pyridin-4-yl]oxy}phenyl)-3,4-dihydropyrido[2,1-c][1,2,4]thiadiazine 2,2-dioxide A mixture of 5-chloro-3-(4-(2-(trifluoromethyl)pyridin-4-yloxy)phenyl)pyridin-2-amine (220 mg) in THF (dry) (10 mL) was added to a mixture of NaH (60%, 120 mg) and 2-chloroethanesulfonyl chloride (294 mg) in THF (dry) (10 mL) at room temperature. The mixture was stirred at 70° C. for 1 hr. MeOH and NH silica gel were added and the mixture was concentrated in vacuo. The residue was purified by column chromatography (NH silica gel, eluted with MeOH in EtOAc) to give the titled compound (253 mg) as a white solid. The solid was crystallized from $CH_3CN$-IPE to give a white solid.

$^1$H NMR (300 MHz, DMSO-$d_6$) δ 3.44-3.56 (2H, m), 4.54-4.73 (2H, m), 7.22 (1H, dd, J=5.7, 2.3 Hz), 7.29-7.41 (2H, m), 7.50 (1H, d, J=2.3 Hz), 7.67-7.76 (2H, m), 7.80 (1H, d, J=2.3 Hz), 8.13 (1H, d, J=2.3 Hz), 8.67 (1H, d, J=5.7 Hz).

mp 239-240° C.

Anal. Calcd for $C_{19}H_{13}N_3O_3SClF_3$: C, 50.06; H, 2.87; N, 9.22. Found: C, 50.08; H, 3.13; N, 9.08.

Example 80

9-(4-pyrrolidin-1-ylphenyl)-3,4-dihydropyrido[2,1-c][1,2,4]thiadiazine 2,2-dioxide

A) 1-(4-iodophenyl)pyrrolidin-2-one

A mixture of 4-bromobutanoyl chloride (15.0 g) in THF (dry) (150 mL) was added to a mixture of 4-iodoaniline (7.50 g) and $Et_3N$ (9.55 mL) in THF (dry) (150 mL) at 0° C. The mixture was stirred at 60° C. overnight. A mixture of NaH (60%, 4.11 g) in DMF (dry) (50 mL) was added to the mixture at 0° C. The mixture was stirred at 120° C. overnight. The mixture was poured into water and extracted with EtOAc. The organic layer was separated, washed with brine, dried over anhydrous magnesium sulfate and concentrated in vacuo. The residue was purified by column chromatography (silica gel, eluted with EtOAc in hexane) to give the title compound (3.84 g) as a white solid.
MS (API+). found: 287.9

B) 1-(4-iodophenyl)pyrrolidine

A mixture of borane-tetrahydrofuran complex (1.2 M in THF, 5.81 mL) and 1-(4-iodophenyl)pyrrolidin-2-one (1.00 g) in THF (dry) (20 mL) was stirred at 70° C. under $N_2$ for 3 hr. The mixture was poured into 1N HCl aq., sat.NaHCO$_3$ aq. was added and the mixture was extracted with EtOAc. The organic layer was separated, washed with brine, dried over anhydrous magnesium sulfate and concentrated in vacuo to give the title compound (0.954 g) as a white solid.
MS (API+). found: 274.0

C) 3-(4-pyrrolidin-1-ylphenyl)-1,2-dihydropyridin-2-amine n-Butyllithium (1.6 M in hexane, 48.3 mL) was added dropwise to a solution of N,N,N',N'-tetramethylethane-1,2-diamine (8.08 g) and tert-butyl pyridin-2-ylcarbamate (5.00 g) in THF (dry) (50 mL) at −78° C. The mixture was stirred at 0° C. under $N_2$ for 2 hr. Triisopropyl borate (17.0 g) was added to the mixture at −78° C. The mixture was stirred at 0° C. under $N_2$ for 30 min. The mixture was quenched with sat.NH$_4$Cl aq. at 0° C. and added with Et$_2$O to give a yellow precipitate (11.7 g, wet). A mixture of the precipitate (349 mg), sodium carbonate (155 mg), tetrakis(triphenylphosphine)palladium(0) (42.3 mg) and 1-(4-iodophenyl)pyrrolidine (200 mg) in DME (25 mL) and water (5 mL) was stirred at 80° C. under $N_2$ overnight. NH silica gel was added and the mixture was concentrated in vacuo. The residue was purified by column chromatography (NH silica gel, eluted with EtOAc in hexane) to give the title compound (17.1 mg) as a white solid.
MS (API+). found: 240.1

D) 9-(4-pyrrolidin-1-ylphenyl)-3,4-dihydropyrido[2,1-c][1,2,4]thiadiazine 2,2-dioxide A mixture of 3-(4-(pyrrolidin-1-yl)phenyl)pyridin-2-amine (17.0 mg) in THF (dry) (5 mL) was added to a mixture of NaH (60%, 14.2 mg) and 2-chloroethanesulfonyl chloride (34.7 mg) in THF (dry) (5.00 mL) at room temperature. The mixture was stirred at 50° C. for 1 hr. Water and NH silica gel were added and the mixture was concentrated in vacuo. The residue was purified by column chromatography (NH silica gel, eluted with MeOH in EtOAc) to give the title compound (14.8 mg) as a pale yellow solid.
$^1$H NMR (300 MHz, CDCl$_3$) δ 1.89-2.09 (4H, m), 3.27-3.35 (4H, m), 3.35-3.44 (2H, m), 4.55-4.71 (2H, m), 6.46-6.64 (3H, m), 7.10 (1H, dd, J=6.8, 1.5 Hz), 7.43 (1H, dd, J=7.2, 1.5 Hz), 7.48-7.57 (2H, m).

Example 81

7-chloro-9-(4-phenoxyphenyl)-3,4-dihydropyrido[2,1-c][1,2,4]thiadiazine 2,2-dioxide A) 5-chloro-3-(4-phenoxyphenyl)pyridin-2-amine A mixture of sodium carbonate decahydrate (20.7 g), tetrakis(triphenylphosphine)palladium(0) (0.836 g), 4-phenoxyphenylboronic acid (9.28 g) and 4-phenoxyphenylboronic acid (9.28 g) in DME (150 mL) and water (30 mL) was stirred at 80° C. under $N_2$ overnight. NH silica gel was added and the mixture was concentrated in vacuo. The residue was purified by column chromatography (NH silica gel, eluted with EtOAc in hexane) to give the title compound (10.6 g) as a yellow solid.
MS (API+). found: 297.1

B) 7-chloro-9-(4-phenoxyphenyl)-3,4-dihydropyrido[2,1-c][1,2,4]thiadiazine 2,2-dioxide To a mixture of NaH (60%, 2.59 g) and 2-chloroethanesulfonyl chloride (6.33 g) in THF (dry) (50 mL) was added a solution of 5-chloro-3-(4-phenoxyphenyl)pyridin-2-amine (3.84 g) in THF (dry) (50 mL) at room temperature. The mixture was stirred at room temperature overnight. Water and NH silica gel were added and the mixture was concentrated in vacuo. The residue was purified by column chromatography (NH silica gel, eluted with MeOH in EtOAc) to give the title compound (3.07 g) as a pale yellow solid. The solid was crystallized from DMSO (15 mL)-EtOH (90 mL) to give a white solid.
$^1$H NMR (300 MHz, DMSO-d$_6$) δ 3.38-3.58 (2H, m), 4.50-4.72 (2H, m), 6.88-7.14 (4H, m), 7.14-7.28 (1H, m), 7.29-7.49 (2H, m), 7.50-7.64 (2H, m), 7.71 (1H, d, J=2.6 Hz), 8.09 (1H, d, J=2.3 Hz).
mp 248-249° C.
Anal. Calcd for $C_{19}H_{15}N_2O_3SCl \cdot 0.25H_2O$: C, 58.31; H, 3.99; N, 7.16.
Found: C, 58.32; H, 3.97; N, 7.13.

Example 82

9-{4-[(3-fluorobenzyl)oxy]phenyl}-3,4-dihydropyrido[2,1-c][1,2,4]thiadiazine 2,2-dioxide A) 4-(2-aminopyridin-3-yl)phenol Tetrakis(triphenylphosphine)palladium(0) (0.967 g) was added to a suspension of 3-bromopyridin-2-amine (4.82 g), 4-hydroxyphenylboronic acid (5.00 g) and sodium carbonate (5.91 g) in DME (250 mL) and water (50.0 mL) and the mixture was stirred at 80° C. under nitrogen for 4 hr. Water and EtOAc were added and the organic layer was separated, washed with brine, dried over anhydrous sodium sulfate and concentrated in vacuo. The residue was purified by column chromatography (silica gel, eluted with EtOAc in hexane) and washed with IPE to give the title compound (2.80 g) as a white solid.
MS (ESI+). found: 187.0.

B) 3-{4-[(3-fluorobenzyl)oxy]phenyl}pyridin-2-amine

Diisopropylazadicarboxylate (1.19 mL) was added dropwise to a solution of triphenylphosphine (1585 mg), 4-(2-aminopyridin-3-yl)phenol (750 mg) and (3-fluorophenyl)methanol (0.434 mL) in THF (dry) (15 mL) at room temperature and the mixture was stirred overnight and concentrated in vacuo. The residue was purified by column chromatography (1st; NH-silica gel, eluted with EtOAc in hexane, 2nd; silica gel, eluted with EtOAc in hexane) to give the title compound (210 mg) as a white powder.
MS (ESI+). found: 295.1.

C) 9-{4-[(3-fluorobenzyl)oxy]phenyl}-3,4-dihydropyrido[2,1-c][1,2,4]thiadiazine 2,2-dioxide To a suspension of NaH (60%, 136 mg) in THF (dry) (10 mL) was added 2-chloroethanesulfonyl chloride (0.214 mL)

at 0° C. and the mixture was stirred for 5 min at the same temperature. A solution of 3-{4-[(3-fluorobenzyl)oxy]phenyl}pyridin-2-amine (200 mg) in THF (dry) (10 mL) was added at 0° C. and the mixture was stirred at room temperature under nitrogen overnight. The mixture was quenched with water at 0° C. carefully. Water was added to form precipitates which were washed with water, hexane and collected. The precipitate was sonicated in EtOAc and the insoluble material was collected to give 9-{4-[(3-fluorobenzyl)oxy]phenyl}-3,4-dihydropyrido[2,1-c][1,2,4]thiadiazine 2,2-dioxide (317.7 mg) as an off-white solid. This was crystallized from MeOH-THF/IPE to give an off-white crystal.

$^1$H NMR (300 MHz, DMSO-d$_6$) δ 3.43-3.55 (2H, m), 4.58-4.73 (2H, m), 5.18 (2H, s), 6.69 (1H, t, J=7.0 Hz), 7.05 (2H, d, J=9.0 Hz), 7.16 (1H, td, J=8.7, 2.6 Hz), 7.25-7.36 (2H, m), 7.40-7.52 (3H, m), 7.59 (1H, dd, J=7.2, 1.5 Hz), 7.74 (1H, dd, J=6.8, 1.9 Hz).

Example 83

9-{4-[(3-fluorobenzyl)oxy]phenyl}-3,4,6,7,8,9-hexahydropyrido[2,1-c][1,2,4]thiadiazine 2,2-dioxide Example 84

9-{4-[(3-fluorobenzyl)oxy]phenyl}-3,4,6,7,8,9-hexahydropyrido[2,1-c][1,2,4]thiadiazin-9-ol 2,2-dioxide Diisopropylazadicarboxylate (0.241 mL) was added to a suspension of triphenylphosphine (321 mg), 2,2-dioxido-4-(3,4,6,7,8,9-hexahydropyrido[2,1-c][1,2,4]thiadiazin-9-yl)phenol (229 mg) and (3-fluorophenyl)methanol (0.106 mL) in THF (dry) (80 mL) at room temperature and the mixture was stirred overweekend and concentrated in vacuo. The residue was washed with EtOAc-THF (1:1) and the insoluble material was removed by filtration, and the filtrate was concentrated in vacuo (starting phenol was recovered, 95.6 mg). The residue was purified by column chromatography (1st; silica gel, eluted with EtOAc in hexane and MeOH in EtOAc, 2nd; NH-silica gel, eluted with MeOH in EtOAc, 3rd; silica gel, eluted with EtOAc in hexane) to give 9-{4-[(3-fluorobenzyl)oxy]phenyl}-3,4,6,7,8,9-hexahydropyrido[2,1-c][1,2,4]thiadiazine 2,2-dioxide and 9-{4-[(3-fluorobenzyl)oxy]phenyl}-3,4,6,7,8,9-hexahydropyrido[2,1-c][1,2,4]thiadiazin-9-ol 2,2-dioxide. 9-{4-[(3-fluorobenzyl)oxy]phenyl}-3,4,6,7,8,9-hexahydropyrido[2,1-c][1,2,4]thiadiazine 2,2-dioxide was recrystallized from THF/IPE to give colorless crystals (40.3 mg). 9-{4-[(3-fluorobenzyl)oxy]phenyl}-3,4,6,7,8,9-hexahydropyrido[2,1-c][1,2,4]thiadiazin-9-ol 2,2-dioxide was recrystallized from THF/IPE to give a white solid (1.4 mg). 9-{4-[(3-fluorobenzyl)oxy]phenyl}-3,4,6,7,8,9-hexahydropyrido[2,1-c][1,2,4]thiadiazine 2,2-dioxide $^1$H NMR (300 MHz, DMSO-d$_6$) δ 1.63-1.81 (3H, m), 1.88-2.09 (1H, m), 3.21-3.29 (2H, m), 3.41-3.55 (2H, m), 3.67-3.74 (1H, m), 3.76-3.88 (2H, m), 5.06-5.16 (2H, m), 6.92-7.00 (2H, m), 7.08-7.19 (3H, m), 7.24-7.33 (2H, m), 7.39-7.49 (1H, m). 9-{4-[(3-fluorobenzyl)oxy]phenyl}-3,4,6,7,8,9-hexahydropyrido[2,1-c][1,2,4]thiadiazin-9-ol 2,2-dioxide $^1$H NMR (300 MHz, DMSO-d$_6$) δ 1.44-1.61 (1H, m), 1.76-2.02 (3H, m), 3.41-3.55 (4H, m), 3.78-3.96 (2H, m), 5.13 (2H, s), 5.72 (1H, s), 6.91-7.01 (2H, m), 7.10-7.19 (1H, m), 7.24-7.34 (4H, m), 7.44 (1H, td, J=8.0, 5.8 Hz).

Example 85

9-[4-(3-chlorophenoxy)phenyl]-3,4-dihydropyrido[2,1-c][1,2,4]thiadiazine 2,2-dioxide A) 3-(4-(3-chlorophenoxy)phenyl)pyridin-2-amine To a mixture of 4-(2-aminopyridin-3-yl)phenol (400 mg), 1-chloro-3-iodobenzene (615 mg), picoline acid (52.9 mg) and tripotassium phosphate (1368 mg) in DMSO (6 mL) was added copper (I) iodide (82.0 mg). The reaction mixture was stirred under a nitrogen atmosphere at 120° C. for 4 hr. To the reaction mixture was added water, and the mixture was extracted with ethyl acetate. The extract was washed with saturated brine, dried over anhydrous sodium sulfate, and the solvent was evaporated under reduced pressure. The residue was purified by silica gel column chromatography (ethyl acetate/hexane) and concentrated under reduced pressure to give the title compound (307 mg) as a yellow solid.
MS (ESI+). found: 297.0.

B) 9-[4-(3-chlorophenoxy)phenyl]-3,4-dihydropyrido[2,1-c][1,2,4]thiadiazine 2,2-dioxide To a suspension of NaH (60%, 202 mg) in THF (dry) (10 mL) was added 2-chloroethanesulfonyl chloride (0.319 mL) at 0° C. and the mixture was stirred for 5 min at the same temperature. A solution of 3-(4-(3-chlorophenoxy)phenyl)pyridin-2-amine (300 mg) in THF (dry) (10 mL) was added at 0° C. and the mixture was stirred at room temperature under nitrogen overnight. The mixture was quenched with water at 0° C. carefully. Water was added to form precipitates which were washed with water, hexane and collected. The precipitate was sonicated in EtOAc and the insoluble material was collected to give the title compound (248 mg) as an off-white solid. This was crystallized from THF-MeOH/IPE to give colorless crystals.

$^1$H NMR (300 MHz, DMSO-d$_6$) δ 3.42-3.51 (2H, m), 4.61-4.70 (2H, m), 6.71 (1H, t, J=7.0 Hz), 7.01-7.06 (1H, m), 7.07-7.12 (2H, m), 7.14 (1H, t, J=2.1 Hz), 7.21-7.26 (1H, m), 7.41-7.47 (1H, m), 7.55-7.61 (2H, m), 7.65 (1H, dd, J=7.2, 1.9 Hz), 7.78 (1H, dd, J=6.8, 1.5 Hz).

Example 86

9-{4-[2-(trifluoromethyl)phenoxy]phenyl}-3,4,6,7,8,9-hexahydropyrido[2,1-c][1,2,4]thiadiazine 2,2-dioxide Platinum(IV) oxide (20.0 mg) was added to a solution of 9-{4-[2-(trifluoromethyl)phenoxy]phenyl}-3,4-dihydropyrido[2,1-c][1,2,4]thiadiazine 2,2-dioxide (100 mg) in THF (dry) (10 mL) and MeOH (10 mL) and the mixture was stirred at room temperature under hydrogen overnight. The insoluble solid was removed by filtration through Celite-pad (eluted with EtOAc) and the filtrate was concentrated in vacuo. The residue was crystallized from THF/IPE to give 9-{4-[2-(trifluoromethyl)phenoxy]phenyl}-3,4,6,7,8,9-hexahydropyrido[2,1-c][1,2,4]thiadiazine 2,2-dioxide (77.3 mg) as colorless crystals.

$^1$H NMR (300 MHz, DMSO-d$_6$) δ1.69-1.82 (3H, m), 1.93-2.09 (1H, m), 3.26-3.31 (2H, m), 3.43-3.55 (2H, m), 3.76-3.89 (3H, m), 7.00 (2H, d, J=8.7 Hz), 7.06 (1H, d, J=7.9 Hz), 7.26 (2H, d, J=8.7 Hz), 7.29-7.36 (1H, m), 7.62-7.69 (1H, m), 7.79 (1H, d, J=7.6 Hz).

Example 87

4-(2,2-dioxido-3,4-dihydropyrido[2,1-c][1,2,4]thiadiazin-9-yl)phenol

A) 3-(4-{[tert-butyl(dimethyl)silyl]oxy}phenyl)pyridin-2-amine

Tetrakis(triphenylphosphine)palladium(0) (1.38 g) was added to a suspension of 3-bromopyridin-2-amine (20.6 g), 4-(tert-butyldimethylsilyloxy)phenylboronic acid (39.0 g) and sodium carbonate (25.2 g) in DME (650 mL) and water (130 mL) and the mixture was stirred at 100° C. under nitrogen 6 hr. Volatiles were removed in vacuo, water and EtOAc were added and the organic layer was separated, washed with brine, dried over anhydrous sodium sulfate and concentrated in vacuo. The residue was crystallized from EtOAc-hexane to give 4-(2-aminopyridin-3-yl)phenol (7.90 g) as yellow crystals. The filtrate of crystallization was purified by column chromatography (silica gel, eluted with EtOAc in hexane) to give 3-(4-{[tert-butyl(dimethyl)silyl]oxy}phenyl)pyridin-2-amine (23.4 g) as a white powder.

MS (ESI+). found: 301.3.

B) 9-(4-{[tert-butyl(dimethyl)silyl]oxy}phenyl)-3,4-dihydropyrido[2,1-c][1,2,4]thiadiazine 2,2-dioxide To a suspension of NaH (60%, 6.66 g) in THF (dry) (200 mL) was added 2-chloroethanesulfonyl chloride (7.00 mL) at 0° C. and the mixture was stirred for 10 min at the same temperature. A solution of 3-(4-{[tert-butyl(dimethyl)silyl]oxy}phenyl)pyridin-2-amine (10 g) in THF (dry) (200 mL) was added at 0° C. and the mixture was stirred at room temperature under nitrogen overnight. The mixture was quenched with water at 0° C. carefully. Water was added to form precipitates which were washed with water and EtOAc, and collected to give 9-(4-{[(tert-butyl(dimethyl)silyl]oxy}phenyl)-3,4-dihydropyrido[2,1-c][1,2,4]thiadiazine 2,2-dioxide (11.2 g) as an off-white solid.

MS (ESI+). found: 391.2.

C) 4-(2,2-dioxido-3,4-dihydropyrido[2,1-c][1,2,4]thiadiazin-9-yl)phenol

TBAF (1 M in THF) (40.0 mL) was added to a solution of 9-(4-{[tert-butyl(dimethyl)silyl]oxy}phenyl)-3,4-dihydropyrido[2,1-c][1,2,4]thiadiazine 2,2-dioxide (14.9 g) in THF (dry)(2.0 L) at 0° C. and the mixture was stirred at ambient temperature for 30 min. The mixture was neutralized with sat. NH$_4$Cl aq. and extracted with EtOAc. The organic layer was separated, dried over anhydrous sodium sulfate and concentrated in vacuo. The residue was washed with EtOAc/hexane to give the title compound (10.2 g) as an off-white crystal.

$^1$H NMR (300 MHz, DMSO-d$_6$) δ 3.36-3.54 (2H, m), 4.57-4.74 (2H, m), 6.67 (1H, t, J=6.8 Hz), 6.78 (2H, d, J=8.7 Hz), 7.35 (2H, d, J=8.7 Hz), 7.54 (1H, dd, J=7.2, 1.5 Hz), 7.71 (1H, dd, J=6.8, 1.5 Hz), 9.58 (1H, s).

Example 88

9-[4-(cycloheptyloxy)phenyl]-3,4-dihydropyrido[2,1-c][1,2,4]thiadiazine 2,2-dioxide To a mixture of 4-(2,2-dioxido-3,4-dihydropyrido[2,1-c][1,2,4]thiadiazin-9-yl)phenol (300 mg), potassium carbonate (390 mg) in DMSO (5 mL) was added bromocycloheptane (250 mg). The mixture was stirred at 130° C. for 1 hr. Another bromocycloheptane (100 uL) was added and the mixture was stirred at room temperature overnight. 0.5 N NaOH aq., EtOAc and THF were added and the extracted organic layer was washed with water and brine, dried over anhydrous sodium sulfate and concentrated in vacuo. The residue was crystallized from MeCN/IPE to give the title compound (144 mg) as colorless crystals.

$^1$H NMR (300 MHz, DMSO-d$_6$) δ 1.40-1.79 (10H, m), 1.90-2.05 (2H, m), 3.40-3.49 (2H, m), 4.49-4.59 (1H, m), 4.60-4.68 (2H, m), 6.65-6.72 (1H, m), 6.92 (2H, d, J=8.7 Hz), 7.44 (2H, d, J=8.7 Hz), 7.58 (1H, dd, J=7.2, 1.5 Hz), 7.73 (1H, dd, J=6.8, 1.5 Hz).

Example 89

9-[4-(cyclohexyloxy)phenyl]-7-fluoro-3,4-dihydropyrido[2,1-c][1,2,4]thiadiazine 2,2-dioxide

A) 3-[4-(cyclohexyloxy)phenyl]-5-fluoropyridin-2-amine

Tetrakis(triphenylphosphine)palladium(0) (54.5 mg) was added to a suspension of 3-bromo-5-fluoropyridin-2-amine (300 mg), 4-(cyclohexyloxy)phenylboronic acid (449 mg) and sodium carbonate (333 mg) in DME (15 mL) and water (3 mL) and the mixture was stirred at 100° C. under nitrogen for 2 hr. Water and EtOAc were added and the organic layer was separated, washed with brine, dried over anhydrous sodium sulfate and concentrated in vacuo. The residue was purified by column chromatography (silica gel, eluted with EtOAc in hexane) and washed with IPE to give the title compound (366 mg) as a yellow solid.

MS (ESI+). found: 287.2.

B) 9-[4-(cyclohexyloxy)phenyl]-7-fluoro-3,4-dihydropyrido[2,1-c][1,2,4]thiadiazine 2,2-dioxide To a suspension of NaH (60%, 153 mg) in THF (dry) (15 mL) was added 2-chloroethanesulfonyl chloride (0.403 mL) at 0° C. and the mixture was stirred for 5 min at the same temperature. A solution of 3-[4-(cyclohexyloxy)phenyl]-5-fluoropyridin-2-amine (366 mg) in THF (dry) (15 mL) was added at 0° C. and the mixture was stirred at room temperature under nitrogen for 15 hr and at 50° C. for 1 hr. The mixture was quenched with water at 0° C. carefully and water was added to form precipitates. The precipitate was crystallized from THF-MeOH/IPE to give the title compound (170 mg) as colorless crystals.

$^1$H NMR (300 MHz, DMSO-d$_6$) δ 1.19-1.58 (6H, m), 1.65-1.80 (2H, m), 1.89-2.04 (2H, m), 3.39-3.51 (2H, m), 4.34-4.47 (1H, m), 4.54-4.67 (2H, m), 6.97 (2H, d, J=8.7 Hz), 7.51 (2H, d, J=8.7 Hz), 7.77 (1H, dd, J=8.5, 2.8 Hz), 8.04 (1H, dd, J=4.3, 2.8 Hz).

Example 90

9-[4-(3-methoxyphenoxy)phenyl]-3,4-dihydropyrido[2,1-c][1,2,4]thiadiazine 2,2-dioxide

A) 3-[4-(3-methoxyphenoxy)phenyl]pyridin-2-amine

Copper(I) iodide (102 mg) was added to a mixture of picolinic acid (66.1 mg), 4-(2-aminopyridin-3-yl)phenol (500 mg), tripotassium phosphate (1710 mg), 1-iodo-3-methoxybenzene (754 mg) and DMSO (8 mL). The mixture was stirred at 120° C. under nitrogen for 6 hr. The insoluble material was removed by silica-filtration with EtOAc, and the filtrate was extracted with EtOAc. The organic layer was separated, washed with water and brine, dried over anhydrous sodium sulfate and concentrated in vacuo. The residue was purified by column chromatography (NH silica gel, eluted with EtOAc in hexane) to give the title compound (349 mg) as a yellow solid.

MS (ESI+). found: 293.3.

B) 9-[4-(3-methoxyphenoxy)phenyl]-3,4-dihydropyrido[2,1-c][1,2,4]thiadiazine 2,2-dioxide To a suspension of NaH (60%, 143 mg) in THF (dry) (15 mL) was added 2-chloroethanesulfonyl chloride (0.376 mL) at 0° C. and the mixture was stirred for 5 min at the same temperature. A solution of 3-(4-(3-methoxyphenoxy)phenyl) pyridin-2-amine (348 mg) in THF (dry) (15 mL) was added at 0° C. and the mixture was stirred at room temperature under nitrogen for 15 hr. The mixture was quenched with water at 0° C. carefully and water was added to form precipitates. The precipitate was crystallized from MeCN-THF-MeOH/IPE to give the title compound (304 mg) as colorless crystals.

$^1$H NMR (300 MHz, DMSO-d$_6$) δ 3.42-3.51 (2H, m), 3.75 (3H, s), 4.61-4.70 (2H, m), 6.58-6.79 (4H, m), 7.03 (2H, d, J=8.7 Hz), 7.27-7.36 (1H, m), 7.54 (2H, d, J=8.7 Hz), 7.63 (1H, dd, J=7.2, 1.5 Hz), 7.77 (1H, dd, J=6.8, 1.5 Hz).

Example 91

9-[4-(cyclobutyloxy)phenyl]-3,4-dihydropyrido[2,1-c][1,2,4]thiadiazine 2,2-dioxide A mixture of 4-(2,2-dioxido-3,4-dihydropyrido[2,1-c][1,2,4]thiadiazin-9-yl)phenol (300 mg), potassium carbonate (390 mg) and bromocyclobutane (191 mg) in DMSO (5 mL) was stirred at 130° C. for 1 hr. Bromocyclobutane (100 mg) was added, and the mixture was stirred at room temperature overnight. 0.5N Aqueous sodium hydroxide solution, ethyl acetate and THF were added and the mixture was extracted. The extract was washed with water and saturated brine, dried over anhydrous sodium sulfate, and the solvent was evaporated under reduced pressure. The residue was separated by HPLC (C18, mobile phase: water/acetonitrile (0.1% TFA containing system)). To the obtained fraction was added a saturated aqueous sodium hydrogen carbonate solution, and the mixture was extracted with ethyl acetate, dried over anhydrous sodium sulfate, and concentrated under reduced pressure. The residue was crystallized from acetonitrile, THF and diisopropyl ether to give the title compound (71.9 mg) as a white solid.

$^1$H NMR (300 MHz, CDCl$_3$) δ 1.62-1.76 (1H, m), 1.81-1.93 (1H, m), 2.12-2.26 (2H, m), 2.41-2.53 (2H, m), 3.36-3.44 (2H, m), 4.61-4.72 (3H, m), 6.56 (1H, t, J=6.8 Hz), 6.82 (2H, d, J=8.7 Hz), 7.16 (1H, dd, J=6.8, 1.5 Hz), 7.45 (1H, dd, J=7.2, 1.5 Hz), 7.52 (2H, d, J=8.7 Hz).

Example 92

7-chloro-9-[6-(cyclohexyloxy)pyridin-3-yl]-3,4-dihydropyrido[2,1-c][1,2,4]thiadiazine 2,2-dioxide A) 5-bromo-2-(cyclohexyloxy)pyridine Cyclohexanol (3.99 mL) was added to a mixture of NaH (60%, 1.50 g) in N,N-dimethylacetoamide (10 mL) at 0° C. The mixture was stirred at room temperature for 30 min. The solution of 5-bromo-2-chloropyridine (6.00 g) in N,N-dimethylacetoamide (10 mL) was added and the mixture was stirred at 100° C. for 1.5 hr. The mixture was quenched with water at room temperature and extracted with EtOAc. The organic layer was separated, washed with brine, dried over anhydrous sodium sulfate and concentrated in vacuo. The residue was purified by column chromatography (silica gel, eluted with EtOAc in hexane) to give the title compound (7.67 g) as colorless oil.

MS (ESI+). found: 256.0, 258.0.

B) 5-chloro-6'-(cyclohexyloxy)-3,3'-bipyridin-2-amine n-Butyllithium (1.6 M in hexane) (20.5 mL) was dropwised to a mixture of 5-bromo-2-(cyclohexyloxy)pyridine (7.00 g) and THF (dry) (75 mL) at −78° C. and the mixture was stirred at the same temperature under nitrogen for 40 min. Triisopropyl borate (7.71 g) was dropwised to the mixture at −78° C. and the mixture was stirred at the same temperature for 5 min. Then the mixture was warmed up to room temperature and stirred for additional 30 min. The mixture was poured into 1N NaOH aq. (75 mL)/water (120 mL) and stirred for 1 hr. The organic layer was separated and the aqueous phase was washed with Et$_2$O (100 mL×2) and neutralized by 1N HCl aq. The mixture was extracted with EtOAc, dried over anhydrous sodium sulfate and concentrated in vacuo to give [6-(cyclohexyloxy)pyridin-3-yl]boronic acid (5.15 g) as pale yellow solid.

Tetrakis(triphenylphosphine)palladium(0) (107 mg) was added to a suspension of 3-bromo-5-chloropyridin-2-amine (640 mg), [6-(cyclohexyloxy)pyridin-3-yl]boronic acid (750 mg) and sodium carbonate (654 mg) in DME (15 mL) and water (3 mL) and the mixture was stirred at 100° C. under nitrogen for 2.5 hr. Water and EtOAc were added and the organic layer was separated, washed with brine, dried over anhydrous sodium sulfate and concentrated in vacuo. The residue was purified by column chromatography (silica gel, eluted with EtOAc in hexane) to give the title compound (846 mg) as colorless gum.

MS (ESI+). found: 304.1.

C) 7-chloro-9-[6-(cyclohexyloxy)pyridin-3-yl]-3,4-dihydropyrido[2,1-c][1,2,4]thiadiazine 2,2-dioxide To a suspension of NaH (60%, 553 mg) in THF (dry) (30 mL) was added 2-chloroethanesulfonyl chloride (0.582 mL) at 0° C. and the mixture was stirred for 10 min at the same temperature. A solution of 5-chloro-6'-(cyclohexyloxy)-3,3'-bipyridin-2-amine (840 mg) in THF (dry) (30 mL) was added at 0° C. and the mixture was stirred at room temperature under nitrogen overnight. The mixture was quenched with water at 0° C. carefully. EtOAc and THF were added and the organic layer was separated, washed with brine, dried over anhydrous sodium sulfate and concentrated in vacuo. The residue was purified by column chromatography (silica gel, eluted with EtOAc in hexane). The residue was crystallized from THF/IPE to give the title compound (336 mg) as colorless crystals.

$^1$H NMR (300 MHz, DMSO-d$_6$) δ 1.18-1.61 (6H, m), 1.69-1.79 (2H, m), 1.94-2.01 (2H, m), 3.42-3.58 (2H, m), 4.55-4.68 (2H, m), 4.94-5.14 (1H, m), 6.81 (1H, d, J=9.1 Hz), 7.78 (1H, d, J=2.6 Hz), 7.88 (1H, dd, J=8.7, 2.6 Hz), 8.10 (1H, d, J=2.3 Hz), 8.27 (1H, d, J=2.3 Hz).

Example 93

9-[6-(cyclohexyloxy)pyridin-3-yl]-7-fluoro-3,4-dihydropyrido[2,1-c][1,2,4]thiadiazine 2,2-dioxide

A) 6'-(cyclohexyloxy)-5-fluoro-3,3'-bipyridin-2-amine

Tetrakis(triphenylphosphine)palladium(0) (36.3 mg) was added to a suspension of 3-bromo-5-fluoropyridin-2-amine (200 mg), 6-(cyclohexyloxy)pyridin-3-ylboronic acid (255 mg) and sodium carbonate (222 mg) in DME (5 mL) and water (1 mL) and the mixture was stirred at 90° C. under nitrogen for 3 hr. Water and EtOAc were added and the organic layer was separated, washed with brine, dried over anhydrous sodium sulfate and concentrated in vacuo. The residue was purified by column chromatography (silica gel, eluted with EtOAc in hexane) and washed with IPE to give the title compound (280 mg) as a yellow solid.

MS (ESI+). found: 288.1.

B) 9-[6-(cyclohexyloxy)pyridin-3-yl]-7-fluoro-3,4-dihydropyrido[2,1-c][1,2,4]thiadiazine 2,2-dioxide To a suspension of NaH (60%, 195 mg) in THF (dry) (10 mL) was added 2-chloroethanesulfonyl chloride (0.307 mL) at 0° C. and the mixture was stirred for 10 min at the same temperature. A solution of 6'-(cyclohexyloxy)-5-fluoro-3,3'-bipyridin-2-amine (280 mg) in THF (dry) (10 mL) was added at 0° C. and the mixture was stirred at room temperature under nitrogen for 1 day. The mixture was quenched with water at 0° C. carefully. EtOAc and THF were added and the organic layer was separated, washed with brine, dried over anhydrous sodium sulfate and concentrated in vacuo. The residue was crystallized from MeCN-THF/IPE to give the title compound (81.1 mg) as colorless crystals.

$^1$H NMR (300 MHz, DMSO-$d_6$) δ 1.26-1.60 (6H, m), 1.68-1.78 (2H, m), 1.92-2.03 (2H, m), 3.43-3.51 (2H, m), 4.50-4.69 (2H, m), 4.94-5.11 (1H, m), 6.82 (1H, d, J=8.7 Hz), 7.84-7.97 (2H, m), 8.10 (1H, dd, J=4.3, 2.8 Hz), 8.30 (1H, d, J=1.9 Hz).

Example 94

9-[6-(cyclohexyloxy)pyridin-3-yl]-3,4-dihydropyrazino[2,1-c][1,2,4]thiadiazine 2,2-dioxide

A) 3-[6-(cyclohexyloxy)pyridin-3-yl]pyrazin-2-amine

Tetrakis(triphenylphosphine)palladium(0) (53.5 mg) was added to a suspension of 3-chloropyrazin-2-amine (200 mg), 6-(cyclohexyloxy)pyridin-3-ylboronic acid (375 mg) and sodium carbonate (327 mg) in DME (5 mL) and water (1 mL) and the mixture was stirred at 90° C. under nitrogen for 3 hr. Water and EtOAc were added and the organic layer was separated, washed with brine, dried over anhydrous sodium sulfate and concentrated in vacuo. The residue was purified by column chromatography (silica gel, eluted with EtOAc in hexane) and washed with IPE to give the title compound (332 mg) as brown gum.

MS (ESI+). found: 271.1.

B) 9-[6-(cyclohexyloxy)pyridin-3-yl]-3,4-dihydropyrazino[2,1-c][1,2,4]thiadiazine 2,2-dioxide To a suspension of NaH (60%, 246 mg) in THF (dry) (10 mL) was added 2-chloroethanesulfonyl chloride (0.388 mL) at 0° C. and the mixture was stirred for 10 min at the same temperature. A solution of 3-[6-(cyclohexyloxy)pyridin-3-yl]pyrazin-2-amine (332 mg) in THF (dry) (10 mL) was added at 0° C. and the mixture was stirred at room temperature under nitrogen for 1 day. The mixture was quenched with water at 0° C. carefully. EtOAc and THF were added and the organic layer was separated, washed with brine, dried over anhydrous sodium sulfate and concentrated in vacuo. The residue was crystallized from MeCN-THF/IPE to give the title compound (104 mg) as colorless crystals.

$^1$H NMR (300 MHz, DMSO-$d_6$) δ 1.19-1.62 (6H, m), 1.65-1.83 (2H, m), 1.85-2.11 (2H, m), 3.49-3.65 (2H, m), 4.51-4.73 (2H, m), 4.97-5.20 (1H, m), 6.84 (1H, d, J=8.7 Hz), 7.58-7.76 (2H, m), 8.27 (1H, dd, J=8.7, 2.6 Hz), 8.82 (1H, d, J=2.3 Hz).

Example 95

9-[6-(cyclohexyloxy)pyridin-3-yl]-7-methyl-3,4-dihydropyrazino[2,1-c][1,2,4]thiadiazine 2,2-dioxide

A) 3-[6-(cyclohexyloxy)pyridin-3-yl]-5-methylpyrazin-2-amine

Tetrakis(triphenylphosphine)palladium(0) (48.3 mg) was added to a suspension of 3-chloro-5-methylpyrazin-2-amine (200 mg), 6-(cyclohexyloxy)pyridin-3-ylboronic acid (339 mg) and sodium carbonate (295 mg) in DME (5 mL) and water (1 mL) and the mixture was stirred at 90° C. under nitrogen for 3 hr. Water and EtOAc were added and the organic layer was separated, washed with brine, dried over anhydrous sodium sulfate and concentrated in vacuo. The residue was purified by column chromatography (silica gel, eluted with EtOAc in hexane) to give the title compound (339 mg) as light brown gum.

MS (ESI+). found: 285.1.

B) 9-[6-(cyclohexyloxy)pyridin-3-yl]-7-methyl-3,4-dihydropyrazino[2,1-c][1,2,4]thiadiazine 2,2-dioxide To a suspension of NaH (60%, 238 mg) in THF (dry) (10 mL) was added 2-chloroethanesulfonyl chloride (0.375 mL) at 0° C. and the mixture was stirred for 10 min at the same temperature. A solution of 3-[6-(cyclohexyloxy)pyridin-3-yl]-5-methylpyrazin-2-amine (338 mg) in THF (dry) (10 mL) was added at 0° C. and the mixture was stirred at room temperature under nitrogen for 1 day. The mixture was quenched with water at 0° C. carefully. EtOAc and THF were added and the organic layer was separated, washed with brine, dried over anhydrous sodium sulfate and concentrated in vacuo. The residue was crystallized from MeCN-THF/IPE to give the title compound (84.5 mg) as colorless crystals.

$^1$H NMR (300 MHz, DMSO-$d_6$) δ 1.20-1.62 (6H, m), 1.63-1.83 (2H, m), 1.92-2.07 (2H, m), 2.30 (3H, s), 3.43-3.58 (2H, m), 4.48-4.69 (2H, m), 4.96-5.16 (1H, m), 6.84 (1H, d, J=8.7 Hz), 7.58 (1H, s), 8.27 (1H, dd, J=8.7, 1.9 Hz), 8.85 (1H, d, J=1.9 Hz).

Example 96

9-(2-fluorobiphenyl-4-yl)-3,4,6,7,8,9-hexahydropyrido[2,1-c][1,2,4]thiadiazine 2,2-dioxide A racemate (357 mg) of 9-(2-fluorobiphenyl-4-yl)-3,4,6, 7,8,9-hexahydropyrido[2,1-c][1,2,4]thiadiazine 2,2-dioxide was separated by SFC (column: CHIRALPAK AYH (OC006), 20 mmID×250 mmL, manufactured by DAICEL CHEMICAL INDUSTRIES, LTD., mobile phase:carbon dioxide/ethanol/acetonitrile=600/200/200) to give the title compound (156 mg) with a shorter retention time. Crystallization from acetonitrile and diisopropyl ether gave a white solid.

$^1$H NMR (300 MHz, DMSO-$d_6$) δ 1.69-1.87 (3H, m), 1.94-2.15 (1H, m), 3.20-3.26 (2H, m), 3.41-3.59 (2H, m), 3.75-3.91 (3H, m), 7.10-7.27 (2H, m), 7.34-7.63 (6H, m).

Example 97

9-(2-fluorobiphenyl-4-yl)-3,4,6,7,8,9-hexahydropyrido[2,1-c][1,2,4]thiadiazine 2,2-dioxide A racemate (357 mg) of 9-(2-fluorobiphenyl-4-yl)-3,4,6,7,8,9-hexahydropyrido[2,1-c][1,2,4]thiadiazine 2,2-dioxide was separated by SFC (column: CHIRALPAK AYH (OC006), mmID×250 mmL, manufactured by DAICEL CHEMICAL INDUSTRIES, LTD., mobile phase:carbon dioxide/ethanol/acetonitrile=600/200/200) to give the title compound (158 mg) with a longer retention time. Crystallization from acetonitrile and diisopropyl ether gave a white solid.

$^1$H NMR (300 MHz, DMSO-$d_6$) δ 1.64-1.91 (3H, m), 1.91-2.17 (1H, m), 3.19-3.28 (2H, m), 3.39-3.62 (2H, m), 3.69-3.91 (3H, m), 7.10-7.27 (2H, m), 7.31-7.60 (6H, m).

Example 98

9-[4-(3-methoxyphenoxy)phenyl]-3,4,6,7,8,9-hexahydropyrido[2,1-c][1,2,4]thiadiazine 2,2-dioxide Platinum(IV) oxide (37 mg) was added to a solution of 9-[4-(3-methoxyphenoxy)phenyl]-3,4-dihydropyrido[2,1-c][1,2,4]thiadiazine 2,2-dioxide (129 mg) in THF (dry) (20 mL) and MeOH (20 mL) and the mixture was stirred at room temperature under hydrogen overnight. The insoluble material was removed by filtration, and the filtrate was concentrated in vacuo. The residue was crystallized from THF/IPE to give the title compound (70.2 mg) as colorless crystals.

$^1$H NMR (300 MHz, DMSO-$d_6$) δ 1.68-1.82 (3H, m), 1.91-2.09 (1H, m), 3.24-3.29 (2H, m), 3.41-3.54 (2H, m), 3.72-3.87 (6H, m), 6.51-6.62 (2H, m), 6.72 (1H, dd, J=7.6, 2.3 Hz), 6.90-6.98 (2H, m), 7.17-7.33 (3H, m).

Example 99

7-methyl-9-(4-phenoxyphenyl)-3,4,6,7,8,9-hexahydropyrido[2,1-c][1,2,4]thiadiazine 2,2-dioxide A) 5-methyl-3-(4-phenoxyphenyl)pyridin-2-amine Tetrakis(triphenylphosphine)palladium(0) (40.8 mg) was added to a suspension of 3-bromo-5-methylpyridin-2-amine (220 mg), 4-phenoxyphenylboronic acid (327 mg) and sodium carbonate (249 mg) in DME (8 mL) and water (1.5 mL) and the mixture was stirred at 85° C. under nitrogen overnight. Silica-gel was added and the volatiles were removed in vacuo. The mixture supported on silica-gel was purified by column chromatography (NH-silica gel, eluted with EtOAc in hexane) to give the title compound (315 mg) as a white solid.

MS (ESI+). found: 277.1.

B) 7-methyl-9-(4-phenoxyphenyl)-3,4,6,7,8,9-hexahydropyrido[2,1-c][1,2,4]thiadiazine 2,2-dioxide To a suspension of NaH (60%, 229 mg) in THF (dry) (10 mL) was added 2-chloroethanesulfonyl chloride (0.361 mL) at 0° C. and the mixture was stirred for 5 min at the same temperature. A solution of 5-methyl-3-(4-phenoxyphenyl)pyridin-2-amine (316 mg) in THF (dry) (20 mL) was added at 0° C. and the mixture was stirred at room temperature for 30 min. The mixture was quenched with water. Water and EtOAc were added and the extracted organic layer was washed with brine. Silica-gel was added and the volatiles were removed in vacuo. The mixture supported on silica-gel was purified by column chromatography (silica gel, eluted with MeOH in EtOAc) to give 7-methyl-9-(4-phenoxyphenyl)-3,4-dihydropyrido[2,1-c][1,2,4]thiadiazine 2,2-dioxide (158.2 mg) as a white solid. Platinum(IV) oxide (30.0 mg) was added to a solution of 7-methyl-9-(4-phenoxyphenyl)-3,4-dihydropyrido[2,1-c][1,2,4]thiadiazine 2,2-dioxide (141 mg) in THF (dry) (15 mL) and MeOH (15 mL) and the mixture was stirred at 50° C. under hydrogen overnight. Platinum(IV) oxide (30.0 mg) was added and the mixture was stirred at 50° C. under hydrogen for 1 day. The insoluble material was removed by filtration, silica-gel was added and the volatiles were removed in vacuo. The mixture supported on silica-gel was purified by column chromatography (silica gel, eluted with MeOH in EtOAc) and crystallized from THF/IPE to give the title compound (35.4 mg) as colorless crystals.

$^1$H NMR (300 MHz, DMSO-$d_6$) δ 0.85-1.01 (3H, m), 1.41-1.58 (1H, m), 1.64-2.18 (3H, m), 3.17-3.26 (2H, m), 3.38-3.48 (1H, m), 3.74-3.87 (3H, m), 6.88-6.98 (2H, m), 6.99-7.05 (2H, m), 7.10-7.24 (3H, m), 7.36-7.44 (2H, m).

Example 100

9-(2'-fluorobiphenyl-4-yl)-3,4,6,7,8,9-hexahydropyrido[2,1-c][1,2,4]thiadiazine 2,2-dioxide A) 9-[4-(4,4,5,5-tetramethyl-1,3,2-dioxaborolan-2-yl)phenyl]-3,4-dihydropyrido[2,1-c][1,2,4]thiadiazine 2,2-dioxide 9-(4-Chlorophenyl)-3,4-dihydropyrido[2,1-c][1,2,4]thiadiazine 2,2-dioxide (224 mg), potassium acetate (149 mg), 4,4,4',4',5,5,5',5'-octamethyl-2,2'-bi(1,3,2-dioxaborolane) (232 mg), tricyclohexylphosphine (42.6 mg), and tris(dibenzylideneacetone)dipalladium(0) (34.8 mg) in DME (5 mL) was stirred at 70° C. overnight. After cooling to room temperature, the mixture was purified by column chromatography (silica gel with Celite, eluted with EtOAc in hexane then MeOH in EtOAc) then recrystallized from EtOH-EtOAc to give the title compound (142 mg) as white powder.

MS (ESI+). found: 387.1.

B) 9-(2'-fluorobiphenyl-4-yl)-3,4,6,7,8,9-hexahydropyrido[2,1-c][1,2,4]thiadiazine 2,2-dioxide Tetrakis(triphenylphosphine)palladium(0) (18.0 mg) was added to a suspension of 1-fluoro-2-iodobenzene (69.0 mg), 9-[4-(4,4,5,5-tetramethyl-1,3,2-dioxaborolan-2-yl)phenyl]-3,4-dihydropyrido[2,1-c][1,2,4]thiadiazine 2,2-dioxide (60.0 mg) and cesium carbonate (152 mg) in toluene (3 mL) and EtOH (3 mL) and the mixture was stirred at 80° C. under nitrogen for 24 hr. Silica-gel was added and the volatiles were removed in vacuo. The mixture supported on silica-gel was purified by column chromatography (NH-silica gel, eluted with EtOAc in hexane) and dissolved in THF (dry) (5 mL) and MeOH (5 mL) and platinum(IV) oxide (6.00 mg) was added and the mixture was stirred at room temperature under hydrogen for 2 days. The insoluble solid was removed by filtration through Celite-pad (eluted with EtOAc). Silica-gel was added and the volatiles were removed in vacuo. The mixture supported on silica-gel was purified by column chromatography (NH silica gel, eluted with MeOH in EtOAc) and crystallized from THF/IPE to give the title compound (0.80 mg) as colorless crystals.

$^1$H NMR (300 MHz, DMSO-$d_6$) δ 1.63-1.91 (4H, m), 1.98-2.12 (1H, m), 3.24-3.28 (1H, m), 3.43-3.56 (2H, m), 3.76-3.87 (3H, m), 7.18-7.61 (8H, m).

Example 101

9-(2-methylbiphenyl-4-yl)-3,4-dihydropyrido[2,1-c][1,2,4]thiadiazine 2,2-dioxide A) 3-(2-methylbiphenyl-4-yl)pyridin-2-amine Pd(dppf)Cl$_2$ (0.089 g) was added to a mixture of 4-bromo-2-methylbiphenyl (1.5 g), potassium acetate (1.787 g) and 4,4,4',4',5,5,5',5'-octamethyl-2,2'-bi(1,3,2-dioxaborolane) (2.312 g) in DME (25 mL) and DMSO (1.25 mL). The mixture was stirred at 80° C. under nitrogen overnight. Activated-carbon powder was added and the mixture was stirred for 5 min. The insoluble material was removed by filtration, and the filtrate was concentrated in vacuo to give crude 4,4,5,5-tetramethyl-2-(2-methylbiphenyl-4-yl)-1,3,2-dioxaborolane. Tetrakis(triphenylphosphine)palladium(0) (173 mg) was added to a suspension of 3-bromopyridin-2-amine (865 mg), the prepared 4,4,5,5-tetramethyl-2-(2-methylbiphenyl-4-yl)-1,3,2-dioxaborolane and sodium carbonate decahydrate (2861 mg) in DME (30 mL) and water (6 mL) and the mixture was stirred at 80° C. under nitrogen for 6 hr. Silica-gel was added and the volatiles were removed in vacuo. The mixture supported on silica-gel was purified by column chromatography (NH-silica gel, eluted with EtOAc in hexane) to give the title compound (1.25 g) as a light yellow solid.

MS (ESI+). found: 261.1.

B) 9-(2-methylbiphenyl-4-yl)-3,4-dihydropyrido[2,1-c][1,2,4]thiadiazine 2,2-dioxide To a suspension of NaH (60%, 1.163 g) in THF (dry) (30 mL) was added 2-chloroethanesulfonyl chloride (1.22 mL) at 0° C. and the mixture was stirred for 5 min at the same temperature. A solution of 3-(2-methylbiphenyl-4-yl)pyridin-2-amine (1.51 g) in THF (dry) (50 mL) was added at 0° C. and the mixture was stirred at room temperature overnight. The mixture was quenched with water at 0° C. carefully. Water and EtOAc were added and the precipitates were collected and washed with water and EtOAc, dried in vacuo to give the title compound (339 mg) as a white solid. A part of this was recrystallized from MeCN-THF/IPE.

$^1$H NMR (300 MHz, DMSO-$d_6$) δ 2.26 (3H, s), 3.42-3.54 (2H, m), 4.60-4.73 (2H, m), 6.72 (1H, t, J=7.0 Hz), 7.24 (1H, d, J=8.3 Hz), 7.33-7.51 (7H, m), 7.66 (1H, dd, J=7.2, 1.9 Hz), 7.79 (1H, dd, J=6.8, 1.5 Hz).

Example 102

9-(2-methylbiphenyl-4-yl)-3,4,6,7,8,9-hexahydropyrido[2,1-c][1,2,4]thiadiazine 2,2-dioxide Platinum(IV) oxide (60 mg) was added to a solution of 9-(2-methylbiphenyl-4-yl)-3,4-dihydropyrido[2,1-c][1,2,4] thiadiazine 2,2-dioxide (265 mg) in THF (dry) (75 mL), MeOH (75 mL) and the mixture was stirred at room temperature under hydrogen for 12 hr. Activated carbon was added and the insoluble solid was removed by filtration through NH-silica gel/Celite pad (eluted with EtOAc). The filtrate was concentrated and the residue was crystallized from MeCN-THF/IPE to give the title compound (200 mg) as a colorless crystal.

$^1$H NMR (300 MHz, DMSO-$d_6$) δ 1.63-1.91 (3H, m), 1.91-2.11 (1H, m), 2.22 (3H, s), 3.25-3.30 (2H, m), 3.43-3.63 (2H, m), 3.73-3.96 (3H, m), 7.02-7.20 (3H, m), 7.28-7.51 (5H, m).

Example 103

9-(2-methylbiphenyl-4-yl)-3,4,6,7,8,9-hexahydropyrido[2,1-c][1,2,4]thiadiazine 2,2-dioxide A racemate (166.3 mg) of 9-(2-methylbiphenyl-4-yl)-3,4,6,7,8,9-hexahydropyrido[2,1-c][1,2,4]thiadiazine 2,2-dioxide was separated by HPLC (column: CHIRALPAK AD (LF001), 50 mmID×500 mmL, manufactured by DAICEL CHEMICAL INDUSTRIES, LTD., mobile phase:methanol 100%) to give the title compound (75.4 mg) with a longer retention time. Crystallization from acetonitrile and diisopropyl ether gave a white solid.

$^1$H NMR (300 MHz, DMSO-$d_6$) δ 1.70-1.87 (3H, m), 1.96-2.11 (1H, m), 2.22 (3H, s), 3.25-3.29 (2H, m), 3.39-3.59 (2H, m), 3.71-3.94 (3H, m), 7.01-7.18 (3H, m), 7.29-7.48 (5H, m).

Example 104

9-(2-methylbiphenyl-4-yl)-3,4,6,7,8,9-hexahydropyrido[2,1-c][1,2,4]thiadiazine 2,2-dioxide A racemate (166.3 mg) of 9-(2-methylbiphenyl-4-yl)-3,4,6,7,8,9-hexahydropyrido[2,1-c][1,2,4]thiadiazine 2,2-dioxide was separated by HPLC (column: CHIRALPAK AD (LF001), 50 mmID×500 mmL, manufactured by DAICEL CHEMICAL INDUSTRIES, LTD., mobile phase:methanol 100%) to give the title compound (76.4 mg) with a shorter retention time. Crystallization from acetonitrile and diisopropyl ether gave a white solid.

$^1$H NMR (300 MHz, DMSO-$d_6$) δ 1.68-1.87 (3H, m), 1.89-2.12 (1H, m), 2.22 (3H, s), 3.25-3.29 (2H, m), 3.37-3.60 (2H, m), 3.67-3.94 (3H, m), 7.01-7.20 (3H, m), 7.27-7.51 (5H, m).

Example 105

9-(4'-methylbiphenyl-4-yl)-3,4,6,7,8,9-hexahydropyrido[2,1-c][1,2,4]thiadiazine 2,2-dioxide Trifluoromethanesulfonyl chloride (0.035 mL) was added to a mixture of 4-(2,2-dioxido-3,4,6,7,8,9-hexahydropyrido[2,1-c][1,2,4]thiadiazin-9-yl)phenol (46 mg) in DMF (dry) (1 mL) at 0° C. The mixture was stirred at 0° C. for 5 min and at room temperature for 2 hr. Water and EtOAc were added and the extracted organic layer was washed with brine, dried over anhydrous sodium sulfate and concentrated in vacuo. EtOH (3 mL), water (1.5 mL) and DMF (dry) (2 mL) was added to the residue. Tetrakis(triphenylphosphine) palladium(0) (16 mg), p-tolylboronic acid (59.3 mg) and sodium carbonate decahydrate (125 mg) was added and the mixture was stirred at 50° C. under nitrogen overnight. Water and EtOAc were added and the extracted organic layer was washed with brine. Silica-gel was added to the organic phase and the volatiles were removed in vacuo. The mixture supported on silica-gel was purified by column chromatography (silica gel, eluted with EtOAc in hexane) and crystallized from MeCN/IPE to give the title compound (7.3 mg) as colorless crystals.

$^1$H NMR (300 MHz, DMSO-d$_6$) δ 1.65-1.88 (3H, m), 1.88-2.10 (1H, m), 2.34 (3H, s), 3.24-3.29 (2H, m), 3.41-3.60 (2H, m), 3.73-3.91 (3H, m), 7.17-7.35 (4H, m), 7.47-7.64 (4H, m).

Example 106

9-(3'-methoxybiphenyl-4-yl)-3,4,6,7,8,9-hexahydro-pyrido[2,1-c][1,2,4]thiadiazine 2,2-dioxide Platinum(IV) oxide (9.7 mg) was added to a solution of 9-(3'-methoxybiphenyl-4-yl)-3,4-dihydropyrido[2,1-c][1,2,4]thiadiazine 2,2-dioxide (17.4 mg) in THF (dry) (15 mL) and MeOH (15 mL) and the mixture was stirred at 50° C. under hydrogen overnight. Activated carbon was added and the insoluble solid was removed by filtration through NH-silica gel/Celite pad (eluted with EtOAc). Silica-gel was added to the filtrate and the volatiles were removed in vacuo. The mixture supported on silica-gel was purified by column chromatography (NH silica gel, eluted with MeOH in EtOAc) to give the title compound (6.5 mg) as colorless gum.

$^1$H NMR (300 MHz, CDCl$_3$) δ 1.78-2.02 (3H, m), 2.08-2.23 (1H, m), 3.25-3.35 (2H, m), 3.40-3.56 (2H, m), 3.86 (3H, s), 3.89-4.01 (3H, m), 6.89 (1H, dd, J=8.1, 2.5 Hz), 7.08-7.11 (1H, m), 7.12-7.17 (1H, m), 7.22 (2H, d, J=8.3 Hz), 7.32-7.38 (1H, m), 7.53 (2H, d, J=8.3 Hz).

Example 107

9-[4-(4-methylphenoxy)phenyl]-3,4-dihydropyrido[2,1-c][1,2,4]thiadiazine 2,2-dioxide A) 3-(4-(4-methylphenoxy)phenyl)pyridin-2-amine Copper(I) iodide (0.507 g) was added to a mixture of picolinic acid (0.328 g), 4-(2-aminopyridin-3-yl)phenol (2.48 g), tripotassium phosphate (8.48 g), 1-iodo-4-methylbenzene (3.19 g) and DMSO (150 mL). The mixture was stirred at 130° C. under nitrogen for 4.5 hr. The insoluble solid was removed by filtration through NH-silica gel/Celite pad (eluted with EtOAc). Water was added and the mixture was extracted. The extracted organic layer was washed with brine. Silica-gel was added to the organic phase and the volatiles were removed in vacuo. The mixture supported on silica-gel was purified by column chromatography (NH-silica gel, eluted with EtOAc in hexane) to give the title compound (2.17 g) as a yellow solid.

MS (ESI+). found: 277.1.

B) 9-[4-(4-methylphenoxy)phenyl]-3,4-dihydropyrido[2,1-c][1,2,4]thiadiazine 2,2-dioxide To a suspension of NaH (60%, 1.57 g) in THF (dry) (60 mL) was added 2-chloroethanesulfonyl chloride (1.652 mL) at 0° C. and the mixture was stirred for 10 min at the same temperature. A solution of 3-(4-(4-methylphenoxy)phenyl)pyridin-2-amine (2.17 g) in THF (dry) (40 mL) was added at 0° C. and the mixture was stirred at room temperature under nitrogen overnight. The mixture was quenched with water at 0° C. Water, EtOAc and IPE were added and the precipitates were collected, washed with water/EtOAc, and dried in vacuo. The precipitates were crystallized from DMSO (15 mL)/EtOH (200 mL) at 80° C. to room temperature to give the title compound (1.91 g) as colorless crystals.

$^1$H NMR (300 MHz, DMSO-d$_6$) δ 2.30 (3H, s), 3.39-3.51 (2H, m), 4.59-4.71 (2H, m), 6.70 (1H, t, J=7.0 Hz), 6.94-7.03 (4H, m), 7.22 (2H, d, J=8.3 Hz), 7.47-7.54 (2H, m), 7.61 (1H, dd, J=7.2, 1.5 Hz), 7.76 (1H, dd, J=6.8, 1.5 Hz).

mp 248-249° C.

Anal. Calcd for C$_{20}$H$_{18}$N$_2$O$_3$S: C, 65.55; H, 4.95; N, 7.64. Found: C, 65.46; H, 5.00; N, 7.55.

Example 108

9-[4-(4-methylphenoxy)phenyl]-3,4,6,7,8,9-hexahydropyrido[2,1-c][1,2,4]thiadiazine 2,2-dioxide Platinum(IV) oxide (30 mg) was added to a solution of 9-[4-(4-methylphenoxy)phenyl]-3,4-dihydropyrido[2,1-c][1,2,4]thiadiazine 2,2-dioxide (278 mg) in THF (dry) (30 mL) and MeOH (30 mL) and the mixture was stirred at 50° C. under hydrogen for 3 hr. Activated carbon was added and the insoluble solid was removed by filtration through NH-silica gel/Celite pad (eluted with EtOAc). The filtrate was concentrated and the residue was crystallized from MeCN/IPE to give the title compound (195.4 mg) as colorless crystals.

$^1$H NMR (300 MHz, DMSO-d$_6$) δ 1.68-1.80 (3H, m), 1.90-2.07 (1H, m), 2.29 (3H, s), 3.24-3.30 (2H, m), 3.47 (2H, q, J=6.4 Hz), 3.70-3.89 (3H, m), 6.84-6.97 (4H, m), 7.14-7.24 (4H, m).

Example 109

9-[4-(4-methylphenoxy)phenyl]-3,4,6,7,8,9-hexahydropyrido[2,1-c][1,2,4]thiadiazine 2,2-dioxide A racemate (160.7 mg) of 9-[4-(4-methylphenoxy)phenyl]-3,4,6,7,8,9-hexahydropyrido[2,1-c][1,2,4]thiadiazine 2,2-dioxide was separated by SFC (column: CHIRALPAK IC (ME001), 50 mmID×500 mmL, manufactured by DAICEL CHEMICAL INDUSTRIES, LTD., mobile phase:acetonitrile 100%) to give the title compound (79.9 mg) with a shorter retention time. Crystallization from THF and diisopropyl ether gave a white solid.

$^1$H NMR (300 MHz, DMSO-d$_6$) δ 1.56-1.84 (3H, m), 1.87-2.11 (1H, m), 2.29 (3H, s), 3.23-3.29 (2H, m), 3.38-3.59 (2H, m), 3.63-4.01 (3H, m), 6.81-7.04 (4H, m), 7.07-7.31 (4H, m).

Example 110

9-[4-(4-methylphenoxy)phenyl]-3,4,6,7,8,9-hexahydro-pyrido[2,1-c][1,2,4]thiadiazine 2,2-dioxide A racemate (160.7 mg) of 9-[4-(4-methylphenoxy)phenyl]-3,4,6,7,8,9-hexahydropyrido[2,1-c][1,2,4]thiadiazine 2,2-dioxide was separated by SFC (column: CHIRALPAK IC (ME001), 50 mmID×500 mmL, manufactured by DAICEL CHEMICAL INDUSTRIES, LTD., mobile phase:acetonitrile 100%) to give the title compound (78 mg) with a longer retention time. Crystallization from THF and diisopropyl ether gave a white solid.

$^1$H NMR (300 MHz, DMSO-d$_6$) δ 1.67-1.84 (3H, m), 1.90-2.11 (1H, m), 2.29 (3H, s), 3.23-3.29 (2H, m), 3.36-3.56 (2H, m), 3.65-3.95 (3H, m), 6.78-7.01 (4H, m), 7.11-7.28 (4H, m).

Example 111

9-[4-(4-fluoro-3-methylphenoxy)phenyl]-3,4-dihydropyrido[2,1-c][1,2,4]thiadiazine 2,2-dioxide A) 3-(4-(4-fluoro-3-methylphenoxy)phenyl)pyridin-2-amine Copper(I) iodide (102 mg) was added to a mixture of picolinic acid (66.1 mg), 4-(2-aminopyridin-3-yl)phenol (500 mg), tripotassium phosphate (1710 mg), 4-bromo-1-fluoro-2-methylbenzene (609 mg) and DMSO (8 mL). The mixture was stirred at 130° C. under nitrogen for 5 hr. Activated carbon was added and the insoluble solid was removed by filtration through NH-silica gel/Celite pad (eluted with EtOAc). Water was added and the extracted organic layer was washed with brine. Silica-gel was added to the organic layer and the volatiles were removed in vacuo. The mixture supported on silica-gel was purified by column chromatography (NH-silica gel, eluted with EtOAc in hexane) to give the title compound (362.3 mg) as a pale-yellow solid.

MS (ESI+). found: 295.1.

B) 9-[4-(4-fluoro-3-methylphenoxy)phenyl]-3,4-dihydropyrido[2,1-c][1,2,4]thiadiazine 2,2-dioxide To a suspension of NaH (60%, 245 mg) in THF (dry) (15 mL) was added 2-chloroethanesulfonyl chloride (0.386 mL) at 0° C. and the mixture was stirred for 5 min at the same temperature. A solution of 3-(4-(4-fluoro-3-methylphenoxy)phenyl)pyridin-2-amine (360 mg) in THF (dry) (20 mL) was added at 0° C. and the mixture was stirred at room temperature for 5 hr. The mixture was quenched with water at 0° C. Water, EtOAc and IPE were added and the precipitates were collected, washed with water/EtOAc, dried in vacuo to give the title compound (359.2 mg) as a white solid. A part of this was recrystallized from MeCN/IPE.

$^1$H NMR (300 MHz, DMSO-$d_6$) δ 2.24 (3H, d, J=1.9 Hz), 3.41-3.52 (2H, m), 4.58-4.71 (2H, m), 6.70 (1H, t, J=7.0 Hz), 6.88-7.02 (3H, m), 7.06 (1H, dd, J=6.4, 3.0 Hz), 7.18 (1H, t, J=9.3 Hz), 7.47-7.55 (2H, m), 7.61 (1H, dd, J=7.2, 1.5 Hz), 7.77 (1H, dd, J=6.8, 1.5 Hz).

Example 112

9-[4-(4-fluoro-3-methylphenoxy)phenyl]-3,4,6,7,8,9-hexahydropyrido[2,1-c][1,2,4]thiadiazine 2,2-dioxide Platinum(IV) oxide (30 mg) was added to a solution of 9-[4-(4-fluoro-3-methylphenoxy)phenyl]-3,4-dihydropyrido[2,1-c][1,2,4]thiadiazine 2,2-dioxide (256 mg) in THF (dry) (30 mL) and MeOH (30 mL) and the mixture was stirred at 50° C. under hydrogen for 3 hr. Activated carbon was added and the insoluble solid was removed by filtration through NH-silica gel/Celite pad (eluted with EtOAc). The filtrate was concentrated and the residue was crystallized from MeCN/IPE to give the title compound (169.3 mg) as colorless crystals.

$^1$H NMR (300 MHz, DMSO-$d_6$) δ 1.67-1.81 (3H, m), 1.93-2.06 (1H, m), 2.22 (3H, d, J=1.9 Hz), 3.25-3.30 (2H, m), 3.39-3.54 (2H, m), 3.69-3.89 (3H, m), 6.83-6.94 (3H, m), 7.01 (1H, dd, J=6.4, 3.0 Hz), 7.08-7.23 (3H, m).

Example 113

9-[4-(4-fluoro-3-methylphenoxy)phenyl]-3,4,6,7,8,9-hexahydropyrido[2,1-c][1,2,4]thiadiazine 2,2-dioxide A racemate (135 mg) of 9-[4-(4-fluoro-3-methylphenoxy)phenyl]-3,4,6,7,8,9-hexahydropyrido[2,1-c][1,2,4]thiadiazine 2,2-dioxide was separated by SFC (column: CHIRALPAK AYH (OC006), 20 mmID×250 mmL, manufactured by DAICEL CHEMICAL INDUSTRIES, LTD., mobile phase: carbon dioxide/acetonitrile/ethanol=700/150/150) to give the title compound (56.8 mg) with a shorter retention time. Crystallization from THF and diisopropyl ether gave a white solid.

$^1$H NMR (300 MHz, DMSO-$d_6$) δ 1.61-1.81 (3H, m), 1.88-2.07 (1H, m), 2.22 (3H, d, J=1.9 Hz), 3.24-3.30 (2H, m), 3.41-3.55 (2H, m), 3.68-3.89 (3H, m), 6.83-6.94 (3H, m), 7.01 (1H, dd, J=6.0, 3.4 Hz), 7.09-7.23 (3H, m).

Example 114

9-[4-(4-fluoro-3-methylphenoxy)phenyl]-3,4,6,7,8,9-hexahydropyrido[2,1-c][1,2,4]thiadiazine 2,2-dioxide A racemate (135 mg) of 9-[4-(4-fluoro-3-methylphenoxy)phenyl]-3,4,6,7,8,9-hexahydropyrido[2,1-c][1,2,4]thiadiazine 2,2-dioxide was separated by SFC (column: CHIRALPAK AYH (OC006), 20 mmID×250 mmL, manufactured by DAICEL CHEMICAL INDUSTRIES, LTD., mobile phase: carbon dioxide/acetonitrile/ethanol=700/150/150) to give the title compound (56.8 mg) with a longer retention time. Crystallization from THF and diisopropyl ether gave a white solid.

$^1$H NMR (300 MHz, DMSO-$d_6$) δ 1.67-1.82 (3H, m), 1.89-2.06 (1H, m), 2.22 (3H, d, J=1.9 Hz), 3.24-3.30 (2H, m), 3.47 (2H, dq, J=12.4, 6.4 Hz), 3.70-3.88 (3H, m), 6.83-6.94 (3H, m), 7.01 (1H, dd, J=6.4, 3.0 Hz), 7.12-7.23 (3H, m).

Example 115

9-[4-(2-methylphenoxy)phenyl]-3,4-dihydropyrido[2,1-c][1,2,4]thiadiazine 2,2-dioxide A) 3-(4-(2-methylphenoxy)phenyl)pyridin-2-amine Copper(I) iodide (102 mg) was added to a mixture of picolinic acid (66.1 mg), 4-(2-aminopyridin-3-yl)phenol (500 mg), tripotassium phosphate (1710 mg), 1-iodo-2-methylbenzene (703 mg) and DMSO (8 mL). The mixture was stirred at 130° C. under nitrogen for 5 hr. Activated carbon was added and the insoluble solid was removed by filtration through NH-silica gel/Celite pad (eluted with EtOAc). Water was added and the extracted organic layer was washed with brine. Silica-gel was added to the organic layer and the volatiles were removed in vacuo. The mixture supported on silica-gel was purified by column chromatography (NH-silica gel, eluted with EtOAc in hexane) to give the title compound (392.8 mg) as a yellow solid.

MS (ESI+). found: 277.1.

B) 9-[4-(2-methylphenoxy)phenyl]-3,4-dihydropyrido[2,1-c][1,2,4]thiadiazine 2,2-dioxide To a suspension of NaH (60%, 284 mg) in THF (dry) (15 mL) was added 2-chloroethanesulfonyl chloride (0.448 mL)

at 0° C. and the mixture was stirred for 5 min at the same temperature. A solution of 3-(4-(2-methylphenoxy)phenyl)pyridin-2-amine (392 mg) in THF (dry) (20 mL) was added at 0° C. and the mixture was stirred at room temperature for 5 hr. The mixture was quenched with water at 0° C. Water, EtOAc and IPE were added and the precipitates were collected, washed with water/EtOAc, dried in vacuo to give the title compound (415.4 mg) as a white solid. A part of this was recrystallized from MeCN/IPE.

$^1$H NMR (300 MHz, DMSO-$d_6$) δ 2.19 (3H, s), 3.40-3.51 (2H, m), 4.59-4.69 (2H, m), 6.70 (1H, t, J=7.0 Hz), 6.86-6.93 (2H, m), 6.99 (1H, dd, J=7.9, 1.1 Hz), 7.10-7.18 (1H, m), 7.21-7.29 (1H, m), 7.35 (1H, d, J=7.2 Hz), 7.47-7.53 (2H, m), 7.61 (1H, dd, J=7.2, 1.5 Hz), 7.76 (1H, dd, J=6.6, 1.7 Hz).

Example 116

9-[4-(2-methylphenoxy)phenyl]-3,4,6,7,8,9-hexahydropyrido[2,1-c][1,2,4]thiadiazine 2,2-dioxide Platinum(IV) oxide (30 mg) was added to a solution of 9-[4-(2-methylphenoxy)phenyl]-3,4-dihydropyrido[2,1-c][1,2,4]thiadiazine 2,2-dioxide (281 mg) in THF (dry) (150 mL) and MeOH (150 mL) and the mixture was stirred at 50° C. under hydrogen overnight. Activated carbon was added and the insoluble solid was removed by filtration through NH-silica gel/Celite pad (eluted with EtOAc). The filtrate was concentrated and the residue was crystallized from MeCN/IPE to give the title compound (144.1 mg) as colorless crystals.

$^1$H NMR (300 MHz, DMSO-$d_6$) δ 1.68-1.80 (3H, m), 1.91-2.09 (1H, m), 2.18 (3H, s), 3.25-3.29 (2H, m), 3.47 (2H, q, J=5.7 Hz), 3.70-3.86 (3H, m), 6.82 (2H, d, J=8.7 Hz), 6.91 (1H, d, J=7.6 Hz), 7.06-7.25 (4H, m), 7.32 (1H, dd, J=7.4, 0.9 Hz).

Example 117

9-[4-(3-methylphenoxy)phenyl]-3,4-dihydropyrido[2,1-c][1,2,4]thiadiazine 2,2-dioxide A) 3-(4-(3-methylphenoxy)phenyl)pyridin-2-amine Copper(I) iodide (102 mg) was added to a mixture of picolinic acid (66.1 mg), 4-(2-aminopyridin-3-yl)phenol (500 mg), tripotassium phosphate (1710 mg), 1-iodo-3-methylbenzene (703 mg) and DMSO (8 mL). The mixture was stirred at 130° C. under nitrogen for 5 hr. Activated carbon was added and the insoluble solid was removed by filtration through NH-silica gel/Celite pad (eluted with EtOAc). Water was added and the extracted organic layer was washed with brine. Silica-gel was added to the organic layer and the volatiles were removed in vacuo. The mixture supported on silica-gel was purified by column chromatography (NH-silica gel, eluted with EtOAc in hexane) to give the title compound (511.5 mg) as a yellow solid.

MS (ESI+). found: 277.1.

B) 9-[4-(3-methylphenoxy)phenyl]-3,4-dihydropyrido[2,1-c][1,2,4]thiadiazine 2,2-dioxide To a suspension of NaH (60%, 370 mg) in THF (dry) (25 mL) was added 2-chloroethanesulfonyl chloride (0.583 mL) at 0° C. and the mixture was stirred for 5 min at the same temperature. A solution of 3-(4-(3-methylphenoxy)phenyl)pyridin-2-amine (511 mg) in THF (dry) (40 mL) was added at 0° C. and the mixture was stirred at room temperature overnight. The mixture was quenched with water at 0° C. Water, EtOAc and IPE were added and the precipitates were collected, washed with water/EtOAc, dried in vacuo to give the title compound (514 mg) as a white solid. A part of this was recrystallized from MeCN/IPE.

$^1$H NMR (300 MHz, DMSO-$d_6$) δ 2.31 (3H, s), 3.42-3.50 (2H, m), 4.61-4.69 (2H, m), 6.71 (1H, t, J=7.0 Hz), 6.83-6.95 (2H, m), 6.96-7.05 (3H, m), 7.30 (1H, t, J=7.8 Hz), 7.53 (2H, d, J=8.3 Hz), 7.64 (1H, d, J=1.1 Hz), 7.77 (1H, dd, J=6.6, 1.3 Hz).

Example 118

9-[4-(3-methylphenoxy)phenyl]-3,4,6,7,8,9-hexahydropyrido[2,1-c][1,2,4]thiadiazine 2,2-dioxide Platinum(IV) oxide (30 mg) was added to a solution of 9-[4-(3-methylphenoxy)phenyl]-3,4-dihydropyrido[2,1-c][1,2,4]thiadiazine 2,2-dioxide (357 mg) in THF (dry) (80 mL) and MeOH (80 mL) and the mixture was stirred at 50° C. under hydrogen for 6 hr. Activated carbon was added and the insoluble solid was removed by filtration through NH-silica gel/Celite pad (eluted with EtOAc) and the filtrate was concentrated in vacuo. The residue was crystallized from MeCN-THF/IPE to give the title compound (243.5 mg) as colorless crystals.

$^1$H NMR (300 MHz, DMSO-$d_6$) δ 1.65-1.80 (3H, m), 1.90-2.09 (1H, m), 2.29 (3H, s), 3.25-3.31 (2H, m), 3.41-3.53 (2H, m), 3.72-3.88 (3H, m), 6.77-7.00 (5H, m), 7.14-7.31 (3H, m).

Example 119

9-[4-(3-methylphenoxy)phenyl]-3,4,6,7,8,9-hexahydropyrido[2,1-c][1,2,4]thiadiazine 2,2-dioxide A racemate (200.3 mg) of 9-[4-(3-methylphenoxy)phenyl]-3,4,6,7,8,9-hexahydropyrido[2,1-c][1,2,4]thiadiazine 2,2-dioxide was separated by SFC (column: CHIRALPAK IC (ME001), 50 mmID×500 mmL, manufactured by DAICEL CHEMICAL INDUSTRIES, LTD., mobile phase:acetonitrile 100%) to give the title compound (94.9 mg) with a shorter retention time. Crystallization from THF and diisopropyl ether gave a white solid.

$^1$H NMR (300 MHz, DMSO-$d_6$) δ 1.66-1.83 (3H, m), 1.92-2.09 (1H, m), 2.29 (3H, s), 3.24-3.28 (2H, m), 3.38-3.56 (2H, m), 3.69-3.88 (3H, m), 6.75-7.00 (5H, m), 7.13-7.32 (3H, m).

Example 120

9-[4-(3-methylphenoxy)phenyl]-3,4,6,7,8,9-hexahydropyrido[2,1-c][1,2,4]thiadiazine 2,2-dioxide A racemate (200.3 mg) of 9-[4-(3-methylphenoxy)phenyl]-3,4,6,7,8,9-hexahydropyrido[2,1-c][1,2,4]thiadiazine 2,2-dioxide was separated by SFC (column: CHIRALPAK IC (ME001), 50 mmID×500 mmL, manufactured by DAICEL CHEMICAL INDUSTRIES, LTD., mobile phase:acetonitrile 100%) to give the title compound (93.2 mg) with a longer retention time. Crystallization from THF and diisopropyl ether gave a white solid.

$^1$H NMR (300 MHz, DMSO-$d_6$) δ 1.66-1.82 (3H, m), 1.92-2.09 (1H, m), 2.29 (3H, s), 3.24-3.29 (2H, m), 3.38-3.57 (2H, m), 3.70-3.90 (3H, m), 6.76-6.99 (5H, m), 7.15-7.32 (3H, m).

Example 121

9-{4-[2-methyl-4-(trifluoromethyl)phenoxy]phenyl}-3,4-dihydropyrido[2,1-c][1,2,4]thiadiazine 2,2-dioxide

A) 3-(4-(2-methyl-4-(trifluoromethyl)phenoxy)phenyl)pyridin-2-amine

Copper(I) iodide (102 mg) was added to a mixture of picolinic acid (66.1 mg), 4-(2-aminopyridin-3-yl)phenol (500 mg), tripotassium phosphate (1710 mg), 1-bromo-2-methyl-4-(trifluoromethyl)benzene (770 mg) and DMSO (8 mL). The mixture was stirred at 130° C. under nitrogen for 5 hr. Activated carbon was added and the insoluble solid was removed by filtration through NH-silica gel/Celite pad (eluted with EtOAc). Water was added and the extracted organic layer was washed with brine. Silica-gel was added to the organic layer and the volatiles were removed in vacuo. The mixture supported on silica-gel was purified by column chromatography (NH-silica gel, eluted with EtOAc in hexane) to give the title compound (489 mg) as a yellow solid.
MS (ESI+). found: 345.1.

B) 9-{4-[2-methyl-4-(trifluoromethyl)phenoxy]phenyl}-3,4-dihydropyrido[2,1-c][1,2,4]thiadiazine 2,2-dioxide To a suspension of NaH (60%, 284 mg) in THF (dry) (25 mL) was added 2-chloroethanesulfonyl chloride (0.448 mL) at 0° C. and the mixture was stirred for 5 min at the same temperature. A solution of 3-(4-(2-methyl-4-(trifluoromethyl)phenoxy)phenyl)pyridin-2-amine (489 mg) in THF (dry) (40 mL) was added at 0° C. and the mixture was stirred at room temperature overnight. The mixture was quenched with water at 0° C. Water, EtOAc and THF were added and the extracted organic layer was washed with brine. Silica-gel was added to the organic layer and the volatiles were removed in vacuo. The mixture supported on silica-gel was purified by column chromatography (NH silica gel, eluted with MeOH in EtOAc) and washed with IPE to give the title compound (390 mg) as a white solid. A part of this was recrystallized from MeCN/IPE.
$^1$H NMR (300 MHz, DMSO-$d_6$) δ 2.33 (3H, s), 3.41-3.51 (2H, m), 4.58-4.71 (2H, m), 6.71 (1H, t, J=6.8 Hz), 7.00-7.10 (3H, m), 7.53-7.67 (4H, m), 7.72-7.81 (2H, m).

Example 122

9-{4-[2-methyl-4-(trifluoromethyl)phenoxy]phenyl}-3,4,6,7,8,9-hexahydropyrido[2,1-c][1,2,4]thiadiazine 2,2-dioxide Platinum(IV) oxide (30 mg) was added to a solution of 9-{4-[2-methyl-4-(trifluoromethyl)phenoxy]phenyl}-3,4-dihydropyrido[2,1-c][1,2,4]thiadiazine 2,2-dioxide (315 mg) in THF (dry) (10 mL) and MeOH (10 mL) and the mixture was stirred at room temperature under hydrogen for 4 hr. Activated carbon was added and the insoluble solid was removed by filtration through NH-silica gel/Celite pad (eluted with EtOAc) and the filtrate was concentrated in vacuo. The residue was crystallized from THF/IPE to give the title compound (206.1 mg) as colorless crystals.
$^1$H NMR (300 MHz, DMSO-$d_6$) δ 1.67-1.81 (3H, m), 1.93-2.12 (1H, m), 2.32 (3H, s), 3.26-3.31 (2H, m), 3.38-3.54 (2H, m), 3.72-3.90 (3H, m), 6.90-7.03 (3H, m), 7.25 (2H, d, J=8.7 Hz), 7.54 (1H, dd, J=8.7, 2.3 Hz), 7.71 (1H, d, J=1.9 Hz).

Example 123

9-{4-[2-methyl-4-(trifluoromethyl)phenoxy]phenyl}-3,4,6,7,8,9-hexahydropyrido[2,1-c][1,2,4]thiadiazine 2,2-dioxide A racemate (166 mg) of 9-{4-[2-methyl-4-(trifluoromethyl)phenoxy]phenyl}-3,4,6,7,8,9-hexahydropyrido[2,1-c][1,2,4]thiadiazine 2,2-dioxide was separated by SFC (column: CHIRALPAK ODH (OG010), 20 mmID×250 mmL, manufactured by DAICEL CHEMICAL INDUSTRIES, LTD., mobile phase:carbon dioxide/acetonitrile/ethanol=800/100/100) to give the title compound (62.8 mg) with a shorter retention time. Crystallization from THF and diisopropyl ether gave a white solid.
$^1$H NMR (300 MHz, DMSO-$d_6$) δ 1.68-1.82 (3H, m), 1.93-2.10 (1H, m), 2.31 (3H, s), 3.26-3.29 (2H, m), 3.43-3.54 (2H, m), 3.71-3.89 (3H, m), 6.91-7.02 (3H, m), 7.25 (2H, d, J=8.7 Hz), 7.54 (1H, dd, J=8.7, 1.9 Hz), 7.71 (1H, d, J=1.9 Hz).

Example 124

9-{4-[2-methyl-4-(trifluoromethyl)phenoxy]phenyl}-3,4,6,7,8,9-hexahydropyrido[2,1-c][1,2,4]thiadiazine 2,2-dioxide A racemate (166 mg) of 9-{4-[2-methyl-4-(trifluoromethyl)phenoxy]phenyl}-3,4,6,7,8,9-hexahydropyrido[2,1-c][1,2,4]thiadiazine 2,2-dioxide was separated by SFC (column: CHIRALPAK ODH (OG010), 20 mmID×250 mmL, manufactured by DAICEL CHEMICAL INDUSTRIES, LTD., mobile phase:carbon dioxide/acetonitrile/ethanol=800/100/100) to give the title compound (76.8 mg) with a longer retention time. Crystallization from THF and diisopropyl ether gave a white solid.
$^1$H NMR (300 MHz, DMSO-$d_6$) δ 1.68-1.82 (3H, m), 1.92-2.10 (1H, m), 2.31 (3H, s), 3.25-3.30 (2H, m), 3.39-3.56 (2H, m), 3.69-3.91 (3H, m), 6.89-7.04 (3H, m), 7.25 (2H, d, J=8.7 Hz), 7.54 (1H, dd, J=8.9, 2.1 Hz), 7.71 (1H, d, J=2.3 Hz).

Example 125

9-{4-[4-(trifluoromethyl)phenoxy]phenyl}-3,4,6,7,8,9-hexahydropyrido[2,1-c][1,2,4]thiadiazine 2,2-dioxide

A) 3-(4-(4-(trifluoromethyl)phenoxy)phenyl)pyridin-2-amine

Copper(I) iodide (102 mg) was added to a mixture of picolinic acid (66.1 mg), 4-(2-aminopyridin-3-yl)phenol (500 mg), tripotassium phosphate (1710 mg), 1-bromo-4-(trifluoromethyl)benzene (725 mg) and DMSO (8 mL). The mixture was stirred at 130° C. under nitrogen for 5 hr. Activated carbon was added and the insoluble solid was removed by filtration through NH-silica gel/Celite pad (eluted with EtOAc). Water was added and the extracted organic layer was washed with brine. Silica-gel was added to the organic layer and the volatiles were removed in vacuo. The mixture supported on silica-gel was purified by column chromatography (NH-silica gel, eluted with EtOAc in hexane) to give the title compound (690.4 mg) as a yellow solid.

MS (ESI+). found: 331.1.

B) 9-{4-[4-(trifluoromethyl)phenoxy]phenyl}-3,4,6,7,8,9-hexahydropyrido[2,1-c][1,2,4]thiadiazine 2,2-dioxide To a suspension of NaH (60%, 418 mg) in THF (dry) (25 mL) was added 2-chloroethanesulfonyl chloride (0.659 mL) at 0° C. and the mixture was stirred for 5 min at the same temperature. A solution of 3-(4-(4-(trifluoromethyl)phenoxy)phenyl)pyridin-2-amine (690 mg) in THF (dry) (40 mL) was added at 0° C. and the mixture was stirred at room temperature overnight. The mixture was quenched with water at 0° C. Water, EtOAc and THF were added and the extracted organic layer was washed with brine, dried over anhydrous magnesium sulfate and concentrated in vacuo. The residue was washed with IPE/EtOAc, dried in vacuo to give 9-{4-[4-(trifluoromethyl)phenoxy]phenyl}-3,4-dihydropyrido[2,1-c][1,2,4]thiadiazine 2,2-dioxide (579.1 mg) as a slightly yellow solid. Platinum(IV) oxide (30 mg) was added to a solution of 9-{4-[4-(trifluoromethyl)phenoxy]phenyl}-3,4-dihydropyrido[2,1-c][1,2,4]thiadiazine 2,2-dioxide (505 mg) in THF (dry) (15 mL) and MeOH (15 mL) and the mixture was stirred at room temperature under hydrogen for 6 hr. Platinum(IV) oxide (30 mg), MeOH (15 mL) and THF (dry) (15 mL) were added and the mixture was stirred at 50° C. under hydrogen overnight. Activated carbon was added and the insoluble solid was removed by filtration through NH-silica gel/Celite pad (eluted with EtOAc) and the filtrate was concentrated in vacuo. The residue was crystallized from THF/IPE to give the title compound (297.2 mg) as colorless crystals.

$^1$H NMR (300 MHz, DMSO-$d_6$) δ 1.68-1.83 (3H, m), 1.92-2.12 (1H, m), 3.25-3.30 (2H, m), 3.40-3.56 (2H, m), 3.74-3.90 (3H, m), 7.02-7.19 (4H, m), 7.29 (2H, d, J=8.7 Hz), 7.74 (2H, d, J=8.7 Hz).

mp 191-193° C.

Anal. Calcd for $C_{20}H_9N_2O_3SF_3$: C, 56.60; H, 4.51; N, 6.60. Found: C, 56.51; H, 4.59; N, 6.59.

Example 126

9-(6-methoxynaphthalen-2-yl)-3,4-dihydropyrido[2,1-c][1,2,4]thiadiazine 2,2-dioxide A) 3-(6-methoxynaphthalen-2-yl)pyridin-2-amine Tetrakis(triphenylphosphine)palladium(0) (95 mg) was added to a suspension of 3-bromopyridin-2-amine (713.7 mg), 6-methoxynaphthalen-2-ylboronic acid (1000 mg) and sodium carbonate decahydrate (2361 mg) in DME (15 mL) and water (3 mL) and the mixture was stirred at 80° C. under nitrogen for 3 hr and at 70° C. overnight. Activated carbon was added and the insoluble solid was removed by filtration through NH-silica gel/Celite pad (eluted with EtOAc) and the volatiles were removed in vacuo to give the title compound (1194 mg) as a crude orange solid. This product was subjected to the next reaction without further purification.

MS (ESI+). found: 251.1.

B) 9-(6-methoxynaphthalen-2-yl)-3,4-dihydropyrido[2,1-c][1,2,4]thiadiazine 2,2-dioxide To a suspension of NaH (60%, 951 mg) in THF (dry) (40 mL) was added 2-chloroethanesulfonyl chloride (1.50 mL) at 0° C. and the mixture was stirred for 5 min at the same temperature. A solution of 3-(6-methoxynaphthalen-2-yl)pyridin-2-amine (1190 mg) in THF (dry) (25 mL) was added at 0° C. and the mixture was stirred at room temperature overnight. The mixture was quenched with water. Water and EtOAc were added and the precipitates were collected, washed with water/EtOAc, dried in vacuo to give the title compound (835.3 mg). A part of this was recrystallized from MeCN-THF/IPE.

$^1$H NMR (300 MHz, DMSO-$d_6$) δ 3.43-3.51 (2H, m), 3.89 (3H, s), 4.62-4.71 (2H, m), 6.75 (1H, t, J=7.0 Hz), 7.18 (1H, dd, J=8.9, 2.5 Hz), 7.35 (1H, d, J=2.6 Hz), 7.64 (1H, dd, J=8.7, 1.9 Hz), 7.72 (1H, dd, J=7.0, 1.7 Hz), 7.78-7.87 (3H, m), 7.91 (1H, s).

Example 127

9-(6-methoxynaphthalen-2-yl)-3,4,6,7,8,9-hexahydropyrido[2,1-c][1,2,4]thiadiazine 2,2-dioxide Platinum(IV) oxide (30 mg) was added to a solution of 9-(6-methoxynaphthalen-2-yl)-3,4-dihydropyrido[2,1-c][1,2,4]thiadiazine 2,2-dioxide (218 mg) in THF (dry) (75 mL) and MeOH (75 mL) and the mixture was stirred at room temperature under hydrogen overnight and at 50° C. overnight. Activated carbon was added and the insoluble solid was removed by filtration through NH-silica gel/Celite pad (eluted with EtOAc). The filtrate was concentrated and the residue was crystallized from MeCN-THF/IPE to give the title compound (153 mg) as colorless crystals.

$^1$H NMR (300 MHz, DMSO-$d_6$) δ 1.75-1.90 (3H, m), 1.95-2.13 (1H, m), 3.27-3.30 (2H, m), 3.43-3.66 (2H, m), 3.75-3.95 (6H, m), 7.15 (1H, dd, J=9.1, 2.6 Hz), 7.24-7.39 (2H, m), 7.61 (1H, s), 7.77 (2H, dd, J=8.7, 3.8 Hz).

Example 128

9-(6-methoxynaphthalen-2-yl)-3,4,6,7,8,9-hexahydropyrido[2,1-c][1,2,4]thiadiazine 2,2-dioxide A racemate (114 mg) of 9-(6-methoxynaphthalen-2-yl)-3,4,6,7,8,9-hexahydropyrido[2,1-c][1,2,4]thiadiazine 2,2-dioxide was separated by SFC (column: CHIRALPAK ADH (KG010), mmID×250 mmL, manufactured by DAICEL CHEMICAL INDUSTRIES, LTD., mobile phase:carbon dioxide/acetonitrile/ethanol=800/100/100) to give the title compound (52 mg) with a shorter retention time. Crystallization from acetonitrile and diisopropyl ether gave a white solid.

$^1$H NMR (300 MHz, DMSO-$d_6$) δ 1.75-1.90 (3H, m), 1.95-2.13 (1H, m), 3.27-3.30 (2H, m), 3.43-3.66 (2H, m), 3.75-3.95 (6H, m), 7.15 (1H, dd, J=9.1, 2.6 Hz), 7.24-7.39 (2H, m), 7.61 (1H, s), 7.77 (2H, dd, J=8.7, 3.8 Hz).

Example 129

9-(6-methoxynaphthalen-2-yl)-3,4,6,7,8,9-hexahydropyrido[2,1-c][1,2,4]thiadiazine 2,2-dioxide A racemate (114 mg) of 9-(6-methoxynaphthalen-2-yl)-3,4,6,7,8,9-hexahydropyrido[2,1-c][1,2,4]thiadiazine 2,2-dioxide was separated by SFC (column: CHIRALPAK ADH (KG010), mmID×250 mmL, manufactured by DAICEL CHEMICAL INDUSTRIES, LTD., mobile phase:carbon dioxide/acetonitrile/ethanol=800/100/100) to give the title compound (56 mg) with a longer retention time. Crystallization from acetonitrile and diisopropyl ether gave a white solid.

$^1$H NMR (300 MHz, DMSO-d$_6$) δ 1.73-1.90 (3H, m), 1.98-2.11 (1H, m), 3.29-3.31 (2H, m), 3.44-3.62 (2H, m), 3.77-3.94 (6H, m), 7.15 (1H, dd, J=8.9, 2.5 Hz), 7.29-7.34 (2H, m), 7.61 (1H, s), 7.77 (2H, dd, J=8.7, 3.8 Hz).

Example 130

9-[4-(3-ethylphenoxy)phenyl]-3,4-dihydropyrido[2,1-c][1,2,4]thiadiazine 2,2-dioxide A) 3-(4-(3-ethylphenoxy)phenyl)pyridin-2-amine Copper(I) iodide (102 mg) was added to a mixture of picolinic acid (66.1 mg), 4-(2-aminopyridin-3-yl)phenol (500 mg), tripotassium phosphate (1710 mg), 1-bromo-3-ethylbenzene (596 mg) and DMSO (8 mL). The mixture was stirred at 130° C. under nitrogen for 4 hr. Activated carbon was added and the insoluble solid was removed by filtration through NH-silica gel/Celite pad (eluted with EtOAc). Water and EtOAc were added and the extracted organic layer was washed with brine. Silica-gel was added to the organic layer and the volatiles were removed in vacuo. The mixture supported on silica-gel was purified by column chromatography (NH-silica gel, eluted with EtOAc in hexane) to give the title compound (312.5 mg) as a pale yellow crystalline solid.

MS (ESI+). found: 291.1.

B) 9-[4-(3-ethylphenoxy)phenyl]-3,4-dihydropyrido[2,1-c][1,2,4]thiadiazine 2,2-dioxide To a suspension of NaH (60%, 215 mg) in THF (dry) (20 mL) was added 2-chloroethanesulfonyl chloride (0.339 mL) at 0° C. and the mixture was stirred for 5 min at the same temperature. A solution of 3-(4-(3-ethylphenoxy)phenyl)pyridin-2-amine (312 mg) in THF (dry) (30 mL) was added at 0° C. and the mixture was stirred at room temperature for 1 hr. The mixture was quenched with water at 0° C. Water and EtOAc/THF were added and the extracted organic layer was washed with brine. Silica-gel was added to the organic layer and the volatiles were removed in vacuo. The mixture supported on silica-gel was purified by column chromatography (NH silica gel, eluted with MeOH in EtOAc) and washed with IPE/EtOAc to give the title compound (295 mg) as a white solid. A part of this was recrystallized from THF/IPE.

$^1$H NMR (300 MHz, DMSO-d$_6$) δ 1.18 (3H, t, J=7.6 Hz), 2.62 (2H, q, J=7.6 Hz), 3.40-3.51 (2H, m), 4.57-4.71 (2H, m), 6.70 (1H, t, J=7.0 Hz), 6.87 (1H, dd, J=7.7, 2.1 Hz), 6.93-7.06 (4H, m), 7.27-7.36 (1H, m), 7.50-7.57 (2H, m), 7.62 (1H, dd, J=7.2, 1.5 Hz), 7.76 (1H, dd, J=6.6, 1.7 Hz).

Example 131

9-[4-(3-ethylphenoxy)phenyl]-3,4,6,7,8,9-hexahydropyrido[2,1-c][1,2,4]thiadiazine 2,2-dioxide Platinum(IV) oxide (30 mg) was added to a solution of 9-[4-(3-ethylphenoxy)phenyl]-3,4-dihydropyrido[2,1-c][1,2,4]thiadiazine 2,2-dioxide (247 mg) in THF (dry) (20 mL) and MeOH (20 mL). The mixture was stirred at 50° C. under hydrogen for 40 min and at room temperature under hydrogen for 4 h. Activated carbon was added and the insoluble solid was removed by filtration through NH-silica gel/Celite pad (eluted with EtOAc) and the filtrate was concentrated in vacuo. The residue was crystallized from THF/IPE to give the title compound (167.0 mg) as colorless crystals.

$^1$H NMR (300 MHz, DMSO-d$_6$) δ 1.16 (3H, t, J=7.7 Hz), 1.62-1.82 (3H, m), 1.89-2.09 (1H, m), 2.60 (2H, q, J=7.7 Hz), 3.23-3.29 (2H, m), 3.38-3.55 (2H, m), 3.69-3.91 (3H, m), 6.80 (1H, dd, J=8.1, 1.7 Hz), 6.87-6.95 (3H, m), 6.99 (1H, d, J=7.6 Hz), 7.15-7.23 (2H, m), 7.29 (1H, t, J=7.9 Hz).

Example 132

9-[4-(3-ethylphenoxy)phenyl]-3,4,6,7,8,9-hexahydropyrido[2,1-c][1,2,4]thiadiazine 2,2-dioxide A racemate (140 mg) of 9-[4-(3-ethylphenoxy)phenyl]-3,4,6,7,8,9-hexahydropyrido[2,1-c][1,2,4]thiadiazine 2,2-dioxide was separated by SFC (column: CHIRALPAK ADH (OC006), mmIDx250 mmL, manufactured by DAICEL CHEMICAL INDUSTRIES, LTD., mobile phase:carbon dioxide/acetonitrile/ethanol=700/150/150) to give the title compound (73 mg) with a shorter retention time as a white solid.

$^1$H NMR (300 MHz, DMSO-d$_6$) δ 1.16 (3H, t, J=7.5 Hz), 1.64-1.84 (3H, m), 1.91-2.11 (1H, m), 2.60 (2H, q, J=7.5 Hz), 3.22-3.28 (2H, m), 3.38-3.56 (2H, m, J=6.2, 6.2, 6.2 Hz), 3.69-3.91 (3H, m), 6.80 (1H, dd, J=7.5, 2.3 Hz), 6.86-6.95 (3H, m), 7.00 (1H, d, J=7.5 Hz), 7.20 (2H, d, J=8.7 Hz), 7.29 (1H, t, J=7.7 Hz).

Example 133

9-[4-(3-ethylphenoxy)phenyl]-3,4,6,7,8,9-hexahydropyrido[2,1-c][1,2,4]thiadiazine 2,2-dioxide A racemate (140 mg) of 9-[4-(3-ethylphenoxy)phenyl]-3,4,6,7,8,9-hexahydropyrido[2,1-c][1,2,4]thiadiazine 2,2-dioxide was separated by SFC (column: CHIRALPAK ADH (OC006), mmIDx250 mmL, manufactured by DAICEL CHEMICAL INDUSTRIES, LTD., mobile phase:carbon dioxide/acetonitrile/ethanol=700/150/150) to give the title compound (56 mg) with a longer retention time as a white solid.

$^1$H NMR (300 MHz, DMSO-d$_6$) δ 1.16 (3H, t, J=7.7 Hz), 1.64-1.84 (3H, m), 1.91-2.11 (1H, m), 2.60 (2H, q, J=7.5 Hz), 3.23-3.28 (2H, m), 3.38-3.57 (2H, m), 3.70-3.88 (3H, m), 6.80 (1H, dd, J=7.7, 2.1 Hz), 6.88-6.95 (3H, m), 7.00 (1H, d, J=6.8 Hz), 7.20 (2H, d, J=8.3 Hz), 7.29 (1H, t, J=7.9 Hz).

Example 134

9-[4-(3,4-dimethylphenoxy)phenyl]-3,4-dihydropyrido[2,1-c][1,2,4]thiadiazine 2,2-dioxide A) 3-(4-(3,4-dimethylphenoxy)phenyl)pyridin-2-amine Copper(I) iodide (102 mg) was added to a mixture of picolinic acid (66.1 mg), 4-(2-aminopyridin-3-yl)phenol (500 mg), tripotassium phosphate (1710 mg), 4-bromo-1,2-dimethylbenzene (596 mg) and DMSO (8 mL). The mixture was stirred at 130° C. under nitrogen for 3 hr and at 110° C. under nitrogen overnight. Activated carbon was added and the insoluble solid was removed by filtration through NH-silica gel/Celite pad (eluted with EtOAc). Water and EtOAc were added and the extracted organic layer was washed with brine. Silica-gel was added to the organic layer and the volatiles were removed in vacuo. The mixture supported on silica-gel was purified by column chromatography (NH-silica gel, eluted with EtOAc in hexane) to give the title compound (144 mg) as a pale yellow crystalline solid.

MS (ESI+). found: 291.1.

B) 9-[4-(3,4-dimethylphenoxy)phenyl]-3,4-dihydropyrido[2,1-c][1,2,4]thiadiazine 2,2-dioxide To a suspension of NaH (60%, 99 mg) in THF (dry) (10 mL) was added 2-chloroethanesulfonyl chloride (0.156 mL) at 0° C. and the mixture was stirred for 10 min at the same temperature. A solution of 3-(4-(3,4-dimethylphenoxy)phenyl)pyridin-2-amine (144 mg) in THF (dry) (10 mL) was added at 0° C. and the mixture was stirred at room temperature under nitrogen overnight. The mixture was quenched with water at 0° C. and extracted with EtOAc/THF. Silica-gel was added to the organic phase and the volatiles were removed in vacuo. The mixture supported on silica-gel was purified by column chromatography (silica gel, eluted with MeOH in EtOAc) to give the title compound (119.7 mg). A part of product was recrystallized from MeCN/IPE.

$^1$H NMR (300 MHz, DMSO-$d_6$) δ 2.21 (6H, s), 3.40-3.52 (2H, m), 4.58-4.71 (2H, m), 6.70 (1H, t, J=7.0 Hz), 6.81 (1H, dd, J=8.3, 2.6 Hz), 6.91 (1H, d, J=2.6 Hz), 6.92-6.99 (2H, m), 7.17 (1H, d, J=8.3 Hz), 7.45-7.53 (2H, m), 7.61 (1H, dd, J=7.2, 1.5 Hz), 7.76 (1H, dd, J=6.6, 1.7 Hz).

Example 135

9-[4-(3,4-dimethylphenoxy)phenyl]-3,4,6,7,8,9-hexahydropyrido[2,1-c][1,2,4]thiadiazine 2,2-dioxide Platinum(IV) oxide (25 mg) was added to a solution of 9-[4-(3,4-dimethylphenoxy)phenyl]-3,4-dihydropyrido[2,1-c][1,2,4]thiadiazine 2,2-dioxide (93.8 mg) in THF (dry) (10 mL) and MeOH (10 mL). The mixture was stirred at room temperature under hydrogen for 3 hr. Activated carbon was added and the insoluble solid was removed by filtration through NH-silica gel/Celite pad (eluted with EtOAc) and the filtrate was concentrated in vacuo. The residue was crystallized from THF/IPE to give the title compound (71.8 mg) as colorless crystals.

$^1$H NMR (300 MHz, DMSO-$d_6$) δ 1.66-1.81 (3H, m), 1.86-2.06 (1H, m), 2.20 (6H, s), 3.24-3.29 (2H, m), 3.39-3.56 (2H, m), 3.67-3.91 (3H, m), 6.75 (1H, dd, J=8.3, 2.6 Hz), 6.80-6.96 (3H, m), 7.05-7.30 (3H, m).

Example 136

9-{4-[difluoro(4-methylphenyl)methyl]phenyl}-3,4-dihydropyrido[2,1-c][1,2,4]thiadiazine 2,2-dioxide

A) (4-bromophenyl)(4-methylphenyl)methanone

To a mixture of N,O-dimethylhydroxylamine hydrochloride (8.20 g) in THF (dry) (75 mL) was added TEA (23.4 mL) at 0° C. After being stirred at 0° C. for 20 min, 4-methylbenzoyl chloride (10 g) in THF (dry) (20 mL) was added to the reaction mixture. The mixture was stirred at room temperature for 2 days. The mixture was quenched with water at room temperature and extracted with EtOAc. The organic layer was separated, washed with brine, dried over anhydrous magnesium sulfate and concentrated in vacuo to give N-methoxy-N,4-dimethylbenzamide (11.7 g) as a yellow oil. n-Butyllithium (1.6 M in hexane) (25.1 mL) was added dropwise to a mixture of 1,4-dibromobenzene (8.29 g) in THF (dry) (105 mL) at −78° C. for 10 min. The mixture was stirred at the same temperature under nitrogen for 30 min to form white precipitates. A solution of N-methoxy-N,4-dimethylbenzamide (6 g) in THF (dry) (20 mL) was added to the reaction mixture at −78° C. and the mixture was stirred at the same temperature under nitrogen for 30 min and then at room temperature under a dry atmosphere with anhydrous calcium chloride tube overnight. The mixture was quenched with sat. NH$_4$Cl aq. at room temperature and extracted with EtOAc. The organic layer was separated, washed with water and brine, dried over anhydrous magnesium sulfate and concentrated in vacuo. The residue was purified by column chromatography (silica gel, eluted with EtOAc in hexane) to give the title compound (7.18 g) as a pale yellow solid.

$^1$H NMR (300 MHz, DMSO-$d_6$) δ 2.41 (3H, s), 7.38 (2H, d, J=7.9 Hz), 7.65 (4H, d, J=7.9 Hz), 7.74-7.80 (2H, m).

B) 1-bromo-4-(difluoro(4-methylphenyl)methyl)benzene

Bis(2-methoxyethyl)aminosulfur trifluoride (4.79 mL) was added dropwise under nitrogen to (4-bromophenyl)(4-methylphenyl)methanone (3 g) at room temperature. The mixture was stirred at 75° C. under nitrogen for 10 min. Toluene (1.5 mL) was added and the mixture was stirred at 75° C. under nitrogen overnight. The mixture was quenched with sat. NaHCO$_3$ aq. at room temperature and extracted with EtOAc. The organic layer was separated, washed with water and brine, dried over anhydrous magnesium sulfate and concentrated in vacuo. The residue was washed with hexane and the insoluble material was removed by filtration, and the filtrate was concentrated in vacuo. The residue was purified by column chromatography (silica gel, eluted with EtOAc in hexane) to give the title compound (646.4 mg) as pale yellow oil.

$^1$H NMR (300 MHz, DMSO-$d_6$) δ 2.34 (3H, s), 7.27-7.33 (2H, m), 7.37-7.42 (2H, m), 7.42-7.50 (2H, m), 7.70 (2H, d, J=8.3 Hz).

C) 3-(4-(difluoro(4-methylphenyl)methyl)phenyl)pyridin-2-amine

Pd(dppf)Cl$_2$ (31.8 mg) was added to a mixture of 1-bromo-4-(difluoro(4-methylphenyl)methyl)benzene (646 mg), potassium acetate (640 mg) and 4,4,4',4',5,5,5',5'-octamethyl-2,2'-bi(1,3,2-dioxaborolane) (828 mg) in DME (20 mL) and DMSO (1 mL). The mixture was stirred at 80° C. under nitrogen overnight. Activated-carbon powder was added and the mixture was stirred for 5 min. The insoluble material was removed by filtration. The filtrate was concentrated in vacuo. To the residual brown oil was added potassium acetate (640 mg), 4,4,4',4',5,5,5',5'-octamethyl-2,2'-bi(1,3,2-dioxaborolane) (828 mg), Pd(dppf)Cl$_2$ (60 mg) and DME (20 mL), and the mixture was stirred at 80° C. under nitrogen for 5 hr. Activated-carbon powder was added and the mixture was stirred for 5 min. The insoluble material was removed by filtration. Silica-gel was added and the volatiles were removed in vacuo. The mixture supported on silica-gel was purified by column chromatography (NH silica gel, eluted with EtOAc in hexane) to give crude of 2-(4-(difluoro(4-methylphenyl)methyl)phenyl)-4,4,5,5-tetramethyl-1,3,2-dioxaborolane as a pale yellow amorphous solid. Tetrakis(triphenylphosphine)palladium(0) (62.8 mg) was added to a suspension of 3-bromopyridin-2-amine (313 mg), the prepared 2-(4-(difluoro(4-methylphenyl)methyl) phenyl)-4,4,5,5-tetramethyl-1,3,2-dioxaborolane and sodium carbonate decahydrate (1036 mg) in DME (20 mL) and water (4 mL) and the mixture was stirred at 80° C. under nitrogen for 4 hr. Silica-gel was added and the volatiles were removed in vacuo. The mixture supported on silica-gel was purified by column chromatography (silica gel, eluted with EtOAc in hexane) to give a pale yellow solid (1.12 g) including the title compound. This was used for the next step without further purification.

MS (ESI+). found: 311.1.

D) 9-{4-[difluoro(4-methylphenyl)methyl]phenyl}-3,4-dihydropyrido[2,1-c][1,2,4]thiadiazine 2,2-dioxide To a suspension of NaH (60%, 362 mg) in THF (dry) (20 mL) was added 2-chloroethanesulfonyl chloride (0.571 mL) at 0° C. and the mixture was stirred for 10 min at the same temperature. A solution of 3-(4-(difluoro(4-methylphenyl) methyl)phenyl)pyridin-2-amine obtained by step C of Example 136 in THF (dry) (10 mL) was added at 0° C. and the mixture was stirred at room temperature under a dry atmosphere with anhydrous calcium chloride tube overnight. The mixture was quenched with water/THF then water at 0° C. and extracted with EtOAc/THF. Silica-gel was added to the organic phase and the volatiles were removed in vacuo. The mixture supported on silica-gel was purified by column chromatography (silica gel, eluted with MeOH in EtOAc) and concentrated in vacuo and washed with IPE to give the title compound (197 mg) as an off-white powder. A part of product was recrystallized from MeCN/IPE.

$^1$H NMR (300 MHz, DMSO-$d_6$) δ 2.35 (3H, s), 3.41-3.51 (2H, m), 4.58-4.73 (2H, m), 6.72 (1H, t, J=7.0 Hz), 7.27-7.36 (2H, m), 7.44 (2H, d, J=8.3 Hz), 7.49-7.58 (2H, m), 7.59-7.70 (3H, m), 7.80 (1H, dd, J=6.8, 1.5 Hz).

Example 137

9-{4-[difluoro(4-methylphenyl)methyl]phenyl}-3,4,6,7,8,9-hexahydropyrido[2,1-c][1,2,4]thiadiazine 2,2-dioxide Platinum(IV) oxide (30 mg) was added to a solution of 9-{4-[difluoro(4-methylphenyl)methyl]phenyl}-3,4-dihydropyrido[2,1-c][1,2,4]thiadiazine 2,2-dioxide (156 mg) in THF (dry) (20 mL) and MeOH (20 mL). The mixture was stirred at room temperature under hydrogen for 3 h. Activated carbon was added and the insoluble solid was removed by filtration through NH-silica gel/Celite pad (eluted with EtOAc). Platinum(IV) oxide (30 mg) was added and the mixture was stirred at room temperature under hydrogen overnight. Activated carbon was added and the insoluble solid was removed by filtration through NH-silica gel/Celite pad (eluted with EtOAc) and the filtrate was concentrated in vacuo. The residue was crystallized from THF/IPE to give the title compound (72.0 mg) as colorless crystals.

$^1$H NMR (300 MHz, DMSO-$d_6$) δ 1.70-1.80 (3H, m), 1.95-2.04 (1H, m), 2.34 (3H, s), 3.25-3.28 (2H, m), 3.40-3.55 (2H, m), 3.82 (3H, q, J=6.4 Hz), 7.25-7.36 (4H, m), 7.36-7.47 (4H, m).

mp 190-191° C.

Anal. Calcd for $C_{21}H_{22}N_2O_2SF_2$: C, 62.36; H, 5.48; N, 6.93. Found: C, 62.35; H, 5.59; N, 6.80.

Example 138

9-{4-[difluoro(4-methylphenyl)methyl]phenyl}-3,4,6,7,8,9-hexahydropyrido[2,1-c][1,2,4]thiadiazine 2,2-dioxide A racemate (33 mg) of 9-{4-[difluoro(4-methylphenyl) methyl]phenyl}-3,4,6,7,8,9-hexahydropyrido[2,1-c][1,2,4] thiadiazine 2,2-dioxide was separated by SFC (column: CHIRALPAK AY-H (OC006), 20 mmID×250 mmL, manufactured by DAICEL CHEMICAL INDUSTRIES, LTD., mobile phase:carbon dioxide/acetonitrile/ethanol=740/130/130) to give the title compound (15 mg) with a shorter retention time as a white solid.

$^1$H NMR (300 MHz, DMSO-$d_6$) δ 1.66-1.81 (3H, m), 1.90-2.10 (1H, m), 2.34 (3H, s), 3.24-3.30 (2H, m), 3.42-3.54 (2H, m), 3.76-3.89 (3H, m), 7.27-7.35 (4H, m), 7.38-7.47 (4H, m).

Example 139

9-{4-[difluoro(4-methylphenyl)methyl]phenyl}-3,4,6,7,8,9-hexahydropyrido[2,1-c][1,2,4]thiadiazine 2,2-dioxide A racemate (33 mg) of 9-{4-[difluoro(4-methylphenyl) methyl]phenyl}-3,4,6,7,8,9-hexahydropyrido[2,1-c][1,2,4] thiadiazine 2,2-dioxide was separated by SFC (column: CHIRALPAK AY-H (OC006), 20 mmID×250 mmL, manufactured by DAICEL CHEMICAL INDUSTRIES, LTD., mobile phase:carbon dioxide/acetonitrile/ethanol=740/130/130) to give the title compound (16.8 mg) with a longer retention time as a white solid.

$^1$H NMR (300 MHz, DMSO-$d_6$) δ 1.64-1.83 (3H, m), 2.00 (1H, s), 2.34 (3H, s), 3.23-3.30 (2H, m), 3.40-3.57 (2H, m), 3.73-3.89 (3H, m), 7.25-7.35 (4H, m), 7.37-7.46 (4H, m).

Example 140

9-{4-[difluoro(4-fluoro-3-methylphenyl)methyl] phenyl}-3,4,6,7,8,9-hexahydropyrido[2,1-c][1,2,4] thiadiazine 2,2-dioxide Platinum(IV) oxide (30 mg) was added to a solution of 9-{4-[difluoro(4-fluoro-3-methylphenyl)methyl]phenyl}-3,4-dihydropyrido[2,1-c][1,2,4]thiadiazine 2,2-dioxide (148 mg) in THF (dry) (50 mL) and MeOH (50 mL). The mixture was stirred at room temperature under hydrogen for 3 hr. Activated carbon was added and the insoluble solid was removed by filtration through NH-silica gel/Celite pad (eluted with EtOAc) and the filtrate was concentrated in vacuo. The residue was crystallized from THF/IPE to give the title compound (46.5 mg) as colorless crystals.

$^1$H NMR (300 MHz, DMSO-$d_6$) δ 1.68-1.83 (3H, m), 1.92-2.07 (1H, m), 2.27 (3H, d, J=1.9 Hz), 3.24-3.28 (2H, m), 3.40-3.55 (2H, m), 3.74-3.89 (3H, m), 7.19-7.55 (7H, m).

Example 141

9-[4-(2,3-dihydro-1-benzofuran-6-yloxy)phenyl]-3,4,6,7,8,9-hexahydropyrido[2,1-c][1,2,4]thiadiazine 2,2-dioxide Platinum(IV) oxide (20 mg) was added to a solution of 9-[4-(2,3-dihydro-1-benzofuran-6-yloxy)phenyl]-3,4-dihydropyrido[2,1-c][1,2,4]thiadiazine 2,2-dioxide (100 mg) in THF (dry) (50 mL) and MeOH (50 mL). The mixture was stirred at room temperature under hydrogen for 3 hr. Activated carbon was added and the insoluble solid was removed by filtration through NH-silica gel/Celite pad (eluted with EtOAc). Platinum(IV) oxide (20 mg) was added and the mixture was stirred at room temperature under hydrogen overnight. Activated carbon was added and the insoluble solid was removed by filtration through NH-silica gel/Celite pad (eluted with EtOAc) and the filtrate was concentrated in vacuo. The residue was crystallized from THF/IPE to give the title compound (68.8 mg) as colorless crystals.

$^1$H NMR (300 MHz, DMSO-$d_6$) δ 1.64-1.83 (3H, m), 1.92-2.07 (1H, m), 3.14 (2H, t, J=8.7 Hz), 3.24-3.27 (2H, m), 3.38-3.56 (2H, m, J=5.7 Hz), 3.70-3.86 (3H, m), 4.56 (2H, t, J=8.7 Hz), 6.38-6.51 (2H, m), 6.91 (2H, d, J=8.7 Hz), 7.12-7.24 (3H, m).

Example 142

9-{4-[4-bromo-3-(trifluoromethyl)phenoxy]phenyl}-3,4,6,7,8,9-hexahydropyrido[2,1-c][1,2,4]thiadiazine 2,2-dioxide A mixture of platinum (IV) oxide (30 mg) and 9-{4-[4-bromo-3-(trifluoromethyl)phenoxy]phenyl}-3,4-dihydropyrido[2,1-c][1,2,4]thiadiazine 2,2-dioxide (192 mg) in THF (20 mL) was stirred under a hydrogen atmosphere overnight. To the reaction mixture was added activated carbon, and the mixture was filtered through basic silica gel and celite. To the filtrate was added silica gel and the mixture was concentrated under reduced pressure. The residue was purified by silica gel column chromatography (methanol/ethyl acetate) and concentrated under reduced pressure. The residue was separated by HPLC (C18, mobile phase: water/acetonitrile (0.1% TFA containing system)). To the obtained fraction was added a saturated aqueous sodium hydrogen carbonate solution, and the mixture was extracted with ethyl acetate, dried over anhydrous magnesium sulfate, and concentrated under reduced pressure. The obtained residue was crystallized from THF and diisopropyl ether to give the title compound (30 mg) as a white solid.

$^1$H NMR (300 MHz, DMSO-$d_6$) δ 1.65-1.85 (3H, m), 1.90-2.12 (1H, m), 3.25-3.29 (2H, m), 3.48 (2H, dq, J=12.8, 6.3 Hz), 3.74-3.89 (3H, m), 7.07 (2H, d, J=8.7 Hz), 7.19 (1H, dd, J=8.9, 2.8 Hz), 7.28 (2H, d, J=8.7 Hz), 7.46 (1H, d, J=3.0 Hz), 7.86 (1H, d, J=8.7 Hz).

Example 143

9-[4-(4-fluoro-2-methylphenoxy)phenyl]-3,4-dihydropyrido[2,1-c][1,2,4]thiadiazine 2,2-dioxide A) 3-(4-(4-fluoro-2-methylphenoxy)phenyl)pyridin-2-amine Copper(I) iodide (102 mg) was added to a mixture of picolinic acid (66.1 mg), 4-(2-aminopyridin-3-yl)phenol (500 mg), tripotassium phosphate (1710 mg), 4-fluoro-1-iodo-2-methylbenzene (761 mg) and DMSO (8 mL). The mixture was stirred at 130° C. under nitrogen for 5 hr. Activated carbon was added and the insoluble solid was removed by filtration through NH-silica gel/Celite pad (eluted with EtOAc). Water was added and the extracted organic layer was washed with brine. Silica-gel was added to the organic layer and the volatiles were removed in vacuo. The mixture supported on silica-gel was purified by column chromatography (NH-silica gel, eluted with EtOAc in hexane) to give the title compound (354 mg) as a yellow solid.

MS (ESI+). found: 295.1.

B) 9-[4-(4-fluoro-2-methylphenoxy)phenyl]-3,4-dihydropyrido[2,1-c][1,2,4]thiadiazine 2,2-dioxide To a suspension of NaH (60%, 241 mg) in THF (dry) (25 mL) was added 2-chloroethanesulfonyl chloride (0.380 mL) at 0° C. and the mixture was stirred for 5 min at the same temperature. A solution of 3-(4-(4-fluoro-2-methylphenoxy)phenyl)pyridin-2-amine (354 mg) in THF (dry) (40 mL) was added at 0° C. and the mixture was stirred at room temperature overnight. The mixture was quenched with water at 0° C. Water, EtOAc and THF were added and the extracted organic layer was washed with brine, dried over anhydrous magnesium sulfate and concentrated in vacuo. The residue was washed with IPE/EtOAc, dried in vacuo to give the title compound (375 mg) as a slightly yellow solid. A part of this was recrystallized from MeCN/IPE.

$^1$H NMR (300 MHz, DMSO-$d_6$) δ 2.18 (3H, s), 3.41-3.49 (2H, m), 4.58-4.70 (2H, m), 6.70 (1H, t, J=6.8 Hz), 6.88 (2H, d, J=8.7 Hz), 7.03-7.10 (2H, m), 7.23 (1H, dd, J=9.1, 1.9 Hz), 7.50 (2H, d, J=8.7 Hz), 7.60 (1H, dd, J=7.2, 1.5 Hz), 7.76 (1H, dd, J=6.4, 1.5 Hz).

mp 240-242° C.

Anal. Calcd for $C_{20}H_7N_2O_3SF \cdot 0.2H_2O$: C, 61.91; H, 4.52; N, 7.22. Found: C, 61.94; H, 4.60; N, 7.37.

Example 144

9-[4-(4-fluoro-2-methylphenoxy)phenyl]-3,4,6,7,8,9-hexahydropyrido[2,1-c][1,2,4]thiadiazine 2,2-dioxide Platinum(IV) oxide (30 mg) was added to a solution of 9-[4-(4-fluoro-2-methylphenoxy)phenyl]-3,4-dihydropyrido[2,1-c][1,2,4]thiadiazine 2,2-dioxide (303 mg) in THF (dry) (30 mL) and MeOH (30 mL) and the mixture was stirred at 50° C. under hydrogen for 4 hr. The starting material was purified by column chromatography (NH silica gel, eluted with MeOH in EtOAc) and recovered. Platinum (IV) oxide (30 mg) was added to a solution of the purified starting material in THF (dry) (30 mL) and MeOH (30 mL) and the mixture was stirred at 50° C. under hydrogen overnight. Activated carbon was added and the insoluble solid was removed by filtration through NH-silica gel/Celite pad (eluted with EtOAc) and the filtrate was concentrated in vacuo. The residue was crystallized from MeCN/IPE to give the title compound (115 mg) as colorless crystals.

$^1$H NMR (300 MHz, DMSO-$d_6$) δ 1.64-1.80 (3H, m), 1.89-2.06 (1H, m), 2.17 (3H, s), 3.27 (2H, t, J=6.4 Hz), 3.37-3.54 (2H, m), 3.69-3.88 (3H, m), 6.73-6.84 (2H, m), 6.92-7.10 (2H, m), 7.13-7.25 (3H, m).

Example 145

9-[4-(4-fluoro-2-methylphenoxy)phenyl]-3,4,6,7,8,9-hexahydropyrido[2,1-c][1,2,4]thiadiazine 2,2-dioxide A racemate (140 mg) of 9-[4-(4-fluoro-2-methylphenoxy)phenyl]-3,4,6,7,8,9-hexahydropyrido[2,1-c][1,2,4]thiadiazine 2,2-dioxide was separated by SFC (column: CHIRALPAK AYH (OC006), 20 mmID×250 mmL, manufactured by DAICEL CHEMICAL INDUSTRIES, LTD., mobile phase:

carbon dioxide/acetonitrile/ethanol=740/130/130) to give the title compound (42 mg) with a shorter retention time as a white solid.

$^1$H NMR (300 MHz, DMSO-d$_6$) δ 1.65-1.81 (3H, m), 1.90-2.05 (1H, m), 2.17 (3H, s), 3.24-3.28 (2H, m), 3.39-3.55 (2H, m), 3.67-3.88 (3H, m), 6.80 (2H, d, J=8.7 Hz), 6.91-7.09 (2H, m), 7.10-7.26 (3H, m).

Example 146

9-[4-(4-fluoro-2-methylphenoxy)phenyl]-3,4,6,7,8,9-hexahydropyrido[2,1-c][1,2,4]thiadiazine 2,2-dioxide A racemate (140 mg) of 9-[4-(4-fluoro-2-methylphenoxy)phenyl]-3,4,6,7,8,9-hexahydropyrido[2,1-c][1,2,4]thiadiazine 2,2-dioxide was separated by SFC (column: CHIRALPAK AYH (OC006), 20 mmID×250 mmL, manufactured by DAICEL CHEMICAL INDUSTRIES, LTD., mobile phase: carbon dioxide/acetonitrile/ethanol=740/130/130) to give the title compound (32 mg) with a longer retention time as a white solid.

$^1$H NMR (300 MHz, DMSO-d$_6$) δ 1.64-1.82 (3H, m), 1.89-2.07 (1H, m), 2.17 (3H, s), 3.23-3.28 (2H, m), 3.41-3.56 (2H, m), 3.67-3.90 (3H, m), 6.76-6.87 (2H, m), 6.93-7.10 (2H, m), 7.12-7.26 (3H, m).

Example 147

9-[4-(4-chlorophenoxy)phenyl]-3,4-dihydropyrido[2,1-c][1,2,4]thiadiazine 2,2-dioxide A mixture of 4-chlorophenylboronic acid (407 mg), 4-(2,2-dioxido-3,4-dihydropyrido[2,1-c][1,2,4]thiadiazin-9-yl)phenol (240 mg), diacetoxycopper (316 mg), triethylamine (0.604 mL), and powdered 4A MS (1.5 g) in DMF (10 mL) was stirred at room temperature overnight. The mixture was added with NH silica gel, concentrated in vacuo, and purified by column chromatography (NH silica gel, eluted with MeOH in EtOAc) to give the title compound (132 mg) as a white solid.

$^1$H NMR (300 MHz, DMSO-d$_6$) δ 3.43-3.50 (2H, m), 4.62-4.69 (2H, m), 6.71 (1H, t, J=7.0 Hz), 7.03-7.13 (4H, m), 7.43-7.49 (2H, m), 7.53-7.59 (2H, m), 7.63 (1H, dd, J=7.2, 1.5 Hz), 7.78 (1H, dd, J=6.8, 1.9 Hz).

mp 232-234° C.

Anal. Calcd for C$_{19}$H$_{15}$N$_2$O$_3$SCl: C, 58.99; H, 3.91; N, 7.24. Found: C, 58.83; H, 4.02; N, 7.11.

Example 148

9-[4-(4-chlorophenoxy)phenyl]-3,4,6,7,8,9-hexahydropyrido[2,1-c][1,2,4]thiadiazine 2,2-dioxide A) 4-(2-aminopyridin-3-yl)phenol A mixture of sodium carbonate decahydrate (86.0 g), tetrakis(triphenylphosphine)palladium(0) (7.76 g), (4-((tert-butyldimethylsilyl)oxy)phenyl)boronic acid (40 g) and 3-bromopyridin-2-amine (26.9 g) in DME (500 mL) and water (50 mL) was stirred at 90° C. for 24 hr. After cooling to room temperature, the aqueous layer was removed. The organic layer was filtered with NH-silica gel cartridge, and washed with EtOAc. The filtrate was concentrated in vacuo. The residue was recrystallized from EtOAc-IPE to give the title compound (25.0 g) as a pale yellow solid.

MS (ESI+). found: 187.1.

B) 3-(4-((tert-butyl(dimethyl)silyl)oxy)phenyl)pyridin-2-amine

A mixture of 4-(2-aminopyridin-3-yl)phenol (19.8 g), tert-butyldimethylchlorosilane (21.8 mL) and 1H-imidazol (8.69 g) in DMF (200 mL) was stirred at room temperature for 20 hr. To the mixture was added water, and the resulting precipitate was collected by filtration, and then washed with water to give the title compound (30.5 g) as a white solid.

MS (ESI+). found: 301.1.

C) 9-(4-((tert-butyl(dimethyl)silyl)oxy)phenyl)-3,4-dihydropyrido[2,1-c][1,2,4]thiadiazine 2,2-dioxide To a suspension of NaH (60%, 42.0 g) in THF (dry) (350 mL) was added 2-chloroethanesulfonyl chloride (44.5 mL) at 0° C. and the mixture was stirred for 10 min at the same temperature. A solution of 3-(4-((tert-butyl(dimethyl)silyl)oxy)phenyl)pyridin-2-amine (78.8 g) in THF (dry) (350 mL) was added at 0° C. and the mixture was stirred at room temperature under N$_2$ overnight. The mixture was quenched with water at 0° C. carefully. Additional water was added to form precipitates which were washed with water and EtOAc and collected to give the title compound (65.5 g) as an off-white solid.

MS (ESI+). found: 391.2.

D) 9-(4-((tert-butyl(dimethyl)silyl)oxy)phenyl)-3,4,6,7,8,9-hexahydropyrido[2,1-c][1,2,4]thiadiazine 2,2-dioxide Platinum(IV) oxide (2.0 g) was added to a solution of 9-(4-((tert-butyl(dimethyl)silyl)oxy)phenyl)-3,4-dihydropyrido[2,1-c][1,2,4]thiadiazine 2,2-dioxide (20.0 g) in THF (dry) (500 mL) and MeOH (300 mL) and the mixture was stirred at room temperature under H$_2$ for 4 hr. The mixture was passed through NH silica gel cartridge with Celite (eluted with THF). The filtrate was concentrated in vacuo. The residual solid was recrystallized from THF (100 mL)-IPE (300 mL) to give the title compound (17.3 g).

MS (ESI+). found: 395.2.

E) 4-(2,2-dioxido-3,4,6,7,8,9-hexahydropyrido[2,1-c][1,2,4]thiadiazin-9-yl)phenol A mixture of 9-(4-((tert-butyldimethylsilyl)oxy)phenyl)-3,4,6,7,8,9-hexahydropyrido[2,1-c][1,2,4]thiadiazine 2,2-dioxide (6.97 g) and 6 M HCl aq. (10.0 mL) in AcOH (100 mL) was stirred at 60° C. for 2 hr. After cooling to room temperature, the solvent was removed in vacuo. The residual solid was recrystallized from MeOH-IPE to give the title compound (5.01 g) as a white solid.

MS (ESI+). found: 281.1.

F) 9-[4-(4-chlorophenoxy)phenyl]-3,4,6,7,8,9-hexahydropyrido[2,1-c][1,2,4]thiadiazine 2,2-dioxide A mixture of 4-chlorophenylboronic acid (167 mg), 4-(2,2-dioxido-3,4,6,7,8,9-hexahydropyrido[2,1-c][1,2,4]thiadiazin-9-yl)phenol (100 mg), pyridine (0.087 mL), diacetoxycopper (130 mg), and cesium carbonate (116 mg) in DMSO (3.0 mL) was stirred at room temperature for 24 hr. The mixture was diluted with water, and extracted with EtOAc (40 mL). The organic layer was washed with 0.1N NaOH aq. (2×40 mL) and then brine, dried over anhydrous magnesium sulfate, and concentrated in vacuo. The residue was purified by column chromatography (silica gel, eluted with MeOH in EtOAc) to give the title compound (23.0 mg) as a white solid.

$^1$H NMR (300 MHz, DMSO-$d_6$) δ 1.70-1.82 (3H, m), 1.96-2.06 (1H, m), 3.23-3.29 (2H, m), 3.44-3.52 (2H, m), 3.75-3.86 (3H, m), 6.95-7.07 (4H, m), 7.23 (2H, d, J=8.3 Hz), 7.39-7.47 (2H, m).

mp 215-216° C.

Anal. Calcd for $C_{19}H_{19}N_2O_3SCl$: C, 58.38; H, 4.90; N, 7.17. Found: C, 58.38; H, 4.97; N, 6.89.

Example 149

(9S)-9-[4-(4-chlorophenoxy)phenyl]-3,4,6,7,8,9-hexahydropyrido[2,1-c][1,2,4]thiadiazine 2,2-dioxide Diacetoxycopper (1037 mg) was added to a mixture of triethylamine (1.983 mL), 4-chlorophenylboronic acid (1339 mg), 4-[(9S)-2,2-dioxido-3,4,6,7,8,9-hexahydropyrido[2,1-c][1,2,4]thiadiazin-9-yl]phenol (800 mg) and in DMF (dry) (30 mL). The mixture was stirred at room temperature under a dry atmosphere with anhydrous calcium chloride tube for 15 hr. Then 4-chlorophenylboronic acid (1339 mg) and diacetoxycopper (1037 mg) were added and the mixture was stirred at room temperature under a dry atmosphere with anhydrous calcium chloride tube for 2 days. The insoluble material was removed by filtration, and the filtrate was diluted with water, and extracted with EtOAc. The organic layer was washed with 0.1N NaOH aq., dried over anhydrous magnesium sulfate. Silica-gel was added and the volatiles were removed in vacuo. The mixture supported on silica-gel was purified by column chromatography (NH silica gel, eluted with MeOH in EtOAc) then crystallized from THF/IPE to give the title compound (177 mg) as an off-white solid.

$^1$H NMR (300 MHz, DMSO-$d_6$) δ 1.64-1.83 (3H, m), 1.93-2.09 (1H, m), 3.25-3.30 (2H, m), 3.40-3.55 (2H, m), 3.71-3.89 (3H, m), 6.93-7.08 (4H, m), 7.23 (2H, d, J=8.7 Hz), 7.37-7.48 (2H, m). X-ray powder diffraction pattern with specific peaks at d value (or d-spacing)=15.60, 7.80, 5.21, 5.06, 4.64, 3.97, 3.90 and 3.75 Å.

Example 150

9-[4-(4-chlorophenoxy)phenyl]-3,4,6,7,8,9-hexahydropyrido[2,1-c][1,2,4]thiadiazine 2,2-dioxide A racemate (214 mg) of 9-[4-(4-chlorophenoxy)phenyl]-3,4,6,7,8,9-hexahydropyrido[2,1-c][1,2,4]thiadiazine 2,2-dioxide was separated by HPLC (column: CHIRALPAK IC (ME001), 50 mmID×500 mmL, manufactured by DAICEL CHEMICAL INDUSTRIES, LTD., mobile phase:acetonitrile 100%) to give the title compound (101 mg) with a longer retention time. Crystallization from THF and diisopropyl ether gave a white solid.

$^1$H NMR (300 MHz, DMSO-$d_6$) δ 1.62-1.85 (3H, m), 1.89-2.10 (1H, m), 3.25-3.28 (2H, m), 3.41-3.56 (2H, m), 3.69-3.89 (3H, m), 6.92-7.09 (4H, m), 7.23 (2H, d, J=8.3 Hz), 7.38-7.48 (2H, m).

mp 183-185° C.

Anal. Calcd for $C_{19}H_{19}N_2O_3SCl$: C, 58.38; H, 4.90; N, 7.17. Found: C, 58.42; H, 5.01; N, 6.93.

Example 151

9-[4-(3,4-dichlorophenoxy)phenyl]-3,4,6,7,8,9-hexahydropyrido[2,1-c][1,2,4]thiadiazine 2,2-dioxide A mixture of 2,4,6-tris(3,4-dichlorophenyl)-1,3,5,2,4,6-trioxatriborinane (277 mg), 4-(2,2-dioxido-3,4,6,7,8,9-hexahydropyrido[2,1-c][1,2,4]thiadiazin-9-yl)phenol (100 mg), pyridine (0.087 mL), diacetoxycopper (130 mg), and cesium carbonate (116 mg) in MeCN (10 mL) was stirred at room temperature for 16 hr. The mixture was filtered by Celite. The filtrate was diluted with water, and extracted with EtOAc (40 mL). The organic layer was washed with 0.1N NaOH aq. (2×40 mL) and then brine, dried over anhydrous magnesium sulfate, and concentrated in vacuo. The residue was purified by column chromatography (NH silica gel, eluted with MeOH in EtOAc) and then recrystallized from EtOAc-IPE to give the title compound (37.0 mg) as a white solid.

$^1$H NMR (300 MHz, DMSO-$d_6$) δ 1.68-1.81 (3H, m), 1.95-2.08 (1H, m), 3.24-3.29 (2H, m), 3.48 (2H, dq, J=12.8, 6.4 Hz), 3.75-3.90 (3H, m), 6.97-7.08 (3H, m), 7.26 (2H, d, J=8.7 Hz), 7.31 (1H, d, J=3.0 Hz), 7.63 (1H, d, J=8.7 Hz).

mp 195-197° C.

Anal. Calcd for $C_{19}H_{18}N_2O_3SCl_2 \cdot 0.25H_2O$: C, 53.09; H, 4.34; N, 6.52. Found: C, 53.18; H, 4.29; N, 6.34.

Example 152

9-[4-(3,4-dichlorophenoxy)phenyl]-3,4,6,7,8,9-hexahydropyrido[2,1-c][1,2,4]thiadiazine 2,2-dioxide A racemate (312 mg) of 9-[4-(3,4-dichlorophenoxy)phenyl]-3,4,6,7,8,9-hexahydropyrido[2,1-c][1,2,4]thiadiazine 2,2-dioxide was separated by HPLC (column: CHIRALPAK IC (ME001), 50 mmID×500 mmL, manufactured by DAICEL CHEMICAL INDUSTRIES, LTD., mobile phase:acetonitrile 100%) to give the title compound (145 mg) with a shorter retention time. Crystallization from THF and diisopropyl ether gave a white solid.

$^1$H NMR (300 MHz, DMSO-$d_6$) δ 1.73-1.79 (3H, m), 1.93-2.08 (1H, m), 3.25-3.29 (2H, m), 3.40-3.55 (2H, m), 3.72-3.91 (3H, m), 6.95-7.10 (3H, m), 7.21-7.36 (3H, m), 7.63 (1H, d, J=9.1 Hz).

Example 153

9-[4-(3,4-dichlorophenoxy)phenyl]-3,4,6,7,8,9-hexahydropyrido[2,1-c][1,2,4]thiadiazine 2,2-dioxide A racemate (312 mg) of 9-[4-(3,4-dichlorophenoxy)phenyl]-3,4,6,7,8,9-hexahydropyrido[2,1-c][1,2,4]thiadiazine 2,2-dioxide was separated by HPLC (column: CHIRALPAK IC (ME001), 50 mmID×500 mmL, manufactured by DAICEL CHEMICAL INDUSTRIES, LTD., mobile phase:acetonitrile 100%) to give the title compound (143 mg) with a longer retention time. Crystallization from THF and diisopropyl ether gave a white solid.

$^1$H NMR (300 MHz, DMSO-$d_6$) δ 1.73-1.78 (3H, m), 1.92-2.08 (1H, m), 3.25-3.29 (2H, m), 3.40-3.54 (2H, m), 3.74-3.88 (3H, m), 6.94-7.08 (3H, m), 7.21-7.34 (3H, m), 7.63 (1H, d, J=9.1 Hz).

Example 154

9-[4-(4-chloro-3-methoxyphenoxy)phenyl]-3,4-dihydropyrido[2,1-c][1,2,4]thiadiazine 2,2-dioxide A) 3-(4-(4-chloro-3-methoxyphenoxy)phenyl)pyridin-2-amine Copper(I) iodide (102 mg) was added to a mixture of picolinic acid (66.1 mg), 4-(2-aminopyridin-3-yl)phenol (500 mg), tripotassium phosphate (1710 mg), 4-bromo-1-chloro-2-methoxybenzene (714 mg) and DMSO (8 mL). The mixture was stirred at 130° C. under nitrogen for 4 hr. Activated carbon was added and the insoluble solid was removed by filtration through NH-silica gel/Celite pad (eluted with EtOAc). Silica-gel was added to the filtrate and the volatiles were removed in vacuo. The mixture supported on silica-gel was purified by column chromatography (NH-silica gel, eluted with EtOAc in hexane) and concentrated. The residue was purified by column chromatography (silica gel, eluted with EtOAc in hexane) to give the title compound (359 mg) as pale yellow oil.
MS (ESI+). found: 327.1.

B) 9-[4-(4-chloro-3-methoxyphenoxy)phenyl]-3,4-dihydropyrido[2,1-c][1,2,4]thiadiazine 2,2-dioxide To a suspension of NaH (60%, 220 mg) in THF (dry) (20 mL) was added 2-chloroethanesulfonyl chloride (0.347 mL) at 0° C. and the mixture was stirred for 10 min at the same temperature. A solution of 3-(4-(4-chloro-3-methoxyphenoxy)phenyl)pyridin-2-amine (359 mg) in THF (dry) (10 mL) was added at 0° C. and the mixture was stirred at room temperature under a dry atmosphere with anhydrous calcium chloride tube overnight. The mixture was quenched with water/THF then water at 0° C. and extracted with EtOAc/THF. Silica-gel was added to the organic phase and the volatiles were removed in vacuo. The mixture supported on silica-gel was purified by column chromatography (silica gel, eluted with MeOH in EtOAc) and concentrated in vacuo and washed with IPE to give the title compound (306 mg) as a white solid. A part of product was recrystallized from MeCN/IPE.
$^1$H NMR (300 MHz, DMSO-$d_6$) δ 3.42-3.49 (2H, m), 3.85 (3H, s), 4.62-4.68 (2H, m), 6.59 (1H, dd, J=8.7, 2.7 Hz), 6.71 (1H, t, J=7.0 Hz), 6.97 (1H, q, J=3.2 Hz), 7.06 (2H, d, J=8.7 Hz), 7.42 (1H, d, J=8.7 Hz), 7.52-7.58 (2H, m), 7.63 (1H, dd, J=7.2, 1.5 Hz), 7.77 (1H, d, J=5.3 Hz).

Example 155

9-[4-(4-chloro-3-methoxyphenoxy)phenyl]-3,4,6,7,8,9-hexahydropyrido[2,1-c][1,2,4]thiadiazine 2,2-dioxide Platinum(IV) oxide (30 mg) was added to a solution of 9-[4-(4-chloro-3-methoxyphenoxy)phenyl]-3,4-dihydropyrido[2,1-c][1,2,4]thiadiazine 2,2-dioxide (262.3 mg) in THF (dry) (60 mL) and MeOH (30 mL). The mixture was stirred at room temperature under hydrogen for 3 hr. Platinum(IV) oxide (30 mg) was added and the mixture was stirred at room temperature under hydrogen for 4 hr. The insoluble solid was removed by filtration through NH-silica gel/Celite pad (eluted with EtOAc) and the filtrate was concentrated in vacuo. MeCN (13 mL) was added and this mixture was purified by preparative HPLC (C18, eluted with water in acetonitrile containing 0.1% TFA). The desired fractions were neutralized with sat.NaHCO$_3$ aq. and the mixture was extracted with EtOAc. The combined organic layer was dried over anhydrous magnesium sulfate and concentrated in vacuo. The residue was crystallized from THF/IPE to give the title compound (80.1 mg) as colorless crystals.
$^1$H NMR (300 MHz, DMSO-$d_6$) δ 1.63-1.85 (3H, m), 1.93-2.08 (1H, m), 3.22-3.28 (2H, m), 3.39-3.56 (2H, m), 3.74-3.89 (6H, m), 6.51 (1H, dd, J=8.7, 2.7 Hz), 6.91 (1H, d, J=2.7 Hz), 6.98 (2H, d, J=8.7 Hz), 7.23 (2H, d, J=8.7 Hz), 7.39 (1H, d, J=8.7 Hz).

Example 156

9-{4-[3-(1,1-difluoroethyl)phenoxy]phenyl}-3,4-dihydropyrido[2,1-c][1,2,4]thiadiazine 2,2-dioxide A) 3-(4-(3-(1,1-difluoroethyl)phenoxy)phenyl)pyridin-2-amine Copper(I) iodide (102 mg) was added to a mixture of picolinic acid (66.1 mg), 4-(2-aminopyridin-3-yl)phenol (500 mg), tripotassium phosphate (1710 mg), 1-bromo-3-(1,1-difluoroethyl)benzene (712 mg) and DMSO (8 mL). The mixture was stirred at 130° C. under nitrogen for 10 hr. Activated carbon was added and the insoluble solid was removed by filtration through NH-silica gel/Celite pad (eluted with EtOAc). Silica-gel was added to the filtrate and the volatiles were removed in vacuo. The mixture supported on silica-gel was purified by column chromatography (NH-silica gel, eluted with EtOAc in hexane) and concentrated. The residue was purified by column chromatography (silica gel, eluted with EtOAc in hexane) to give the title compound (499 mg) as pale yellow oil.
MS (ESI+). found: 327.1.

B) 9-{4-[3-(1,1-difluoroethyl)phenoxy]phenyl}-3,4-dihydropyrido[2,1-c][1,2,4]thiadiazine 2,2-dioxide To a suspension of NaH (60%, 306 mg) in THF (dry) (25 mL) was added 2-chloroethanesulfonyl chloride (0.483 mL) at 0° C. and the mixture was stirred for 10 min at the same temperature. A solution of 3-(4-(3-(1,1-difluoroethyl)phenoxy)phenyl)pyridin-2-amine (499 mg) in THF (dry) (15 mL) was added at 0° C. and the mixture was stirred at room temperature under a dry atmosphere with anhydrous calcium chloride tube overnight. The mixture was quenched with water/THF then water at 0° C. and extracted with EtOAc/THF. Silica-gel was added to the organic phase and the volatiles were removed in vacuo. The mixture supported on silica-gel was purified by column chromatography (silica gel, eluted with MeOH in EtOAc) and concentrated in vacuo and washed with IPE to give the title compound (254 mg) as a white solid. A part of product was recrystallized from MeCN/IPE.
$^1$H NMR (300 MHz, DMSO-$d_6$) δ 1.97 (3H, t, J=18.9 Hz), 3.41-3.50 (2H, m), 4.61-4.70 (2H, m), 6.71 (1H, t, J=7.0 Hz), 7.07 (2H, d, J=8.7 Hz), 7.14-7.21 (1H, m), 7.23-7.28 (1H, m), 7.36 (1H, d, J=7.6 Hz), 7.49-7.54 (1H, m), 7.57 (2H, d, J=8.7 Hz), 7.64 (1H, dd, J=7.2, 1.9 Hz), 7.77 (1H, dd, J=6.6, 1.7 Hz).

Example 157

9-{4-[3-(1,1-difluoroethyl)phenoxy]phenyl}-3,4,6,7,8,9-hexahydropyrido[2,1-c][1,2,4]thiadiazine 2,2-dioxide Platinum(IV) oxide (30 mg) was added to a solution of 9-{4-[3-(1,1-difluoroethyl)phenoxy]phenyl}-3,4-dihydropyrido[2,1-c][1,2,4]thiadiazine 2,2-dioxide (230 mg) in THF (dry) (20 mL) and MeOH (20 mL). The mixture was stirred at room temperature under hydrogen overnight. Activated carbon was added and the insoluble solid was removed by filtration through NH-silica gel/Celite pad (eluted with EtOAc) and the filtrate was concentrated in vacuo. The residue was purified by column chromatography (silica gel, eluted with MeOH in EtOAc) and concentrated. The residue was crystallized from EtOAc/hexane to give the title compound (79.4 mg) as colorless crystals.

$^1$H NMR (300 MHz, DMSO-$d_6$) δ 1.67-1.83 (3H, m), 1.87-2.08 (4H, m), 3.23-3.29 (2H, m), 3.41-3.55 (2H, m), 3.72-3.89 (3H, m), 6.93-7.02 (2H, m), 7.07-7.14 (1H, m), 7.18-7.27 (3H, m), 7.33 (1H, d, J=8.0 Hz), 7.45-7.55 (1H, m).

mp 117-118° C.

Anal. Calcd for $C_{21}H_{22}N_2O_3SF_2$: C, 59.99; H, 5.27; N, 6.66. Found: C, 60.00; H, 5.30; N, 6.66.

Example 158

9-{4-[3-(1,1-difluoroethyl)phenoxy]phenyl}-3,4,6,7,8,9-hexahydropyrido[2,1-c][1,2,4]thiadiazine 2,2-dioxide A racemate (49 mg) of 9-{4-[3-(1,1-difluoroethyl)phenoxy]phenyl}-3,4,6,7,8,9-hexahydropyrido[2,1-c][1,2,4]thiadiazine 2,2-dioxide was separated by SFC (column: CHIRALPAK ADH (KG010), 20 mmID×250 mmL, manufactured by DAICEL CHEMICAL INDUSTRIES, LTD., mobile phase:carbon dioxide/methanol=740/260) to give the title compound (21 mg) with a shorter retention time as a white solid.

$^1$H NMR (300 MHz, DMSO-$d_6$) δ 1.66-1.82 (3H, m), 1.85-2.07 (4H, m), 3.22-3.29 (2H, m), 3.38-3.57 (2H, m), 3.72-3.91 (3H, m), 6.99 (2H, d, J=8.7 Hz), 7.11 (1H, d, J=8.3 Hz), 7.18-7.27 (3H, m), 7.33 (1H, d, J=7.5 Hz), 7.45-7.55 (1H, m).

Example 159

9-{4-[3-(1,1-difluoroethyl)phenoxy]phenyl}-3,4,6,7,8,9-hexahydropyrido[2,1-c][1,2,4]thiadiazine 2,2-dioxide A racemate (49 mg) of 9-{4-[3-(1,1-difluoroethyl)phenoxy]phenyl}-3,4,6,7,8,9-hexahydropyrido[2,1-c][1,2,4]thiadiazine 2,2-dioxide was separated by SFC (column: CHIRALPAK ADH (KG010), 20 mmID×250 mmL, manufactured by DAICEL CHEMICAL INDUSTRIES, LTD., mobile phase:carbon dioxide/methanol=740/260) to give the title compound (20 mg) with a longer retention time as a white solid.

$^1$H NMR (300 MHz, DMSO-$d_6$) δ 1.67-1.82 (3H, m), 1.85-2.09 (4H, m), 3.24-3.30 (2H, m), 3.40-3.57 (2H, m), 3.72-3.90 (3H, m), 6.99 (2H, d, J=8.7 Hz), 7.11 (1H, d, J=8.3 Hz), 7.16-7.28 (3H, m), 7.33 (1H, d, J=7.5 Hz), 7.46-7.55 (1H, m).

Example 160

(9S)-9-{4-[2-chloro-5-(trifluoromethyl)phenoxy]phenyl}-3,4,6,7,8,9-hexahydropyrido[2,1-c][1,2,4]thiadiazine 2,2-dioxide Diacetoxycopper (907 mg) was added to a mixture of pyridine (0.606 mL), 2-chloro-5-(trifluoromethyl)phenylboronic acid (459 mg), 4-[(9S)-2,2-dioxido-3,4,6,7,8,9-hexahydropyrido[2,1-c][1,2,4]thiadiazin-9-yl]phenol (700 mg) and cesium carbonate (814 mg) in MeCN (25 mL). The mixture was stirred at room temperature under a dry atmosphere with anhydrous calcium chloride tube for 2 days. The insoluble material was removed by filtration, and the filtrate was diluted with water, and extracted with EtOAc. The organic layer was washed with brine and dried over anhydrous magnesium sulfate. Silica-gel was added and the volatiles were removed in vacuo. The mixture supported on silica-gel was purified by column chromatography (NH silica gel, eluted with MeOH in EtOAc) and concentrated in vacuo to give the title compound (5.9 mg) as pale yellow gum.

$^1$H NMR (300 MHz, CDCl$_3$) δ 1.79-2.03 (3H, m), 2.05-2.19 (1H, m), 3.24-3.33 (2H, m), 3.40-3.53 (2H, m), 3.82-3.99 (3H, m), 6.88-6.97 (2H, m), 7.13-7.19 (2H, m), 7.24 (1H, d, J=1.5 Hz), 7.34 (1H, dd, J=8.3, 1.5 Hz), 7.58 (1H, d, J=8.3 Hz).

Example 161

9-[4-(4-ethylphenoxy)phenyl]-3,4,6,7,8,9-hexahydropyrido[2,1-c][1,2,4]thiadiazine 2,2-dioxide A) 3-(4-(4-ethylphenoxy)phenyl)pyridin-2-amine Copper(I) iodide (102 mg) was added to a mixture of picolinic acid (66.1 mg), 4-(2-aminopyridin-3-yl)phenol (500 mg), tripotassium phosphate (1710 mg), 1-bromo-4-ethylbenzene (596 mg) and DMSO (8 mL). The mixture was stirred at 130° C. under nitrogen for 4 hr. Activated carbon was added and the insoluble solid was removed by filtration through silica gel/Celite pad (eluted with EtOAc). Silica-gel was added to the filtrate and the volatiles were removed in vacuo. The mixture supported on silica-gel was purified by column chromatography (NH-silica gel, eluted with EtOAc in hexane) and concentrated to give the title compound (117 mg) as an off-white solid.

MS (ESI+). found: 291.1.

B) 9-[4-(4-ethylphenoxy)phenyl]-3,4,6,7,8,9-hexahydropyrido[2,1-c][1,2,4]thiadiazine 2,2-dioxide To a suspension of NaH (60%, 81 mg) in THF (dry) (10 mL) was added 2-chloroethanesulfonyl chloride (0.085 mL) at 0° C. and the mixture was stirred for 10 min at the same temperature. A solution of 3-(4-(4-ethylphenoxy)phenyl)pyridin-2-amine (117 mg) in THF (dry) (10 mL) was added at 0° C. and the mixture was stirred at room temperature under nitrogen for 4 hr. The mixture was quenched with water at 0° C. Water, EtOAc and THF were added and the mixture was extracted. Silica-gel was added to the organic phase and the volatiles were removed in vacuo. The mixture supported on silica-gel was purified by column chromatography (silica gel, eluted with MeOH in EtOAc) and concentrated in vacuo to give 9-[4-(4-ethylphenoxy)phenyl]-3,4-dihydropyrido[2,1-c][1,2,4]thiadiazine 2,2-dioxide as a white solid. Platinum(IV) oxide (20 mg) was added to a solution of 9-[4-(4-ethylphenoxy)phenyl]-3,4-dihydropyrido[2,1-c][1,2,4]thiadiazine 2,2-dioxide (153 mg) in THF (dry) (20 mL) and MeOH (20 mL). The mixture was stirred at room temperature under hydrogen for 3 hr. Activated carbon was added and the insoluble solid was removed by filtration through silica gel/Celite pad (eluted with EtOAc). Platinum(IV) oxide (20 mg) was added and the mixture was stirred at room temperature under hydrogen overnight. Activated carbon was added and the insoluble solid was removed by filtration through silica gel/Celite pad (eluted with EtOAc) and the filtrate was concentrated in vacuo. The residue was crystallized from THF/IPE to give the title compound (46.7 mg) as colorless crystals.

¹H NMR (300 MHz, DMSO-d₆) δ 1.18 (3H, t, J=7.6 Hz), 1.64-1.84 (3H, m), 1.90-2.09 (1H, m), 2.59 (2H, q, J=7.6 Hz), 3.28 (2H, t, J=6.2 Hz), 3.40-3.55 (2H, m), 3.70-3.89 (3H, m), 6.86-6.99 (4H, m), 7.13-7.28 (4H, m).

Example 162

9-{4-[difluoro(phenyl)methyl]phenyl}-3,4-dihydropyrido[2,1-c][1,2,4]thiadiazine 2,2-dioxide A) 1-bromo-4-(difluoro(phenyl)methyl)benzene Bis(2-methoxyethyl)aminosulfur trifluoride (2.02 mL) was added dropwise under nitrogen to (4-bromophenyl)(phenyl)methanone (1 g) at room temperature. The mixture was stirred at 75° C. under nitrogen for 11 hr and at room temperature for 2 days. The mixture was quenched with sat. NaHCO₃ aq. at room temperature and extracted with EtOAc. The organic layer was separated, washed with water and brine, dried over anhydrous magnesium sulfate and concentrated in vacuo. The residue was purified by column chromatography (silica gel, eluted with EtOAc in hexane) to give the title compound (436 mg) as a colorless amorphous solid.
¹H NMR (300 MHz, DMSO-d₆) δ 7.37-7.58 (7H, m), 7.71 (2H, d, J=8.3 Hz).

B) 3-(4-(difluoro(phenyl)methyl)phenyl)pyridin-2-amine

Pd(dppf)Cl₂ (19.4 mg) was added to a mixture of 1-bromo-4-(difluoro(phenyl)methyl)benzene (376 mg), potassium acetate (391 mg) and 4,4,4',4',5,5,5',5'-octamethyl-2,2'-bi(1,3,2-dioxaborolane) (506 mg) in DME (10 mL) and DMSO (0.5 mL). The mixture was stirred at 80° C. under nitrogen overnight. Activated-carbon powder was added and the mixture was stirred for 5 min. The insoluble material was removed by filtration. The filtrate was concentrated in vacuo to give a brown oil of 2-(4-(difluoro(phenyl)methyl)phenyl)-4,4,5,5-tetramethyl-1,3,2-dioxaborolane. Tetrakis(triphenylphosphine)palladium(0) (38.4 mg) was added to a suspension of 3-bromopyridin-2-amine (192 mg), the prepared 2-(4-(difluoro(phenyl)methyl)phenyl)-4,4,5,5-tetramethyl-1,3,2-dioxaborolane and sodium carbonate decahydrate (634 mg) in DME (10 mL) and water (2 mL) and the mixture was stirred at 80° C. under nitrogen for 3 hr. Silica-gel was added and the volatiles were removed in vacuo. The mixture supported on silica-gel was purified by column chromatography (NH silica gel, eluted with EtOAc in hexane) to give the title compound (291 mg) as a colorless oil.
MS (ESI+). found: 297.1.

C) 9-{4-[difluoro(phenyl)methyl]phenyl}-3,4-dihydropyrido[2,1-c][1,2,4]thiadiazine 2,2-dioxide To a suspension of NaH (60%, 196 mg) in THF (dry) (20 mL) was added 2-chloroethanesulfonyl chloride (0.310 mL) at 0° C. and the mixture was stirred for 10 min at the same temperature. A solution of 3-(4-(difluoro(phenyl)methyl)phenyl)pyridin-2-amine (291 mg) in THF (dry) (10 mL) was added at 0° C. and the mixture was stirred at room temperature under a dry atmosphere with anhydrous calcium chloride tube for 2 hr. The mixture was quenched with water/THF then water at 0° C. and extracted with EtOAc/THF. Silica-gel was added to the organic phase and the volatiles were removed in vacuo. The mixture supported on silica-gel was purified by column chromatography (silica gel, eluted with MeOH in EtOAc) and concentrated in vacuo. The residue was washed with IPE to give the title compound (49 mg) as a white solid.
¹H NMR (300 MHz, DMSO-d₆) δ 3.41-3.51 (2H, m), 4.60-4.70 (2H, m), 6.72 (1H, t, J=6.8 Hz), 7.45-7.70 (10H, m), 7.80 (1H, dd, J=6.8, 1.5 Hz).

Example 163

9-{4-[difluoro(phenyl)methyl]phenyl}-3,4,6,7,8,9-hexahydropyrido[2,1-c][1,2,4]thiadiazine 2,2-dioxide Platinum(IV) oxide (14 mg) was added to a solution of 9-{4-[difluoro(phenyl)methyl]phenyl}-3,4-dihydropyrido[2,1-c][1,2,4]thiadiazine 2,2-dioxide (49 mg) in THF (dry) (10 mL) and MeOH (10 mL). The mixture was stirred at room temperature under hydrogen for 4 hr. Activated carbon was added and the insoluble solid was removed by filtration through NH-silica gel/Celite pad (eluted with EtOAc) and the filtrate was concentrated in vacuo. The residue was crystallized from THF/IPE to give the title compound (18.8 mg) as colorless crystals.
¹H NMR (300 MHz, DMSO-d₆) δ 1.64-1.82 (3H, m), 1.91-2.10 (1H, m), 3.24-3.28 (2H, m), 3.42-3.53 (2H, m), 3.74-3.89 (3H, m), 7.28-7.37 (2H, m), 7.42-7.58 (7H, m).

Example 164

9-[4-(4-fluoro-3-methoxyphenoxy)phenyl]-7-methyl-3,4,6,7,8,9-hexahydropyrido[2,1-c][1,2,4]thiadiazine 2,2-dioxide A) 4-(2-amino-5-methylpyridin-3-yl)phenol Tetrakis(triphenylphosphine)palladium(0) (0.716 g) was added to a suspension of 3-bromo-5-methylpyridin-2-amine (3.86 g), 4-(4,4,5,5-tetramethyl-1,3,2-dioxaborolan-2-yl)phenol (5 g) and sodium carbonate (2.19 g) in DME (150 mL) and water (30 mL) and the mixture was stirred at 80° C. under nitrogen for 5 hr. Silica-gel was added and the volatiles were removed in vacuo. The mixture supported on silica-gel was purified by column chromatography (silica gel, eluted with EtOAc in hexane) to give the title compound (1.99 g) as a pale yellow solid.
MS (ESI+). found: 201.1.

B) 3-(4-(4-fluoro-3-methoxyphenoxy)phenyl)-5-methylpyridin-2-amine

Copper(I) iodide (95 mg) was added to a mixture of picolinic acid (61.5 mg), 4-(2-amino-5-methylpyridin-3-yl)phenol (500 mg), tripotassium phosphate (1590 mg), 4-bromo-1-fluoro-2-methoxybenzene (614 mg) and DMSO (8 mL). The mixture was stirred at 130° C. under nitrogen for 10 hr. The insoluble solid was removed by filtration through silica gel/Celite pad (eluted with EtOAc). Silica-gel was added to the filtrate and the volatiles were removed in vacuo. The mixture supported on silica-gel was purified by column chromatography (NH-silica gel, eluted with EtOAc in hexane) to give the title compound (361 mg) as pale yellow oil.
MS (ESI+). found: 325.1.

C) 9-[4-(4-fluoro-3-methoxyphenoxy)phenyl]-7-methyl-3,4-dihydropyrido[2,1-c][1,2,4]thiadiazine 2,2-dioxide To a suspension of NaH (60%, 222 mg) in THF (dry) (20 mL) was added 2-chloroethanesulfonyl chloride (0.233 mL)

at 0° C. and the mixture was stirred for 10 min at the same temperature. A solution of 3-(4-(4-fluoro-3-methoxyphenoxy)phenyl)-5-methylpyridin-2-amine (360 mg) in THF (dry) (20 mL) was added at 0° C. and the mixture was stirred at room temperature under nitrogen overnight. The mixture was quenched with water at 0° C. Water, EtOAc and THF were added to the mixture and the organic phase was separated. Silica-gel was added to the organic phase and the volatiles were removed in vacuo. The mixture supported on silica-gel was purified by column chromatography (silica gel, eluted with MeOH in EtOAc) and concentrated in vacuo to give 9-[4-(4-fluoro-3-methoxyphenoxy)phenyl]-7-methyl-3,4-dihydropyrido[2,1-c][1,2,4]thiadiazine 2,2-dioxide as a white solid. This product was subjected to the next reaction without further purification. A part of the product was crystallized from EtOAc/IPE to give the title compound as a colorless solid.

MS (ESI+). found: 415.1.

D) 9-[4-(4-fluoro-3-methoxyphenoxy)phenyl]-7-methyl-3,4,6,7,8,9-hexahydropyrido[2,1-c][1,2,4]thiadiazine 2,2-dioxide Platinum(IV) oxide (30 mg) was added to a solution of 9-[4-(4-fluoro-3-methoxyphenoxy)phenyl]-7-methyl-3,4-dihydropyrido[2,1-c][1,2,4]thiadiazine 2,2-dioxide (400 mg) in THF (dry) (15 mL) and MeOH (15 mL). The mixture was stirred at room temperature under hydrogen for 3 hr. Activated carbon was added and the insoluble solid was removed by filtration through silica gel/Celite pad (eluted with EtOAc). Platinum(IV) oxide (30 mg) was added and the mixture was stirred at room temperature under hydrogen overnight. AcOH (10 mL) and platinum(IV) oxide (30 mg) were added and the mixture was stirred at room temperature under hydrogen for 1 day and at 50° C. for 1 day. Activated carbon was added and the insoluble solid was removed by filtration through silica gel/Celite pad (eluted with EtOAc) and the filtrate was concentrated in vacuo. The residue was purified by column chromatography (NH silica gel, eluted with MeOH in EtOAc) and concentrated in vacuo. The residue was crystallized from THF/IPE to give the title compound (30.3 mg) as colorless crystals.

$^1$H NMR (300 MHz, DMSO-$d_6$) δ 0.83-0.99 (3H, m), 1.49 (1H, q, J=12.3 Hz), 1.70-2.17 (2H, m), 3.04-3.25 (3H, m), 3.37-3.63 (1H, m), 3.74-3.87 (6H, m), 6.52 (1H, dt, J=9.1, 3.2 Hz), 6.87-6.98 (3H, m), 7.15-7.26 (3H, m).

Example 165

9-[4-(cyclohexyloxy)phenyl]-3,4-dihydropyrido[2,1-c][1,2,4]thiadiazine 2,2-dioxide

A) 1-bromo-4-(cyclohexyloxy)benzene

Boron trifluoride etherate (5.83 mL) was added to a mixture of 4-bromophenol (39.8 g) and cyclohexene (187 mL) in toluene (160 mL) to form bright orange-red solution. The mixture was stirred at 40° C. under nitrogen for 5 hr. The mixture was quenched with 2N NaOH aq. (40 mL) and water at room temperature and extracted with EtOAc. The organic layer was separated, washed with water and brine, dried over anhydrous sodium sulfate and concentrated in vacuo. The residue was purified by column chromatography (silica gel, eluted with hexane) to give the title compound (46.3 g) as pale yellow oil.

$^1$H NMR (300 MHz, DMSO-$d_6$) δ 1.22-1.53 (6H, m), 1.70-1.85 (2H, m), 1.95 (2H, dt, J=6.5, 3.3 Hz), 4.14-4.24 (1H, m), 6.77 (2H, d, J=9.0 Hz), 7.34 (2H, d, J=9.0 Hz).

B) 3-[4-(cyclohexyloxy)phenyl]pyridin-2-amine n-Butyllithium (1.6 M in hexane) (136 mL) was dropwised to a mixture of 1-bromo-4-(cyclohexyloxy)benzene (46.3 g) and THF (dry) (500 mL) at −78° C. and the mixture was stirred at the same temperature under nitrogen for 40 min. Triisopropyl borate (51.2 g) was dropwised to the mixture at −78° C. for 15 min and the mixture was stirred at the same temperature for 5 min. Then the mixture was warmed up to room temperature and stirred for additional 30 min. The mixture was poured into 1N NaOH aq. (250 mL) and water (750 mL) and the mixture was further stirred for 30 min. The organic layer was separated and the aqueous phase was washed with Et$_2$O (300 mL×2) and acidified by 6N HCl aq. The mixture was extracted with EtOAc, dried over anhydrous sodium sulfate and concentrated in vacuo to give 4-(cyclohexyloxy)phenylboronic acid (29.5 g) as a white powder. Tetrakis(triphenylphosphine)palladium(0) (0.656 g) was added to a suspension of 3-bromopyridin-2-amine (9.83 g), 4-(cyclohexyloxy)phenylboronic acid (15.0 g) and sodium carbonate (12.0 g) in DME (325 mL) and water (65.0 mL) and the mixture was stirred at 100° C. under nitrogen for 3 hr and at 90° C. for 12 hr. Volatiles were removed in vacuo with silica-gel. The silica-supported mixture was purified by column chromatography (silica gel, eluted with EtOAc in hexane) to give the title compound (14.1 g) as a white powder.

MS (ESI+). found: 269.1.

C) 9-[4-(cyclohexyloxy)phenyl]-3,4-dihydropyrido[2,1-c][1,2,4]thiadiazine 2,2-dioxide To a suspension of NaH (60%, 10.5 g) in THF (dry) (200 mL) was added 2-chloroethanesulfonyl chloride (11.0 mL) at 0° C. and the mixture was stirred for 10 min at the same temperature. A solution of 3-[4-(cyclohexyloxy)phenyl]pyridin-2-amine (14.1 g) in THF (dry) (150 mL) was added at 0° C. and the mixture was stirred at room temperature under nitrogen for 14 hr. The mixture was quenched with water at 0° C. carefully. Water and hexane were added to form precipitates which were washed with EtOAc and collected to give 9-[4-(cyclohexyloxy)phenyl]-3,4-dihydropyrido[2,1-c][1,2,4]thiadiazine 2,2-dioxide (17.4 g) as an off-white solid. To 9-[4-(cyclohexyloxy)phenyl]-3,4-dihydropyrido[2,1-c][1,2,4]thiadiazine 2,2-dioxide (16.0 g) was added DMSO (280 mL) under heating with oil bath (ca. 90° C.). After being stirred for 10 min., EtOH (520 mL) was dropwised at 85° C. to form precipitates. The mixture was stirred for further 15 min at same temperature and then cooled to room temperature (the oil bath was removed and stirred for 50 min and stirred for 60 min in water bath). The precipitates were collected, washed with EtOH (40 mL) and dried in air for 2 days to give the title compound (13.1 g) as colorless crystals.

$^1$H NMR (300 MHz, DMSO-$d_6$) δ 1.19-1.59 (6H, m), 1.63-1.80 (2H, m), 1.88-2.01 (2H, m), 3.41-3.49 (2H, m), 4.32-4.44 (1H, m), 4.59-4.68 (2H, m), 6.68 (1H, t, J=7.0 Hz), 6.96 (2H, d, J=8.7 Hz), 7.44 (2H, d, J=8.7 Hz), 7.58 (1H, dd, J=7.3, 1.7 Hz), 7.71-7.76 (1H, m).

mp 275-277° C.

Anal. Calcd for $C_{19}H_{22}N_2O_3S$: C, 63.66; H, 6.19; N, 7.82. Found: C, 63.63; H, 6.30; N, 7.86.

Example 166

9-(4-phenoxyphenyl)-3,4-dihydropyrido[2,1-c][1,2,4]thiadiazine 2,2-dioxide

A mixture of sodium carbonate (121 mg), tetrakis(triphenylphosphine)palladium(0) (13.18 mg), (4-phenoxyphenyl)boronic acid (98 mg) and 9-bromo-3,4-dihydropyrido[2,1-c][1,2,4]thiadiazine 2,2-dioxide (100 mg) in DMF (dry) (10 mL) and water (2 mL) was stirred at 80° C. under $N_2$ overnight. NH silica gel was added and the mixture was concentrated in vacuo. The residue was purified by column chromatography (NH silica gel, eluted with MeOH in EtOAc) to give 9-(4-phenoxyphenyl)-3,4-dihydropyrido[2,1-c][1,2,4]thiadiazine 2,2-dioxide (116 mg) as a white solid. The solid was crystallized from DMSO (1.5 mL)-EtOH (3 mL) to give the title compound (90.7 mg) as a white solid.

$^1$H NMR (300 MHz, DMSO-$d_6$) δ 3.37-3.52 (2H, m), 4.55-4.76 (2H, m), 6.70 (1H, t, J=7.0 Hz), 6.96-7.13 (4H, m), 7.14-7.23 (1H, m), 7.36-7.48 (2H, m), 7.49-7.58 (2H, m), 7.63 (1H, dd, J=7.2, 1.5 Hz), 7.77 (1H, dd, J=6.6, 1.7 Hz).

mp 251-252° C.

Anal. Calcd for $C_{19}H_6N_2O_3S$: C, 64.76; H, 4.58; N, 7.95. Found: C, 64.63; H, 4.65; N, 7.88.

Example 167

9-(4-phenoxyphenyl)-3,4-dihydropyrido[2,1-c][1,2,4]thiadiazine 2,2-dioxide

A) 3-(4-phenoxyphenyl)pyridin-2-amine

A mixture of 4-phenoxyphenylboronic acid (40.2 g), 3-bromopyridin-2-amine (25 g), tetrakis(triphenylphosphine)palladium(0) (5.01 g) and sodium carbonate (30.6 g) in DME (722 mL) and water (145 mL) was stirred at 80° C. under $N_2$ for 20 hr. NH silica gel was added and the mixture was concentrated in vacuo. The residue was purified by column chromatography (NH silica gel, eluted with EtOAc in hexane) to give a white solid. The solid was crystallized from EtOAc and hexane to give the title compound (33.8 g) as a white solid.

MS (API+). found: 263.1

B) 9-(4-phenoxyphenyl)-3,4-dihydropyrido[2,1-c][1,2,4]thiadiazine 2,2-dioxide

To a suspension of NaH (60%, 20.4 g) in THF (dry) (250 mL) was added 2-chloroethanesulfonyl chloride (32.2 mL) at 0° C. and the mixture was stirred for 5 min at the same temperature. A solution of 3-(4-phenoxyphenyl)pyridin-2-amine (29.09 g) in THF (dry) (150 mL) was dropwised at 0° C. and the mixture was stirred at room temperature under $N_2$ for 2 days. The mixture was quenched with THF/water (v/v=5/1) at 0° C. under $N_2$ carefully. Water (500 mL) and EtOAc (400 mL) were added to form precipitates (stirred for 30 min) which were washed with water and EtOAc, collected and crystallized from DMSO/EtOH (500 mL/1000 ml, at 90° C.) to give the title compound (36.0 g) as colorless crystals.

$^1$H NMR (300 MHz, DMSO-$d_6$) δ 3.40-3.53 (2H, m), 4.60-4.71 (2H, m), 6.71 (1H, t, J=6.8 Hz), 6.96-7.05 (2H, m), 7.05-7.13 (2H, m), 7.13-7.23 (1H, m), 7.38-7.47 (2H, m), 7.50-7.57 (2H, m), 7.63 (1H, dd, J=7.2, 1.5 Hz), 7.77 (1H, dd, J=6.8, 1.5 Hz).

mp 253-255° C.

MS (API+). found: 353.1

X-ray powder diffraction pattern with specific peaks at d value (or d-spacing)=10.99, 7.23, 5.83, 5.05, 4.95, 4.69, 4.57, 4.19, 4.14 and 4.01 Å.

Example 168

9-[4-(4-methylphenoxy)phenyl]-3,4-dihydropyrido[2,1-c][1,2,4]thiadiazine 2,2-dioxide A) 1-bromo-4-(4-methylphenoxy)benzene A mixture of 4-methylphenol (30.0 g), 1,4-dibromobenzene (54.5 g), copper(I) iodide (4.40 g), potassium carbonate (5.11 g) and N,N-dimethylglycine (2.86 g) in DMF (300 mL) was stirred at 100° C. under $N_2$ for 18 hr. The mixture was diluted with sat. $NH_4Cl$ aq. at 0° C. and extracted with EtOAc. The organic layer was separated, washed with sat. $NH_4Cl$ aq., 1N NaOH aq. and brine, dried over anhydrous magnesium sulfate and concentrated in vacuo. The residue was purified by column chromatography (silica gel, eluted with hexane) to give the title compound (39.5 g) as a colorless solid.

$^1$H NMR (300 MHz, CDCl$_3$) δ 2.34 (3H, s), 6.83-6.91 (4H, m), 7.14 (2H, d, J=8.3 Hz), 7.40 (2H, d, J=9.0 Hz).

B) 4,4,5,5-tetramethyl-2-[4-(4-methylphenoxy)phenyl]-1,3,2-dioxaborolane

A mixture of 1-bromo-4-(4-methylphenoxy)benzene (37.0 g), 4,4,4',4',5,5,5',5'-octamethyl-2,2'-bi(1,3,2-dioxaborolane) (42.8 g), potassium acetate (27.6 g) and [1,1'-bis(diphenylphosphino)ferrocene]dichloropalladium(II) (5.14 g) in DMF (370 mL) was stirred at 100° C. under $N_2$ for 16 hr. The mixture was neutralized with sat. $NaHCO_3$ aq. at 0° C. and the solid was removed by filtration, and the filtrate was extracted with EtOAc. The organic layer was separated, washed with brine, dried over anhydrous magnesium sulfate and concentrated in vacuo. The residue was purified by column chromatography (silica gel, eluted with EtOAc in hexane) to give the title compound (43.5 g) as an off-white solid.

$^1$H NMR (300 MHz, CDCl$_3$) δ 1.33 (12H, s), 2.34 (3H, s), 6.88-6.99 (4H, m), 7.15 (2H, d, J=8.3 Hz), 7.76 (2H, d, J=8.7 Hz).

C) 3-[4-(4-methylphenoxy)phenyl]pyridin-2-amine

Tetrakis(triphenylphosphine)palladium(0) (12.5 g) was added to a suspension of 3-bromopyridin-2-amine (31.2 g), 4,4,5,5-tetramethyl-2-[4-(4-methylphenoxy)phenyl]-1,3,2-dioxaborolane (72.8 g) and sodium carbonate (38.3 g) in 1,2-dimethoxyethane (500 mL) and water (250 mL) and the mixture was stirred at 100° C. under $N_2$ for 16 hr. The mixture was diluted with water at room temperature and extracted with EtOAc-THF (3:1). The separated organic layer was washed with brine, dried over anhydrous magnesium sulfate and concentrated in vacuo. The residue was purified by column chromatography (NH silica gel, eluted with EtOAc in hexane) to give a crude product, which was washed with diisopropyl ether to give the title compound (35.2 g) as a colorless solid.

MS (ESI+). found: 277.0.

¹H NMR (300 MHz, CDCl₃) δ 2.35 (3H, s), 4.54 (2H, brs), 6.74 (1H, dd, J=7.3, 5.1 Hz), 6.97 (2H, d, J=8.7 Hz), 7.05 (2H, d, J=8.7 Hz), 7.18 (2H, d, J=8.3 Hz), 7.32-7.41 (3H, m), 8.06 (1H, dd, J=4.9, 1.9 Hz).

D) 9-[4-(4-methylphenoxy)phenyl]-3,4-dihydropyrido[2,1-c][1,2,4]thiadiazine 2,2-dioxide 2-Chloroethanesulfonyl chloride (19.5 mL) was added dropwise to a mixture of NaH (60%, 12.5 g) in THF (100 mL) at 0° C. in an ice bath. After being stirred at 0° C. for 10 min, a solution of 3-[4-(4-methylphenoxy)phenyl]pyridin-2-amine (17.2 g) in THF (100 mL) was added dropwise to the mixture at 0° C. The ice-bath was removed and the mixture was stirred at room temperature under N₂ for 14 hr. The mixture was quenched with EtOH at 0° C. and water was added dropwise to the mixture at 0° C. The mixture was stirred at room temperature for 1 h. The precipitate was collected by filtration, and washed with water and EtOAc to give the title compound (8.68 g) as colorless powder.

E) 9-[4-(4-methylphenoxy)phenyl]-3,4-dihydropyrido[2,1-c][1,2,4]thiadiazine 2,2-dioxide 9-[4-(4-Methylphenoxy)phenyl]-3,4-dihydropyrido[2,1-c][1,2,4]thiadiazine 2,2-dioxide (10.4 g) was crystallized from DMSO-EtOH to give the title compound (8.04 g) as colorless crystals.

MS (ESI+). found: 367.1.

¹H NMR (300 MHz, DMSO-d₆) δ 2.29 (3H, s), 3.38-3.50 (2H, m), 4.58-4.68 (2H, m), 6.68 (1H, t, J=7.0 Hz), 6.92-7.00 (4H, m), 7.21 (2H, d, J=8.0 Hz), 7.45-7.53 (2H, m), 7.59 (1H, dd, J=7.1, 1.6 Hz), 7.75 (1H, dd, J=6.6, 1.6 Hz).

mp 248-250° C.

Anal. Calcd for C₂₀H₈N₂O₃S: C, 65.55; H, 4.95; N, 7.64; S, 8.75.

Found: C, 65.56; H, 5.02; N, 7.63; S, 8.69.

X-ray powder diffraction pattern with specific peaks at d value (or d-spacing)=12.62, 7.78, 7.34, 6.96, 6.25, 5.89, 5.53, 5.16 Å.

Example 169

9-[4-(cyclohexyloxy)phenyl]-7-methyl-3,4-dihydropyrazino[2,1-c][1,2,4]thiadiazine 2,2-dioxide A) 3-(4-(cyclohexyloxy)phenyl)-5-methylpyrazin-2-amine Tetrakis(triphenylphosphine)palladium(0) (0.922 g) was added to a suspension of 3-bromo-5-methylpyrazin-2-amine (5 g), 4-(cyclohexyloxy)phenylboronic acid (7.61 g) and sodium carbonate decahydrate (15.2 g) in DME (200 mL) and water (40 mL) and the mixture was stirred at 80° C. under nitrogen overnight. The insoluble material was removed by filtration (eluted with EtOAc), and silica-gel was added and the volatiles were removed in vacuo. The mixture supported on silica-gel was purified by column chromatography (silica gel, eluted with EtOAc in hexane) to give the title compound (7.5 g) as a pale orange solid.

MS (ESI+). found: 284.1.

B) 9-[4-(cyclohexyloxy)phenyl]-7-methyl-3,4-dihydropyrazino[2,1-c][1,2,4]thiadiazine 2,2-dioxide To a suspension of NaH (60%, 5.29 g) in THF (dry) (100 mL) was added 2-chloroethanesulfonyl chloride (5.57 mL) at 0° C. and the mixture was stirred for 10 min at the same temperature. A solution of 3-(4-(cyclohexyloxy)phenyl)-5-methylpyrazin-2-amine (7.5 g) in THF (dry) (75 mL) was added at 0° C. and the mixture was stirred at room temperature under nitrogen for 2 days. The mixture was quenched with water/THF at 0° C. carefully and water was added to form precipitates which were washed with EtOAc and water and dried in vacuo to give crude title compound (4.7 g). The part of this material (ca. 4.3 g) was crystallized from DMSO (200 mL)-EtOH (40 mL)/water (400 mL) to give 9-[4-(cyclohexyloxy)phenyl]-7-methyl-3,4-dihydropyrazino[2,1-c][1,2,4]thiadiazine 2,2-dioxide as light-yellow crystals (3.6 g), which was recrystallized from DMSO (100 mL)-EtOH (15 mL)/water (100 mL) at 80° C. to room temperature to give the title compound (3.09 g) as light-yellow crystals.

¹H NMR (300 MHz, DMSO-d₆) δ 1.17-1.59 (6H, m), 1.62-1.82 (2H, m), 1.85-2.03 (2H, m), 2.29 (3H, s), 3.42-3.55 (2H, m), 4.34-4.50 (1H, m), 4.51-4.62 (2H, m), 6.99 (2H, d, J=8.7 Hz), 7.52 (1H, s), 8.00 (2H, d, J=8.7 Hz).

X-ray powder diffraction pattern with specific peaks at d value (or d-spacing)=23.99, 7.98, 5.99, 4.60, 3.99 and 3.42 Å.

Example 170

9-{4-[4-(1,1-difluoroethyl)phenoxy]phenyl}-3,4,6,7,8,9-hexahydropyrido[2,1-c][1,2,4]thiadiazine 2,2-dioxide Platinum(IV) oxide (15 mg) was added to a mixture of 9-{4-[4-(1,1-difluoroethyl)phenoxy]phenyl}-3,4-dihydropyrido[2,1-c][1,2,4]thiadiazine 2,2-dioxide (300 mg) in THF (dry) (10 mL) and MeOH (10 mL). The mixture was stirred at room temperature under hydrogen overnight. The insoluble solid was removed by filtration through silica gel/Celite pad (eluted with EtOAc) and the filtrate was concentrated in vacuo. The residue was crystallized from THF/IPE to give the title compound (77.7 mg) as colorless crystals.

¹H NMR (300 MHz, DMSO-d₆) δ 1.67-1.83 (3H, m), 1.85-2.12 (4H, m), 3.24-3.29 (2H, m), 3.41-3.55 (2H, m), 3.74-3.90 (3H, m), 6.93-7.16 (4H, m), 7.25 (2H, d, J=8.3 Hz), 7.57 (2H, d, J=8.7 Hz).

mp 171-172° C.

Anal. Calcd for C₂₁H₂₂N₂O₃SF₂: C, 59.99; H, 5.27; N, 6.66. Found: C, 60.06; H, 5.51; N, 6.44.

Example 171

9-{4-[3-(1,1-difluoroethyl)phenoxy]phenyl}-7-methyl-3,4,6,7,8,9-hexahydropyrido[2,1-c][1,2,4]thiadiazine 2,2-dioxide A) 3-(4-(3-(1,1-difluoroethyl)phenoxy)phenyl)-5-methylpyridin-2-amine Copper(I) iodide (39.2 mg) was added to a mixture of picolinic acid (25.4 mg), 4-(2-aminopyridin-3-yl)phenol (206 mg), tripotassium phosphate (656 mg), 1-bromo-3-(1,1-difluoroethyl)benzene (239 mg) and DMSO (3 mL). The mixture was stirred at 130° C. under nitrogen for 10 hr. The insoluble solid was removed by filtration through silica gel/Celite pad (eluted with EtOAc). Silica-gel was added to the filtrate and the volatiles were removed in vacuo. The mixture supported on silica-gel was purified by column

B) 9-{4-[3-(1,1-difluoroethyl)phenoxy]phenyl}-7-methyl-3,4,6,7,8,9-hexahydropyrido[2,1-c][1,2,4]thiadiazine 2,2-dioxide To a suspension of NaH (60%, 96 mg) in THF (dry) (10 mL) was added 2-chloroethanesulfonyl chloride (0.101 mL) at 0° C. and the mixture was stirred for 10 min at the same temperature. A solution of 3-(4-(3-(1,1-difluoroethyl)phenoxy)phenyl)-5-methylpyridin-2-amine (164 mg) in THF (dry) (10 mL) was added at 0° C. and the mixture was stirred at room temperature under nitrogen overnight. The mixture was quenched with water at 0° C. Water, EtOAc and THF were added and the mixture was extracted. Silica-gel was added to the organic phase and the volatiles were removed in vacuo. The mixture supported on silica-gel was purified by column chromatography (silica gel, eluted with MeOH in EtOAc) and concentrated in vacuo to give 9-{4-[3-(1,1-difluoroethyl)phenoxy]phenyl}-7-methyl-3,4-dihydropyrido[2,1-c][1,2,4]thiadiazine 2,2-dioxide as a white solid. Platinum(IV) oxide (30 mg) was added to a solution of the prepared 9-{4-[3-(1,1-difluoroethyl)phenoxy]phenyl}-7-methyl-3,4-dihydropyrido[2,1-c][1,2,4]thiadiazine 2,2-dioxide in THF (dry) (15 mL) and MeOH (15 mL). The mixture was stirred at room temperature under hydrogen for 3 hr. Activated carbon was added and the insoluble solid was removed by filtration through silica gel/Celite pad (eluted with EtOAc, to remove catalyst poison). Platinum(IV) oxide (30 mg) was added and the mixture was stirred at room temperature under hydrogen overnight. Activated carbon was added and the insoluble solid was removed by filtration through silica gel/Celite pad (eluted with EtOAc) and the filtrate was concentrated in vacuo. The residue was crystallized from THF/IPE to give the title compound (47.6 mg) as colorless crystals.

$^1$H NMR (300 MHz, DMSO-$d_6$) δ 0.95 (3H, d, J=6.4 Hz), 1.51 (1H, q, J=12.2 Hz), 1.86-2.18 (5H, m), 3.19-3.26 (3H, m), 3.42 (1H, dd, J=12.1, 4.5 Hz), 3.74-3.86 (3H, m), 6.97 (2H, d, J=8.7 Hz), 7.11 (1H, dd, J=8.1, 2.1 Hz), 7.17-7.28 (3H, m), 7.33 (1H, d, J=7.2 Hz), 7.46-7.55 (1H, m).

Example 172

9-{4-[3-(1,1-difluoroethyl)phenoxy]phenyl}-7-methyl-3,4,6,7,8,9-hexahydropyrido[2,1-c][1,2,4]thiadiazine 2,2-dioxide A diastereomer mixture (30 mg) of 9-{4-[3-(1,1-difluoroethyl)phenoxy]phenyl}-7-methyl-3,4,6,7,8,9-hexahydropyrido[2,1-c][1,2,4]thiadiazine 2,2-dioxide was separated by HPLC (C18, mobile phase:water/acetonitrile (5 mM ammonium acetate-containing system)), a saturated aqueous sodium hydrogen carbonate solution was added to a fraction having a longer retention time, and the mixture was extracted with ethyl acetate, dried over anhydrous magnesium sulfate and concentrated under reduced pressure. The obtained racemate (27 mg) of 9-{4-[3-(1,1-difluoroethyl)phenoxy]phenyl}-7-methyl-3,4,6,7,8,9-hexahydropyrido[2,1-c][1,2,4]thiadiazine 2,2-dioxide was separated by SFC (column: CHIRALPAK IC (MB001), 20 mmID×250 mmL, manufactured by DAICEL CHEMICAL INDUSTRIES, LTD., mobile phase:carbon dioxide/methanol=740/260) to give the title compound (14 mg) with a shorter retention time as a white solid.

$^1$H NMR (300 MHz, DMSO-$d_6$) δ 0.95 (3H, d, J=6.4 Hz), 1.51 (1H, q, J=12.4 Hz), 1.84-2.19 (5H, m), 3.13-3.26 (3H, m), 3.42 (1H, dd, J=11.9, 4.7 Hz), 3.72-3.87 (3H, m), 6.97 (2H, d, J=8.3 Hz), 7.11 (1H, d, J=7.5 Hz), 7.17-7.26 (3H, m), 7.33 (1H, d, J=7.9 Hz), 7.45-7.55 (1H, m).

Example 173

9-{4-[3-(1,1-difluoroethyl)phenoxy]phenyl}-7-methyl-3,4,6,7,8,9-hexahydropyrido[2,1-c][1,2,4]thiadiazine 2,2-dioxide A diastereomer mixture (30 mg) of 9-{4-[3-(1,1-difluoroethyl)phenoxy]phenyl}-7-methyl-3,4,6,7,8,9-hexahydropyrido[2,1-c][1,2,4]thiadiazine 2,2-dioxide was separated by HPLC (C18, mobile phase: water/acetonitrile (5 mM ammonium acetate-containing system)), a saturated aqueous sodium hydrogen carbonate solution was added to a fraction having a longer retention time, and the mixture was extracted with ethyl acetate, dried over anhydrous magnesium sulfate and concentrated under reduced pressure. The obtained racemate (27 mg) of 9-{4-[3-(1,1-difluoroethyl)phenoxy]phenyl}-7-methyl-3,4,6,7,8,9-hexahydropyrido[2,1-c][1,2,4]thiadiazine 2,2-dioxide was separated by SFC (column: CHIRALPAK IC (MB001), 20 mmID×250 mmL, manufactured by DAICEL CHEMICAL INDUSTRIES, LTD., mobile phase:carbon dioxide/methanol=740/260) to give the title compound (14 mg) with a longer retention time as a white solid.

$^1$H NMR (300 MHz, DMSO-$d_6$) δ 0.95 (3H, d, J=6.4 Hz), 1.51 (1H, q, J=12.2 Hz), 1.82-2.19 (5H, m), 3.13-3.26 (3H, m), 3.36-3.48 (1H, m), 3.69-3.88 (3H, m), 6.97 (2H, d, J=8.3 Hz), 7.11 (1H, d, J=7.9 Hz), 7.17-7.26 (3H, m), 7.33 (1H, d, J=7.5 Hz), 7.45-7.56 (1H, m).

Example 174

9-[4-(1,1-difluoroethyl)phenyl]-3,4,6,7,8,9-hexahydropyrido[2,1-c][1,2,4]thiadiazine 2,2-dioxide Platinum(IV) oxide (45 mg) was added to a mixture of 9-(4-(1,1-difluoroethyl)phenyl)-3,4-dihydropyrido[2,1-c][1,2,4]thiadiazine 2,2-dioxide (207 mg) in THF (dry) (120 mL) and MeOH (120 mL). The mixture was stirred at room temperature under hydrogen overnight. Activated carbon powder was added and the insoluble solid was removed by filtration through silica gel/Celite pad (eluted with EtOAc) and the filtrate was concentrated in vacuo. The residue was crystallized from THF/IPE to give the title compound (80.4 mg) as colorless crystals.

$^1$H NMR (300 MHz, DMSO-$d_6$) δ 1.63-1.82 (3H, m), 1.86-2.09 (4H, m), 3.23-3.29 (2H, m), 3.38-3.58 (2H, m), 3.72-3.91 (3H, m), 7.32 (2H, d, J=8.3 Hz), 7.50 (2H, d, J=8.3 Hz).

Example 175

9-[4-(trifluoromethyl)phenyl]-3,4,6,7,8,9-hexahydropyrido[2,1-c][1,2,4]thiadiazine 2,2-dioxide A mixture of 9-[4-(trifluoromethyl)phenyl]-3,4-dihydropyrido[2,1-c][1,2,4]thiadiazine 2,2-dioxide (250 mg) and platinum(IV) oxide (25.9 mg) in MeOH (10 mL) was stirred at room temperature under H$_2$ for 20 hr. The reaction mixture was filtered by Celite and the filtrate was concentrated in vacuo. The residue was recrystallized from EtOAc-MeOH to give the title compound (68.0 mg) as a white solid.

$^1$H NMR (300 MHz, DMSO-d$_6$) δ 1.72-1.80 (3H, m), 1.97-2.06 (1H, m), 3.25-3.32 (2H, m), 3.43-3.59 (2H, m), 3.78-3.96 (3H, m), 7.46 (2H, d, J=8.3 Hz), 7.68 (2H, d, J=8.3 Hz).

mp 226-227° C.

Anal. Calcd for C$_{14}$H$_{15}$N$_2$O$_2$SF$_3$-0.75H$_2$O: C, 48.62; H, 4.81; N, 8.10.

Found: C, 48.29; H, 4.39; N, 7.99.

Example 176

9-[4-(trifluoromethyl)phenyl]-3,4,6,7,8,9-hexahydropyrido[2,1-c][1,2,4]thiadiazine 2,2-dioxide A racemate (45.3 mg) of 9-[4-(trifluoromethyl)phenyl]-3,4,6,7,8,9-hexahydropyrido[2,1-c][1,2,4]thiadiazine 2,2-dioxide was separated by HPLC (column: CHIRALPAK AD (LF001), 50 mmID×500 mmL, manufactured by DAICEL CHEMICAL INDUSTRIES, LTD., mobile phase:hexane/ethanol=200/800) to give the title compound (23.3 mg) with a shorter retention time. Crystallization from THF and diisopropyl ether gave a white solid.

$^1$H NMR (300 MHz, CDCl$_3$) δ 1.83-2.02 (3H, m), 2.07-2.23 (1H, m), 3.24-3.33 (2H, m), 3.40-3.57 (2H, m), 3.84-4.03 (3H, m), 7.28 (2H, d, J=7.9 Hz), 7.58 (2H, d, J=7.9 Hz).

Example 177

9-[4-(trifluoromethyl)phenyl]-3,4,6,7,8,9-hexahydropyrido[2,1-c][1,2,4]thiadiazine 2,2-dioxide A racemate (45.3 mg) of 9-[4-(trifluoromethyl)phenyl]-3,4,6,7,8,9-hexahydropyrido[2,1-c][1,2,4]thiadiazine 2,2-dioxide was separated by HPLC (column: CHIRALPAK AD (LF001), 50 mmID×500 mmL, manufactured by DAICEL CHEMICAL INDUSTRIES, LTD., mobile phase:hexane/ethanol=200/800) to give the title compound (21.3 mg) with a longer retention time. Crystallization from THF and diisopropyl ether gave a white solid.

$^1$H NMR (300 MHz, CDCl$_3$) δ 1.79-2.01 (3H, m), 2.05-2.24 (1H, m), 3.30 (2H, t, J=6.4 Hz), 3.49 (2H, q, J=6.4 Hz), 3.87-4.05 (3H, m), 7.27-7.32 (2H, m), 7.59 (2H, d, J=8.3 Hz).

Example 178

9-[4-(trifluoromethoxy)phenyl]-3,4,6,7,8,9-hexahydropyrido[2,1-c][1,2,4]thiadiazine 2,2-dioxide A racemate (85.4 mg) of 9-[4-(trifluoromethoxy)phenyl]-3,4,6,7,8,9-hexahydropyrido[2,1-c][1,2,4]thiadiazine 2,2-dioxide was separated by HPLC (column: CHIRALPAK AD (LF001), 50 mmID×500 mmL, manufactured by DAICEL CHEMICAL INDUSTRIES, LTD., mobile phase:hexane/ethanol=500/500) to give the title compound (43.6 mg) with a shorter retention time. Crystallization from THF and diisopropyl ether gave a white solid.

$^1$H NMR (300 MHz, CDCl$_3$) δ 1.79-2.01 (3H, m), 2.06-2.20 (1H, m), 3.23-3.33 (2H, m), 3.39-3.54 (2H, m), 3.82-4.03 (3H, m), 7.11-7.23 (4H, m).

Example 179

9-[4-(trifluoromethoxy)phenyl]-3,4,6,7,8,9-hexahydropyrido[2,1-c][1,2,4]thiadiazine 2,2-dioxide A racemate (85.4 mg) of 9-[4-(trifluoromethoxy)phenyl]-3,4,6,7,8,9-hexahydropyrido[2,1-c][1,2,4]thiadiazine 2,2-dioxide was separated by HPLC (column: CHIRALPAK AD (LF001), 50 mmID×500 mmL, manufactured by DAICEL CHEMICAL INDUSTRIES, LTD., mobile phase:hexane/ethanol=500/500) to give the title compound (42.8 mg) with a longer retention time. Crystallization from THF and diisopropyl ether gave a white solid.

$^1$H NMR (300 MHz, CDCl$_3$) δ 1.80-2.01 (3H, m), 2.06-2.21 (1H, m), 3.24-3.35 (2H, m), 3.41-3.55 (2H, m), 3.83-4.02 (3H, m), 7.13-7.22 (4H, m).

Example 180

9-[4-(cyclohexyloxy)phenyl]-7-methyl-3,4-dihydropyrazino[2,1-c][1,2,4]thiadiazine 2,2-dioxide A) 3-(4-(cyclohexyloxy)phenyl)-5-methylpyrazin-2-amine Tetrakis(triphenylphosphine)palladium(0) (55.3 mg) was added to a suspension of 3-bromo-5-methylpyrazin-2-amine (300 mg), 4-(cyclohexyloxy)phenylboronic acid (456 mg) and sodium carbonate (338 mg) in DME (15 mL) and water (3 mL) and the mixture was stirred at 100° C. under nitrogen for 2 hr. Water and EtOAc were added and the organic layer was separated, washed with brine, dried over anhydrous sodium sulfate and concentrated in vacuo. The residue was purified by column chromatography (silica gel, eluted with EtOAc in hexane) and washed with hexane/IPE to give the title compound (236 mg) as a white powder.

MS (ESI+). found: 284.3.

B) 9-[4-(cyclohexyloxy)phenyl]-7-methyl-3,4-dihydropyrazino[2,1-c][1,2,4]thiadiazine 2,2-dioxide To a suspension of NaH (60%, 100 mg) in THF (dry) (10 mL) was added 2-chloroethanesulfonyl chloride (0.263 mL) at 0° C. and the mixture was stirred for 5 min at the same temperature. A solution of 3-(4-(cyclohexyloxy)phenyl)-5-methylpyrazin-2-amine (236 mg) in THF (dry) (10 mL) was added at 0° C. and the mixture was stirred at room temperature under nitrogen for 15 hr and at 50° C. for 1 hr. The mixture was quenched with water at 0° C. carefully and water was added to form precipitates. The precipitate was crystallized from THF/IPE to give the title compound (128 mg) as yellow crystals.

$^1$H NMR (300 MHz, DMSO-d$_6$) δ 1.21-1.60 (6H, m), 1.62-1.79 (2H, m), 1.88-2.01 (2H, m), 2.29 (3H, s), 3.45-3.55 (2H, m), 4.36-4.48 (1H, m), 4.52-4.62 (2H, m), 6.99 (2H, d, J=8.7 Hz), 7.52 (1H, s), 8.00 (2H, d, J=8.7 Hz).

mp 216-217° C.

Anal. Calcd for C$_{19}$H$_{23}$N$_3$O$_3$S: C, 61.10; H, 6.21; N, 11.25. Found: C, 61.10; H, 6.33; N, 11.04.

Example 181

9-[4-(2-methylpropoxy)phenyl]-3,4-dihydropyrido[2,1-c][1,2,4]thiadiazine 2,2-dioxide To a mixture of 4-(2,2-dioxido-3,4-dihydropyrido[2,1-c][1,2,4]thiadiazin-9-yl)phenol (200 mg), potassium carbonate (260 mg) in DMSO (4 mL) was added 1-iodo-2-methylpropane (173 mg). The mixture was stirred at 130° C. for 1 hr. Another 1-iodo-2-methylpropane (0.10 mL) was added and the mixture was stirred at room temperature overnight. 0.5N NaOHaq, EtOAc and THF were added and the extracted organic layer was washed with water and brine, dried over anhydrous sodium sulfate and concentrated in vacuo. The residue was crystallized from THF-MeOH/IPE to give the title compound (104 mg) as colorless crystals.

$^1$H NMR (300 MHz, DMSO-d$_6$) δ 0.99 (6H, d, J=6.4 Hz), 1.95-2.11 (1H, m), 3.41-3.51 (2H, m), 3.78 (2H, d, J=6.8 Hz), 4.60-4.71 (2H, m), 6.65-6.72 (1H, m), 6.96 (2H, d, J=8.7 Hz), 7.45 (2H, d, J=8.7 Hz), 7.58 (1H, dd, J=7.2, 1.5 Hz), 7.74 (1H, dd, J=6.6, 1.5 Hz).

Example 182

9-[4-(cyclohexyloxy)phenyl]-3,4-dihydropyrido[2,1-c][1,2,4]thiadiazine 2,2-dioxide A) 3-[4-(cyclohexyloxy)phenyl]pyridin-2-amine DEAD (in toluene) (1.57 mL) was added dropwise to a solution of triphenylphosphine (909 mg), 4-(2-aminopyridin-3-yl)phenol (430 mg) and cyclohexanol (0.369 mL) in THF (dry) (15 mL) at room temperature and the mixture was stirred for 2 hr. Another DEAD, triphenylphosphine and cyclohexanol were added (0.5 eq, respectively) and the mixture was stirred at room temperature for 2 hr. The mixture was concentrated in vacuo and the residue was purified by column chromatography (NH silica gel, eluted with EtOAc in hexane, and silica gel, eluted with EtOAc in hexane) to give the title compound (172 mg) as a white solid.

MS (ESI+). found: 269.1.

B) 9-[4-(cyclohexyloxy)phenyl]-3,4-dihydropyrido[2,1-c][1,2,4]thiadiazine 2,2-dioxide To a suspension of NaH (60%, 127 mg) in THF (dry) (5 mL) was added 2-chloroethanesulfonyl chloride (0.200 mL) at 0° C. and the mixture was stirred for 5 min at the same temperature. A solution of 3-[4-(cyclohexyloxy)phenyl]pyridin-2-amine (170 mg) in THF (dry) (5 mL) was added at 0° C. and the mixture was stirred at room temperature under nitrogen overnight. The mixture was quenched with water at 0° C. carefully. Water was added to form precipitates which were washed with water and hexane, collected and dried in vacuo to give the title compound (148 mg) as a white powder. A part of this product was crystallized from MeCN-THF/IPE to give a colorless crystal.

$^1$H NMR (300 MHz, DMSO-d$_6$) δ 1.19-1.59 (6H, m), 1.67-1.80 (2H, m), 1.88-2.01 (2H, m), 3.39-3.50 (2H, m), 4.31-4.45 (1H, m), 4.58-4.70 (2H, m), 6.68 (1H, t, J=7.0 Hz), 6.95 (2H, d, J=8.7 Hz), 7.44 (2H, d, J=8.7 Hz), 7.58 (1H, dd, J=7.2, 1.5 Hz), 7.70-7.79 (1H, m).

mp 272-274° C.

Anal. Calcd for C$_{19}$H$_{22}$N$_2$O$_3$S-0.2H$_2$O: C, 63.03; H, 6.24; N, 7.74. Found: C, 63.01; H, 6.29; N, 7.58.

Example 183

2-chloro-4-[4-(2,2-dioxido-3,4,6,7,8,9-hexahydropyrido[2,1-c][1,2,4]thiadiazin-9-yl)phenoxy]benzonitrile Potassium carbonate (73.9 mg) was added to a mixture of 4-(2,2-dioxido-3,4,6,7,8,9-hexahydropyrido[2,1-c][1,2,4] thiadiazin-9-yl)phenol (50 mg) and 2-chloro-4-fluorobenzonitrile (41.6 mg) in DMF (dry) (1 mL). The mixture was stirred at 60° C. under atmosphere overnight. The mixture was quenched with water and extracted with EtOAc. The organic layer was separated, washed with water and brine, dried over anhydrous magnesium sulfate and concentrated in vacuo. The residue was purified by column chromatography (silica gel, eluted with MeOH in EtOAc) and concentrated. The residue was crystallized from MeCN-THF/IPE to give the title compound (32.2 mg) as colorless crystals.

$^1$H NMR (300 MHz, DMSO-d$_6$) δ 1.70-1.83 (3H, m), 1.99-2.07 (1H, m), 3.23-3.28 (2H, m), 3.42-3.55 (2H, m), 3.78-3.89 (3H, m, J=4.5 Hz), 7.04 (1H, dd, J=8.7, 2.3 Hz), 7.15 (2H, d, J=8.7 Hz), 7.28-7.37 (3H, m), 7.96 (1H, d, J=9.1 Hz).

mp 219-220° C.

Anal. Calcd for C$_{20}$H$_8$N$_3$O$_3$SCl: C, 57.76; H, 4.36; N, 10.10. Found: C, 57.73; H, 4.47; N, 9.90.

Example 184

2-chloro-4-[4-(9-hydroxy-2,2-dioxido-3,4,6,7,8,9-hexahydropyrido[2,1-c][1,2,4]thiadiazin-9-yl)phenoxy]benzonitrile Crude title compound was obtained as a byproduct of Example 183. The title compound (2.1 mg) was obtained as a white solid by crystallization from THF and diisopropyl ether.

$^1$H NMR (300 MHz, DMSO-d$_6$) δ 1.48-1.67 (1H, m), 1.85-2.04 (3H, m), 3.51 (2H, t, J=5.9 Hz), 3.77-3.93 (2H, m), 5.96-6.05 (1H, m), 7.03 (1H, dd, J=8.7, 2.3 Hz), 7.16 (2H, d, J=9.1 Hz), 7.30 (1H, d, J=2.3 Hz), 7.48 (2H, d, J=8.7 Hz), 7.97 (1H, d, J=9.1 Hz). 2 protons were hidden in a peak of water.

Example 185

9-(4-phenylcyclohexyl)-3,4-dihydropyrido[2,1-c][1,2,4]thiadiazine 2,2-dioxide

A) tert-butyl (3-bromopyridin-2-yl)carbamate

A solution of 3-bromopyridin-2-amine (5.8 g) in t-BuOH (25 mL) was added to a solution of di-tert-butyl dicarbonate (8.78 g) in t-BuOH (45 mL) at 0° C. The mixture was stirred at room temperature overnight and 65° C. overweekend. The reaction mixture was concentrated in vacuo. The residue was purified by column chromatography (silica gel, eluted with EtOAc in hexane) to give the title compound (5.99 g) as a white solid.

$^1$H NMR (300 MHz, CDCl$_3$) δ 1.55 (9H, s), 6.89 (1H, dd, J=7.9, 4.9 Hz), 7.30 (1H, brs), 7.82 (1H, dd, J=7.7, 1.7 Hz), 8.41 (1H, dd, J=4.9, 1.5 Hz).

B) tert-butyl [3-(1-hydroxy-4-phenylcyclohexyl)pyridin-2-yl]carbamate

To a solution of tert-butyl (3-bromopyridin-2-yl)carbamate (4 g) in THF (dry) (20 mL) was added dropwise n-butyllithium (1.6 M in hexane) (20.1 mL) at −78° C. and the mixture was stirred at the same temperature under nitrogen for 1 hr to give a yellow suspension. A solution of 4-phenylcyclohexanone (3.06 g) in THF (dry) (30 mL) was added dropwise at −78° C. and the mixture was stirred at room temperature under nitrogen overnight. The mixture was quenched with water at 0° C. and extracted with EtOAc.

The organic layer was separated, washed with brine and dried over anhydrous sodium sulfate and concentrated in vacuo. The residue was purified by column chromatography (silica gel, eluted with EtOAc in hexane) to give the title compound (560 mg) as a pale yellow solid.

MS (ESI+). found: 369.2.

C) 1-(2-aminopyridin-3-yl)-4-phenylcyclohexanol

4N HCl-EtOAc (5 mL) was added to tert-butyl [3-(1-hydroxy-4-phenylcyclohexyl)pyridin-2-yl]carbamate (450 mg) and the mixture was stirred at room temperature overnight. The resulted precipitates were collected and dried in vacuo to give 1-(2-aminopyridin-3-yl)-4-phenylcyclohexanol hydrochloride. 1-(2-aminopyridin-3-yl)-4-phenylcyclohexanol hydrochloride $^1$H NMR (300 MHz, DMSO-d$_6$) δ 1.44-1.71 (2H, m), 1.77-2.03 (4H, m), 2.23-2.38 (2H, m), 2.69-2.85 (1H, m), 5.80-6.05 (1H, m), 6.83-6.98 (1H, m), 7.07-7.38 (5H, m), 7.61-7.89 (2H, m), 7.91-8.12 (2H, m), 13.34-13.80 (1H, m).

This material was resolved in EtOAc and washed with sat. NaHCO$_3$ aq. and NaOH aq. The organic layer was separated, washed with brine, dried over anhydrous magnesium sulfate and concentrated in vacuo to give 1-(2-aminopyridin-3-yl)-4-phenylcyclohexanol (246 mg) as a colorless oil.

D) 3-(4-phenylcyclohexyl)pyridin-2-amine

TFA (3 mL) was added to 1-(2-aminopyridin-3-yl)-4-phenylcyclohexanol (246 mg) and the mixture was stirred at 40° C. under nitrogen for 6 hr. TFA was removed in vacuo and this product was subjected to the next reaction without further purification. MeOH (1 mL) and Pd/C (10 mg) were added and the mixture was stirred at room temperature under hydrogen for 2 days. The insoluble solid was removed by filtration through Celite-pad (eluted with EtOAc) and the filtrate was concentrated in vacuo. The residue was purified by column chromatography (NH silica gel, eluted with EtOAc in hexane) to give the title compound (38.6 mg) as colorless oil.

$^1$H NMR (300 MHz, CDCl$_3$) δ 1.63-1.92 (5H, m), 1.95-2.14 (2H, m), 2.28-2.43 (2H, m), 2.53-2.67 (1H, m), 5.52 (2H, brs), 6.62 (1H, dd, J=7.9, 4.9 Hz), 7.18-7.25 (1H, m), 7.28-7.37 (4H, m), 7.40 (1H, dd, J=7.6, 1.5 Hz), 7.98 (1H, dd, J=4.9, 1.9 Hz).

E) 9-(4-phenylcyclohexyl)-3,4-dihydropyrido[2,1-c][1,2,4]thiadiazine 2,2-dioxide To a suspension of NaH (60%, 29.2 mg) in THF (dry) (2 mL) was added 2-chloroethanesulfonyl chloride (0.046 mL) at 0° C. and the mixture was stirred for 5 min at the same temperature. A solution of 3-(4-phenylcyclohexyl)pyridin-2-amine (36.8 mg) in THF (dry) (2 mL) was added at 0° C. and the mixture was stirred at room temperature under nitrogen overnight. The mixture was quenched with water at 0° C. carefully and extracted with EtOAc. The organic layer was separated, washed with brine, dried over anhydrous sodium sulfate and concentrated in vacuo. The residue was purified by column chromatography (silica gel, eluted with EtOAc in hexane) and crystallized from EtOAc-hexane to give the title compound (15.7 mg) as an off-white crystals.

$^1$H NMR (300 MHz, DMSO-d$_6$) δ 1.52-2.13 (8H, m), 2.85-3.11 (2H, m), 3.37-3.53 (2H, m), 4.50-4.69 (2H, m), 6.52-6.69 (1H, m), 7.11-7.25 (1H, m), 7.27-7.38 (4H, m), 7.44-7.58 (1H, m), 7.58-7.72 (1H, m).

Example 186

9-{[4-(1-methylpropyl)phenoxy]methyl}-3,4-dihydropyrido[2,1-c][1,2,4]thiadiazine 2,2-dioxide A) 3-{[4-(1-methylpropyl)phenoxy]methyl}pyridin-2-amine The solution of (2-aminopyridin-3-yl)methanol (1.0 g) in THF (dry) (10 mL) was added dropwise to a solution of thionyl chloride (0.736 mL) in THF (dry) (30 mL) at 0° C. The mixture was stirred at room temperature for 30 min and concentrated in vacuo to give 3-(chloromethyl)pyridin-2-amine hydrochloride as a yellow gum. NaH (60%, 147 mg) was added to a mixture of 4-(1-methylpropyl)phenol (503 mg) in DMF (dry) (7 mL) at 0° C. The mixture was stirred at the same temperature for 20 min, then was added with the prepared 3-(chloromethyl)pyridin-2-amine hydrochloride (300 mg) at the same temperature. The mixture was stirred at 0° C. for 20 min, room temperature for 1 hr and 60° C. for 1 hr. Silica-gel was added to the mixture and the volatiles were removed in vacuo. The mixture supported on silica-gel was purified by column chromatography (silica gel, eluted with EtOAc in hexane) to give the title compound (151 mg) as pale yellow crystals.

MS (ESI+). found: 257.1.

B) 9-{[4-(1-methylpropyl)phenoxy]methyl}-3,4-dihydropyrido[2,1-c][1,2,4]thiadiazine 2,2-dioxide To a suspension of NaH (60%, 117 mg) in THF (dry) (4 mL) was added 2-chloroethanesulfonyl chloride (0.185 mL) at 0° C. and the mixture was stirred for 10 min at the same temperature. A solution of 3-{[4-(1-methylpropyl)phenoxy]methyl}pyridin-2-amine (150 mg) in THF (dry) (4 mL) was added at 0° C. and the mixture was stirred at room temperature under nitrogen for 1 day. The mixture was quenched with water at 0° C. carefully. EtOAc and THF were added and the organic layer was separated, washed with brine, dried over anhydrous sodium sulfate and concentrated in vacuo. The residue was purified by column chromatography (silica gel, eluted with EtOAc in hexane) and crystallized from THF/IPE to give the title compound (34.9 mg) as colorless crystals.

$^1$H NMR (300 MHz, DMSO-d$_6$) δ 0.75 (3H, t, J=7.4 Hz), 1.15 (3H, d, J=6.8 Hz), 1.43-1.60 (2H, m), 2.54-2.57 (1H, m), 3.39-3.54 (2H, m), 4.53-4.68 (2H, m), 4.85 (2H, s), 6.63-6.76 (1H, m), 6.91 (2H, d, J=8.7 Hz), 7.12 (2H, d, J=8.7 Hz), 7.69 (1H, d, J=7.2 Hz), 7.76 (1H, d, J=6.8 Hz).

Example 187

9-{4-[3-(trifluoromethyl)phenoxy]phenyl}-3,4-dihydropyrido[2,1-c][1,2,4]thiadiazine 2,2-dioxide A) 3-(4-(3-(trifluoromethyl)phenoxy)phenyl)pyridin-2-amine Copper(I) iodide (61.4 mg) was added to a mixture of tripotassium phosphate (1026 mg), picolinic acid (39.7 mg), 4-(2-aminopyridin-3-yl)phenol (300 mg) and 1-iodo-3-(trifluoromethyl)benzene (526 mg) in DMSO (6 mL). The mixture was stirred at 120° C. under nitrogen for 2 hr. The mixture was purified by column chromatography (silica gel, eluted with EtOAc in hexane) to give the title compound (348 mg) as a pale yellow solid.

MS (ESI+). found: 331.2.

B) 9-{4-[3-(trifluoromethyl)phenoxy]phenyl}-3,4-dihydropyrido[2,1-c][1,2,4]thiadiazine 2,2-dioxide To a suspension of NaH (60%, 210 mg) in THF (dry) (10 mL) was added 2-chloroethanesulfonyl chloride (0.331 mL) at 0° C. and the mixture was stirred for 5 min at the same temperature. A solution of 3-(4-(3-(trifluoromethyl)phenoxy)phenyl)pyridin-2-amine (347 mg) in THF (dry) (10 mL) was added at 0° C. and the mixture was stirred at room temperature under nitrogen overnight. The mixture was quenched with water at 0° C. carefully. Water was added to form precipitates which were washed with water and hexane, collected and dried in vacuo to give the title compound (234 mg) as a white powder. A part of this product was crystallized from MeCN-THF/IPE as colorless crystals.

$^1$H NMR (300 MHz, DMSO-d$_6$) δ 3.42-3.53 (2H, m), 4.59-4.71 (2H, m), 6.72 (1H, t, J=7.0 Hz), 7.12 (2H, d, J=9.1 Hz), 7.33-7.44 (2H, m), 7.49-7.56 (1H, m), 7.57-7.69 (4H, m), 7.79 (1H, dd, J=6.6, 1.7 Hz).

Example 188

9-{4-[(4,4-dimethylcyclohex-1-en-1-yl)oxy]phenyl}-3,4-dihydropyrido[2,1-c][1,2,4]thiadiazine 2,2-dioxide

A) 3-(4-((4,4-dimethylcyclohex-1-en-1-yl)oxy)phenyl)pyridin-2-amine

Copper(I) iodide (102 mg) was added to a mixture of picolinic acid (66.1 mg), 4-(2-aminopyridin-3-yl)phenol (500 mg), tripotassium phosphate (1710 mg), 1-bromo-4,4-dimethylcyclohex-1-ene (609 mg) and DMSO (8 mL). The mixture was stirred at 130° C. under nitrogen for 16 hr. The insoluble solid was removed by filtration through silica gel/Celite pad (eluted with EtOAc). Silica-gel was added to the filtrate and the volatiles were removed in vacuo. The mixture supported on silica-gel was purified by column chromatography (NH-silica gel, eluted with EtOAc in hexane) to give the title compound (563 mg) as an off-white amorphous solid.

MS (ESI+). found: 295.1.

B) 9-{4-[(4,4-dimethylcyclohex-1-en-1-yl)oxy]phenyl}-3,4-dihydropyrido[2,1-c][1,2,4]thiadiazine 2,2-dioxide To a suspension of NaH (60%, 382 mg) in THF (dry) (30 mL) was added 2-chloroethanesulfonyl chloride (0.402 mL) at 0° C. and the mixture was stirred for 10 min at the same temperature. A solution of 3-(4-((4,4-dimethylcyclohex-1-en-1-yl)oxy)phenyl)pyridin-2-amine (563 mg) in THF (dry) (30 mL) was added at 0° C. and the mixture was stirred at room temperature under nitrogen for 3 hr. The mixture was quenched with water at 0° C. Water and EtOAc were added and the mixture was extracted. Silica-gel was added to the organic phase and the volatiles were removed in vacuo. The mixture supported on silica-gel was purified by column chromatography (silica gel, eluted with MeOH in EtOAc) and concentrated in vacuo to give the title compound (369 mg) as a pale yellow solid. A part of the product was crystallized from MeCN/IPE to give a pale yellow crystal.

$^1$H NMR (300 MHz, DMSO-d$_6$) δ 0.97 (6H, s), 1.49 (2H, t, J=6.4 Hz), 1.83-1.94 (2H, m), 2.07-2.18 (2H, m), 3.40-3.51 (2H, m), 4.59-4.70 (2H, m), 5.03 (1H, t, J=3.8 Hz), 6.70 (1H, t, J=7.0 Hz), 6.99 (2H, d, J=8.7 Hz), 7.50 (2H, d, J=8.7 Hz), 7.60 (1H, d, J=6.4 Hz), 7.76 (1H, d, J=5.7 Hz).

Example 189

9-{4-[(4,4-dimethylcyclohexyl)oxy]phenyl}-3,4,6,7,8,9-hexahydropyrido[2,1-c][1,2,4]thiadiazine 2,2-dioxide Platinum(IV) oxide (40 mg) was added to a solution of 9-{4-[(4,4-dimethylcyclohex-1-en-1-yl)oxy]phenyl}-3,4-dihydropyrido[2,1-c][1,2,4]thiadiazine 2,2-dioxide (340 mg) in THF (dry) (30 mL), MeOH (30 mL) and AcOH (10 mL). The mixture was stirred at room temperature under hydrogen overnight. Activated carbon was added and the insoluble solid was removed by filtration through silica gel/Celite pad (eluted with EtOAc, to remove catalytic poison). Platinum(IV) oxide (40 mg) was added and the mixture was stirred at 50° C. under hydrogen for 6 hr. Platinum(IV) oxide was added and the mixture was stirred 50° C. under hydrogen for 12 hr. The insoluble solid was removed by filtration through silica gel/Celite pad (eluted with EtOAc) and the filtrate was concentrated in vacuo with silica-gel. The mixture supported on silica-gel was purified by column chromatography (silica gel, eluted with MeOH in EtOAc) and concentrated in vacuo. The residue was crystallized from EtOAc/hexane. This was dissolved in THF, silica-gel was added to the solution and the volatiles were removed in vacuo. The mixture supported on silica-gel was purified by column chromatography (silica gel, eluted with MeOH in EtOAc). The residue was crystallized from THF-EtOAc/IPE to give the title compound (37.6 mg) as colorless crystals.

$^1$H NMR (300 MHz, DMSO-d$_6$) δ 0.83-1.02 (6H, m), 1.19-1.34 (2H, m), 1.37-2.14 (10H, m), 3.22-3.29 (2H, m), 3.38-3.55 (2H, m, J=12.7, 6.4, 6.4, 6.4 Hz), 3.63-3.90 (3H, m), 4.21-4.34 (1H, m), 6.81-6.92 (2H, m), 7.02-7.18 (2H, m).

Example 190

9-(4-propoxyphenyl)-3,4,6,7,8,9-hexahydropyrido[2,1-c][1,2,4]thiadiazine 2,2-dioxide A mixture of 9-(4-propoxyphenyl)-3,4-dihydropyrido[2,1-c][1,2,4]thiadiazine 2,2-dioxide (300 mg) and platinum (IV) oxide (32.1 mg) in MeOH (10 mL) was stirred at room temperature under H$_2$ for 20 hr. The reaction mixture was filtered by Celite and the filtrate was concentrated in vacuo. The residue was recrystallized from EtOAc-MeOH to give the title compound (114 mg) as a white solid.

$^1$H NMR (300 MHz, DMSO-d$_6$) δ 0.97 (3H, t, J=7.4 Hz), 1.67-1.78 (5H, m), 1.90-2.03 (1H, m), 3.23-3.29 (2H, m), 3.41-3.51 (2H, m), 3.69 (1H, t, J=5.3 Hz), 3.81 (2H, q, J=5.8 Hz), 3.90 (2H, t, J=6.4 Hz), 6.86 (2H, d, J=8.7 Hz), 7.09 (2H, d, J=8.7 Hz).

mp 169-170° C.

Anal. Calcd for C$_{16}$H$_{22}$N$_2$O$_3$S-0.75H$_2$O: C, 57.21; H, 7.05; N, 8.34. Found: C, 57.21; H, 6.56; N, 8.33.

Example 191

9-(6-phenoxypyridin-3-yl)-3,4-dihydropyrido[2,1-c][1,2,4]thiadiazine 2,2-dioxide

A) 6'-fluoro-3,3'-bipyridin-2-amine

A mixture of sodium carbonate (5.79 g), tetrakis(triphenylphosphine)palladium(0) (0.631 g), 6-fluoropyridin-3- ylboronic acid (5 g) and 3-bromopyridin-2-amine (4.72 g) in DME (75 mL) and water (15 mL) was stirred at 80° C. overnight. The mixture was poured into water and extracted with EtOAc. The organic layer was separated, washed with brine, dried over anhydrous magnesium sulfate and concentrated in vacuo. The residue was purified by column chromatography (silica gel, eluted with EtOAc in hexane, then NH silica gel, eluted with EtOAc in hexane) to give the title compound (4.53 g) as a colorless solid.

MS (API+). found: 190.0

B) 6'-phenoxy-3,3'-bipyridin-2-amine

A mixture of potassium carbonate (3287 mg), phenol (821 mg) and 6'-fluoro-3,3'-bipyridin-2-amine (1500 mg) in DMSO (15 mL) was stirred for 1 hr at 150° C. The mixture was poured into water and extracted with EtOAc. The organic layer was separated, washed with brine, dried over anhydrous magnesium sulfate and concentrated in vacuo. The residue was purified by column chromatography (NH silica gel, eluted with EtOAc in hexane) to give the title compound (1750 mg) as a yellow solid.

MS (API+). found: 264.1

C) 9-(6-phenoxypyridin-3-yl)-3,4-dihydropyrido[2,1-c][1,2,4]thiadiazine 2,2-dioxide A mixture of 6'-phenoxy-3,3'-bipyridin-2-amine (350 mg) in THF (dry) (15 mL) was added to a mixture of NaH (60%, 266 mg) and 2-chloroethanesulfonyl chloride (542 mg) in THF (dry) (15.0 mL) at room temperature. The mixture was stirred at 50° C. overnight. The mixture was poured into water and extracted with EtOAc. The organic layer was separated, washed with brine, dried over anhydrous magnesium sulfate and concentrated in vacuo. The residue was purified by column chromatography (NH silica gel, eluted with MeOH in EtOAc) to give the title compound (419 mg) as a pale yellow solid. The solid was crystallized from $CH_3CN$-IPE to give a pale yellow solid.

$^1$H NMR (300 MHz, DMSO-$d_6$) δ 3.40-3.55 (2H, m), 4.57-4.71 (2H, m), 6.72 (1H, t, J=7.0 Hz), 7.08 (1H, d, J=8.7 Hz), 7.14-7.20 (2H, m), 7.20-7.28 (1H, m), 7.36-7.50 (2H, m), 7.70 (1H, dd, J=7.2, 1.5 Hz), 7.80 (1H, dd, J=6.8, 1.5 Hz), 8.03 (1H, dd, J=8.5, 2.4 Hz), 8.23 (1H, d, J=2.3 Hz).

mp 244-245° C.

Anal. Calcd for $C_{18}H_5N_3O_3S$: C, 61.18; H, 4.28; N, 11.89. Found: C, 60.98; H, 4.39; N, 11.89.

Example 192

9-(4-phenoxyphenyl)-3,4-dihydropyrido[2,1-c][1,2,4]thiadiazine 2,2-dioxide

A solution of 3-(4-phenoxyphenyl)pyridin-2-amine (301 mg) in N,N-dimethylacetoamide (3 mL) was added dropwise to 2-chloroethanesulfonyl chloride (382 mg) and additional N,N-dimethylacetoamide (2 mL) was used to complete the addition of above solution. After being stirred at 60° C. for 4 hr, the mixture was cooled to room temperature. Water (10 mL) was added dropwise to the reaction mixture and the whole was stirred at room temperature for 0.5 hr. The precipitate was collected by filtration, washed with water (10 mL) and THF (3 mL), and dried in vacuo at 60° C. to give the title compound (346.7 mg) as an off-white powder.

MS (ESI+). found: 353.2.

$^1$H NMR (300 MHz, DMSO-$d_6$) δ 3.40-3.54 (2H, m), 4.59-4.73 (2H, m), 6.65-6.79 (1H, m), 6.96-7.14 (4H, m), 7.14-7.27 (1H, m), 7.34-7.50 (2H, m), 7.50-7.60 (2H, m), 7.60-7.71 (1H, m), 7.74-7.83 (1H, m).

Example 193

9-(4-tert-butylphenyl)-3,4-dihydropyrido[2,1-c][1,2,4]thiadiazine 2,2-dioxide

A solution of 3-(4-tert-butylphenyl)pyridin-2-amine (301 mg) in N,N-dimethylacetoamide (4 mL) was added dropwise to 2-chloroethanesulfonyl chloride (437 mg) and additional N,N-dimethylacetoamide (1 mL) was used to complete the addition of above solution. After being stirred at 60° C. for 3 hr, the mixture was cooled to room temperature. Water (10 mL) was added dropwise to the reaction mixture and the whole was stirred at room temperature for 0.5 hr. The precipitate was collected by filtration, washed with water (10 mL) and diisopropyl ether (3 mL), and dried in vacuo at 60° C. to give the title compound (366 mg) as an off-white powder.

MS (ESI+). found: 317.2.

$^1$H NMR (300 MHz, DMSO-$d_6$) δ 1.31 (9H, s), 3.38-3.52 (2H, m), 4.52-4.75 (2H, m), 6.70 (1H, t, J=6.8 Hz), 7.35-7.53 (4H, m), 7.61 (1H, dd, J=7.2, 1.5 Hz), 7.76 (1H, dd, J=6.8, 1.5 Hz).

Example 194

9-(3-fluorobiphenyl-4-yl)-3,4-dihydropyrido[2,1-c][1,2,4]thiadiazine 2,2-dioxide A solution of 2-chloroethanesulfonyl chloride (208.2 mg) in N,N-dimethylacetoamide (2 mL) was added dropwise to a suspension of 3-(3-fluorobiphenyl-4-yl)pyridin-2-amine (149.5 mg) in N,N-dimethylacetoamide (2 mL) and additional N,N-dimethylacetoamide (1 mL) was used to complete the addition of above solution. After being stirred at 60° C. for 3 h, the mixture was cooled to room temperature. Water (10 mL) was added dropwise to the reaction mixture and the whole was stirred at room temperature for 0.5 hr. The precipitate was collected by filtration, washed with water (10 mL) and THF (3 mL), and dried in vacuo at 60° C. to give the title compound (143 mg) as an off-white powder.

MS (ESI+). found: 355.1.

$^1$H NMR (300 MHz, DMSO-$d_6$) δ 3.46-3.54 (2H, m), 4.63-4.72 (2H, m), 6.75 (1H, t, J=7.0 Hz), 7.39-7.64 (8H, m), 7.76 (1H, dd, J=7.2, 1.9 Hz), 7.83 (1H, dd, J=6.8, 1.5 Hz).

Example 195

9-(6-phenoxypyridin-3-yl)-3,4-dihydropyrido[2,1-c][1,2,4]thiadiazine 2,2-dioxide A solution of 2-chloroethanesulfonyl chloride (386 mg) in N,N-dimethylacetoamide (2 mL) was added dropwise to a solution of 6'-phenoxy-3,3'-bipyridin-2-amine (302 mg) in N,N-dimethylacetoamide (2 mL) and additional N,N-dimethylacetoamide (1 mL) was used to complete the addition of above solution. After being stirred at 60° C. for 4 h, the mixture was cooled to room temperature. Water (10 mL) was added dropwise to the reaction mixture and the whole was stirred at room temperature for 0.5 hr. The precipitate was collected by filtration, washed with water (10 mL) and diisopropyl ether (3 mL), and dried in vacuo at 60° C. to give the title compound (323 mg) as an off-white powder.

MS (ESI+). found: 354.2.

$^1$H NMR (300 MHz, DMSO-d$_6$) δ3.40-3.55 (2H, m), 4.57-4.71 (2H, m), 6.72 (1H, t, J=7.0 Hz), 7.08 (1H, d, J=8.7 Hz), 7.14-7.20 (2H, m), 7.20-7.28 (1H, m), 7.36-7.50 (2H, m), 7.70 (1H, dd, J=7.2, 1.5 Hz), 7.80 (1H, dd, J=6.8, 1.5 Hz), 8.03 (1H, dd, J=8.5, 2.4 Hz), 8.23 (1H, d, J=2.3 Hz).

Example 196

9-[4-(cyclohexyloxy)phenyl]-3,4-dihydropyrido[2,1-c][1,2,4]thiadiazine 2,2-dioxide A solution of 2-chloroethanesulfonyl chloride (381 mg) in N,N-dimethylacetoamide (2 mL) was added dropwise to a suspension of 3-[4-(cyclohexyloxy)phenyl]pyridin-2-amine (301 mg) in N,N-dimethylacetoamide (2 mL) and additional N,N-dimethylacetoamide (1 mL) was used to complete the addition of above solution. After being stirred at 60° C. for 3 hr, the mixture was cooled to room temperature. Water (10 mL) was added dropwise to the reaction mixture and the whole was stirred at room temperature for 0.5 hr. The precipitate was collected by filtration, washed with water (10 mL) and diisopropyl ether (3 mL), and dried in vacuo at 60° C. to give the title compound (342 mg) as an off-white powder.

MS (ESI+). found: 359.2.

$^1$H NMR (300 MHz, DMSO-d$_6$) δ 1.19-1.59 (6H, m), 1.67-1.80 (2H, m), 1.88-2.01 (2H, m), 3.39-3.50 (2H, m), 4.31-4.45 (1H, m), 4.58-4.70 (2H, m), 6.68 (1H, t, J=7.0 Hz), 6.95 (2H, d, J=8.7 Hz), 7.44 (2H, d, J=8.7 Hz), 7.58 (1H, dd, J=7.2, 1.5 Hz), 7.70-7.79 (1H, m).

Example 197

9-[4-(4-methylphenoxy)phenyl]-3,4-dihydropyrido[2,1-c][1,2,4]thiadiazine 2,2-dioxide A) 9-[4-(4-methylphenoxy)phenyl]-3,4-dihydropyrido[2,1-c][1,2,4]thiadiazine 2,2-dioxide 2-Chloroethanesulfonyl chloride (0.885 g) in N,N-dimethylacetoamide (7.0 mL) was added dropwise to a solution of 3-[4-(4-methylphenoxy)phenyl]pyridin-2-amine (1.00 g) in N,N-dimethylacetoamide (3.0 mL) at 0° C. The mixture was stirred at 70° C. under N$_2$ overnight. EtOAc and IPE was added dropwise to the mixture at room temperature. The solid was isolated by filtration and washed with water, IPE and EtOAc to give the title compound (1.07 g) as a gray solid.

B) 9-[4-(4-methylphenoxy)phenyl]-3,4-dihydropyrido[2,1-c][1,2,4]thiadiazine 2,2-dioxide 9-[4-(4-Methylphenoxy)phenyl]-3,4-dihydropyrido[2,1-c][1,2,4]thiadiazine 2,2-dioxide was crystallized from DMSO-EtOH to give the title compound (0.870 g) as colorless crystals.

MS (ESI+). found: 367.1.

$^1$H NMR (300 MHz, DMSO-d$_6$) δ 2.30 (3H, s), 3.39-3.53 (2H, m), 4.58-4.73 (2H, m), 6.70 (1H, t, J=7.0 Hz), 6.98 (4H, dd, J=8.9, 3.2 Hz), 7.22 (2H, d, J=8.3 Hz), 7.51 (2H, d, J=9.0 Hz), 7.61 (1H, dd, J=7.2, 1.5 Hz), 7.76 (1H, dd, J=6.8, 1.5 Hz).

Example 198

4-[4-(2,2-dioxido-3,4-dihydropyrido[2,1-c][1,2,4]thiadiazin-9-yl)phenoxy]phenol

A) 9-[4-(4-{[tert-butyl(dimethyl)silyl]oxy}phenoxy)phenyl]-3,4-dihydropyrido[2,1-c][1,2,4]thiadiazine 2,2-dioxide A mixture of 4-(tert-butyldimethylsilyloxy)phenylboronic acid (6.11 g), 4-(2,2-dioxido-3,4-dihydropyrido[2,1-c][1,2,4]thiadiazin-9-yl)phenol (2.23 g), triethylamine (5.61 mL), diacetoxycopper (2.93 g), and 4A MS (2.0 g) in DMF (80 mL) was stirred at room temperature overnight. The mixture was added with silica gel, concentrated in vacuo, and purified by column chromatography (silica gel, eluted with EtOAc in hexane) to give the title compound (1.82 g) as a white solid.

MS (ESI+). found: 483.2.

B) 4-[4-(2,2-dioxido-3,4-dihydropyrido[2,1-c][1,2,4]thiadiazin-9-yl)phenoxy]phenol A solution of 9-[4-(4-{[tert-butyl(dimethyl)silyl]oxy}phenoxy)phenyl]-3,4-dihydropyrido[2,1-c][1,2,4]thiadiazine 2,2-dioxide (1.82 g) in THF (dry) (55 mL) was added to tetrabutylammonium fluoride (1 M in THF) (6.79 mL) at room temperature. After stirring for 0.5 hr, the mixture was added with sat.NH$_4$Cl aq. and silica gel, then concentrated in vacuo. The residue was purified by column chromatography (silica gel, eluted with EtOAc in hexane then MeOH in EtOAc), recrystallized from THF-IPE, then preparative HPLC (C18, eluent; H$_2$O/MeCN with 0.1% TFA). The collected fraction was concentrated in vacuo. The residue was recrystallized from MeCN—H$_2$O to give the title compound (492 mg) as a white solid.

$^1$H NMR (300 MHz, DMSO-d$_6$) δ 3.41-3.49 (2H, m), 4.60-4.68 (2H, m), 6.69 (1H, t, J=7.0 Hz), 6.77-6.84 (2H, m), 6.87-6.97 (4H, m), 7.44-7.50 (2H, m), 7.59 (1H, dd, J=7.2, 1.9 Hz), 7.75 (1H, dd, J=6.8, 1.9 Hz), 9.39 (1H, s).

mp 289-290° C.

Anal. Calcd for C$_{19}$H$_{16}$N$_2$O$_4$S: C, 61.94; H, 4.38; N, 7.60. Found: C, 61.86; H, 4.42; N, 7.64.

Example 199

9-[4-(4-fluorophenoxy)phenyl]-3,4-dihydropyrido[2,1-c][1,2,4]thiadiazine 2,2-dioxide A mixture of 4-fluorophenylboronic acid (365 mg), 4-(2,2-dioxido-3,4-dihydropyrido[2,1-c][1,2,4]thiadiazin-9-yl)phenol (240 mg), diacetoxycopper (316 mg), triethylamine (0.60 mL), and powdered 4A MS (1.5 g) in DMF (10 mL) was stirred at room temperature overnight. The mixture was added with NH silica gel, concentrated in vacuo, and purified by column chromatography (NH silica gel, eluted with MeOH in EtOAc) to give the title compound (139 mg) as a white solid.

$^1$H NMR (300 MHz, DMSO-d$_6$) δ 3.42-3.49 (2H, m), 4.61-4.68 (2H, m), 6.67-6.73 (1H, m), 7.00 (2H, d, J=8.7 Hz), 7.10-7.30 (4H, m), 7.53 (2H, d, J=8.7 Hz), 7.62 (1H, dd, J=7.2, 1.5 Hz), 7.73-7.81 (1H, m).

mp 266-267° C.

Anal. Calcd for C$_{19}$H$_5$N$_2$O$_3$SF: C, 61.61; H, 4.08; N, 7.56. Found: C, 61.67; H, 4.17; N, 7.60.

Example 200

9-{4-[4-(trifluoromethyl)phenoxy]phenyl}-3,4-dihydropyrido[2,1-c][1,2,4]thiadiazine 2,2-dioxide A mixture of 4-(trifluoromethyl)phenylboronic acid (495 mg), 4-(2,2-dioxido-3,4-dihydropyrido[2,1-c][1,2,4]thiadiazin-9-yl)phenol (240 mg), diacetoxycopper (316 mg), triethylamine (0.60 mL), and powdered 4A MS (1.5 g) in DMF (10 mL) was stirred at room temperature overnight. The mixture was added with NH silica gel, concentrated in vacuo, and purified by column chromatography (NH silica gel, eluted with MeOH in EtOAc) to give the title compound (45 mg) as a white solid.

$^1$H NMR (300 MHz, DMSO-d$_6$) δ 3.43-3.51 (2H, m), 4.62-4.70 (2H, m), 6.72 (1H, t, J=7.0 Hz), 7.14-7.26 (4H, m), 7.58-7.69 (3H, m), 7.72-7.82 (3H, m).

mp 253-255° C.

Anal. Calcd for $C_{20}H_5N_2O_3SF_3$: C, 57.14; H, 3.60; N, 6.66. Found: C, 57.21; H, 3.73; N, 6.68.

Example 201

9-[4-(3-chlorophenoxy)phenyl]-3,4,6,7,8,9-hexahydropyrido[2,1-c][1,2,4]thiadiazine 2,2-dioxide A mixture of 3-chlorophenylboronic acid (167 mg), 4-(2,2-dioxido-3,4,6,7,8,9-hexahydropyrido[2,1-c][1,2,4]thiadiazin-9-yl)phenol (100 mg), diacetoxycopper (130 mg), triethylamine (0.248 mL), and powdered 4A MS (1.00 g) in MeCN (10 mL) was stirred at room temperature overnight. The mixture was added with NH silica gel, concentrated in vacuo, and purified by column chromatography (NH silica gel, eluted with MeOH in EtOAc), and then recrystallized from EtOAc-IPE to give the title compound (37.0 mg) as a white solid.

$^1$H NMR (300 MHz, DMSO-d$_6$) δ 1.67-1.83 (3H, m), 1.96-2.08 (1H, m), 3.24-3.29 (2H, m), 3.42-3.53 (2H, m), 3.75-3.87 (3H, m), 6.94-7.04 (3H, m), 7.07 (1H, t, J=2.3 Hz), 7.16-7.29 (3H, m), 7.36-7.45 (1H, m).

mp 165-167° C.

Anal. Calcd for $C_{19}H_{19}N_2O_3SCl$: C, 58.38; H, 4.90; N, 7.17. Found: C, 58.38; H, 5.03; N, 6.96.

Example 202

(9R)-9-[4-(3-chlorophenoxy)phenyl]-3,4,6,7,8,9-hexahydropyrido[2,1-c][1,2,4]thiadiazine 2,2-dioxide A) (9S)-9-(4-((tert-butyldimethylsilyl)oxy)phenyl)-3,4,6,7,8,9-hexahydropyrido[2,1-c][1,2,4]thiadiazine 2,2-dioxide (9R)-9-(4-((tert-butyldimethylsilyl)oxy)phenyl)-3,4,6,7,8,9-hexahydropyrido[2,1-c][1,2,4]thiadiazine 2,2-dioxide 9-(4-((tert-Butyldimethylsilyl)oxy)phenyl)-3,4,6,7,8,9-hexahydropyrido[2,1-c][1,2,4]thiadiazine 2,2-dioxide (28.8 g) was separated by preparative HPLC (column; CHIRALPAK AS (CC001), 50 mmID×500 mmL, DAICEL CHEMICAL INDUSTRIES, LTD., eluent; MeCN/2-propanol=100/900) to give (9S)-9-(4-((tert-butyldimethylsilyl)oxy)phenyl)-3,4,6,7,8,9-hexahydropyrido[2,1-c][1,2,4]thiadiazine 2,2-dioxide (13.7 g) as a white solid and (9R)-9-(4-((tert-butyldimethylsilyl)oxy)phenyl)-3,4,6,7,8,9-hexahydropyrido[2,1-c][1,2,4]thiadiazine 2,2-dioxide (11.8 g) as a white solid.

(9S)-9-(4-((tert-butyldimethylsilyl)oxy)phenyl)-3,4,6,7,8,9-hexahydropyrido[2,1-c][1,2,4]thiadiazine 2,2-dioxide MS (ESI+). found: 395.2.

(9R)-9-(4-((tert-butyldimethylsilyl)oxy)phenyl)-3,4,6,7,8,9-hexahydropyrido[2,1-c][1,2,4]thiadiazine 2,2-dioxide MS (ESI+). found: 395.2.

B) (9R)-9-(4-hydroxyphenyl)-3,4,6,7,8,9-hexahydropyrido[2,1-c][1,2,4]thiadiazine 2,2-dioxide A mixture of (9R)-9-(4-((tert-butyldimethylsilyl)oxy)phenyl)-3,4,6,7,8,9-hexahydropyrido[2,1-c][1,2,4]thiadiazine 2,2-dioxide (11.8 g) and 6 M HCl aq. (15.0 mL) in MeOH (100 mL) was stirred at 60° C. for 2 hr. After cooling to room temperature, the precipitate was collected and washed with MeOH to give the title compound (8.04 g) as a white solid.

MS (ESI+). found: 281.0.

C) (9R)-9-[4-(3-chlorophenoxy)phenyl]-3,4,6,7,8,9-hexahydropyrido[2,1-c][1,2,4]thiadiazine 2,2-dioxide A mixture of 3-chlorophenylboronic acid (167 mg), (9R)-9-(4-hydroxyphenyl)-3,4,6,7,8,9-hexahydropyrido[2,1-c][1,2,4]thiadiazine 2,2-dioxide (100 mg), diacetoxycopper (130 mg), triethylamine (0.248 mL), and powdered 4A MS (1.50 g) in DMF (10 mL) was stirred at room temperature overnight. The mixture was added with NH silica gel, concentrated in vacuo, and purified by column chromatography (NH silica gel, eluted with MeOH in EtOAc) to give the title compound (32.0 mg) as a white solid.

$^1$H NMR (300 MHz, DMSO-d$_6$) δ 1.70-1.80 (3H, m), 1.95-2.06 (1H, m), 3.23-3.29 (2H, m), 3.48 (2H, q, J=6.3 Hz), 3.76-3.86 (3H, m), 6.94-7.03 (3H, m), 7.07 (1H, t, J=2.3 Hz), 7.15-7.28 (3H, m), 7.36-7.46 (1H, m).

Example 203

(9S)-9-[4-(3-chlorophenoxy)phenyl]-3,4,6,7,8,9-hexahydropyrido[2,1-c][1,2,4]thiadiazine 2,2-dioxide A) 4-[(9S)-2,2-dioxido-3,4,6,7,8,9-hexahydropyrido[2,1-c][1,2,4]thiadiazin-9-yl]phenol A mixture of (9S)-9-(4-((tert-butyldimethylsilyl)oxy)phenyl)-3,4,6,7,8,9-hexahydropyrido[2,1-c][1,2,4]thiadiazine 2,2-dioxide (13.7 g) and 6 M HCl aq. (17.4 mL) in MeOH (350 mL) was stirred at 60° C. for 2 hr. After cooling to room temperature, the precipitate was collected and washed with MeOH to give the title compound (8.20 g) as a white solid.

MS (ESI+). found: 281.0.

B) (9S)-9-[4-(3-chlorophenoxy)phenyl]-3,4,6,7,8,9-hexahydropyrido[2,1-c][1,2,4]thiadiazine 2,2-dioxide A mixture of (3-chlorophenyl)boronic acid (167 mg), 4-[(9S)-2,2-dioxido-3,4,6,7,8,9-hexahydropyrido[2,1-c][1, 2,4]thiadiazin-9-yl]phenol (100 mg), diacetoxycopper (130 mg), triethylamine (0.248 mL), and powdered 4A MS (1.50 g) in DMF (10 mL) was stirred at room temperature overnight. The mixture was added with NH silica gel, concentrated in vacuo, and purified by column chromatography (NH silica gel, eluted with MeOH in EtOAc) to give the title compound (34.0 mg) as a white solid.

$^1$H NMR (300 MHz, DMSO-$d_6$) δ 1.71-1.80 (3H, m), 2.02 (1H, d, J=6.1 Hz), 3.24-3.29 (2H, m), 3.48 (2H, q, J=6.4 Hz), 3.76-3.86 (3H, m), 6.94-7.03 (3H, m), 7.07 (1H, t, J=2.3 Hz), 7.17-7.28 (3H, m), 7.36-7.45 (1H, m).

Anal. Calcd for $C_{19}H_{19}N_2O_3SCl$: C, 58.38; H, 4.90; N, 7.17. Found: C, 58.39; H, 4.91; N, 7.11.

Example 204

8-methoxy-9-(4-phenoxyphenyl)-3,4-dihydropyrido [2,1-c][1,2,4]thiadiazine 2,2-dioxide A) 4-methoxy-3-(4-phenoxyphenyl)pyridin-2-amine A mixture of sodium carbonate (122 mg), tetrakis(triphenylphosphine)palladium(0) (33.2 mg), 4-phenoxyphenylboronic acid (160 mg) and 3-iodo-4-methoxypyridin-2-amine (144 mg) in DME (10 mL) and water (3 mL) was stirred at 80° C. overnight. The mixture was added with silica gel, concentrated in vacuo, and purified by column chromatography (silica gel, eluted with EtOAc in hexane) to give the title compound (124 mg) as a pale yellow solid.

MS (ESI+). found: 293.1.

B) 8-methoxy-9-(4-phenoxyphenyl)-3,4-dihydropyrido[2,1-c][1,2,4]thiadiazine 2,2-dioxide A solution of 4-methoxy-3-(4-phenoxyphenyl)pyridin-2-amine (124 mg) in THF (dry) (5 mL) was added to a suspension of NaH (60%, 85.0 mg) and 2-chloroethanesulfonyl chloride (0.133 mL) in THF (dry) (5 mL) at 0° C. The mixture was stirred at room temperature overnight. Water and hexane were added to give a white precipitate. The precipitate was collected by filtration and washed with water and EtOAc then crystallized from THF-IPE to give the title compound (60.0 mg) as a white solid.

$^1$H NMR (300 MHz, DMSO-$d_6$) δ 3.32-3.39 (2H, m), 3.81 (3H, s), 4.52-4.65 (2H, m), 6.79 (1H, d, J=8.0 Hz), 6.96 (2H, d, J=8.7 Hz), 7.05-7.25 (5H, m), 7.36-7.49 (2H, m), 7.87 (1H, d, J=7.6 Hz).

mp 269-270° C.

Anal. Calcd for $C_{20}H_8N_2O_4S$-0.25$H_2O$: C, 62.08; H, 4.82; N, 7.24. Found: C, 62.08; H, 4.76; N, 7.23.

Example 205

8-chloro-9-(4-phenoxyphenyl)-3,4-dihydropyrido[2,1-c][1,2,4]thiadiazine 2,2-dioxide A) 4-chloro-3-(4-phenoxyphenyl)pyridin-2-amine A mixture of sodium carbonate (122 mg), tetrakis(triphenylphosphine)palladium(0) (33.2 mg), 4-phenoxyphenylboronic acid (160 mg) and 4-chloro-3-iodopyridin-2-amine (146 mg) in DME (10 mL) and water (3 mL) was stirred at 80° C. overnight. The mixture was added with silica gel, concentrated in vacuo, and purified by column chromatography (silica gel, eluted with EtOAc in hexane) to give the title compound (111 mg) as a pale yellow solid.

MS (ESI+). found: 297.1.

B) 8-chloro-9-(4-phenoxyphenyl)-3,4-dihydropyrido [2,1-c][1,2,4]thiadiazine 2,2-dioxide A solution of 4-chloro-3-(4-phenoxyphenyl)pyridin-2-amine (124 mg) in THF (dry) (5 mL) was added to a suspension of NaH (60%, 84.0 mg) and 2-chloroethanesulfonyl chloride (0.131 mL) in THF (dry) (5 mL) at 0° C. The mixture was stirred at room temperature overnight. Water and hexane were added to give a white precipitate. The precipitate was collected by filtration and washed with water and EtOAc, and then crystallized from THF-IPE to give the title compound (60.0 mg) as a white solid.

$^1$H NMR (300 MHz, DMSO-$d_6$) δ 3.39-3.49 (2H, m), 4.57-4.67 (2H, m), 6.86 (1H, d, J=7.2 Hz), 6.99-7.25 (7H, m), 7.39-7.49 (2H, m), 7.80 (1H, d, J=7.6 Hz).

mp 283-284° C.

Anal. Calcd for $C_{19}H_5ClN_2O_3S$-0.25$H_2O$-0.25AcOEt: C, 58.11; H, 4.27; N, 6.78.

Found: C, 58.26; H, 4.08; N, 6.81.

Example 206

7-fluoro-9-(4-phenoxyphenyl)-3,4-dihydropyrido[2,1-c][1,2,4]thiadiazine 2,2-dioxide A) 5-fluoro-3-(4-phenoxyphenyl)pyridin-2-amine A mixture of sodium carbonate (122 mg), tetrakis(triphenylphosphine)palladium(0) (33.2 mg), 4-phenoxyphenylboronic acid (160 mg) and 3-bromo-5-fluoropyridin-2-amine (110 mg) in DME (10 mL) and water (3 mL) was stirred at 80° C. overnight. The mixture was added with silica gel, concentrated in vacuo, and purified by column chromatography (silica gel, eluted with EtOAc in hexane) to give the title compound (132 mg) as a pale yellow solid.

MS (ESI+). found: 281.1.

B) 7-fluoro-9-(4-phenoxyphenyl)-3,4-dihydropyrido [2,1-c][1,2,4]thiadiazine 2,2-dioxide A solution of 5-fluoro-3-(4-phenoxyphenyl)pyridin-2-amine (124 mg) in THF (dry) (5 mL) was added to a suspension of NaH (60%, 88.0 mg) and 2-chloroethanesulfonyl chloride (0.139 mL) in THF (dry) (5 mL) at 0° C. The mixture was stirred at room temperature overnight. Water and hexane were added to give a white precipitate. The precipitate was collected by filtration and washed with water and EtOAc, then recrystallized from EtOAc-EtOH to give the title compound (29.0 mg) as a white solid.

$^1$H NMR (300 MHz, DMSO-$d_6$) δ 3.41-3.51 (2H, m), 4.57-4.65 (2H, m), 7.00-7.12 (4H, m), 7.15-7.24 (1H, m), 7.38-7.48 (2H, m), 7.60 (2H, d, J=8.7 Hz), 7.84 (1H, dd, J=8.3, 3.0 Hz), 8.04-8.14 (1H, m).

mp 91.9-92.0° C.

Anal. Calcd for $C_{19}H_{15}N_2O_3SF$-1.0$H_2O$: C, 58.75; H, 4.41; N, 7.21. Found: C, 58.85; H, 4.05; N, 6.82.

Example 207

7-methyl-9-(4-phenoxyphenyl)-3,4-dihydropyrazino [2,1-c][1,2,4]thiadiazine 2,2-dioxide A) 5-methyl-3-(4-phenoxyphenyl)pyrazin-2-amine A mixture of sodium carbonate (122 mg), tetrakis(triphenylphosphine)palladium(0) (33.2 mg), 4-phenoxyphenylboronic acid (160 mg) and 3-bromo-5-methylpyrazin-2- amine (108 mg) in DME (10 mL) and water (3 mL) was stirred at 80° C. overnight. The mixture was added with silica gel, concentrated in vacuo, and purified by column chromatography (silica gel, eluted with EtOAc in hexane) to give the title compound (148 mg) as a pale yellow solid.

MS (ESI+). found: 278.1.

B) 7-methyl-9-(4-phenoxyphenyl)-3,4-dihydropyrazino[2,1-c][1,2,4]thiadiazine 2,2-dioxide A solution of 5-methyl-3-(4-phenoxyphenyl)pyrazin-2-amine (124 mg) in THF (dry) (5 mL) was added to a suspension of NaH (60%, 89.0 mg) and 2-chloroethanesulfonyl chloride (0.140 mL) in THF (dry) (5 mL) at 0° C. The mixture was stirred at room temperature overnight. Water and hexane were added to give a white precipitate. The precipitate was collected by filtration and washed with water and EtOAc then recrystallized from EtOAc-EtOH to give the title compound (86.0 mg) as a white solid.

$^1$H NMR (300 MHz, DMSO-d$_6$) δ 2.30 (3H, s), 3.46-3.56 (2H, m), 4.54-4.63 (2H, m), 7.01-7.13 (4H, m), 7.16-7.24 (1H, m), 7.39-7.49 (2H, m), 7.57 (1H, s), 7.98-8.07 (2H, m).

mp 92.0-92.5° C.

Anal. Calcd for $C_{19}H_7N_3O_3S$-0.5H$_2$O: C, 60.62; H, 4.82; N, 11.16. Found: C, 60.67; H, 4.61; N, 10.87.

Example 208

9-[3-chloro-4-(1-methylethoxyl)phenyl]-3,4-dihydropyrido[2,1-c][1,2,4]thiadiazine 2,2-dioxide

A) 3-(3-chloro-4-isopropoxyphenyl)pyridin-2-amine

A mixture of sodium carbonate (760 mg), tetrakis(triphenylphosphine)palladium(0) (207 mg), 3-chloro-4-isopropoxyphenylboronic acid (1.00 g) and 3-bromopyridin-2-amine (621 mg) in DME (10 mL) and water (3 mL) was stirred at 80° C. overnight. The mixture was added with silica gel, concentrated in vacuo, and purified by column chromatography (silica gel, eluted with EtOAc in hexane) to give the title compound (770 mg) as a pale yellow solid.

MS (ESI+). found: 264.2.

B) 9-[3-chloro-4-(1-methylethoxyl)phenyl]-3,4-dihydropyrido[2,1-c][1,2,4]thiadiazine 2,2-dioxide A solution of 3-(3-chloro-4-isopropoxyphenyl)pyridin-2-amine (770 mg) in THF (dry) (10 mL) was added to a suspension of NaH (60%, 586 mg) and 2-chloroethanesulfonyl chloride (0.919 mL) in THF (dry) (10 mL) at 0° C. The mixture was stirred at room temperature overnight. Water and hexane were added to give a white precipitate. The precipitate was collected by filtration, washed with water and EtOAc and crystallized from THF-IPE to give the title compound (600 mg) as a white solid.

$^1$H NMR (300 MHz, DMSO-d$_6$) δ 1.32 (6H, d, J=6.0 Hz), 3.43-3.50 (2H, m), 4.60-4.79 (3H, m), 6.70 (1H, t, J=7.0 Hz), 7.21 (1H, d, J=8.7 Hz), 7.44 (1H, dd, J=8.7, 2.3 Hz), 7.61 (1H, d, J=2.3 Hz), 7.64 (1H, dd, J=7.2, 1.9 Hz), 7.77 (1H, dd, J=6.6, 1.7 Hz).

mp 239-240° C.

Anal. Calcd for $C_{16}H_7N_2O_3SCl$: C, 54.46; H, 4.86; N, 7.94. Found: C, 54.28; H, 4.86; N, 7.86.

Example 209

9-(4-butoxyphenyl)-3,4-dihydropyrido[2,1-c][1,2,4]thiadiazine 2,2-dioxide

A) 3-(4-butoxyphenyl)pyridin-2-amine

A mixture of sodium carbonate (0.978 g), tetrakis(triphenylphosphine)palladium(0) (0.267 g), 4-butoxyphenylboronic acid (1.16 g) and 3-bromopyridin-2-amine (0.799 g,) in DME (23 mL) and water (4.6 mL) was stirred at 80° C. overnight. The mixture was added with silica gel, concentrated in vacuo, and purified by column chromatography (silica gel, eluted with EtOAc in hexane) to give the title compound (0.690 g) as a pale yellow solid.

MS (ESI+). found: 243.1.

B) 9-(4-butoxyphenyl)-3,4-dihydropyrido[2,1-c][1,2,4]thiadiazine 2,2-dioxide A solution of 3-(4-butoxyphenyl)pyridin-2-amine (690 mg) in THF (dry) (5 mL) was added to a suspension of NaH (60%, 569 mg) and 2-chloroethanesulfonyl chloride (0.893 mL) in THF (dry) (5 mL) at 0° C. The mixture was stirred at room temperature overnight. Water and hexane were added to give a white precipitate. The precipitate was collected by filtration and washed with water and EtOAc, and then recrystallized from IPE-EtOH to give the title compound (502 mg) as a white solid.

$^1$H NMR (300 MHz, DMSO-d$_6$) δ 0.94 (3H, t, J=7.4 Hz), 1.38-1.52 (2H, m), 1.65-1.78 (2H, m), 3.39-3.49 (2H, m), 4.01 (2H, t, J=6.4 Hz), 4.59-4.69 (2H, m), 6.68 (1H, t, J=7.0 Hz), 6.93-6.99 (2H, m), 7.42-7.49 (2H, m), 7.58 (1H, dd, J=7.2, 1.5 Hz), 7.73 (1H, dd, J=6.8, 1.9 Hz).

mp 230-232° C.

Anal. Calcd for $C_{17}H_{20}N_2O_3S$-0.1IPE: C, 61.69; H, 6.30; N, 8.18. Found: C, 61.85; H, 6.34; N, 8.01.

Example 210

9-(4-phenoxyphenyl)-3,4-dihydropyrazino[2,1-c][1,2,4]thiadiazine 2,2-dioxide

A) 3-(4-phenoxyphenyl)pyrazin-2-amine

Tetrakis(triphenylphosphine)palladium(0) (0.268 g) was added to a suspension of 3-chloropyrazin-2-amine (1.00 g), 4-phenoxyphenylboronic acid (2.15 g) and sodium carbonate (1.64 g) in DME (37.5 mL) and water (7.5 mL) and the mixture was stirred at 80° C. under N$_2$ for 4 hr. The reaction mixture was added with water and EtOAc. The organic layer was separated, washed with brine, dried over anhydrous magnesium sulfate and concentrated in vacuo. The residue was purified by column chromatography (silica gel, eluted with EtOAc in hexane) to give the title compound (1.97 g) as a white solid.

MS (ESI+). found: 264.1.

B) 9-(4-phenoxyphenyl)-3,4-dihydropyrazino[2,1-c][1,2,4]thiadiazine 2,2-dioxide A solution of 3-(4-phenoxyphenyl)pyrazin-2-amine (1.97 g) in THF (dry) (20 mL) was added to a suspension of NaH (60%, 1.50 g) and 2-chloroethanesulfonyl chloride (2.35 mL) in THF (dry) (20 mL) at 0° C. The mixture was stirred at room temperature overnight then at 80° C. for 4 hr. After cooling to room temperature, the mixture was added with water and EtOAc. The precipitate was collected by filtration, washed with water and EtOAc, and then recrystallized from EtOH-EtOAc to give the title compound (1.68 g) as a pale yellow solid.

$^1$H NMR (300 MHz, DMSO-$d_6$) δ 3.51-3.60 (2H, m), 4.59-4.67 (2H, m), 7.02-7.14 (4H, m), 7.17-7.24 (1H, m), 7.39-7.48 (2H, m), 7.65-7.76 (2H, m), 7.99-8.07 (2H, m).

Anal. Calcd for $C_{18}H_{15}N_3O_3S$-0.5$H_2O$: C, 59.66; H, 4.45; N, 11.59. Found: C, 59.50; H, 4.33; N, 11.40.

Example 211

9-(4-phenoxyphenyl)-3,4,6,7,8,9-hexahydropyrazino[2,1-c][1,2,4]thiadiazine 2,2-dioxide A mixture of 9-(4-phenoxyphenyl)-3,4-dihydropyrazino[2,1-c][1,2,4]thiadiazine 2,2-dioxide (96.0 mg), and platinum(IV) oxide (15.0 mg) in EtOH (5 mL) was stirred at room temperature for 2.5 hr under $H_2$. The mixture was added with NH silica gel, concentrated, purified by column chromatography (NH silica gel, eluted with MeOH in EtOAc), then recrystallized from EtOAc-IPE to give the title compound (32.0 mg) as white powder.

$^1$H NMR (300 MHz, DMSO-$d_6$) δ 2.85-2.95 (2H, m), 3.01-3.09 (1H, m), 3.26-3.43 (4H, m), 3.75-3.88 (2H, m), 4.49 (1H, d, J=4.9 Hz), 6.91-7.06 (4H, m), 7.10-7.20 (1H, m), 7.30-7.45 (4H, m). Anal. Calcd for $C_{18}H_9N_3O_3S$-0.2$H_2O$: C, 59.88; H, 5.42; N, 11.64. Found: C, 60.13; H, 5.52; N, 11.46.

Example 212

(9S)-(4-phenoxyphenyl)-3,4,6,7,8,9-hexahydropyrazino[2,1-c][1,2,4]thiadiazine 2,2-dioxide Example 213

(9R)-9-(4-phenoxyphenyl)-3,4,6,7,8,9-hexahydropyrazino[2,1-c][1,2,4]thiadiazine 2,2-dioxide A mixture of 9-(4-phenoxyphenyl)-3,4-dihydropyrazino[2,1-c][1,2,4]thiadiazine 2,2-dioxide (1.24 g), and platinum (IV) oxide (124 mg) in EtOH (20 mL) was stirred at room temperature for 20 hr under $H_2$. The mixture was filtered by Celite, and the filtrate was concentrated in vacuo. The residue was separated by SFC (column; CHIRALPAK IC (MB001), 20 mmID×250 mmL, DAICEL CHEMICAL INDUSTRIES, LTD., eluent; $CO_2$/MeOH=660/340) to give two materials (retention time; short (510 mg) and retention time; long (420 mg)). The material (retention time; short) (510 mg) was recrystallized from MeOH-IPE to give (9S)-(4-phenoxyphenyl)-3,4,6,7,8,9-hexahydropyrazino[2,1-c][1,2,4]thiadiazine 2,2-dioxide (386 mg) as a white solid. The material (retention time; long)(420 mg) was recrystallized from MeOH-EtOAc to give (9R)-9-(4-phenoxyphenyl)-3,4,6,7,8,9-hexahydropyrazino[2,1-c][1,2,4]thiadiazine 2,2-dioxide (149 mg) as a white solid.

(9S)-(4-phenoxyphenyl)-3,4,6,7,8,9-hexahydropyrazino[2,1-c][1,2,4]thiadiazine 2,2-dioxide $^1$H NMR (300 MHz, DMSO-$d_6$) δ 2.85-2.93 (2H, m), 3.02-3.11 (1H, m), 3.25-3.31 (2H, m), 3.35-3.42 (2H, m), 3.76-3.86 (2H, m), 4.48 (1H, d, J=4.5 Hz), 6.93-7.05 (4H, m), 7.11-7.19 (1H, m), 7.32-7.44 (4H, m).
mp 124-125° C.

Anal. Calcd for $C_{18}H_9N_3O_3S$-0.25$H_2O$: C, 59.73; H, 5.43; N, 11.61.
Found: C, 59.62; H, 5.57; N, 11.40.

(9R)-9-(4-phenoxyphenyl)-3,4,6,7,8,9-hexahydropyrazino[2,1-c][1,2,4]thiadiazine 2,2-dioxide $^1$H NMR (300 MHz, DMSO-$d_6$) δ 2.83-2.94 (2H, m), 3.01-3.10 (1H, m), 3.25-3.31 (2H, m), 3.34-3.43 (2H, m), 3.75-3.87 (2H, m), 4.49 (1H, d, J=4.5 Hz), 6.93-7.06 (4H, m), 7.11-7.19 (1H, m), 7.31-7.45 (4H, m).
mp 124-125° C.
Anal. Calcd for $C_{18}H_{19}N_3O_3S$: C, 60.49; H, 5.36; N, 11.76. Found: C, 60.25; H, 5.56; N, 11.60.

Example 214

4-[(9S)-2,2-dioxido-3,4,6,7,8,9-hexahydropyrido[2,1-c][1,2,4]thiadiazin-9-yl]phenyl trifluoromethanesulfonate To a suspension of 4-[(9S)-2,2-dioxido-3,4,6,7,8,9-hexahydropyrido[2,1-c][1,2,4]thiadiazin-9-yl]phenol (1.00 g) and potassium carbonate (1.23 g) in DMF (dry)(30 mL) was added trifluoromethanesulfonyl chloride (0.939 mL) at 0° C. The mixture was stirred at 0° C. for 5 min then at room temperature for 2 hr. The mixture was added with water. The resulting precipitate was collected, washed with water, and dried at 60° C. in vacuo to give the title compound (1.27 g) as a white solid.

$^1$H NMR (300 MHz, DMSO-$d_6$) δ 1.69-1.84 (3H, m), 2.01 (1H, dd, J=8.7, 5.3 Hz), 3.23-3.34 (2H, m), 3.39-3.57 (2H, m), 3.72-3.95 (3H, m), 7.24-7.55 (4H, m).
Anal. Calcd for $C_{14}H_{15}N_2O_5S_2F_3$: C, 40.77; H, 3.67; N, 6.79. Found: C, 40.85; H, 3.69; N, 6.72.

Example 215

(9S)-9-[4-(4-chloro-2-methylphenoxy)phenyl]-3,4,6,7,8,9-hexahydropyrido[2,1-c][1,2,4]thiadiazine 2,2-dioxide A mixture of (4-chloro-2-methylphenyl)boronic acid (912 mg), 4-[(9S)-2,2-dioxido-3,4,6,7,8,9-hexahydropyrido[2,1-c][1,2,4]thiadiazin-9-yl]phenol (500 mg), pyridine (3.60 mL), cesium carbonate (581 mg), diacetoxycopper (648 mg) and powdered 4A MS (5.00 g) in MeCN (18 mL) was stirred at room temperature overnight. The mixture was added with NH silica gel, concentrated in vacuo, and purified by column chromatography (NH silica gel, eluted with MeOH in EtOAc) to give the title compound (37.0 mg) as a white solid.

$^1$H NMR (300 MHz, DMSO-$d_6$) δ 1.68-1.80 (3H, m), 1.94-2.07 (1H, m), 2.19 (3H, s), 3.23-3.30 (2H, m), 3.47 (2H, d, J=5.3 Hz), 3.72-3.87 (3H, m), 6.82-6.96 (3H, m), 7.16-7.29 (3H, m), 7.38-7.46 (1H, m).
192-193° C.
Anal. Calcd for $C_{20}H_{21}N_2O_3SCl$: C, 59.33; H, 5.23; N, 6.92. Found: C, 59.09; H, 5.30; N, 6.67.

Example 216

(9S)-9-[4-(3,4-dimethylphenoxy)phenyl]-3,4,6,7,8,9-hexahydropyrido[2,1-c][1,2,4]thiadiazine 2,2-dioxide A mixture of (3,4-dimethylphenyl)boronic acid (802 mg), 4-[(9S)-2,2-dioxido-3,4,6,7,8,9-hexahydropyrido[2,1-c][1, 2,4]thiadiazin-9-yl]phenol (500 mg), pyridine (3.60 mL), cesium carbonate (581 mg), diacetoxycopper (648 mg) and powdered 4A MS (5.00 g) in MeCN (18 mL) was stirred at room temperature overnight. The mixture was added with NH silica gel, concentrated in vacuo, and purified by column chromatography (NH silica gel, eluted with MeOH in EtOAc) then recrystallized from EtOAc to give the title compound (40.0 mg) as a white solid.

$^1$H NMR (300 MHz, DMSO-d$_6$) δ 1.69-1.79 (3H, m), 1.96-2.05 (1H, m), 2.20 (6H, s), 3.24-3.30 (2H, m), 3.43-3.51 (2H, m), 3.69-3.88 (3H, m), 6.75 (1H, dd, J=8.1, 2.8 Hz), 6.83-6.92 (3H, m), 7.09-7.21 (3H, m).

mp 170-171° C.

Anal. Calcd for C$_{21}$H$_{24}$N$_2$O$_3$S-0.1H$_2$O: C, 65.29; H, 6.31; N, 7.25. Found: C, 65.18; H, 6.29; N, 7.14.

Example 217

(9R)-9-[4-(4-ethylphenoxy)phenyl]-3,4,6,7,8,9-hexahydropyrido[2,1-c][1,2,4]thiadiazine 2,2-dioxide A mixture of (4-ethylphenyl)boronic acid (1.34 g), (9R)-9-(4-hydroxyphenyl)-3,4,6,7,8,9-hexahydropyrido[2,1-c][1,2,4]thiadiazine 2,2-dioxide (500 mg), diacetoxycopper (648 mg), triethylamine (1.24 mL), and powdered 4A MS (1.50 g) in DMF (20 mL) was stirred at room temperature overnight. The mixture was added with NH silica gel, concentrated in vacuo, and purified by column chromatography (NH silica gel, eluted with MeOH in EtOAc) then recrystallized from EtOAc-IPE to give the title compound (53.0 mg) as a white solid.

$^1$H NMR (300 MHz, DMSO-d$_6$) δ 1.18 (3H, t, J=7.6 Hz), 1.67-1.81 (3H, m), 1.93-2.07 (1H, m), 2.59 (2H, q, J=7.6 Hz), 3.24-3.29 (2H, m), 3.47 (2H, dq, J=12.3, 6.4 Hz), 3.70-3.88 (3H, m), 6.86-6.99 (4H, m), 7.14-7.27 (4H, m).

mp 152-153° C.

Anal. Calcd for C$_{21}$H$_{24}$N$_2$O$_3$S: C, 65.60; H, 6.29; N, 7.29. Found: C, 65.48; H, 6.30; N, 7.21.

Example 218

(9S)-9-[4-(4-ethylphenoxy)phenyl]-3,4,6,7,8,9-hexahydropyrido[2,1-c][1,2,4]thiadiazine 2,2-dioxide A mixture of (4-ethylphenyl)boronic acid (802 mg), 4-[(9S)-2,2-dioxido-3,4,6,7,8,9-hexahydropyrido[2,1-c][1,2,4]thiadiazin-9-yl]phenol (500 mg), pyridine (3.60 mL), cesium carbonate (581 mg), diacetoxycopper (648 mg), and powdered 4A MS (5.00 g) in MeCN (18 mL) was stirred at room temperature overnight. The mixture was added with NH silica gel, concentrated in vacuo, and purified by column chromatography (NH silica gel, eluted with MeOH in EtOAc) then recrystallized from EtOAc to give the title compound (132 mg) as a white solid.

$^1$H NMR (300 MHz, DMSO-d$_6$) δ 1.18 (3H, t, J=7.6 Hz), 1.69-1.80 (3H, m), 1.95-2.03 (1H, m), 2.59 (2H, q, J=7.6 Hz), 3.24-3.30 (2H, m), 3.43-3.53 (2H, m), 3.72-3.85 (3H, m), 6.87-6.98 (4H, m), 7.15-7.25 (4H, m).

mp 156-157° C.

Anal. Calcd for C$_{21}$H$_{24}$N$_2$O$_3$S: C, 65.60; H, 6.29; N, 7.29. Found: C, 65.39; H, 6.30; N, 7.17.

Example 219

(9S)-9-[4-(3-methoxyphenoxy)phenyl]-3,4,6,7,8,9-hexahydropyrido[2,1-c][1,2,4]thiadiazine 2,2-dioxide A mixture of (3-methoxyphenyl)boronic acid (813 mg), 4-[(9S)-2,2-dioxido-3,4,6,7,8,9-hexahydropyrido[2,1-c][1,2,4]thiadiazin-9-yl]phenol (500 mg), pyridine (3.60 mL), cesium carbonate (581 mg), diacetoxycopper (648 mg), and powdered 4A MS (5.00 g) in MeCN (18 mL) was stirred at room temperature overnight. The mixture was added with NH silica gel, concentrated in vacuo, and purified by column chromatography (NH silica gel, eluted with MeOH in EtOAc) then recrystallized from EtOAc to give the title compound (80.0 mg) as a white solid.

$^1$H NMR (300 MHz, DMSO-d$_6$) δ 1.74 (3H, d, J=3.4 Hz), 1.95-2.06 (1H, m), 3.23-3.31 (2H, m), 3.42-3.54 (2H, m), 3.71-3.87 (6H, m), 6.52-6.62 (2H, m), 6.69-6.75 (1H, m), 6.88-7.04 (2H, m), 7.11-7.37 (3H, m).

mp 139-140° C.

Anal. Calcd for C$_{20}$H$_{22}$N$_2$O$_4$S: C, 62.16; H, 5.74; N, 7.25. Found: C, 62.05; H, 5.75; N, 7.18.

Example 220

(9S)-9-(2'-chlorobiphenyl-4-yl)-3,4,6,7,8,9-hexahydropyrido[2,1-c][1,2,4]thiadiazine 2,2-dioxide Tetrakis(triphenylphosphine)palladium(0) (16.0 mg) was added to a mixture of (2-chlorophenyl)boronic acid (76.0 mg), 4-[(9S)-2,2-dioxido-3,4,6,7,8,9-hexahydropyrido[2,1-c][1,2,4]thiadiazin-9-yl]phenyl trifluoromethanesulfonate (100 mg) and sodium carbonate (51.4 mg) in EtOH (3 mL), water (1.5 mL) and DMF (dry) (2 mL). The mixture was stirred at 50° C. under nitrogen for 19 hr. Silica-gel was added and the volatiles were removed in vacuo. The mixture supported on silica-gel was purified by column chromatography (NH silica gel, eluted with MeOH in EtOAc), dissolved in MeCN/DMSO (4700/300 μM) and purified by preparative HPLC (C18, eluted with water in acetonitrile containing 0.1% TFA). The desired fractions were neutralized with sat.NaHCO$_3$aq., extracted with EtOAc and washed with brine. The organic layer was separated, dried over anhydrous magnesium sulfate and concentrated in vacuo. The residue was crystallized from MeCN-THF/hexane to give the title compound (38.4 mg) as colorless crystals.

$^1$H NMR (300 MHz, DMSO-d$_6$) δ 1.66-1.88 (3H, m), 1.93-2.19 (1H, m), 3.41-3.65 (2H, m), 3.68-4.02 (3H, m), 7.28-7.35 (2H, m), 7.37-7.46 (5H, m), 7.51-7.65 (1H, m). The peaks of two protons were hidden behind water.

Example 221

The compound of Example 221 was produced in the same manner as in Example 220.

Example 222

9-{4-[(E)-2-phenylethenyl]phenyl}-3,4-dihydropyrido[2,1-c][1,2,4]thiadiazine 2,2-dioxide A) (E)-3-(4-styrylphenyl)pyridin-2-amine Pd(dppf)Cl$_2$ (0.141 g) was added to a mixture of (E)-1-bromo-4-styrylbenzene (1.00 g), potassium acetate (1.14 g) and 4,4,4',4',5,5,5',5'-octamethyl-2,2'-bi(1,3,2-dioxaborolane) (1.03 g) in DMF (dry) (10 mL). The mixture was stirred at 90° C. under nitrogen for 12 hr. The insoluble solid was removed by filtration through Celite pad (eluted with EtOAc). The organic layer was separated, washed with water and brine, dried over anhydrous magnesium sulfate. Activated-carbon powder and silica-gel were added and the mixture was shaken, sonicated and filtered through silica-gel/Celite pad (eluted with EtOAc). The filtrate was concentrated in vacuo to give the crude (E)-4,4,5,5-tetramethyl-2-(4-styrylphenyl)-1,3,2-dioxaborolane. Tetrakis(triphenylphosphine)palladium(0) (0.186 g) was added to a suspension of 3-bromopyridin-2-amine (0.557 g), the prepared (E)-4,4,5,5-tetramethyl-2-(4-styrylphenyl)-1,3,2-dioxaborolane and sodium carbonate (1.02 g) in DME (20 mL) and water (4 mL) and the mixture was stirred at 80° C. under nitrogen overnight. Silica-gel was added and the volatiles were removed in vacuo. The mixture supported on silica-gel was purified by column chromatography (silica gel, eluted with EtOAc in hexane) to give the title compound (532 mg) as a pale yellow solid.

MS (ESI+). found: 273.1.

B) 9-{4-[(E)-2-phenylethenyl]phenyl}-3,4-dihydropyrido[2,1-c][1,2,4]thiadiazine 2,2-dioxide 2-Chloroethanesulfonyl chloride (0.410 mL) was added to a mixture of NaH (60%, 390 mg) in THF (dry) (8 mL) at 0° C. under nitrogen flow. The mixture was stirred at 0° C. for 5 min. The mixture of (E)-3-(4-styrylphenyl)pyridin-2-amine (531 mg) in THF (dry) (20 mL) was added dropwise and the mixture was stirred at room temperature under atmosphere overnight. The mixture was quenched with water at 0° C., and water, EtOAc and THF were added. The insoluble material was collected by filtration and crystallized from DMSO-EtOH to give the title compound (340 mg) as slightly pale yellow crystals.

$^1$H NMR (300 MHz, DMSO-d$_6$) δ 3.42-3.53 (2H, m), 4.59-4.72 (2H, m), 6.72 (1H, t, J=7.0 Hz), 7.22-7.44 (5H, m), 7.51-7.70 (7H, m), 7.78 (1H, dd, J=6.6, 1.3 Hz).

Example 223

(9S)-9-(4'-chlorobiphenyl-4-yl)-3,4,6,7,8,9-hexahydropyrido[2,1-c][1,2,4]thiadiazine 2,2-dioxide Tetrakis(triphenylphosphine)palladium(0) (16.0 mg) was added to a mixture of (4-chlorophenyl)boronic acid (76.0 mg), 4-[(9S)-2,2-dioxido-3,4,6,7,8,9-hexahydropyrido[2,1-c][1,2,4]thiadiazin-9-yl]phenyl trifluoromethanesulfonate (100 mg) and sodium carbonate (51.4 mg) in EtOH (3 mL), water (1.5 mL) and DMF (dry) (2 mL). The mixture was stirred at 50° C. under nitrogen for 16 hr. Silica-gel was added and the volatiles were removed in vacuo. The mixture supported on silica-gel was purified by column chromatography (NH silica gel, eluted with MeOH in EtOAc) and crystallized from MeCN-THF/IPE to give the title compound (26.7 mg) as a colorless crystal.

$^1$H NMR (300 MHz, DMSO-d$_6$) δ 1.67-1.87 (3H, m), 1.91-2.13 (1H, m), 3.26-3.29 (2H, m), 3.41-3.60 (2H, m), 3.75-3.92 (3H, m), 7.31 (2H, d, J=8.3 Hz), 7.51 (2H, d, J=8.7 Hz), 7.61 (2H, d, J=8.7 Hz), 7.70 (2H, d, J=8.3 Hz).

Example 224

The compound of Example 224 was produced in the same manner as in Example 223.

Example 225

(9S)-9-(4'-chloro-3'-fluorobiphenyl-4-yl)-3,4,6,7,8,9-hexahydropyrido[2,1-c][1,2,4]thiadiazine 2,2-dioxide Tetrakis(triphenylphosphine)palladium(0) (16.0 mg) was added to a mixture of (4-chloro-3-fluorophenyl)boronic acid (85.0 mg), 4-[(9S)-2,2-dioxido-3,4,6,7,8,9-hexahydropyrido[2,1-c][1,2,4]thiadiazin-9-yl]phenyl trifluoromethanesulfonate (100 mg) and sodium carbonate (51.4 mg) in EtOH (3 mL), water (1.5 mL) and DMF (dry) (2 mL). The mixture was stirred at 50° C. under nitrogen for 16 hr. Silica-gel was added and the volatiles were removed in vacuo. The mixture supported on silica-gel was purified by column chromatography (NH silica gel, eluted with MeOH in EtOAc) and concentrated. The residue was dissolved in MeCN/DMSO (1900/100 μM) and purified by preparative HPLC (C18, eluted with water in acetonitrile containing 0.1% TFA). The desired fractions were neutralized with sat. NaHCO$_3$ aq., extracted with EtOAc and washed with brine. The organic layer was separated, dried over anhydrous magnesium sulfate and concentrated in vacuo to give the title compound (5.00 mg) as a white solid.

$^1$H NMR (300 MHz, CDCl$_3$) δ 1.81-2.03 (3H, m), 2.10-2.22 (1H, m), 3.27-3.34 (2H, m), 3.41-3.56 (2H, m), 3.86-4.02 (3H, m), 7.24 (2H, d, J=8.3 Hz), 7.28-7.36 (2H, m), 7.39-7.53 (3H, m).

Example 226

(9S)-9-(3'-chloro-4'-fluorobiphenyl-4-yl)-3,4,6,7,8,9-hexahydropyrido[2,1-c][1,2,4]thiadiazine 2,2-dioxide Tetrakis(triphenylphosphine)palladium(0) (16 mg) was added to a mixture of (3-chloro-4-fluorophenyl)boronic acid (85 mg), 4-[(9S)-2,2-dioxido-3,4,6,7,8,9-hexahydropyrido[2,1-c][1,2,4]thiadiazin-9-yl]phenyl trifluoromethanesulfonate (100 mg) and sodium carbonate (51.4 mg) in EtOH (3 mL), water (1.5 mL) and DMF (dry) (2 mL). The mixture was stirred at 50° C. under nitrogen for 16 hr. Silica-gel was added and the volatiles were removed in vacuo. The mixture supported on silica-gel was purified by column chromatography (NH silica gel, eluted with MeOH in EtOAc), dissolved in MeCN/DMSO (2500/300 μM) and purified by preparative HPLC (C18, eluted with water in acetonitrile containing 0.1% TFA). The desired fractions were neutralized with sat. NaHCO$_3$ aq., extracted with EtOAc and washed with brine. The organic layer was separated, dried over anhydrous magnesium sulfate and concentrated in vacuo to give the title compound (20 mg) as a white solid.

$^1$H NMR (300 MHz, CDCl$_3$) δ 1.81-2.03 (3H, m), 2.08-2.24 (1H, m), 3.27-3.34 (2H, m), 3.41-3.57 (2H, m), 3.86-4.03 (3H, m), 7.15-7.25 (3H, m), 7.40 (1H, ddd, J=8.7, 4.5, 2.3 Hz), 7.44-7.49 (2H, m), 7.57 (1H, dd, J=6.8, 2.3 Hz).

Example 227

(9S)-9-[4-(3,4,5-trifluorophenoxy)phenyl]-3,4,6,7,8,9-hexahydropyrido[2,1-c][1,2,4]thiadiazine 2,2-dioxide A mixture of (3,4,5-trifluorophenyl)boronic acid (1882 mg), 4-[(9S)-2,2-dioxido-3,4,6,7,8,9-hexahydropyrido[2,1-c][1,2,4]thiadiazin-9-yl]phenol (1000 mg), pyridine (7.21 mL), cesium carbonate (1162 mg), diacetoxycopper (1296 mg) and powdered 4A MS (10.0 g) in MeCN (36 mL) was stirred at room temperature overnight. The mixture was added with NH silica gel, concentrated in vacuo, and purified by column chromatography (NH silica gel, eluted with MeOH in EtOAc) then recrystallized from EtOAc to give the title compound (196 mg) as a white solid.

¹H NMR (300 MHz, DMSO-d₆) δ 1.65-1.83 (3H, m), 1.90-2.09 (1H, m), 3.23-3.28 (2H, m), 3.39-3.57 (2H, m), 3.71-3.90 (3H, m), 6.95-7.13 (4H, m), 7.19-7.34 (2H, m).

mp 180-181° C.

Anal. Calcd for $C_{19}H_{17}N_2O_3SF_3$: C, 55.60; H, 4.18; N, 6.83. Found: C, 55.66; H, 4.22; N, 6.68.

Example 228

(9S)-9-[4-(4-bromophenoxy)phenyl]-3,4,6,7,8,9-hexahydropyrido[2,1-c][1,2,4]thiadiazine 2,2-dioxide Diacetoxycopper (648 mg) was added to a mixture of pyridine (0.433 mL), (4-bromophenyl)boronic acid (1075 mg), cesium carbonate (581 mg) and 4-[(9S)-2,2-dioxido-3,4,6,7,8,9-hexahydropyrido[2,1-c][1,2,4]thiadiazin-9-yl]phenol (500 mg) in MeCN (35 mL). The mixture was stirred at room temperature under a dry atmosphere (anhydrous calcium chloride tube) for 19 hr. The insoluble, light-blue precipitates were removed by filtration through Celite-pad (eluted with EtOAc). Silica-gel was added to the filtrate and the volatiles were removed in vacuo. The mixture supported on silica-gel was purified by column chromatography (NH silica gel, eluted with MeOH in EtOAc) and concentrated in vacuo. The residue was crystallized from THF/IPE to give the title compound (50.6 mg) as colorless crystals.

¹H NMR (300 MHz, DMSO-d₆) δ 1.66-1.82 (3H, m), 1.93-2.11 (1H, m), 3.25-3.29 (2H, m), 3.41-3.54 (2H, m), 3.74-3.86 (3H, m), 6.94-7.04 (4H, m), 7.24 (2H, d, J=8.7 Hz), 7.51-7.59 (2H, m).

Example 229

9-[4-(difluoromethoxy)phenyl]-3,4,6,7,8,9-hexahydropyrido[2,1-c][1,2,4]thiadiazine 2,2-dioxide A mixture of 9-(4-hydroxyphenyl)-3,4,6,7,8,9-hexahydropyrido[2,1-c][1,2,4]thiadiazine 2,2-dioxide (736 mg) and N-benzyl-N,N-diethylethanaminium chloride (59.8 mg) in THF (dry) (20 mL) and 8N NaOH aq. (3.28 mL) was stirred at room temperature under $CHF_2Cl$ atmosphere overnight. $Et_2O$ was added and the aqueous phase was removed. Then EtOAc was added and the extracted organic layer was washed with brine and concentrated. The residue was purified by column chromatography (NH silica gel, eluted with MeOH in EtOAc) and crystallized from THF/hexane to give the title compound (22.5 mg) as colorless crystals.

Example 230

9-[4-(1,1-difluoroethyl)phenyl]-3,4,6,7,8,9-hexahydropyrido[2,1-c][1,2,4]thiadiazine 2,2-dioxide A racemate (45 mg) of 9-[4-(1,1-difluoroethyl)phenyl]-3,4,6,7,8,9-hexahydropyrido[2,1-c][1,2,4]thiadiazine 2,2-dioxide was separated by HPLC (column: CHIRALPAK AD (AK001), 50 mmID×500 mmL, manufactured by DAICEL CHEMICAL INDUSTRIES, LTD., mobile phase:methanol/diethylamine=1000/1) to give the title compound (20 mg) with a shorter retention time. Crystallization from THF and diisopropyl ether gave a white solid.

¹H NMR (300 MHz, DMSO-d₆) δ 1.70-1.81 (3H, m), 1.85-2.09 (4H, m), 3.24-3.29 (2H, m), 3.43-3.55 (2H, m), 3.72-3.91 (3H, m), 7.32 (2H, d, J=7.6 Hz), 7.50 (2H, d, J=7.6 Hz).

Example 231

9-[4-(1,1-difluoroethyl)phenyl]-3,4,6,7,8,9-hexahydropyrido[2,1-c][1,2,4]thiadiazine 2,2-dioxide A racemate (45 mg) of 9-[4-(1,1-difluoroethyl)phenyl]-3,4,6,7,8,9-hexahydropyrido[2,1-c][1,2,4]thiadiazine 2,2-dioxide was separated by HPLC (column: CHIRALPAK AD (AK001), 50 mmID×500 mmL, manufactured by DAICEL CHEMICAL INDUSTRIES, LTD., mobile phase:methanol/diethylamine=1000/1) to give the title compound (21 mg) with a longer retention time. Crystallization from THF and diisopropyl ether gave a white solid.

¹H NMR (300 MHz, DMSO-d₆) δ 1.64-1.83 (3H, m), 1.85-2.09 (4H, m), 3.24-3.30 (2H, m), 3.39-3.61 (2H, m), 3.73-3.93 (3H, m), 7.32 (2H, d, J=7.6 Hz), 7.50 (2H, d, J=7.6 Hz).

Example 232

9-{4-[4-(trifluoromethyl)phenoxy]phenyl}-3,4,6,7,8,9-hexahydropyrido[2,1-c][1,2,4]thiadiazine 2,2-dioxide A racemate (255 mg) of 9-{4-[4-(trifluoromethyl)phenoxy]phenyl}-3,4,6,7,8,9-hexahydropyrido[2,1-c][1,2,4]thiadiazine 2,2-dioxide was separated by SFC (column: CHIRALPAK IC (MB001), 20 mmID×250 mmL, manufactured by DAICEL CHEMICAL INDUSTRIES, LTD., mobile phase:carbon dioxide/acetonitrile/methanol=770/115/115) to give the title compound (115 mg) with a shorter retention time as a white solid. Crystallization from THF and diisopropyl ether gave a white solid.

¹H NMR (300 MHz, DMSO-d₆) δ 1.64-1.83 (3H, m), 1.93-2.09 (1H, m), 3.25-3.29 (2H, m), 3.39-3.57 (2H, m), 3.74-3.90 (3H, m), 7.03-7.18 (4H, m), 7.29 (2H, d, J=8.7 Hz), 7.74 (2H, d, J=8.7 Hz).

mp 174-176° C.

Anal. Calcd for $C_{20}H_9N_2O_3SF_3$: C, 56.60; H, 4.51; N, 6.60. Found: C, 56.51; H, 4.59; N, 6.43.

Example 233

9-{4-[4-(trifluoromethyl)phenoxy]phenyl}-3,4,6,7,8,9-hexahydropyrido[2,1-c][1,2,4]thiadiazine 2,2-dioxide A racemate (255 mg) of 9-{4-[4-(trifluoromethyl)phenoxy]phenyl}-3,4,6,7,8,9-hexahydropyrido[2,1-c][1,2,4]thiadiazine 2,2-dioxide was separated by SFC (column: CHIRALPAK IC (MB001), 20 mmID×250 mmL, manufactured by DAICEL CHEMICAL INDUSTRIES, LTD., mobile phase:carbon dioxide/acetonitrile/methanol=770/115/115) to give the title compound (120 mg) with a longer retention time as a white solid. Crystallization from THF and diisopropyl ether gave a white solid.

¹H NMR (300 MHz, DMSO-d₆) δ 1.70-1.82 (3H, m), 1.95-2.09 (1H, m), 3.26-3.29 (2H, m), 3.39-3.55 (2H, m), 3.75-3.87 (3H, m), 7.03-7.18 (4H, m), 7.29 (2H, d, J=8.7 Hz), 7.74 (2H, d, J=8.7 Hz).

mp 177-179° C.

Anal. Calcd for $C_{20}H_9N_2O_3SF_3$: C, 56.60; H, 4.51; N, 6.60. Found: C, 56.53; H, 4.53; N, 6.50.

Example 234

9-{4-[4-(1,1-difluoroethyl)phenoxy]phenyl}-3,4,6,7,
8,9-hexahydropyrido[2,1-c][1,2,4]thiadiazine 2,2-
dioxide A racemate (45.0 mg) of 9-{4-[4-(1,1-difluoroethyl)phenoxy]phenyl}-3,4,6,7,8,9-hexahydropyrido[2,1-c][1,2,4]thiadiazine 2,2-dioxide was separated by HPLC (column: CHIRALPAK AD (AK001), 50 mmID×500 mmL, manufactured by DAICEL CHEMICAL INDUSTRIES, LTD., mobile phase:isopropanol/diethylamine=1000/1) to give the title compound (20.0 mg) with a shorter retention time. Crystallization from THF and diisopropyl ether gave a white solid.

$^1$H NMR (300 MHz, DMSO-$d_6$) δ 1.68-1.82 (3H, m), 1.86-2.12 (4H, m), 3.26-3.29 (2H, m), 3.39-3.59 (2H, m), 3.66-3.93 (3H, m), 6.95-7.11 (4H, m), 7.25 (2H, d, J=8.7 Hz), 7.57 (2H, d, J=8.7 Hz).
mp 153-154° C.

Example 235

9-{4-[4-(1,1-difluoroethyl)phenoxy]phenyl}-3,4,6,7,
8,9-hexahydropyrido[2,1-c][1,2,4]thiadiazine 2,2-
dioxide A racemate (45.0 mg) of 9-{4-[4-(1,1-difluoroethyl)phenoxy]phenyl}-3,4,6,7,8,9-hexahydropyrido[2,1-c][1,2,4]thiadiazine 2,2-dioxide was separated by HPLC (column: CHIRALPAK AD (AK001), 50 mmID×500 mmL, manufactured by DAICEL CHEMICAL INDUSTRIES, LTD., mobile phase:isopropanol/diethylamine=1000/1) to give the title compound (22.0 mg) with a longer retention time. Crystallization from THF and diisopropyl ether gave a white solid.

$^1$H NMR (300 MHz, DMSO-$d_6$) δ 1.61-1.82 (3H, m), 1.86-2.12 (4H, m), 3.23-3.29 (2H, m), 3.38-3.58 (2H, m), 3.69-3.91 (3H, m), 6.95-7.12 (4H, m), 7.25 (2H, d, J=8.7 Hz), 7.57 (2H, d, J=8.7 Hz).
mp 154-155° C.

Example 236

(9S)-9-[4-(3-fluoro-5-methylphenoxy)phenyl]-3,4,6,
7,8,9-hexahydropyrido[2,1-c][1,2,4]thiadiazine 2,2-
dioxide A mixture of (3-fluoro-5-methylphenyl)boronic acid (824 mg), 4-[(9S)-2,2-dioxido-3,4,6,7,8,9-hexahydropyrido[2,1-c][1,2,4]thiadiazin-9-yl]phenol (500 mg), pyridine (3.60 mL), cesium carbonate (581 mg), diacetoxycopper (648 mg), and powdered 4A MS (5.0 g) in MeCN (18 mL) was stirred at room temperature overnight. The mixture was added with NH silica gel, concentrated in vacuo, and purified by column chromatography (NH silica gel, eluted with EtOAc in hexane then MeOH in EtOAc) then recrystallized from EtOAc to give the title compound (267 mg) as a white solid.

$^1$H NMR (300 MHz, DMSO-$d_6$) δ 1.69-1.83 (3H, m), 1.95-2.07 (1H, m), 2.29 (3H, s), 3.23-3.30 (2H, m), 3.42-3.55 (2H, m), 3.74-3.90 (3H, m), 6.61-6.71 (2H, m), 6.81 (1H, dd, J=9.7, 2.1 Hz), 6.95-7.03 (2H, m), 7.13-7.33 (2H, m).
mp 158-159° C.

Anal. Calcd for $C_{20}H_{21}N_2O_3SF$: C, 61.84; H, 5.45; N, 7.21. Found: C, 61.64; H, 5.41; N, 7.03.

Example 237

9-(5,6,7,8-tetrahydronaphthalen-2-yloxy)-3,4-dihy-
dropyrido[2,1-c][1,2,4]thiadiazine 2,2-dioxide The title compound was obtained in the same manner as in Example 15.

Example 238

9-(5,6,7,8-tetrahydronaphthalen-2-yloxy)-3,4,6,7,8,
9-hexahydropyrido[2,1-c][1,2,4]thiadiazine 2,2-di-
oxide The title compound was obtained in the same manner as in Examples 59 and 60.

Example 239

9-[4-(1H-pyrazol-1-yl)phenyl]-3,4-dihydropyrido[2,
1-c][1,2,4]thiadiazine 2,2-dioxide The title compound was obtained in the same manner as in Example 14.

Example 240

9-[(2,2,3,3-tetrafluoro-2,3-dihydro-1,4-benzodioxin-
6-yl)oxy]-3,4-dihydropyrido[2,1-c][1,2,4]thiadiazine
2,2-dioxide The title compound was obtained in the same manner as in Example 15.

Example 241

9-{[7-(2,2,2-trifluoroethoxy)naphthalen-2-yl]oxy}-3,
4-dihydropyrido[2,1-c][1,2,4]thiadiazine 2,2-dioxide A) 7-[(2-aminopyridin-3-yl)oxy]naphthalen-2-ol The title compound was obtained in the same manner as in Example 15, step A.
MS (API+). found: 253.1

B) 3-{[7-(2,2,2-trifluoroethoxy)naphthalen-2-yl]
oxy}pyridin-2-amine

To a mixture of sodium hydride (60%, 116 mg), 7-[(2-aminopyridin-3-yl)oxy]naphthalen-2-ol (477 mg) and dehydrated THF (10 mL) was added a mixture of 2,2,2-trifluoroethyl 4-methylbenzenesulfonate (370 mg) and dehydrated THF (5 mL) at room temperature. The reaction mixture was stirred at 70° C. over the weekend, DMSO (10.00 mL) was added and the mixture was stirred at 120° C. for 1 hr. The reaction mixture was added to a saturated aqueous ammonium chloride solution, and the mixture was extracted with ethyl acetate. The organic layer was washed with saturated brine, dried over magnesium sulfate, and concentrated under reduced pressure. The residue was purified by silica gel column chromatography (ethyl acetate/hexane) to give the title compound (82 mg) as a pale-yellow viscous product.
MS (API+). found: 335.0

C) 9-{[7-(2,2,2-trifluoroethoxy)naphthalen-2-yl]
oxy}-3,4-dihydropyrido[2,1-c][1,2,4]thiadiazine
2,2-dioxide The title compound was obtained in the same manner as in Example 14, step B.

Example 242

9-[4-(1-methylpropoxy)phenyl]-3,4-dihydropyrido
[2,1-c][1,2,4]thiadiazine 2,2-dioxide The title compound was obtained in the same manner as in Example 66.

Example 243

9-[4-(1,4-dioxaspiro[4.5]dec-8-yloxy)phenyl]-3,4-
dihydropyrido[2,1-c][1,2,4]thiadiazine 2,2-dioxide The title compound was obtained in the same manner as in Example 66.

Example 244

4-[4-(2,2-dioxido-3,4-dihydropyrido[2,1-c][1,2,4]
thiadiazin-9-yl)phenoxy]cyclohexanone A mixture of 9-[4-(1,4-dioxaspiro[4.5]dec-8-yloxy)phenyl]-3,4-dihydropyrido[2,1-c][1,2,4]thiadiazine 2,2-dioxide (130 mg), 1M hydrochloric acid (15 mL) and dehydrated THF (15 mL) was stirred at room temperature for 8 hr. The reaction mixture was neutralized with 1M aqueous sodium hydroxide solution, and extracted with ethyl acetate. The organic layer was washed with saturated brine, dried over magnesium sulfate, and concentrated under reduced pressure. The residue was washed with diethyl ether to give the title compound (109 mg) as a pale-yellow solid.

Example 245

9-(4-{[tert-butyl(dimethyl)silyl]oxy}phenyl)-7-
chloro-3,4-dihydropyrido[2,1-c][1,2,4]thiadiazine
2,2-dioxide The title compound was obtained in the same manner as in Example 14, step B.

Example 246

9-{4-[(6-methylpyridin-2-yl)oxy]phenyl}-3,4-dihydropyrido[2,1-c][1,2,4]thiadiazine 2,2-dioxide The title compound was obtained in the same manner as in Example 76.

Example 247

9-{4-[(5-chloropyridin-2-yl)oxy]phenyl}-3,4-dihydropyrido[2,1-c][1,2,4]thiadiazine 2,2-dioxide The title compound was obtained in the same manner as in Example 76.

Example 248

9-(4-{[4-(trifluoromethyl)pyridin-2-yl]oxy}phenyl)-
3,4-dihydropyrido[2,1-c][1,2,4]thiadiazine 2,2-dioxide The title compound was obtained in the same manner as in Example 76.

Example 249

7-chloro-9-{4-[(6-methylpyridin-2-yl)oxy]phenyl}-
3,4-dihydropyrido[2,1-c][1,2,4]thiadiazine 2,2-dioxide The title compound was obtained in the same manner as in Example 76.

Example 250

9-(4-{[3-(trifluoromethyl)pyridin-2-yl]oxy}phenyl)-
3,4-dihydropyrido[2,1-c][1,2,4]thiadiazine 2,2-dioxide The title compound was obtained in the same manner as in Example 76.

Example 251

7-chloro-9-[4-(tetrahydrofuran-2-ylmethoxy)phenyl]-3,4-dihydropyrido[2,1-c][1,2,4]thiadiazine 2,2-dioxide The title compound was obtained in the same manner as in Example 66.

Example 252

7-chloro-9-[4-(tetrahydro-2H-pyran-4-yloxy)phenyl]-3,4-dihydropyrido[2,1-c][1,2,4]thiadiazine 2,2-dioxide The title compound was obtained in the same manner as in Example 66.

Example 253

7-chloro-9-[4-(tetrahydro-2H-pyran-4-ylmethoxy)
phenyl]-3,4-dihydropyrido[2,1-c][1,2,4]thiadiazine
2,2-dioxide The title compound was obtained in the same manner as in Example 66.

Example 254

9-(4-{[6-(trifluoromethyl)pyridin-3-yl]oxy}phenyl)-
3,4-dihydropyrido[2,1-c][1,2,4]thiadiazine 2,2-dioxide The title compound was obtained in the same manner as in Example 79.

Example 255

9-(4-{[4-(trifluoromethyl)pyridin-3-yl]oxy}phenyl)-3,4-dihydropyrido[2,1-c][1,2,4]thiadiazine 2,2-dioxide The title compound was obtained in the same manner as in Example 79.

Example 256

7-chloro-9-(4-{[6-(trifluoromethyl)pyridin-3-yl]oxy}phenyl)-3,4-dihydropyrido[2,1-c][1,2,4]thiadiazine 2,2-dioxide The title compound was obtained in the same manner as in Example 79.

Example 257

9-(4-{[2-(trifluoromethyl)pyridin-4-yl]oxy}phenyl)-3,4-dihydropyrido[2,1-c][1,2,4]thiadiazine 2,2-dioxide The title compound was obtained in the same manner as in Example 79.

Example 258

9-(5-phenoxypyridin-2-yl)-3,4-dihydropyrido[2,1-c][1,2,4]thiadiazine 2,2-dioxide A) 5-bromo-2,3'-bipyridin-2'-amine n-Butyllithium (1.6 M in hexane, 48.3 mL) was added dropwise to a solution of N1,N1,N2,N2-tetramethylethane-1,2-diamine (8.08 g) and tert-butyl pyridin-2-ylcarbamate (5 g) in THF (dry) (50 mL) at −78° C. The mixture was stirred at 0° C. under $N_2$ for 2 hr. Triisopropyl borate (16.95 g) was added to the mixture at −78° C. The mixture was stirred at 0° C. under $N_2$ for 30 min. The mixture was quenched with sat. $NH_4Cl$ aq. at 0° C. and added with $Et_2O$ to give a yellow precipitate (11.68 g, wet). A mixture of potassium carbonate (438 mg), tetrakis(triphenylphosphine)palladium(0) (61.0 mg), 2,5-dibromopyridine (250 mg) and the precipitate (250 mg) in toluene (10 mL) and MeOH (5 mL) was stirred at 80° C. under $N_2$ overnight. NH silica gel was added and the mixture was concentrated in vacuo. The residue was purified by column chromatography (NH silica gel, eluted with EtOAc in hexane) to give the title compound (132 mg) as a yellow solid.
MS (API+). found: 250.0

B) 9-(5-phenoxypyridin-2-yl)-3,4-dihydropyrido[2,1-c][1,2,4]thiadiazine 2,2-dioxide The title compound was synthesized by following the procedure of example 79.

Example 259

9-(4-{[5-(trifluoromethyl)pyridin-3-yl]oxy}phenyl)-3,4-dihydropyrido[2,1-c][1,2,4]thiadiazine 2,2-dioxide The title compound was obtained in the same manner as in Example 79.

Example 260

7-chloro-9-(4-{[5-(trifluoromethyl)pyridin-3-yl]oxy}phenyl)-3,4-dihydropyrido[2,1-c][1,2,4]thiadiazine 2,2-dioxide The title compound was obtained in the same manner as in Example 79.

Example 261

9-[4-(cyclohexyloxy)phenyl]-3,4,6,7,8,9-hexahydropyrido[2,1-c][1,2,4]thiadiazine 2,2-dioxide In the same manner as in Example 98, the title compound (48.0 mg) was obtained from 9-[4-(cyclohexyloxy)phenyl]-3,4-dihydropyrido[2,1-c][1,2,4]thiadiazine 2,2-dioxide.
$^1$H NMR (300 MHz, $CDCl_3$) δ 1.23-1.53 (6H, m), 1.72-2.14 (8H, m), 3.20-3.37 (2H, m), 3.37-3.53 (2H, m), 3.82 (1H, t, J=5.1 Hz), 3.91 (2H, t, J=6.4 Hz), 4.08-4.30 (1H, m), 6.84 (2H, d, J=8.3 Hz), 7.04 (2H, d, J=8.3 Hz).

Example 262

9-{4-[3-(trifluoromethyl)phenoxy]phenyl}-3,4,6,7,8,9-hexahydropyrido[2,1-c][1,2,4]thiadiazine 2,2-dioxide In the same manner as in Example 98, the title compound (36.5 mg) was obtained from 9-{4-[3-(trifluoromethyl)phenoxy]phenyl}-3,4-dihydropyrido[2,1-c][1,2,4]thiadiazine 2,2-dioxide.
$^1$H NMR (300 MHz, DMSO-$d_6$) δ 1.72-1.83 (3H, m), 1.95-2.10 (1H, m), 3.25-3.27 (2H, m), 3.44-3.56 (2H, m), 3.76-3.88 (3H, m), 7.04 (2H, d, J=8.7 Hz), 7.24-7.36 (4H, m), 7.47-7.53 (1H, m), 7.58-7.66 (1H, m).

Example 263

9-[4-(pyridin-2-yloxy)phenyl]-3,4-dihydropyrido[2,1-c][1,2,4]thiadiazine 2,2-dioxide 2-Chloropyridine (0.132 mL) was added to a solution of 4-(2,2-dioxido-3,4-dihydropyrido[2,1-c][1,2,4]thiadiazin-9-yl)phenol (300 mg) and potassium carbonate (390 mg) in DMSO (6 mL). The mixture was stirred at 120° C. under nitrogen overnight. The mixture was quenched with water and extracted with EtOAc. The organic layer was separated, washed with water and brine, dried over anhydrous sodium sulfate and concentrated in vacuo. The residue was purified by column chromatography (NH silica gel, eluted with MeOH in EtOAc) and crystallized from THF-IPE to give the title compound (3.3 mg) as colorless crystals.
$^1$H NMR (300 MHz, $CDCl_3$) δ 3.37-3.45 (2H, m), 4.63-4.71 (2H, m), 6.54-6.63 (1H, m), 6.90-7.05 (2H, m), 7.12-7.23 (2H, m), 7.30-7.37 (1H, m), 7.51 (1H, dd, J=7.0, 1.7 Hz), 7.60-7.76 (3H, m), 8.22 (1H, dd, J=4.5, 2.3 Hz).

Example 264

The compound of Example 264 was produced in the same manner as in Example 88.

Example 265

9-[4-(2,2,2-trifluoroethoxy)phenyl]-3,4,6,7,8,9-hexahydropyrido[2,1-c][1,2,4]thiadiazine 2,2-dioxide In the same manner as in Example 98, the title compound (49.7 mg) was obtained from 9-[4-(2,2,2-trifluoroethoxy)phenyl]-3,4-dihydropyrido[2,1-c][1,2,4]thiadiazine 2,2-dioxide.
$^1$H NMR (300 MHz, DMSO-$d_6$) δ 1.66-1.79 (3H, m), 1.93-2.04 (1H, m), 3.23-3.28 (2H, m), 3.41-3.52 (2H, m), 3.70-3.76 (1H, m), 3.78-3.87 (2H, m), 4.74 (2H, q, J=8.8 Hz), 6.99 (2H, d, J=8.7 Hz), 7.16 (2H, d, J=8.7 Hz).

Example 266

9-{4-[2-(trifluoromethyl)phenoxy]phenyl}-3,4-dihydropyrido[2,1-c][1,2,4]thiadiazine 2,2-dioxide A) 3-(4-(2-(trifluoromethyl)phenoxy)phenyl)pyridin-2-amine In the same manner as in Example 85, step A, the title compound (206 mg) was obtained from 4-(2-aminopyridin-3-yl)phenol (400 mg) and 1-iodo-2-(trifluoromethyl)benzene (701 mg).
MS (ESI+). found: 331.0.

B) 9-{4-[2-(trifluoromethyl)phenoxy]phenyl}-3,4-dihydropyrido[2,1-c][1,2,4]thiadiazine 2,2-dioxide The title compound was obtained in the same manner as in Example 85, step B.
$^1$H NMR (300 MHz, DMSO-$d_6$) δ 3.41-3.51 (2H, m), 4.59-4.72 (2H, m), 6.71 (1H, t, J=7.0 Hz), 7.03-7.12 (2H, m), 7.17 (1H, d, J=8.3 Hz), 7.31-7.43 (1H, m), 7.54-7.60 (2H, m), 7.62-7.72 (2H, m), 7.75-7.86 (2H, m).

Example 267-269

The compounds of Examples 267-269 were produced in the same manner as in Example 88.

Example 270

9-[4-(2-methoxyphenoxy)phenyl]-3,4-dihydropyrido[2,1-c][1,2,4]thiadiazine 2,2-dioxide A)
3-(4-(2-methoxyphenoxy)phenyl)pyridin-2-amine In the same manner as in Example 85, step A, the title compound (113.4 mg) was obtained from 4-(2-aminopyridin-3-yl)phenol (500 mg) and 1-iodo-2-methoxybenzene (754 mg).
MS (ESI+). found: 293.3.

B) 9-[4-(2-methoxyphenoxy)phenyl]-3,4-dihydropyrido[2,1-c][1,2,4]thiadiazine 2,2-dioxide The title compound was obtained in the same manner as in Example 85, step B.
$^1$H NMR (300 MHz, DMSO-$d_6$) δ 3.41-3.50 (2H, m), 3.77 (3H, s), 4.60-4.67 (2H, m), 6.66-6.72 (1H, m), 6.83 (2H, d, J=8.7 Hz), 6.96-7.29 (4H, m), 7.46 (2H, d, J=8.7 Hz), 7.59 (1H, dd, J=7.2, 1.9 Hz), 7.75 (1H, dd, J=6.8, 1.5 Hz).

Example 271

The compound of Example 271 was produced in the same manner as in Example 88.

Example 272

9-[(4-cyclopentylphenoxy)methyl]-3,4-dihydropyrido[2,1-c][1,2,4]thiadiazine 2,2-dioxide A)
3-((4-cyclopentylphenoxy)methyl)pyridin-2-amine Diisopropylazodicarboxylate (0.714 mL) was added to a solution of triphenylphosphine (951 mg), (2-aminopyridin-3-yl)methanol (300 mg) and 4-cyclopentylphenol (392 mg) in THF (dry) (20 mL) at room temperature and the mixture was stirred for 20 hr. Volatiles were removed in vacuo with silica-gel. The silica-supported mixture was purified by column chromatography (1st; NH-silica gel, eluted with EtOAc in hexane, 2nd; silica gel, eluted with EtOAc in hexane) to give the title compound (55.4 mg) as a white powder.
MS (ESI+). found: 269.1.

B) 9-[(4-cyclopentylphenoxy)methyl]-3,4-dihydropyrido[2,1-c][1,2,4]thiadiazine 2,2-dioxide The title compound was obtained in the same manner as in Example 85, step B.
$^1$H NMR (300 MHz, DMSO-$d_6$) δ 1.38-1.81 (6H, m), 1.87-2.05 (2H, m), 2.82-2.99 (1H, m), 3.42-3.55 (2H, m), 4.56-4.72 (2H, m), 4.85 (2H, s), 6.68 (1H, t, J=6.8 Hz), 6.90 (2H, d, J=8.7 Hz), 7.17 (2H, d, J=8.7 Hz), 7.67 (1H, d, J=7.2 Hz), 7.76 (1H, d, J=5.7 Hz).

Example 273

The compound of Example 273 was produced in the same manner as in Example 186.

Example 274

The compound of Example 274 was produced in the same manner as in Example 88.

Example 275

The compound of Example 275 was produced in the same manner as in Example 92.

Example 276

9-[(3-chlorobenzyl)oxy]-3,4-dihydropyrido[2,1-c][1,2,4]thiadiazine 2,2-dioxide

A) 3-(3-chlorobenzyloxy)pyridin-2-amine

To the mixture of 2-aminopyridin-3-ol (500 mg) and DMF (dry) (15 mL) was added NaH (60%, 200 mg) at room temperature and the mixture was stirred at room temperature for 20 min. 1-(Bromomethyl)-3-chlorobenzene (933 mg) was added and the mixture was stirred at the same temperature for 1 hr. Water and EtOAc were added and the extracted organic layer was washed with brine, dried over anhydrous sodium sulfate and concentrated in vacuo. The residue was purified by column chromatography (silica gel, eluted with EtOAc in hexane) to give the title compound (1.01 g) as a brown crystalline solid.
MS (ESI+). found: 235.1.

B) 9-[(3-chlorobenzyl)oxy]-3,4-dihydropyrido[2,1-c][1,2,4]thiadiazine 2,2-dioxide The title compound was obtained in the same manner as in Example 85, step B.
$^1$H NMR (300 MHz, DMSO-$d_6$) δ 3.39-3.47 (2H, m), 4.52-4.66 (2H, m), 5.12 (2H, s), 6.56 (1H, dd, J=7.6, 6.8 Hz), 7.13 (1H, dd, J=7.7, 1.3 Hz), 7.31-7.58 (5H, m).

Example 277

9-{[3,5-bis(trifluoromethyl)benzyl]oxy}-3,4,6,7,8,9-hexahydropyrido[2,1-c][1,2,4]thiadiazine 2,2-dioxide A) 9-{[3,5-bis(trifluoromethyl)benzyl]oxy}-3,4-dihydropyrido[2,1-c][1,2,4]thiadiazine 2,2-dioxide The title compound was obtained in the same manner as in Example 276.
MS (ESI+). found: 427.1.

B) 9-{[3,5-bis(trifluoromethyl)benzyl]oxy}-3,4,6,7,8,9-hexahydropyrido[2,1-c][1,2,4]thiadiazine 2,2-dioxide In the same manner as in Example 98, the title compound (61.4 mg) was obtained from 9-{[3,5-bis(trifluoromethyl)benzyl]oxy}-3,4-dihydropyrido[2,1-c][1,2,4]thiadiazine 2,2-dioxide.
$^1$H NMR (300 MHz, DMSO-$d_6$) δ 1.63-2.05 (4H, m), 3.20-3.27 (2H, m), 3.35-3.44 (2H, m), 3.64-3.79 (2H, m), 4.02 (1H, t, J=4.5 Hz), 4.77-5.03 (2H, m), 7.96-8.11 (3H, m).

Example 278

7-methyl-9-(3-phenoxyazetidin-1-yl)-3,4-dihydropyrazino[2,1-c][1,2,4]thiadiazine 2,2-dioxide A) 5-methyl-3-(3-phenoxyazetidin-1-yl)pyrazin-2-amine Potassium carbonate (18.53 mg) was added to a mixture of 3-phenoxyazetidine (20 mg) and 3-bromo-5-methylpyrazin-2-amine (25 mg) in DMF (dry) (1 mL). The mixture was stirred at 120° C. for 4 hr. Water and EtOAc were added and the extracted organic layer was washed with brine, dried over anhydrous sodium sulfate and concentrated in vacuo. The residue was purified by column chromatography (silica gel, eluted with EtOAc in hexane) to give the title compound (12 mg) as white solid.
MS (ESI+). found: 257.1.

B) 7-methyl-9-(3-phenoxyazetidin-1-yl)-3,4-dihydropyrazino[2,1-c][1,2,4]thiadiazine 2,2-dioxide The title compound was obtained in the same manner as in Example 85, step B.
$^1$H NMR (300 MHz, DMSO-$d_6$) δ 1.97-2.12 (3H, m), 3.40-3.44 (2H, m), 4.00-4.20 (2H, m), 4.31-4.44 (2H, m), 4.59-4.80 (2H, m), 4.96-5.14 (1H, m), 6.78-6.90 (3H, m), 6.99 (1H, t, J=7.9 Hz), 7.25-7.40 (2H, m).

Example 279

The compound of Example 279 was produced in the same manner as in Example 278.

Example 280

The compound of Example 280 was produced in the same manner as in Example 14.

Example 281

9-(1-methyl-1H-indol-5-yl)-3,4,6,7,8,9-hexahydropyrido[2,1-c][1,2,4]thiadiazine 2,2-dioxide In the same manner as in Example 98, the title compound (93.2 mg) was obtained from 9-(1-methyl-1H-indol-5-yl)-3,4-dihydropyrido[2,1-c][1,2,4]thiadiazine 2,2-dioxide.
$^1$H NMR (300 MHz, DMSO-$d_6$) δ 1.64-1.87 (3H, m), 1.96-2.09 (1H, m), 3.25-3.29 (2H, m), 3.42-3.61 (2H, m), 3.73-3.94 (6H, m), 6.36 (1H, dd, J=3.0, 0.8 Hz), 6.98 (1H, dd, J=8.5, 1.7 Hz), 7.27-7.39 (3H, m).

Example 282

The compound of Example 282 was produced in the same manner as in Example 14.

Example 283

9-(4-{[4-(trifluoromethyl)pyridin-2-yl]oxy}phenyl)-3,4,6,7,8,9-hexahydropyrido[2,1-c][1,2,4]thiadiazine 2,2-dioxide In the same manner as in Example 98, the title compound (28 mg) was obtained from 9-(4-{[4-(trifluoromethyl)pyridin-2-yl]oxy}phenyl)-3,4-dihydropyrido[2,1-c][1,2,4]thiadiazine 2,2-dioxide.
$^1$H NMR (300 MHz, DMSO-$d_6$) δ 1.72-1.83 (3H, m), 1.95-2.09 (1H, m), 3.26-3.30 (2H, m), 3.45-3.54 (2H, m), 3.76-3.89 (3H, m), 7.14 (2H, d, J=8.7 Hz), 7.27 (2H, d, J=8.7 Hz), 7.45-7.51 (2H, m), 8.42 (1H, d, J=5.7 Hz).

Example 285

9-(1-ethyl-1H-indol-5-yl)-3,4,6,7,8,9-hexahydropyrido[2,1-c][1,2,4]thiadiazine 2,2-dioxide A) tert-butyl 5-(2,2-dioxido-3,4-dihydropyrido[2,1-c][1,2,4]thiadiazin-9-yl)-1H-indole-1-carboxylate The title compound was obtained in the same manner as in Example 14.
MS (ESI+). found: 400.2.

B) 9-(1H-indol-5-yl)-3,4-dihydropyrido[2,1-c][1,2,4]thiadiazine 2,2-dioxide

To a mixture of tert-butyl 5-(2,2-dioxido-3,4-dihydropyrido[2,1-c][1,2,4]thiadiazin-9-yl)-1H-indole-1-carboxylate (500 mg) in THF (dry) (80 mL) was added 8 M NaOH aq. (8 mL). The mixture was stirred at 50° C. for 30 min. MeOH (20 mL) was added and the mixture was stirred at 50°

C. for 4 hr. The precipitate was collected by filtration and dried in vacuo to give the title compound (324.1 mg) as a white solid.

MS (ESI+). found: 300.1.

C) 9-(1-ethyl-1H-indol-5-yl)-3,4-dihydropyrido[2,1-c][1,2,4]thiadiazine 2,2-dioxide To a mixture of 9-(1H-indol-5-yl)-3,4-dihydropyrido[2,1-c][1,2,4]thiadiazine 2,2-dioxide (131 mg) in DMF (dry) (15 mL) was added NaH (60%, 18.38 mg) at room temperature. The mixture was stirred at the same temperature for 10 min. Iodoethane (0.039 mL) was added and the mixture was stirred at room temperature overnight. Water and EtOAc were added and the extracted organic layer was washed with brine. Silica-gel was added to the organic layer and the volatiles were removed in vacuo. The mixture supported on silica-gel was purified by column chromatography (NH-silica gel, eluted with MeOH in EtOAc) to give the title compound (34.6 mg) as a white solid.

$^1$H NMR (300 MHz, CDCl$_3$) δ 1.47 (3H, t, J=7.2 Hz), 3.36-3.45 (2H, m), 4.18 (2H, q, J=7.2 Hz), 4.62-4.71 (2H, m), 6.50 (1H, d, J=2.3 Hz), 6.54-6.64 (1H, m), 7.12 (1H, d, J=3.4 Hz), 7.15-7.20 (1H, m), 7.34 (1H, d, J=8.7 Hz), 7.46-7.55 (2H, m), 7.77 (1H, d, J=1.1 Hz).

D) 9-(1-ethyl-1H-indol-5-yl)-3,4,6,7,8,9-hexahydropyrido[2,1-c][1,2,4]thiadiazine 2,2-dioxide In the same manner as in Example 98, the title compound (24.1 mg) was obtained from 9-(1-ethyl-1H-indol-5-yl)-3,4-dihydropyrido[2,1-c][1,2,4]thiadiazine 2,2-dioxide.

$^1$H NMR (300 MHz, DMSO-d$_6$) δ 1.35 (3H, t, J=7.2 Hz), 1.64-1.88 (3H, m), 1.97-2.12 (1H, m), 3.23-3.28 (2H, m), 3.42-3.56 (2H, m), 3.76-3.90 (3H, m), 4.12-4.25 (2H, m), 6.37 (1H, d, J=3.0 Hz), 6.96 (1H, d, J=8.3 Hz), 7.28-7.43 (3H, m).

Example 286

7-(2,2-dioxido-3,4-dihydropyrido[2,1-c][1,2,4]thiadiazin-9-yl)-2,2-dimethyl-3,4-dihydronaphthalen-1(2H)-one A) 7-(2-aminopyridin-3-yl)-2,2-dimethyl-3,4-dihydronaphthalen-1(2H)-one The title compound was obtained in the same manner as in Example 101, step A.

MS (ESI+). found: 267.2.

B) 7-(2,2-dioxido-3,4-dihydropyrido[2,1-c][1,2,4]thiadiazin-9-yl)-2,2-dimethyl-3,4-dihydronaphthalen-1 (2H)-one The title compound was obtained in the same manner as in Example 85, step B.

$^1$H NMR (300 MHz, DMSO-d$_6$) δ 1.15 (6H, s), 1.96 (2H, t, J=6.2 Hz), 3.00 (2H, t, J=6.2 Hz), 3.40-3.52 (2H, m), 4.58-4.71 (2H, m), 6.71 (1H, t, J=7.0 Hz), 7.38 (1H, d, J=8.3 Hz), 7.60-7.71 (2H, m), 7.79 (1H, dd, J=6.6, 1.7 Hz), 7.95 (1H, d, J=1.9 Hz).

Example 287

5-(2,2-dioxido-3,4-dihydropyrido[2,1-c][1,2,4]thiadiazin-9-yl)-2,2-dimethyl-2,3-dihydro-1H-inden-1-one A) 5-(2-aminopyridin-3-yl)-2,2-dimethyl-2,3-dihydro-1H-inden-1-one The title compound was obtained in the same manner as in Example 101, step A.

MS (ESI+). found: 253.1.

B) 5-(2,2-dioxido-3,4-dihydropyrido[2,1-c][1,2,4]thiadiazin-9-yl)-2,2-dimethyl-2,3-dihydro-1H-inden-1-one The title compound was obtained in the same manner as in Example 85, step B.

$^1$H NMR (300 MHz, DMSO-d$_6$) δ 1.17 (6H, s), 3.04 (2H, s), 3.44-3.54 (2H, m), 4.63-4.72 (2H, m), 6.74 (1H, t, J=7.0 Hz), 7.53-7.58 (1H, m), 7.64 (1H, s), 7.67-7.72 (2H, m), 7.84 (1H, dd, J=6.8, 1.5 Hz).

Example 288

7-(2,2-dioxido-3,4,6,7,8,9-hexahydropyrido[2,1-c][1,2,4]thiadiazin-9-yl)-2,2-dimethyl-3,4-dihydronaphthalen-1(2H)-one In the same manner as in Example 98, the title compound (220.1 mg) was obtained from 7-(2,2-dioxido-3,4-dihydropyrido[2,1-c][1,2,4]thiadiazin-9-yl)-2,2-dimethyl-3,4-dihydronaphthalen-1 (2H)-one.

$^1$H NMR (300 MHz, DMSO-d$_6$) δ 1.13 (6H, s), 1.63-1.86 (3H, m), 1.88-2.05 (3H, m), 2.94 (2H, t, J=6.0 Hz), 3.17-3.27 (2H, m), 3.41-3.63 (2H, m), 3.70-3.96 (3H, m), 7.19-7.33 (1H, m), 7.33-7.45 (1H, m), 7.71 (1H, d, J=1.9 Hz).

Example 289

5-(2,2-dioxido-3,4,6,7,8,9-hexahydropyrido[2,1-c][1,2,4]thiadiazin-9-yl)-2,2-dimethyl-2,3-dihydro-1H-inden-1-one In the same manner as in Example 98, the title compound (163.3 mg) was obtained from 5-(2,2-dioxido-3,4-dihydropyrido[2,1-c][1,2,4]thiadiazin-9-yl)-2,2-dimethyl-2,3-dihydro-1H-inden-1-one.

$^1$H NMR (300 MHz, DMSO-d$_6$) δ 1.14 (6H, s), 1.65-1.86 (3H, m), 1.93-2.13 (1H, m), 2.99 (2H, s), 3.26-3.30 (2H, m), 3.41-3.61 (2H, m), 3.68-4.00 (3H, m), 7.29 (1H, d, J=7.9 Hz), 7.40 (1H, s), 7.60 (1H, d, J=7.9 Hz).

Example 290

9-[4-(1H-pyrazol-1-yl)phenyl]-3,4,6,7,8,9-hexahydropyrido[2,1-c][1,2,4]thiadiazine 2,2-dioxide A) 9-(4-(1H-pyrazol-1-yl)phenyl)-3,4-dihydropyrido[2,1-c][1,2,4]thiadiazine 2,2-dioxide The title compound was obtained in the same manner as in Example 14.

MS (ESI+). found: 327.1.

B) 9-[4-(1H-pyrazol-1-yl)phenyl]-3,4,6,7,8,9-hexahydropyrido[2,1-c][1,2,4]thiadiazine 2,2-dioxide In the same manner as in Example 98, the title compound (165.7 mg) was obtained from 9-(4-(1H-pyrazol-1-yl)phenyl)-3,4-dihydropyrido[2,1-c][1,2,4]thiadiazine 2,2-dioxide.

$^1$H NMR (300 MHz, DMSO-$d_6$) δ 1.68-1.87 (3H, m), 1.93-2.13 (1H, m), 3.24-3.29 (2H, m), 3.44-3.62 (2H, m), 3.74-3.95 (3H, m), 6.45-6.62 (1H, m), 7.33 (2H, d, J=8.7 Hz), 7.66-7.84 (3H, m), 8.47 (1H, d, J=3.0 Hz).

Example 291

1-[4-(2,2-dioxido-3,4,6,7,8,9-hexahydropyrido[2,1-c][1,2,4]thiadiazin-9-yl)phenyl]ethanone A) 1-[4-(2,2-dioxido-3,4-dihydropyrido[2,1-c][1,2,4]thiadiazin-9-yl)phenyl]ethanone The title compound was obtained in the same manner as in Example 14.
MS (ESI+). found: 303.1.

B) 1-[4-(2,2-dioxido-3,4,6,7,8,9-hexahydropyrido[2,1-c][1,2,4]thiadiazin-9-yl)phenyl]ethanone In the same manner as in Example 98, the title compound (278.6 mg) was obtained from 1-[4-(2,2-dioxido-3,4-dihydropyrido[2,1-c][1,2,4]thiadiazin-9-yl)phenyl]ethanone.

$^1$H NMR (300 MHz, DMSO-$d_6$) δ 1.67-1.85 (3H, m), 1.95-2.12 (1H, m), 2.57 (3H, s), 3.24-3.31 (2H, m), 3.40-3.60 (2H, m), 3.74-3.96 (3H, m), 7.37 (2H, d, J=8.3 Hz), 7.90 (2H, d, J=8.3 Hz).

Example 292

The compound of Example 292 was produced in the same manner as in Example 284.

Example 293

9-[1-(2-methylpropyl)-1H-indol-5-yl]-3,4-dihydropyrido[2,1-c][1,2,4]thiadiazine 2,2-dioxide A) 5-bromo-1-isobutyl-1H-indole To a mixture of 5-bromo-1H-indole (1 g) in DMF (dry) (10 mL) was added NaH (60%, 0.612 g) at room temperature. The mixture was stirred at 80° C. for 10 min. 1-Iodo-2-methylpropane (0.587 mL) was added at room temperature and the mixture was stirred at 80° C. for 1 hr. Another 1-iodo-2-methylpropane (0.587 mL) was added and the mixture was stirred at 80° C. for 1 hr. Water and EtOAc were added and the extracted organic layer was washed with brine. Silica-gel was added to the organic layer and the volatiles were removed in vacuo. The mixture supported on silica-gel was purified by column chromatography (silica gel, eluted with EtOAc in hexane) to give the title compound (554 mg) as colorless oil.

$^1$H NMR (300 MHz, DMSO-$d_6$) δ 0.91 (6H, d, J=6.8 Hz), 2.04-2.27 (1H, m), 3.88 (2H, d, J=7.2 Hz), 6.42 (1H, d, J=2.6 Hz), 7.07 (1H, d, J=3.0 Hz), 7.16-7.22 (1H, m), 7.24-7.25 (1H, m), 7.74 (1H, d, J=1.5 Hz).

B) 3-(1-isobutyl-1H-indol-5-yl)pyridin-2-amine

The title compound was obtained in the same manner as in Example 101, step A.
MS (ESI+). found: 266.2.

C) 9-[1-(2-methylpropyl)-1H-indol-5-yl]-3,4-dihydropyrido[2,1-c][1,2,4]thiadiazine 2,2-dioxide The title compound was obtained in the same manner as in Example 85, step B.

$^1$H NMR (300 MHz, DMSO-$d_6$) δ 0.86 (6H, d, J=6.4 Hz), 2.16 (1H, d, J=6.8 Hz), 3.41-3.50 (2H, m), 3.99 (2H, d, J=7.6 Hz), 4.61-4.71 (2H, m), 6.46 (1H, d, J=2.6 Hz), 6.67-6.74 (1H, m), 7.27 (1H, dd, J=8.5, 1.7 Hz), 7.38 (1H, d, J=3.0 Hz), 7.49 (1H, d, J=8.3 Hz), 7.59-7.64 (1H, m), 7.67 (1H, s), 7.74 (1H, dd, J=6.8, 1.5 Hz).

Example 294

9-(1-butyl-1H-indol-5-yl)-3,4,6,7,8,9-hexahydropyrido[2,1-c][1,2,4]thiadiazine 2,2-dioxide In the same manner as in Example 98, the title compound (49.7 mg) was obtained from 9-(1-butyl-1H-indol-5-yl)-3,4-dihydropyrido[2,1-c][1,2,4]thiadiazine 2,2-dioxide.

$^1$H NMR (300 MHz, DMSO-$d_6$) δ 0.85-0.92 (3H, m), 1.17-1.31 (2H, m), 1.67-1.84 (5H, m), 1.97-2.10 (1H, m), 3.25-3.30 (2H, m), 3.43-3.59 (2H, m), 3.77-3.91 (3H, m), 4.14 (2H, t, J=7.0 Hz), 6.36 (1H, d, J=3.0 Hz), 6.96 (1H, dd, J=8.5, 1.7 Hz), 7.30-7.41 (3H, m).

Example 295

9-{1-[2-(4-fluorophenyl)ethyl]-1H-indol-5-yl}-3,4,6,7,8,9-hexahydropyrido[2,1-c][1,2,4]thiadiazine 2,2-dioxide To a mixture of cesium carbonate (435 mg) and 9-(1H-indol-5-yl)-3,4-dihydropyrido[2,1-c][1,2,4]thiadiazine 2,2-dioxide (200 mg) in DMSO (5 mL) was added 1-(2-bromoethyl)-4-fluorobenzene (136 mg). The mixture was stirred at room temperature for 1 day. Water and EtOAc were added and the extracted organic layer was washed with brine, dried over anhydrous sodium sulfate. Silica-gel was added to the organic layer and the volatiles were removed in vacuo. The mixture supported on silica-gel was purified by column chromatography (silica gel, eluted with MeOH in EtOAc), concentrated and dissolved in THF (dry) (25 mL) and MeOH (25 mL). Then platinum(IV) oxide (46 mg) was added and the mixture was stirred at room temperature under hydrogen overnight. Activated carbon was added and the insoluble solid was removed by filtration through NH-silica gel/Celite pad (eluted with EtOAc). The filtrate was concentrated and the residue was purified by column chromatography (1st: NH silica gel, eluted with MeOH in EtOAc, 2nd: silica gel, eluted with EtOAc) to give the title compound (5.7 mg) as a white solid.

$^1$H NMR (300 MHz, CDCl$_3$) δ 1.75-2.23 (4H, m), 3.05 (2H, t, J=7.2 Hz), 3.24-3.35 (2H, m), 3.36-3.58 (2H, m), 3.88-4.03 (3H, m), 4.29 (2H, t, J=7.2 Hz), 6.36 (1H, d, J=3.0 Hz), 6.84 (1H, d, J=3.0 Hz), 6.87-7.14 (5H, m), 7.23 (1H, s), 7.35-7.40 (1H, m).

Example 296

9-[1-(2-methylpropyl)-1H-indol-5-yl]-3,4,6,7,8,9-hexahydropyrido[2,1-c][1,2,4]thiadiazine 2,2-dioxide In the same manner as in Example 98, the title compound (5.3 mg) was obtained from 9-[1-(2-methylpropyl)-1H-indol-5-yl]-3,4-dihydropyrido[2,1-c][1,2,4]thiadiazine 2,2-dioxide.

$^1$H NMR (300 MHz, DMSO-$d_6$) δ 0.85 (6H, d, J=6.4 Hz), 1.62-1.87 (3H, m), 1.93-2.20 (2H, m), 3.23-3.30 (2H, m), 3.42-3.58 (2H, m), 3.72-3.91 (3H, m), 3.95 (2H, d, J=7.2 Hz), 6.37 (1H, d, J=2.3 Hz), 6.95 (1H, dd, J=8.5, 1.7 Hz), 7.26-7.34 (2H, m), 7.39 (1H, d, J=8.7 Hz).

Example 297

9-(3'-methoxybiphenyl-4-yl)-3,4-dihydropyrido[2,1-c][1,2,4]thiadiazine 2,2-dioxide

A) 3-(4-(1H-naphtho[1,8-de][1,3,2]diazaborinin-2(3H)-yl)phenyl)pyridin-2-amine Tetrakis(triphenylphosphine)palladium(0) (57.7 mg) was added to a suspension of 3-bromopyridin-2-amine (432 mg), 2-(4-(4,4,5,5-tetramethyl-1,3,2-dioxaborolan-2-yl)phenyl)-2,3-dihydro-1H-naphtho[1,8-de][1,3,2]diazaborinine (1016 mg) and sodium carbonate decahydrate (1429 mg) in DME (10 mL) and water (2 mL) and the mixture was stirred at 80° C. under nitrogen for 3 hr and at 70° C. overnight. Activated carbon was added and the insoluble solid was removed by filtration through NH-silica gel/Celite pad (eluted with EtOAc). The filtrate was concentrated and the residue was purified by column chromatography (silica gel, eluted with EtOAc in hexane) to give the title compound (397 mg) as a brown solid.

MS (ESI+). found: 337.2.

B) 4-(2-aminopyridin-3-yl)phenylboronic acid

6N HCl aq. (1.1 mL) was added to a mixture of 3-(4-(1H-naphtho[1,8-de][1,3,2]diazaborinin-2 (3H)-yl)phenyl)pyridin-2-amine (396 mg) in THF (dry) (12 mL). The mixture was stirred at room temperature for 3 hr. The mixture was added with sat. NaHCO$_3$ aq, EtOAc and 2N NaOH aq., and the separated aqueous phase was acidified by 6N HCl aq., then controlled pH ca.8 by sat. NaHCO$_3$ aq. The aqueous mixture was extracted with EtOAc, and the organic layer was separated, washed with brine dried over anhydrous magnesium sulfate and concentrated in vacuo to give the title compound (52.4 mg) as a white solid.

MS (ESI+). found: 215.1.

C) 3-(3'-methoxybiphenyl-4-yl)pyridin-2-amine

Tetrakis(triphenylphosphine)palladium(0) (8.49 mg) was added to a suspension of 1-iodo-3-methoxybenzene (68.8 mg), 4-(2-aminopyridin-3-yl)phenylboronic acid (52.4 mg) and sodium carbonate decahydrate (210 mg) in DME (5 mL), water (1 mL) and THF (dry) (5 mL). The mixture was stirred at 80° C. under nitrogen overnight. Silica-gel was added and the volatiles were removed in vacuo. The mixture supported on silica-gel was purified by column chromatography (NH silica gel, eluted with EtOAc in hexane) to give the title compound (49.1 mg) as a white solid.

MS (ESI+). found: 277.1.

D) 9-(3'-methoxybiphenyl-4-yl)-3,4-dihydropyrido[2,1-c][1,2,4]thiadiazine 2,2-dioxide To a suspension of NaH (60%, 35.5 mg) in THF (dry) (5 mL) was added 2-chloroethanesulfonyl chloride (0.056 mL) at 0° C. and the mixture was stirred for 5 min at the same temperature. A solution of 3-(3'-methoxybiphenyl-4-yl)pyridin-2-amine (49 mg) in THF (dry) (5 mL) was added at 0° C. and the mixture was stirred at room temperature overnight. The mixture was quenched with water. Water and EtOAc were added and the extracted organic layer was washed with brine, dried over anhydrous magnesium sulfate and concentrated in vacuo. The residue was washed with EtOAc and dried in vacuo to give the title compound (18 mg) as a white solid.

$^1$H NMR (300 MHz, DMSO-$d_6$) δ 3.41-3.56 (2H, m), 3.84 (3H, s), 4.58-4.76 (2H, m), 6.74 (1H, t, J=7.0 Hz), 6.96 (1H, dd, J=7.7, 2.1 Hz), 7.21-7.31 (2H, m), 7.35-7.45 (1H, m), 7.56-7.65 (2H, m), 7.65-7.76 (3H, m), 7.76-7.86 (1H, m).

Example 298

The compound of Example 298 was produced in the same manner as in Example 14.

Example 299

9-{4-[5-cyclopropyl-3-(trifluoromethyl)-1H-pyrazol-1-yl]phenyl}-3,4-dihydropyrido[2,1-c][1,2,4]thiadiazine 2,2-dioxide

A) 1-(4-bromophenyl)-5-cyclopropyl-3-(trifluoromethyl)-1H-pyrazole

1-Cyclopropyl-4,4,4-trifluorobutane-1,3-dione (1.330 g) was added to a mixture of (4-bromophenyl)hydrazine hydrochloride (1.65 g) and AcOH (10 mL). The mixture was stirred at 120° C. for 1 hr. AcOH was removed in vacuo and the residue was purified by column chromatography (NH silica gel, eluted with EtOAc in hexane) to give 1-(4-bromophenyl)-5-cyclopropyl-3-(trifluoromethyl)-1H-pyrazole (2.2059 g) as a yellow oil.

$^1$H NMR (300 MHz, CDCl$_3$) δ 0.60-0.93 (2H, m), 0.93-1.15 (2H, m), 1.68-1.88 (1H, m), 6.22 (1H, s), 7.51 (2H, d), 7.63 (2H, d, J=9.1 Hz).

B) 3-(4-(5-cyclopropyl-3-(trifluoromethyl)-1H-pyrazol-1-yl)phenyl)pyridin-2-amine The title compound was obtained in the same manner as in Example 101, step A.

MS (ESI+). found: 345.1.

C) 9-{4-[5-cyclopropyl-3-(trifluoromethyl)-1H-pyrazol-1-yl]phenyl}-3,4-dihydropyrido[2,1-c][1,2,4]thiadiazine 2,2-dioxide The title compound was obtained in the same manner as in Example 85, step B.

$^1$H NMR (300 MHz, DMSO-$d_6$) δ 0.79-0.95 (2H, m), 0.95-1.11 (2H, m), 1.85-2.00 (1H, m), 3.43-3.58 (2H, m), 4.59-4.76 (2H, m), 6.66 (1H, s), 6.75 (1H, t, J=7.0 Hz), 7.60-7.78 (5H, m), 7.83 (1H, dd, J=6.6, 1.7 Hz).

Example 300

The compound of Example 300 was produced in the same manner as in Example 299.

Example 301

9-{4-[5-cyclopropyl-3-(trifluoromethyl)-1H-pyrazol-1-yl]phenyl}-3,4,6,7,8,9-hexahydropyrido[2,1-c][1,2,4]thiadiazine 2,2-dioxide In the same manner as in Example 98, the title compound (60.3 mg) was obtained from 9-{4-[5-cyclopropyl-3-(trifluoromethyl)-1H-pyrazol-1-yl]phenyl}-3,4-dihydropyrido[2,1-c][1,2,4]thiadiazine 2,2-dioxide.
$^1$H NMR (300 MHz, DMSO-$d_6$) δ 0.73-0.93 (2H, m), 0.93-1.07 (2H, m), 1.68-1.91 (4H, m), 1.99-2.14 (1H, m), 3.26-3.29 (2H, m), 3.44-3.60 (2H, m), 3.76-4.01 (3H, m), 6.62 (1H, s), 7.42 (2H, d, J=8.3 Hz), 7.60 (2H, d, J=8.7 Hz).

Example 302

9-{4-[5-methyl-3-(trifluoromethyl)-1H-pyrazol-1-yl]phenyl}-3,4,6,7,8,9-hexahydropyrido[2,1-c][1,2,4]thiadiazine 2,2-dioxide In the same manner as in Example 98, the title compound (176 mg) was obtained from 9-{4-[5-methyl-3-(trifluoromethyl)-1H-pyrazol-1-yl]phenyl}-3,4-dihydropyrido[2,1-c][1,2,4]thiadiazine 2,2-dioxide.
$^1$H NMR (300 MHz, DMSO-$d_6$) δ 1.73-1.85 (3H, m), 1.94-2.15 (1H, m), 2.36 (3H, s), 3.26-3.31 (2H, m), 3.42-3.62 (2H, m), 3.73-3.99 (3H, m), 6.76 (1H, s), 7.35-7.46 (2H, m), 7.46-7.56 (2H, m).

Example 303

9-[(5,6,7,8-tetrahydronaphthalen-2-yloxy)methyl]-3,4,6,7,8,9-hexahydropyrido[2,1-c][1,2,4]thiadiazine 2,2-dioxide In the same manner as in Example 98, the title compound (6.50 mg) was obtained from 9-[(5,6,7,8-tetrahydronaphthalen-2-yloxy)methyl]-3,4-dihydropyrido[2,1-c][1,2,4]thiadiazine 2,2-dioxide.
$^1$H NMR (300 MHz, CDCl$_3$) δ 1.67-1.91 (6H, m), 1.96-2.20 (2H, m), 2.57-2.80 (4H, m), 2.80-2.96 (1H, m), 3.11-3.29 (2H, m), 3.29-3.49 (2H, m), 3.74-3.90 (2H, m), 4.03-4.25 (1H, m), 4.39 (1H, dd, J=9.4, 3.8 Hz), 6.56-6.75 (2H, m), 6.86-7.02 (1H, m).

Example 304

[4-(2,2-dioxido-3,4,6,7,8,9-hexahydropyrido[2,1-c][1,2,4]thiadiazin-9-yl)phenyl](phenyl)methanone In the same manner as in Example 98, the title compound (11.3 mg) was obtained from [4-(2,2-dioxido-3,4-dihydropyrido[2,1-c][1,2,4]thiadiazin-9-yl)phenyl](phenyl)methanone.
$^1$H NMR (300 MHz, DMSO-$d_6$) δ 1.71-1.84 (3H, m), 1.95-2.13 (1H, m), 3.32-3.35 (2H, m), 3.42-3.59 (2H, m), 3.76-3.96 (3H, m), 7.41 (2H, d, J=8.3 Hz), 7.51-7.61 (2H, m), 7.64-7.80 (5H, m).

Example 305

9-{[4-(trifluoromethyl)phenoxy]methyl}-3,4,6,7,8,9-hexahydropyrido[2,1-c][1,2,4]thiadiazine 2,2-dioxide In the same manner as in Example 98, the title compound (1.40 mg) was obtained from 9-{[4-(trifluoromethyl)phenoxy]methyl}-3,4-dihydropyrido[2,1-c][1,2,4]thiadiazine 2,2-dioxide.
$^1$H NMR (300 MHz, CDCl$_3$) δ 1.73-1.96 (2H, m), 1.97-2.22 (2H, m), 2.87-3.00 (1H, m), 3.14-3.33 (2H, m), 3.33-3.51 (2H, m), 3.86 (2H, t, J=6.6 Hz), 4.27 (1H, dd, J=9.4, 7.5 Hz), 4.46 (1H, dd, J=9.4, 3.8 Hz), 6.99 (2H, d, J=8.7 Hz), 7.54 (2H, d, J=8.7 Hz).

Example 306

[4-(2,2-dioxido-3,4-dihydropyrido[2,1-c][1,2,4]thiadiazin-9-yl)phenyl](3-methoxyphenyl)methanone A) (4-bromophenyl)(3-methoxyphenyl)methanone The title compound was obtained in the same manner as in Example 136, step A.
$^1$H NMR (300 MHz, CDCl$_3$) δ 3.86 (3H, s), 7.10-7.18 (1H, m), 7.28-7.84 (7H, m).

B) [4-(2-aminopyridin-3-yl)phenyl](3-methoxyphenyl)methanone

The title compound was obtained in the same manner as in Example 101, step A.
MS (ESI+). found: 305.1.

C) [4-(2,2-dioxido-3,4-dihydropyrido[2,1-c][1,2,4]thiadiazin-9-yl)phenyl](3-methoxyphenyl)methanone The title compound was obtained in the same manner as in Example 85, step B.
$^1$H NMR (300 MHz, DMSO-$d_6$) δ 3.41-3.54 (2H, m), 3.83 (3H, s), 4.60-4.74 (2H, m), 6.75 (1H, t, J=7.0 Hz), 7.22-7.36 (3H, m), 7.45-7.55 (1H, m), 7.64-7.90 (6H, m).

Example 307

9-{4-[3-methyl-4-(trifluoromethyl)phenoxy]phenyl}-3,4-dihydropyrido[2,1-c][1,2,4]thiadiazine 2,2-dioxide A) 3-{4-[3-methyl-4-(trifluoromethyl)phenoxy]phenyl}pyridin-2-amine In the same manner as in Example 85, step A, the title compound (482 mg) was obtained from 4-(2-aminopyridin-3-yl)phenol (500 mg) and 4-bromo-2-methyl-1-(trifluoromethyl)benzene (770 mg).
MS (ESI+). found: 345.1.

B) 9-{4-[3-methyl-4-(trifluoromethyl)phenoxy]phenyl}-3,4-dihydropyrido[2,1-c][1,2,4]thiadiazine 2,2-dioxide The title compound was obtained in the same manner as in Example 85, step B.

¹H NMR (300 MHz, DMSO-d₆) δ 2.43 (3H, d, J=1.5 Hz), 3.41-3.52 (2H, m), 4.55-4.71 (2H, m), 6.72 (1H, t, J=7.0 Hz), 6.97 (1H, dd, J=8.7, 1.9 Hz), 7.08-7.20 (3H, m), 7.53-7.83 (5H, m).

Example 308

9-{4-[3-methyl-4-(trifluoromethyl)phenoxy]phenyl}-3,4,6,7,8,9-hexahydropyrido[2,1-c][1,2,4]thiadiazine 2,2-dioxide In the same manner as in Example 98, the title compound (187 mg) was obtained from 9-{4-[3-methyl-4-(trifluoromethyl)phenoxy]phenyl}-3,4-dihydropyrido[2,1-c][1,2,4]thiadiazine 2,2-dioxide.

¹H NMR (300 MHz, DMSO-d₆) δ 1.65-1.86 (3H, m), 1.91-2.09 (1H, m), 2.41 (3H, d, J=1.5 Hz), 3.24-3.29 (2H, m), 3.39-3.55 (2H, m, J=6.4, 6.4, 6.4 Hz), 3.69-3.92 (3H, m), 6.90 (1H, d, J=8.7 Hz), 6.98-7.16 (3H, m), 7.27 (2H, d, J=8.7 Hz), 7.66 (1H, d, J=8.7 Hz).

Example 309

9-{4-[2-methyl-5-(trifluoromethyl)phenoxy]phenyl}-3,4-dihydropyrido[2,1-c][1,2,4]thiadiazine 2,2-dioxide A) 3-{4-[2-methyl-5-(trifluoromethyl)phenoxy]phenyl}pyridin-2-amine In the same manner as in Example 85, step A, the title compound (456 mg) was obtained from 4-(2-aminopyridin-3-yl)phenol (500 mg) and 2-bromo-1-methyl-4-(trifluoromethyl)benzene (770 mg).

MS (ESI+). found: 345.1.

B) 9-{4-[2-methyl-5-(trifluoromethyl)phenoxy]phenyl}-3,4-dihydropyrido[2,1-c][1,2,4]thiadiazine 2,2-dioxide The title compound was obtained in the same manner as in Example 85, step B.

¹H NMR (300 MHz, DMSO-d₆) δ 2.30 (3H, s), 3.40-3.50 (2H, m), 4.60-4.70 (2H, m), 6.70 (1H, t, J=7.0 Hz), 6.92-7.04 (2H, m), 7.27 (1H, s), 7.47-7.66 (5H, m), 7.77 (1H, dd, J=6.6, 1.7 Hz).

Example 310

9-{4-[2-methyl-5-(trifluoromethyl)phenoxy]phenyl}-3,4,6,7,8,9-hexahydropyrido[2,1-c][1,2,4]thiadiazine 2,2-dioxide In the same manner as in Example 98, the title compound (173 mg) was obtained from 9-{4-[2-methyl-5-(trifluoromethyl)phenoxy]phenyl}-3,4-dihydropyrido[2,1-c][1,2,4]thiadiazine 2,2-dioxide.

¹H NMR (300 MHz, DMSO-d₆) δ 1.65-1.84 (3H, m), 1.92-2.10 (1H, m), 2.28 (3H, s), 3.23-3.29 (2H, m), 3.41-3.55 (2H, m), 3.70-3.90 (3H, m), 6.84-6.96 (2H, m, J=8.7 Hz), 7.11-7.29 (3H, m), 7.42-7.51 (1H, m), 7.57 (1H, d, J=7.9 Hz).

Example 311

9-{4-[4-bromo-3-(trifluoromethyl)phenoxy]phenyl}-3,4-dihydropyrido[2,1-c][1,2,4]thiadiazine 2,2-dioxide A) 3-{4-[4-bromo-3-(trifluoromethyl)phenoxy]phenyl}pyridin-2-amine Tripotassium phosphate (3.42 g) was added to a mixture of 4-(2-aminopyridin-3-yl)phenol (1.00 g) and 1-bromo-4-fluoro-2-(trifluoromethyl)benzene (1.57 g) in DMSO (15 mL). The mixture was stirred at 140° C. under nitrogen for 7 hr. Water and EtOAc were added and the extracted organic layer was washed with brine. Silica-gel was added to the organic layer and the volatiles were removed in vacuo. The mixture supported on silica-gel was purified by column chromatography (NH-silica gel, eluted with EtOAc in hexane) and concentrated to give 3-{4-[4-bromo-3-(trifluoromethyl)phenoxy]phenyl}pyridin-2-amine (1.52 g) as orange oil.

¹H NMR (300 MHz, DMSO-d₆) δ 5.60 (2H, s), 6.66 (1H, dd, J=7.2, 4.9 Hz), 7.15-7.23 (2H, m), 7.26 (1H, dd, J=9.0, 3.0 Hz), 7.34 (1H, dd, J=7.2, 1.9 Hz), 7.44-7.54 (3H, m), 7.88 (1H, d, J=9.0 Hz), 7.95 (1H, dd, J=4.9, 1.9 Hz).

B) 9-{4-[4-bromo-3-(trifluoromethyl)phenoxy]phenyl}-3,4-dihydropyrido[2,1-c][1,2,4]thiadiazine 2,2-dioxide The title compound was obtained in the same manner as in Example 85, step B.

¹H NMR (300 MHz, DMSO-d₆) δ 3.41-3.51 (2H, m), 4.59-4.71 (2H, m), 6.71 (1H, t, J=6.8 Hz), 7.12-7.19 (2H, m), 7.26 (1H, dd, J=8.9, 2.8 Hz), 7.53 (1H, d, J=3.0 Hz), 7.56-7.69 (3H, m), 7.78 (1H, dd, J=6.8, 1.5 Hz), 7.89 (1H, d, J=9.0 Hz).

Example 312

The compound of Example 312 was produced in the same manner as in Example 136.

Example 313

9-[4-(2,3-dihydro-1-benzofuran-6-yloxy)phenyl]-3,4-dihydropyrido[2,1-c][1,2,4]thiadiazine 2,2-dioxide A) 3-[4-(2,3-dihydrobenzofuran-6-yloxy)phenyl]pyridin-2-amine In the same manner as in Example 85, step A, the title compound (295 mg) was obtained from 4-(2-aminopyridin-3-yl)phenol (500 mg) and 6-bromo-2,3-dihydrobenzofuran (641 mg).

MS (ESI+). found: 305.0.

B) 9-[4-(2,3-dihydro-1-benzofuran-6-yloxy)phenyl]-3,4-dihydropyrido[2,1-c][1,2,4]thiadiazine 2,2-dioxide The title compound was obtained in the same manner as in Example 85, step B.

¹H NMR (300 MHz, DMSO-d₆) δ 3.16 (2H, t, J=8.5 Hz), 3.40-3.50 (2H, m, J=6.4 Hz), 4.51-4.71 (4H, m), 6.47-6.55

(2H, m), 6.70 (1H, t, J=7.2 Hz), 6.99 (2H, d, J=8.7 Hz), 7.22 (1H, d, J=7.9 Hz), 7.51 (2H, d, J=8.3 Hz), 7.62 (1H, d, J=6.8 Hz), 7.76 (1H, d, J=5.3 Hz).

Example 314

The compound of Example 314 was produced in the same manner as in Example 313.

Example 315

The compound of Example 315 was produced in the same manner as in Example 310.

Example 316

The compound of Example 316 was produced in the same manner as in Example 313.

Example 317

9-[4-(4-fluoro-3-methoxyphenoxy)phenyl]-7-methyl-3,4-dihydropyrido[2,1-c][1,2,4]thiadiazine 2,2-dioxide A) 3-[4-(4-fluoro-3-methoxyphenoxy)phenyl]-5-methylpyridin-2-amine In the same manner as in Example 85, step A, the title compound (361 mg) was obtained from 4-(2-amino-5-methylpyridin-3-yl)phenol (500 mg) and 4-bromo-1-fluoro-2-methoxybenzene (614 mg).
MS (ESI+). found: 325.1.

B) 9-[4-(4-fluoro-3-methoxyphenoxy)phenyl]-7-methyl-3,4-dihydropyrido[2,1-c][1,2,4]thiadiazine 2,2-dioxide The title compound was obtained in the same manner as in Example 85, step B.
$^1$H NMR (300 MHz, DMSO-$d_6$) δ 2.14 (3H, s), 3.39-3.44 (2H, m), 3.83 (3H, s), 4.56-4.62 (2H, m), 6.58 (1H, dt, J=8.7, 3.2 Hz), 6.97-7.04 (3H, m), 7.24 (1H, dd, J=11.2, 8.9 Hz), 7.49-7.56 (3H, m), 7.63 (1H, s).

Example 318

The compound of Example 318 was produced in the same manner as in Example 310.

Example 319

The compound of Example 319 was produced in the same manner as in Example 313.

Example 320

The compound of Example 320 was produced in the same manner as in Example 310.

Example 321

9-[4-(1-phenylcyclobutyl)phenyl]-3,4,6,7,8,9-hexahydropyrido[2,1-c][1,2,4]thiadiazine 2,2-dioxide A) 4-[1-(4-hydroxyphenyl)cyclobutyl]phenyl trifluoromethanesulfonate Trifluoromethanesulfonic anhydride (0.350 mL) was added to a solution of 4,4'-(cyclobutane-1,1-diyl)diphenol (500 mg) and pyridine (0.505 mL) in MeCN (10 mL) at 0° C. The mixture was stirred at room temperature for 40 min. The mixture was neutralized with 1N HCl at 0° C. and extracted with EtOAc. The organic layer was separated, washed with water and brine, dried over anhydrous magnesium sulfate and concentrated in vacuo. The residue was purified by column chromatography (silica gel, eluted with EtOAc in hexane) to give 4-[1-(4-hydroxyphenyl)cyclobutyl]phenyl trifluoromethanesulfonate (160 mg) as colorless oil.
$^1$H NMR (300 MHz, CDCl$_3$) δ 1.89-2.03 (2H, m), 2.59-2.78 (4H, m), 4.56-4.61 (1H, m), 6.72-6.80 (2H, m), 7.11-7.19 (4H, m), 7.29-7.36 (2H, m).

B) 4,4,5,5-tetramethyl-2-[4-(1-phenylcyclobutyl)phenyl]-1,3,2-dioxaborolane

Pd—C (40.0 mg) was added to a mixture of 4-[1-(4-hydroxyphenyl)cyclobutyl]phenyl trifluoromethanesulfonate (160 mg) in MeOH (10 mL). The mixture was stirred at room temperature under hydrogen for 2 hr. The insoluble solid was removed by filtration through silica gel/Celite pad (eluted with EtOAc) and the filtrate was concentrated in vacuo. The residue was dissolved in MeCN (5 mL) and TEA (0.119 mL) and trifluoromethanesulfonyl chloride (0.054 mL) were added at 0° C. The mixture was stirred at room temperature overnight. Trifluoromethanesulfonyl chloride (0.054 mL) and TEA (0.119 mL) were added at 0° C. and the mixture was stirred at room temperature under a dry atmosphere (anhydrous calcium chloride tube) for 1 day. MeOH (1 mL) was added and the volatiles were removed in vacuo to give an orange residue. This material (153 mg) was dissolved in DMF (dry) (5 mL), and was added potassium acetate (126 mg), 4,4,4',4',5,5,5',5'-octamethyl-2,2'-bi(1,3,2-dioxaborolane) (164 mg), and Pd(dppf)Cl$_2$ (15.7 mg). The mixture was stirred at 90° C. under nitrogen for 6 hr. The mixture was poured into water and extracted with EtOAc. The organic layer was separated, washed with water and brine, dried over anhydrous magnesium sulfate and concentrated in vacuo. The residue was purified by column chromatography (silica gel, eluted with EtOAc in hexane) to give the title compound (26.7 mg) as a white solid.
$^1$H NMR (300 MHz, CDCl$_3$) δ 1.31 (12H, s), 1.87-2.04 (2H, m), 2.75 (4H, t, J=7.6 Hz), 7.07-7.16 (1H, m), 7.20-7.24 (1H, m), 7.26-7.37 (5H, m), 7.73 (2H, d, J=8.3 Hz).

C) 9-[4-(1-phenylcyclobutyl)phenyl]-3,4,6,7,8,9-hexahydropyrido[2,1-c][1,2,4]thiadiazine 2,2-dioxide The title compound was obtained in the same manner as in Example 31 and Example 98.
$^1$H NMR (300 MHz, CDCl$_3$) δ 1.62-2.19 (6H, m), 2.67-2.79 (4H, m), 3.21-3.33 (2H, m), 3.35-3.49 (2H, m), 3.77-3.97 (3H, m), 7.04 (2H, d, J=8.3 Hz), 7.13 (1H, s), 7.21-7.25 (2H, m), 7.27-7.32 (4H, m).

Example 322

The compound of Example 322 was obtained in the same manner as in Example 31 and Example 98.

Example 323

9-{4-[4-(1,1-difluoroethyl)phenoxy]phenyl}-3,4-dihydropyrido[2,1-c][1,2,4]thiadiazine 2,2-dioxide A) 3-(4-(4-(1,1-difluoroethyl)phenoxy)phenyl)pyridin-2-amine In the same manner as in Example 85, step A, the title compound (347 mg) was obtained from 4-(2-aminopyridin-3-yl)phenol (400 mg) and 1-bromo-4-(1,1-difluoroethyl)benzene (570 mg).
MS (ESI+). found: 327.1.

B) 9-{4-[4-(1,1-difluoroethyl)phenoxy]phenyl}-3,4-dihydropyrido[2,1-c][1,2,4]thiadiazine 2,2-dioxide The title compound was obtained in the same manner as in Example 85, step B.
$^1$H NMR (300 MHz, DMSO-$d_6$) δ 1.97 (3H, t, J=18.9 Hz), 3.40-3.54 (2H, m), 4.60-4.71 (2H, m), 6.71 (1H, t, J=7.0 Hz), 7.04-7.18 (4H, m), 7.53-7.67 (5H, m), 7.78 (1H, dd, J=6.4, 1.5 Hz).

Example 324

9-[4-(4-methylbenzyl)phenyl]-3,4,6,7,8,9-hexahydropyrido[2,1-c][1,2,4]thiadiazine 2,2-dioxide A) 3-(4-(4-methylbenzyl)phenyl)pyridin-2-amine The title compound was obtained in the same manner as in Example 101, step A.
MS (ESI+). found: 275.1.

B) 9-[4-(4-methylbenzyl)phenyl]-3,4-dihydropyrido[2,1-c][1,2,4]thiadiazine 2,2-dioxide The title compound was obtained in the same manner as in Example 85, step B.
MS (ESI+). found: 365.1.

C) 9-[4-(4-methylbenzyl)phenyl]-3,4,6,7,8,9-hexahydropyrido[2,1-c][1,2,4]thiadiazine 2,2-dioxide In the same manner as in Example 98, the title compound (18.4 mg) was obtained from 9-[4-(4-methylbenzyl)phenyl]-3,4-dihydropyrido[2,1-c][1,2,4]thiadiazine 2,2-dioxide.
$^1$H NMR (300 MHz, DMSO-$d_6$) δ 1.61-1.80 (3H, m), 1.86-2.08 (1H, m), 2.25 (3H, s), 3.22-3.29 (2H, m), 3.37-3.54 (2H, m), 3.64-3.91 (5H, m), 6.91-7.20 (8H, m).

Example 325

9-[4-(1-methyl-1-phenylethyl)phenyl]-3,4-dihydropyrido[2,1-c][1,2,4]thiadiazine 2,2-dioxide A) 4-(2-phenylpropan-2-yl)phenyl trifluoromethanesulfonate Trifluoromethanesulfonic anhydride (1.99 mL) was added dropwise to a solution of 4-(2-phenylpropan-2-yl)phenol (1.68 g) and pyridine (1.277 mL) in MeCN (10 mL) at 0° C. The mixture was stirred at room temperature for 2 days. The mixture was quenched with 0.1 N HCl aq. at 0° C. and extracted with EtOAc. The organic layer was separated, washed with water and brine, dried over anhydrous magnesium sulfate, filtered through silica-Celite pad (eluted with EtOAc) and concentrated in vacuo to give 4-(2-phenylpropan-2-yl)phenyl trifluoromethanesulfonate (2.65 g) as a yellow oil.
$^1$H NMR (300 MHz, CDCl$_3$) δ1.68 (6H, s), 7.11-7.25 (5H, m), 7.26-7.34 (4H, m).

B) 3-(4-(2-phenylpropan-2-yl)phenyl)pyridin-2-amine

The title compound was obtained in the same manner as in Example 101, step A.
MS (ESI+). found: 289.1.

C) 9-[4-(1-methyl-1-phenylethyl)phenyl]-3,4-dihydropyrido[2,1-c][1,2,4]thiadiazine 2,2-dioxide The title compound was obtained in the same manner as in Example 85, step B.
$^1$H NMR (300 MHz, DMSO-$d_6$) δ 1.67 (6H, s), 3.37-3.52 (2H, m), 4.55-4.72 (2H, m), 6.69 (1H, t, J=7.0 Hz), 7.07-7.35 (7H, m), 7.43 (2H, d, J=8.7 Hz), 7.61 (1H, dd, J=7.0, 1.7 Hz), 7.71-7.83 (1H, m).

Example 326

9-[4-(1-methyl-1-phenylethyl)phenyl]-3,4,6,7,8,9-hexahydropyrido[2,1-c][1,2,4]thiadiazine 2,2-dioxide In the same manner as in Example 98, the title compound (214 mg) was obtained from 9-[4-(1-methyl-1-phenylethyl)phenyl]-3,4-dihydropyrido[2,1-c][1,2,4]thiadiazine 2,2-dioxide.
$^1$H NMR (300 MHz, DMSO-$d_6$) δ 1.64 (6H, s), 1.66-1.75 (3H, m), 1.87-2.08 (1H, m), 3.22-3.28 (2H, m), 3.39-3.52 (2H, m), 3.67-3.73 (1H, m), 3.75-3.87 (2H, m), 7.03-7.20 (5H, m), 7.20-7.33 (4H, m).

Example 328

9-[4-(pentafluorosulfanyl)phenyl]-3,4,6,7,8,9-hexahydropyrido[2,1-c][1,2,4]thiadiazine 2,2-dioxide A) 3-[4-(pentafluorosulfanyl)phenyl]pyridin-2-amine The title compound was obtained in the same manner as in Example 101, step A.
MS (ESI+). found: 297.0.

B) 9-[4-(pentafluorosulfanyl)phenyl]-3,4-dihydropyrido[2,1-c][1,2,4]thiadiazine 2,2-dioxide The title compound was obtained in the same manner as in Example 85, step B.
$^1$H NMR (300 MHz, CDCl$_3$) δ 3.44-3.52 (2H, m), 4.62-4.70 (2H, m), 6.75 (1H, t, J=6.8 Hz), 7.69-7.77 (3H, m), 7.85 (1H, dd, J=6.8, 1.5 Hz), 7.96 (2H, d, J=8.7 Hz).

C) 9-[4-(pentafluorosulfanyl)phenyl]-3,4,6,7,8,9-hexahydropyrido[2,1-c][1,2,4]thiadiazine 2,2-dioxide In the same manner as in Example 98, the title compound (2.7 mg) was obtained from 9-[4-(pentafluorosulfanyl)phenyl]-3,4-dihydropyrido[2,1-c][1,2,4]thiadiazine 2,2-dioxide.

¹H NMR (300 MHz, DMSO-d₆) δ 1.72-1.84 (3H, m), 1.96-2.11 (1H, m), 3.41-3.58 (4H, m), 3.79-3.86 (2H, m), 3.89-3.98 (1H, m), 7.46 (2H, d, J=8.7 Hz), 7.85 (2H, d, J=8.7 Hz).

Example 329

The compound of Example 329 was produced in the same manner as in Example 325.

Example 330

9-{4-[1-methyl-1-(4-methylphenyl)ethyl]phenyl}-3,4,6,7,8,9-hexahydropyrido[2,1-c][1,2,4]thiadiazine 2,2-dioxide In the same manner as in Example 98, the title compound (63.5 mg) was obtained from 9-{4-[1-methyl-1-(4-methylphenyl)ethyl]phenyl}-3,4-dihydropyrido[2,1-c][1,2,4]thiadiazine 2,2-dioxide.
¹H NMR (300 MHz, DMSO-d₆) δ 1.61 (6H, s), 1.65-1.78 (3H, m), 1.90-2.07 (1H, m), 2.25 (3H, s), 3.22-3.29 (2H, m), 3.39-3.52 (2H, m, J=4.1 Hz), 3.70 (1H, t, J=5.5 Hz), 3.75-3.88 (2H, m), 7.03-7.16 (8H, m).

Example 331

9-[4-(1,1-difluoroethyl)phenyl]-3,4-dihydropyrido[2,1-c][1,2,4]thiadiazine 2,2-dioxide A) 3-(4-(1,1-difluoroethyl)phenyl)pyridin-2-amine The title compound was obtained in the same manner as in Example 101, step A.
MS (ESI+). found: 235.1.

B) 9-[4-(1,1-difluoroethyl)phenyl]-3,4-dihydropyrido[2,1-c][1,2,4]thiadiazine 2,2-dioxide The title compound was obtained in the same manner as in Example 85, step B.
¹H NMR (300 MHz, DMSO-d₆) δ 2.00 (3H, t, J=18.8 Hz), 3.41-3.51 (2H, m), 4.61-4.70 (2H, m), 6.73 (1H, t, J=7.0 Hz), 7.56-7.69 (5H, m), 7.81 (1H, dd, J=6.8, 1.5 Hz).

Example 332

The compound of Example 332 was produced in the same manner as in Example 186.

Example 333-337

The compounds of Examples 333-337 were produced in the same manner as in Example 67.

Example 338

(9S)-8-methyl-9-(4-phenoxyphenyl)-3,4,6,7,8,9-hexahydropyrazino[2,1-c][1,2,4]thiadiazine 2,2-dioxide A mixture of (9S)-9-(4-phenoxyphenyl)-3,4,6,7,8,9-hexahydropyrazino[2,1-c][1,2,4]thiadiazine 2,2-dioxide (129 mg), potassium carbonate (100 mg) and iodomethane (0.022 mL) in DMF (4 mL) was stirred at 0° C. to room temperature for 20 hr. The reaction mixture was added with NH silica gel, evaporated, and purified by column chromatography (NH silica gel, eluted with EtOAc in hexane then 20% MeOH in EtOAc) then preparative HPLC (C18, MeCN in H₂O with 0.1% TFA). The combined collected fractions were concentrated in vacuo. The resulting aqueous solution was added with NaHCO₃ and NaCl, then extracted with EtOAc (2×100 mL). The organic layer was combined, dried over anhydrous magnesium sulfate, and concentrated in vacuo. The residue was recrystallized from EtOAc-IPE to give the title compound (18 mg) as a white solid.
1H NMR (300 MHz, DMSO-d6) δ 2.11 (3H, s), 2.55-2.67 (1H, m), 2.90-3.01 (1H, m), 3.13-3.29 (2H, m), 3.41-3.51 (1H, m), 3.55-3.69 (1H, m), 3.79-3.90 (2H, m), 3.96 (1H, s), 6.90-6.99 (2H, m), 7.01-7.08 (2H, m), 7.11-7.21 (1H, m), 7.24-7.34 (2H, m), 7.35-7.46 (2H, m).

Example 339

The compound of Example 339 was produced in the same manner as in Example 338.

Example 340

(9S)-8-acetyl-9-(4-phenoxyphenyl)-3,4,6,7,8,9-hexahydropyrazino[2,1-c][1,2,4]thiadiazine 2,2-dioxide A mixture of (9S)-9-(4-phenoxyphenyl)-3,4,6,7,8,9-hexahydropyrazino[2,1-c][1,2,4]thiadiazine 2,2-dioxide (129 mg), triethylamine (0.100 mL) and acetyl chloride (0.026 mL) in THF (4 mL) was stirred at 0° C. to room temperature for 20 hr. The reaction mixture was added with water, and the precipitate was filtered. The collected solid was purified by recrystallization from MeOH-EtOAc then preparative HPLC (C18, MeCN in H₂O with 10 mM NH₄HCO₃). The combined collected fractions were concentrated in vacuo. The resulting solid was recrystallized from EtOAc-IPE to give the title compound (60 mg) as a white solid.
¹H NMR (300 MHz, DMSO-d₆) δ 2.07-2.14 (3H, m), 3.34-3.69 (5H, m), 3.80-3.96 (3H, m), 5.95 (1H, s), 6.96-7.08 (4H, m), 7.12-7.21 (1H, m), 7.30-7.47 (4H, m).

Example 341

The compound of Example 341 was produced in the same manner as in Example 340.

Example 342

The compound of Example 342 was produced in the same manner as in Example 98.

Example 343

The compound of Example 343 was produced in the same manner as in Example 14 and Example 98.

Example 344

The compound of Example 344 was produced in the same manner as in Example 14.

Example 345

The compound of Example 345 was produced in the same manner as in Example 98.

Example 346

9-(2-fluorobiphenyl-4-yl)-9-methyl-3,4,6,7,8,9-hexahydropyrazino[2,1-c][1,2,4]thiadiazine 2,2-dioxide hydrochloride

A) tert-butyl 9-(2-fluorobiphenyl-4-yl)-3,4,6,7-tetrahydropyrazino[2,1-c][1,2,4]thiadiazine-8 (9H)-carboxylate 2,2-dioxide A suspension of 9-(2-fluorobiphenyl-4-yl)-3,4,6,7,8,9-hexahydropyrazino[2,1-c][1,2,4]thiadiazine 2,2-dioxide (1.13 g) and di-tert-butyl dicarbonate (1.59 mL) in THF (200 mL) was stirred at room temperature overnight. The mixture was added with silica gel, concentrated in vacuo, then purified by column chromatography (silica gel, eluted with EtOAc in hexane) to give the title compound (1.45 g) as a colorless amorphous powder.
MS (ESI+). found: 460.2.

B) tert-butyl 9-(2-fluorobiphenyl-4-yl)-9-methyl-3,4,6,7-tetrahydropyrazino[2,1-c][1,2,4]thiadiazine-8 (9H)-carboxylate 2,2-dioxide A suspension of tert-butyl 9-(2-fluorobiphenyl-4-yl)-3,4,6,7-tetrahydropyrazino[2,1-c][1,2,4]thiadiazine-8 (9H)-carboxylate 2,2-dioxide (0.71 g), iodomethane (0.115 mL) and NaH (60%, 93 mg) in DMF (16 mL) was stirred at 0° C. to room temperature overnight. The reaction mixture was added with water and extracted with EtOAc. The organic layer was washed with brine and water, dried over anhydrous magnesium sulfate and concentrated. The residue was purified by column chromatography (silica gel, eluted with EtOAc in hexane). The obtained material was purified by column chromatography (silica gel, eluted with EtOAc in hexane) to give the title compound (150 mg) as a white solid.
MS (ESI+). found: 474.2.

C) 9-(2-fluorobiphenyl-4-yl)-9-methyl-3,4,6,7,8,9-hexahydropyrazino[2,1-c][1,2,4]thiadiazine 2,2-dioxide hydrochloride A suspension of tert-butyl 9-(2-fluorobiphenyl-4-yl)-9-methyl-3,4,6,7-tetrahydropyrazino[2,1-c][1,2,4]thiadiazine-8 (9H)-carboxylate 2,2-dioxide (150 mg) and 4 N HCl/EtOAc (5 mL) in EtOAc (5 mL) was stirred at room temperature overnight. After removing solvent, the residue was recrystallized from MeOH to give the title compound (65 mg) as a white solid.
$^1$H NMR (300 MHz, DMSO-$d_6$) δ 1.99 (3H, s), 2.92-3.21 (1H, m), 3.28-4.25 (7H, m), 7.31-7.85 (8H, m), 10.77 (2H, brs).

Example 347

The compound of Example 347 was produced in the same manner as in Example 98.

Example 348

9-(2-fluorobiphenyl-4-yl)(9-$^2$H)-3,4,6,7,8,9-hexahydropyrazino[2,1-c][1,2,4]thiadiazine 2,2-dioxide hydrochloride

A) tert-butyl 9-(2-fluorobiphenyl-4-yl)(9-$^2$H)-3,4,6,7-tetrahydropyrazino[2,1-c][1,2,4]thiadiazine-8 (9H)-carboxylate 2,2-dioxide A suspension of NaH (60%, 35 mg) and tert-butyl 9-(2-fluorobiphenyl-4-yl)-3,4,6,7-tetrahydropyrazino[2,1-c][1,2,4]thiadiazine-8 (9H)-carboxylate 2,2-dioxide (200 mg) in DMF (3 mL) was stirred at 0° C. for 0.5 hr. To the reaction mixture was added D$_2$O (3.0 mL) and the mixture was stirred at 0° C. to room temperature overnight. The mixture was added with water, and extracted with EtOAc. The organic layer was washed with brine and water, dried over anhydrous magnesium sulfate and concentrated. The residue was purified by column chromatography (silica gel, eluted with EtOAc in hexane) to give the title compound (95 mg) as a colorless amorphous powder.
MS (ESI+). found: 461.2.

B) 9-(2-fluorobiphenyl-4-yl) (9-$^2$H)-3,4,6,7,8,9-hexahydropyrazino[2,1-c][1,2,4]thiadiazine 2,2-dioxide hydrochloride A suspension of tert-butyl 9-(2-fluorobiphenyl-4-yl)(9-$^2$H)-3,4,6,7-tetrahydropyrazino[2,1-c][1,2,4]thiadiazine-8 (9H)-carboxylate 2,2-dioxide (95 mg) and 4N HCl/EtOAc (1 mL) in EtOAc (3 mL) was stirred at room temperature for 2 hr. After removing solvent, the residue was recrystallized from EtOAc-EtOH to give the title compound (61 mg) as a white solid.
$^1$H NMR (300 MHz, DMSO-$d_6$) δ 3.31-3.52 (4H, m), 3.64-4.04 (4H, m), 7.31-7.81 (8H, m), 9.20-10.64 (2H, m).

Example 349

9-(3-fluoro-4-propoxyphenyl)-3,4-dihydropyrido[2,1-c][1,2,4]thiadiazine 2,2-dioxide

A) 3-(4-(benzyloxy)-3-fluorophenyl)pyridin-2-amine

A mixture of sodium carbonate (7.18 g), tetrakis(triphenylphosphine)palladium(0) (1.957 g), 4-(benzyloxy)-3-fluorophenylboronic acid (10 g), and 3-bromopyridin-2-amine (5.86 g) in DME (120 mL) and water (24 mL) was stirred at 80° C. overnight. The mixture was added with silica gel, concentrated in vacuo, and purified by column chromatography (silica gel, eluted with EtOAc in hexane) to give the title compound (9.97 g) as a pale yellow solid.
MS (ESI+). found: 295.1.

B) 4-(2-aminopyridin-3-yl)-2-fluorophenol

A mixture of 3-(4-(benzyloxy)-3-fluorophenyl)pyridin-2-amine (8.5 g), and platinum(IV) oxide (400 mg) in EtOH (200 mL) was stirred at room temperature under hydrogen overweekend. The mixture was added with NH silica gel, concentrated in vacuo, and purified by column chromatography (NH silica gel, eluted with MeOH in EtOAc) to give the title compound (3.20 g) as a pale yellow solid.
MS (ESI+). found: 205.0.

C) 3-(3-fluoro-4-propoxyphenyl)pyridin-2-amine

In the same manner as in Example 67, the title compound was obtained from 4-(2-aminopyridin-3-yl)-2-fluorophenol and 1-iodopropane.
MS (ESI+). found: 261.1.

D) 9-(3-fluoro-4-propoxyphenyl)-3,4-dihydropyrido[2,1-c][1,2,4]thiadiazine 2,2-dioxide In the same manner as in Example 14, step B, the title compound was obtained from 3-(3-fluoro-4-propoxyphenyl)pyridin-2-amine.

Example 350

The compound of Example 350 was produced in the same manner as in Example 98.

Example 351

The compound of Example 351 was produced in the same manner as in Example 349.

Example 352

The compound of Example 352 was produced in the same manner as in Example 98.

Example 353

The compound of Example 353 was produced in the same manner as in Example 349.

Example 354

The compound of Example 354 was produced in the same manner as in Example 76.

Example 355

The compound of Example 355 was produced in the same manner as in Example 67.

Example 356

The compound of Example 356 was produced in the same manner as in Example 98.

Example 357

The compound of Example 357 was produced in the same manner as in Example 203.

Example 358

The compound of Example 358 was produced in the same manner as in Example 98.

Example 359

The compound of Example 359 was produced in the same manner as in Example 214.

Example 360

9-(2,4-dichlorophenyl)-3,4-dihydropyrido[2,1-c][1,2,4]thiadiazine 2,2-dioxide

To 9-bromo-3,4-dihydropyrido[2,1-c][1,2,4]thiadiazine 2,2-dioxide (26 mg) were added a solution of 2,4-dichlorophenylboronic acid (38 mg) in ethanol (0.5 mL), toluene (0.5 mL), tetrakis(triphenylphosphine)palladium(0) (11 mg) and cesium carbonate (98 mg), and the mixture was stirred at 100° C. overnight. To the reaction solution were added saturated aqueous sodium hydrogen carbonate solution (1 mL) and ethyl acetate (3 mL) and the mixture was stirred. The organic layer was passed through a phase separation filter, and the solvent was evaporated from the separated solution by an air blowing apparatus. The residue was purified by HPLC (C18, mobile phase: acetonitrile/10 mM aqueous ammonium acetate solution) to give the title compound (20.7 mg).

MS (ESI+): [M+H]+ 329.

Examples 361-398, 400-403, 405-412, 414-432

The compounds of Examples 361-398, 400-403, 405-412, 414-432 were produced in the same manner as in Example 360.

Example 433

9-[4-(2-chlorophenoxy)phenyl]-3,4,6,7,8,9-hexahydropyrido[2,1-c][1,2,4]thiadiazine 2,2-dioxide To 4-(2,2-dioxido-3,4,6,7,8,9-hexahydropyrido[2,1-c][1,2,4]thiadiazin-9-yl)phenol (28 mg) were added a solution of 2-chlorophenylboronic acid (47 mg) in acetonitrile (1 mL), pyridine (0.2 mL), cesium carbonate (32 mg) and copper(II) acetate (36 mg), and the mixture was stirred at room temperature overnight.

To the reaction solution were added aqueous ammonium chloride solution (1 mL) and ethyl acetate (3 mL) and the mixture was stirred. The organic layer was passed through a phase separation filter, and the solvent was evaporated from the separated solution by an air blowing apparatus. The residue was purified by HPLC (C18, mobile phase: acetonitrile/10 mM aqueous ammonium acetate solution) to give the title compound (4.1 mg).

MS (ESI+): [M+H]$^+$ 391.

Example 434-456

The compounds of Examples 434-456 were produced in the same manner as in Example 433.

Example 457

(9S)-9-[4-(3-chloro-4-fluorophenoxy)phenyl]-3,4,6,7,8,9-hexahydropyrido[2,1-c][1,2,4]thiadiazine 2,2-dioxide A mixture of (3-chloro-4-fluorophenyl)boronic acid (933 mg), 4-[(9S)-2,2-dioxido-3,4,6,7,8,9-hexahydropyrido[2,1-c][1,2,4]thiadiazin-9-yl]phenol (500 mg), pyridine (3.60 mL), cesium carbonate (581 mg), diacetoxycopper (648 mg) and powdered 4A MS (4 g) in MeCN (18 mL) was stirred at room temperature for 3 days. The mixture was added with NH silica gel, concentrated in vacuo, and purified by column chromatography (NH silica gel, eluted with MeOH in EtOAc) then recrystallized from EtOAc-THF/IPE to give (95)-9-[4-(3-chloro-4-fluorophenoxy)phenyl]-3,4,6,7,8,9-hexahydropyrido[2,1-c][1,2,4]thiadiazine 2,2-dioxide (290.6 mg) as a white solid.

$^1$H NMR (300 MHz, DMSO-d$_6$) δ1.64-1.85 (3H, m), 1.88-2.10 (1H, m, J=6.0 Hz), 3.23-3.29 (2H, m), 3.38-3.57 (2H, m), 3.71-3.91 (3H, m), 6.94-7.10 (3H, m), 7.18-7.34 (3H, m), 7.44 (1H, t, J=9.1 Hz).

mp 154-156° C.

Anal. Calcd for $C_{19}H_{18}N_2O_3SClF$: C, 55.81; H, 4.44; N, 6.85. Found: C, 55.83; H, 4.43; N, 6.68.

Example 458-460

The compounds of Examples 458-460 were produced in the same manner as in Example 433.

Example 461

9-[(7-methoxynaphthalen-2-yl)oxy]-3,4,6,7,8,9-hexahydropyrido[2,1-c][1,2,4]thiadiazine 2,2-dioxide A racemate (67.7 mg) of 9-[(7-methoxynaphthalen-2-yl)oxy]-3,4,6,7,8,9-hexahydropyrido[2,1-c][1,2,4]thiadiazine 2,2-dioxide was separated by HPLC (column: CHIRALPAK AD (LF001), 50 mmID×500 mmL, manufactured by DAICEL CHEMICAL INDUSTRIES, LTD., mobile phase: methanol 100%) to give the title compound (30.4 mg) with a shorter retention time. Crystallization from THF and diisopropyl ether gave a white solid.

$^1$H NMR (300 MHz, DMSO-$d_6$) δ 1.74-1.92 (1H, m), 1.93-2.11 (3H, m), 3.38-3.60 (2H, m), 3.70-3.97 (5H, m), 5.03 (1H, t, J=3.4 Hz), 7.04 (2H, ddd, J=17.3, 8.9, 2.4 Hz), 7.18 (1H, d, J=2.3 Hz), 7.40 (1H, d, J=2.3 Hz), 7.75 (2H, dd, J=8.9, 4.0 Hz). The 2H peak was hidden behind water.

mp 153-154° C.

Example 462

9-[(7-methoxynaphthalen-2-yl)oxy]-3,4,6,7,8,9-hexahydropyrido[2,1-c][1,2,4]thiadiazine 2,2-dioxide A racemate (67.7 mg) of 9-[(7-methoxynaphthalen-2-yl)oxy]-3,4,6,7,8,9-hexahydropyrido[2,1-c][1,2,4]thiadiazine 2,2-dioxide was separated by HPLC (column: CHIRALPAK AD (LF001), 50 mmID×500 mmL, manufactured by DAICEL CHEMICAL INDUSTRIES, LTD., mobile phase: methanol 100%) to give the title compound (30.5 mg) with a longer retention time. Crystallization from THF and diisopropyl ether gave a white solid.

$^1$H NMR (300 MHz, DMSO-$d_6$) δ 1.75-1.90 (1H, m), 1.94-2.08 (3H, m), 3.38-3.58 (2H, m), 3.73-3.91 (5H, m), 4.95-5.07 (1H, m), 7.04 (2H, ddd, J=17.3, 8.9, 2.4 Hz), 7.18 (1H, d, J=2.3 Hz), 7.40 (1H, d, J=2.3 Hz), 7.75 (2H, dd, J=8.9, 4.0 Hz). The 2H peak was hidden behind water.

mp 154-155° C.

The compounds of Examples 59-283, 285-326, 328-398, 400-403, 405-412 and 414-462 are shown in the following Tables. In the Tables, MS means Found.

In the structural formulas in the Tables, the indication of hydrogen atom bonded to nitrogen atom may be omitted.

TABLE 8

| Ex. No. | IUPAC Name | Structure | Salt | MS |
|---|---|---|---|---|
| 59 | 9-[(7-methoxynaphthalen-2-yl)oxy]-3,4-dihydropyrido[2,1-c][1,2,4]thiadiazine 2,2-dioxide | 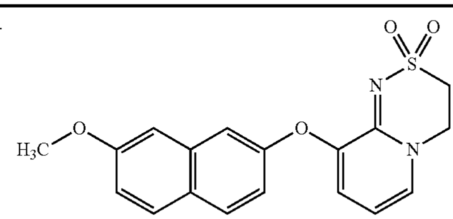 | | 357.1 |
| 60 | 9-[(7-methoxynaphthalen-2-yl)oxy]-3,4,6,7,8,9-hexahydropyrido[2,1-c][1,2,4]thiadiazine 2,2-dioxide | 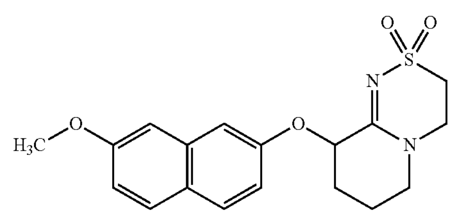 [SMILES: COc1ccc2ccc(OC3CCCN4CCS(=O)(=O)N=C34)cc2c1] | | 361.3 |
| 61 | 9-{[4-(1-methylethyl)phenoxy]methyl}-3,4-dihydropyrido[2,1-c][1,2,4]thiadiazine 2,2-dioxide | 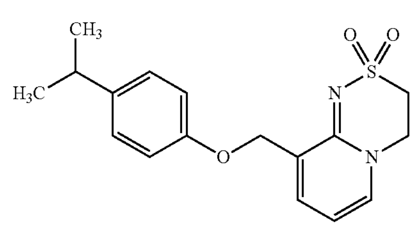 [SMILES: CC(C)c1ccc(OCC2=CC=CN3CCS(=O)(=O)N=C23)cc1] | | 333.1 |
| 62 | (9R)-9-(4-phenoxyphenyl)-3,4,6,7,8,9-hexahydropyrido[2,1-c][1,2,4]thiadiazine 2,2-dioxide | 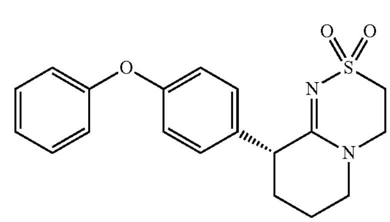 [SMILES: O=S1(=O)CCN2CCC[C@H](c3ccc(Oc4ccccc4)cc3)C2=N1] | | 357.3 |

TABLE 8-continued

| Ex. No. | IUPAC Name | Structure | Salt | MS |
|---|---|---|---|---|
| 63 | (9S)-9-(4-phenoxyphenyl)-3,4,6,7,8,9-hexahydropyrido[2,1-c][1,2,4]thiadiazine 2,2-dioxide | 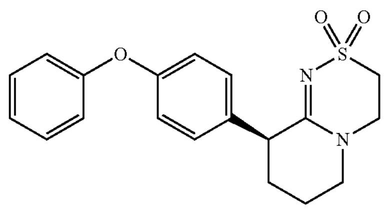 [SMILES: O=S1(=O)CCN2CCC[C@@H](c3ccc(Oc4ccccc4)cc3)C2=N1] | | 357.3 |
| 64 | 9-biphenyl-4-yl-3,4,6,7,8,9-hexahydropyrido[2,1-c][1,2,4]thiadiazine 2,2-dioxide | 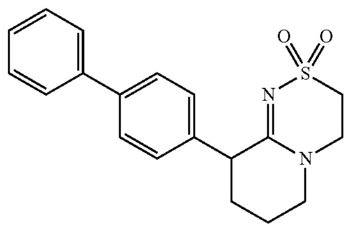 [SMILES: O=S1(=O)CCN2CCCC(c3ccc(-c4ccccc4)cc3)C2=N1] | | 341.3 |
| 65 | 9-biphenyl-4-yl-3,4,6,7,8,9-hexahydropyrido[2,1-c][1,2,4]thiadiazine 2,2-dioxide | 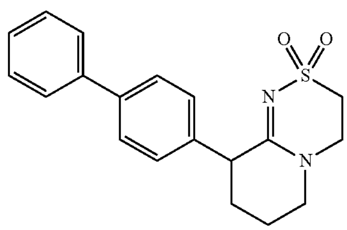 [SMILES: O=S1(=O)CCN2CCCC(c3ccc(-c4ccccc4)cc3)C2=N1] | | 341.3 |
| 66 | 9-[4-(cyclopentyloxy)phenyl]-3,4-dihydropyrido[2,1-c][1,2,4]thiadiazine 2,2-dioxide | 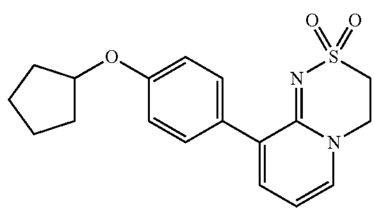 [SMILES: O=S1(=O)CCN2C=CC=C(c3ccc(OC4CCCC4)cc3)C2=N1] | | 345.1 |
| 67 | 9-[4-(2,2-dimethylpropoxy)phenyl]-3,4-dihydropyrido[2,1-c][1,2,4]thiadiazine 2,2-dioxide | 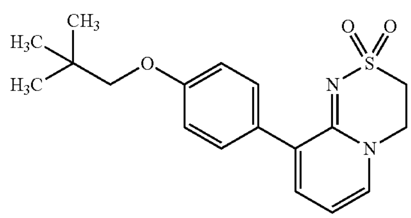 [SMILES: CC(C)(C)COc1ccc(C2=CC=CN3CCS(=O)(=O)N=C23)cc1] | | 347.1 |
| 68 | 9-[4-(cyclohexyloxy)phenyl]-3,4-dihydropyrazino[2,1-c][1,2,4]thiadiazine 2,2-dioxide | 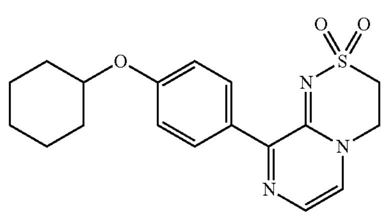 | | 360.1 |
| 69 | 9-[4-(tetrahydro-2H-pyran-4-ylmethoxy)phenyl]-3,4-dihydropyrido[2,1-c][1,2,4]thiadiazine 2,2-dioxide | 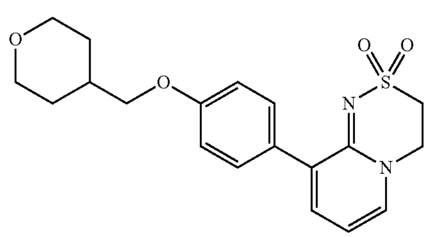 [SMILES: O=S1(=O)CCN2C=CC=C(c3ccc(OCC4CCOCC4)cc3)C2=N1] | | 375.1 |

TABLE 8-continued

| Ex. No. | IUPAC Name | Structure | Salt | MS |
|---|---|---|---|---|
| 70 | 9-[4-(cyclopropyloxy)phenyl]-3,4-dihydropyrido[2,1-c][1,2,4]thiadiazine 2,2-dioxide | 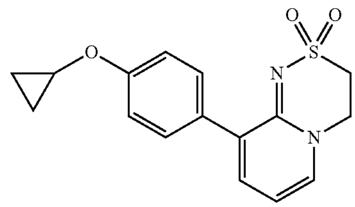 [SMILES: O=S1(=O)CCN2C=CC=C(c3ccc(OC4CC4)cc3)C2=N1] | | 317.0 |

TABLE 9

| Ex. No. | IUPAC Name | Structure | Salt | MS |
|---|---|---|---|---|
| 71 | 9-[4-(tetrahydro-2H-pyran-4-yloxy)phenyl]-3,4-dihydropyrido[2,1-c][1,2,4]thiadiazine 2,2-dioxide | | | 361.2 |
| 72 | 9-[4-(1-ethylpropoxy)phenyl]-3,4-dihydropyrido[2,1-c][1,2,4]thiadiazine 2,2-dioxide | | | 347.1 |
| 73 | 7-chloro-9-[4-(cyclohexyloxy)phenyl]-3,4-dihydropyrido[2,1-c][1,2,4]thiadiazine 2,2-dioxide | | | 393.1 |
| 74 | 9-[4-(cyclopentylmethoxy)phenyl]-3,4-dihydropyrido[2,1-c][1,2,4]thiadiazine 2,2-dioxide | | | 359.1 |
| 75 | 9-[4-(tetrahydrofuran-2-ylmethoxy)phenyl]-3,4-dihydropyrido[2,1-c][1,2,4]thiadiazine 2,2-dioxide | | | 361.1 |

TABLE 9-continued

| | | | |
|---|---|---|---|
| 76 | 7-chloro-9-(4-{[4-(trifluoromethyl)pyridin-2-yl]oxy}phenyl)-3,4-dihydropyrido[2,1-c][1,2,4]thiadiazine 2,2-dioxide | 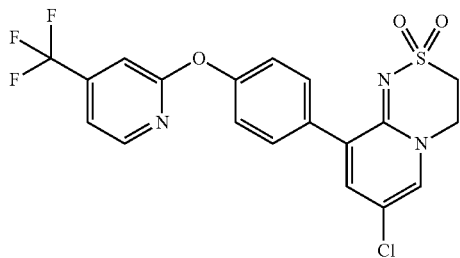 [SMILES: O=S1(=O)CCN2C=C(Cl)C=C(c3ccc(Oc4cc(C(F)(F)F)ccn4)cc3)C2=N1] | 456.0 |
| 77 | 7-chloro-9-{4-[(5-chloropyridin-2-yl)oxy]phenyl}-3,4-dihydropyrido[2,1-c][1,2,4]thiadiazine 2,2-dioxide | 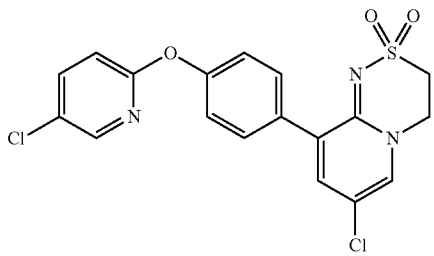 [SMILES: O=S1(=O)CCN2C=C(Cl)C=C(c3ccc(Oc4ccc(Cl)cn4)cc3)C2=N1] | 422.1 |
| 78 | 7-chloro-9-(4-{[3-(trifluoromethyl)pyridin-2-yl]oxy}phenyl)-3,4-dihydropyrido[2,1-c][1,2,4]thiadiazine 2,2-dioxide | 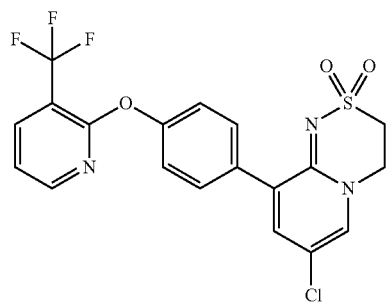 [SMILES: O=S1(=O)CCN2C=C(Cl)C=C(c3ccc(Oc4ncccc4C(F)(F)F)cc3)C2=N1] | 456.0 |
| 79 | 7-chloro-9-(4-{[2-(trifluoromethyl)pyridin-4-yl]oxy}phenyl)-3,4-dihydropyrido[2,1-c][1,2,4]thiadiazine 2,2-dioxide | 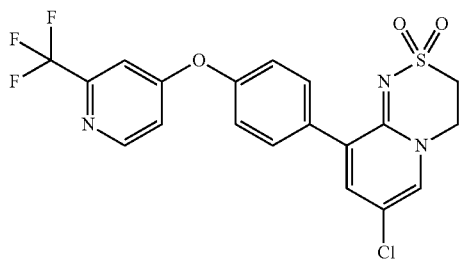 [SMILES: O=S1(=O)CCN2C=C(Cl)C=C(c3ccc(Oc4ccnc(C(F)(F)F)c4)cc3)C2=N1] | 456.1 |
| 80 | 9-(4-pyrrolidin-1-ylphenyl)-3,4-dihydropyrido[2,1-c][1,2,4]thiadiazine 2,2-dioxide | 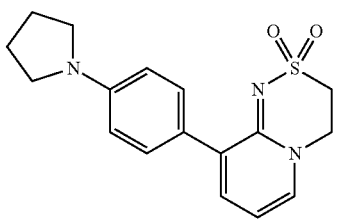 [SMILES: O=S1(=O)CCN2C=CC=C(c3ccc(N4CCCC4)cc3)C2=N1] | 330.1 |
| 81 | 7-chloro-9-(4-phenoxyphenyl)-3,4-dihydropyrido[2,1-c][1,2,4]thiadiazine 2,2-dioxide | 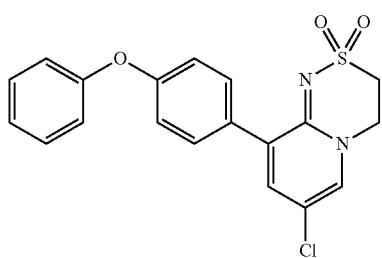 | 387.0 |

TABLE 9-continued

| | | | |
|---|---|---|---|
| 82 | 9-{4-[(3-fluorobenzyl)oxy]phenyl}-3,4-dihydropyrido[2,1-c][1,2,4]thiadiazine 2,2-dioxide | 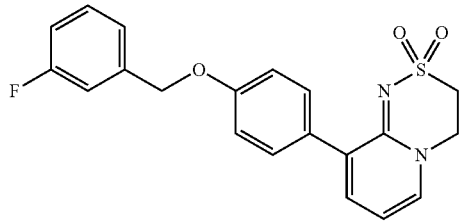 [SMILES: O=S1(=O)CCN2C=CC=C(c3ccc(OCc4cccc(F)c4)cc3)C2=N1] | 385.2 |

TABLE 10

| | | | |
|---|---|---|---|
| 83 | 9-{4-[(3-fluorobenzyl)oxy]phenyl}-3,4,6,7,8,9-hexahydropyrido[2,1-c][1,2,4]thiadiazine 2,2-dioxide | 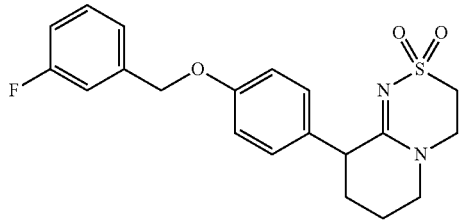 [SMILES: O=S1(=O)CCN2CCCC(c3ccc(OCc4cccc(F)c4)cc3)C2=N1] | 389.2 |
| 84 | 9-{4-[(3-fluorobenzyl)oxy]phenyl}-3,4,6,7,8,9-hexahydropyrido[2,1-c][1,2,4]thiadiazin-9-ol 2,2-dioxide | 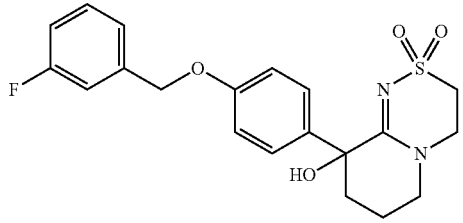 [SMILES: O=S1(=O)CCN2CCCC(O)(c3ccc(OCc4cccc(F)c4)cc3)C2=N1] | 405.2 |
| 85 | 9-[4-(3-chlorophenoxy)phenyl]-3,4-dihydropyrido[2,1-c][1,2,4]thiadiazine 2,2-dioxide | 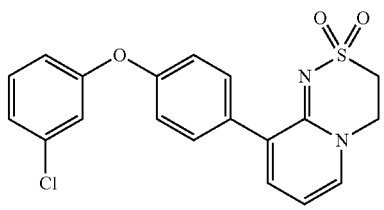 [SMILES: O=S1(=O)CCN2C=CC=C(c3ccc(Oc4cccc(Cl)c4)cc3)C2=N1] | 387.1 |
| 86 | 9-{4-[2-(trifluoromethyl)phenoxy]phenyl}-3,4,6,7,8,9-hexahydropyrido[2,1-c][1,2,4]thiadiazine 2,2-dioxide | 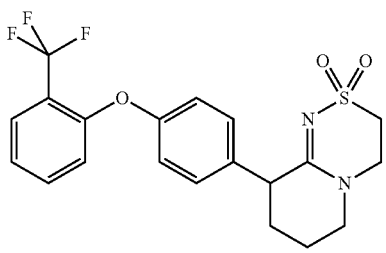 [SMILES: O=S1(=O)CCN2CCCC(c3ccc(Oc4ccccc4C(F)(F)F)cc3)C2=N1] | 425.1 |
| 87 | 4-(2,2-dioxido-3,4-dihydropyrido[2,1-c][1,2,4]thiadiazin-9-yl)phenol |  | 277.0 |

TABLE 10-continued

| | | | |
|---|---|---|---|
| 88 | 9-[4-(cycloheptyloxy)phenyl]-3,4-dihydropyrido[2,1-c][1,2,4]thiadiazine 2,2-dioxide | 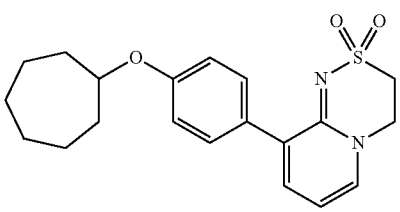 [SMILES: O=S1(=O)CCN2C=CC=C(c3ccc(OC4CCCCCC4)cc3)C2=N1] | 373.1 |
| 89 | 9-[4-(cyclohexyloxy)phenyl]-7-fluoro-3,4-dihydropyrido[2,1-c][1,2,4]thiadiazine 2,2-dioxide | 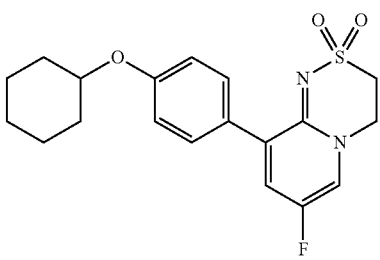 [SMILES: O=S1(=O)CCN2C=C(F)C=C(c3ccc(OC4CCCCC4)cc3)C2=N1] | 377.2 |
| 90 | 9-[4-(3-methoxyphenoxy)phenyl]-3,4-dihydropyrido[2,1-c][1,2,4]thiadiazine 2,2-dioxide | 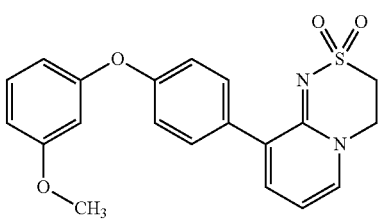 | 383.1 |
| 91 | 9-[4-(cyclobutyloxy)phenyl]-3,4-dihydropyrido[2,1-c][1,2,4]thiadiazine 2,2-dioxide | 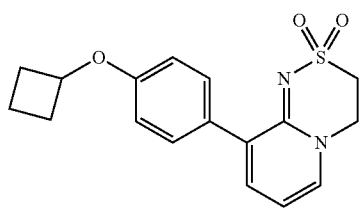 [SMILES: O=S1(=O)CCN2C=CC=C(c3ccc(OC4CCC4)cc3)C2=N1] | 331.1 |
| 92 | 7-chloro-9-[6-(cyclohexyloxy)pyridin-3-yl]-3,4-dihydropyrido[2,1-c][1,2,4]thiadiazine 2,2-dioxide | 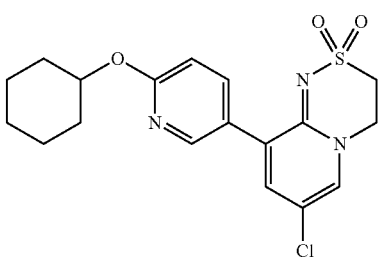 [SMILES: O=S1(=O)CCN2C=C(F)C=C(c3ccc(OC4CCCCC4)nc3)C2=N1] | 394.1 |
| 93 | 9-[6-(cyclohexyloxy)pyridin-3-yl]-7-fluoro-3,4-dihydropyrido[2,1-c][1,2,4]thiadiazine 2,2-dioxide | 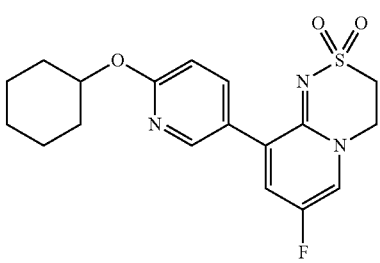 | 378.2 |

TABLE 10-continued

| | | | |
|---|---|---|---|
| 94 | 9-[6-(cyclohexyloxy)pyridin-3-yl]-3,4-dihydropyrazino[2,1-c][1,2,4]thiadiazine 2,2-dioxide | 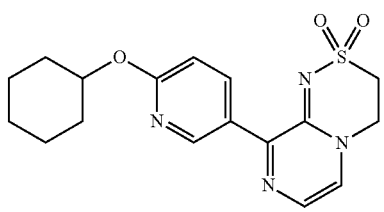 | 361.2 |

TABLE 11

| | | | |
|---|---|---|---|
| 95 | 9-[6-(cyclohexyloxy)pyridin-3-yl]-7-methyl-3,4-dihydropyrazino[2,1-c][1,2,4]thiadiazine 2,2-dioxide | 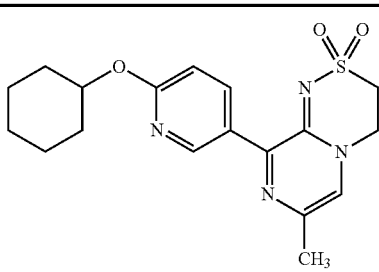 | 375.2 |
| 96 | 9-(2-fluorobiphenyl-4-yl)-3,4,6,7,8,9-hexahydropyrido[2,1-c][1,2,4]thiadiazine 2,2-dioxide | 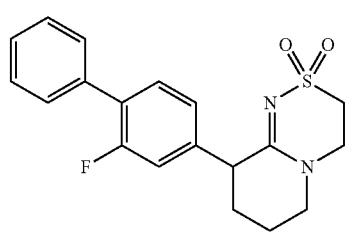 [SMILES: O=S1(=O)CCN2CCCC(c3ccc(-c4ccccc4)c(F)c3)C2=N1] | 359.0 |
| 97 | 9-(2-fluorobiphenyl-4-yl)-3,4,6,7,8,9-hexahydropyrido[2,1-c][1,2,4]thiadiazine 2,2-dioxide | 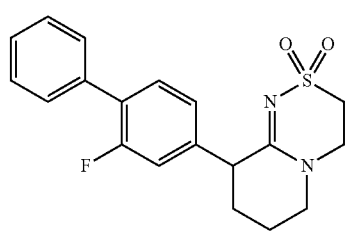 [SMILES: O=S1(=O)CCN2CCCC(c3ccc(-c4ccccc4)c(F)c3)C2=N1] | 359.0 |
| 98 | 9-[4-(3-methoxyphenoxy)phenyl]-3,4,6,7,8,9-hexahydropyrido[2,1-c][1,2,4]thiadiazine 2,2-dioxide | 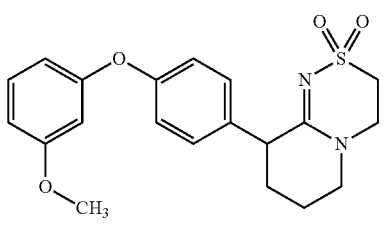 [SMILES: COc1cccc(Oc2ccc(C3CCCN4CCS(=O)(=O)N=C34)cc2)c1] | 387.2 |
| 99 | 7-methyl-9-(4-phenoxyphenyl)-3,4,6,7,8,9-hexahydropyrido[2,1-c][1,2,4]thiadiazine 2,2-dioxide | 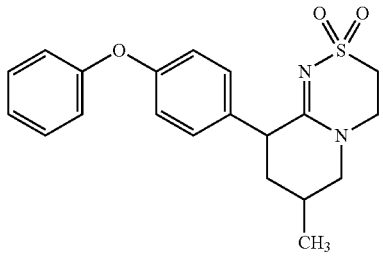 [SMILES: CC1CC(c2ccc(Oc3ccccc3)cc2)C2=NS(=O)(=O)CCN2C1] | 371.2 |

TABLE 11-continued

| | | | |
|---|---|---|---|
| 100 | 9-(2'-fluorobiphenyl-4-yl)-3,4,6,7,8,9-hexahydropyrido[2,1-c][1,2,4]thiadiazine 2,2-dioxide | 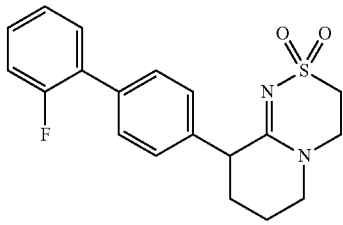 [SMILES: O=S1(=O)CCN2CCCC(c3ccc(-c4ccccc4F)cc3)C2=N1] | 359.1 |
| 101 | 9-(2-methylbiphenyl-4-yl)-3,4-dihydropyrido[2,1-c][1,2,4]thiadiazine 2,2-dioxide | 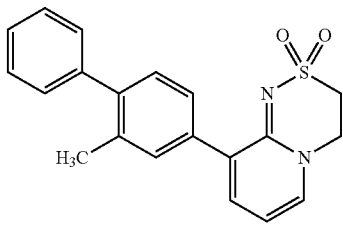 [SMILES: Cc1cc(C2=CC=CN3CCS(=O)(=O)N=C23)ccc1-c1ccccc1] | 351.1 |
| 102 | 9-(2-methylbiphenyl-4-yl)-3,4,6,7,8,9-hexahydropyrido[2,1-c][1,2,4]thiadiazine 2,2-dioxide | 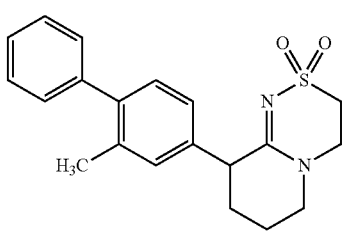 [SMILES: Cc1cc(C2CCCN3CCS(=O)(=O)N=C23)ccc1-c1ccccc1] | 355.2 |
| 103 | 9-(2-methylbiphenyl-4-yl)-3,4,6,7,8,9-hexahydropyrido[2,1-c][1,2,4]thiadiazine 2,2-dioxide | 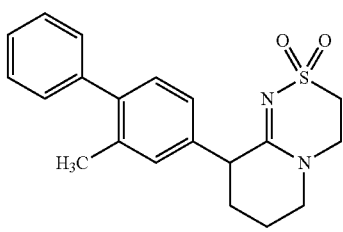 [SMILES: Cc1cc(C2CCCN3CCS(=O)(=O)N=C23)ccc1-c1ccccc1] | 355.1 |
| 104 | 9-(2-methylbiphenyl-4-yl)-3,4,6,7,8,9-hexahydropyrido[2,1-c][1,2,4]thiadiazine 2,2-dioxide | 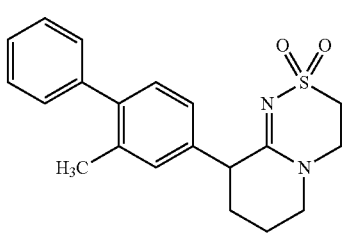 [SMILES: Cc1cc(C2CCCN3CCS(=O)(=O)N=C23)ccc1-c1ccccc1] | 355.1 |
| 105 | 9-(4'-methylbiphenyl-4-yl)-3,4,6,7,8,9-hexahydropyrido[2,1-c][1,2,4]thiadiazine 2,2-dioxide | 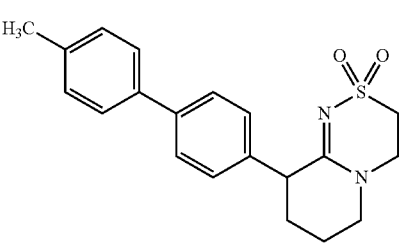 [SMILES: Cc1ccc(-c2ccc(C3CCCN4CCS(=O)(=O)N=C34)cc2)cc1] | 355.1 |

TABLE 11-continued

| | | | |
|---|---|---|---|
| 106 | 9-(3'-methoxybiphenyl-4-yl)-3,4,6,7,8,9-hexahydropyrido[2,1-c][1,2,4]thiadiazine 2,2-dioxide | 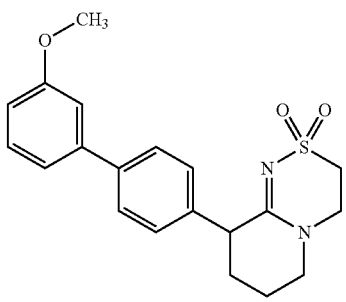 [SMILES: COc1cccc(-c2ccc(C3CCCN4CCS(=O)(=O)N=C34)cc2)c1] | 371.1 |

TABLE 12

| | | | |
|---|---|---|---|
| 107 | 9-[4-(4-methylphenoxy)phenyl]-3,4-dihydropyrido[2,1-c][1,2,4]thiadiazine 2,2-dioxide | 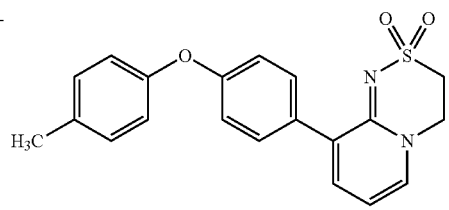 | 367.1 |
| 108 | 9-[4-(4-methylphenoxy)phenyl]-3,4,6,7,8,9-hexahydropyrido[2,1-c][1,2,4]thiadiazine 2,2-dioxide | 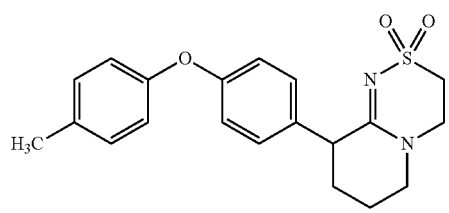 [SMILES: Cc1ccc(Oc2ccc(C3CCCN4CCS(=O)(=O)N=C34)cc2)cc1] | 371.1 |
| 109 | 9-[4-(4-methylphenoxy)phenyl]-3,4,6,7,8,9-hexahydropyrido[2,1-c][1,2,4]thiadiazine 2,2-dioxide | 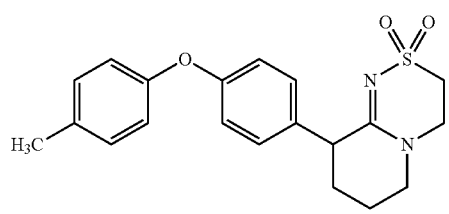 [SMILES: Cc1ccc(Oc2ccc(C3CCCN4CCS(=O)(=O)N=C34)cc2)cc1] | 371.1 |
| 110 | 9-[4-(4-methylphenoxy)phenyl]-3,4,6,7,8,9-hexahydropyrido[2,1-c][1,2,4]thiadiazine 2,2-dioxide | 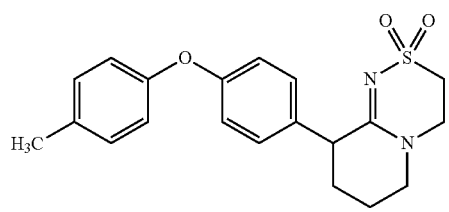 [SMILES: Cc1ccc(Oc2ccc(C3CCCN4CCS(=O)(=O)N=C34)cc2)cc1] | 371.1 |
| 111 | 9-[4-(4-fluoro-3-methylphenoxy)phenyl]-3,4-dihydropyrido[2,1-c][1,2,4]thiadiazine 2,2-dioxide | 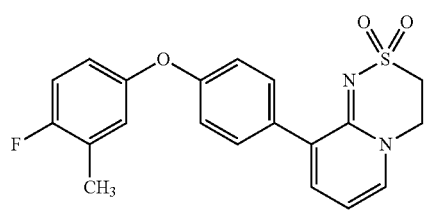 [SMILES: Cc1cc(Oc2ccc(C3=CC=CN4CCS(=O)(=O)N=C34)cc2)ccc1F] | 385.1 |

TABLE 12-continued

| | | | |
|---|---|---|---|
| 112 | 9-[4-(4-fluoro-3-methylphenoxy)phenyl]-3,4,6,7,8,9-hexahydropyrido[2,1-c][1,2,4]thiadiazine 2,2-dioxide | 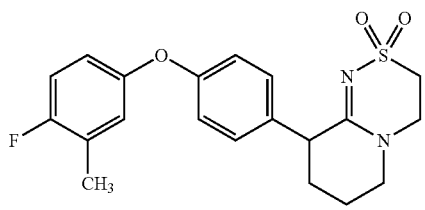 [SMILES: Cc1cc(Oc2ccc(C3CCCN4CCS(=O)(=O)N=C34)cc2)ccc1F] | 389.1 |
| 113 | 9-[4-(4-fluoro-3-methylphenoxy)phenyl]-3,4,6,7,8,9-hexahydropyrido[2,1-c][1,2,4]thiadiazine 2,2-dioxide | 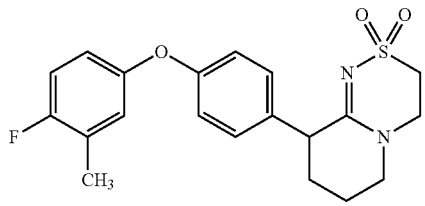 [SMILES: Cc1cc(Oc2ccc(C3CCCN4CCS(=O)(=O)N=C34)cc2)ccc1F] | 389.1 |
| 114 | 9-[4-(4-fluoro-3-methylphenoxy)phenyl]-3,4,6,7,8,9-hexahydropyrido[2,1-c][1,2,4]thiadiazine 2,2-dioxide | 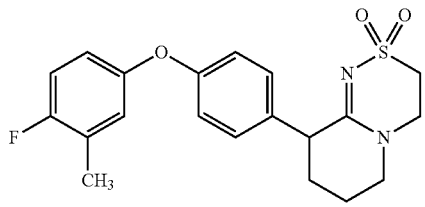 [SMILES: Cc1cc(Oc2ccc(C3CCCN4CCS(=O)(=O)N=C34)cc2)ccc1F] | 389.1 |
| 115 | 9-[4-(2-methylphenoxy)phenyl]-3,4-dihydropyrido[2,1-c][1,2,4]thiadiazine 2,2-dioxide | 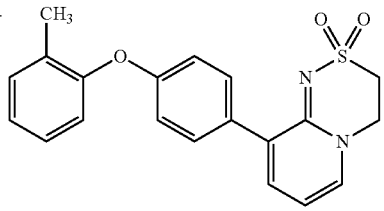 | 367.1 |
| 116 | 9-[4-(2-methylphenoxy)phenyl]-3,4,6,7,8,9-hexahydropyrido[2,1-c][1,2,4]thiadiazine 2,2-dioxide | 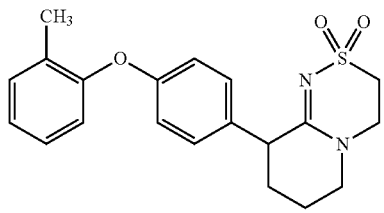 [SMILES: Cc1ccccc1Oc1ccc(C2CCCN3CCS(=O)(=O)N=C23)cc1] | 371.1 |
| 117 | 9-[4-(3-methylphenoxy)phenyl]-3,4-dihydropyrido[2,1-c][1,2,4]thiadiazine 2,2-dioxide | 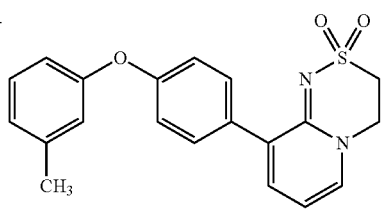 | 367.1 |
| 118 | 9-[4-(3-methylphenoxy)phenyl]-3,4,6,7,8,9-hexahydropyrido[2,1-c][1,2,4]thiadiazine 2,2-dioxide | 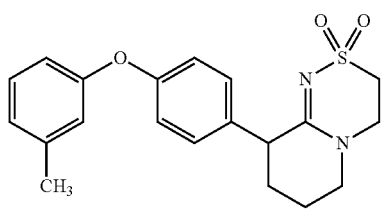 [SMILES: Cc1cccc(Oc2ccc(C3CCCN4CCS(=O)(=O)N=C34)cc2)c1] | 371.1 |

TABLE 13

| | | | |
|---|---|---|---|
| 119 | 9-[4-(3-methylphenoxy)phenyl]-3,4,6,7,8,9-hexahydropyrido[2,1-c][1,2,4]thiadiazine 2,2-dioxide | 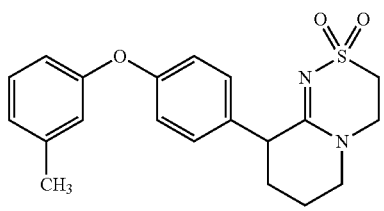 | 371.1 |
| 120 | 9-[4-(3-methylphenoxy)phenyl]-3,4,6,7,8,9-hexahydropyrido[2,1-c][1,2,4]thiadiazine 2,2-dioxide | 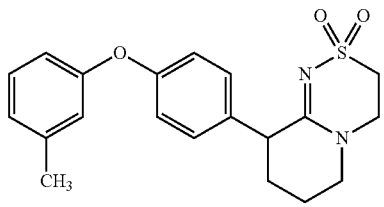 [SMILES: Cc1cccc(Oc2ccc(C3CCCN4CCS(=O)(=O)N=C34)cc2)c1] | 371.1 |
| 121 | 9-{4-[2-methyl-4-(trifluoromethyl)phenoxy]phenyl}-3,4-dihydropyrido[2,1-c][1,2,4]thiadiazine 2,2-dioxide | 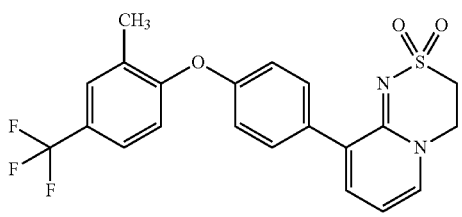 [SMILES: Cc1cc(C(F)(F)F)ccc1Oc1ccc(C2=CC=CN3CCS(=O)(=O)N=C23)cc1] | 435.1 |
| 122 | 9-{4-[2-methyl-4-(trifluoromethyl)phenoxy]phenyl}-3,4,6,7,8,9-hexahydropyrido[2,1-c][1,2,4]thiadiazine 2,2-dioxide | 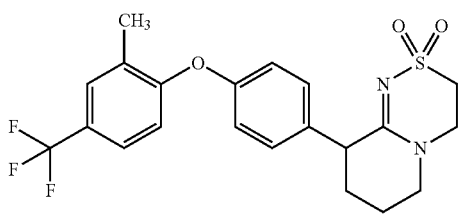 [SMILES: Cc1cc(C(F)(F)F)ccc1Oc1ccc(C2CCCN3CCS(=O)(=O)N=C23)cc1] | 439.1 |
| 123 | 9-{4-[2-methyl-4-(trifluoromethyl)phenoxy]phenyl}-3,4,6,7,8,9-hexahydropyrido[2,1-c][1,2,4]thiadiazine 2,2-dioxide | 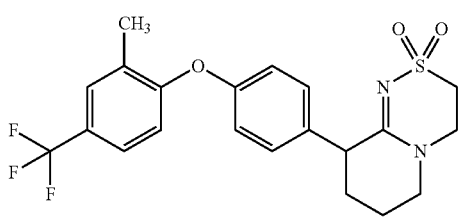 [SMILES: Cc1cc(C(F)(F)F)ccc1Oc1ccc(C2CCCN3CCS(=O)(=O)N=C23)cc1] | 439.1 |
| 124 | 9-{4-[2-methyl-4-(trifluoromethyl)phenoxy]phenyl}-3,4,6,7,8,9-hexahydropyrido[2,1-c][1,2,4]thiadiazine 2,2-dioxide | 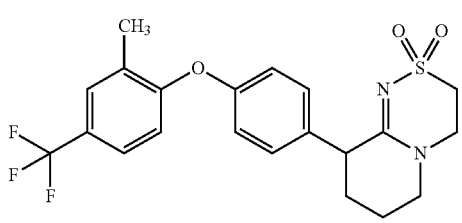 [SMILES: Cc1cc(C(F)(F)F)ccc1Oc1ccc(C2CCCN3CCS(=O)(=O)N=C23)cc1] | 439.1 |
| 125 | 9-{4-[4-(trifluoromethyl)phenoxy]phenyl}-3,4,6,7,8,9-hexahydropyrido[2,1-c][1,2,4]thiadiazine 2,2-dioxide | 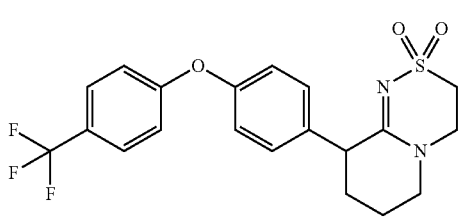 [SMILES: O=S1(=O)CCN2CCCC(c3ccc(Oc4ccc(C(F)(F)F)cc4)cc3)C2=N1] | 425.1 |

TABLE 13-continued

| | | | |
|---|---|---|---|
| 126 | 9-(6-methoxynaphthalen-2-yl)-3,4-dihydropyrido[2,1-c][1,2,4]thiadiazine 2,2-dioxide | 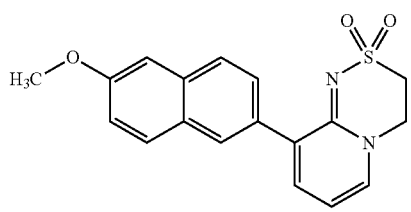 [SMILES: COc1ccc2cc(C3=CC=CN4CCS(=O)(=O)N=C34)ccc2c1] | 341.0 |
| 127 | 9-(6-methoxynaphthalen-2-yl)-3,4,6,7,8,9-hexahydropyrido[2,1-c][1,2,4]thiadiazine 2,2-dioxide | 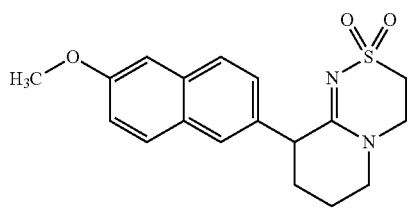 [SMILES: COc1ccc2cc(C3CCCN4CCS(=O)(=O)N=C34)ccc2c1] | 345.1 |
| 128 | 9-(6-methoxynaphthalen-2-yl)-3,4,6,7,8,9-hexahydropyrido[2,1-c][1,2,4]thiadiazine 2,2-dioxide | 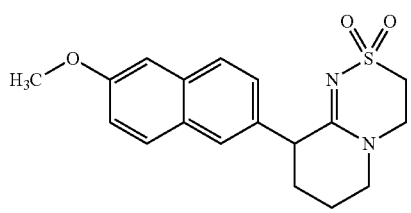 [SMILES: COc1ccc2cc(C3CCCN4CCS(=O)(=O)N=C34)ccc2c1] | 345.1 |
| 129 | 9-(6-methoxynaphthalen-2-yl)-3,4,6,7,8,9-hexahydropyrido[2,1-c][1,2,4]thiadiazine 2,2-dioxide | 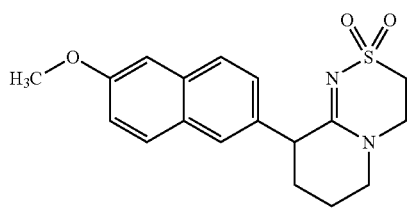 [SMILES: COc1ccc2cc(C3CCCN4CCS(=O)(=O)N=C34)ccc2c1] | 345.1 |
| 130 | 9-[4-(3-ethylphenoxy)phenyl]-3,4-dihydropyrido[2,1-c][1,2,4]thiadiazine 2,2-dioxide | 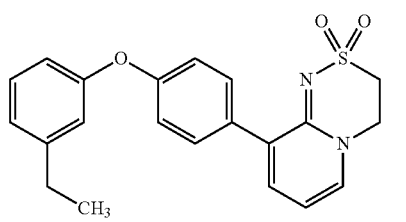 [SMILES: CCc1cccc(Oc2ccc(C3=CC=CN4CCS(=O)(=O)N=C34)cc2)c1] | 381.1 |

TABLE 14

| | | | |
|---|---|---|---|
| 131 | 9-[4-(3-ethylphenoxy)phenyl]-3,4,6,7,8,9-hexahydropyrido[2,1-c][1,2,4]thiadiazine 2,2-dioxide | 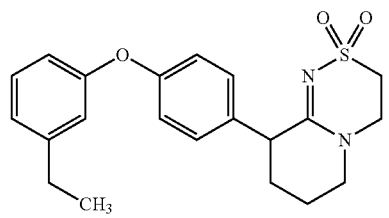 [SMILES: CCc1cccc(Oc2ccc(C3CCCN4CCS(=O)(=O)N=C34)cc2)c1] | 385.2 |
| 132 | 9-[4-(3-ethylphenoxy)phenyl]-3,4,6,7,8,9-hexahydropyrido[2,1-c][1,2,4]thiadiazine 2,2-dioxide | 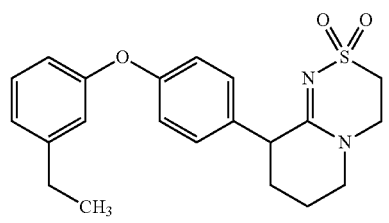 | 385.1 |

TABLE 14-continued

| | | | |
|---|---|---|---|
| 133 | 9-[4-(3-ethylphenoxy)phenyl]-3,4,6,7,8,9-hexahydropyrido[2,1-c][1,2,4]thiadiazine 2,2-dioxide | 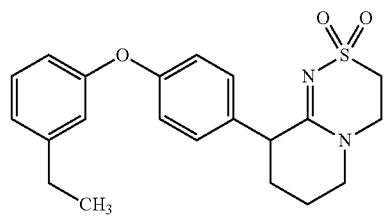 | 385.1 |
| 134 | 9-[4-(3,4-dimethylphenoxy)phenyl]-3,4-dihydropyrido[2,1-c][1,2,4]thiadiazine 2,2-dioxide | 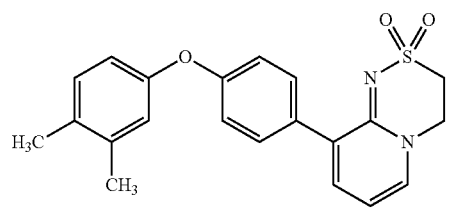 [SMILES: Cc1ccc(Oc2ccc(C3=CC=CN4CCS(=O)(=O)N=C34)cc2)cc1C] | 381.1 |
| 135 | 9-[4-(3,4-dimethylphenoxy)phenyl]-3,4,6,7,8,9-hexahydropyrido[2,1-c][1,2,4]thiadiazine 2,2-dioxide | 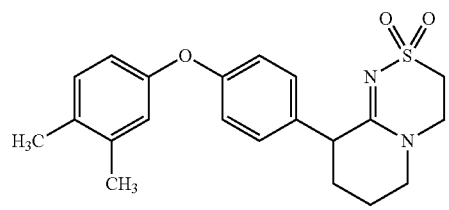 [SMILES: Cc1ccc(Oc2ccc(C3CCCN4CCS(=O)(=O)N=C34)cc2)cc1C] | 385.1 |
| 136 | 9-{4-[difluoro(4-methylphenyl)methyl]phenyl}-3,4-dihydropyrido[2,1-c][1,2,4]thiadiazine 2,2-dioxide | 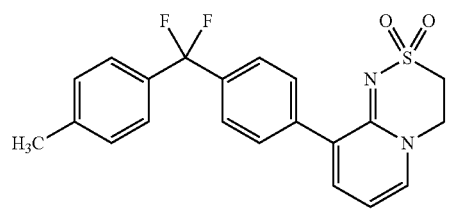 [SMILES: Cc1ccc(C(F)(F)c2ccc(C3=CC=CN4CCS(=O)(=O)N=C34)cc2)cc1] | 401.1 |
| 137 | 9-{4-[difluoro(4-methylphenyl)methyl]phenyl}-3,4,6,7,8,9-hexahydropyrido[2,1-c][1,2,4]thiadiazine 2,2-dioxide | 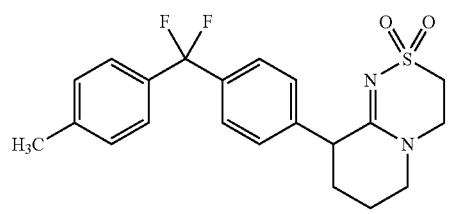 [SMILES: Cc1ccc(C(F)(F)c2ccc(C3CCCN4CCS(=O)(=O)N=C34)cc2)cc1] | 405.1 |
| 138 | 9-{4-[difluoro(4-methylphenyl)methyl]phenyl}-3,4,6,7,8,9-hexahydropyrido[2,1-c][1,2,4]thiadiazine 2,2-dioxide | 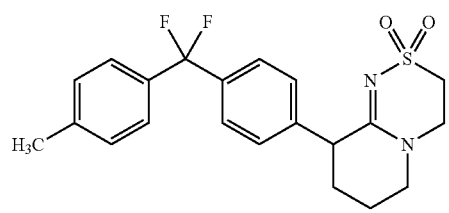 [SMILES: Cc1ccc(C(F)(F)c2ccc(C3CCCN4CCS(=O)(=O)N=C34)cc2)cc1] | 405.1 |
| 139 | 9-{4-[difluoro(4-methylphenyl)methyl]phenyl}-3,4,6,7,8,9-hexahydropyrido[2,1-c][1,2,4]thiadiazine 2,2-dioxide | 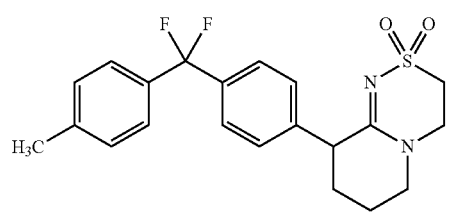 [SMILES: Cc1ccc(C(F)(F)c2ccc(C3CCCN4CCS(=O)(=O)N=C34)cc2)cc1] | 405.1 |

TABLE 14-continued

| # | Name | Structure | Mass |
|---|------|-----------|------|
| 140 | 9-{4-[difluoro(4-fluoro-3-methylphenyl)methyl]phenyl}-3,4,6,7,8,9-hexahydropyrido[2,1-c][1,2,4]thiadiazine 2,2-dioxide | 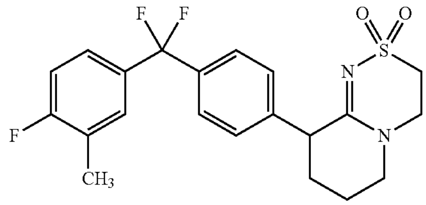 [SMILES: Cc1cc(C(F)(F)c2ccc(C3CCCN4CCS(=O)(=O)N=C34)cc2)ccc1F] | 423.1 |
| 141 | 9-[4-(2,3-dihydro-1-benzofuran-6-yloxy)phenyl]-3,4,6,7,8,9-hexahydropyrido[2,1-c][1,2,4]thiadiazine 2,2-dioxide | 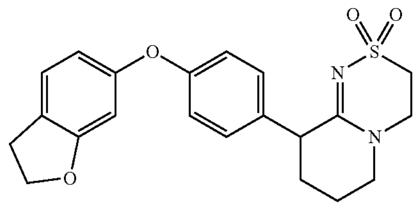 [SMILES: O=S1(=O)CCN2CCCC(c3ccc(Oc4ccc5c(c4)OCC5)cc3)C2=N1] | 399.1 |
| 142 | 9-{4-[4-bromo-3-(trifluoromethyl}phenoxy]phenyl}-3,4,6,7,8,9-hexahydropyrido[2,1-c][1,2,4]thiadiazine 2,2-dioxide | 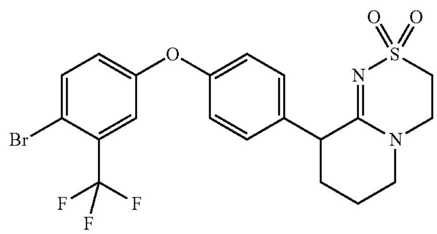 [SMILES: O=S1(=O)CCN2CCCC(c3ccc(Oc4ccc(Br)c(C(F)(F)F)c4)cc3)C2=N1] | 503.0 505.0 |

TABLE 15

| # | Name | Structure | Mass |
|---|------|-----------|------|
| 143 | 9-[4-(4-fluoro-2-methylphenoxy)phenyl]-3,4-dihydropyrido[2,1-c][1,2,4]thiadiazine 2,2-dioxide | 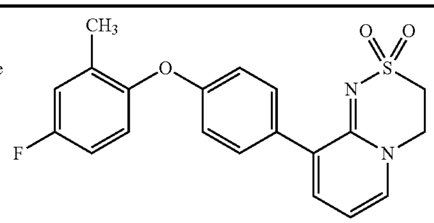 | 385.1 |
| 144 | 9-[4-(4-fluoro-2-methylphenoxy)phenyl]-3,4,6,7,8,9-hexahydropyrido[2,1-c][1,2,4]thiadiazine 2,2-dioxide | 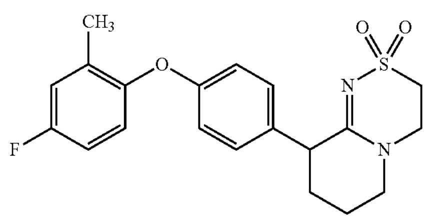 [SMILES: Cc1cc(F)ccc1Oc1ccc(C2CCCN3CCS(=O)(=O)N=C23)cc1] | 389.1 |
| 145 | 9-[4-(4-fluoro-2-methylphenoxy)phenyl]-3,4,6,7,8,9-hexahydropyrido[2,1-c][1,2,4]thiadiazine 2,2-dioxide | 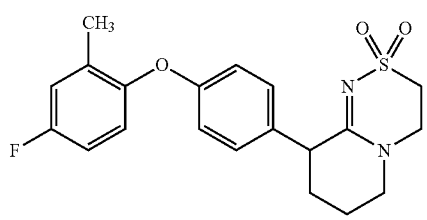 [SMILES: Cc1cc(F)ccc1Oc1ccc(C2CCCN3CCS(=O)(=O)N=C23)cc1] | 389.1 |
| 146 | 9-[4-(4-fluoro-2-methylphenoxy)phenyl]-3,4,6,7,8,9-hexahydropyrido[2,1-c][1,2,4]thiadiazine 2,2-dioxide | 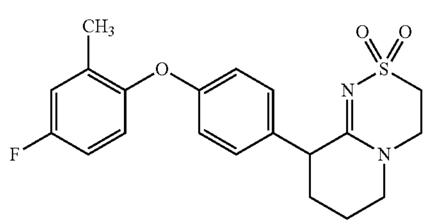 [SMILES: Cc1cc(F)ccc1Oc1ccc(C2CCCN3CCS(=O)(=O)N=C23)cc1] | 389.1 |

TABLE 15-continued

| | | | |
|---|---|---|---|
| 147 | 9-[4-(4-chlorophenoxy)phenyl]-3,4-dihydropyrido[2,1-c][1,2,4]thiadiazine 2,2-dioxide | 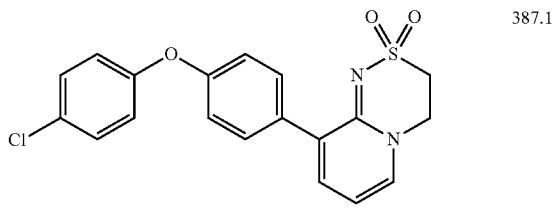 | 387.1 |
| 148 | 9-[4-(4-chlorophenoxy)phenyl]-3,4,6,7,8,9-hexahydropyrido[2,1-c][1,2,4]thiadiazine 2,2-dioxide | 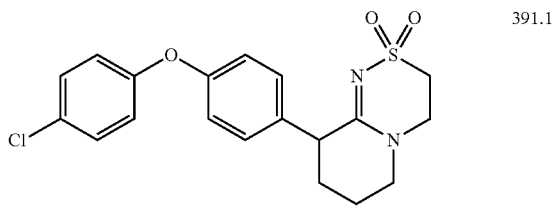 | 391.1 |
| 149 | (9S)-9-[4-(4-chlorophenoxy)phenyl]-3,4,6,7,8,9-hexahydropyrido[2,1-c][1,2,4]thiadiazine 2,2-dioxide | 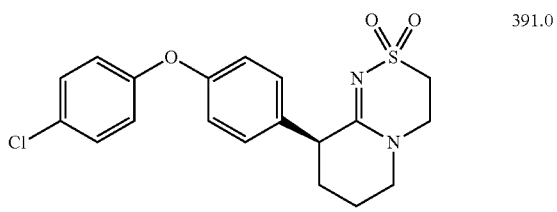 | 391.0 |
| 150 | 9-[4-(4-chlorophenoxy)phenyl]-3,4,6,7,8,9-hexahydropyrido[2,1-c][1,2,4]thiadiazine 2,2-dioxide | 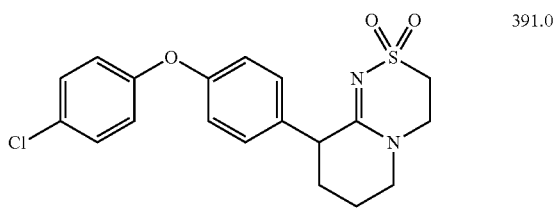 | 391.0 |
| 151 | 9-[4-(3,4-dichlorophenoxy)phenyl]-3,4,6,7,8,9-hexahydropyrido[2,1-c][1,2,4]thiadiazine 2,2-dioxide | 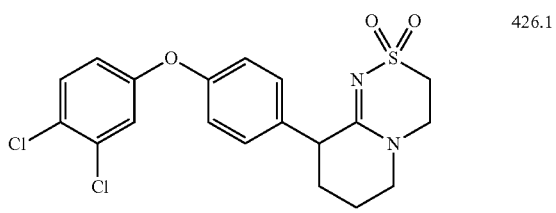 | 426.1 |
| 152 | 9-[4-(3,4-dichlorophenoxy)phenyl]-3,4,6,7,8,9-hexahydropyrido[2,1-c][1,2,4]thiadiazine 2,2-dioxide | 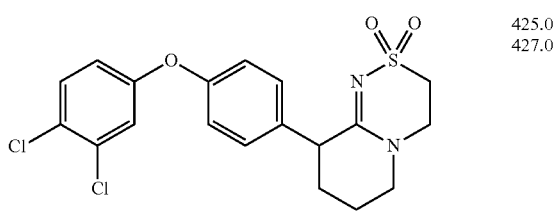 | 425.0<br>427.0 |
| 153 | 9-[4-(3,4-dichlorophenoxy)phenyl]-3,4,6,7,8,9-hexahydropyrido[2,1-c][1,2,4]thiadiazine 2,2-dioxide | 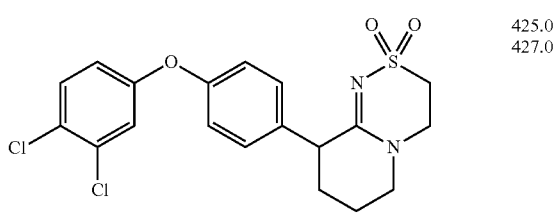 | 425.0<br>427.0 |

| | | | |
|---|---|---|---|
| | TABLE 15-continued | | |
| 154 | 9-[4-(4-chloro-3-methoxyphenoxy)phenyl]-3,4-dihydropyrido[2,1-c][1,2,4]thiadiazine 2,2-dioxide | 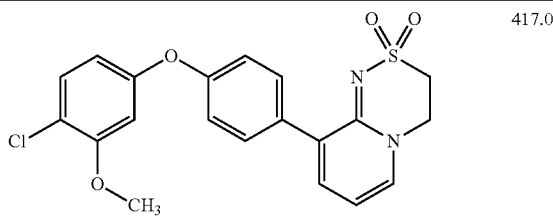 | 417.0 |

| | | | |
|---|---|---|---|
| | TABLE 16 | | |
| 155 | 9-[4-(4-chloro-3-methoxyphenoxy)phenyl]-3,4,6,7,8,9-hexahydropyrido[2,1-c][1,2,4]thiadiazine 2,2-dioxide | 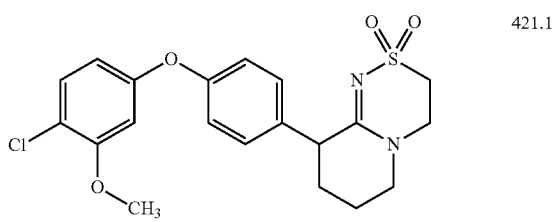 | 421.1 |
| 156 | 9-{4-[3-(1,1-difluoroethyl)phenoxy]phenyl}-3,4-dihydropyrido[2,1-c][1,2,4]thiadiazine 2,2-dioxide | 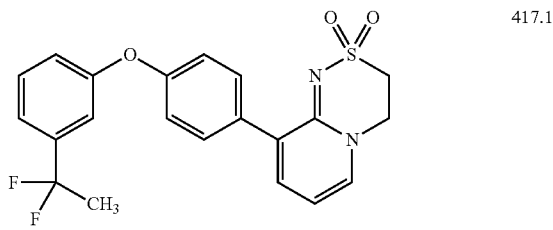 | 417.1 |
| 157 | 9-{4-[3-(1,1-difluoroethyl)phenoxy]phenyl}-3,4,6,7,8,9-hexahydropyrido[2,1-c][1,2,4]thiadiazine 2,2-dioxide | 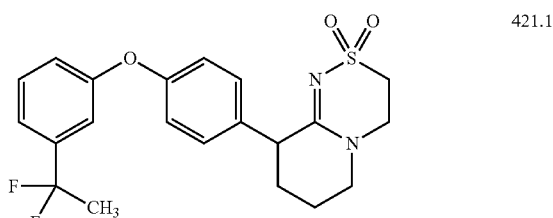 | 421.1 |
| 158 | 9-{4-[3-(1,1-difluoroethyl)phenoxy]phenyl}-3,4,6,7,8,9-hexahydropyrido[2,1-c][1,2,4]thiadiazine 2,2-dioxide | 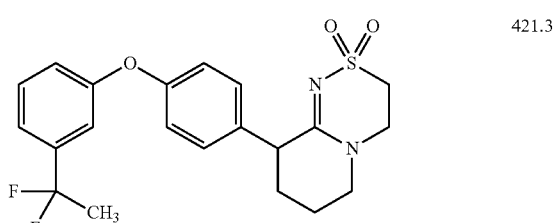 | 421.3 |
| 159 | 9-{4-[3-(1,1-difluoroethyl)phenoxy]phenyl}-3,4,6,7,8,9-hexahydropyrido[2,1-c][1,2,4]thiadiazine 2,2-dioxide | 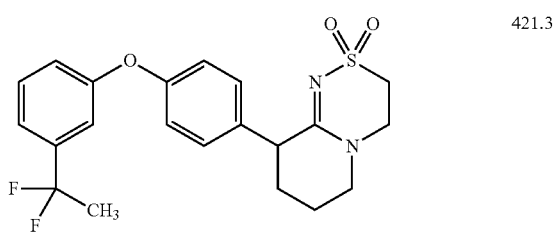 | 421.3 |

TABLE 16-continued

| | | | |
|---|---|---|---|
| 160 | (9S)-9-{4-[2-chloro-5-(trifluoromethyl)phenoxy]phenyl}-3,4,6,7,8,9-hexahydropyrido[2,1-c][1,2,4]thiadiazine 2,2-dioxide | 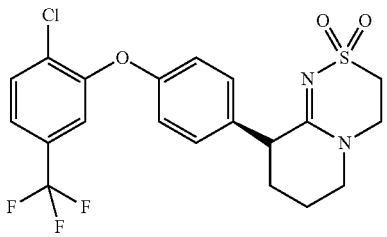 | 459.1 |
| 161 | 9-[4-(4-ethylphenoxy)phenyl]-3,4,6,7,8,9-hexahydropyrido[2,1-c][1,2,4]thiadiazine 2,2-dioxide | 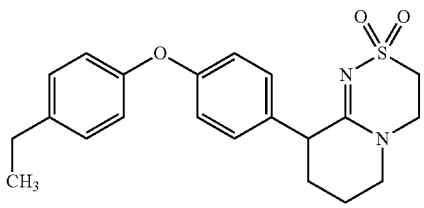 [SMILES: CCc1ccc(Oc2ccc(C3CCCN4CCS(=O)(=O)N=C34)cc2)cc1] | 385.1 |
| 162 | 9-{4-[difluoro(phenyl)methyl]phenyl}-3,4-dihydropyrido[2,1-c][1,2,4]thiadiazine 2,2-dioxide | 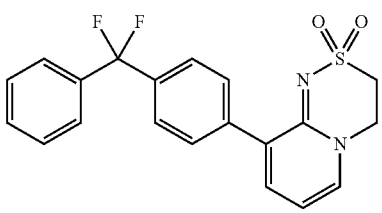 [SMILES: O=S1(=O)CCN2C=CC=C(c3ccc(C(F)(F)c4ccccc4)cc3)C2=N1] | 387.1 |
| 163 | 9-{4-[difluoro(phenyl)methyl]phenyl}-3,4,6,7,8,9-hexahydropyrido[2,1-c][1,2,4]thiadiazine 2,2-dioxide | 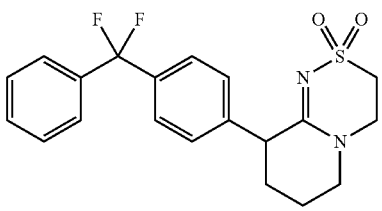 [SMILES: O=S1(=O)CCN2CCCC(c3ccc(C(F)(F)c4ccccc4)cc3)C2=N1] | 391.1 |
| 164 | 9-[4-(4-fluoro-3-methoxyphenoxy)phenyl]-7-methyl-3,4,6,7,8,9-hexahydropyrido[2,1-c][1,2,4]thiadiazine 2,2-dioxide | 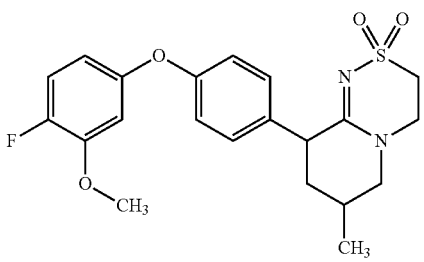 [SMILES: COc1cc(Oc2ccc(C3CC(C)CN4CCS(=O)(=O)N=C34)cc2)ccc1F] | 419.1 |
| 165 | 9-[4-(cyclohexyloxy)phenyl]-3,4-dihydropyrido[2,1-c][1,2,4]thiadiazine 2,2-dioxide | 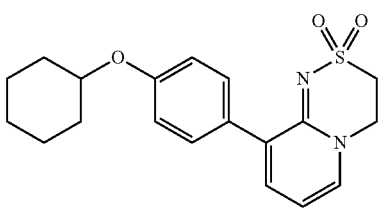 [SMILES: O=S1(=O)CCN2C=CC=C(c3ccc(OC4CCCCC4)cc3)C2=N1] | 359.1 |
| 166 | 9-(4-phenoxyphenyl)-3,4-dihydropyrido[2,1-c][1,2,4]thiadiazine 2,2-dioxide | 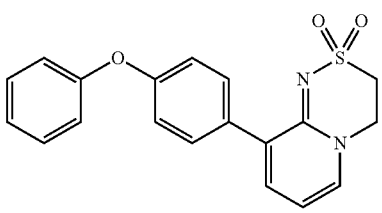 [SMILES: O=S1(=O)CCN2C=CC=C(c3ccc(Oc4ccccc4)cc3)C2=N1] | 353.1 |

TABLE 17

| | | | |
|---|---|---|---|
| 167 | 9-(4-phenoxyphenyl)-3,4-dihydropyrido[2,1-c][1,2,4]thiadiazine 2,2-dioxide | 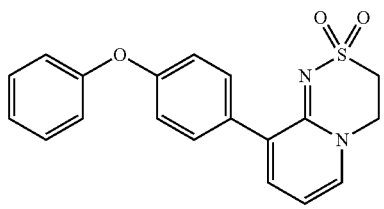 [SMILES: O=S1(=O)CCN2C=CC=C(c3ccc(Oc4ccccc4)cc3)C2=N1] | 353.1 |
| 168 | 9-[4-(4-methylphenoxy)phenyl]-3,4-dihydropyrido[2,1-c][1,2,4]thiadiazine 2,2-dioxide | 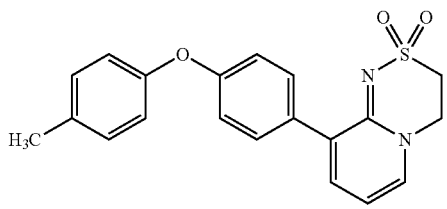 [SMILES: Cc1ccc(Oc2ccc(C3=CC=CN4CCS(=O)(=O)N=C34)cc2)cc1] | 367.1 |
| 169 | 9-[4-(cyclohexyloxy)phenyl]-7-methyl-3,4-dihydropyrazino[2,1-c][1,2,4]thiadiazine 2,2-dioxide | 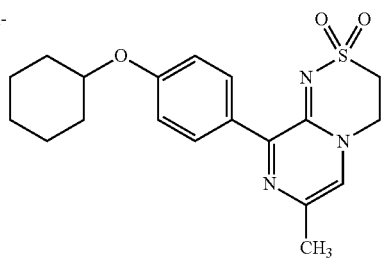 | 374.1 |
| 170 | 9-{4-[4-(1,1-difluoroethyl)-phenoxy]phenyl}-3,4,6,7,8,9-hexahydropyrido[2,1-c][1,2,4]thiadiazine 2,2-dioxide | 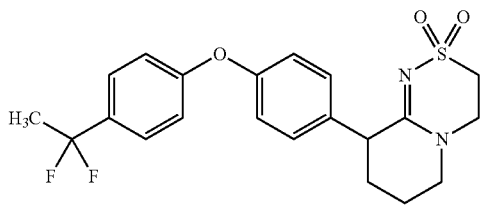 [SMILES: CC(F)(F)c1ccc(Oc2ccc(C3CCCN4CCS(=O)(=O)N=C34)cc2)cc1] | 421.1 |
| 171 | 9-{4-[3-(1,1-difluoroethyl)-phenoxy]phenyl}-7-methyl-3,4,6,7,8,9-hexahydropyrido[2,1-c][1,2,4]thiadiazine 2,2-dioxide | 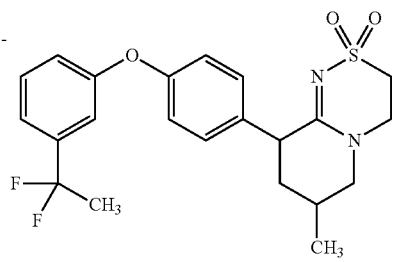 | 435.1 |
| 172 | 9-(4-[3-(1,1-difluoroethyl)-phenoxy]phenyl}-7-methyl-3,4,6,7,8,9-hexahydropyrido[2,1-c][1,2,4]thiadiazine 2,2-dioxide | 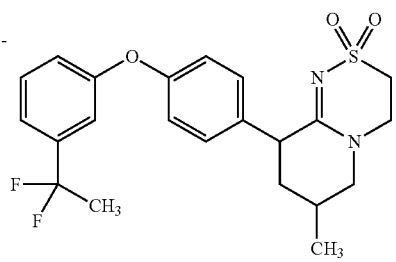 | 435.3 |

TABLE 17-continued

| | | | |
|---|---|---|---|
| 173 | 9-{4-[3-(1,1-difluoroethyl)-phenoxy]phenyl}-7-methyl-3,4,6,7,8,9-hexahydropyrido[2,1-c][1,2,4]thiadiazine 2,2-dioxide | 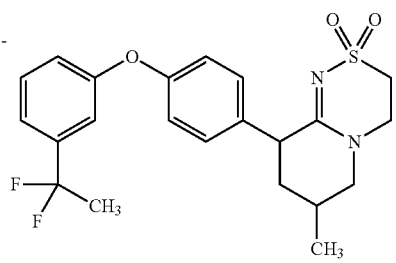 | 435.3 |
| 174 | 9-(4-(1,1-difluoroethyl)phenyl]-3,4,6,7,8,9-hexahydropyrido[2,1-c][1,2,4]thiadiazine 2,2-dioxide | 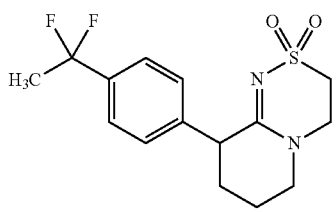 [SMILES: CC(F)(F)c1ccc(C2CCCN3CCS(=O)(=O)N=C23)cc1] | 329.1 |
| 175 | 9-[4-(trifluoromethyl)phenyl]-3,4,6,7,8,9-hexahydropyrido[2,1-c][1,2,4]thiadiazine 2,2-dioxide | 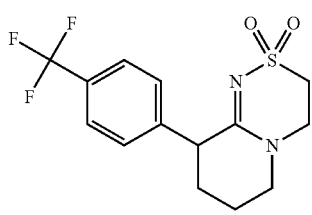 [SMILES: O=S1(=O)CCN2CCCC(c3ccc(C(F)(F)F)cc3)C2=N1] | 333.1 |
| 176 | 9-[4-(trifluoromethyl)phenyl]-3,4,6,7,8,9-hexahydropyrido[2,1-c][1,2,4]thiadiazine 2,2-dioxide | 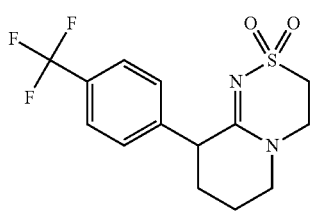 [SMILES: O=S1(=O)CCN2CCCC(c3ccc(C(F)(F)F)cc3)C2=N1] | 333.0 |
| 177 | 9-[4-(trifluoromethyl)phenyl]-3,4,6,7,8,9-hexahydropyrido[2,1-c][1,2,4]thiadiazine 2,2-dioxide | 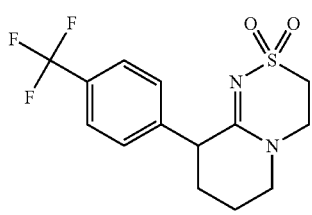 [SMILES: O=S1(=O)CCN2CCCC(c3ccc(C(F)(F)F)cc3)C2=N1] | 332.9 |
| 178 | 9-[4-(trifluoromethoxy)phenyl]-3,4,6,7,8,9-hexahydropyrido[2,1-c][1,2,4]thiadiazine 2,2-dioxide | 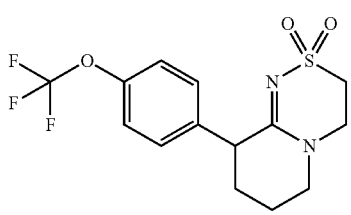 [SMILES: O=S1(=O)CCN2CCCC(c3ccc(OC(F)(F)F)cc3)C2=N1] | 348.9 |

TABLE 18

| | | | |
|---|---|---|---|
| 179 | 9-[4-(trifluoromethoxy)phenyl]-3,4,6,7,8,9-hexahydropyrido[2,1-c][1,2,4]thiadiazine 2,2-dioxide | 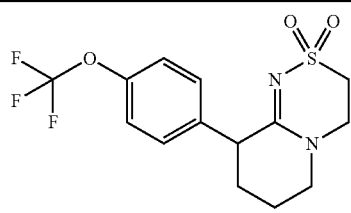 | 349.0 |

TABLE 18-continued

| | | | |
|---|---|---|---|
| 180 | 9-[4-(cyclohexyloxy)phenyl]-7-methyl-3,4-dihydropyrazino[2,1-c][1,2,4]thiadiazine 2,2-dioxide | 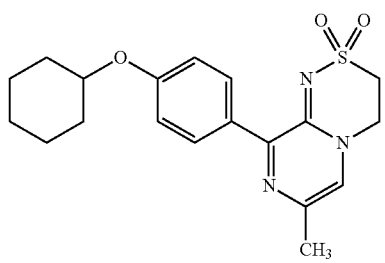 [SMILES: CC1=CN2CCS(=O)(=O)N=C2C(c2ccc(OC3CCCCC3)cc2)=N1] | 374.1 |
| 181 | 9-[4-(2-methylpropoxy)phenyl]-3,4-dihydropyrido[2,1-c][1,2,4]thiadiazine 2,2-dioxide | 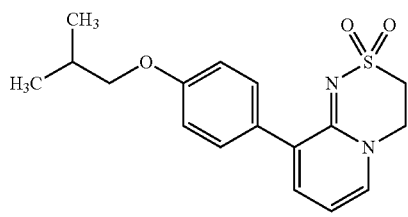 [SMILES: CC(C)COc1ccc(C2=CC=CN3CCS(=O)(=O)N=C23)cc1] | 333.1 |
| 182 | 9-[4-(cyclohexyloxy)phenyl]-3,4-dihydropyrido[2,1-c][1,2,4]thiadiazine 2,2-dioxide | 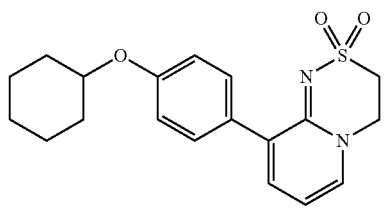 [SMILES: O=S1(=O)CCN2C=CC=C(c3ccc(OC4CCCCC4)cc3)C2=N1] | 359.1 |
| 183 | 2-chloro-4-[4-(2,2-dioxido-3,4,6,7,8,9-hexahydropyrido[2,1-c][1,2,4]-thiadiazin-9-yl)phenoxy]benzonitrile | 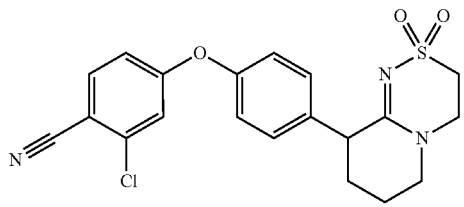 [SMILES: N#Cc1ccc(Oc2ccc(C3CCCN4CCS(=O)(=O)N=C34)cc2)cc1Cl] | 416.1 |
| 184 | 2-chloro-4-[4-(9-hydroxy-2,2-dioxido-3,4,6,7,8,9-hexahydropyrido[2,1-c][1,2,4]thiadiazin-9-yl)phenoxy]benzonitrile | 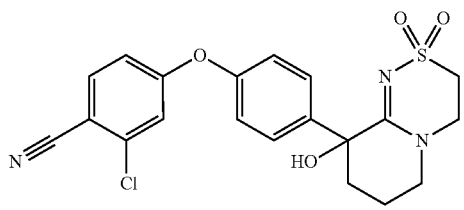 [SMILES: N#Cc1ccc(Oc2ccc(C3(O)CCCN4CCS(=O)(=O)N=C43)cc2)cc1Cl] | 432.1 |
| 185 | 9-(4-phenylcyclohexyl)-3,4-dihydropyrido[2,1-c][1,2,4]thiadiazine 2,2-dioxide | 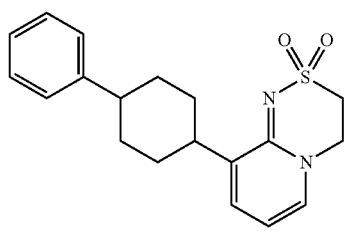 [SMILES: O=S1(=O)CCN2C=CC=C(C3CCC(c4ccccc4)CC3)C2=N1] | 343.1 |
| 186 | 9-{[4-(1-methylpropyl)phenoxy]methyl}-3,4-dihydropyrido[2,1-c][1,2,4]thiadiazine 2,2-dioxide | 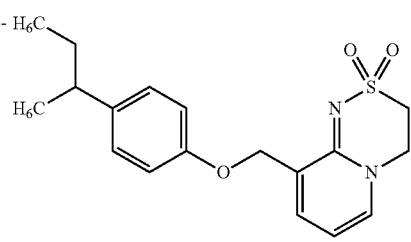 | 347.1 |

TABLE 18-continued

| | | | |
|---|---|---|---|
| 187 | 9-{4-[3-(trifluoromethyl)phenoxy]phenyl}-3,4-dihydropyrido[2,1-c][1,2,4]thiadiazine 2,2-dioxide | | 421.1 |
| 188 | 9-{4-[(4,4-dimethylcyclohex-1-en-1-yl)oxy]phenyl)-3,4-dihydropyrido[2,1-c][1,2,4]thiadiazine 2,2-dioxide | | 385.1 |
| 189 | 9-{4-[(4,4-dimethylcyclohexyl)oxy]phenyl}-3,4,6,7,8,9-hexahydropyrido[2,1-c][1,2,4]thiadiazine 2,2-dioxide | | 391.2 |
| 190 | 9-(4-propoxyphenyl)-3,4,6,7,8,9-hexahydropyrido[2,1-c][1,2,4]thiadiazine 2,2-dioxide | | 323.1 |

TABLE 19

| | | | |
|---|---|---|---|
| 191 | 9-(6-phenoxypyridin-3-yl)-3,4-dihydropyrido[2,1-c][1,2,4]thiadiazine 2,2-dioxide | | 354.1 |
| 192 | 9-(4-phenoxyphenyl)-3,4-dihydropyrido[2,1-c][1,2,4]thiadiazine 2,2-dioxide | | 353.2 |
| 193 | 9-(4-tert-butylphenyl)-3,4-dihydropyrido[2,1-c][1,2,4]thiadiazine 2,2-dioxide | | 317.2 |

| | | | |
|---|---|---|---|
| 194 | 9-(3-fluorobiphenyl-4-yl)-3,4-dihydropyrido[2,1-c][1,2,4]thiadiazine 2,2-dioxide | 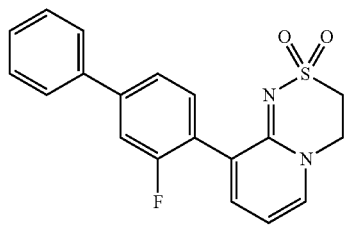 | 355.1 |
| 195 | 9-(6-phenoxypyridin-3-yl)-3,4-dihydropyrido[2,1-c][1,2,4]thiadiazine 2,2-dioxide | 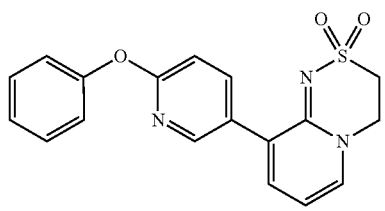 | 354.1 |
| 196 | 9-[4-(cyclohexyloxy)phenyl]-3,4-dihydropyrido[2,1-c][1,2,4]thiadiazine 2,2-dioxide | 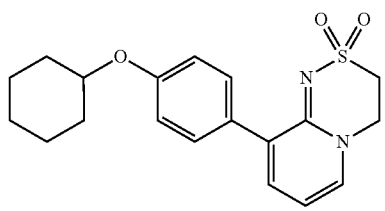 [SMILES: O=S1(=O)CCN2C=CC=C(c3ccc(OC4CCCCC4)cc3)C2=N1] | 359.2 |
| 197 | 9-[4-(4-methylphenoxy)phenyl]-3,4-dihydropyrido[2,1-c][1,2,4]thiadiazine 2,2-dioxide | 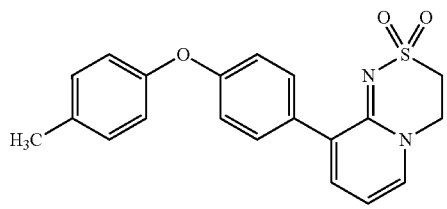 [SMILES: Cc1ccc(Oc2ccc(C3=CC=CN4CCS(=O)(=O)N=C34)cc2)cc1] | 367.1 |
| 198 | 4-[4-(2,2-dioxido-3,4-dihydropyrido[2,1-c][1,2,4]thiadiazin-9-yl)phenoxy]phenol | 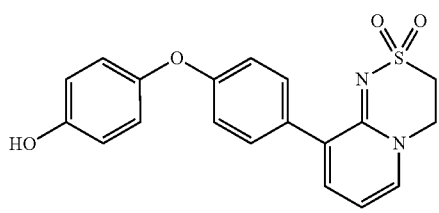 [SMILES: O=S1(=O)CCN2C=CC=C(c3ccc(Oc4ccc(O)cc4)cc3)C2=N1] | 369.1 |
| 199 | 9-[4-(4-fluorophenoxy)phenyl]-3,4-dihydropyrido[2,1-c][1,2,4]thiadiazine 2,2-dioxide | 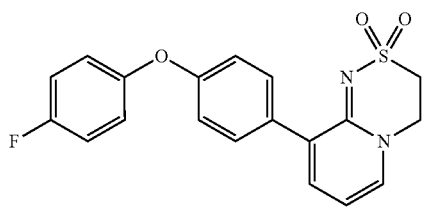 [SMILES: O=S1(=O)CCN2C=CC=C(c3ccc(Oc4ccc(F)cc4)cc3)C2=N1] | 371.0 |
| 200 | 9-{4-[4-(trifluoromethyl)phenoxy]phenyl}-3,4-dihydropyrido[2,1-c][1,2,4]thiadiazine 2,2-dioxide | 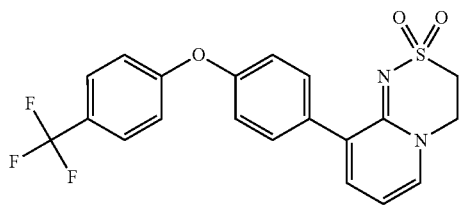 [SMILES: O=S1(=O)CCN2C=CC=C(c3ccc(Oc4ccc(C(F)(F)F)cc4)cc3)C2=N1] | 421.1 |

TABLE 19-continued

| | | | |
|---|---|---|---|
| 201 | 9-[4-(3-chlorophenoxy)phenyl]-3,4,6,7,8,9-hexahydropyrido[2,1-c][1,2,4]thiadiazine 2,2-dioxide | 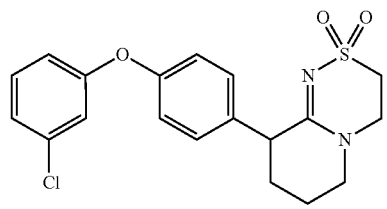 [SMILES: O=S1(=O)CCN2CCCC(c3ccc(Oc4cccc(Cl)c4)cc3)C2=N1] | 391.1 |
| 202 | (9R)-9-[4-(3-chlorophenoxy)phenyl]-3,4,6,7,8,9-hexahydropyrido[2,1-c][1,2,4]thiadiazine 2,2-dioxide | 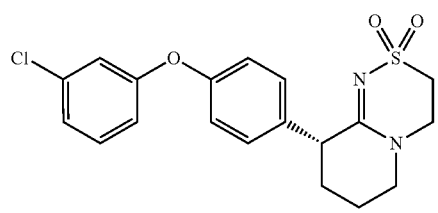 [SMILES: O=S1(=O)CCN2CCC[C@H](c3ccc(Oc4cccc(Cl)c4)cc3)C2=N1] | 391.1 |

TABLE 20

| | | | |
|---|---|---|---|
| 203 | (9S)-9-[4-(3-chlorophenoxy)phenyl]-3,4,6,7,8,9-hexahydropyrido[2,1-c][1,2,4]thiadiazine 2,2-dioxide | 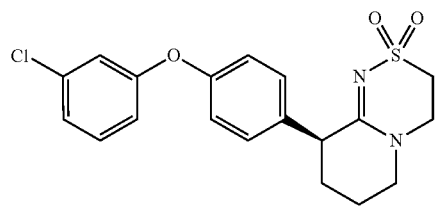 [SMILES: O=S1(=O)CCN2CCC[C@@H](c3ccc(Oc4cccc(Cl)c4)cc3)C2=N1] | 391.1 |
| 204 | 8-methoxy-9-(4-phenoxyphenyl)-3,4-dihydropyrido[2,1-c][1,2,4]thiadiazine 2,2-dioxide | 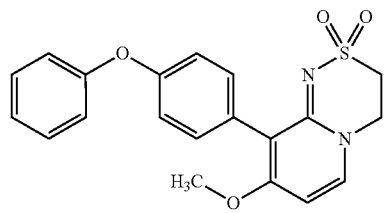 [SMILES: COC1=C(c2ccc(Oc3ccccc3)cc2)C2=NS(=O)(=O)CCN2C=C1] | 383.1 |
| 205 | 8-chloro-9-(4-phenoxyphenyl)-3,4-dihydropyrido[2,1-c][1,2,4]thiadiazine 2,2-dioxide | 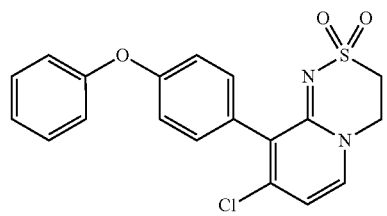 [SMILES: O=S1(=O)CCN2C=CC(Cl)=C(c3ccc(Oc4ccccc4)cc3)C2=N1] | 387.1 |
| 206 | 7-fluoro-9-(4-phenoxyphenyl)-3,4-dihydropyrido[2,1-c][1,2,4]thiadiazine 2,2-dioxide | 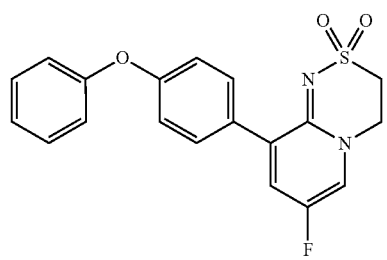 [SMILES: O=S1(=O)CCN2C=C(F)C=C(c3ccc(Oc4ccccc4)cc3)C2=N1] | 371.1 |

TABLE 20-continued

| | | | |
|---|---|---|---|
| 207 | 7-methyl-9-(4-phenoxyphenyl)-3,4-dihydropyrazino[2,1-c][1,2,4]thiadiazine 2,2-dioxide | 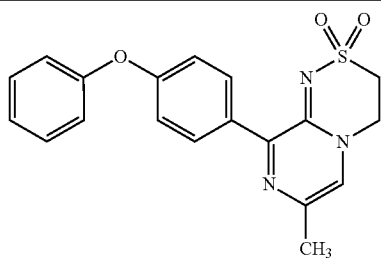 | 368.1 |
| 208 | 9-[3-chloro-4-(1-methylethoxy)phenyl]-3,4-dihydropyrido[2,1-c][1,2,4]thiadiazine 2,2-dioxide | 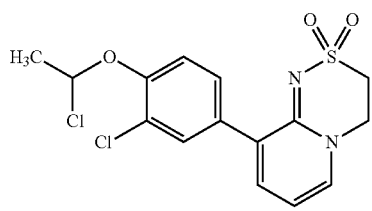 [SMILES: CC(Cl)Oc1ccc(C2=CC=CN3CCS(=O)(=O)N=C23)cc1Cl] | 353.2 |
| 209 | 9-(4-butoxyphenyl)-3,4-dihydropyrido[2,1-c][1,2,4]thiadiazine 2,2-dioxide | 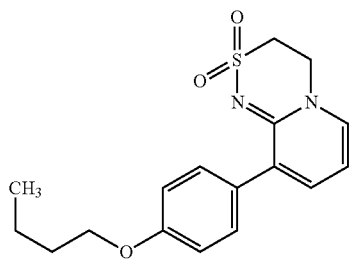 [SMILES: CCCCOc1ccc(C2=CC=CN3CCS(=O)(=O)N=C23)cc1] | 333.1 |
| 210 | 9-(4-phenoxyphenyl)-3,4-dihydropyrazino[2,1-c][1,2,4]thiadiazine 2,2-dioxide | 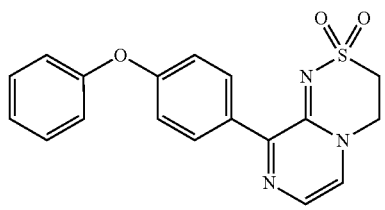 | 354.1 |
| 211 | 9-(4-phenoxyphenyl)-3,4,6,7,8,9-hexahydropyrazino[2,1-c][1,2,4]thiadiazine 2,2-dioxide | 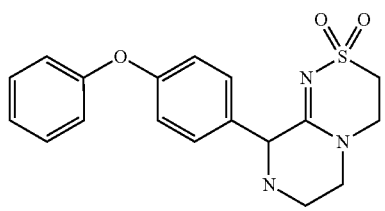 | 358.1 |
| 212 | (9S)-9-(4-phenoxyphenyl)-3,4,6,7,8,9-hexahydropyrazino[2,1-c][1,2,4]thiadiazine 2,2-dioxide | 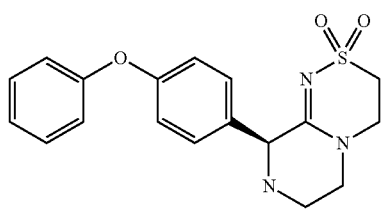 [SMILES: O=S1(=O)CCN2CCN[C@@H](c3ccc(Oc4ccccc4)cc3)C2=N1] | 358.1 |
| 213 | (9R)-9-(4-phenoxyphenyl)-3,4,6,7,8,9-hexahydropyrazino[2,1-c][1,2,4]thiadiazine 2,2-dioxide | 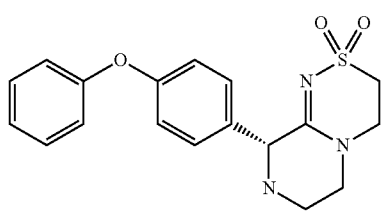 | 358.1 |

TABLE 20-continued

| | | | |
|---|---|---|---|
| 214 | 4-[(9S)-2,2-dioxido-3,4,6,7,8,9-hexahydropyrido[2,1-c][1,2,4]thiadiazin-9-yl]phenyl trifluoromethanesulfonate | 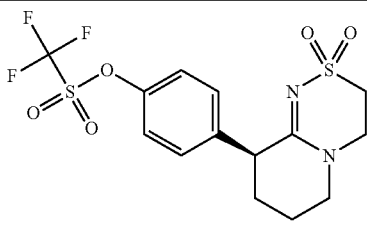 | 413.1 |

TABLE 21

| | | | |
|---|---|---|---|
| 215 | (9S)-9-[4-(4-chloro-2-methylphenoxy)phenyl]-3,4,6,7,8,9-hexahydropyrido[2,1-c][1,2,4]thiadiazine 2,2-dioxide | 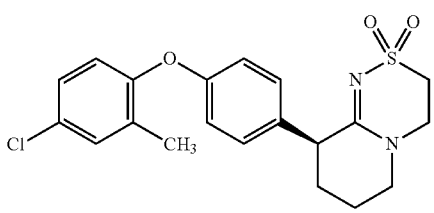 [SMILES: Cc1cc(Cl)ccc1Oc1ccc([C@@H]2CCCN3CCS(=O)(=O)N=C23)cc1] | 405.1 |
| 216 | (9S)-9-[4-(3,4-dimethylphenoxy)phenyl]-3,4,6,7,8,9-hexahydropyrido[2,1-c][1,2,4]thiadiazine 2,2-dioxide | 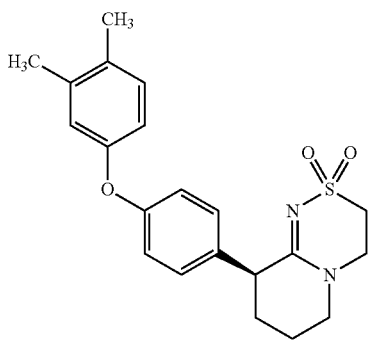 [SMILES: Cc1ccc(Oc2ccc([C@@H]3CCCN4CCS(=O)(=O)N=C34)cc2)cc1C] | 385.1 |
| 217 | (9R)-9-[4-(4-ethylphenoxy)phenyl]-3,4,6,7,8,9-hexahydropyrido[2,1-c][1,2,4]thiadiazine 2,2-dioxide | 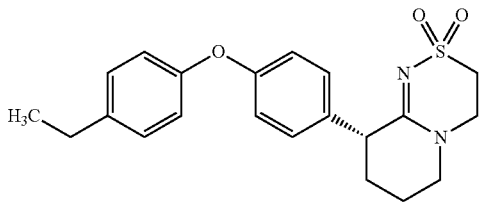 [SMILES: CCc1ccc(Oc2ccc([C@H]3CCCN4CCS(=O)(=O)N=C34)cc2)cc1] | 385.2 |
| 218 | (9S)-9-[4-(4-ethylphenoxy)phenyl]-3,4,6,7,8,9-hexahydropyrido[2,1-c][1,2,4]thiadiazine 2,2-dioxide | 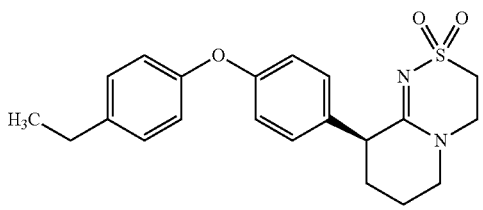 [SMILES: CCc1ccc(Oc2ccc([C@@H]3CCCN4CCS(=O)(=O)N=C34)cc2)cc1] | 385.1 |
| 219 | (9S)-9-[4-(3-methoxyphenoxy)phenyl]-3,4,6,7,8,9-hexahydropyrido[2,1-c][1,2,4]thiadiazine 2,2-dioxide | 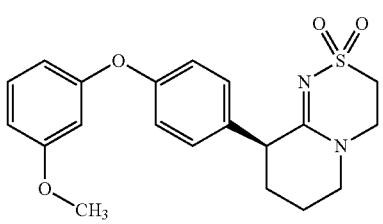 [SMILES: COc1cccc(Oc2ccc([C@@H]3CCCN4CCS(=O)(=O)N=C34)cc2)c1] | 387.1 |

| | | | |
|---|---|---|---|
| 220 | (9S)-9-(2'-chlorobiphenyl-4-yl)-3,4,6,7,8,9-hexahydropyrido[2,1-c][1,2,4]thiadiazine 2,2-dioxide | 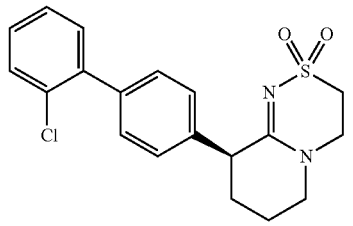 [SMILES: O=S1(=O)CCN2CCC[C@@H](c3ccc(-c4ccccc4Cl)cc3)C2=N1] | 375.1 |
| 221 | 9-(2'-chlorobiphenyl-4-yl)-3,4,6,7,8,9-hexahydropyrido[2,1-c][1,2,4]thiadiazine 2,2-dioxide | 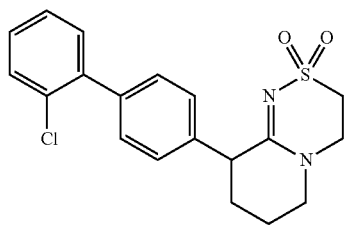 [SMILES: O=S1(=O)CCN2CCCC(c3ccc(-c4ccccc4Cl)cc3)C2=N1] | 375.1 |
| 222 | 9-{4-[(E)-2-phenylethenyl]phenyl}-3,4-dihydropyrido[2,1-c][1,2,4]thiadiazine 2,2-dioxide | 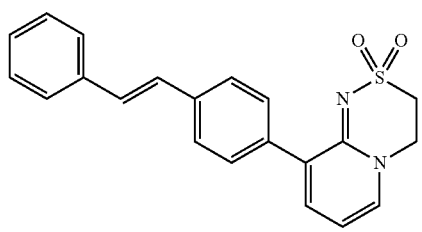 [SMILES: O=S1(=O)CCN2C=CC=C(c3ccc(/C=C/c4ccccc4)cc3)C2=N1] | 363.1 |
| 223 | (9S)-9-(4'-chlorobiphenyl-4-yl)-3,4,6,7,8,9-hexahydropyrido[2,1-c][1,2,4]thiadiazine 2,2-dioxide | 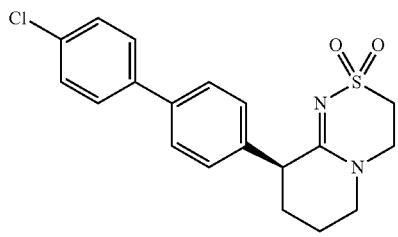 [SMILES: O=S1(=O)CCN2CCC[C@@H](c3ccc(-c4ccc(Cl)cc4)cc3)C2=N1] | 375.1 |
| 224 | 9-(4'-chlorobiphenyl-4-yl)-3,4,6,7,8,9-hexahydropyrido[2,1-c][1,2,4]thiadiazine 2,2-dioxide | 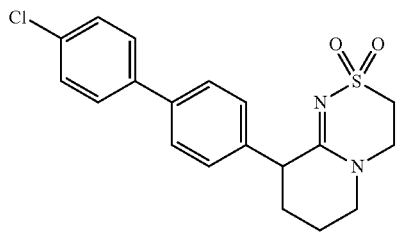 [SMILES: O=S1(=O)CCN2CCCC(c3ccc(-c4ccc(Cl)cc4)cc3)C2=N1] | 375.1 |
| 225 | (9S)-9-(4'-chloro-3'-fluorobiphenyl-4-yl)-3,4,6,7,8,9-hexahydropyrido[2,1-c][1,2,4]thiadiazine 2,2-dioxide | 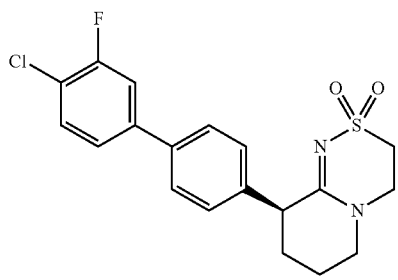 [SMILES: O=S1(=O)CCN2CCC[C@@H](c3ccc(-c4ccc(Cl)c(F)c4)cc3)C2=N1] | 393.1 |

TABLE 21-continued
| | | | |
|---|---|---|---|
| 226 | (9S)-9-(3'-chloro-4'-fluorobiphenyl-4-yl)-3,4,6,7,8,9-hexahydropyrido[2,1-c][1,2,4]thiadiazine 2,2-dioxide | 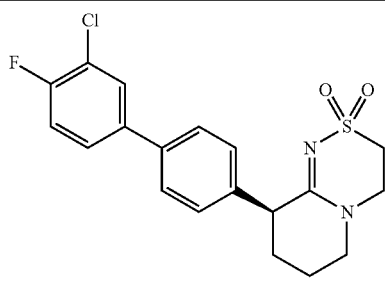 | 393.1 |
TABLE 22
| | | | |
|---|---|---|---|
| 227 | (9S)-9-[4-(3,4,5-trifluorophenoxy)phenyl]-3,4,6,7,8,9-hexahydropyrido[2,1-c][1,2,4]thiadiazine 2,2-dioxide | 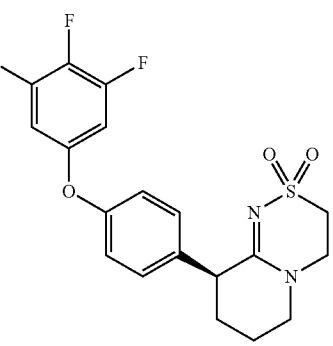 | 411.1 |
| 228 | (9S)-9-[4-(4-bromophenoxy)phenyl]-3,4,6,7,8,9-hexahydropyrido[2,1-c][1,2,4]thiadiazine 2,2-dioxide | 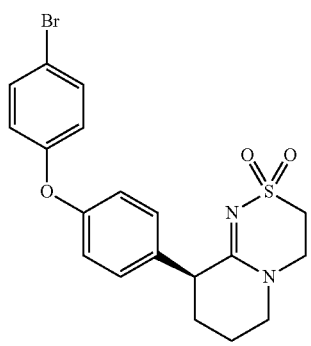 [SMILES: O=S1(=O)CCN2CCC[C@@H](c3ccc(Oc4ccc(Br)cc4)cc3)C2=N1] | 435.0<br>437.0 |
| 229 | 9-[4-(difluoromethoxy)phenyl]-3,4,6,7,8,9-hexahydropyrido[2,1-c][1,2,4]thiadiazine 2,2-dioxide | 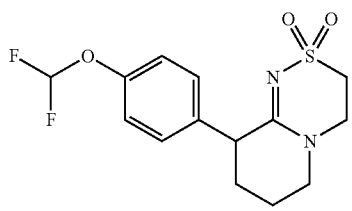 [SMILES: O=S1(=O)CCN2CCCC(c3ccc(OC(F)F)cc3)C2=N1] | 331.0 |
| 230 | 9-[4-(1,1-difluoroethyl)phenyl]-3,4,6,7,8,9-hexahydropyrido[2,1-c][1,2,4]thiadiazine 2,2-dioxide | 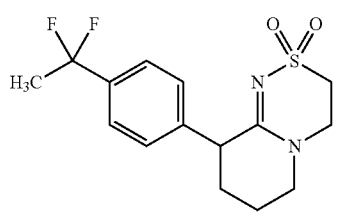 [SMILES: CC(F)(F)c1ccc(C2CCCN3CCS(=O)(=O)N=C23)cc1] | 329.1 |

| # | Name | Structure | Mass |
|---|---|---|---|
| 231 | 9-[4-(1,1-difluoroethyl)phenyl]-3,4,6,7,8,9-hexahydropyrido[2,1-c][1,2,4]thiadiazine 2,2-dioxide | 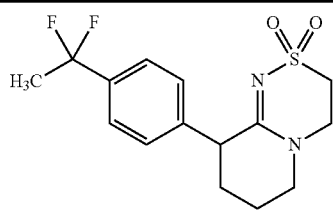 | 329.1 |
| 232 | 9-{4-[4-(trifluoromethyl)phenoxy]phenyl}-3,4,6,7,8,9-hexahydropyrido[2,1-c][1,2,4]thiadiazine 2,2-dioxide | 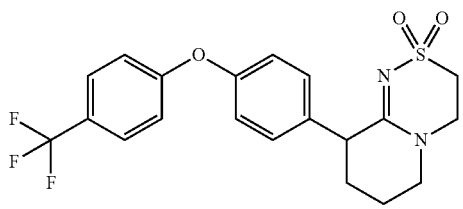 [SMILES: O=S1(=O)CCN2CCCC(c3ccc(Oc4ccc(C(F)(F)F)cc4)cc3)C2=N1] | 425.1 |
| 233 | 9-{4-[4-(trifluoromethyl)phenoxy]phenyl}-3,4,6,7,8,9-hexahydropyrido[2,1-c][1,2,4]thiadiazine 2,2-dioxide | 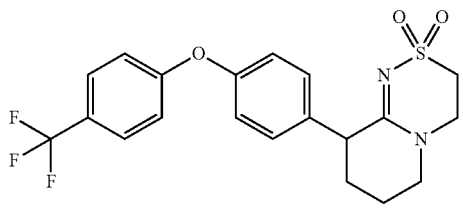 [SMILES: O=S1(=O)CCN2CCCC(c3ccc(Oc4ccc(C(F)(F)F)cc4)cc3)C2=N1] | 425.1 |
| 234 | 9-{4-[4-(1,1-difluoroethyl)phenoxy]phenyl}-3,4,6,7,8,9-hexahydropyrido[2,1-c][1,2,4]thiadiazine 2,2-dioxide | 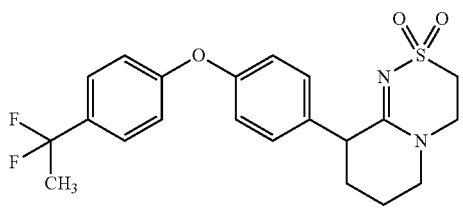 [SMILES: CC(F)(F)c1ccc(Oc2ccc(C3CCCN4CCS(=O)(=O)N=C34)cc2)cc1] | 421.1 |
| 235 | 9-{4-[4-(1,1-difluoroethyl)phenoxy]phenyl}-3,4,6,7,8,9-hexahydropyrido[2,1-c][1,2,4]thiadiazine 2,2-dioxide | 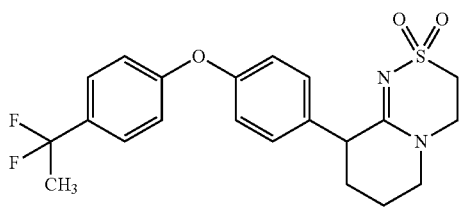 [SMILES: CC(F)(F)c1ccc(Oc2ccc(C3CCCN4CCS(=O)(=O)N=C34)cc2)cc1] | 421.1 |
| 236 | (9S)-9-[4-(3-fluoro-5-methylphenoxy)phenyl]-3,4,6,7,8,9-hexahydropyrido[2,1-c][1,2,4]thiadiazine 2,2-dioxide | 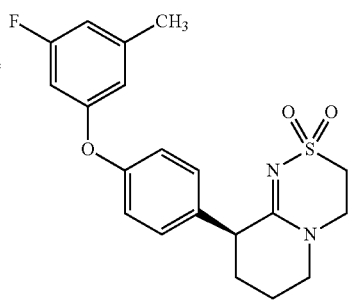 | 389.1 |
| 237 | 9-(5,6,7,8-tetrahydronaphthalen-2-yloxy)-3,4-dihydropyrido[2,1-c][1,2,4]thiadiazine 2,2-dioxide | 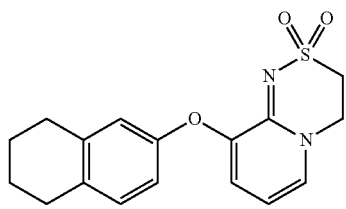 [SMILES: O=S1(=O)CCN2C=CC=C(Oc3ccc4c(c3)CCCC4)C2=N1] | 331.1 |

TABLE 22-continued

| | | | |
|---|---|---|---|
| 238 | 9-(5,6,7,8-tetrahydronaphthalen-2-yloxy)-3,4,6,7,8,9-hexahydropyrido[2,1-c][1,2,4]thiadiazine 2,2-dioxide | 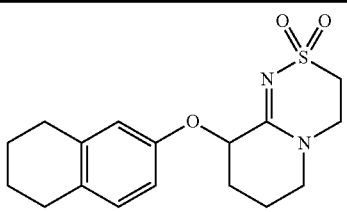 | 335.1 |

TABLE 23

| | | | |
|---|---|---|---|
| 239 | 9-[4-(1H-pyrazol-1-yl)phenyl]-3,4-dihydropyrido[2,1-c][1,2,4]thiadiazine 2,2-dioxide | 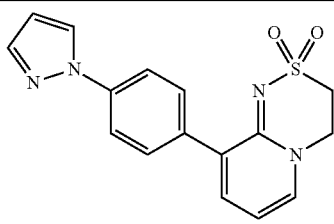 | 327.1 |
| 240 | 9-[(2,2,3,3-tetrafluoro-2,3-dihydro-1,4-benzodioxin-6-yl)oxy]-3,4-dihydropyrido[2,1-c][1,2,4]thiadiazine 2,2-dioxide | 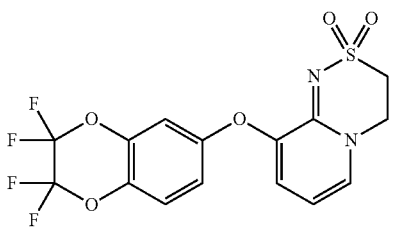 [SMILES: O=S1(=O)CCN2C=CC=C(Oc3ccc4c(c3)OC(F)(F)C(F)(F)O4)C2=N1] | 407.0 |
| 241 | 9-{[7-(2,2,2-trifluoroethoxy)naphthalen-2-yl]oxy}-3,4-dihydropyrido[2,1-c][1,2,4]thiadiazine 2,2-dioxide | 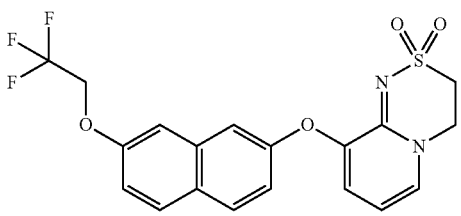 [SMILES: O=S1(=O)CCN2C=CC=C(Oc3ccc4ccc(OCC(F)(F)F)cc4c3)C2=N1] | 425.1 |
| 242 | 9-[4-(1-methylpropoxy)phenyl]-3,4-dihydropyrido[2,1-c][1,2,4]thiadiazine 2,2-dioxide | 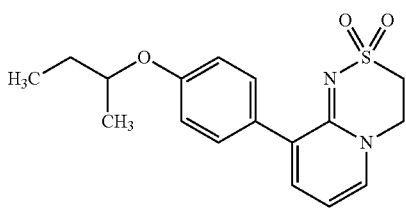 [SMILES: CCC(C)Oc1ccc(C2=CC=CN3CCS(=O)(=O)N=C23)cc1] | 333.1 |
| 243 | 9-[4-(1,4-dioxaspiro[4.5]dec-8-yloxy)phenyl]-3,4-dihydropyrido[2,1-c][1,2,4]thiadiazine 2,2-dioxide | 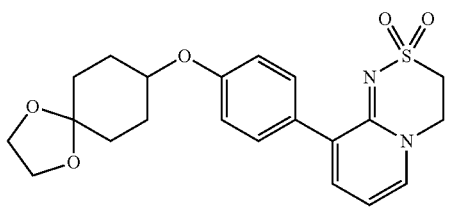 [SMILES: O=S1(=O)CCN2C=CC=C(c3ccc(OC4CCC5(CC4)OCCO5)cc3)C2=N1] | 417.1 |
| 244 | 4-[4-(2,2-dioxido-3,4-dihydropyrido[2,1-c][1,2,4]thiadiazin-9-yl)phenoxy]cyclohexanone | 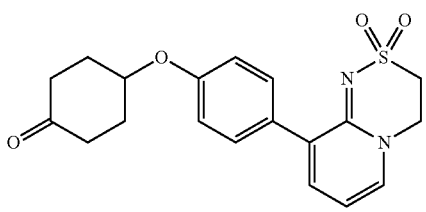 [SMILES: O=C1CCC(Oc2ccc(C3=CC=CN4CCS(=O)(=O)N=C34)cc2)CC1] | 373.1 |

TABLE 23-continued

| | | | |
|---|---|---|---|
| 245 | 9-(4-{[tert-butyl(dimethyl)silyl]oxy}phenyl)-7-chloro-3,4-dihydropyrido[2,1-c][1,2,4]thiadiazine 2,2-dioxide | 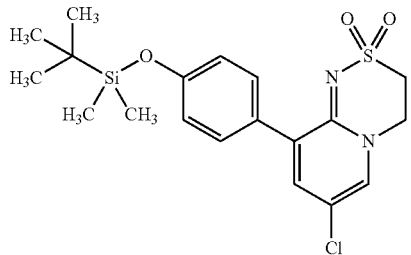 [SMILES: CC(C)(C)[Si](C)(C)Oc1ccc(C2=CC(Cl)=CN3CCS(=O)(=O)N=C23)cc1] | 425.1 |
| 246 | 9-{4-[(6-methylpyridin-2-yl)oxy]phenyl}-3,4-dihydropyrido[2,1-c][1,2,4]thiadiazine 2,2-dioxide | 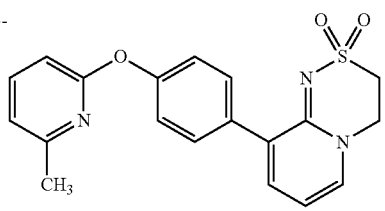 | 368.1 |
| 247 | 9-{4-[(5-chloropyridin-2-yl)oxy]phenyl}-3,4-dihydropyrido[2,1-c][1,2,4]thiadiazine 2,2-dioxide | 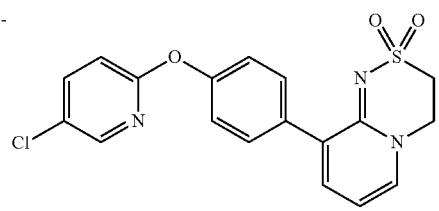 | 388.0 |
| 248 | 9-(4-{[4-(trifluoromethyl)pyridin-2-yl]oxy}phenyl)-3,4-dihydropyrido[2,1-c][1,2,4]thiadiazine 2,2-dioxide | 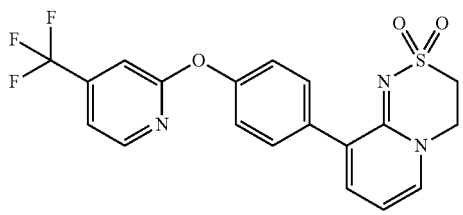 [SMILES: O=S1(=O)CCN2C=CC=C(c3ccc(Oc4cc(C(F)(F)F)ccn4)cc3)C2=N1] | 422.1 |
| 249 | 7-chloro-9-{4-[(6-methylpyridin-2-yl)oxy]phenyl}-3,4-dihydropyrido[2,1-c][1,2,4]thiadiazine 2,2-dioxide | 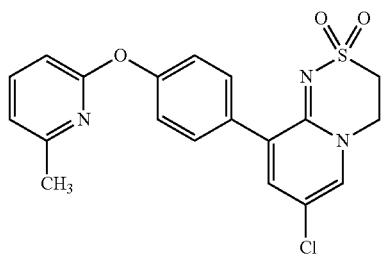 [SMILES: Cc1cccc(Oc2ccc(C3=CC(Cl)=CN4CCS(=O)(=O)N=C34)cc2)n1] | 402.0 |
| 250 | 9-(4-{[3-(trifluoromethyl)pyridin-2-yl]oxy}phenyl)-3,4-dihydropyrido[2,1-c][1,2,4]thiadiazine 2,2-dioxide | 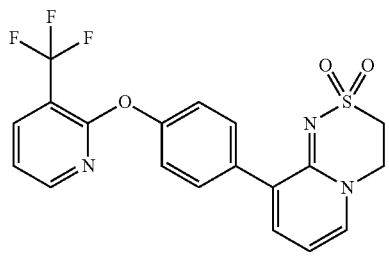 [SMILES: O=S1(=O)CCN2C=CC=C(c3ccc(Oc4ncccc4C(F)(F)F)cc3)C2=N1] | 422.1 |

TABLE 24

| | | | |
|---|---|---|---|
| 251 | 7-chloro-9-[4-(tetrahydrofuran-2-ylmethoxy)phenyl]-3,4-dihydropyrido[2,1-c][1,2,4]thiadiazine 2,2-dioxide | 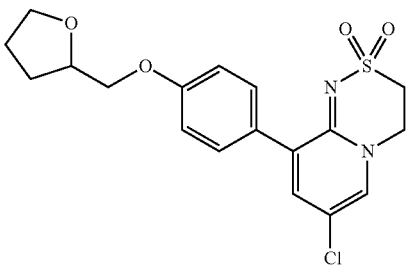 [SMILES: O=S1(=O)CCN2C=C(Cl)C=C(c3ccc(OCC4CCCO4)cc3)C2=N1] | 395.1 |
| 252 | 7-chloro-9-[4-(tetrahydro-2H-pyran-4-yloxy)phenyl]-3,4-dihydropyrido[2,1-c][1,2,4]thiadiazine 2,2-dioxide | 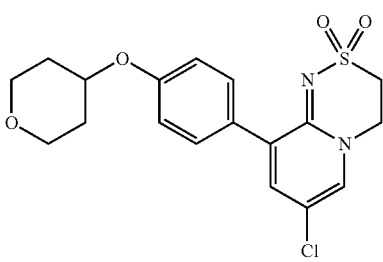 [SMILES: O=S1(=O)CCN2C=C(Cl)C=C(c3ccc(OC4CCOCC4)cc3)C2=N1] | 395.1 |
| 253 | 7-chloro-9-[4-(tetrahydro-2H-pyran-4-ylmethoxy)phenyl]-3,4-dihydropyrido[2,1-c][1,2,4]thiadiazine 2,2-dioxide | 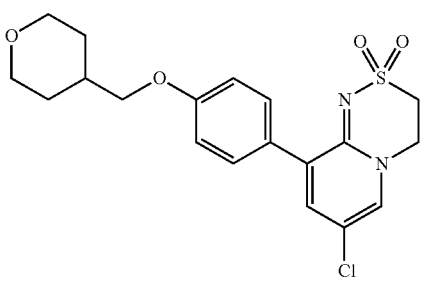 [SMILES: O=S1(=O)CCN2C=C(Cl)C=C(c3ccc(OCC4CCOCC4)cc3)C2=N1] | 409.2 |
| 254 | 9-(4-{[6-(trifluoromethyl)pyridin-3-yl]oxy}phenyl)-3,4-dihydropyrido[2,1-c][1,2,4]thiadiazine 2,2-dioxide | 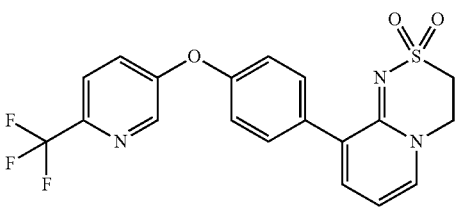 [SMILES: O=S1(=O)CCN2C=CC=C(c3ccc(Oc4ccc(C(F)(F)F)nc4)cc3)C2=N1] | 422.1 |
| 255 | 9-(4-{[4-(trifluoromethyl)pyridin-3-yl]oxy}phenyl)-3,4-dihydropyrido[2,1-c][1,2,4]thiadiazine 2,2-dioxide | 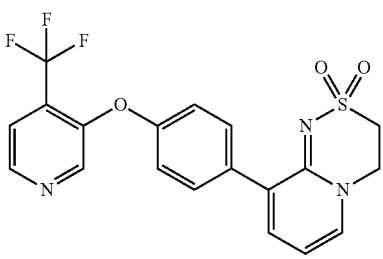 [SMILES: O=S1(=O)CCN2C=CC=C(c3ccc(Oc4cnccc4C(F)(F)F)cc3)C2=N1] | 422.0 |
| 256 | 7-chloro-9-(4-{[6-(trifluoromethyl)pyridin-3-yl]oxy}phenyl)-3,4-dihydropyrido[2,1-c][1,2,4]thiadiazine 2,2-dioxide | 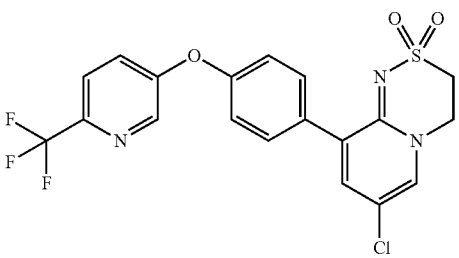 [SMILES: O=S1(=O)CCN2C=C(Cl)C=C(c3ccc(Oc4ccc(C(F)(F)F)nc4)cc3)C2=N1] | 456.0 |

TABLE 24-continued

| # | Name | Structure | Mass |
|---|------|-----------|------|
| 257 | 9-(4-{[2-(trifluoromethyl)pyridin-4-yl]oxy}phenyl)-3,4-dihydropyrido[2,1-c][1,2,4]thiadiazine 2,2-dioxide | 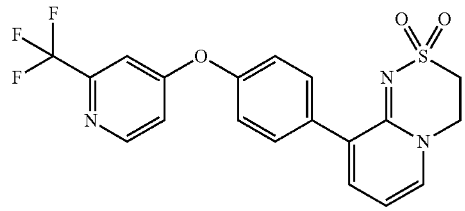 [SMILES: O=S1(=O)CCN2C=CC=C(c3ccc(Oc4ccnc(C(F)(F)F)c4)cc3)C2=N1] | 422.1 |
| 258 | 9-(5-phenoxypyridin-2-yl)-3,4-dihydropyrido[2,1-c][1,2,4]thiadiazine 2,2-dioxide | 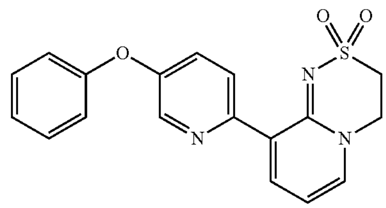 | 354.1 |
| 259 | 9-(4-{[5-(trifluoromethyl)pyridin-3-yl]oxy}phenyl)-3,4-dihydropyrido[2,1-c][1,2,4]thiadiazine 2,2-dioxide | 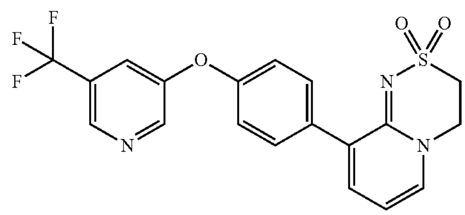 [SMILES: O=S1(=O)CCN2C=CC=C(c3ccc(Oc4cncc(C(F)(F)F)c4)cc3)C2=N1] | 422.1 |
| 260 | 7-chloro-9-(4-{[5-(trifluoromethyl)pyridin-3-yl]oxy}phenyl)-3,4-dihydropyrido[2,1-c][1,2,4]thiadiazine 2,2-dioxide | 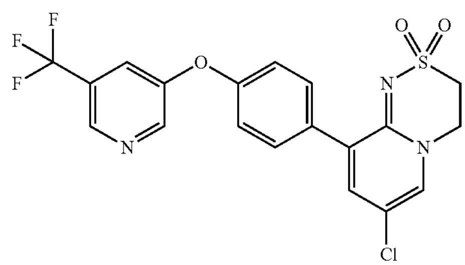 [SMILES: O=S1(=O)CCN2C=C(Cl)C=C(c3ccc(Oc4cncc(C(F)(F)F)c4)cc3)C2=N1] | 456.0 |
| 261 | 9-[4-(cyclohexyloxy)phenyl]-3,4,6,7,8,9-hexahydropyrido[2,1-c][1,2,4]thiadiazine 2,2-dioxide | 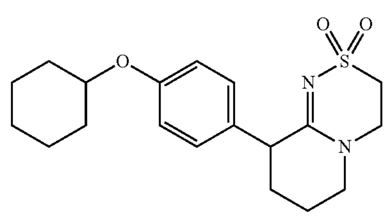 [SMILES: O=S1(=O)CCN2CCCC(c3ccc(OC4CCCCC4)cc3)C2=N1] | 363.2 |
| 262 | 9-{4-[3-(trifluoromethyl)-phenoxy]phenyl}-3,4,6,7,8,9-hexahydropyrido[2,1-c][1,2,4]thiadiazine 2,2-dioxide | 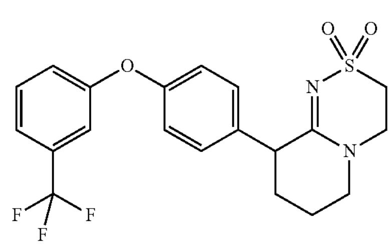 [SMILES: O=S1(=O)CCN2CCCC(c3ccc(Oc4cccc(C(F)(F)F)c4)cc3)C2=N1] | 425.1 |

TABLE 25

| | | | |
|---|---|---|---|
| 263 | 9-[4-(pyridin-2-yloxy)phenyl]-3,4-dihydropyrido[2,1-c][1,2,4]thiadiazine 2,2-dioxide | 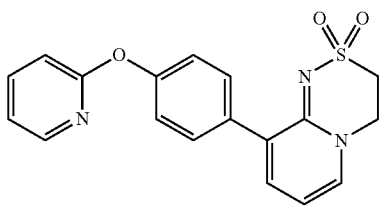 [SMILES: O=S1(=O)CCN2C=CC=C(c3ccc(Oc4ccccn4)cc3)C2=N1] | 354.1 |
| 264 | 9-[4-(2,2,2-trifluoroethoxy)phenyl]-3,4-dihydropyrido[2,1-c][1,2,4]thiadiazine 2,2-dioxide | 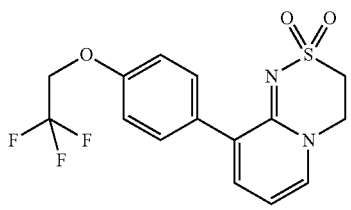 [SMILES: O=S1(=O)CCN2C=CC=C(c3ccc(OCC(F)(F)F)cc3)C2=N1] | 359.1 |
| 265 | 9-[4-(2,2,2-trifluoroethoxy)phenyl]-3,4,6,7,8,9-hexahydropyrido[2,1-c][1,2,4]thiadiazine 2,2-dioxide | 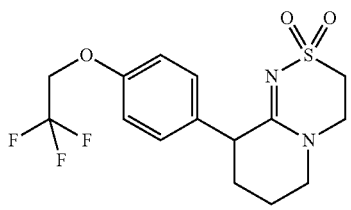 [SMILES: O=S1(=O)CCN2CCCC(c3ccc(OCC(F)(F)F)cc3)C2=N1] | 363.1 |
| 266 | 9-{4-[2-(trifluoromethyl)phenoxy]phenyl}-3,4-dihydropyrido[2,1-c][1,2,4]thiadiazine 2,2-dioxide | 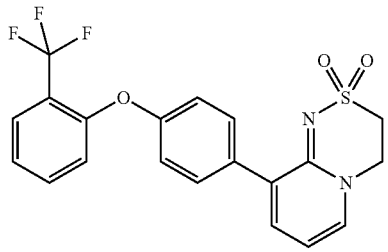 [SMILES: O=S1(=O)CCN2C=CC=C(c3ccc(Oc4ccccc4C(F)(F)F)cc3)C2=N1] | 421.1 |
| 267 | 9-[4-(benzyloxy)phenyl]-3,4-dihydropyrido[2,1-c][1,2,4]thiadiazine 2,2-dioxide | 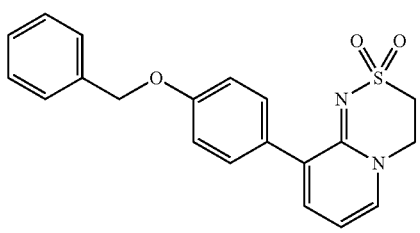 [SMILES: O=S1(=O)CCN2C=CC=C(c3ccc(OCc4ccccc4)cc3)C2=N1] | 367.1 |
| 268 | 9-[4-(cyclohexylmethoxy)phenyl]-3,4-dihydropyrido[2,1-c][1,2,4]thiadiazine 2,2-dioxide | 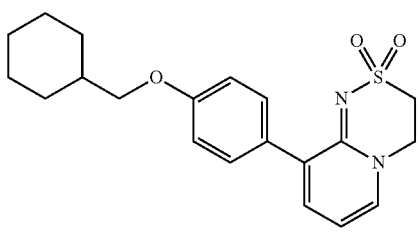 [SMILES: O=S1(=O)CCN2C=CC=C(c3ccc(OCC4CCCCC4)cc3)C2=N1] | 373.1 |
| 269 | 9-[4-(cyclopropylmethoxy)phenyl]-3,4-dihydropyrido[2,1-c][1,2,4]thiadiazine 2,2-dioxide | 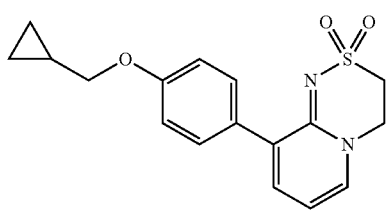 [SMILES: O=S1(=O)CCN2C=CC=C(c3ccc(OCC4CC4)cc3)C2=N1] | 331.1 |

TABLE 25-continued

| | | | |
|---|---|---|---|
| 270 | 9-[4-(2-methoxyphenoxy)phenyl]-3,4-dihydropyrido[2,1-c][1,2,4]thiadiazine 2,2-dioxide | 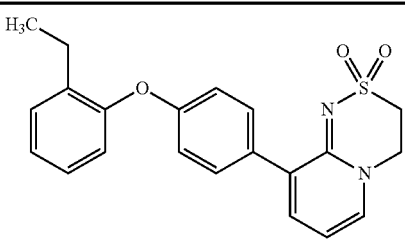 | 383.1 |
| 271 | 9-[4-(cyclohex-2-en-1-yloxy)phenyl]-3,4-dihydropyrido[2,1-c][1,2,4]thiadiazine 2,2-dioxide | 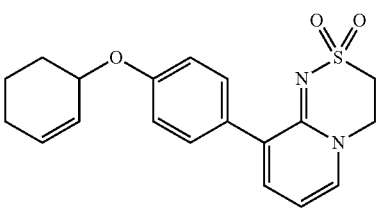 [SMILES: O=S1(=O)CCN2C=CC=C(c3ccc(OC4C=CCCC4)cc3)C2=N1] | 357.1 |
| 272 | 9-[(4-cyclopentylphenoxy)methyl]-3,4-dihydropyrido[2,1-c][1,2,4]thiadiazine 2,2-dioxide | 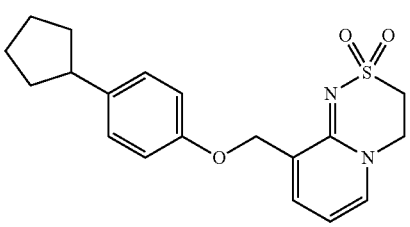 [SMILES: O=S1(=O)CCN2C=CC=C(COc3ccc(C4CCCC4)cc3)C2=N1] | 359.0 |
| 273 | 9-[(5,6,7,8-tetrahydronaphthalen-2-yloxy)methyl]-3,4-dihydropyrido[2,1-c][1,2,4]thiadiazine 2,2-dioxide | 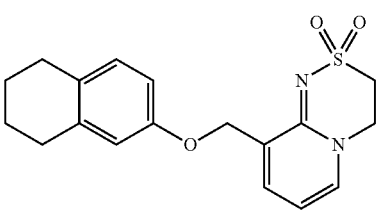 [SMILES: O=S1(=O)CCN2C=CC=C(COc3ccc4c(c3)CCCC4)C2=N1] | 345.0 |
| 274 | 2-[4-(2,2-dioxido-3,4-dihydropyrido[2,1-c][1,2,4]thiadiazin-9-yl)phenoxy]cyclohexanone | 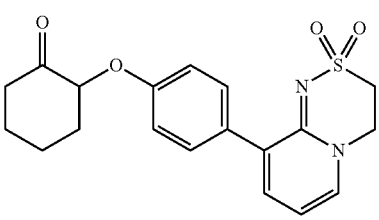 [SMILES: O=C1CCCCC1Oc1ccc(C2=CC=CN3CCS(=O)(=O)N=C23)cc1] | 373.2 |

TABLE 26

| | | | |
|---|---|---|---|
| 275 | 9-[6-(cyclohexyloxy)pyridin-3-yl]-3,4-dihydropyrido[2,1-c][1,2,4]thiadiazine 2,2-dioxide | 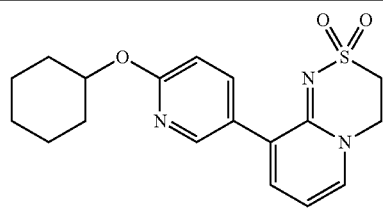 | 360.2 |
| 276 | 9-[(3-chlorobenzyl)oxy]-3,4-dihydropyrido[2,1-c][1,2,4]thiadiazine 2,2-dioxide | 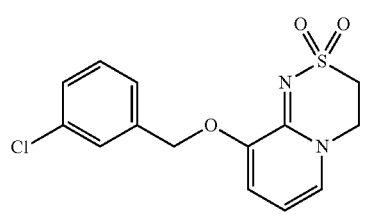 [SMILES: O=S1(=O)CCN2C=CC=C(OCc3cccc(Cl)c3)C2=N1] | 325.1 |

TABLE 26-continued

| | | | |
|---|---|---|---|
| 277 | 9-{[3,5-bis(trifluoromethyl)benzyl]oxy}-3,4,6,7,8,9-hexahydropyrido[2,1-c][1,2,4]thiadiazine 2,2-dioxide | 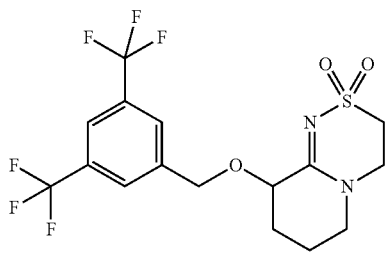 [SMILES: O=S1(=O)CCN2CCCC(OCc3cc(C(F)(F)F)cc(C(F)(F)F)c3)C2=N1] | 431.2 |
| 278 | 7-methyl-9-(3-phenoxyazetidin-1-yl)-3,4-dihydropyrazino[2,1-c][1,2,4]thiadiazine 2,2-dioxide | 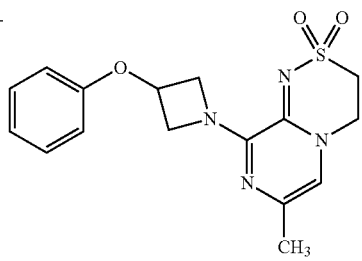 | 347.2 |
| 279 | 9-(4-phenylpiperidin-1-yl)-3,4-dihydropyrazino[2,1-c][1,2,4]thiadiazine 2,2-dioxide | 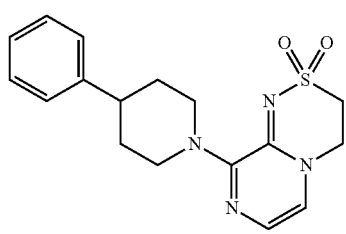 [SMILES: O=S1(=O)CCN2C=CN=C(N3CCC(c4ccccc4)CC3)C2=N1] | 345.2 |
| 280 | 9-(4-phenoxyphenyl)-7-(trifluoromethyl)-3,4-dihydropyrido[2,1-c][1,2,4]thiadiazine 2,2-dioxide | 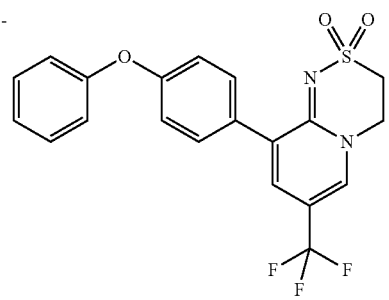 | 421.1 |
| 281 | 9-(1-methyl-1H-indol-5-yl)-3,4,6,7,8,9-hexahydropyrido[2,1-c][1,2,4]thiadiazine 2,2-dioxide | 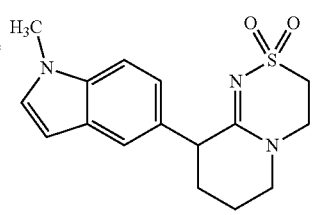 [SMILES: Cn1ccc2cc(C3CCCN4CCS(=O)(=O)N=C34)ccc21] | 318.2 |
| 282 | 9-(6-phenylpyridin-3-yl)-3,4-dihydropyrido[2,1-c][1,2,4]thiadiazine 2,2-dioxide | 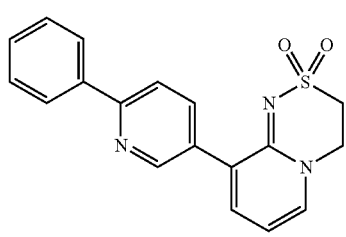 [SMILES: O=S1(=O)CCN2C=CC=C(c3ccc(-c4ccccc4)nc3)C2=N1] | 338.1 |

TABLE 26-continued

| # | Name | Structure | Mass |
|---|---|---|---|
| 283 | 9-(4-{[4-(trifluoromethyl)pyridin-2-yl]oxy}phenyl)-3,4,6,7,8,9-hexahydropyrido[2,1-c][1,2,4]thiadiazine 2,2-dioxide | 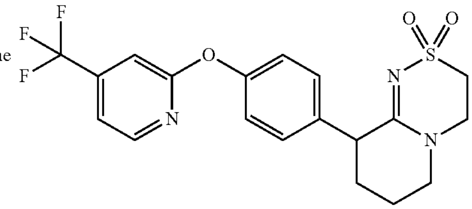 | 426.2 |
| 285 | 9-(1-ethyl-1H-indol-5-yl)-3,4,6,7,8,9-hexahydropyrido[2,1-c][1,2,4]thiadiazine 2,2-dioxide | 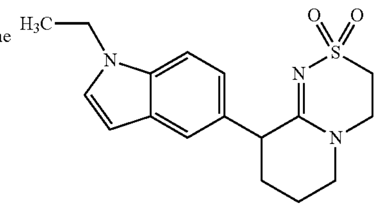 | 332.2 |
| 286 | 7-(2,2-dioxido-3,4-dihydropyrido[2,1-c][1,2,4]thiadiazin-9-yl)-2,2-dimethyl-3,4-dihydronaphthalen-1(2H)-one | 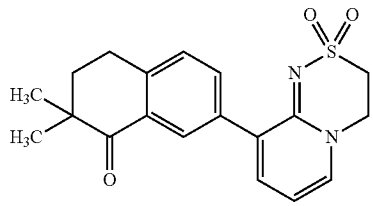 [SMILES: CC1(C)CCc2ccc(C3=CC=CN4CCS(=O)(=O)N=C34)cc2C1=O] | 357.2 |
| 287 | 5-(2,2-dioxido-3,4-dihydropyrido[2,1-c][1,2,4]thiadiazin-9-yl)-2,2-dimethyl-2,3-dihydro-1H-inden-1-one | 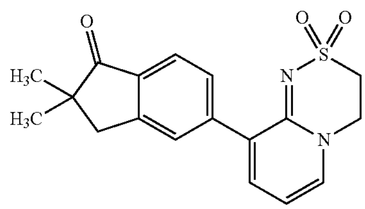 [SMILES: CC1(C)Cc2cc(C3=CC=CN4CCS(=O)(=O)N=C34)ccc2C1=O] | 343.1 |

TABLE 27

| # | Name | Structure | Mass |
|---|---|---|---|
| 288 | 7-(2,2-dioxido-3,4,6,7,8,9-hexahydropyrido[2,1-c][1,2,4]thiadiazin-9-yl)-2,2-dimethyl-3,4-dihydronaphthalen-1(2H)-one | 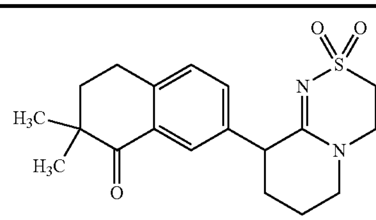 | 361.2 |
| 289 | 5-(2,2-dioxido-3,4,6,7,8,9-hexahydropyrido[2,1-c][1,2,4]thiadiazin-9-yl)-2,2-dimethyl-2,3-dihydro-1H-inden-1-one | 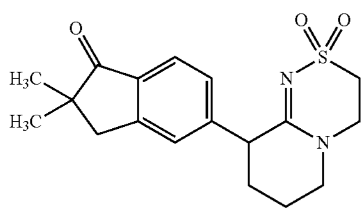 [SMILES: CC1(C)Cc2cc(C3CCCN4CCS(=O)(=O)N=C34)ccc2C1=O] | 347.2 |
| 290 | 9-[4-(1H-pyrazol-1-yl)phenyl]-3,4,6,7,8,9-hexahydropyrido[2,1-c][1,2,4]thiadiazine 2,2-dioxide | 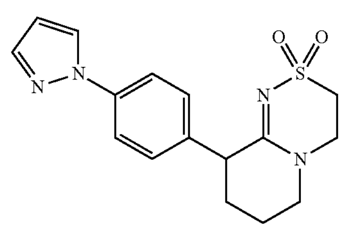 [SMILES: O=S1(=O)CCN2CCCC(c3ccc(-n4cccn4)cc3)C2=N1] | 331.1 |

TABLE 27-continued

| | | | |
|---|---|---|---|
| 291 | 1-[4-(2,2-dioxido-3,4,6,7,8,9-hexahydropyrido[2,1-c][1,2,4]thiadiazin-9-yl)phenyl]ethanone | 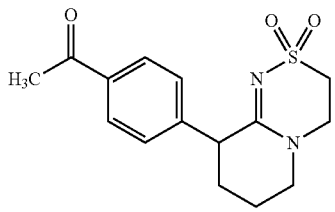 [SMILES: CC(=O)c1ccc(C2CCCN3CCS(=O)(=O)N=C23)cc1] | 307.1 |
| 292 | 9-(1-butyl-1H-indol-5-yl)-3,4-dihydropyrido[2,1-c][1,2,4]thiadiazine 2,2-dioxide | 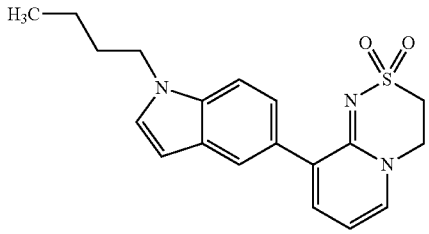 [SMILES: CCCCn1ccc2cc(C3=CC=CN4CCS(=O)(=O)N=C34)ccc21] | 356.2 |
| 293 | 9-[1-(2-methylpropyl)-1H-indol-5-yl]-3,4-dihydropyrido[2,1-c][1,2,4]thiadiazine 2,2-dioxide | 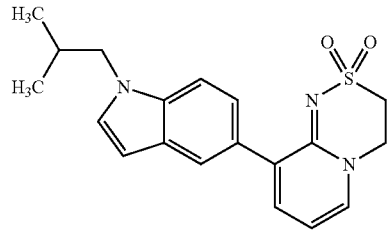 [SMILES: CC(C)Cn1ccc2cc(C3=CC=CN4CCS(=O)(=O)N=C34)ccc21] | 356.1 |
| 294 | 9-(1-butyl-1H-indol-5-yl)-3,4,6,7,8,9-hexahydropyrido[2,1-c][1,2,4]thiadiazine 2,2-dioxide | 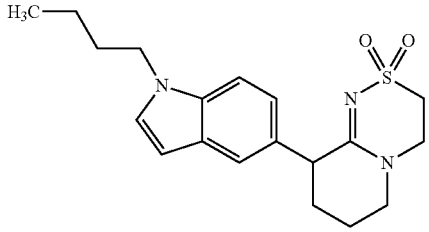 [SMILES: CCCCn1ccc2cc(C3CCCN4CCS(=O)(=O)N=C34)ccc21] | 360.1 |
| 295 | 9-{1-[2-(4-fluorophenyl)ethyl]-1H-indol-5-yl}-3,4,6,7,8,9-hexahydropyrido[2,1-c][1,2,4]thiadiazine 2,2-dioxide | 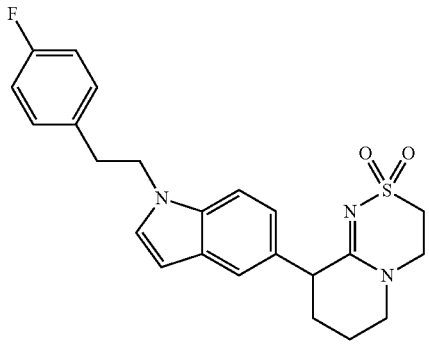 [SMILES: O=S1(=O)CCN2CCCC(c3ccc4c(ccn4CCc4ccc(F)cc4)c3)C2=N1] | 426.2 |
| 296 | 9-[1-(2-methylpropyl)-1H-indol-5-yl]-3,4,6,7,8,9-hexahydropyrido[2,1-c][1,2,4]thiadiazine 2,2-dioxide | 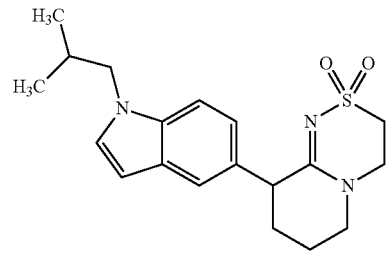 [SMILES: CC(C)Cn1ccc2cc(C3CCCN4CCS(=O)(=O)N=C34)ccc21] | 360.2 |

TABLE 27-continued

| | | | |
|---|---|---|---|
| 297 | 9-(3'-methoxybiphenyl-4-yl)-3,4-dihydropyrido[2,1-c][1,2,4]thiadiazine 2,2-dioxide | 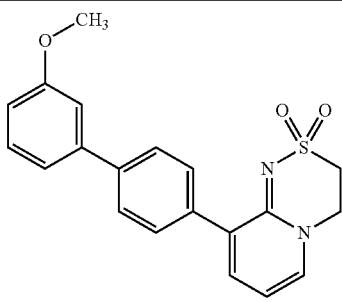 | 367.1 |
| 298 | [4-(2,2-dioxido-3,4-dihydropyrido[2,1-c][1,2,4]thiadiazin-9-yl)phenyl](phenyl)methanone | 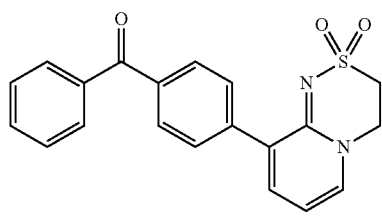 [SMILES: O=C(c1ccccc1)c1ccc(C2=CC=CN3CCS(=O)(=O)N=C23)cc1] | 365.1 |
| 299 | 9-{4-[5-cyclopropyl-3-(trifluoromethyl)-1H-pyrazol-1-yl]phenyl}-3,4-dihydropyrido[2,1-c][1,2,4]thiadiazine 2,2-dioxide | 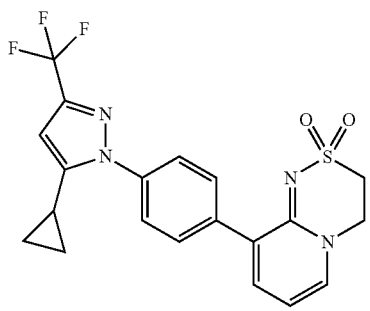 [SMILES: O=S1(=O)CCN2C=CC=C(c3ccc(-n4nc(C(F)(F)F)cc4C4CC4)cc3)C2=N1] | 435.1 |

TABLE 28

| | | | |
|---|---|---|---|
| 300 | 9-{4-[5-methyl-3-(trifluoromethyl)-1H-pyrazol-1-yl]phenyl}-3,4-dihydropyrido[2,1-c][1,2,4]thiadiazine 2,2-dioxide | 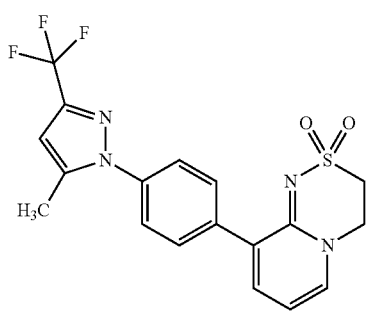 [SMILES: Cc1cc(C(F)(F)F)nn1-c1ccc(C2=CC=CN3CCS(=O)(=O)N=C23)cc1] | 409.1 |
| 301 | 9-{4-[5-cyclopropyl-3-(trifluoromethyl)-1H-pyrazol-1-yl]-phenyl}-3,4,6,7,8,9-hexahydropyrido-[2,1-c][1,2,4]thiadiazine 2,2-dioxide | 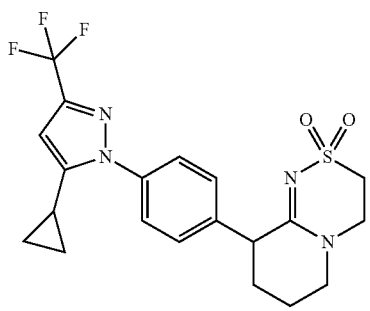 [SMILES: O=S1(=O)CCN2CCCC(c3ccc(-n4nc(C(F)(F)F)cc4C4CC4)cc3)C2=N1] | 439.1 |

| | | | |
|---|---|---|---|
| 302 | 9-{4-[5-methyl-3-(trifluoromethyl)-1H-pyrazol-1-yl]phenyl}-3,4,6,7,8,9-hexahydropyrido[2,1-c][1,2,4]thiadiazine 2,2-dioxide | 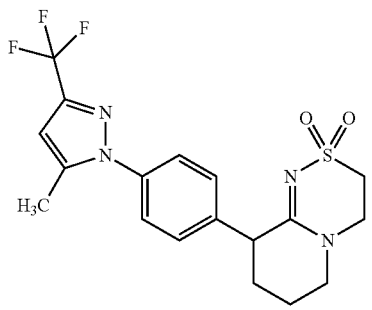 [SMILES: Cc1cc(C(F)(F)F)nn1-c1ccc(C2CCCN3CCS(=O)(=O)N=C23)cc1] | 413.1 |
| 303 | 9-[(5,6,7,8-tetrahydronaphthalen-2-yloxy)methyl]-3,4,6,7,8,9-hexahydropyrido[2,1-c][1,2,4]thiadiazine 2,2-dioxide | 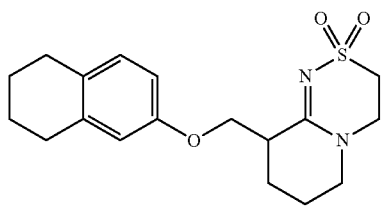 [SMILES: O=S1(=O)CCN2CCCC(COc3ccc4c(c3)CCCC4)C2=N1] | 349.1 |
| 304 | [4-(2,2-dioxido-3,4,6,7,8,9-hexahydropyrido[2,1-c][1,2,4]thiadiazin-9-yl)phenyl](phenyl)methanone | 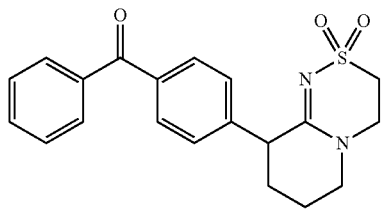 [SMILES: O=C(c1ccccc1)c1ccc(C2CCCN3CCS(=O)(=O)N=C23)cc1] | 369.1 |
| 305 | 9-{[4-(trifluoromethyl)phenoxy]methyl}-3,4,6,7,8,9-hexahydropyrido[2,1-c][1,2,4]thiadiazine 2,2-dioxide | 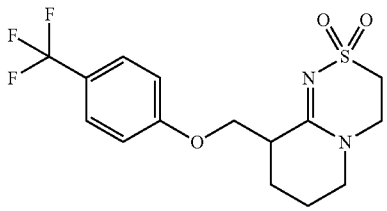 [SMILES: O=S1(=O)CCN2CCCC(COc3ccc(C(F)(F)F)cc3)C2=N1] | 363.1 |
| 306 | [4-(2,2-dioxido-3,4-dihydropyrido[2,1-c][1,2,4]thiadiazin-9-yl)phenyl](3-methoxyphenyl)methanone | 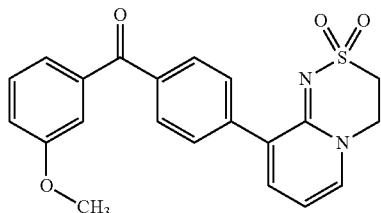 | 395.1 |
| 307 | 9-{4-[3-methyl-4-(trifluoromethyl)phenoxy]phenyl}-3,4-dihydropyrido[2,1-c][1,2,4]thiadiazine 2,2-dioxide | 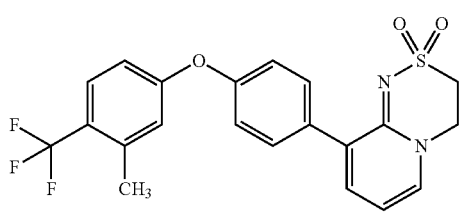 [SMILES: Cc1cc(Oc2ccc(C3=CC=CN4CCS(=O)(=O)N=C34)cc2)ccc1C(F)(F)F] | 435.1 |
| 308 | 9-{4-[3-methyl-4-(trifluoromethyl)phenoxy]phenyl}-3,4,6,7,8,9-hexahydropyrido[2,1-c][1,2,4]thiadiazine 2,2-dioxide | 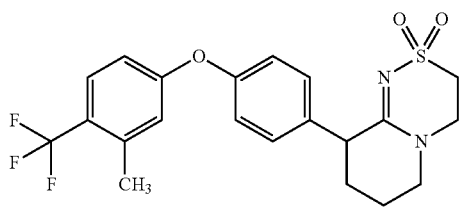 [SMILES: Cc1cc(Oc2ccc(C3CCCN4CCS(=O)(=O)N=C34)cc2)ccc1C(F)(F)F] | 439.1 |

TABLE 28-continued

| | | | |
|---|---|---|---|
| 309 | 9-{4-[2-methyl-5-(trifluoromethyl)phenoxy]phenyl}-3,4-dihydropyrido[2,1-c][1,2,4]thiadiazine 2,2-dioxide | 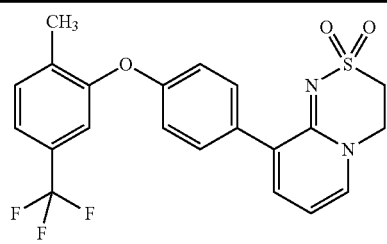 | 435.0 |
| 310 | 9-{4-[2-methyl-5-(trifluoromethyl)phenoxy]phenyl}-3,4,6,7,8,9-hexahydropyrido[2,1-c][1,2,4]thiadiazine 2,2-dioxide | 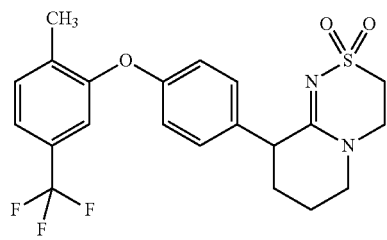 [SMILES: Cc1ccc(C(F)(F)F)cc1Oc1ccc(C2CCCN3CCS(=O)(=O)N=C23)cc1] | 439.1 |
| 311 | 9-{4-[4-bromo-3-(trifluoromethyl)phenoxy]phenyl}-3,4-dihydropyrido[2,1-c][1,2,4]thiadiazine 2,2-dioxide | 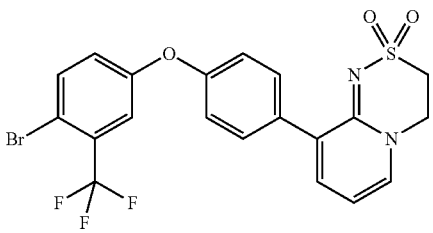 [SMILES: O=S1(=O)CCN2C=CC=C(c3ccc(Oc4ccc(Br)c(C(F)(F)F)c4)cc3)C2=N1] | 499.0<br>501.0 |

TABLE 29

| | | | |
|---|---|---|---|
| 312 | 9-{4-[difluoro(4-fluoro-3-methylphenyl)methyl]phenyl}-3,4-dihydropyrido[2,1-c][1,2,4]thiadiazine 2,2-dioxide | 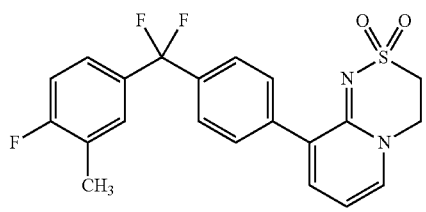 [SMILES: Cc1cc(C(F)(F)c2ccc(C3=CC=CN4CCS(=O)(=O)N=C34)cc2)ccc1F] | 419.1 |
| 313 | 9-[4-(2,3-dihydro-1-benzofuran-6-yloxy)phenyl]-3,4-dihydropyrido[2,1-c][1,2,4]thiadiazine 2,2-dioxide | 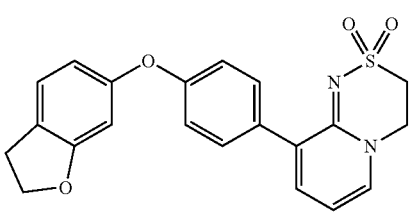 [SMILES: O=S1(=O)CCN2C=CC=C(c3ccc(Oc4ccc5c(c4)OCC5)cc3)C2=N1] | 395.1 |
| 314 | 9-{4-[2,4-bis(trifluoromethyl)phenoxy]phenyl}-3,4-dihydropyrido[2,1-c][1,2,4]thiadiazine 2,2-dioxide | 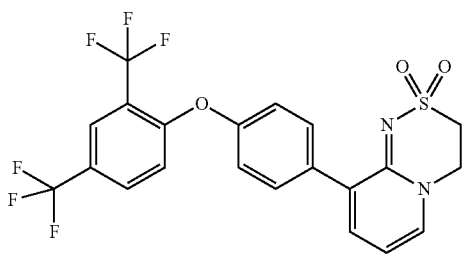 [SMILES: O=S1(=O)CCN2C=CC=C(c3ccc(Oc4ccc(C(F)(F)F)cc4C(F)(F)F)cc3)C2=N1] | 489.1 |

TABLE 29-continued

| | | | |
|---|---|---|---|
| 315 | 9-{4-[2,4-bis(trifluoromethyl)phenoxy]phenyl}-3,4,6,7,8,9-hexahydropyrido[2,1-c][1,2,4]thiadiazine 2,2-dioxide | 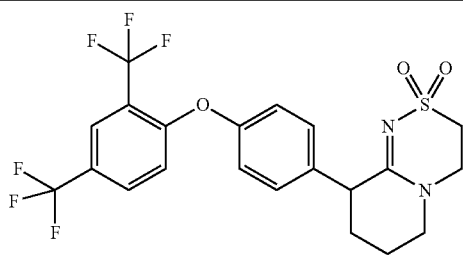 | 493.1 |
| 316 | 9-[4-(4-fluoro-3-methoxyphenoxy)phenyl]-3,4-dihydropyrido[2,1-c][1,2,4]thiadiazine 2,2-dioxide | 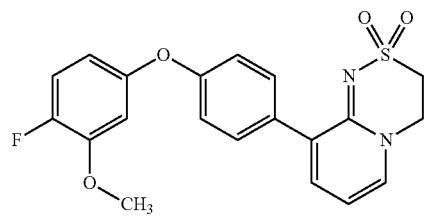 [SMILES: COc1cc(Oc2ccc(C3=CC=CN4CCS(=O)(=O)N=C34)cc2)ccc1F] | 401.1 |
| 317 | 9-[4-(4-fluoro-3-methoxyphenoxy)phenyl]-7-methyl-3,4-dihydropyrido[2,1-c][1,2,4]thiadiazine 2,2-dioxide | 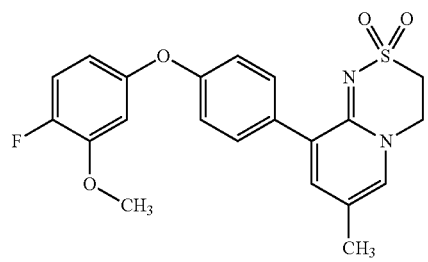 [SMILES: COc1cc(Oc2ccc(C3=CC(C)=CN4CCS(=O)(=O)N=C34)cc2)ccc1F] | 415.1 |
| 318 | 9-[4-(4-fluoro-3-methoxyphenoxy)phenyl]-3,4,6,7,8,9-hexahydropyrido[2,1-c][1,2,4]thiadiazine 2,2-dioxide | 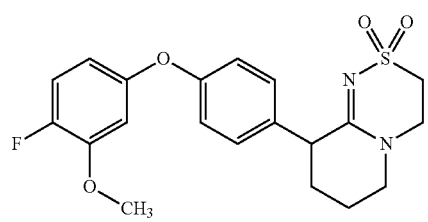 [SMILES: COc1cc(Oc2ccc(C3CCCN4CCS(=O)(=O)N=C34)cc2)ccc1F] | 405.1 |
| 319 | 9-[4-(2,3-dihydro-1-benzofuran-5-yloxy)phenyl]-3,4-dihydropyrido[2,1-c][1,2,4]thiadiazine 2,2-dioxide | 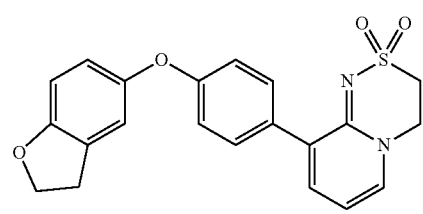 [SMILES: O=S1(=O)CCN2C=CC=C(c3ccc(Oc4ccc5c(c4)CCO5)cc3)C2=N1] | 395.1 |
| 320 | 9-[4-(2,3-dihydro-1-benzofuran-5-yloxy)phenyl]-3,4,6,7,8,9-hexahydropyrido[2,1-c][1,2,4]thiadiazine 2,2-dioxide | 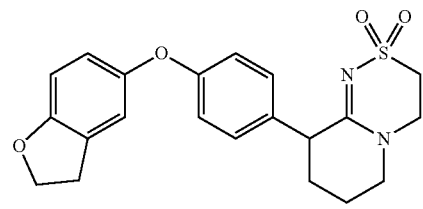 [SMILES: O=S1(=O)CCN2CCCC(c3ccc(Oc4ccc5c(c4)CCO5)cc3)C2=N1] | 399.1 |
| 321 | 9-[4-(1-phenylcyclobutyl)phenyl]-3,4,6,7,8,9-hexahydropyrido[2,1-c][1,2,4]thiadiazine 2,2-dioxide | 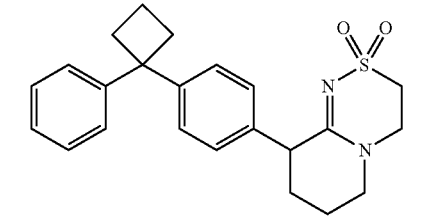 [SMILES: O=S1(=O)CCN2CCCC(c3ccc(C4(c5ccccc5)CCC4)cc3)C2=N1] | 395.1 |

TABLE 29-continued

| | | | |
|---|---|---|---|
| 322 | 9-(3-phenoxyphenyl)-3,4,6,7,8,9-hexahydropyrido[2,1-c][1,2,4]thiadiazine 2,2-dioxide | 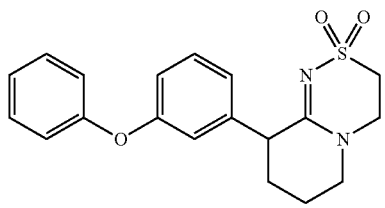 [SMILES: O=S1(=O)CCN2CCCC(c3cccc(Oc4ccccc4)c3)C2=N1] | 357.1 |
| 323 | 9-{4-[4-(1,1-difluoroethyl)phenoxy]phenyl}-3,4-dihydropyrido[2,1-c][1,2,4]thiadiazine 2,2-dioxide | 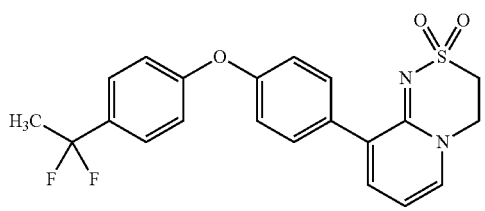 [SMILES: CC(F)(F)c1ccc(Oc2ccc(C3=CC=CN4CCS(=O)(=O)N=C34)cc2)cc1] | 417.1 |

TABLE 30

| | | | |
|---|---|---|---|
| 324 | 9-[4-(4-methylbenzyl)phenyl]-3,4,6,7,8,9-hexahydropyrido[2,1-c][1,2,4]thiadiazine 2,2-dioxide | 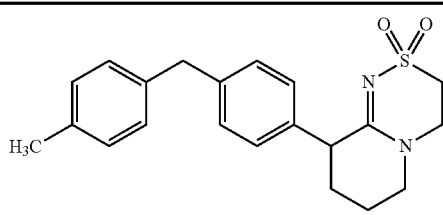 | 369.2 |
| 325 | 9-[4-(1-methyl-1-phenylethyl)phenyl]-3,4-dihydropyrido[2,1-c][1,2,4]thiadiazine 2,2-dioxide | 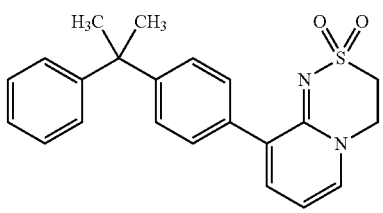 [SMILES: CC(C)(c1ccccc1)c1ccc(C2=CC=CN3CCS(=O)(=O)N=C23)cc1] | 379.1 |
| 326 | 9-[4-(1-methyl-1-phenylethyl)phenyl]-3,4,6,7,8,9-hexahydropyrido[2,1-c][1,2,4]thiadiazine 2,2-dioxide | 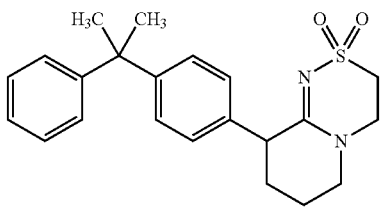 [SMILES: CC(C)(c1ccccc1)c1ccc(C2CCCN3CCS(=O)(=O)N=C23)cc1] | 383.1 |
| 328 | 9-[4-(pentafluoro-lambda$^6$-sulfanyl)phenyl]-3,4,6,7,8,9-hexahydropyrido[2,1-c][1,2,4]thiadiazine 2,2-dioxide | 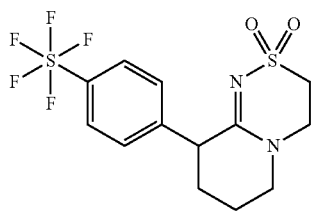 [SMILES: O=S1(=O)CCN2CCCC(c3ccc(S(F)(F)(F)(F)F)cc3)C2=N1] | 391.0 |
| 329 | 9-{4-[1-methyl-1-(4-methylphenyl)ethyl]phenyl}-3,4-dihydropyrido[2,1-c][1,2,4]thiadiazine 2,2-dioxide | 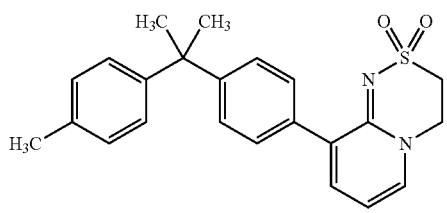 [SMILES: Cc1ccc(C(C)(C)c2ccc(C3=CC=CN4CCS(=O)(=O)N=C34)cc2)cc1] | 393.2 |

TABLE 30-continued

| | | | |
|---|---|---|---|
| 330 | 9-{4-[1-methyl-1-(4-methylphenyl)ethyl]phenyl}-3,4,6,7,8,9-hexahydropyrido[2,1-c][1,2,4]thiadiazine 2,2-dioxide | 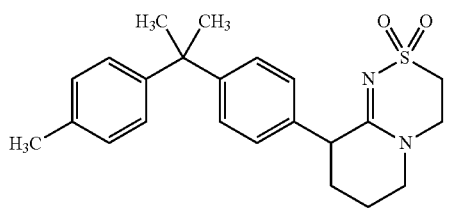 [SMILES: Cc1ccc(C(C)(C)c2ccc(C3CCCN4CCS(=O)(=O)N=C34)cc2)cc1] | 397.2 |
| 331 | 9-[4-(1,1-difluoroethyl)phenyl]-3,4-dihydropyrido[2,1-c][1,2,4]thiadiazine 2,2-dioxide | 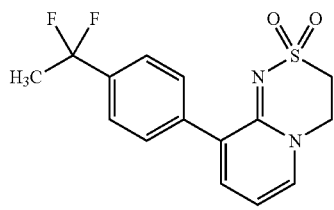 [SMILES: CC(F)(F)c1ccc(C2=CC=CN3CCS(=O)(=O)N=C23)cc1] | 325.1 |
| 332 | 9-{[4-(trifluoromethyl)phenoxy]methyl}-3,4-dihydropyrido[2,1-c][1,2,4]thiadiazine 2,2-dioxide | 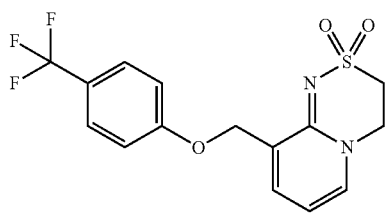 [SMILES: O=S1(=O)CCN2C=CC=C(COc3ccc(C(F)(F)F)cc3)C2=N1] | 359.1 |
| 333 | 9-(4-methoxyphenyl)-3,4-dihydropyrazino[2,1-c][1,2,4]thiadiazine 2,2-dioxide | 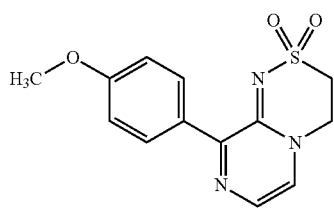 [SMILES: COc1ccc(C2=NC=CN3CCS(=O)(=O)N=C23)cc1] | 292.1 |
| 334 | 9-(4-ethoxyphenyl)-3,4-dihydropyrazino[2,1-c][1,2,4]thiadiazine 2,2-dioxide | 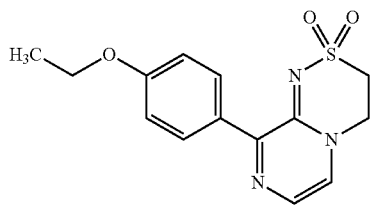 [SMILES: CCOc1ccc(C2=NC=CN3CCS(=O)(=O)N=C23)cc1] | 306.0 |
| 335 | 9-(4-propoxyphenyl)-3,4-dihydropyrazino[2,1-c][1,2,4]thiadiazine 2,2-dioxide | 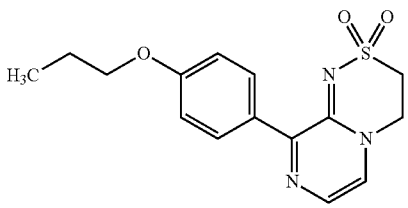 [SMILES: CCCOc1ccc(C2=NC=CN3CCS(=O)(=O)N=C23)cc1] | 320.1 |
| 336 | 9-[4-(1-methylethoxy)phenyl]-3,4-dihydropyrazino[2,1-c][1,2,4]thiadiazine 2,2-dioxide | 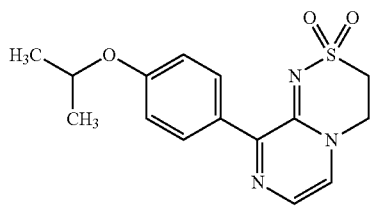 [SMILES: CC(C)Oc1ccc(C2=NC=CN3CCS(=O)(=O)N=C23)cc1] | 320.1 |

TABLE 31

| | | |
|---|---|---|
| 337 9-[4-(cyclopentyloxy)phenyl]-3,4-dihydropyrazino[2,1-c][1,2,4]thiadiazine 2,2-dioxide | 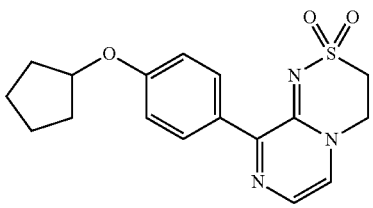 [SMILES: O=S1(=O)CCN2C=CN=C(c3ccc(OC4CCCC4)cc3)C2=N1] | 346.1 |
| 338 (9S)-8-methyl-9-(4-phenoxyphenyl)-3,4,6,7,8,9-hexahydropyrazino[2,1-c][1,2,4]thiadiazine 2,2-dioxide | 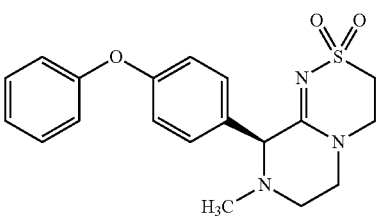 [SMILES: CN1CCN2CCS(=O)(=O)N=C2[C@@H]1c1ccc(Oc2ccccc2)cc1] | 372.1 |
| 339 (9R)-8-methyl-9-(4-phenoxyphenyl)-3,4,6,7,8,9-hexahydropyrazino[2,1-c][1,2,4]thiadiazine 2,2-dioxide | 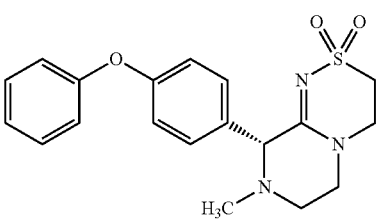 [SMILES: CN1CCN2CCS(=O)(=O)N=C2[C@H]1c1ccc(Oc2ccccc2)cc1] | 372.1 |
| 340 (9S)-8-acetyl-9-(4-phenoxyphenyl)-3,4,6,7,8,9-hexahydropyrazino[2,1-c][1,2,4]thiadiazine 2,2-dioxide | 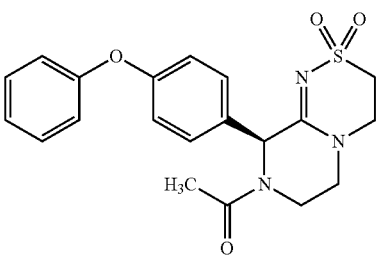 [SMILES: CC(=O)N1CCN2CCS(=O)(=O)N=C2[C@@H]1c1ccc(Oc2ccccc2)cc1] | 400.1 |
| 341 (9R)-8-acetyl-9-(4-phenoxyphenyl)-3,4,6,7,8,9-hexahydropyrazino[2,1-c][1,2,4]thiadiazine 2,2-dioxide | 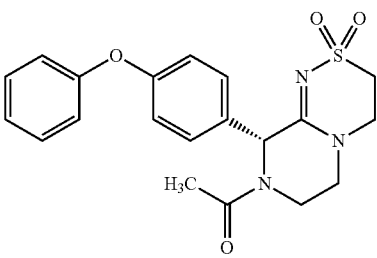 [SMILES: CC(=O)N1CCN2CCS(=O)(=O)N=C2[C@H]1c1ccc(Oc2ccccc2)cc1] | 400.1 |
| 342 9-(4-butoxyphenyl)-3,4,6,7,8,9-hexahydropyrido[2,1-c][1,2,4]thiadiazine 2,2-dioxide | 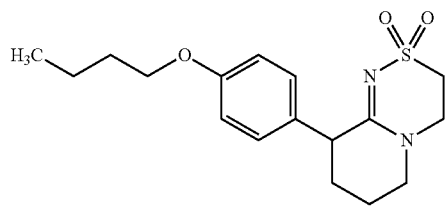 [SMILES: CCCCOc1ccc(C2CCCN3CCS(=O)(=O)N=C23)cc1] | 337.1 |
| 343 9-(4-morpholin-4-ylphenyl)-3,4,6,7,8,9-hexahydropyrido[2,1-c][1,2,4]thiadiazine 2,2-dioxide | 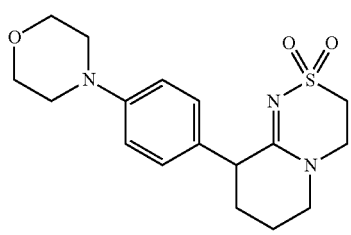 [SMILES: O=S1(=O)CCN2CCCC(c3ccc(N4CCOCC4)cc3)C2=N1] | 350.1 |

TABLE 31-continued

| | | | |
|---|---|---|---|
| 344 | 9-(2-fluorobiphenyl-4-yl)-3,4-dihydropyrazino[2,1-c][1,2,4]thiadiazine 2,2-dioxide | 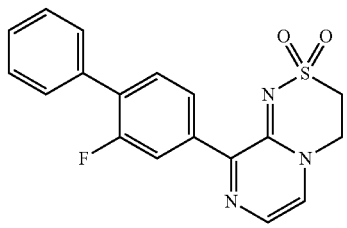 [SMILES: O=S1(=O)CCN2C=CN=C(c3ccc(-c4ccccc4)c(F)c3)C2=N1] | 356.1 |
| 345 | 9-(2-fluorobiphenyl-4-yl)-3,4,6,7,8,9-hexahydropyrazino[2,1-c][1,2,4]thiadiazine 2,2-dioxide | 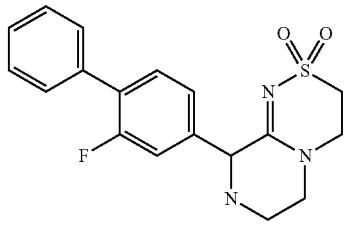 [SMILES: O=S1(=O)CCN2CCNC(c3ccc(-c4ccccc4)c(F)c3)C2=N1] | 360.1 |
| 346 | 9-(2-fluorobiphenyl-4-yl)-9-methyl-3,4,6,7,8,9-hexahydropyrazino[2,1-c][1,2,4]thiadiazine 2,2-dioxide | 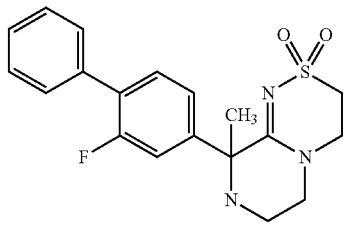 [SMILES: CC1(c2ccc(-c3ccccc3)c(F)c2)NCCN2CCS(=O)(=O)N=C21] | HCl 374.1 |
| 347 | 9-(3-fluoro-4-phenoxyphenyl)-3,4,6,7,8,9-hexahydropyrido[2,1-c][1,2,4]thiadiazine 2,2-dioxide | 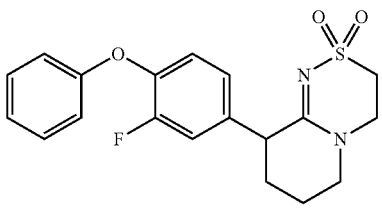 [SMILES: O=S1(=O)CCN2CCCC(c3ccc(Oc4ccccc4)c(F)c3)C2=N1] | 375.1 |
| 348 | 9-(2-fluorobiphenyl-4-yl)(9-~2~H)-3,4,6,7,8,9-hexahydropyrazino[2,1-c][1,2,4]thiadiazine 2,2-dioxide | 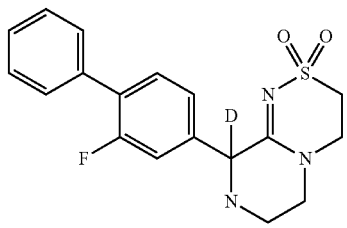 [SMILES: [2H]C1(c2ccc(-c3ccccc3)c(F)c2)NCCN2CCS(=O)(=O)N=C21] | HCl 361.1 |

TABLE 32

| | | | |
|---|---|---|---|
| 349 | 9-(3-fluoro-4-propoxyphenyl)-3,4-dihydropyrido[2,1-c][1,2,4]thiadiazine 2,2-dioxide | 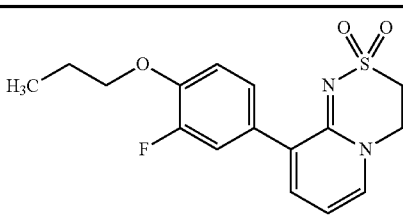 | 337.1 |

TABLE 32-continued

| | | | |
|---|---|---|---|
| 350 | 9-(3-fluoro-4-propoxyphenyl)-3,4,6,7,8,9-hexahydropyrido[2,1-c][1,2,4]thiadiazine 2,2-dioxide | 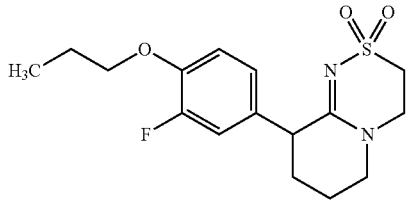 [SMILES: CCCOc1ccc(C2CCCN3CCS(=O)(=O)N=C23)cc1F] | 341.1 |
| 351 | 9-(4-butoxy-3-fluorophenyl)-3,4-dihydropyrido[2,1-c][1,2,4]thiadiazine 2,2-dioxide |  | 351.2 |
| 352 | 9-(4-butoxy-3-fluorophenyl)-3,4,6,7,8,9-hexahydropyrido[2,1-c][1,2,4]thiadiazine 2,2-dioxide | 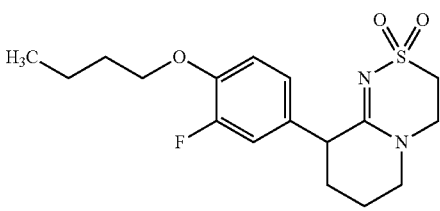 [SMILES: CCCCOc1ccc(C2CCCN3CCS(=O)(=O)N=C23)cc1F] | 355.1 |
| 353 | 9-(3-fluoro-4-{[4-(trifluoromethyl)pyridin-2-yl]oxy}phenyl)-3,4-dihydropyrido[2,1-c][1,2,4]thiadiazine 2,2-dioxide | 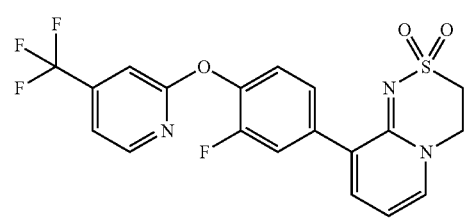 [SMILES: O=S1(=O)CCN2C=CC=C(c3ccc(Oc4cc(C(F)(F)F)ccn4)c(F)c3)C2=N1] | 440.1 |
| 354 | 9-(4-{[4-(trifluoromethyl)pyridin-2-yl]oxy}phenyl)-3,4-dihydropyrazino[2,1-c][1,2,4]thiadiazine 2,2-dioxide | 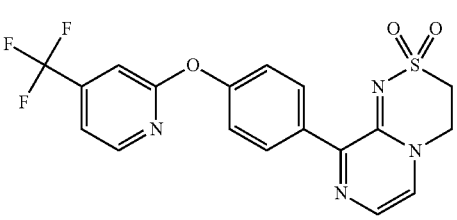 [SMILES: O=S1(=O)CCN2C=CN=C(c3ccc(Oc4cc(C(F)(F)F)ccn4)cc3)C2=N1] | 423.1 |
| 355 | 9-(4-butoxyphenyl)-3,4-dihydropyrazino[2,1-c][1,2,4]thiadiazine 2,2-dioxide | 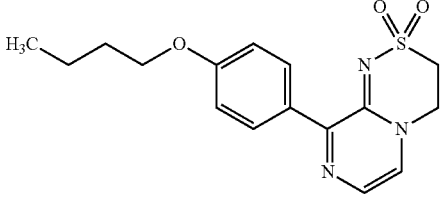 [SMILES: CCCCOc1ccc(C2=NC=CN3CCS(=O)(=O)N=C23)cc1] | 334.1 |
| 356 | 9-(3-fluoro-4-{[4-(trifluoromethyl)pyridin-2-yl]oxy}phenyl)-3,4,6,7,8,9-hexahydropyrido[2,1-c][1,2,4]thiadiazine 2,2-dioxide | 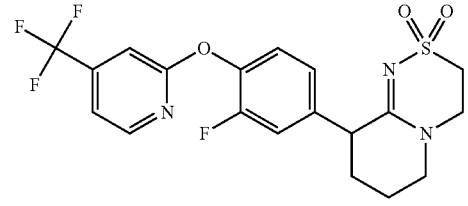 [SMILES: O=S1(=O)CCN2CCCC(c3ccc(Oc4cc(C(F)(F)F)ccn4)c(F)c3)C2=N1] | 444.1 |

TABLE 32-continued

| | | | |
|---|---|---|---|
| 357 | 9-[4-(4-fluorophenoxy)phenyl]-3,4,6,7,8,9-hexahydropyrido[2,1-c][1,2,4]thiadiazine 2,2-dioxide | 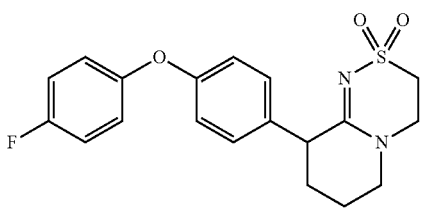 [SMILES: O=S1(=O)CCN2CCCC(c3ccc(Oc4ccc(F)cc4)cc3)C2=N1] | 375.1 |
| 358 | 9-[4-(cycloheptyloxy)phenyl]-3,4,6,7,8,9-hexahydropyrido[2,1-c][1,2,4]thiadiazine 2,2-dioxide | 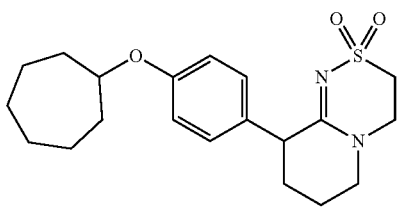 [SMILES: O=S1(=O)CCN2CCCC(c3ccc(OC4CCCCCC4)cc3)C2=N1] | 377.2 |
| 359 | 4-(2,2-dioxido-3,4,6,7,8,9-hexahydropyrido[2,1-c][1,2,4]thiadiazin-9-yl)phenyl trifluoromethanesulfonate | 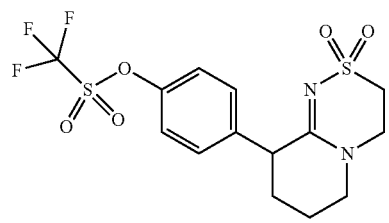 [SMILES: O=S1(=O)CCN2CCCC(c3ccc(OS(=O)(=O)C(F)(F)F)cc3)C2=N1] | 413.1 |
| 360 | 9-(2,4-dichlorophenyl)-3,4-dihydropyrido[2,1-c][1,2,4]thiadiazine 2,2-dioxide | 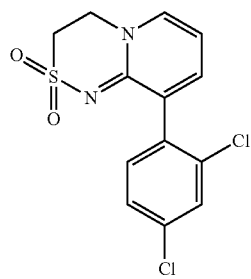 [SMILES: O=S1(=O)CCN2C=CC=C(c3ccc(Cl)cc3Cl)C2=N1] | 330.9 |

TABLE 33

| | | | |
|---|---|---|---|
| 361 | 9-[3-fluoro-4-(1-methylethoxy)phenyl]-3,4-dihydropyrido[2,1-c][1,2,4]thiadiazine 2,2-dioxide | 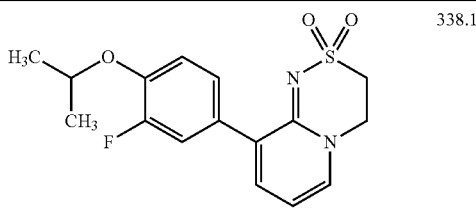 | 338.1 |
| 362 | 9-(4-fluorophenyl)-3,4-dihydropyrido[2,1-c][1,2,4]thiadiazine 2,2-dioxide | 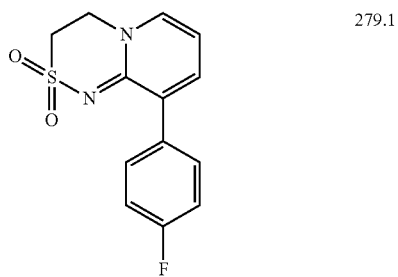 | 279.1 |

TABLE 33-continued
| | | | |
|---|---|---|---|
| 363 | 9-(3-chloro-4-fluorophenyl)-3,4-dihydropyrido[2,1-c][1,2,4]thiadiazine 2,2-dioxide | 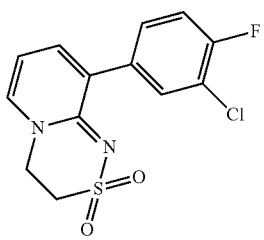 [SMILES: O=S1(=O)CCN2C=CC=C(c3ccc(F)c(Cl)c3)C2=N1] | 312.9 |
| 364 | 9-(3-chlorophenyl)-3,4-dihydropyrido[2,1-c][1,2,4]thiadiazine 2,2-dioxide | 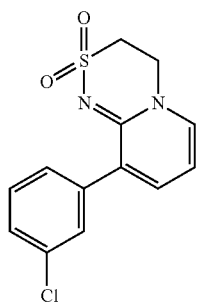 [SMILES: O=S1(=O)CCN2C=CC=C(c3cccc(Cl)c3)C2=N1] | 295.0 |
| 365 | 9-(3-fluorophenyl)-3,4-dihydropyrido[2,1-c][1,2,4]thiadiazine 2,2-dioxide | 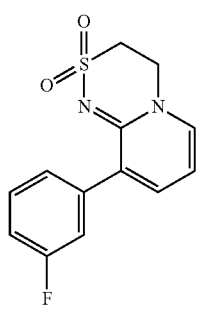 [SMILES: O=S1(=O)CCN2C=CC=C(c3cccc(F)c3)C2=N1] | 279.1 |
| 366 | 9-(2-chlorophenyl)-3,4-dihydropyrido[2,1-c][1,2,4]thiadiazine 2,2-dioxide | 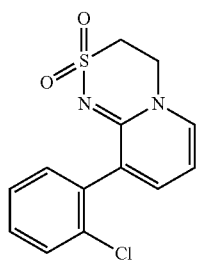 [SMILES: O=S1(=O)CCN2C=CC=C(c3ccccc3Cl)C2=N1] | 294.9 |
| 367 | 9-(2-fluorophenyl)-3,4-dihydropyrido[2,1-c][1,2,4]thiadiazine 2,2-dioxide | 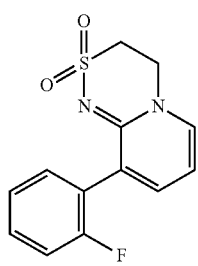 [SMILES: O=S1(=O)CCN2C=CC=C(c3ccccc3F)C2=N1] | 279.1 |
| 368 | 9-(3,4-difluorophenyl)-3,4-dihydropyrido[2,1-c][1,2,4]thiadiazine 2,2-dioxide | 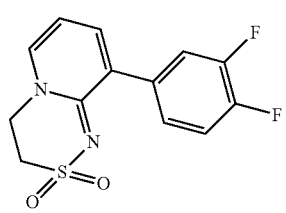 [SMILES: O=S1(=O)CCN2C=CC=C(c3ccc(F)c(F)c3)C2=N1] | 297.0 |

TABLE 33-continued
| | | | |
|---|---|---|---|
| 369 | 9-(3,4-dichlorophenyl)-3,4-dihydropyrido[2,1-c][1,2,4]thiadiazine 2,2-dioxide | 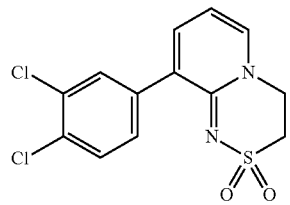 [SMILES: O=S1(=O)CCN2C=CC=C(c3ccc(Cl)c(Cl)c3)C2=N1] | 330.9 |
| 370 | 9-(2,3-dichlorophenyl)-3,4-dihydropyrido[2,1-c][1,2,4]thiadiazine 2,2-dioxide | 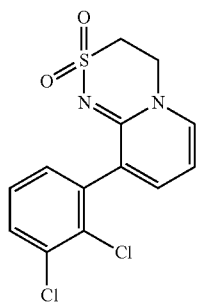 [SMILES: O=S1(=O)CCN2C=CC=C(c3cccc(Cl)c3Cl)C2=N1] | 330.9 |
| 371 | 9-(3,5-difluorophenyl)-3,4-dihydropyrido[2,1-c][1,2,4]thiadiazine 2,2-dioxide | 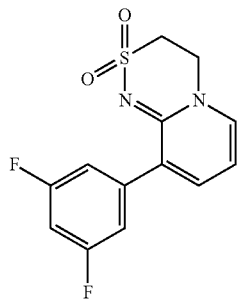 [SMILES: O=S1(=O)CCN2C=CC=C(c3cc(F)cc(F)c3)C2=N1] | 298.0 |
| 372 | 9-(2,4-difluorophenyl)-3,4-dihydropyrido[2,1-c][1,2,4]thiadiazine 2,2-dioxide | 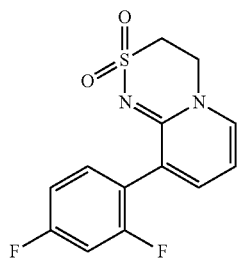 [SMILES: O=S1(=O)CCN2C=CC=C(c3ccc(F)cc3F)C2=N1] | 297.0 |
TABLE 34
| | | | |
|---|---|---|---|
| 373 | 9-(4-chloro-3-fluorophenyl)-3,4-dihydropyrido[2,1-c][1,2,4]thiadiazine 2,2-dioxide | 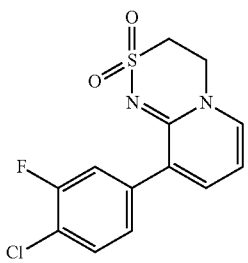 [SMILES: O=S1(=O)CCN2C=CC=C(c3ccc(Cl)c(F)c3)C2=N1] | 314.0 |

TABLE 34-continued
| | | |
|---|---|---|
| 374 9-(2,4,5-trifluorophenyl)-3,4-dihydropyrido[2,1-c][1,2,4]thiadiazine 2,2-dioxide | 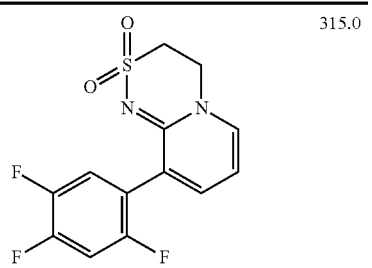 | 315.0 |
| 375 9-(2,3,4-trifluorophenyl)-3,4-dihydropyrido[2,1-c][1,2,4]thiadiazine 2,2-dioxide | 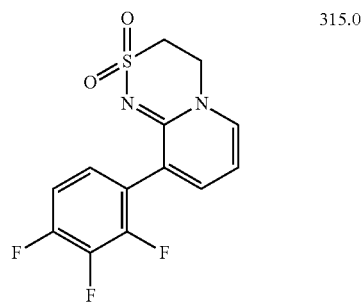 | 315.0 |
| 376 9-(2,3-difluorophenyl)-3,4-dihydropyrido[2,1-c][1,2,4]thiadiazine 2,2-dioxide | 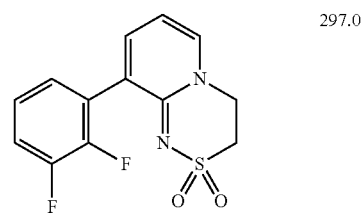 | 297.0 |
| 377 9-phenyl-3,4-dihydropyrido[2,1-c][1,2,4]thiadiazine 2,2-dioxide | 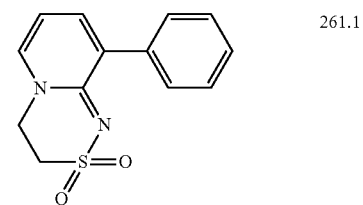 | 261.1 |
| 378 9-(2,5-dichlorophenyl)-3,4-dihydropyrido[2,1-c][1,2,4]thiadiazine 2,2-dioxide | 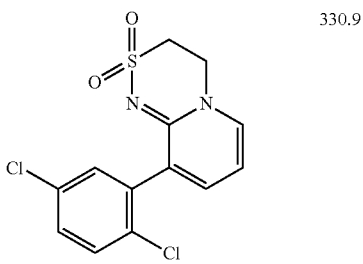 | 330.9 |
| 379 9-(1-benzyl-1H-pyrazol-4-yl)-3,4-dihydropyrido[2,1-c][1,2,4]thiadiazine 2,2-dioxide | 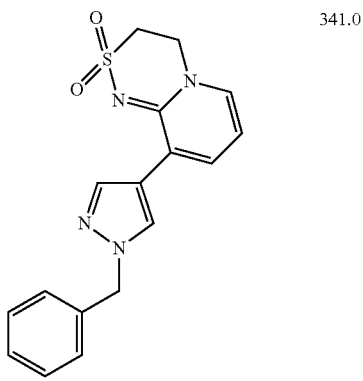 | 341.0 |

TABLE 34-continued
| | | |
|---|---|---|
| 380 9-(2-chloro-4-fluorophenyl)-3,4-dihydropyrido[2,1-c][1,2,4]thiadiazine 2,2-dioxide | 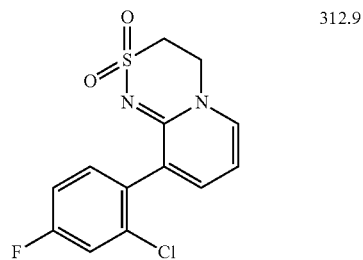 | 312.9 |
| 381 9-(3-chloro-2-fluorophenyl)-3,4-dihydropyrido[2,1-c][1,2,4]thiadiazine 2,2-dioxide | 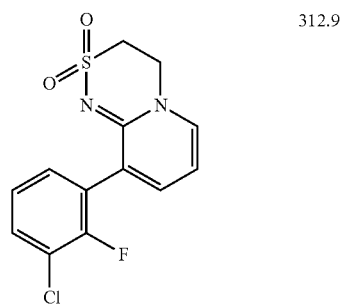 | 312.9 |
| 382 9-(5-chloro-2-fluorophenyl)-3,4-dihydropyrido[2,1-c][1,2,4]thiadiazine 2,2-dioxide | 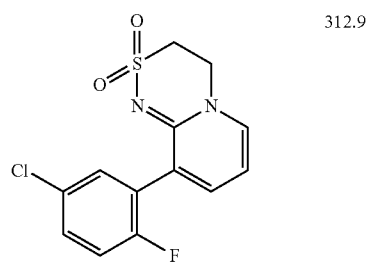 | 312.9 |
| 383 9-(2-chloro-5-fluorophenyl)-3,4-dihydropyrido[2,1-c][1,2,4]thiadiazine 2,2-dioxide | 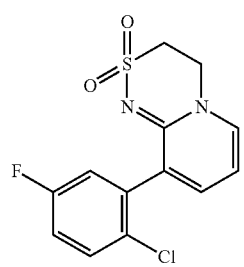 [SMILES: O=S1(=O)CCN2C=CC=C(c3cc(F)ccc3Cl)C2=N1] | 312.9 |
| 384 9-(3-chloro-5-fluorophenyl)-3,4-dihydropyrido[2,1-c][1,2,4]thiadiazine 2,2-dioxide | 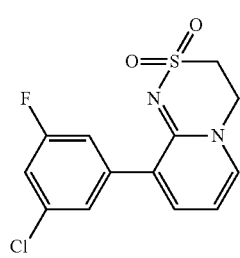 [SMILES: O=S1(=O)CCN2C=CC=C(c3cc(F)cc(Cl)c3)C2=N1] | 312.9 |

TABLE 35
| | | | |
|---|---|---|---|
| 385 | 9-[3-methyl-4-(1-methylethoxy)phenyl]-3,4-dihydropyrido[2,1-c][1,2,4]thiadiazine 2,2-dioxide | 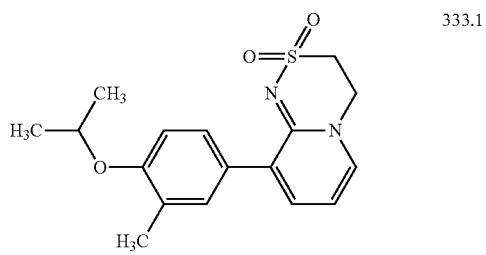 | 333.1 |
| 386 | 9-[4-(benzyloxy)-3,5-dichlorophenyl]-3,4-dihydropyrido[2,1-c][1,2,4]thiadiazine 2,2-dioxide | 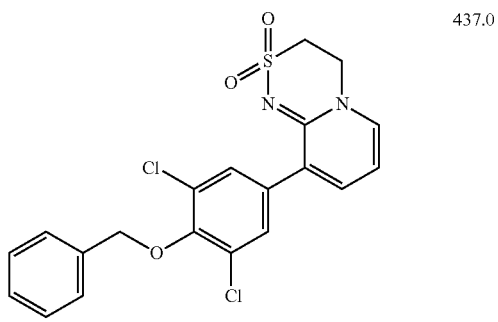 | 437.0 |
| 387 | 9-(4-propoxyphenyl)-3,4-dihydropyrido[2,1-c][1,2,4]thiadiazine 2,2-dioxide | 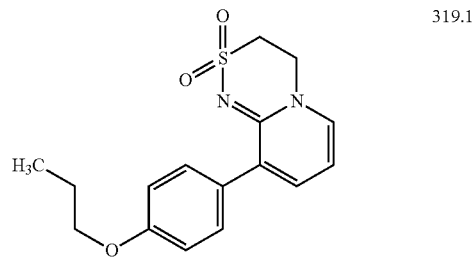 | 319.1 |
| 388 | 9-(2-chloro-4-methoxyphenyl)-3,4-dihydropyrido[2,1-c][1,2,4]thiadiazine 2,2-dioxide | 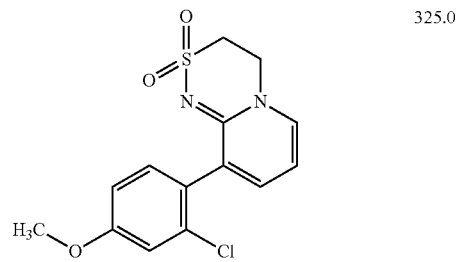 | 325.0 |
| 389 | 9-(2,3-dihydro-1-benzofuran-5-yl)-3,4-dihydropyrido[2,1-c][1,2,4]thiadiazine 2,2-dioxide | 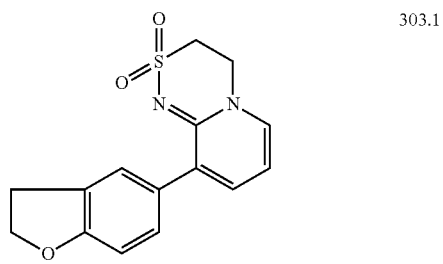 | 303.1 |

TABLE 35-continued
| | | |
|---|---|---|
| 390 | 9-(4-ethoxyphenyl)-3,4-dihydropyrido[2,1-c][1,2,4]thiadiazine 2,2-dioxide | 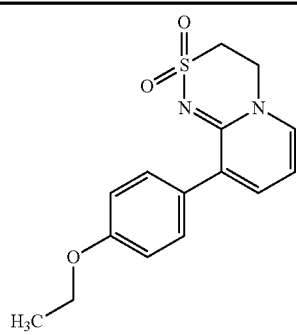 306.1 |
| 391 | 9-(4-methoxyphenyl)-3,4-dihydropyrido[2,1-c][1,2,4]thiadiazine 2,2-dioxide | 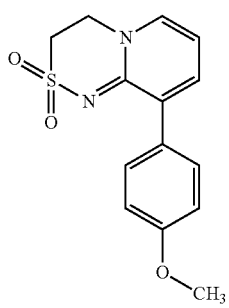 [SMILES: COc1ccc(C2=CC=CN3CCS(=O)(=O)N=C23)cc1] 291.0 |
| 392 | 9-[4-chloro-2-(trifluoromethyl)phenyl]-3,4-dihydropyrido[2,1-c][1,2,4]thiadiazine 2,2-dioxide | 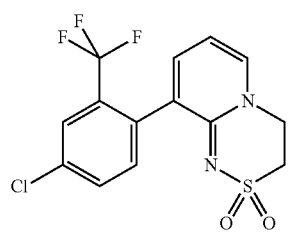 [SMILES: O=S1(=O)CCN2C=CC=C(c3ccc(Cl)cc3C(F)(F)F)C2=N1] 364.0 |
| 393 | 9-[4-(trifluoromethyl)phenyl]-3,4-dihydropyrido[2,1-c][1,2,4]thiadiazine 2,2-dioxide | 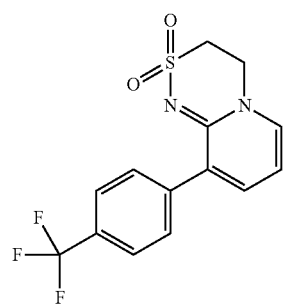 [SMILES: O=S1(=O)CCN2C=CC=C(c3ccc(C(F)(F)F)cc3)C2=N1] 330.0 |
| 394 | 9-(2,2-dimethyl-2,3-dihydro-1-benzofuran-5-yl)-3,4-dihydropyrido[2,1-c][1,2,4]thiadiazine 2,2-dioxide | 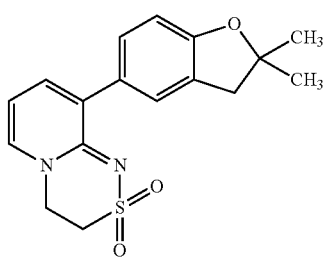 [SMILES: CC1(C)Cc2cc(C3=CC=CN4CCS(=O)(=O)N=C34)ccc2O1] 331.1 |

TABLE 35-continued
| 395 | 9-(4-methoxy-2,6-dimethylphenyl)-3,4-dihydropyrido[2,1-c][1,2,4]thiadiazine 2,2-dioxide | 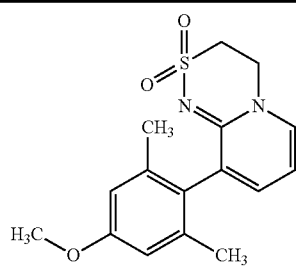 | 319.1 |
| 396 | 9-[4-(3-fluorooxetan-3-yl)phenyl]-3,4-dihydropyrido[2,1-c][1,2,4]thiadiazine 2,2-dioxide | 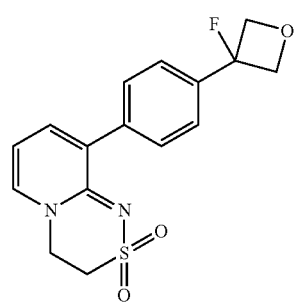 [SMILES: O=S1(=O)CCN2C=CC=C(c3ccc(C4(F)COC4)cc3)C2=N1] | 335.1 |
TABLE 36
| 397 | 9-(4-morpholin-4-ylphenyl)-3,4-dihydropyrido[2,1-c][1,2,4]thiadiazine 2,2-dioxide | 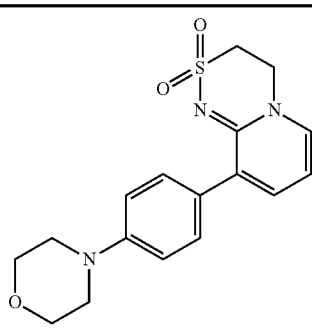 | 346.1 |
| 398 | 9-quinolin-3-yl-3,4-dihydropyrido[2,1-c][1,2,4]thiadiazine 2,2-dioxide | 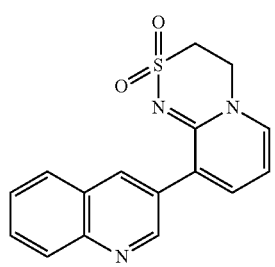 [SMILES: O=S1(=O)CCN2C=CC=C(c3cnc4ccccc4c3)C2=N1] | 312.1 |
| 400 | 1-[4-(2,2-dioxido-3,4-dihydropyrido[2,1-c][1,2,4]thiadiazin-9-yl)phenyl]ethanone | 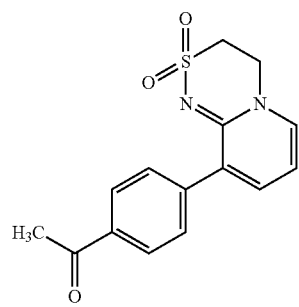 [SMILES: CC(=O)c1ccc(C2=CC=CN3CCS(=O)(=O)N=C23)cc1] | 303.1 |

TABLE 36-continued
| | | |
|---|---|---|
| 401 9-dibenzo[b,d]thiophen-2-yl-3,4-dihydropyrido[2,1-c][1,2,4]thiadiazine 2,2-dioxide | 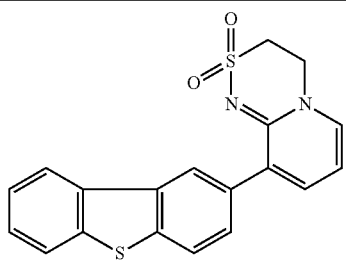 | 367.1 |
| 402 9-(1-methyl-1H-benzimidazol-6-yl)-3,4-dihydropyrido[2,1-c][1,2,4]thiadiazine 2,2-dioxide | 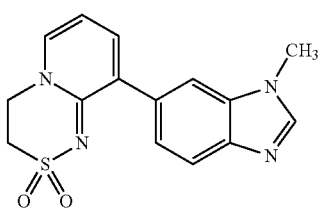 [SMILES: Cn1cnc2ccc(C3=CC=CN4CCS(=O)(=O)N=C34)cc21] | 315.1 |
| 403 9-(1,3-benzodioxol-5-yl)-3,4-dihydropyrido[2,1-c][1,2,4]thiadiazine 2,2-dioxide | 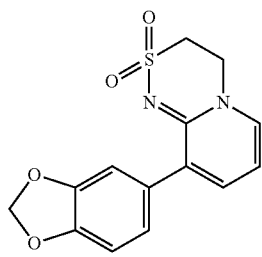 [SMILES: O=S1(=O)CCN2C=CC=C(c3ccc4c(c3)OCO4)C2=N1] | 305.1 |
| 405 9-(1H-indol-5-yl)-3,4-dihydropyrido[2,1-c][1,2,4]thiadiazine 2,2-dioxide | 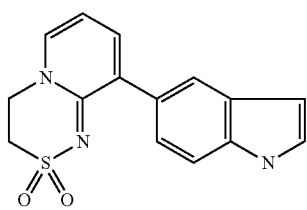 [SMILES: O=S1(=O)CCN2C=CC=C(c3ccc4[nH]ccc4c3)C2=N1] | 300.1 |
| 406 9-(1H-indol-6-yl)-3,4-dihydropyrido[2,1-c][1,2,4]thiadiazine 2,2-dioxide | 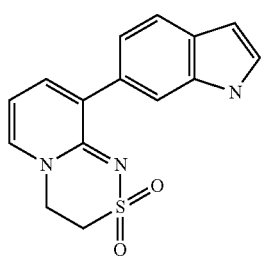 [SMILES: O=S1(=O)CCN2C=CC=C(c3ccc4cc[nH]c4c3)C2=N1] | 300.1 |
| 407 9-(5-chloro-6-methoxypyridin-3-yl)-3,4-dihydropyrido[2,1-c][1,2,4]thiadiazine 2,2-dioxide | 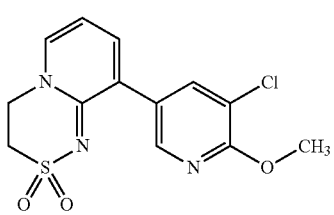 [SMILES: COc1ncc(C2=CC=CN3CCS(=O)(=O)N=C23)cc1Cl] | 327.1 |

TABLE 36-continued
| 408 | 9-[4-(methylsulfanyl)phenyl]-3,4-dihydropyrido[2,1-c][1,2,4]thiadiazine 2,2-dioxide | 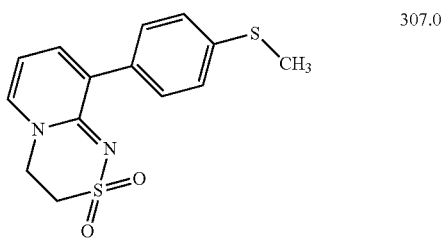 | 307.0 |
| 409 | 9-(1,3-benzothiazol-6-yl)-3,4-dihydropyrido[2,1-c][1,2,4]thiadiazine 2,2-dioxide | 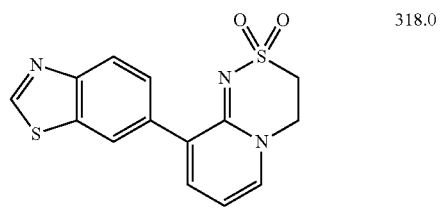 | 318.0 |
| 410 | 9-(1-benzofuran-2-yl)-3,4-dihydropyrido[2,1-c][1,2,4]thiadiazine 2,2-dioxide | 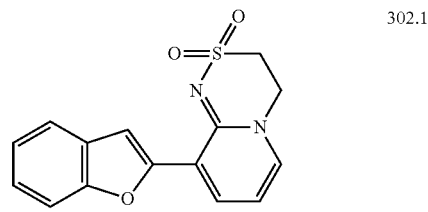 | 302.1 |
TABLE 37
| 411 | 9-(4-tert-butoxyphenyl)-3,4-dihydropyrido[2,1-c][1,2,4]thiadiazine 2,2-dioxide | 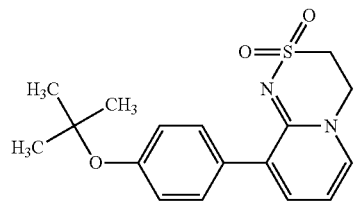 [SMILES: CC(C)(C)Oc1ccc(C2=CC=CN3CCS(=O)(=O)N=C23)cc1] | 333.1 |
| 412 | 9-(1-methyl-1H-indol-5-yl)-3,4-dihydropyrido[2,1-c][1,2,4]thiadiazine 2,2-dioxide | 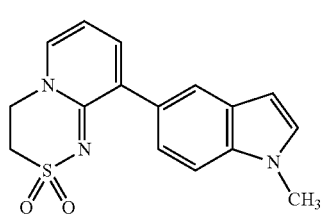 [SMILES: Cn1ccc2cc(C3=CC=CN4CCS(=O)(=O)N=C34)ccc21] | 314.1 |
| 414 | 9-(1H-indazol-6-yl)-3,4-dihydropyrido[2,1-c][1,2,4]thiadiazine 2,2-dioxide | 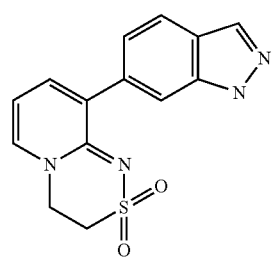 [SMILES: O=S1(=O)CCN2C=CC=C(c3ccc4cn[nH]c4c3)C2=N1] | 301.1 |

TABLE 37-continued

| | | | |
|---|---|---|---|
| 415 | 9-(1-methyl-1H-indazol-6-yl)-3,4-dihydropyrido[2,1-c][1,2,4]thiadiazine 2,2-dioxide | 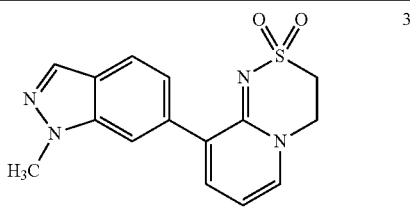 | 315.1 |
| 416 | 9-(4-chloro-2-methylphenyl)-3,4-dihydropyrido[2,1-c][1,2,4]thiadiazine 2,2-dioxide | 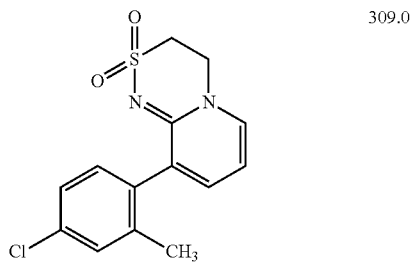 | 309.0 |
| 417 | 9-(2,3-dihydro-1,4-benzodioxin-6-yl)-3,4-dihydropyrido[2,1-c][1,2,4]thiadiazine 2,2-dioxide | 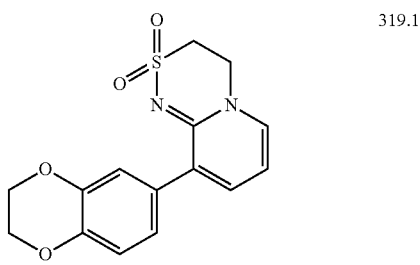 | 319.1 |
| 418 | 9-quinolin-6-yl-3,4-dihydropyrido[2,1-c][1,2,4]thiadiazine 2,2-dioxide | 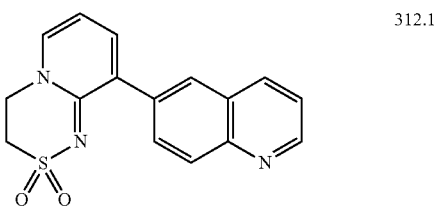 | 312.1 |
| 419 | 9-(2-methyl-2H-indazol-6-yl)-3,4-dihydropyrido[2,1-c][1,2,4]thiadiazine 2,2-dioxide | 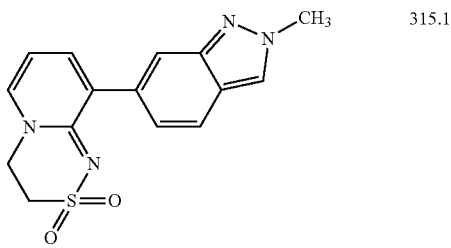 | 315.1 |
| 420 | 9-(2-methyl-2H-indazol-5-yl)-3,4-dihydropyrido[2,1-c][1,2,4]thiadiazine 2,2-dioxide | 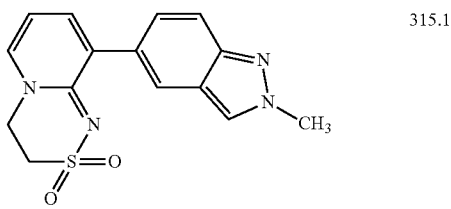 | 315.1 |

TABLE 37-continued
| | | | |
|---|---|---|---|
| 421 | 9-(3,4-dimethylphenyl)-3,4-dihydropyrido[2,1-c][1,2,4]thiadiazine 2,2-dioxide | 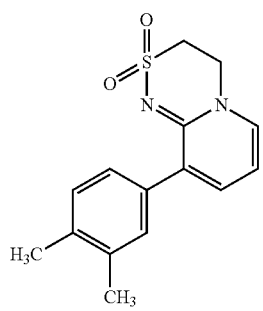 [SMILES: Cc1ccc(C2=CC=CN3CCS(=O)(=O)N=C23)cc1C] | 289.1 |
| 422 | 9-(6-chloropyridin-3-yl)-3,4-dihydropyrido[2,1-c][1,2,4]thiadiazine 2,2-dioxide | 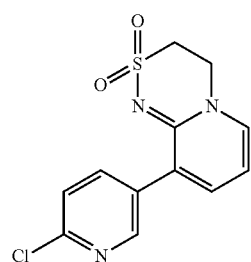 [SMILES: O=S1(=O)CCN2C=CC=C(c3ccc(Cl)nc3)C2=N1] | 296.0 |
| 423 | 9-(3-fluoro-4-methylphenyl)-3,4-dihydropyrido[2,1-c][1,2,4]thiadiazine 2,2-dioxide | 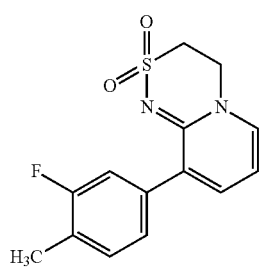 [SMILES: Cc1ccc(C2=CC=CN3CCS(=O)(=O)N=C23)cc1F] | 293.1 |
TABLE 38
| | | | |
|---|---|---|---|
| 424 | 9-[4-chloro-3-(trifluoromethyl)phenyl]-3,4-dihydropyrido[2,1-c][1,2,4]thiadiazine 2,2-dioxide | 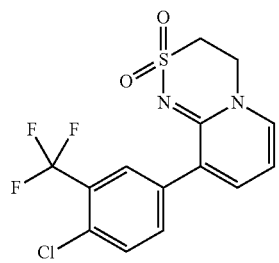 [SMILES: O=S1(=O)CCN2C=CC=C(c3ccc(Cl)c(C(F)(F)F)c3)C2=N1] | 363.0 |
| 425 | 9-(6-ethoxypyridin-3-yl)-3,4-dihydropyrido[2,1-c][1,2,4]thiadiazine 2,2-dioxide | 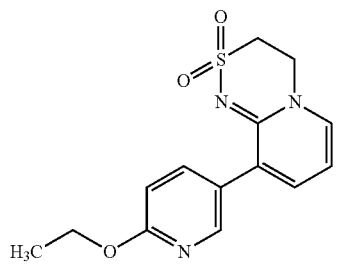 [SMILES: CCOc1ccc(C2=CC=CN3CCS(=O)(=O)N=C23)cn1] | 306.1 |

TABLE 38-continued

| | | | |
|---|---|---|---|
| 426 | 4-(2,2-dioxido-3,4-dihydropyrido[2,1-c][1,2,4]thiadiazin-9-yl)-N,N-diethylbenzamide | 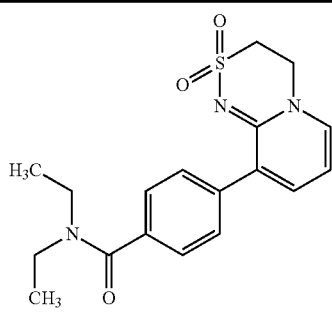 | 360.1 |
| 427 | 9-(6-methoxypyridin-3-yl)-3,4-dihydropyrido[2,1-c][1,2,4]thiadiazine 2,2-dioxide | 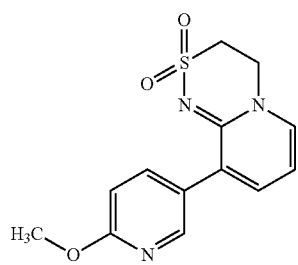 [SMILES: COc1ccc(C2=CC=CN3CCS(=O)(=O)N=C23)cn1] | 292.1 |
| 428 | tert-butyl 4-[(2,2-dioxido-3,4-dihydropyrido[2,1-c][1,2,4]thiadiazin-9-yl)methylidene]piperidine-1-carboxylate | 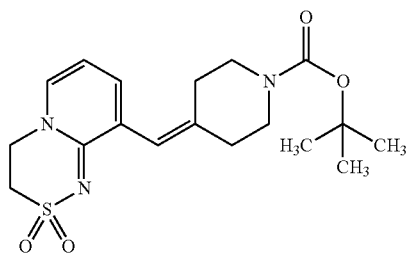 [SMILES: CC(C)(C)OC(=O)N1CCC(=CC2=CC=CN3CCS(=O)(=O)N=C23)CC1] | 280.1 |
| 429 | 9-{(1Z)-3-[4-(trifluoromethyl)piperidin-1-yl]prop-1-en-1-yl}-3,4-dihydropyrido[2,1-c][1,2,4]thiadiazine 2,2-dioxide | 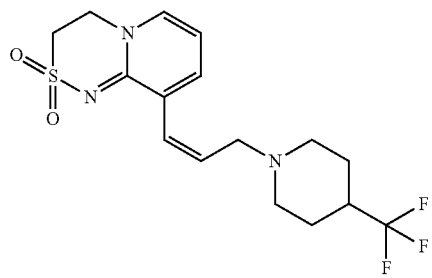 [SMILES: O=S1(=O)CCN2C=CC=C(/C=C\CN3CCC(C(F)(F)F)CC3)C2=N1] | 376.1 |
| 430 | methyl 1-[4-(2,2-dioxido-3,4-dihydropyrido[2,1-c][1,2,4]thiadiazin-9-yl)phenyl]cyclopropanecarboxylate | 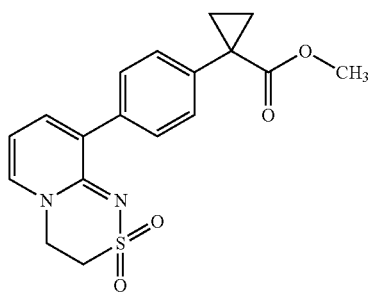 [SMILES: COC(=O)C1(c2ccc(C3=CC=CN4CCS(=O)(=O)N=C34)cc2)CC1] | 359.1 |

TABLE 38-continued
| | | | |
|---|---|---|---|
| 431 | methyl 2-[4-(2,2-dioxido-3,4-dihydropyrido[2,1-c][1,2,4]thiadiazin-9-yl)phenyl]-2-methylpropanoate | 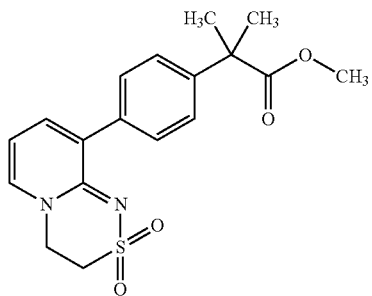 [SMILES: COC(=O)C(C)(C)c1ccc(C2=CC=CN3CCS(=O)(=O)N=C23)cc1] | 361.1 |
| 432 | 9-(5-chlorothiophen-2-yl)-3,4-dihydropyrido[2,1-c][1,2,4]thiadiazine 2,2-dioxide | 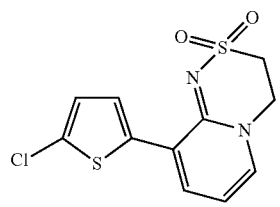 [SMILES: O=S1(=O)CCN2C=CC=C(c3ccc(Cl)s3)C2=N1] | 300.9 |
| 433 | 9-[4-(2-chlorophenoxy)phenyl]-3,4,6,7,8,9-hexahydropyrido[2,1-c][1,2,4]thiadiazine 2,2-dioxide | 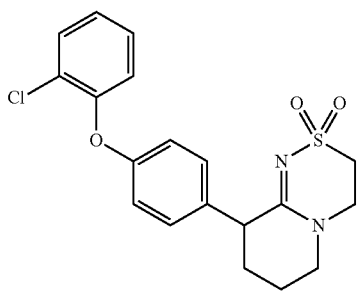 [SMILES: O=S1(=O)CCN2CCCC(c3ccc(Oc4ccccc4Cl)cc3)C2=N1] | 391.1 |
| 434 | 9-[4-(3-fluorophenoxy)phenyl]-3,4,6,7,8,9-hexahydropyrido[2,1-c][1,2,4]thiadiazine 2,2-dioxide | 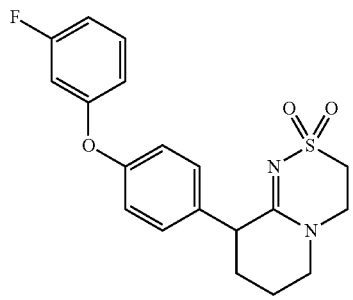 [SMILES: O=S1(=O)CCN2CCCC(c3ccc(Oc4cccc(F)c4)cc3)C2=N1] | 376.1 |
| 435 | 9-[4-(4-tert-butylphenoxy)phenyl]-3,4,6,7,8,9-hexahydropyrido[2,1-c][1,2,4]thiadiazine 2,2-dioxide | 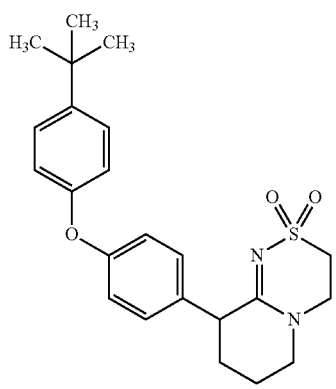 [SMILES: CC(C)(C)c1ccc(Oc2ccc(C3CCCN4CCS(=O)(=O)N=C34)cc2)cc1] | 413.2 |

TABLE 39

| | | | |
|---|---|---|---|
| 436 | 9-{4-[4-(trifluoromethoxy)phenoxy]phenyl}-3,4,6,7,8,9-hexahydropyrido[2,1-c][1,2,4]thiadiazine 2,2-dioxide | 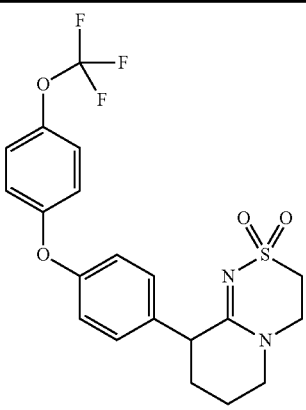 | 441.1 |
| 437 | 3-[4-(2,2-dioxido-3,4,6,7,8,9-hexahydropyrido[2,1-c][1,2,4]thiadiazin-9-yl)phenoxy]benzonitrile | 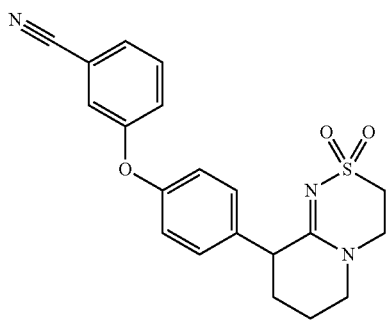 [SMILES: N#Cc1cccc(Oc2ccc(C3CCCN4CCS(=O)(=O)N=C34)cc2)c1] | 382.1 |
| 438 | 9-[4-(2,3-dichlorophenoxy)phenyl]-3,4,6,7,8,9-hexahydropyrido[2,1-c][1,2,4]thiadiazine 2,2-dioxide | 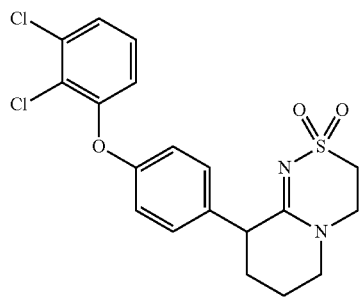 [SMILES: O=S1(=O)CCN2CCCC(c3ccc(Oc4cccc(Cl)c4Cl)cc3)C2=N1] | 426.1 |
| 439 | 9-[4-(3,5-dichlorophenoxy)phenyl]-3,4,6,7,8,9-hexahydropyrido[2,1-c][1,2,4]thiadiazine 2,2-dioxide | 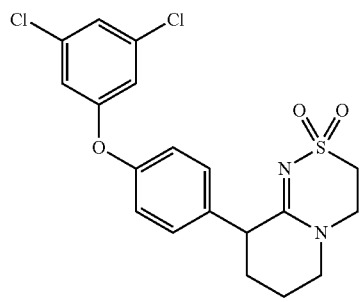 [SMILES: O=S1(=O)CCN2CCCC(c3ccc(Oc4cc(Cl)cc(Cl)c4)cc3)C2=N1] | 428.1 |
| 440 | 9-{4-[2-chloro-5-(trifluoromethyl)phenoxy]phenyl}-3,4,6,7,8,9-hexahydropyrido[2,1-c][1,2,4]thiadiazine 2,2-dioxide | 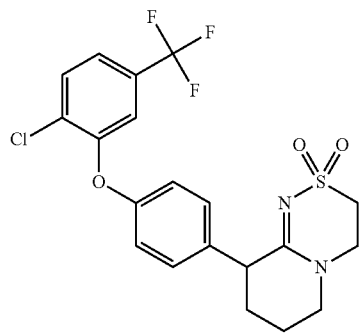 [SMILES: O=S1(=O)CCN2CCCC(c3ccc(Oc4cc(C(F)(F)F)ccc4Cl)cc3)C2=N1] | 459.1 |

TABLE 39-continued

| | | | |
|---|---|---|---|
| 441 | 9-{4-[3-chloro-5-(trifluoromethyl)phenoxy]phenyl}-3,4,6,7,8,9-hexahydropyrido[2,1-c][1,2,4]thiadiazine 2,2-dioxide | 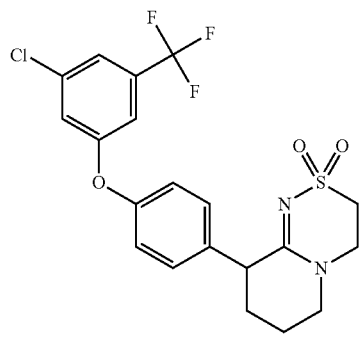 [SMILES: O=S1(=O)CCN2CCCC(c3ccc(Oc4cc(Cl)cc(C(F)(F)F)c4)cc3)C2=N1] | 459.1 |
| 442 | 9-{4-[4-chloro-3-(trifluoromethyl)phenoxy]phenyl}-3,4,6,7,8,9-hexahydropyrido[2,1-c][1,2,4]thiadiazine 2,2-dioxide | 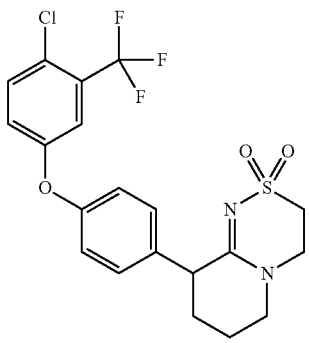 [SMILES: O=S1(=O)CCN2CCCC(c3ccc(Oc4ccc(Cl)c(C(F)(F)F)c4)cc3)C2=N1] | 459.1 |
| 443 | 9-{4-[4-chloro-2-(trifluoromethyl)phenoxy]phenyl}-3,4,6,7,8,9-hexahydropyrido[2,1-c][1,2,4]thiadiazine 2,2-dioxide | 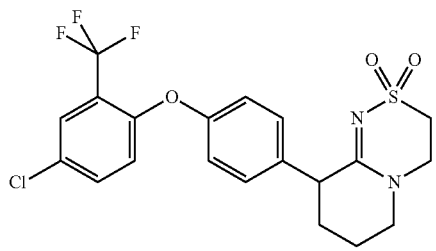 [SMILES: O=S1(=O)CCN2CCCC(c3ccc(Oc4ccc(Cl)cc4C(F)(F)F)cc3)C2=N1] | 459.1 |
| 444 | 9-[4-(5-chloro-2-methylphenoxy)phenyl]-3,4,6,7,8,9-hexahydropyrido[2,1-c][1,2,4]thiadiazine 2,2-dioxide | 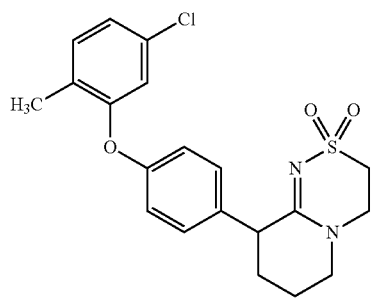 [SMILES: Cc1ccc(Cl)cc1Oc1ccc(C2CCCN3CCS(=O)(=O)N=C23)cc1] | 405.1 |
| 445 | 4-[4-(2,2-dioxido-3,4,6,7,8,9-hexahydropyrido[2,1-c][1,2,4]thiadiazin-9-yl)phenoxy]-3-methylbenzonitrile | 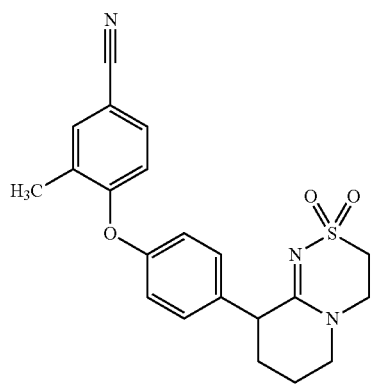 [SMILES: Cc1cc(C#N)ccc1Oc1ccc(C2CCCN3CCS(=O)(=O)N=C23)cc1] | 396.1 |

TABLE 39-continued
| | | | |
|---|---|---|---|
| 446 | 9-[4-(4-chloro-2-methylphenoxy)phenyl]-3,4,6,7,8,9-hexahydropyrido[2,1-c][1,2,4]thiadiazine 2,2-dioxide | 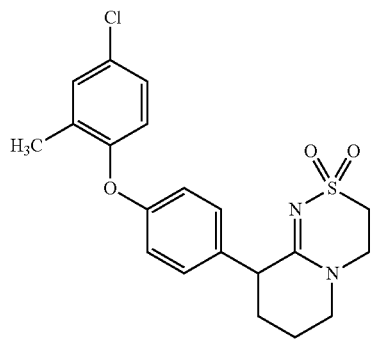 [SMILES: Cc1cc(Cl)ccc1Oc1ccc(C2CCCN3CCS(=O)(=O)N=C23)cc1] | 405.1 |
| 447 | 9-[4-(3-chloro-4-fluorophenoxy)phenyl]-3,4,6,7,8,9-hexahydropyrido[2,1-c][1,2,4]thiadiazine 2,2-dioxide | 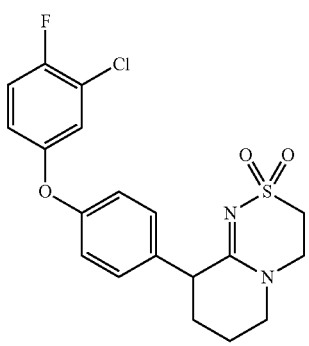 [SMILES: O=S1(=O)CCN2CCCC(c3ccc(Oc4ccc(F)c(Cl)c4)cc3)C2=N1] | 409.1 |
TABLE 40
| | | | |
|---|---|---|---|
| 448 | 9-[4-(3-chloro-5-fluorophenoxy)phenyl]-3,4,6,7,8,9-hexahydropyrido[2,1-c][1,2,4]thiadiazine 2,2-dioxide | 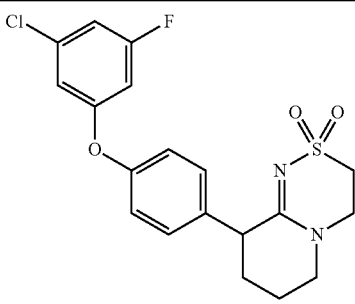 | 409.1 |
| 449 | 9-[4-(2-chloro-5-fluorophenoxy)phenyl]-3,4,6,7,8,9-hexahydropyrido[2,1-c][1,2,4]thiadiazine 2,2-dioxide | 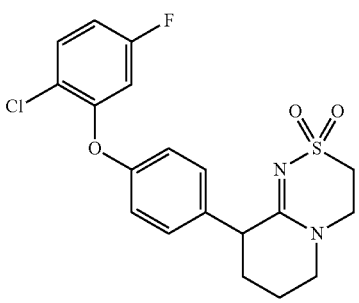 [SMILES: O=S1(=O)CCN2CCCC(c3ccc(Oc4cc(F)ccc4Cl)cc3)C2=N1] | 409.1 |

TABLE 40-continued
| | | | |
|---|---|---|---|
| 450 | (9S)-9-[4-(4-chloro-2-fluorophenoxy)phenyl]-3,4,6,7,8,9-hexahydropyrido[2,1-c][1,2,4]thiadiazine 2,2-dioxide | 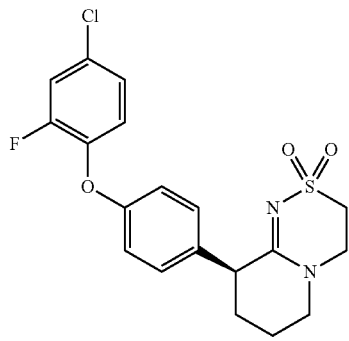 [SMILES: O=S1(=O)CCN2CCC[C@@H](c3ccc(Oc4ccc(Cl)cc4F)cc3)C2=N1] | 409.1 |
| 451 | (9S)-9-[4-(4-chloro-2-fluoro-5-methoxyphenoxy)phenyl]-3,4,6,7,8,9-hexahydropyrido[2,1-c][1,2,4]thiadiazine 2,2-dioxide | 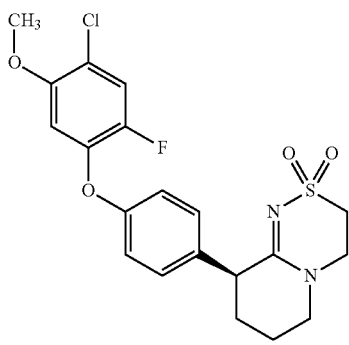 [SMILES: COc1cc(Oc2ccc([C@@H]3CCCN4CCS(=O)(=O)N=C34)cc2)c(F)cc1Cl] | 439.1 |
| 452 | (9S)-9-[4-(4-chloro-2-fluoro-3-methoxyphenoxy)phenyl]-3,4,6,7,8,9-hexahydropyrido[2,1-c][1,2,4]thiadiazine 2,2-dioxide | 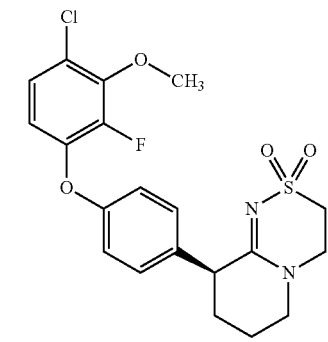 [SMILES: COc1c(Cl)ccc(Oc2ccc([C@@H]3CCCN4CCS(=O)(=O)N=C34)cc2)c1F] | 439.1 |
| 453 | (9S)-9-[4-(2-fluoro-4-methylphenoxy)phenyl]-3,4,6,7,8,9-hexahydropyrido[2,1-c][1,2,4]thiadiazine 2,2-dioxide | 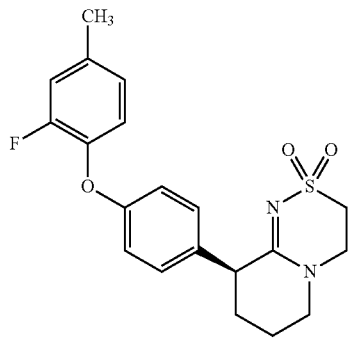 [SMILES: Cc1ccc(Oc2ccc([C@@H]3CCCN4CCS(=O)(=O)N=C34)cc2)c(F)c1] | 389.1 |

TABLE 40-continued
| 454 | (9S)-9-[4-(3-fluoro-4-methylphenoxy)phenyl]-3,4,6,7,8,9-hexahydropyrido[2,1-c][1,2,4]thiadiazine 2,2-dioxide | 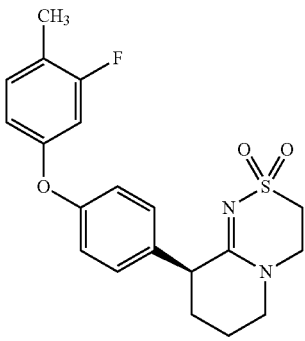 [SMILES: Cc1ccc(Oc2ccc([C@@H]3CCCN4CCS(=O)(=O)N=C34)cc2)cc1F] | 389.1 |
| 455 | (9S)-9-[4-(2,4,5-trimethylphenoxy)phenyl]-3,4,6,7,8,9-hexahydropyrido[2,1-c][1,2,4]thiadiazine 2,2-dioxide | 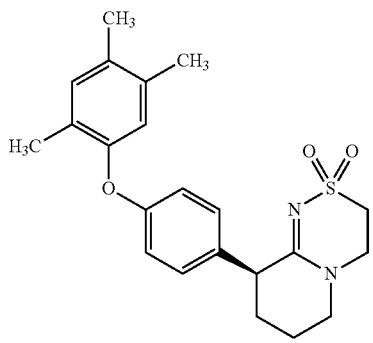 [SMILES: Cc1cc(C)c(Oc2ccc([C@@H]3CCCN4CCS(=O)(=O)N=C34)cc2)cc1C] | 399.2 |
| 456 | (9S)-9-{4-[3-(1-methylethyl)phenoxy]phenyl}-3,4,6,7,8,9-hexahydropyrido[2,1-c][1,2,4]thiadiazine 2,2-dioxide | 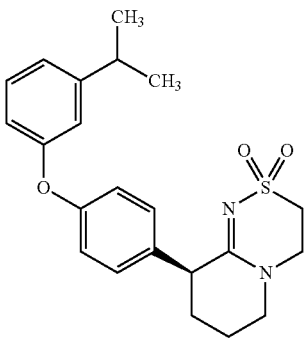 [SMILES: CC(C)c1cccc(Oc2ccc([C@@H]3CCCN4CCS(=O)(=O)N=C34)cc2)c1] | 400.2 |
| 457 | (9S)-9-[4-(3-chloro-4-fluorophenoxy)phenyl]-3,4,6,7,8,9-hexahydropyrido[2,1-c][1,2,4]thiadiazine 2,2-dioxide | 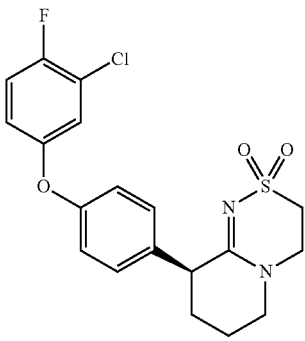 [SMILES: O=S1(=O)CCN2CCC[C@@H](c3ccc(Oc4ccc(F)c(Cl)c4)cc3)C2=N1] | 409.1 |

TABLE 40-continued

| 458 | (9S)-9-[4-(4-methoxy-2-methylphenoxy)phenyl]-3,4,6,7,8,9-hexahydropyrido[2,1-c][1,2,4]thiadiazine 2,2-dioxide | 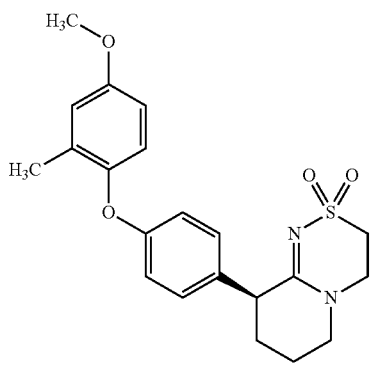 [SMILES: COc1ccc(Oc2ccc([C@@H]3CCCN4CCS(=O)(=O)N=C34)cc2)c(C)c1] | 401.2 |
| 459 | (9S)-9-[4-(3,4-difluorophenoxy)phenyl]-3,4,6,7,8,9-hexahydropyrido[2,1-c][1,2,4]thiadiazine 2,2-dioxide | 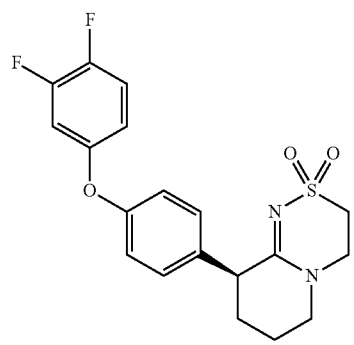 [SMILES: O=S1(=O)CCN2CCC[C@@H](c3ccc(Oc4ccc(F)c(F)c4)cc3)C2=N1] | 393.1 |

TABLE 41

| 460 | (9S)-9-[4-(2,4,5-trifluorophenoxy)phenyl]-3,4,6,7,8,9-hexahydropyrido[2,1-c][1,2,4]thiadiazine 2,2-dioxide | 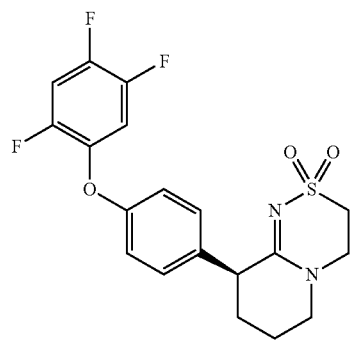 [SMILES: O=S1(=O)CCN2CCC[C@@H](c3ccc(Oc4cc(F)c(F)cc4F)cc3)C2=N1] | 411.1 |
| 461 | 9-[(7-methoxynaphthalen-2-yl)oxy]-3,4,6,7,8,9-hexahydropyrido[2,1-c][1,2,4]thiadiazine 2,2-dioxide | 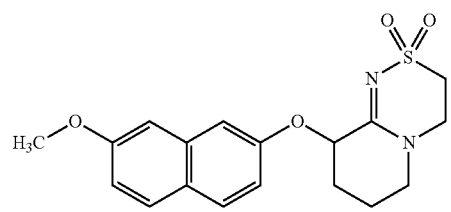 [SMILES: COc1ccc2ccc(OC3CCCN4CCS(=O)(=O)N=C34)cc2c1] | 360.9 |
| 462 | 9-[(7-methoxynaphthalen-2-yl)oxy]-3,4,6,7,8,9-hexahydropyrido[2,1-c][1,2,4]thiadiazine 2,2-dioxide | 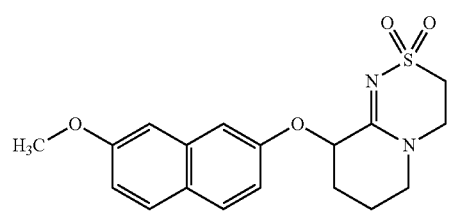 [SMILES: COc1ccc2ccc(OC3CCCN4CCS(=O)(=O)N=C34)cc2c1] | 361.0 |

Experimental Example 1

(1) Construction of Expression Gene

Human GluR1 flip cDNA was amplified by PCR using forward primer ACTGAATTCGCCACCATGCAGCA-CATTTTTGCCTTCTTCTGC (SEQ ID NO: 1) and reverse primer CCGCGGCCGCTTACAATCCCGTGGCTC-CCAAG (SEQ ID NO: 2) artificially synthesized using human brain-derived cDNA (BD Bio science) as a template. The amplified product was digested with restriction enzymes EcoRI, NotI (TAKARA SHUZO CO. LTD.), and incorporated into the same site of pcDNA3.1(+) (Invitrogen) to construct pcDNA3.1(+)/human GluR1 flip gene. Human stargazin cDNA was amplified by PCR using forward primer GGTCTCGAGGCCACCATGGGGCTGTTTGATCGAG-GTGTTCA (SEQ ID NO: 3) and reverse primer GTTG-GATCCTTATACGGGGGTGGTCCGGCGGTTGGCT-GTG (SEQ ID NO: 4) artificially synthesized using human hippocampus cDNA as a template. The amplified product was digested with restriction enzymes XhoI, BamHI (TAKARA SHUZO CO. LTD.), and incorporated into the same site of pcDNA3.1(−) (Invitrogen) to construct pcDNA3.1 Zeo(−)/human stargazin gene.

(2) Construction of GluR1 flip/stargazin expressing cell

CHO-K1 cells passaged in a culture medium (Ham's F12 medium (Invitrogen) added with 10% inactivated fetal bovine serum (Morgate) and penicillin, streptomycin (Invitrogen)) were detached with 0.05% trypsin, 0.53 mM EDTA (Invitrogen) diluted with D-PBS(−). The detached cells were suspended in a culture medium, and recovered by a centrifugation operation at 1,000 rpm. The recovered cells were suspended again in D-PBS(−), and added to a 0.4 cm electroporation cuvette (BioRad). pcDNA3.1(+)/human GluR1 flip gene (5 μg) and pcDNA3.1 Zeo(−)/human stargazin gene (15 μg) were added, and the mixture was introduced into CHO-K1 cells using Gene Pulser II (BioRad) under the conditions of 950 μFd, 250 mV. The introduced cells were cultured overnight in a culture medium and, the next day, plated in a 96 well plate at 250 cells/well using a selection medium (culture medium added with Zeocin (Invitrogen) to 250 μg/mL). Clones showing drug resistance were selected, and GluR1 flip/stargazin expressing clones were selected by an assay method using calcium influx as an index as shown below.

(3) Measurement Method of AMPA Receptor Function Enhancing Activity of Compound Using Calcium Influx as Index CHO-K1/GluR1 flip/stargazin expressing cells were plated on a 96 well black transparent bottom plate (Costar) at $2\times10^4$ cells/well, and cultured in a 37° C., $CO_2$ incubator (SANYO Electric Co., Ltd.) for 2 days. The medium in the cell plate was removed, and assay buffer A (D-MEM (Invitrogen), 0.1% BSA (Serogical Protein), 20 mM HEPES (Invitrogen)) was added at 50 μL/well. A calcium indicator (Calcium 4 Assay Kit, Invitrogen) added with 2.5 mM probenecid (Invitrogen) was added at 50 μL/well and the well was left standing in 37° C., $CO_2$ incubator for 1 hr. The cell plate was set in CellLux (PerkinElmer), a mixture (50 μL) of 9 mM glutamic acid diluted with assay buffer B (HBSS (Invitrogen), 0.1% BSA, 20 mM HEPES) (final concentration 3 mM) and a test compound (test compound concentration 30 μM) was added, and the amount of change in fluorescence level in 3 min was measured. In the definition here, the amount of change in fluorescence level of well added with glutamic acid at final concentration 3 mM and 300 cyclothiazide (TOCRIS) is 100%, the amount of change in fluorescence level of well added only with glutamic acid at final concentration 3 mM is 0%, and the compound activity was calculated according to the following formula.

activity (%)=$(X-C)/(T-C)\times 100$

T: amount of change in fluorescence level of well added with glutamic acid at final concentration 3 mM and 300 μM cyclothiazide
C: amount of change in fluorescence level of well added only with glutamic acid at final concentration 3 mM
X: amount of change in fluorescence level of well added with test compound The results are shown in the following Tables.

TABLE 42

| Example No. | activity (%) |
|---|---|
| 1 | 66 |
| 4 | 85 |
| 14 | 78 |
| 23 | 104 |
| 24 | 78 |
| 25 | 98 |
| 26 | 87 |
| 28 | 80 |
| 31 | 79 |
| 34 | 78 |
| 37 | 95 |
| 43 | 81 |
| 46 | 80 |
| 51 | 87 |
| 52 | 67 |
| 57 | 86 |
| 59 | 72 |
| 60 | 63 |
| 61 | 75 |
| 63 | 77 |
| 64 | 73 |
| 65 | 78 |
| 67 | 68 |
| 68 | 77 |
| 69 | 71 |
| 70 | 86 |
| 72 | 80 |
| 73 | 75 |
| 75 | 81 |
| 78 | 72 |
| 79 | 90 |
| 80 | 88 |
| 81 | 86 |
| 82 | 65 |
| 83 | 57 |
| 85 | 84 |
| 86 | 67 |
| 87 | 51 |
| 88 | 75 |
| 89 | 85 |

TABLE 43

| Example No. | activity (%) |
|---|---|
| 90 | 78 |
| 91 | 81 |
| 94 | 71 |
| 96 | 74 |
| 97 | 86 |
| 98 | 71 |
| 99 | 73 |

TABLE 43-continued

| Example No. | activity (%) |
|---|---|
| 101 | 84 |
| 102 | 71 |
| 103 | 81 |
| 105 | 87 |
| 106 | 98 |
| 107 | 69 |
| 108 | 68 |
| 109 | 88 |
| 111 | 58 |
| 112 | 79 |
| 113 | 86 |
| 115 | 80 |
| 116 | 69 |
| 117 | 90 |
| 118 | 79 |
| 119 | 92 |
| 121 | 71 |
| 122 | 58 |
| 123 | 57 |
| 125 | 53 |
| 126 | 72 |
| 127 | 79 |
| 128 | 98 |
| 129 | 100 |
| 130 | 69 |
| 131 | 58 |
| 132 | 75 |
| 134 | 77 |
| 135 | 59 |
| 136 | 77 |
| 137 | 61 |
| 138 | 71 |
| 141 | 80 |

TABLE 44

| Example No. | activity (%) |
|---|---|
| 142 | 70 |
| 143 | 76 |
| 144 | 76 |
| 145 | 84 |
| 147 | 70 |
| 148 | 73 |
| 149 | 77 |
| 151 | 67 |
| 152 | 80 |
| 154 | 75 |
| 155 | 63 |
| 156 | 90 |
| 157 | 89 |
| 158 | 76 |
| 159 | 90 |
| 160 | 78 |
| 161 | 57 |
| 162 | 56 |
| 163 | 74 |
| 164 | 69 |
| 171 | 87 |
| 172 | 74 |
| 173 | 68 |
| 174 | 79 |
| 175 | 53 |
| 177 | 69 |
| 179 | 69 |
| 180 | 70 |
| 182 | 80 |
| 183 | 91 |
| 185 | 36 |
| 187 | 72 |
| 191 | 74 |
| 198 | 87 |
| 199 | 79 |
| 201 | 74 |
| 203 | 85 |

TABLE 44-continued

| Example No. | activity (%) |
|---|---|
| 204 | 70 |
| 205 | 67 |
| 206 | 84 |

TABLE 45

| Example No. | activity (%) |
|---|---|
| 207 | 78 |
| 208 | 79 |
| 210 | 82 |
| 211 | 71 |
| 215 | 67 |
| 216 | 71 |
| 218 | 74 |
| 219 | 83 |
| 220 | 93 |
| 221 | 96 |
| 226 | 79 |
| 227 | 68 |
| 228 | 78 |
| 230 | 59 |
| 231 | 78 |
| 232 | 60 |
| 235 | 84 |
| 236 | 74 |
| 237 | 66 |
| 238 | 87 |
| 239 | 88 |
| 244 | 76 |
| 246 | 73 |
| 251 | 81 |
| 253 | 80 |
| 254 | 81 |
| 255 | 84 |
| 256 | 86 |
| 257 | 84 |
| 258 | 79 |
| 259 | 90 |
| 260 | 91 |
| 261 | 72 |
| 264 | 80 |
| 266 | 84 |
| 274 | 85 |
| 282 | 84 |
| 287 | 73 |
| 290 | 79 |
| 292 | 90 |

TABLE 46

| Example No. | activity (%) |
|---|---|
| 293 | 80 |
| 294 | 82 |
| 295 | 64 |
| 298 | 99 |
| 299 | 88 |
| 300 | 93 |
| 301 | 76 |
| 303 | 82 |
| 304 | 87 |
| 306 | 89 |
| 313 | 95 |
| 316 | 89 |
| 321 | 64 |
| 323 | 85 |
| 324 | 63 |
| 325 | 99 |
| 329 | 82 |
| 344 | 74 |
| 345 | 63 |
| 347 | 76 |

TABLE 46-continued

| Example No. | activity (%) |
|---|---|
| 348 | 64 |
| 349 | 83 |
| 350 | 74 |
| 352 | 76 |
| 357 | 77 |
| 361 | 85 |
| 396 | 82 |
| 397 | 83 |
| 400 | 83 |
| 408 | 85 |
| 411 | 86 |
| 412 | 91 |
| 423 | 80 |
| 433 | 55 |
| 447 | 78 |
| 462 | 69 |

Experimental Example 2

(1) Animals

Male ICR mice were supplied by CLEA Japan, Inc (Japan). After arrival to the vivarium, animals were allowed a minimum of 1 week for acclimation. They were housed under a 12:12-h light/dark cycle in a temperature- and humidity-controlled laboratory and allowed food and water ad libitum.

(2) Drug Administration

A test compound was suspended in 0.5% methylcellulose in distilled water and orally administered (p.o.). Methamphetamine (Dainippon Sumitomo Pharma Co., Ltd.) was dissolved in saline and subcutaneously administered (s.c.). All drugs were dosed in a volume of 10 mL/kg body weight for mice.

(3) Inhibition of Methamphetamine (MAP)-Induced Hyperlocomotion

The widely used animal models of psychosis have been the measurement of the extent of hyperlocomotion induced by psychostimulants (e.g., amphetamine, cocaine, methamphetamine, MK-801 and phencyclidine) in rodents (Psychopharmacology 1999, vol. 145: 237-250). 4 compounds (A, B, C, D) were tested for its ability to antagonize MAP-induced hyperlocomotion in mice. Male ICR mice were habituated in the locomotor chambers with infrared sensors (BrainScienceIdea Co., Ltd. Japan) to the experiment. After the habituation, animals were treated with either vehicle or the compounds (10 mg/kg, p.o.), and MAP (2 mg/kg, s.c.) was administered 60 min later. Locomotion activities were measured, and accumulated counts (120 min after administration of MAP) were calculated in each treatment group. All data were represented as means plus the standard errors of the means (n=3-9) and analyzed using Student's t-test with significance set at $P<0.01$ and *$P<0.001$ or Welch's t-test with significance set at $^{\$}P<0.05$, $^{\$\$}P<0.01$ and $^{\$\$\$}P<0.001$.

Compound A is 9-(4-phenoxyphenyl)-3,4-dihydropyrido[2,1-c][1,2,4]thiadiazine 2,2-dioxide, compound B is 9-[4-(4-methylphenoxy)phenyl]-3,4-dihydropyrido[2,1-c][1,2,4]thiadiazine 2,2-dioxide, compound C is 9-[4-(cyclohexyloxy)phenyl]-7-methyl-3,4-dihydropyrazino[2,1-c][1,2,4]thiadiazine 2,2-dioxide, and compound D is 9-[4-(cyclohexyloxy)phenyl]-3,4-dihydropyrido[2,1-c][1,2,4]thiadiazine 2,2-dioxide.

The graphs of FIG. 1 show inhibition of methamphetamine (MAP)-induced hyperlocomotion by compound A, B, C and D. By administered 60 min before MAP (2 mg/kg, s.c.) treatment, compound A, B, C, and D produced significant inhibition of MAP-induced hyperlocomotion (0-120 min).

Formulation Example 1

| | |
|---|---|
| (1) compound of Example 1 | 50 mg |
| (2) lactose | 34 mg |
| (3) cornstarch | 10.6 mg |
| (4) cornstarch (paste) | 5 mg |
| (5) magnesium stearate | 0.4 mg |
| (6) calcium carboxymethylcellulose | 20 mg |
| total | 120 mg |

The above-mentioned (1) to (6) are mixed according to a conventional method, and the mixture is compressed by a tableting machine to give a tablet.

INDUSTRIAL APPLICABILITY

The compound of the present invention has an AMPA receptor function enhancing action and is useful as a prophylactic or therapeutic drug for depression, schizophrenia, Alzheimer or attention deficit hyperactivity disorder (ADHD) and the like.

This application is based on patent application No. 2010-179577 filed in Japan, the contents of which are encompassed in full herein.

SEQUENCE LISTING FREE TEXT

SEQ ID NO: 1 is a forward primer for GluR1 flip cDNA.
SEQ ID NO: 2 is a reverse primer for GluR1 flip cDNA.
SEQ ID NO: 3 is a forward primer for stargazin cDNA cDNA.
SEQ ID NO: 4 is a reverse primer for stargazin cDNA cDNA.

The invention claimed is:

1. A method for the treatment of Alzheimer's disease, comprising administering an effective amount of a compound represented by the formula (I):

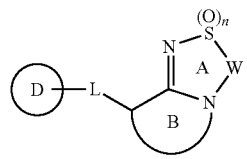

(I)

wherein the partial structural formula represented by the formula:

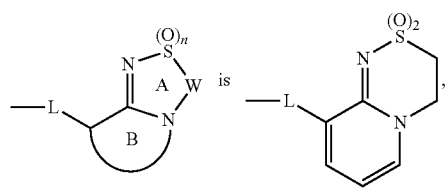

is

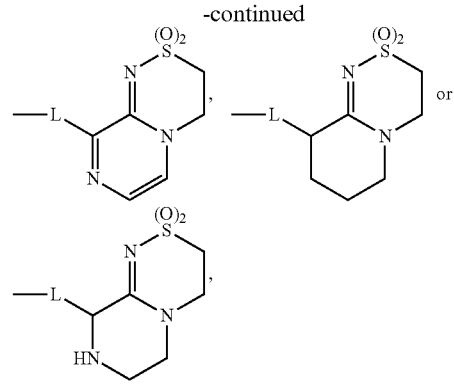

ring B is optionally substituted by substituent selected from
a halogen atom;
hydroxy;
$C_{1-6}$ alkyl optionally substituted by a halogen atom;
$C_{1-6}$ alkoxy; and
$C_{1-6}$ alkyl-carbonyl,
ring D is $C_{3-7}$ cycloalkane, $C_{6-14}$ arene, dihydronaphthalene, tetrahydronaphthalene, dihydroinden, thiophene, azetidine, piperidine, furan, pyridine, pyrazole, 1,2,4-oxadiazole, dihydrobenzodioxin, dihydrobenzofuran, benzodioxole, benzofuran, indole, quinoline, benzimidazole, benzothiazole, indazole or dibenzothiophene, optionally substituted by 1-4 substituents selected from (1) a halogen atom;
(2) cyano;
(3) hydroxy;
(4) oxo;
(5) $C_{1-6}$ alkyl optionally substituted by substituent(s) selected from 1) a halogen atom, 2) phenyl optionally substituted by substituent(s) selected from a halogen atom and $C_{1-6}$ alkyl and 3) $C_{1-6}$ alkoxycarbonyl;
(6) $C_{3-7}$ cycloalkyl optionally substituted by $C_{1-6}$ alkoxycarbonyl or phenyl;
(7) $C_{1-6}$ alkyl-carbonyl;
(8) phenyl-carbonyl optionally substituted by $C_{1-6}$ alkoxy;
(9) $C_{2-6}$ alkenyl substituted by phenyl;
(10) phenyl optionally substituted by 1 to 3 substituents selected from a halogen atom, $C_{1-6}$ alkyl, $C_{3-7}$ cycloalkyl and $C_{1-6}$ alkoxy;
(11) pyrazolyl optionally substituted by 1 to 3 substituents selected from $C_{1-6}$ alkyl optionally substituted by a halogen atom, and $C_{3-7}$ cycloalkyl;
(12) pyrrolidinyl;
(13) dihydrobenzofuranyl;
(14) morpholinyl;
(15) oxetanyl substituted by a halogen atom;
(16) sulfanyl substituted by a halogen atom or $C_{1-6}$ alkyl;
(17) $C_{1-6}$ alkylsulfonyloxy substituted by a halogen atom;
(18) di-$C_{1-6}$ alkylcarbamoyl;
(19) 4,4,5,5-tetramethyl-1,3,2-dioxaborolanyl;
(20) $C_{1-6}$ alkoxy optionally substituted by substituent(s) selected from a halogen atom, $C_{3-7}$ cycloalkyl, phenyl optionally substituted by a halogen atom, tetrahydrofuranyl and tetrahydropyranyl;
(21) $C_{3-7}$ cycloalkyloxy optionally substituted by $C_{1-6}$ alkyl, oxo or $C_{2-6}$ alkylenedioxy;
(22) $C_{3-7}$ cycloalkenyloxy optionally substituted by $C_{1-6}$ alkyl;
(23) phenyloxy optionally substituted by 1 to 3 substituents selected from a halogen atom, cyano, hydroxy, $C_{1-6}$ alkyl optionally substituted by a halogen atom, and $C_{1-6}$ alkoxy optionally substituted by a halogen atom;
(24) pyridyloxy optionally substituted by a halogen atom, or $C_{1-6}$ alkyl optionally substituted by a halogen atom;
(25) silyloxy substituted by $C_{1-6}$ alkyl;
(26) tetrahydrofuranyloxy;
(27) tetrahydropyranyloxy; and
(28) dihydrobenzofuranyloxy, and
L is a bond, —O—, —O—CH$_2$—, —CH$_2$—O—, —CO—NH—, —CO—N($C_{1-6}$ alkyl)-, —S—, —SO—, —SO$_2$—, $C_{1-6}$ alkylene, $C_{2-6}$ alkenylene or $C_{2-6}$ alkynylene,
or a salt thereof to a mammal.

2. The method according to claim 1, wherein the partial structural formula represented by the formula:

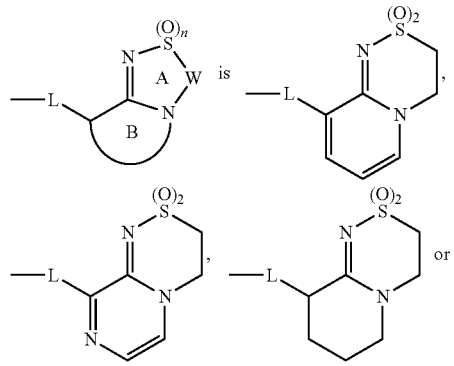

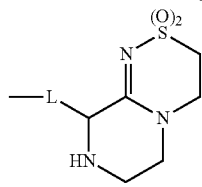

ring B is optionally substituted by substituent selected from a halogen atom, hydroxy, $C_1$-6 alkyl and $C_{1-6}$ alkoxy,
ring D is $C_{3-7}$ cycloalkane, benzene, naphthalene, pyridine or thiophene optionally substituted by 1 to 3 substituents selected from
(1) a halogen atom;
(2) hydroxy;
(3) $C_{1-6}$ alkyl optionally substituted by substituent selected from 1) a halogen atom, and 2) phenyl optionally substituted by substituent selected from a halogen atom and $C_{1-6}$ alkyl;
(4) $C_{3-7}$ cycloalkyl;
(5) phenyl-carbonyl;
(6) $C_{2-6}$ alkenyl substituted by phenyl;
(7) phenyl optionally substituted by a halogen atom or $C_{1-6}$ alkyl;
(8) pyrrolidinyl;
(9) dihydrobenzofuranyl;
(10) $C_{1-6}$ alkylsulfonyloxy substituted by a halogen atom;
(11) $C_{1-6}$ alkoxy optionally substituted by substituent selected from a halogen atom, $C_{3-7}$ cycloalkyl, phenyl substituted by a halogen atom, tetrahydrofuranyl and tetrahydropyranyl;
(12) $C_{3-7}$ cycloalkyloxy optionally substituted by $C_{1-6}$ alkyl;
(13) $C_{3-7}$ cycloalkenyloxy optionally substituted by $C_{1-6}$ alkyl;
(14) phenyloxy optionally substituted by 1 to 3 substituents selected from a halogen atom, cyano, hydroxy, $C_{1-6}$ alkyl optionally substituted by a halogen atom, and $C_{1-6}$ alkoxy;
(15) pyridyloxy substituted by a halogen atom, or $C_{1-6}$ alkyl substituted by a halogen atom;
(16) tetrahydrofuranyloxy;
(17) tetrahydropyranyloxy; and
(18) dihydrobenzofuranyloxy, and
L is a bond, —O—, —O—CH$_2$—, —CO—NH—, $C_{1-6}$ alkylene, or $C_{2-6}$ alkynylene,
or a salt thereof.

3. The method according to claim 1, wherein the partial structural formula represented by the formula:

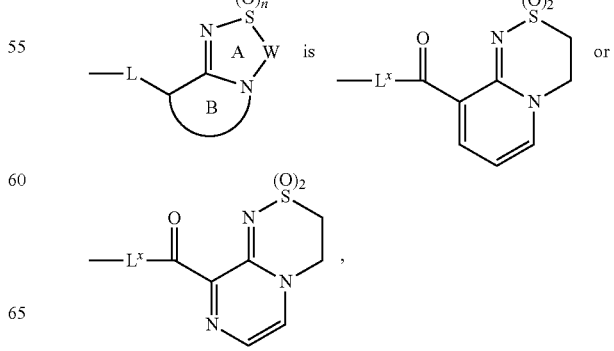

ring B is optionally substituted by $C_{1-6}$ alkyl,
ring D is benzene optionally substituted by 1 to 3 substituents selected from
(1) a halogen atom;
(2) hydroxy;
(3) $C_{1-6}$ alkyl optionally substituted by substituent selected from 1) a halogen atom, and 2) phenyl optionally substituted by substituent selected from a halogen atom and $C_{1-6}$ alkyl;
(4) $C_{3-7}$ cycloalkyl optionally substituted by $C_{1-6}$ alkoxycarbonyl or phenyl;
(5) phenyl-carbonyl;
(6) $C_{2-6}$ alkenyl substituted by phenyl;
(7) phenyl optionally substituted by a halogen atom or $C_{1-6}$ alkyl;
(8) pyrrolidinyl;
(9) dihydrobenzofuranyl;
(10) $C_{1-6}$ alkylsulfonyloxy substituted by a halogen atom;
(11) $C_{1-6}$ alkoxy optionally substituted by substituent selected from a halogen atom, $C_{3-7}$ cycloalkyl, phenyl substituted by a halogen atom, tetrahydrofuranyl and tetrahydropyranyl;
(12) $C_{3-7}$ cycloalkyloxy optionally substituted by $C_{1-6}$ alkyl;
(13) $C_{3-7}$ cycloalkenyloxy optionally substituted by $C_{1-6}$ alkyl;
(14) phenyloxy optionally substituted by 1 to 3 substituents selected from a halogen atom, cyano, hydroxy, $C_{1-6}$ alkyl optionally substituted by a halogen atom, and $C_{1-6}$ alkoxy;
(15) pyridyloxy substituted by a halogen atom, or $C_{1-6}$ alkyl substituted by a halogen atom;
(16) tetrahydrofuranyloxy;
(17) tetrahydropyranyloxy; and
(18) dihydrobenzofuranyloxy, and
L is a bond,
or a salt thereof.

4. A method for the treatment of depression, schizophrenia or attention deficit hyperactivity disorder, comprising administering an effective amount of a compound which is 9-(4-Phenoxyphenyl)-3,4-dihydropyrido[2,1-c][1,2,4]thiadiazine 2,2-dioxide or a salt thereof to a mammal.

5. A method for the treatment of depression, schizophrenia or attention deficit hyperactivity disorder, comprising administering an effective amount of a compound which is 9-[4-(4-Methylphenoxy)phenyl]-3,4-dihydropyrido[2,1-c][1,2,4]thiadiazine 2,2-dioxide or a salt thereof to a mammal.

6. A method for the treatment of depression, schizophrenia or attention deficit hyperactivity disorder, comprising administering an effective amount of a compound which is 9-[4-(Cyclohexyloxy)phenyl]-7-methyl-3,4-dihydropyrazino[2,1-c][1,2,4]thiadiazine 2,2-dioxide to a mammal.

7. The method according to claim 1, wherein the compound represented by the formula (I) is 9-(4-Phenoxyphenyl)-3,4-dihydropyrido[2,1-c][1,2,4]thiadiazine 2,2-dioxide or a salt thereof.

8. The method according to claim 1, wherein the compound represented by the formula (I) is 9-[4-(4-Methylphenoxy)phenyl]-3,4-dihydropyrido[2,1-c][1,2,4]thiadiazine 2,2-dioxide or a salt thereof.

9. The method according to claim 1, wherein the compound represented by the formula (I) is 9-[4-(Cyclohexyloxy)phenyl]-3,4-dihydropyrido[2,1-c][1,2,4]thiadiazine 2,2-dioxide or a salt thereof.

10. The method according to claim 1, wherein the compound represented by the formula (I) is 9-[4-(Cyclohexyloxy)phenyl]-7-methyl-3,4-dihydropyrazino[2,1-c][1,2,4]thiadiazine 2,2-dioxide or a salt thereof.

11. The method according to claim 1, wherein the compound represented by the formula (I) is 9-{4-[Difluoro(phenyl)methyl]phenyl}-3,4-dihydropyrido[2,1-c][1,2,4]thiadiazine 2,2-dioxide or a salt thereof.

12. The method according to claim 1, wherein the compound represented by the formula (I) is 9-[4-(3,4-Dimethylphenoxy)phenyl]-3,4-dihydropyrido[2,1-c][1,2,4]thiadiazine 2,2-dioxide or a salt thereof.

13. The method according to claim 1, wherein the compound represented by the formula (I) is 9-[4-(2,3-Dihydro-1-benzofuran-6-yloxy)phenyl]-3,4-dihydropyrido[2,1-c][1,2,4]thiadiazine 2,2-dioxide or a salt thereof.

14. The method according to claim 1, wherein the compound represented by the formula (I) is 9-[4-(3-Methylphenoxy)phenyl]-3,4-dihydropyrido[2,1-c][1,2,4]thiadiazine 2,2-dioxide or a salt thereof.

15. The method according to claim 1, wherein the compound represented by the formula (I) is 7-Chloro-9-{4-[(5-chloropyridin-2-yl)oxy]phenyl}-3,4-dihydropyrido[2,1-c][1,2,4]thiadiazine 2,2-dioxide or a salt thereof.

16. The method according to claim 1, wherein the compound represented by the formula (I) is 7-Chloro-9-(4-{[2-(trifluoromethyl)pyridin-4-yl]oxy}phenyl)-3,4-dihydropyrido[2,1-c][1,2,4]thiadiazine 2,2-dioxide or a salt thereof.

17. The method according to claim 1, wherein the compound represented by the formula (I) is 9-{4-[Difluoro(4-methylphenyl)methyl]phenyl}-3,4-dihydropyrido[2,1-c][1,2,4]thiadiazine 2,2-dioxide or a salt thereof.

* * * * *